(12) United States Patent
DeGrado et al.

(10) Patent No.: US 10,214,522 B2
(45) Date of Patent: Feb. 26, 2019

(54) ANTI-ALPHAVBETA1 INTEGRIN INHIBITORS AND METHODS OF USE

(71) Applicant: The Regents of the University of California, Oakland, CA (US)

(72) Inventors: William F. DeGrado, San Francisco, CA (US); Dean Sheppard, Oakland, CA (US); Hyunil Jo, Lafayette, CA (US); Nilgun Isik Reed, San Francisco, CA (US); Youzhi Tang, Guangdong Province (KR); Joel McIntosh, Pacifica, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 15/067,124

(22) Filed: Mar. 10, 2016

(65) Prior Publication Data

US 2016/0264566 A1  Sep. 15, 2016

Related U.S. Application Data

(60) Provisional application No. 62/131,166, filed on Mar. 10, 2015, provisional application No. 62/131,735, filed on Mar. 11, 2015.

(51) Int. Cl.

| | | |
|---|---|---|
| *C07D 417/12* | (2006.01) | |
| *C07D 249/06* | (2006.01) | |
| *C07C 279/14* | (2006.01) | |
| *C07D 471/04* | (2006.01) | |
| *C07D 233/50* | (2006.01) | |
| *C07D 217/24* | (2006.01) | |
| *C07D 263/32* | (2006.01) | |
| *C07D 277/30* | (2006.01) | |
| *C07D 401/12* | (2006.01) | |
| *C07D 239/14* | (2006.01) | |
| *C07D 413/12* | (2006.01) | |
| *C07D 403/12* | (2006.01) | |
| *C07D 271/02* | (2006.01) | |
| *C07D 285/04* | (2006.01) | |
| *G01N 33/68* | (2006.01) | |
| *C07D 213/74* | (2006.01) | |
| *G01N 33/573* | (2006.01) | |

(52) U.S. Cl.
CPC .......... *C07D 417/12* (2013.01); *C07C 279/14* (2013.01); *C07D 213/74* (2013.01); *C07D 217/24* (2013.01); *C07D 233/50* (2013.01); *C07D 239/14* (2013.01); *C07D 249/06* (2013.01); *C07D 263/32* (2013.01); *C07D 271/02* (2013.01); *C07D 277/30* (2013.01); *C07D 285/04* (2013.01); *C07D 401/12* (2013.01); *C07D 403/12* (2013.01); *C07D 413/12* (2013.01); *C07D 471/04* (2013.01); *G01N 33/573* (2013.01); *G01N 33/6863* (2013.01); *G01N 2333/7055* (2013.01)

(58) Field of Classification Search
CPC .. C07D 417/12; C07D 213/74; C07D 217/24; C07D 233/50; C07D 239/14; C07D 249/06; C07D 263/32; C07D 271/02; C07D 277/30; C07D 285/04; C07D 401/12; C07D 413/12; C07D 471/04; C07D 403/12; C07C 279/14; G01N 33/573; G01N 33/6863; G01N 2333/7055
USPC ....................................................... 548/400
See application file for complete search history.

(56) References Cited

U.S. PATENT DOCUMENTS

| | | | |
|---|---|---|---|
| 4,676,980 A | 6/1987 | Segal et al. | |
| 4,816,567 A | 3/1989 | Cabilly et al. | |
| 4,946,778 A | 8/1990 | Ladner et al. | |
| 5,545,806 A | 8/1996 | Lonberg et al. | |
| 5,545,807 A | 8/1996 | Surani et al. | |
| 5,569,825 A | 10/1996 | Lonberg et al. | |
| 5,625,126 A | 4/1997 | Lonberg et al. | |
| 5,633,425 A | 5/1997 | Lonberg et al. | |
| 5,661,016 A | 8/1997 | Lonberg et al. | |
| 6,492,421 B1 | 12/2002 | Thorsett | |
| 6,583,139 B1 | 6/2003 | Thorsett | |
| 6,586,602 B2 | 7/2003 | Thorsett | |
| 7,288,526 B2 | 10/2007 | Thorsett | |
| 8,309,735 B2 * | 11/2012 | Zischinsky | C07D 401/12 546/304 |
| 2008/0045521 A1 | 2/2008 | Arnould et al. | |
| 2008/0255183 A1 | 10/2008 | Arnould et al. | |
| 2009/0104116 A1 * | 4/2009 | Zischinsky | C07D 401/12 424/1.65 |
| 2014/0038910 A1 | 2/2014 | Ruminski et al. | |

(Continued)

FOREIGN PATENT DOCUMENTS

| | | |
|---|---|---|
| WO | WO-91/00360 | 1/1991 |
| WO | WO-93/08829 | 5/1993 |
| WO | WO-98/53814 A1 | 12/1998 |

(Continued)

OTHER PUBLICATIONS

Choi, S. et al. (Nov. 1, 2007, e-published Oct. 4, 2007). "Small molecule inhibitors of integrin $\alpha_2\beta_1$," *J Med Chem* 50(22):5457-5462.

(Continued)

*Primary Examiner* — Kristin A Vajda

(74) *Attorney, Agent, or Firm* — Mintz Levin Cohn Ferris Glovsky and Popeo, P.C.; Kenneth E. Jenkins; Joohee Lee

(57) ABSTRACT

Provided herein, inter alia, are methods and compositions for inhibiting $\alpha v\beta 1$ integrin and for treating fibrosis.

19 Claims, 2 Drawing Sheets

(56) References Cited

U.S. PATENT DOCUMENTS

2016/0376266 A1 12/2016 DeGrado et al.

FOREIGN PATENT DOCUMENTS

| WO | WO-2001/042225 A2 | 6/2001 |
|---|---|---|
| WO | WO-2001/042225 A3 | 6/2001 |
| WO | WO-2001/042225 A8 | 6/2001 |
| WO | WO-01/54690 A1 | 8/2001 |
| WO | WO-2002/016329 A1 | 2/2002 |
| WO | WO-2003/008380 A1 | 1/2003 |
| WO | WO-03/089410 A1 | 10/2003 |
| WO | WO-2004/066931 A2 | 8/2004 |
| WO | WO-2004/066931 A3 | 8/2004 |
| WO | WO-2005/000244 A2 | 1/2005 |
| WO | WO-2005/000244 A3 | 1/2005 |
| WO | WO-2005/070921 A1 | 8/2005 |
| WO | WO-2007/060408 A2 | 5/2007 |
| WO | WO-2007/060408 A3 | 5/2007 |
| WO | WO-2007/088041 A1 | 8/2007 |
| WO | WO-2007/131764 A2 | 11/2007 |
| WO | WO-2007/131764 A3 | 11/2007 |
| WO | WO-2007/141473 A1 | 12/2007 |
| WO | WO-2008/062859 A1 | 5/2008 |
| WO | WO-2008/125811 A1 | 10/2008 |
| WO | WO-2009/055487 A1 | 4/2009 |
| WO | WO-2015/048819 A1 | 4/2015 |
| WO | WO-2016/145258 A1 | 9/2016 |

OTHER PUBLICATIONS

Cole, S.P.C. et al. (1985). "The EBV-Hybridoma Technique and Its Application to Human Lung Cancer," *Monoclonal Antibodies and Cancer Therapy* pp. 77-96.

Corbett, J.W. et al. (1997). Solid-Phase Synthesis of a Selective $\alpha_v\beta_3$ Integrin Antagonist Library, *Bioorganic & Miedicinal Chemisty Letters* 7(11):1371-1376.

De Corte, B.L. et al. (Oct. 18, 2004). "Piperidine-containing beta-arylpropionic acids as potent antagonists of $\alpha_v\beta_3/\alpha_v\beta_5$ integrins," *Bioorg Med Chem Lett* 14(20):5227-5232.

Delouvrié, B. et al. (Jun. 15, 2012 e-published Apr. 21, 2012). "Structure-activity relationship of a series of non peptidic RGD integrin antagonists targeting $\alpha 5\beta 1$: part 1," *Bioorg Med Chem Lett* 22(12):4111-41116.

Delouvrié, B. et al. (Jun. 2012, e-published Apr. 21, 2012). "Structure-activity relationship of a series of non peptidic RGD integrin antagonists targeting $\alpha 5\beta 1$: part 2," *Bioorg Med Chem Lett* 22(12):4117-4121.

Fishwild, D.M. et al. (Jul. 1996). "High-avidity human IgGk monoclonal antibodies from a novel strain of minilocus transgenic mice," *Nat Biotechnol* 14(7):845-851.

Ghosh, A.K. et al. (Jan. 1, 2012). "Fibrosis: Is It a Coactivator Disease?," *Frontiers in Bioscience E4*, 1556-1570.

Hagmann, W.K. et al. (Oct. 22, 2001). "The discovery of sulfonylated dipeptides as potent VLA-4 antagonists," *Bioorg Med Chem Lett* 11(20):2709-2713.

Heckmann, D. et al. (2007). "Probing integrin selectivity: rational design of highly active and selective ligands for the $\alpha 5\beta 1$ and $\alpha v\beta 3$ integrin receptor," *Angew Chem Int Ed Engl* 46(19):3571-3574.

Heckmann, D. et al. (Jun. 16, 2008). "Rational design of highly active and selective ligands for the $\alpha 5\beta 1$ integrin receptor," *Chembiochem* 9(9):1397-1407.

Heckmann, D. et al. (2009). "Breaking the dogma of the metal-coordinating carboxylate group in integrin ligands: introducing hydroxamic acids to the MIDAS to tune potency and selectivity," *Angew Chem Int Ed Engl* 48(24):4436-4440.

Henderson, N.C. et al. (Dec. 2013, e-published Nov. 10, 2013). "Targeting of $\alpha v$ integrin identifies a core molecular pathway that regulates fibrosis in several organs," *Nat Med* 19(12):1617-1624.

Hynes, R.O. et al. (Sep. 20, 2002). "Integrins: bidirectional, allosteric signaling machines," *Cell* 110(6):673-687.

International Search Report dated Jan. 16, 2015, for PCT Application No. PCT/US2014/058491, filed on Sep. 30, 2014, 4 pages.
International Search Report dated Jun. 3, 2016, for PCT Application No. PCT/US2016/021879, filed on Mar. 10, 2016 4 pages.
Jones. P.T. et al. (May 29-Jun. 4, 1986). "Replacing the complementarity-determining regions in a human antibody with those from a mouse," *Nature* 321(6069):522-525.

Klingberg, F. et al. (Jan. 2013). "The myofibroblast matrix: implications for tissue repair and fibrosis," *J Pathol* 229(2):298-309.

Kohler, G. et al. (Aug. 7, 1975). "Continuous cultures of fused cells secreting antibody of predefined specificity," *Nature* 256(5517):495-497.

Kozbor, D. et al. (Mar. 1983). "The production of monoclonal antibodies from human lymphocytes," *Immunol Today* 4(3):72-79.

Lonberg, N. et al. (Apr. 28, 1994). "Antigen-specific human antibodies from mice comprising four distinct genetic modifications," *Nature* 368(6474):856-859.

MacDonald, E.M. et al. (Nov. 2012). "TGFβ signaling: its role in fibrosis formation and myopathies," *Curr Opin Rheumatol* 24(6):628-634.

Margadant, C. et al. (Feb. 2010, e-published Jan. 15, 2010). "Integrin-TGF-β crosstalk in fibrosis, cancer and wound healing," *EMBO Rep* 11(2):97-105.

Marks, J.D. et al. (Jul. 1992). "By-passing immunization: building high affinity human antibodies by chain shuffling," *Biotechnology* 10(7):779-783.

McCafferty, J. et al. (Dec. 6, 1990). "Phage antibodies: filamentous phage displaying antibody variable domains," *Nature* 348(6301):552-554.

Miller, M.W. et al. (Jan. 20, 2009, e-published Jan. 13, 2009). "Small-molecule inhibitors of integrin alpha2beta1 that prevent pathological thrombus formation via an allosteric mechanism," *Proc Natl Acad Sci USA* 106(3):719-724.

Morrison, S.L. (Apr. 28, 1994). "Immunology. Success in specification," *Nature* 368(6474):812-813.

Mousa, S.A. et al. (Feb. 1, 1996). "Oral antiplatelet, antithrombotic efficacy of DMP 728, a novel platelet GPIIb/IIIa antagonist," *Circulation* 93(3):537-543.

Neuberger, M. (Jul. 1996). "Generating high-avidity human Mabs in mice," *Nat Biotechnol* 14(7):826.

O'Neil, K.T. et al. (Dec. 1992). "Identification of novel peptide antagonists for GPIIb/IIIa from a conformationally constrained phage peptide library," *Proteins* 14(4):509-515.

Pepinsky, R.B. et al. (Jun. 4, 2002). "Comparative assessment of the ligand and metal ion binding properties of integrins $\alpha 9\beta 1$ and $\alpha 4\beta 1$," *Biochemistry* 41(22):7125-7141.

Perdih, A. et al. (2010). "Small molecule antagonists of integrin receptors," *Curr Med Chem* 17(22):2371-2392.

Presta, L. (1992). "Antibody engineering," *Curr Opin Struc Biol* 2(4):593-596.

Presta, L. (Aug. 2003). "Antibody engineering for therapeutics," *Curr Opin Struc Biol* 13(4):519-525.

Ray, A.M. et al. (Sep. 2014, e-published May 5, 2014). "Single cell tracking assay reveals an opposite effect of selective small non-peptidic $\alpha 5\beta 1$ or $\alpha v\beta 3/\beta 5$ integrin antagonists in U87MG glioma cells," *Biochim Biophys Acta* 1840(9):2978-2987.

Riechmann, L. et al. (Mar. 24, 1988). "Reshaping human antibodies for therapy," *Nature* 332(6162):323-327.

Rockwell, A.L. et al. (Apr. 5, 1999). "Rapid synthesis of RGD mimetics with isoxazoline scaffolds on solid phase: identification of alphavbeta3 antagonists lead compounds," *Bioorg Med Chem Lett* 9(7):937-942.

Ruoslahti, E. et al. (1996). "RGD and other recognition sequences for integrins," *Annu Rev Cell Dev Biol* 12:697-715.

Saku, O. et al. (Feb. 1, 2008, e-published Dec. 14, 2007). "Synthetic study of VLA-4/VCAM-1 inhibitors: synthesis and structure-activity relationship of piperazinylphenylalanine derivatives," *Bioorg Med Chem Lett* 18(3):1053-1057.

Suresh. M.R. et al. (1986). "Bispecific monoclonal antibodies from hybrid hybridomas," *Methods Enzymol* 121:210-228.

Traunecker, A. et al. (Dec. 1991). "Bispecific single chain molecules (Janusins) target cytotoxic lymphocytes on HIV infected cells," *EMBO J* 10(12):3655-3659.

(56) References Cited

OTHER PUBLICATIONS

Verhoeyen, M. et al. (Mar. 25, 1988). "Reshaping human antibodies: grafting an antilysozyme activity," *Science* 239(4847):1534-1536.
Wipff, P.J. et al. (Dec. 17, 2007). "Myofibroblast contraction activates latent TGF-beta1 from the extracellular matrix," J Cell Biol 179(6):1311-1323.
Written Opinion dated Jan. 16, 2015, for PCT Application No. PCT/US2014/058491, filed Sep. 30, 2014, 4 pages.
Written Opinion dated Jun. 3, 2016, for PCT Application No. PCT/US2016/021879, filed Mar. 10, 2016 16 pages.
Xue, C-B. et al. (Apr. 1997). "Design, synthesis, and in vitro activities of benzamide-core glycoprotein IIb/IIIa antagonists: 2,3-diaminopropionic acid derivatives as surrogates of aspartic acid," *Bioorg Med Chem* 5(4):693-705.
Xue, C-B. et al. (Dec. 15, 1998). "Synthesis and antiplatelet effects of an isoxazole series of glycoprotein IIb/IIIa antagonists," *Bioorg Med Chem Lett* 8(24):3499-3504.
Yin, H. et al. (Jul. 1, 2006, e-published May 5, 2006). "Arylamide derivatives as allosteric inhibitors of the integrin $\alpha_2\beta_1$/type I collagen interaction," *Bioorg Med Chem Lett* 16(13):3380-3382.
Zischinsky, G. et al. (Jan. 1, 2010, e-published Nov. 14, 2009). "SAR of N-phenyl piperidine based oral integrin $\alpha5\beta1$ antagonists," *Bioorg Med Chem Lett* 20(1):65-68.
Zischinsky, G. et al. (Jan. 1, 2010, e-published Oct. 28, 2009). "Discovery of orally available integrin alpha5beta1 antagonists," *Bioorg Med Chem Lett* 20(1):380-382.
Takayanagi et al. (2003): STN International, HCAPLUS database, Accession No. 2003:76750, 2 pages.
Thorsett et al. (2003): STN International, HCAPLUS database, Accession No. 2003:485719, 1 page.
Thorsett et al. (2002): STN International, HCAPLUS database, Accession No. 2002:942792, 1 page.
Australian Examination Report dated Dec. 19, 2017, for Australian Application No. 2014324426, 7 pages.
Extended European Search Report dated Jul. 10, 2018, for EP Application No. 16762561.5, filed Mar. 10, 2016, 8 pages.
Jo, H. et al. (Aug. 10, 2014). "Development of a small molecule inhibitor of integrin alpha v beta 1," ACS 248th National Meeting and Exposition, 2 pages.
Reed, N.I. et al. (May 20, 2015). "The $\alpha_v\beta_1$ integrin plays a critical in vivo role in tissue fibrosis," *Sci Transl Med* 7(288):288ra79.
Reed, N.I. et al. (Aug. 30, 2016, e-published Oct. 13, 2016). "Exploring N-Arylsulfonyl-l-proline Scaffold as a Platform for Potent and Selective $\alpha v\beta 1$ Integrin Inhibitors," *ACS Med Chem Lett* 7(10):902-907.

\* cited by examiner

ANTI-ALPHAVBETA1 INTEGRIN INHIBITORS AND METHODS OF USE

CROSS-REFERENCES TO RELATED APPLICATIONS

This application claims the benefit of U.S. Provisional Application No. 62/131,166, filed Mar. 10, 2015, and U.S. Provisional Application No. 62/131,735, filed Mar. 11, 2015 which are incorporated herein by reference in entirety and for all purposes.

STATEMENT AS TO RIGHTS TO INVENTIONS MADE UNDER FEDERALLY SPONSORED RESEARCH AND DEVELOPMENT

This invention was made with government support under grant no. HL123423 awarded by the National Institutes of Health. The government has certain rights in the invention.

BACKGROUND OF THE INVENTION

Fibrosis is a pathologic process, characterized by overproduction of extracellular matrix (ECM) as a response to tissue injury. Nearly 45% of all deaths in the developed world can be attributed to some type of chronic fibroproliferative disease. Despite their high prevalence, current therapeutic options for fibrotic diseases are quite limited to elimination of triggering stimuli and organ transplantation. No effective agent exists that can directly halt the disease progression at the cellular level, which represents a major unmet medical need. Pharmacological modulation of the αvβ1 integrin by small molecules presents one route to test the role of the αvβ1 integrin in tissue fibrosis. Most integrins contain either an αv chain or β1 chain, and targeting either subunit by itself provides little specificity. Accordingly, there is a need in the art for potent, selective αvβ1 integrin inhibitors. Provided herein are solutions to these and other problems in the art.

BRIEF SUMMARY OF THE INVENTION

Herein are provided, inter alia, methods for treating fibrosis using an αvβ1 inhibitor and compositions of αvβ1 inhibitors.

In an aspect is provided a compound having the formula:

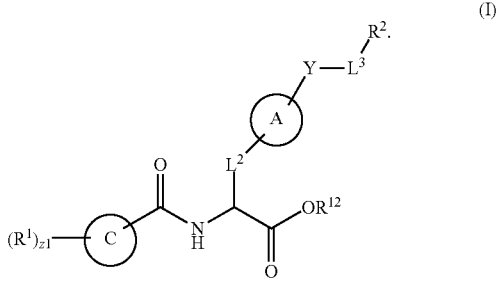

(I)

Ring A is substituted or unsubstituted cycloalkyl, substituted or unsubstituted heterocycloalkyl, substituted or unsubstituted aryl, or substituted or unsubstituted heteroaryl. Ring C is aryl or heteroaryl. $L^2$ is independently a bond, substituted or unsubstituted alkylene, or substituted or unsubstituted heteroalkylene. $L^3$ is a bond, substituted or unsubstituted alkylene, substituted or unsubstituted heteroalkylene, substituted or unsubstituted cycloalkylene, substituted or unsubstituted heterocycloalkylene, substituted or unsubstituted arylene, substituted or unsubstituted heteroarylene, or substituted or unsubstituted alkylarylene. Y is a bond, —C(O)N($R^4$)—, —O—, —C(O)O—, —S—, —N($SO_2R^4$)—, —N(C(O)$R^4$)—, —N(C(O)O$R^4$)—, —N($R^4$)C(O)—, —N($R^4$)—, —N($R^4$)C(O)NH—, —NHC(O)N($R^4$)—, —N($R^4$)C(O)O—, —C(O)—, —N($R^4$)$CH_2$—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. $R^1$ is independently hydrogen, halogen, —$N_3$, —$CX_3$, —$CHX_2$, —$CH_2X$, —CN, —CHO, —OH, —$NH_2$, —COOH, —$CONH_2$, —$NO_2$, —SH, —$SO_2CH_3$—$SO_3H$, —$OSO_3H$, —$SO_2NH_2$, —$SO_2Ph$, —$NHNH_2$, —$ONH_2$, —NHC(O)$NHNH_2$, —$OPO_3H$, —$PO_3H_2$, —$OCF_3$, —$OCHF_2$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, or a detectable moiety. Two $R^1$ substituents may be joined to form a substituted or unsubstituted cycloalkyl, substituted or unsubstituted heterocycloalkyl, substituted or unsubstituted aryl, substituted or unsubstituted heteroaryl. $R^2$ is —$NR^{3A}R^{3B}$, —C(NH)$NH_2$, —C(NH)$R^{3B}$, —C($NR^{3A}$)$NH_2$, —C($NR^{3A}$)$R^{3B}$, —C(NCN)$NH_2$, —$NH_2$, —C(NH)$NHR^{3B}$, —C($NR^{3A}$)$NHR^{3B}$, —C(NCN)$NHR^{3B}$, substituted or unsubstituted cycloalkyl, substituted or unsubstituted heterocycloalkyl, substituted or unsubstituted aryl, substituted or unsubstituted heteroaryl, substituted or unsubstituted fused ring cycloalkyl, substituted or unsubstituted fused ring heterocycloalkyl, substituted or unsubstituted fused ring aryl, or substituted or unsubstituted fused ring heteroaryl. $R^{3A}$ is hydrogen, —C(NH)$NH_2$, —C(NH)$R^{3D}$, —C($NR^{3C}$)$NH_2$, —C($NR^{3C}$)$R^{3D}$, —C(NCN)$NH_2$, $NH_2$, —C(NH)$NHR^{3D}$, —C($NR^{3C}$)$NHR^{3D}$, —C(NCN)$NHR^{3D}$, substituted or unsubstituted cycloalkyl, substituted or unsubstituted heterocycloalkyl, substituted or unsubstituted aryl, substituted or unsubstituted heteroaryl, or $R^{3A}$ and $R^{3B}$ are optionally joined to form a substituted or unsubstituted heterocycloalkyl or substituted or unsubstituted heteroaryl. $R^{3B}$ is hydrogen, —C(NH)$NH_2$, —C(NH)$R^{3D}$, —C($NR^{3C}$)$NH_2$, —C($NR^{3C}$)$R^{3D}$, —C(NCN)$NH_2$, $NH_2$, —C(NH)$NHR^{3D}$, —C($NR^{3C}$)$NHR^{3D}$, —C(NCN)$NHR^{3D}$, substituted or unsubstituted cycloalkyl, substituted or unsubstituted heterocycloalkyl, substituted or unsubstituted aryl, substituted or unsubstituted heteroaryl, or $R^{3A}$ and $R^{3B}$ may optionally be joined to form a substituted or unsubstituted heterocycloalkyl or substituted or unsubstituted heteroaryl. $R^{3C}$ is hydrogen, halogen, —$N_3$, —$CX^{1C}_3$, —$CHX^{1C}_2$, —$CH_2X^{1C}$, —CN, —CHO, —OH, —$NH_2$, —COOH, —$CONH_2$, —$NO_2$, —SH, —$SO_2$, —$SO_2CH_3$—$SO_3H$, —$SO_4H$, —$SO_2NH_2$, —$NHNH_2$, —$ONH_2$, —NHC(O)$NHNH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{3D}$ is hydrogen, halogen, —$N_3$, —$CX^{1D}_3$, —$CHX^{1D}_2$, —$CH_2X^{1D}$, —CN, —CHO, —OH, —$NH_2$, —COOH, —$CONH_2$, —$NO_2$, —SH, —$SO_2$, —$SO_2CH_3$—$SO_3H$, —$SO_4H$, —$SO_2NH_2$, —$NHNH_2$, —$ONH_2$, —NHC(O)$NHNH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^4$ is hydrogen or unsubstituted $C_1$-$C_5$ alkyl. $R^{12}$ is hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, or a prodrug moiety. Each X, $X^{1C}$, and $X^{1D}$ is independently —F, —Cl, —Br, or —I. The symbol z1 is an integer from 0 to 5.

In an aspect is provided a pharmaceutical composition including a compound described herein and a pharmaceutically acceptable excipient.

In an aspect is provided a method for treating fibrosis, the method including administering to a subject in need thereof a compound described herein.

In an aspect is provided a method of detecting αvβ1 expression in a cell, the method including; (i) contacting a cell with a compound described herein; (ii) allowing the compound to bind to the cell; and (iii) detecting the compound, thereby detecting αvβ1 expression in a cell.

In an aspect is provided a method of inhibiting TGFβ activation, the method including: (i) contacting a cell expressing αvβ1 integrin with a compound described herein; (ii) allowing the compound to bind to αvβ1 in the presence of TGFβ; (iii) comparing a level of activated TGFβ to a control to thereby identify a lower level of TGFβ activation and inhibition of TGFβ activation.

BRIEF DESCRIPTION OF THE DRAWINGS

FIG. 1A: Co-immunoprecipitation (IP) and western blot reveals expression of αvβ1 heterodimers in human and murine fibroblasts from the liver and lung. nhLu fb control (normal human lung fibroblasts from an uninjured control subject); IPF fb (lung fibroblasts isolated from a patient with idiopathic pulmonary fibrosis (IPF)); mLu fb (mouse lung fibroblasts); mLi fb (mouse hepatic stellate cells (liver fibroblasts); WI38 (diploid human lung fibroblast cell line); CHO WT (wild type chinese hamster ovary cells, which lack expression of β1); CHO αv (CHO cells with forced expression of αvβ1); hAT2 (human alveolar type II cells, which lack expression of β1); hPAEC (human pulmonary artery endothelial cells, which lack expression of β1). FIG. 1B: Wild type CHO cells (lacking αvβ1) adhere poorly, while CHO cells with forced expression of αvβ1 (CHO αv) and WI38 cells strongly adhere, to TGFβ1LAP.

DETAILED DESCRIPTION

Figure 1A:
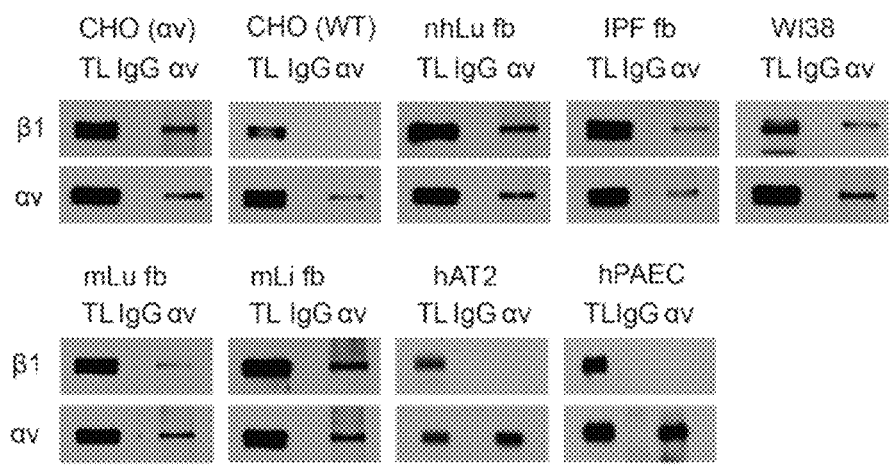
FIGS. 1A-1B.
Figure 1B:
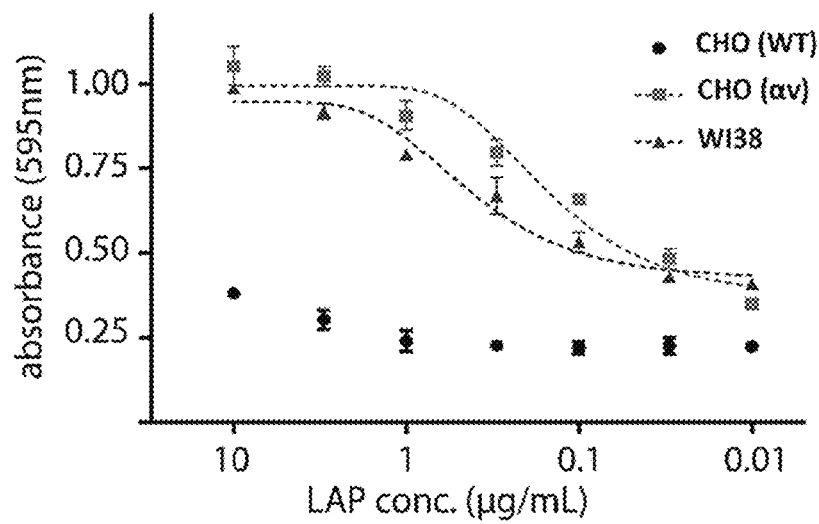
Figure 2:
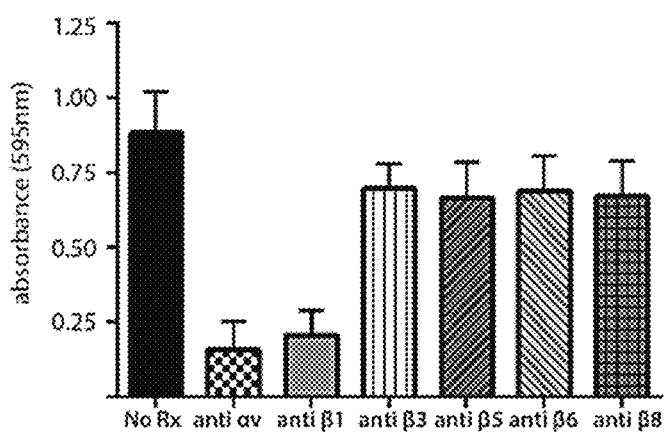
FIG. 2: Adhesion to LAP inhibited by antibodies to either β1 or αv, but not with antibodies to αvβ3, αvβ5, αvβ6 or αvβ8.

Integrins are present in nearly all multi-cellular organisms and play a conserved role in mediating cell adhesion to fixed extracellular ligands and in the maintenance of tissue integrity. In invertebrates, a surprisingly small number of integrin heterodimers mediate these diverse functions. Much has been learned about the critical in vivo functions of most members of the integrin family through the use of mice with global or conditional inactivating mutations of individual subunits and through the use of heterodimer-specific blocking monoclonal antibodies. One major exception is the αvβ1 integrin. This integrin, first identified biochemically more than 2 decades ago, is composed of an α and β subunit that are both present in multiple heterodimers (5 in the case of αv and 12 in the case of β1), which has made it difficult to generate heterodimer-specific antibodies or to infer function from gene knockout studies. As a result, this integrin has been largely ignored.

We have shown that two members of the integrin family, αvβ6 and αvβ8 have as their principal ligands the latency associated peptides of the growth factors TGFβ1-3 that these integrins play major roles in activation of latent forms of this growth factor that are stored in the extracellular matrix in most healthy adult tissues. In mice, inactivation of both of these integrins recapitulates all of the developmental phenotypes of loss of TGFβ1 and 3. Inhibitors of each of these integrins has identified important and distinct roles for each in multiple disease models and has provided new options for therapeutically targeting TGFβ in specific contexts, thereby avoiding potentially undesirable side effects of globally inhibiting this pleiotropic growth factor. However, in contrast to development, it is clear that there are a number of important pathologic circumstances in adults where inhibition of TGFβ is therapeutically effective, but inhibition of αvβ6 and αvβ8 is not. One of these is hepatic fibrosis. We recently used cre-mediated deletion of the integrin αv subunit in activated fibroblasts to demonstrate that loss of all αv integrins from these cells protects mice from fibrosis in multiple organs, including the liver, and that this effect was associated with reduced tissue TGFβ signaling. Tissue fibroblasts can express 4 αv-containing integrins, αvβ1, αvβ3, αvβ5 and αvβ8. We found that individual deletion of αvβ3, αvβ5 or αvβ8 integrin either globally or conditionally in activated fibroblasts (in the case of αvβ8 integrin) had no effect on organ fibrosis, but were previously unable to examine any possible contributions of the αvβ1 integrin because of the lack of suitable experimental tools. Our previous results could thus have been explained either by redundancy of αv integrins or by a specific role for fibroblast αvβ1 in driving fibrosis. To determine the functional relevance of the αvβ1 integrin, we began by examining its possible role in the process of tissue fibrosis. Fibrosis is a critical contributor to many chronic diseases that eventually lead to organ failure. Despite the societal burden of fibrotic diseases, there are currently few approved therapies.

As we reported for hepatic stellate cells, primary murine lung fibroblasts and human fetal and adult lung fibroblasts, as well as lung fibroblasts from patients with Idiopathic Pulmonary Fibrosis, all clearly expressed the αvβ1 integrin as determined by immunoprecipitation (IP) of αv followed by western blotting for β1. In contrast, while both the αv and β1 subunits were easily detectable in primary endothelial cells and epithelial cells, co-immunoprecipitation (IP) did not detect the αvβ1 heterodimer in these cells. We and others have reported that the closely related αv integrins, αvβ6 and αvβ8 can each bind to an amino terminal fragment of the TGFβ1 and 3 gene products called the latency associated peptide (LAP), which normally forms a non-covalent complex with the active cytokine, preventing TGFβ from binding to its receptors and inducing biological effects. When mechanical force is applied to the latent complex by contraction of integrin-expressing cells, the resultant conformational change leads to release of active TGFβ1. Our previous work suggested that an αv integrin on fibroblasts contributed to tissue fibrosis by binding to and activating TGFβ. To determine whether the relevant fibroblast integrin could be αvβ1, we performed cell adhesion assays with either primary fibroblasts, control α5-deficient Chinese Hamster Ovarian (CHO) cells or α5-deficient CHO cells engineered to express the αvβ1 integrin. Both fetal lung fibroblasts (WI-38 cells) and αvβ1 integrin-expressing CHO cells efficiently adhered to a range of concentrations of TGFβ1 LAP, whereas control CHO cells did not. The data suggests that αvβ1 is the principal integrin on fibroblasts responsible for adhesion to TGFβ1 LAP and for activation of latent TGFβ.

Interestingly, a biochemical association between the αvβ1 integrin and TGFβ1 LAP was previously reported based on affinity chromatography, but cells can use this integrin to activate TGFβ. Our finding that αvβ1 is the major integrin on several different primary fibroblasts responsible for binding to TGFβ1 LAP and for mediating activation of latent TGFβ by these cells clarifies several previous reports of integrin-mediated TGFβ activation by contractile fibroblasts. Provided herein is evidence that the αvβ1 integrin is the major integrin on pathologic fibroblasts responsible for activating latent TGFβ and driving tissue fibrosis in multiple organs The abbreviations used herein have their conventional meaning within the chemical and biological arts. The chemical structures and formulae set forth herein are constructed according to the standard rules of chemical valency known in the chemical arts.

Where substituent groups are specified by their conventional chemical formulae, written from left to right, they equally encompass the chemically identical substituents that would result from writing the structure from right to left, e.g., —CH$_2$O— is equivalent to —OCH$_2$—.

The term "alkyl," by itself or as part of another substituent, means, unless otherwise stated, a straight (i.e., unbranched) or branched carbon chain (or carbon), or combination thereof, which may be fully saturated, mono- or polyunsaturated and can include mono-, di- and multivalent radicals, having the number of carbon atoms designated (i.e., $C_1$-$C_{10}$ means one to ten carbons). Alkyl is an uncyclized chain. Examples of saturated hydrocarbon radicals include, but are not limited to, groups such as methyl, ethyl, n-propyl, isopropyl, n-butyl, t-butyl, isobutyl, sec-butyl, (cyclohexyl)methyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. An alkoxy is an alkyl attached to the remainder of the molecule via an oxygen linker (—O—).

The term "alkylene," by itself or as part of another substituent, means, unless otherwise stated, a divalent radical derived from an alkyl, as exemplified, but not limited by, —CH$_2$CH$_2$CH$_2$CH$_2$—. Typically, an alkyl (or alkylene) group will have from 1 to 24 carbon atoms, with those groups having 10 or fewer carbon atoms being preferred herein. A "lower alkyl" or "lower alkylene" is a shorter chain alkyl or alkylene group, generally having eight or fewer carbon atoms. The term "alkenylene," by itself or as part of another substituent, means, unless otherwise stated, a divalent radical derived from an alkene.

The term "heteroalkyl," by itself or in combination with another term, means, unless otherwise stated, a stable straight or branched chain, or combinations thereof, including at least one carbon atom and at least one heteroatom (e.g., O, N, P, Si, and S), and wherein the nitrogen and sulfur atoms may optionally be oxidized, and the nitrogen heteroatom may optionally be quaternized. The heteroatom(s) (e.g., O, N, P, S, B, As, and Si) may be placed at any interior position of the heteroalkyl group or at the position at which the alkyl group is attached to the remainder of the molecule. Heteroalkyl is an uncyclized chain. Examples include, but are not limited to: —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH═CH—O—CH$_3$, —Si(CH$_3$)$_3$, —CH$_2$—CH═N—OCH$_3$, —CH═CH—N(CH$_3$)—CH$_3$, —O—CH$_3$, —O—CH$_2$—CH$_3$, and —CN. Up to two or three heteroatoms may be consecutive, such as, for example, —CH$_2$—NH—OCH$_3$ and —CH$_2$—O—Si(CH$_3$)$_3$. A heteroalkyl moiety may include one heteroatom (e.g., O, N, S, Si, or P). A heteroalkyl moiety may include two optionally different heteroatoms (e.g., O, N, S, Si, or P). A heteroalkyl moiety may include three optionally different heteroatoms (e.g., O, N, S, Si, or P). A heteroalkyl moiety may include four optionally different heteroatoms (e.g., O, N, S, Si, or P). A heteroalkyl moiety may include five optionally different heteroatoms (e.g., O, N, S, Si, or P). A heteroalkyl moiety may include up to 8 optionally different heteroatoms (e.g., O, N, S, Si, or P).

Similarly, the term "heteroalkylene," by itself or as part of another substituent, means, unless otherwise stated, a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula: —C(O)$_2$R'— represents both —C(O)$_2$R'— and —R'C(O)$_2$—. As described above, heteroalkyl groups, as used herein, include those groups that are attached to the remainder of the molecule through a heteroatom, such as —C(O)R', —C(O)NR', —NR'R", —OR', —SR', and/or —SO$_2$R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl," by themselves or in combination with other terms, mean, unless otherwise stated, cyclic versions of "alkyl" and "heteroalkyl," respectively. Cycloalkyl and heteroalkyl are not aromatic. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively.

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo($C_1$-$C_4$)alkyl" includes, but is not limited to, fluoromethyl, difluoromethyl, trifluoromethyl, 2,2,2-trifluoroethyl, 4-chlorobutyl, 3-bromopropyl, and the like.

The term "acyl" means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently. A fused ring aryl refers to multiple rings fused together wherein at least one of the fused rings is an aryl ring. The term "heteroaryl" refers to aryl groups (or rings) that contain at least one heteroatom (e.g., N, O, or S), wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, naphthyl, pyrrolyl, pyrazolyl, pyridazinyl, triazinyl, pyrimidinyl, imidazolyl, pyrazinyl, purinyl, oxazolyl, isoxazolyl, thiazolyl, furyl, thienyl, pyridyl, pyrimidyl, benzothiazolyl, benzoxazoyl benzimidazolyl, benzofuran, isobenzofuranyl, indolyl, isoindolyl, benzothiophenyl, isoquinolyl, quinoxalinyl, quinolyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively. A heteroaryl group substituent may be —O— bonded to a ring heteroatom nitrogen.

Spirocyclic rings are two or more rings wherein adjacent rings are attached through a single atom. The individual rings within spirocyclic rings may be identical or different. Individual rings in spirocyclic rings may be substituted or unsubstituted and may have different substituents from other individual rings within a set of spirocyclic rings. Possible substituents for individual rings within spirocyclic rings are the possible substituents for the same ring when not part of spirocyclic rings (e.g. substituents for cycloalkyl or heterocycloalkyl rings). Spirocylic rings may be substituted or unsubstituted cycloalkyl, substituted or unsubstituted cycloalkylene, substituted or unsubstituted heterocycloalkyl or substituted or unsubstituted heterocycloalkylene and individual rings within a spirocyclic ring group may be any of the immediately previous list, including having all rings of one type (e.g. all rings being substituted heterocycloalkylene wherein each ring may be the same or different substituted heterocycloalkylene). When referring to a spirocyclic ring system, heterocyclic spirocyclic rings means a spirocyclic rings wherein at least one ring is a heterocyclic ring and wherein each ring may be a different ring. When referring to a spirocyclic ring system, substituted spirocyclic rings means that at least one ring is substituted and each substituent may optionally be different.

The symbol "〰" denotes the point of attachment of a chemical moiety to the remainder of a molecule or chemical formula.

The term "oxo," as used herein, means an oxygen that is double bonded to a carbon atom.

The term "alkylarylene" as an arylene moiety covalently bonded to an alkylene moiety (also referred to herein as an alkylene linker). In embodiments, the alkylarylene group has the formula:

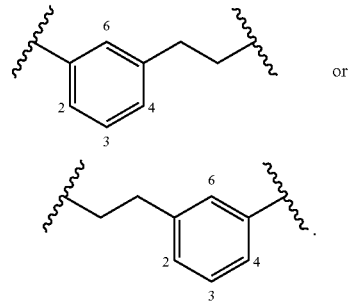

An alkylarylene moiety may be substituted (e.g. with a substituent group) on the alkylene moiety or the arylene linker (e.g. at carbons 2, 3, 4, or 6) with halogen, oxo, —N$_3$, —CF$_3$, —CCl$_3$, —CBr$_3$, —CI$_3$, —CN, —CHO, —OH, —NH$_2$, —COOH, —CONH$_2$, —NO$_2$, —SH, —SO$_2$CH$_3$— SO$_3$H, —OSO$_3$H, —SO$_2$NH$_2$, —NHNH$_2$, —ONH$_2$, —NHC(O)NHNH$_2$, substituted or unsubstituted C$_1$-C$_5$ alkyl or substituted or unsubstituted 2 to 5 membered heteroalkyl). In embodiments, the alkylarylene is unsubstituted.

Each of the above terms (e.g., "alkyl," "heteroalkyl," "aryl," and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —NR'NR"R'", —ONR'R", —NR'C(O) NR"NR'"R"", —CN, —NO$_2$, —NR'SO$_2$R", —NR'C(O)R", —NR'C(O)—OR", —NR'OR", in a number ranging from zero to (2m'+1), where m' is the total number of carbon atoms in such radical. R, R', R", R'", and R"" each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted heteroaryl, substituted or unsubstituted alkyl, alkoxy, or thioalkoxy groups, or arylalkyl groups. When a compound described herein includes more than one R group, for example, each of the R groups is independently selected as are each R', R", R'", and R"" group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are varied and are selected from, for example: —OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —NR'NR"R'", —ONR'R", —NR'C(O)NR"NR'"R"", —CN, —NO$_2$, —R', —N$_3$, —CH(Ph)$_2$, fluoro(C$_1$-C$_4$)alkoxy, and fluoro(C$_1$-C$_4$)alkyl, —NR'SO$_2$R", —NR'C(O)R", —NR'C(O)—OR", —NR'OR", in a number ranging from zero to the total number of open valences on the aromatic ring system; and where R', R", R'", and R"" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound described herein includes more than one R group, for example, each of the R groups is independently selected as are each R', R", R'", and R"" groups when more than one of these groups is present.

Substituents for rings (e.g. cycloalkyl, heterocycloalkyl, aryl, heteroaryl, cycloalkylene, heterocycloalkylene, arylene, or heteroarylene) may be depicted as substituents on the ring rather than on a specific atom of a ring (commonly referred to as a floating substituent). In such a case, the substituent may be attached to any of the ring atoms (obeying the rules of chemical valency) and in the case of fused rings or spirocyclic rings, a substituent depicted as associated with one member of the fused rings or spirocyclic rings (a floating substituent on a single ring), may be a substituent on any of the fused rings or spirocyclic rings (a floating substituent on multiple rings). When a substituent is attached to a ring, but not a specific atom (a floating substituent), and a subscript for the substituent is an integer greater than one, the multiple substituents may be on the same atom, same ring, different atoms, different fused rings, different spirocyclic rings, and each substituent may optionally be different. Where a point of attachment of a ring to the remainder of a molecule is not limited to a single atom (a floating substituent), the attachment point may be any atom of the ring and in the case of a fused ring or spirocyclic ring, any atom of any of the fused rings or spirocyclic rings while obeying the rules of chemical valency. Where a ring, fused rings, or spirocyclic rings contain one or more ring heteroatoms and the ring, fused rings, or spirocyclic rings are shown with one more floating substituents (including, but not limited to, points of attachment to the remainder of the molecule), the floating substituents may be bonded to the heteroatoms. Where the ring heteroatoms are shown bound to one or more hydrogens (e.g. a ring nitrogen with two bonds to ring atoms and a third bond to a hydrogen) in the structure or formula with the floating substituent, when the heteroatom is bonded to the floating substituent, the substituent will be understood to replace the hydrogen, while obeying the rules of chemical valency.

Two or more substituents may optionally be joined to form aryl, heteroaryl, cycloalkyl, or heterocycloalkyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

Two of the substituents on adjacent atoms of the aryl or heteroaryl ring may optionally form a ring of the formula: -T-C(O)—(CRR')$_q$—U—, wherein T and U are independently —NR—, —O—, —CRR'—, or a single bond, and q is an integer of from 0 to 3. Alternatively, two of the substituents on adjacent atoms of the aryl or heteroaryl ring may optionally be replaced with a substituent of the formula: -A-(CH$_2$)$_r$—B—, wherein A and B are independently —CRR'—, —O—, —NR—, —S—, —S(O)—, —S(O)$_2$—, —S(O)$_2$NR'—, or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula: —(CRR')$_s$—X'—(C"R"R'")$_d$—, where s and d are independently integers of from 0 to 3, and X' is —O—, —NR'—, —S—, —S(O)—, —S(O)$_2$—, or —S(O)$_2$NR'—. The substituents R, R', R", and R'" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

As used herein, the terms "heteroatom" or "ring heteroatom" are meant to include oxygen (O), nitrogen (N), sulfur (S), phosphorus (P), and silicon (Si).

A "substituent group," as used herein, means a group selected from the following moieties:
(A) oxo, halogen, —CF$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl, and
(B) alkyl, heteroalkyl, cycloalkyl, heterocycloalkyl, aryl, heteroaryl, substituted with at least one substituent selected from:
(i) oxo, halogen, —CF$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl, and (ii) alkyl, heteroalkyl, cycloalkyl, heterocycloalkyl, aryl, heteroaryl, substituted with at least one substituent selected from:
(a) oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCF_3$, —$OCHF_2$, unsubstituted alkyl, unsubstituted heteroalkyl, unsubstituted cycloalkyl, unsubstituted heterocycloalkyl, unsubstituted aryl, unsubstituted heteroaryl, and
(b) alkyl, heteroalkyl, cycloalkyl, heterocycloalkyl, aryl, heteroaryl, substituted with at least one substituent selected from: oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCF_3$, —$OCHF_2$, unsubstituted alkyl, unsubstituted heteroalkyl, unsubstituted cycloalkyl, unsubstituted heterocycloalkyl, unsubstituted aryl, unsubstituted heteroaryl.

A "size-limited substituent" or "size-limited substituent group," as used herein, means a group selected from all of the substituents described above for a "substituent group," wherein each substituted or unsubstituted alkyl is a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 10 membered heteroaryl.

A "lower substituent" or "lower substituent group," as used herein, means a group selected from all of the substituents described above for a "substituent group," wherein each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 9 membered heteroaryl.

In some embodiments, each substituted group described in the compounds herein is substituted with at least one substituent group. More specifically, in some embodiments, each substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene described in the compounds herein are substituted with at least one substituent group. In other embodiments, at least one or all of these groups are substituted with at least one size-limited substituent group. In other embodiments, at least one or all of these groups are substituted with at least one lower substituent group.

In other embodiments of the compounds herein, each substituted or unsubstituted alkyl may be a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 10 membered heteroaryl. In some embodiments of the compounds herein, each substituted or unsubstituted alkylene is a substituted or unsubstituted $C_1$-$C_{20}$ alkylene, each substituted or unsubstituted heteroalkylene is a substituted or unsubstituted 2 to 20 membered heteroalkylene, each substituted or unsubstituted cycloalkylene is a substituted or unsubstituted $C_3$-$C_8$ cycloalkylene, each substituted or unsubstituted heterocycloalkylene is a substituted or unsubstituted 3 to 8 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 10 membered heteroarylene.

In some embodiments, each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 9 membered heteroaryl. In some embodiments, each substituted or unsubstituted alkylene is a substituted or unsubstituted $C_1$-$C_8$ alkylene, each substituted or unsubstituted heteroalkylene is a substituted or unsubstituted 2 to 8 membered heteroalkylene, each substituted or unsubstituted cycloalkylene is a substituted or unsubstituted $C_3$-$C_7$ cycloalkylene, each substituted or unsubstituted heterocycloalkylene is a substituted or unsubstituted 3 to 7 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 9 membered heteroarylene. In some embodiments, the compound is a chemical species set forth in the Examples section, figures, or tables below.

Certain compounds of the present invention possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the present invention. The compounds of the present invention do not include those that are known in art to be too unstable to synthesize and/or isolate. The present invention is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

As used herein, the term "isomers" refers to compounds having the same number and kind of atoms, and hence the same molecular weight, but differing in respect to the structural arrangement or configuration of the atoms.

The term "tautomer," as used herein, refers to one of two or more structural isomers which exist in equilibrium and which are readily converted from one isomeric form to another.

It will be apparent to one skilled in the art that certain compounds of this invention may exist in tautomeric forms, all such tautomeric forms of the compounds being within the scope of the invention.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}$C- or $^{14}$C-enriched carbon are within the scope of this invention.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}$C- or $^{14}$C-enriched carbon are within the scope of this invention.

The compounds of the present invention may also contain unnatural proportions of atomic isotopes at one or more of the atoms that constitute such compounds. For example, the compounds may be radiolabeled with radioactive isotopes, such as for example tritium ($^{3}$H), iodine-125 ($^{125}$I), or carbon-14 ($^{14}$C). All isotopic variations of the compounds of the present invention, whether radioactive or not, are encompassed within the scope of the present invention.

It should be noted that throughout the application that alternatives are written in Markush groups, for example, each amino acid position that contains more than one possible amino acid. It is specifically contemplated that each member of the Markush group should be considered separately, thereby comprising another embodiment, and the Markush group is not to be read as a single unit.

"Analog," or "analogue" is used in accordance with its plain ordinary meaning within Chemistry and Biology and refers to a chemical compound that is structurally similar to another compound (i.e., a so-called "reference" compound) but differs in composition, e.g., in the replacement of one atom by an atom of a different element, or in the presence of a particular functional group, or the replacement of one functional group by another functional group, or the absolute stereochemistry of one or more chiral centers of the reference compound. Accordingly, an analog is a compound that is similar or comparable in function and appearance but not in structure or origin to a reference compound.

The terms "a" or "an," as used in herein means one or more. In addition, the phrase "substituted with a[n]," as used herein, means the specified group may be substituted with one or more of any or all of the named substituents. For example, where a group, such as an alkyl or heteroaryl group, is "substituted with an unsubstituted $C_1$-$C_{20}$ alkyl, or unsubstituted 2 to 20 membered heteroalkyl," the group may contain one or more unsubstituted $C_1$-$C_{20}$ alkyls, and/or one or more unsubstituted 2 to 20 membered heteroalkyls.

Moreover, where a moiety is substituted with an R substituent, the group may be referred to as "R-substituted." Where a moiety is R-substituted, the moiety is substituted with at least one R substituent and each R substituent is optionally different. Where a particular R group is present in the description of a chemical genus (such as Formula: (I)), a Roman alphabetic symbol may be used to distinguish each appearance of that particular R group. For example, where multiple $R^{13}$ substituents are present, each $R^{13}$ substituent may be distinguished as $R^{13A}$, $R^{13B}$, $R^{13C}$, $R^{13D}$, etc., wherein each of $R^{13A}$, $R^{13B}$, $R^{13C}$, $R^{13D}$, etc. is defined within the scope of the definition of $R^{13}$ and optionally differently.

A "detectable moiety" as used herein refers to a moiety that can be covalently or noncovalently attached to a compound or biomolecule that can be detected for instance, using techniques known in the art. In embodiments, the detectable moiety is covalently attached. The detectable moiety may provide for imaging of the attached compound or biomolecule. The detectable moiety may indicate the contacting between two compounds. Exemplary detectable moieties are fluorophores, antibodies, reactive dies, radiolabeled moieties, magnetic contrast agents, and quantum dots. Exemplary fluorophores include fluorescein, rhodamine, GFP, coumarin, FITC, Alexa fluor, Cy3, Cy5, BODIPY, and cyanine dyes. Exemplary radionuclides include Fluorine-18, Gallium-68, and Copper-64. Exemplary magnetic contrast agents include gadolinium, iron oxide and iron platinum, and manganese. The detectable moiety may be covalently attached through a covalent linker to the remainder of the molecule, wherein the covalent linker forms part of the detectable moiety. Therefore, a detectable moiety may include a detectable portions (e.g. a fluorophore) and covalent linker portion. The covalent linker portion may be $L^{12}$, wherein $L^{12}$ is —O—, —C(O)—, —CO(O)—, substituted or unsubstituted alkylene, substituted or unsubstituted heteroalkylene. The covalent linker portion may be $L^{12}$, wherein $L^{12}$ is a bond, substituted or unsubstituted alkylene, substituted or unsubstituted heteroalkylene, substituted or unsubstituted cycloalkylene, substituted or unsubstituted heterocycloalkylene, substituted or unsubstituted arylene, substituted or unsubstituted heteroarylene, or substituted or unsubstituted alkylarylene.

Description of compounds of the present invention are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

The term "pharmaceutically acceptable salts" is meant to include salts of the active compounds that are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, oxalic, methanesulfonic, and the like. Also included are salts of amino acids such as arginate and the like, and salts of organic acids like glucuronic or galactunoric acids and the like (see, for example, Berge et al., "Pharmaceutical Salts", *Journal of Pharmaceutical Science,* 1977, 66, 1-19). Certain specific compounds of the present invention contain both basic and acidic functionalities that allow the compounds to be converted into either base or acid addition salts.

Thus, the compounds of the present invention may exist as salts, such as with pharmaceutically acceptable acids. The present invention includes such salts. Non-limiting examples of such salts include hydrochlorides, hydrobromides, phosphates, sulfates, methanesulfonates, nitrates, maleates, acetates, citrates, fumarates, proprionates, tartrates (e.g., (+)-tartrates, (−)-tartrates, or mixtures thereof including racemic mixtures), succinates, benzoates, and salts with amino acids such as glutamic acid, and quaternary ammonium salts (e.g. methyl iodide, ethyl iodide, and the like). These salts may be prepared by methods known to those skilled in the art.

The neutral forms of the compounds are preferably regenerated by contacting the salt with a base or acid and isolating the parent compound in the conventional manner. The parent form of the compound may differ from the various salt forms in certain physical properties, such as solubility in polar solvents.

In addition to salt forms, the present invention provides compounds, which are in a prodrug form. Prodrugs of the compounds described herein are those compounds that readily undergo chemical changes under physiological conditions to provide the compounds of the present invention. Prodrugs of the compounds described herein may be converted in vivo after administration. Additionally, prodrugs can be converted to the compounds of the present invention by chemical or biochemical methods in an ex vivo environment, such as, for example, when contacted with a suitable enzyme or chemical reagent.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

"Pharmaceutically acceptable excipient" and "pharmaceutically acceptable carrier" refer to a substance that aids the administration of an active agent to and absorption by a subject and can be included in the compositions of the present invention without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethylcellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the invention. One of skill in the art will recognize that other pharmaceutical excipients are useful in the present invention.

The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

An "αvβ1-inhibitor" as used herein refers to a composition (e.g. a compound, nucleic acid, polynucleotide, peptide, protein, or antibody) capable of reducing the activity of αvβ1 integrin when compared to a control compound (e.g. known to have no reduction in αvβ1 integrin activity) or the absence of the αvβ1-inhibitor compound. An "αvβ1-inhibitor compound" refers to a compound (e.g. compounds described herein) that reduce the activity of αvβ1 integrin when compared to a control, such as absence of the compound or a compound with known inactivity. An "αvβ1-inhibitor-antibody" refers to an antibody that reduces the activity of αvβ1 integrin when compared to a control (e.g. the absence of the antibody). An "αvβ1-inhibitor-RGD peptide" refers to a RGD-peptide that reduces the activity of αvβ1 integrin when compared to a control (e.g. the absence of the peptide).

An "αvβ1-specific moiety", "specific," "specifically", "specificity", or the like of a composition (e.g. a compound, nucleic acid, polynucleotide, peptide, protein, or antibody) refers to the composition's ability to discriminate between particular molecular targets to a significantly greater extent than other proteins in the cell (e.g. a compound having specificity towards αvβ1 integrin binds to αvβ1 integrin whereas the same compound displays little-to-no binding to other integrins such as α5β1, α8β1, αvβ3, αvβ5, or αvβ6). An "αvβ1-specific compound" refers to a compound (e.g. compounds described herein) having specificity towards αvβ1 integrin. An "αvβ1-specific antibody" refers to an antibody having specificity towards αvβ1 integrin. An "αvβ1-specific RGD peptide" refers to a RGD peptide having specificity towards αvβ1 integrin.

The terms "αvβ1-selective," "selective," or "selectivity" or the like of a compound refers to the composition's (e.g. a compound, nucleic acid, polynucleotide, peptide, protein, or antibody) ability to cause a particular action in a particular molecular target (e.g. a compound having selectivity toward αvβ1 integrin would inhibit only αvβ1). An "αvβ1-selective compound" refers to a compound (e.g. compounds described herein) having selectivity towards αvβ1 integrin. An "αvβ1-selective antibody" refers to an antibody having selectivity towards αvβ1 integrin. An "αvβ1-selective RGD peptide" refers to a RGD peptide having selectivity towards αvβ1 integrin.

The terms "polypeptide," "peptide" and "protein" are used interchangeably herein to refer to a polymer of amino acid residues, wherein the polymer may optionally be conjugated to a moiety that does not consist of amino acids. The terms apply to amino acid polymers in which one or more amino acid residue is an artificial chemical mimetic of a corresponding naturally occurring amino acid, as well as to naturally occurring amino acid polymers and non-naturally occurring amino acid polymer.

A polypeptide, or a cell is "recombinant" when it is artificial or engineered, or derived from or contains an artificial or engineered protein or nucleic acid (e.g. non-natural or not wild type). For example, a polynucleotide that is inserted into a vector or any other heterologous location, e.g., in a genome of a recombinant organism, such that it is not associated with nucleotide sequences that normally flank the polynucleotide as it is found in nature is a recombinant polynucleotide. A protein expressed in vitro or in vivo from a recombinant polynucleotide is an example of a recombinant polypeptide. Likewise, a polynucleotide sequence that does not appear in nature, for example a variant of a naturally occurring gene, is recombinant.

"RGD peptide" as used herein refers to a tripeptide comprising Arg., Gly., and Asp. RGD peptides typically act as recognition sequences for integrins and in some embodiments, promote cellular adhesion via integrin binding. RGD peptides as used herein refers to naturally occurring RGD sequences, RGD mimetics (e.g. substitutions of R, G, or D with non-proteinogenic amino acids), RGD peptides covalently bound to a targeting-moiety (e.g. a molecule for targeting the peptide to a specific integrin or specific location in a cell or organism), and cyclized RGD peptides of embodiments described herein. Exemplary RGD peptides include Arg-Gly-Asp, Asp-Gly-Arg, cyclo-Gly-Arg-Gly-Asp-Ser-Pro, and KGD peptides include Cys-Asn-Thr-Leu-Lys-Gly-Asp-Cys and Asn-Thr-Leu-Lys-Gly-Asp, and those found in Ann. Rev. Cell & Dev. Biol., 1996, November, Vol. 12: 697-715 and Proteins, 1992 December; 14(4):509-15.

"Antibody" refers to a polypeptide comprising a framework region from an immunoglobulin gene or fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. Typically, the antigen-binding region of an antibody will be most critical in specificity and affinity of binding.

An exemplary immunoglobulin (antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist, e.g., as intact immunoglobulins or as a number of well-characterized fragments produced by digestion with various peptidases. Thus, for example, pepsin digests an antibody below the disulfide linkages in the hinge region to produce F(ab)'$_2$, a dimer of Fab which itself is a light chain joined to $V_H$—$C_H$1 by a disulfide bond. The F(ab)'$_2$ may be reduced under mild conditions to break the disulfide linkage in the hinge region, thereby converting the F(ab)'$_2$ dimer into an Fab' monomer. The Fab' monomer is essentially Fab with part of the hinge region (see *Fundamental Immunology* (Paul ed., 3d ed. 1993). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g., McCafferty et al., *Nature* 348:552-554 (1990)).

For preparation of suitable antibodies of the invention and for use according to the invention, e.g., recombinant, monoclonal, or polyclonal antibodies, many techniques known in the art can be used (see, e.g., Kohler & Milstein, *Nature* 256:495-497 (1975); Kozbor et al., *Immunology Today* 4: 72 (1983); Cole et al., pp. 77-96 in *Monoclonal Antibodies and Cancer Therapy*, Alan R. Liss, Inc. (1985); Coligan, *Current Protocols in Immunology* (1991); Harlow & Lane, *Antibodies, A Laboratory Manual* (1988); and Goding, *Monoclonal Antibodies: Principles and Practice* (2d ed. 1986)). The genes encoding the heavy and light chains of an antibody of interest can be cloned from a cell, e.g., the genes encoding a monoclonal antibody can be cloned from a hybridoma and used to produce a recombinant monoclonal antibody. Gene libraries encoding heavy and light chains of monoclonal antibodies can also be made from hybridoma or plasma cells. Random combinations of the heavy and light chain gene products generate a large pool of antibodies with different antigenic specificity (see, e.g., Kuby, *Immunology* ($3^{rd}$ ed. 1997)). Techniques for the production of single chain antibodies or recombinant antibodies (U.S. Pat. No. 4,946,778, U.S. Pat. No. 4,816,567) can be adapted to produce antibodies to polypeptides of this invention. Also, transgenic mice, or other organisms such as other mammals, may be used to express humanized or human antibodies (see, e.g., U.S. Pat. Nos. 5,545,807; 5,545,806; 5,569,825; 5,625,126; 5,633,425; 5,661,016, Marks et al., Bio/Technology 10:779-783 (1992); Lonberg et al., *Nature* 368:856-859 (1994); Morrison, *Nature* 368:812-13 (1994); Fishwild et al., *Nature Biotechnology* 14:845-51 (1996); Neuberger, *Nature Biotechnology* 14:826 (1996); and Lonberg & Huszar, *Intern. Rev. Immunol.* 13:65-93 (1995)). Alternatively, phage display technology can be used to identify antibodies and heteromeric Fab fragments that specifically bind to selected antigens (see, e.g., McCafferty et al., *Nature* 348:552-554 (1990); Marks et al., *Biotechnology* 10:779-783 (1992)). Antibodies can also be made bispecific, i.e., able to recognize two different antigens (see, e.g., WO 93/08829, Traunecker et al., *EMBO J.* 10:3655-3659 (1991); and Suresh et al., *Methods in Enzymology* 121:210 (1986)). Antibodies can also be heteroconjugates, e.g., two covalently joined antibodies, or immunotoxins (see, e.g., U.S. Pat. No. 4,676,980, WO 91/00360; WO 92/200373; and EP 03089).

Methods for humanizing or primatizing non-human antibodies are well known in the art. Generally, a humanized antibody has one or more amino acid residues introduced into it from a source which is non-human. These non-human amino acid residues are often referred to as import residues, which are typically taken from an import variable domain. Humanization can be essentially performed following the method of Winter and co-workers (see, e.g., Jones et al., *Nature* 321:522-525 (1986); Riechmann et al., *Nature* 332: 323-327 (1988); Verhoeyen et al., *Science* 239:1534-1536 (1988) and Presta, *Curr. Op. Struct. Biol.* 2:593-596 (1992)), by substituting rodent CDRs or CDR sequences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

A "chimeric antibody" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity. The preferred antibodies of, and for use according to the invention include humanized and/or chimeric monoclonal antibodies.

"Contacting" is used in accordance with its plain ordinary meaning and refers to the process of allowing at least two distinct species (e.g. chemical compounds including biomolecules or cells) to become sufficiently proximal to react, interact or physically touch. It should be appreciated; however, the resulting reaction product can be produced directly from a reaction between the added reagents or from an intermediate from one or more of the added reagents that can be produced in the reaction mixture.

The term "contacting" may include allowing two species to react, interact, or physically touch, wherein the two species may be a compound as described herein and a protein or enzyme. In some embodiments contacting includes allowing a compound described herein to interact with a protein or enzyme that is involved in a signaling pathway.

As defined herein, the term "activation", "activate", "activating" and the like in reference to a protein refers to conversion of a protein into a biologically active derivative from an initial inactive or deactivated state. The terms reference activation, or activating, sensitizing, or up-regulating signal transduction or enzymatic activity or the amount of a protein decreased in a disease.

As defined herein, the term "inhibition", "inhibit", "inhibiting" and the like in reference to a protein-inhibitor interaction means negatively affecting (e.g. decreasing) the activity or function of the protein relative to the activity or function of the protein in the absence of the inhibitor. In embodiments inhibition refers means negatively affecting (e.g. decreasing) the concentration or levels of the protein relative to the concentration or level of the protein in the absence of the inhibitor. In embodiments inhibition refers to reduction of a disease or symptoms of disease. In embodiments, inhibition refers to a reduction in the activity of a particular protein target. Thus, inhibition includes, at least in part, partially or totally blocking stimulation, decreasing, preventing, or delaying activation, or inactivating, desensitizing, or down-regulating signal transduction or enzymatic activity or the amount of a protein. In embodiments, inhibition refers to a reduction of activity of a target protein resulting from a direct interaction (e.g. an inhibitor binds to the target protein). In embodiments, inhibition refers to a reduction of activity of a target protein from an indirect interaction (e.g. an inhibitor binds to a protein that activates the target protein, thereby preventing target protein activation).

Integrins are transmembrane proteins that mediate interactions between adhesion molecules on adjacent cells and/or the extracellular matrix (ECM). Integrins have diverse roles in several biological processes including, for example, cell migration during development and wound healing, cell differentiation, and apoptosis. Integrins typically exist as heterodimers consisting of α subunits (about 120-170 kDa in size) and β subunits (about 90-100 kDa in size).

The terms "αvβ1" and "αvβ1 integrin" refer to an integrin comprised of αv subunit and a β1 subunit and is used according to its common, ordinary meaning. "αvβ1" refers to proteins of the same or similar names, homologs, isoforms, and functional fragments thereof, so long as such fragments retain αvβ1 integrin activity. The term includes any recombinant or naturally-occurring form of αvβ1, or an αvβ1 preprotein, or variants thereof that maintain αvβ1 activity (e.g. within at least 30%, 40%, 50%, 60%, 70%, 80%, 90%, 95%, or 100% activity compared to wildtype αvβ1). In embodiments, αv has the protein sequence corresponding to RefSeq NP 002201.1. In embodiments, αv has the amino acid sequence corresponding to the reference number GI: 4504763. In embodiments, αv has the amino acid sequence corresponding to the reference number GI: 143811408. In embodiments, β1 has the protein sequence corresponding to RefSeq NP_002202.2. In embodiments, β1 has the amino acid sequence corresponding to the reference number GI: 19743813. In embodiments, β1 has the amino acid sequence corresponding to the reference number GI: 218563324.

Fibronectin is used according to its common, ordinary meaning and refers to proteins of the same or similar names, homologs, isoforms, and functional fragments thereof, so long as such fragments retain fibronectin activity. Fibronectin refers to glycoprotein dimers capable of binding integrins and mediating interactions between adhesion molecules in the ECM. The term includes any recombinant or naturally-occurring form of fibronectin, or a fibronectin preprotein, or variants thereof that maintain fibronectin activity (e.g. within at least 30%, 40%, 50%, 60%, 70%, 80%, 90%, 95%, or 100% activity compared to wildtype fibronectin).

"TGF-β," "TGFβ" or "transforming growth factor β" is used according to its common and ordinary meaning. TGFβ refers to proteins of the same or similar names, homologs, isoforms, and functional fragments thereof known to have TGFβ activity.

The term "expression" includes any step involved in the production of the polypeptide including, but not limited to, transcription, post-transcriptional modification, translation, post-translational modification, and secretion. Expression can be detected using conventional techniques for detecting protein (e.g., ELISA, Western blotting, flow cytometry, immunofluorescence, immunohistochemistry, etc.).

The terms "disease" or "condition" refer to a state of being or health status of a patient or subject capable of being treated with the compounds or methods provided herein. The disease may be fibrosis, such as for example, pulmonary fibrosis, liver fibrosis, skin fibrosis, cardiac fibrosis, or kidney fibrosis.

The terms "treating", or "treatment" refers to any indicia of success in the therapy or amelioration of an injury, disease, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation. The term "treating" and conjugations thereof, may include prevention of an injury, pathology, condition, or disease.

"Patient" or "subject in need thereof" refers to a living organism suffering from or prone to a disease or condition that can be treated by administration of a pharmaceutical composition as provided herein. Non-limiting examples include humans, other mammals, bovines, rats, mice, dogs, monkeys, goat, sheep, cows, deer, and other non-mammalian animals. In some embodiments, a patient is human.

A "effective amount" is an amount sufficient for a compound to accomplish a stated purpose relative to the absence of the compound (e.g. achieve the effect for which it is administered, treat a disease, reduce enzyme activity, increase enzyme activity, reduce a signaling pathway, or reduce one or more symptoms of a disease or condition). An example of an "effective amount" is an amount sufficient to contribute to the treatment, prevention, or reduction of a symptom or symptoms of a disease, which could also be referred to as a "therapeutically effective amount." A "reduction" of a symptom or symptoms (and grammatical equivalents of this phrase) means decreasing of the severity or frequency of the symptom(s), or elimination of the symptom (s). A "prophylactically effective amount" of a drug is an amount of a drug that, when administered to a subject, will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms. The full prophylactic effect does not necessarily occur by administration of one dose, and may occur only after administration of a series of doses. Thus, a prophylactically effective amount may be administered in one or more administrations. An "activity decreasing amount," as used herein, refers to an amount of antagonist required to decrease the activity of an enzyme relative to the absence of the antagonist. A "function disrupting amount," as used herein, refers to the amount of antagonist required to disrupt the function of an enzyme or protein relative to the absence of the antagonist. The exact amounts will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy*, 20th Edition, 2003, Gennaro, Ed., Lippincott, Williams & Wilkins).

For any compound described herein, the therapeutically effective amount can be initially determined from cell culture assays. Target concentrations will be those concentrations of active compound(s) that are capable of achieving the methods described herein, as measured using the methods described herein or known in the art.

As is well known in the art, therapeutically effective amounts for use in humans can also be determined from animal models. For example, a dose for humans can be formulated to achieve a concentration that has been found to be effective in animals. The dosage in humans can be adjusted by monitoring compounds effectiveness and adjusting the dosage upwards or downwards, as described above. Adjusting the dose to achieve maximal efficacy in humans based on the methods described above and other methods is well within the capabilities of the ordinarily skilled artisan.

Dosages may be varied depending upon the requirements of the patient and the compound being employed. The dose administered to a patient, in the context of the present invention should be sufficient to effect a beneficial therapeutic response in the patient over time. The size of the dose also will be determined by the existence, nature, and extent of any adverse side-effects. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached. Dosage amounts and intervals can be adjusted individually to provide levels of the administered compound effective for the particular clinical indication being treated. This will provide a therapeutic regimen that is commensurate with the severity of the individual's disease state.

As used herein, the term "administering" means oral administration, administration as a suppository, topical contact, intravenous, intraperitoneal, intramuscular, intralesional, intrathecal, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal) compatible with the preparation. Parenteral administration includes, e.g., intravenous, intramuscular, intraarteriole, intradermal, subcutaneous, intraperitoneal, intraventricular, and intracranial. Other modes of delivery include, but are not limited to, the use of liposomal formulations, intravenous infusion, transdermal patches, etc.

"Co-administer" it is meant that a composition described herein is administered at the same time, just prior to, or just after the administration of one or more additional therapies. The compounds of the invention can be administered alone or can be coadministered to the patient. Coadministration is meant to include simultaneous or sequential administration of the compounds individually or in combination (more than one compound). Thus, the preparations can also be combined, when desired, with other active substances (e.g. to reduce metabolic degradation). The compositions of the present invention can be delivered transdermally, by a topical route, or formulated as applicator sticks, solutions, suspensions, emulsions, gels, creams, ointments, pastes, jellies, paints, powders, and aerosols.

A "cell" as used herein, refers to a cell carrying out metabolic or other function sufficient to preserve or replicate its genomic DNA. A cell can be identified by well-known methods in the art including, for example, presence of an intact membrane, staining by a particular dye, ability to produce progeny or, in the case of a gamete, ability to combine with a second gamete to produce a viable offspring. Cells may include prokaryotic and eukaroytic cells. Prokaryotic cells include but are not limited to bacteria. Eukaryotic cells include but are not limited to yeast cells and cells derived from plants and animals, for example mammalian, insect (e.g., spodoptera) and human cells. Cells may be useful when they are naturally nonadherent or have been treated not to adhere to surfaces, for example by trypsinization.

"Control" or "control experiment" is used in accordance with its plain ordinary meaning and refers to an experiment in which the subjects or reagents of the experiment are treated as in a parallel experiment except for omission of a procedure, reagent, or variable of the experiment. In some instances, the control is used as a standard of comparison in evaluating experimental effects. In some embodiments, a control is the measurement of the activity of a protein in the absence of a compound as described herein (including embodiments and examples).

As used herein "fibrosis" refers to any disease or condition characterized by the formation of excess fibrous connective tissue. The formation of excess fibrous connective tissue may be in response to a reparative or reactive process. Fibrosis may be pulmonary fibrosis, liver fibrosis, myelofibrosis, skin fibrosis (e.g. nephrogenic systemic fibrosis and keloid fibrosis), mediastinal fibrosis, cardiac fibrosis, kidney fibrosis, stromal fibrosis, epidural fibrosis, or idiopathic fibrosis.

The compounds described herein (e.g., compound wherein $R^{12}$ is not hydrogen) may be prodrugs. The term "prodrug" when referring to a prodrug described herein (e.g. αvβ1-inhibitor compound moiety bonded to a prodrug moiety) refers to the compound including the αvβ1-inhibitor compound moiety and the prodrug moiety. A "prodrug moiety" is the portion of a prodrug that may be cleaved from the prodrug resulting in an increased activity of the non-prodrug moiety portion of the prodrug, for example an αvβ1-inhibitor compound having increased αvβ1-inhibitor activity relative to the prodrug of the αvβ1-inhibitor compound. In embodiments, the compounds described herein are prodrugs, wherein the prodrug moiety is the component of the compound that is not an αvβ1-inhibitor compound moiety and is released from the αvβ1-inhibitor compound moiety upon degradation of the prodrug.

In embodiments, degradation of the prodrug includes cleavage of —$OR^{12}$, wherein $R^{12}$ is not hydrogen. In embodiments, degradation of the prodrug includes cleavage of —$R^{12}$, wherein $R^{12}$ is not hydrogen. In embodiments, an αvβ1-inhibitor compound is a compound described herein wherein $R^{12}$ is hydrogen and a prodrug of the αvβ1-inhibitor compound is the identical compound except $R^{12}$ is not a hydrogen. A person having ordinary skill in the art would understand that the αvβ1-inhibitor compound moiety includes only those compounds compatible with the chemistry provided herein for connecting the αvβ1-inhibitor compound moiety to the prodrug moiety and for release of the αvβ1-inhibitor compound from the compound (prodrug) (e.g., in vivo). In embodiments, degradation of the prodrug releases an active agent (e.g., αvβ1-inhibitor compound). In such compounds, the resulting active agent includes a higher level of activity compared to the level of activity of the intact prodrug.

I. Compounds

In an aspect is provided a compound having the formula:

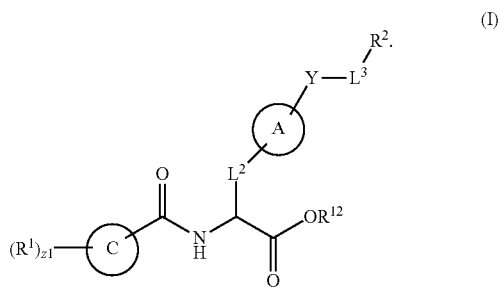

(I)

Ring A is substituted or unsubstituted cycloalkyl, substituted or unsubstituted heterocycloalkyl, substituted or unsubstituted aryl, or substituted or unsubstituted heteroaryl. Ring C is aryl or heteroaryl. $L^2$ is independently a bond, substituted or unsubstituted alkylene, or substituted or unsubstituted heteroalkylene. $L^3$ is a bond, substituted or unsubstituted alkylene, substituted or unsubstituted heteroalkylene, substituted or unsubstituted cycloalkylene, substituted or unsubstituted heterocycloalkylene, substituted or unsubstituted arylene, substituted or unsubstituted heteroarylene, or substituted or unsubstituted alkylarylene. Y is a bond, —C(O)N($R^4$)—, —O—, —C(O)O—, —S—, —N($SO_2R^4$)—, —N(C(O)$R^4$)—, —N(C(O)O$R^4$)—, —N($R^4$)C(O)—, —N($R^4$)—, —N($R^4$)C(O)NH—, —N($R^4$)C(O) N($R^4$)—, —NHC(O)N($R^4$)—, —N($R^4$)C(O)O—, —C(O)—, —N($R^4$)$CH_2$—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. $R^1$ is independently hydrogen, halogen, —$N_3$, —$CX_3$, —$CHX_2$, —$CH_2X$, —CN, —CHO, —OH, —$NH_2$, —COOH, —$CONH_2$, —$NO_2$, —SH, —$SO_2CH_3$—$SO_3H$, —$OSO_3H$, —$SO_2NH_2$, —$SO_2Ph$, —$NHNH_2$, —$ONH_2$, —NHC(O) $NHNH_2$, —$OPO_3H$, —$PO_3H_2$, —$OCF_3$, —$OCHF_2$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, or a detectable moiety. Two $R^1$ substituents may be joined to form a substituted or unsubstituted cycloalkyl, substituted or unsubstituted heterocycloalkyl, substituted or unsubstituted aryl, substituted or unsubstituted heteroaryl. In embodiments, $R^1$ is independently halogen, —$N_3$, —$CF_3$, —CN, —CHO, —OH, —$NH_2$, —COOH, —$CONH_2$, —$NO_2$, —SH, —$SO_2CH_3$—$SO_3H$, —$OSO_3H$, —$SO_2NH_2$, —$SO_2Ph$, —$NHNH_2$, —$ONH_2$, —NHC(O)$NHNH_2$, —$OPO_3H$, —$PO_3H_2$, —$OCF_3$, —$OCHF_2$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, or a detectable moiety. $R^2$ is —$NR^{3A}R^{3B}$, —C(NH)$NH_2$, —C(NH)$R^{3B}$, —C($NR^{3A}$)$NH_2$, —C($NR^{3A}$)$R^{3B}$, —C(NCN)$NH_2$, —$NH_2$, —C(NH)$NHR^{3B}$, —C($NR^{3A}$)$NHR^{3B}$, —C(NCN)$NHR^{3B}$, substituted or unsubstituted cycloalkyl, substituted or unsubstituted heterocycloalkyl (e.g., substituted or unsubstituted fused ring heterocycloalkyl), substituted or unsubstituted aryl (e.g. substituted or unsubstituted fused ring aryl), substituted or unsubstituted heteroaryl (e.g. substituted or unsubstituted fused ring heteroaryl), substituted or unsubstituted fused ring cycloalkyl. $R^{3A}$ is hydrogen, —C(NH) $NH_2$, —C(NH)$R^{3D}$, —C($NR^{3C}$)$NH_2$, —C($NR^{3C}$)$R^{3D}$, —C(NCN)$NH_2$, $NH_2$, —C(NH)$NHR^{3D}$, —C($NR^{3C}$) $NHR^{3D}$, —C(NCN)$NHR^{3D}$, substituted or unsubstituted cycloalkyl, substituted or unsubstituted heterocycloalkyl, substituted or unsubstituted aryl, substituted or unsubstituted heteroaryl, or $R^{3A}$ and $R^{3B}$ are optionally joined to form a substituted or unsubstituted heterocycloalkyl or substituted or unsubstituted heteroaryl. $R^{3B}$ is hydrogen, —C(NH)$NH_2$, —C(NH)$R^{3D}$, —C($NR^{3C}$)$NH_2$, —C($NR^{3C}$)$R^{3D}$, —C(NCN) $NH_2$, $NH_2$, —C(NH)$NHR^{3D}$, —C($NR^{3C}$)$NHR^{3D}$, —C(NCN)$NHR^{3D}$, substituted or unsubstituted cycloalkyl, substituted or unsubstituted heterocycloalkyl, substituted or unsubstituted aryl, substituted or unsubstituted heteroaryl. $R^{3A}$ and $R^{3B}$ may optionally be joined to form a substituted or unsubstituted heterocycloalkyl or substituted or unsubstituted heteroaryl. $R^{3C}$ is hydrogen, halogen, —$N_3$, —$CX^{1C}_3$, —$CHX^{1C}_2$, —$CH_2X^{1C}$, —CN, —CHO, —OH, —$NH_2$, —COOH, —$CONH_2$, —$NO_2$, —SH, —$SO_2$, —$SO_2CH_3$—$SO_3H$, —$SO_4H$, —$SO_2NH_2$, —$NHNH_2$, —$ONH_2$, —NHC(O)$NHNH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{3D}$ is hydrogen, halogen, $-N_3$, $-CX^{1D}_3$, $-CHX^{1D}_2$, $-CH_2X^{1D}$, $-CN$, $-CHO$, $-OH$, $-NH_2$, $-COOH$, $-CONH_2$, $-NO_2$, $-SH$, $-SO_2$, $-SO_2CH_3$—$SO_3H$, $-SO_4H$, $-SO_2NH_2$, $-NHNH_2$, $-ONH_2$, $-NHC(O)NHNH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^4$ is hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl. In embodiments, $R^4$ is hydrogen or substituted or unsubstituted alkyl. In embodiments, $R^4$ is hydrogen or unsubstituted $C_1$-$C_5$ alkyl. $R^{12}$ is hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, or a prodrug moiety. Each X, $X^{1C}$, and $X^{1D}$ is independently $-F$, $-Cl$, $-Br$, or $-I$. The symbol z1 is an integer from 0 to 5.

Ring A may be cycloalkyl, heterocycloalkyl, aryl, or heteroaryl. Ring A may be unsubstituted cycloalkyl, unsubstituted heterocycloalkyl, unsubstituted aryl, or unsubstituted heteroaryl, in that Ring A is only substituted with the Y-$L^3$-$R^2$ moiety (and the remainder of the molecule connected by the $L^2$ linker). $L^2$ may independently be a bond or substituted or unsubstituted $C_1$-$C_{10}$ alkylene. $L^3$ may be a bond, substituted or unsubstituted $C_1$-$C_{10}$ alkylene, substituted or unsubstituted 2 to 10 membered heteroalkylene, substituted or unsubstituted cycloalkylene, substituted or unsubstituted heterocycloalkylene, or substituted or unsubstituted alkylarylene. Y may be a bond, $-C(O)N(R^4)-$, $-O-$, $-C(O)O-$, $-S-$, $-N(SO_2R^4)-$, $-N(C(O)R^4)-$, $-N(C(O)OR^4)-$, $-N(R^4)C(O)-$, $-N(R^4)-$, $-N(R^4)C(O) N(R^4)-$, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. $R^1$ may independently be hydrogen, halogen, $-N_3$, $-CF_3$, $-CCl_3$, $-CBr_3$, $-CI_3$, $-CN$, $-CHO$, $-OH$, $-NH_2$, $-COOH$, $-CONH_2$, $-NO_2$, $-SH$, $-SO_2CH_3$—$SO_3H$, $-OSO_3H$, $-SO_2NH_2$, $-NHNH_2$, $-ONH_2$, $-NHC(O)NHNH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, or a detectable moiety. $R^{3A}$ and $R^{3B}$ may independently be hydrogen, $-C(NH)NH_2$, $-C(NH)R^{3D}$, $-C(NR^{3C})NH_2$, $-C(NR^{3C})R^{3D}$, $-C(NCN)NH_2$, $NH_2$, $-C(NH)NHR^{3D}$, $-C(NR^{3C})NHR^{3D}$, $-C(NCN)NHR^{3D}$, substituted or unsubstituted cycloalkyl, substituted or unsubstituted heterocycloalkyl, substituted or unsubstituted aryl, substituted or unsubstituted heteroaryl, or $R^{3A}$ and $R^{3B}$ may optionally be joined to form a substituted or unsubstituted heterocycloalkyl or substituted or unsubstituted heteroaryl. $R^{3C}$ and $R^{3D}$ may independently be hydrogen, halogen, oxo, $-N_3$, $-CF_3$, $-CCl_3$, $-CBr_3$, $-CI_3$, $-CN$, $-CHO$, $-OH$, $-NH_2$, $-COOH$, $-CONH_2$, $-NO_2$, $-SH$, $-SO_2CH_3$—$SO_3H$, $-SO_4H$, $-SO_2NH_2$, $-NHNH_2$, $-ONH_2$, $-NHC(O)NHNH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^4$ may independently be hydrogen or unsubstituted $C_1$-$C_5$ alkyl. The symbol z1 may be an integer from 0 to 5. Where the compound includes more than one of a given R substituent, each of the R substituents are optionally different. For example, where the compound includes more than one $R^1$ substituent, each $R^1$ is optionally different and may optionally be identified as separate $R^1$ substituents $R^{1A}$, $R^{1B}$, $R^{1C}$, $R^{1D}$, or $R^{1E}$. Each $R^{1A}$, $R^{1B}$, $R^{1C}$, $R^{1D}$, and $R^{1E}$ may be any value of $R^1$ described herein, including each embodiment.

Ring A may be substituted or unsubstituted aryl. Ring A may be substituted or unsubstituted $C_6$-$C_{10}$ aryl. Ring A may be substituted or unsubstituted phenyl. It will be understood that a Ring A may be substituted aryl or substituted phenyl, which is substituted by one or more substituents in addition to the —Y-$L^3$-$R^2$ moiety (and the remainder of the molecule connected by the $L^2$ linker). Likewise, it will be understood that an unsubstituted aryl or unsubstituted phenyl is unsubstituted except for the —Y-$L^3$-$R^2$ moiety (and the remainder of the molecule connected by the $L^2$ linker).

Ring A may be aryl. Ring A may be 6 membered aryl. Ring A may be phenyl. Ring A may be unsubstituted phenyl. Ring A may be unsubstituted triazolyl. Ring A may be substituted triazolyl. Ring A may be unsubstituted tetrazolyl. Ring A may be substituted tetrazolyl. In embodiments, Ring A is phenyl. In embodiments, Ring A is cyclohexyl. In embodiments, Ring A is pyridyl. Ring A may be substituted $C_6$-$C_{10}$ aryl. Ring A may be substituted 5 to 10 membered heteroaryl. Ring A may be substituted aryl. Ring A may be unsubstituted aryl. Ring A may be substituted heteroaryl. Ring A may be unsubstituted heteroaryl. Ring A may be substituted or unsubstituted $C_6$-$C_{10}$ aryl. Ring A may be substituted or unsubstituted 5 to 10 membered heteroaryl. Ring A may be unsubstituted $C_6$-$C_{10}$ aryl. Ring A may be unsubstituted 5 to 10 membered heteroaryl.

Ring A may be a substituted or unsubstituted 4 to 6 membered heterocycloalkyl. Ring A may be a substituted or unsubstituted 5 or 6 membered heterocycloalkyl. Ring A may be substituted or unsubstituted 5 membered heterocycloalkyl. Ring A may be a heterocycloalkyl such as, for example, pyrrolidinyl, imidazolidinyl, oxazolidinyl, thiazolidinyl, dioxolanyl, dithiolanyl, piperidinyl, morpholinyl, dioxanyl, dithianyl, aziridinyl, azetidinyl, azepinyl, oxiranyl, oxetanyl, tetrahydrofuranyl, or tetrahydropyranyl. Ring A may be a substituted or unsubstituted heterocycloalkyl such as, for example, substituted or unsubstituted pyrrolidinyl, substituted or unsubstituted imidazolidinyl, substituted or unsubstituted oxazolidinyl, substituted or unsubstituted thiazolidinyl, substituted or unsubstituted dioxolanyl, substituted or unsubstituted dithiolanyl, substituted or unsubstituted piperidinylen, substituted or unsubstituted morpholinyl, substituted or unsubstituted dioxanyl, substituted or unsubstituted dithianyl, substituted or unsubstituted aziridinyl, substituted or unsubstituted azetidinyl, substituted or unsubstituted azepinyl, substituted or unsubstituted oxiranyl, substituted or unsubstituted oxetanyl, substituted or unsubstituted tetrahydrofuranyl, or substituted or unsubstituted tetrahydropyranyl. Ring A may be a substituted or unsubstituted 6 membered heterocycloalkyl. Ring A may be a unsubstituted 6 membered heterocycloalkyl. Ring A may be a unsubstituted 5 membered heterocycloalkyl. Ring A may be substituted or unsubstituted $C_3$-$C_8$ cycloalkyl. Ring A may be substituted or unsubstituted 3 to 8 membered heterocycloalkyl. Ring A may be unsubstituted $C_3$-$C_8$ cycloalkyl. Ring A may be unsubstituted 3 to 8 membered heterocycloalkyl.

Ring A may be substituted or unsubstituted heteroaryl. Ring A may be substituted or unsubstituted 5 or 6 membered heteroaryl. Ring A may be unsubstituted 5 or 6 membered heteroaryl. Ring A may be a substituted or unsubstituted heteroaryl such as, for example, substituted or unsubstituted pyridinyl, substituted or unsubstituted pyrrolyl, substituted or unsubstituted furanyl, substituted or unsubstituted thiophenyl, substituted or unsubstituted imidazolyl, substituted or unsubstituted pyrazolyl, substituted or unsubstituted oxazolyl, substituted or unsubstituted thiazolyl, substituted or unsubstituted pyranyl, substituted or unsubstituted thiopyranyl, substituted or unsubstituted pyrazinyl, substituted or unsubstituted pyrimindyl, substituted or unsubstituted pyridazinyl, substituted or unsubstituted oxazinyl, substituted or unsubstituted thiazinyl, substituted or unsubstituted doxinyl, substituted or unsubstituted dithiinyl, substituted or unsubstituted azetyl, substituted or unsubstituted oxetyl, substituted or unsubstituted thietyl, substituted or unsubstituted azirinyl, substituted or unsubstituted oxirenyl or substituted or unsubstituted thirenyl. Ring A may be substituted or unsubstituted pyridinyl. Ring A may be substituted cycloalkyl. Ring A may be unsubstituted cycloalkyl. Ring A may be substituted heterocycloalkyl. Ring A may be unsubstituted heterocycloalkyl. Ring A may be substituted $C_3$-$C_8$ cycloalkyl. Ring A may be unsubstituted $C_3$-$C_8$ cycloalkyl. Ring A may be substituted 3 to 8 membered heterocycloalkyl. Ring A may be unsubstituted 3 to 8 membered heterocycloalkyl. In embodiments, Ring A is unsubstituted phenyl. In embodiments, Ring A is unsubstituted 5 to 6 membered heteroaryl.

Ring A may be substituted with —OMe. Ring A may be substituted with —O—$CH_2CH_3$. Ring A may be substituted with —O—$CH_2CH_2CH_3$. Ring A may be substituted with unsubstituted methoxy. Ring A may be substituted with unsubstituted methyl. Ring A may be substituted with unsubstituted ethoxy. Ring A may be substituted with unsubstituted ethyl. Ring A may be substituted with unsubstituted propoxy. Ring A may be substituted with unsubstituted propyl. Ring A may be substituted with unsubstituted n-propyl. Ring A may be substituted with unsubstituted isopropyl. Ring A may be substituted with unsubstituted butoxy. Ring A may be substituted with unsubstituted butyl. Ring A may be substituted with unsubstituted n-butyl. Ring A may be substituted with unsubstituted isobutyl. Ring A may be substituted with unsubstituted tert-butyl. Ring A may be substituted with unsubstituted pentoxy. Ring A may be substituted with unsubstituted pentyl. Ring A may be substituted with unsubstituted n-pentyl.

In embodiments, Ring A is aryl substituted with unsubstituted 2 to 4 membered heteroalkyl. In embodiments, Ring A is unsubstituted 5 to 6 membered heteroaryl. In embodiments, Ring A is unsubstituted $C_5$-$C_6$ cycloalkyl. In embodiments, Ring A is unsubstituted 5 to 6 membered heterocycloalkyl. In embodiments, Ring A is substituted phenyl. In embodiments, Ring A is a methoxy-substituted phenyl. In embodiments, Ring A is

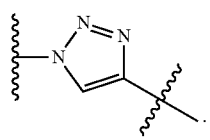

In embodiments, Ring A is

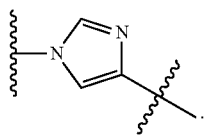 [SMILES: *c1cn(*)cn1]

In embodiments, Ring A is

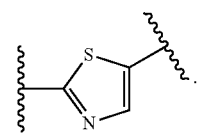 [SMILES: *c1cnc(*)s1]

In embodiments, Ring A is

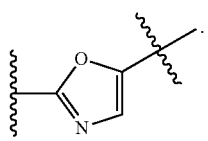 [SMILES: *c1cnc(*)o1]

In embodiments, Ring A is

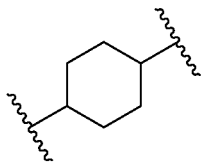

In embodiments, Ring A is

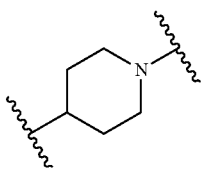

In embodiments, Ring A is

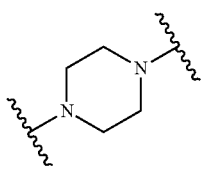

In embodiments, Ring A is

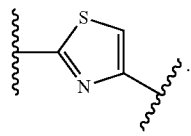

In embodiments, Ring A is

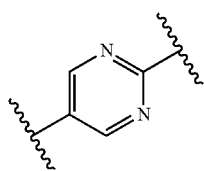 [SMILES: *c1cnc(*)nc1]

In embodiments, Ring A is $R^{26}$-substituted or unsubstituted cycloalkyl, $R^{26}$-substituted or unsubstituted heterocycloalkyl, $R^{26}$-substituted or unsubstituted aryl, or $R^{26}$-substituted or unsubstituted heteroaryl. In embodiments, Ring A is $R^{26}$-substituted cycloalkyl, $R^{26}$-substituted heterocycloalkyl, $R^{26}$-substituted aryl, or $R^{26}$-substituted heteroaryl. In embodiments, Ring A is unsubstituted cycloalkyl, unsubstituted heterocycloalkyl, unsubstituted aryl, or unsubstituted heteroaryl.

$R^{26}$ is independently oxo, halogen, —CF$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCF$_3$, —OCHF$_2$, $R^{27}$-substituted or unsubstituted alkyl (e.g. C$_1$-C$_8$ alkyl, C$_1$-C$_6$ alkyl, or C$_1$-C$_4$ alkyl), $R^{27}$-substituted or unsubstituted heteroalkyl (e.g. 2 to 8 membered heteroalkyl, 2 to 6 membered heteroalkyl, or 2 to 4 membered heteroalkyl), $R^{27}$-substituted or unsubstituted cycloalkyl (e.g. C$_3$-C$_8$ cycloalkyl, C$_4$-C$_8$ cycloalkyl, or C$_5$-C$_6$ cycloalkyl), $R^{27}$-substituted or unsubstituted heterocycloalkyl (e.g. 3 to 8 membered heterocycloalkyl, 4 to 8 membered heterocycloalkyl, or 5 to 6 membered heterocycloalkyl), $R^{27}$-substituted or unsubstituted aryl (e.g. C$_6$-C$_{10}$ aryl or C$_6$ aryl), or $R^{27}$-substituted or unsubstituted heteroaryl (e.g. 5 to 10 membered heteroaryl, 5 to 9 membered heteroaryl, or 5 to 6 membered heteroaryl).

$R^{27}$ is independently oxo, halogen, —CF$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCF$_3$, —OCHF$_2$, $R^{28}$-substituted or unsubstituted alkyl (e.g. C$_1$-C$_8$ alkyl, C$_1$-C$_6$ alkyl, or C$_1$-C$_4$ alkyl), $R^{28}$-substituted or unsubstituted heteroalkyl (e.g. 2 to 8 membered heteroalkyl, 2 to 6 membered heteroalkyl, or 2 to 4 membered heteroalkyl), $R^{28}$-substituted or unsubstituted cycloalkyl (e.g. C$_3$-C$_8$ cycloalkyl, C$_4$-C$_8$ cycloalkyl, or C$_5$-C$_6$ cycloalkyl), $R^{28}$-substituted or unsubstituted heterocycloalkyl (e.g. 3 to 8 membered heterocycloalkyl, 4 to 8 membered heterocycloalkyl, or 5 to 6 membered heterocycloalkyl), $R^{28}$-substituted or unsubstituted aryl (e.g. C$_6$-C$_{10}$ aryl or C$_6$ aryl), or $R^{28}$-substituted or unsubstituted heteroaryl (e.g. 5 to 10 membered heteroaryl, 5 to 9 membered heteroaryl, or 5 to 6 membered heteroaryl).

$R^{28}$ is independently oxo, halogen, —CF$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCF$_3$, —OCHF$_2$, unsubstituted alkyl (e.g. C$_1$-C$_8$ alkyl, C$_1$-C$_6$ alkyl, or C$_1$-C$_4$ alkyl), unsubstituted heteroalkyl (e.g. 2 to 8 membered heteroalkyl, 2 to 6 membered heteroalkyl, or 2 to 4 membered heteroalkyl), unsubstituted cycloalkyl (e.g. C$_3$-C$_8$ cycloalkyl, C$_4$-C$_8$ cycloalkyl, or C$_5$-C$_6$ cycloalkyl), unsubstituted heterocycloalkyl (e.g. 3 to 8 membered heterocycloalkyl, 4 to 8 membered heterocycloalkyl, or 5 to 6 membered heterocycloalkyl), unsubstituted aryl (e.g. C$_6$-C$_{10}$ aryl or C$_6$ aryl), or unsubstituted heteroaryl (e.g. 5 to 10 membered heteroaryl, 5 to 9 membered heteroaryl, or 5 to 6 membered heteroaryl).

Ring C may be heteroaryl. Ring C may be 5 or 6 membered heteroaryl. Ring C may be a 6 membered heteroaryl. Ring C may be a 5 membered heteroaryl. Ring C may be a heteroaryl such as, for example, pyridine, pyrrole, furan, thiophene, imidazole, pyrazole, oxazole, thiazole, pyran, thiopyrane, pyrazine, pyriminde, pyridazine, oxazine, thiazine, doxine, dithiine, azete, oxete, thiete, azirine, oxirene or thirene. Ring C may be pyridinyl. Ring C may be aryl. Ring C may be 6 or 10 membered aryl. Ring C may be phenyl. Ring C may be naphthyl. Ring C may be 1,2,3,4-tetrahydronaphthyl. Ring C may be indenyl. Ring C may be indonyl. Ring C may be indolinyl. Ring C may be substituted phenyl. Ring C may be substituted naphthyl. Ring C may be substituted 1,2,3,4-tetrahydronaphthyl. Ring C may be substituted indenyl. Ring C may be substituted indonyl. Ring C may be substituted indolinyl. Ring C may be unsubstituted phenyl. Ring C may be unsubstituted naphthyl. Ring C may be unsubstituted 1,2,3,4-tetrahydronaphthyl. Ring C may be unsubstituted indenyl. Ring C may be unsubstituted indonyl. Ring C may be unsubstituted indolinyl.

In embodiments, Ring C is fused ring aryl. In embodiments, Ring C is a fused ring aryl-cycloalkyl. In embodiments, Ring C is 9 to 10 membered heteroaryl. In embodiments, Ring C is fused ring 9 to 10 membered heteroaryl.

In embodiments, Ring C is phenyl. In embodiments, Ring C is pyridyl. In embodiments, Ring C is

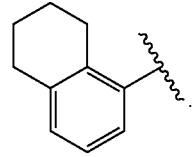 [SMILES: *c1cccc2c1CCCC2]

In embodiments, Ring C is

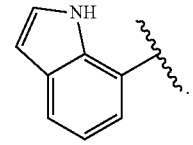

In embodiments, Ring C is

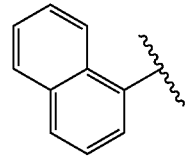

In embodiments, Ring C is

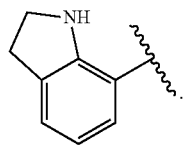 [SMILES: *c1cccc2c1NCC2]

In embodiments, Ring C is

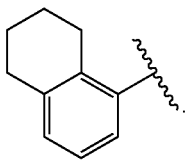 [SMILES: *c1cccc2c1CCCC2]

Ring C may be unsubstituted when z1 is 0. Ring C may be substituted when z1 is an integer between 1 and 5 and one or more $R^1$ substituents is not hydrogen. Ring C may be unsubstituted triazole. Ring C may be substituted triazole. Ring C may be unsubstituted tetrazole. Ring C may be substituted tetrazole.

$L^2$ may be a bond or substituted or unsubstituted $C_1$-$C_{10}$ alkylene or substituted or unsubstituted 2 to 10 membered heteroalkylene. $L^2$ may be a bond or $R^{5A}$-substituted or unsubstituted $C_1$-$C_{10}$ alkylene or $R^{5A}$-substituted or unsubstituted 2 to 10 membered heteroalkylene. $L^2$ may be a bond or substituted or unsubstituted $C_1$-$C_8$ alkylene or substituted or unsubstituted 2 to 8 membered heteroalkylene. $L^2$ may be a bond or $R^{5A}$-substituted $C_1$-$C_8$ alkylene or $R^{5A}$-substituted 2 to 8 membered heteroalkylene. $L^2$ may be 2 to 5 membered heteroalkylene. $L^2$ may be a bond or $R^{5A}$-substituted $C_1$-$C_8$ alkylene or $R^{5A}$-substituted 2 to 5 membered heteroalkylene. $L^2$ may be a bond or substituted or unsubstituted $C_1$-$C_3$ alkylene or substituted or unsubstituted 2 to 3 membered heteroalkylene. $L^2$ may be a bond or $R^{5A}$-substituted $C_1$-$C_3$ alkylene or $R^{5A}$-substituted 2 to 3 membered heteroalkylene.

$L^2$ may be a bond or substituted or unsubstituted $C_1$-$C_{10}$ alkylene. $L^2$ may be a bond or $R^{5A}$-substituted or unsubstituted $C_1$-$C_{10}$ alkylene. $L^2$ may be a bond or substituted or unsubstituted $C_1$-$C_8$ alkylene. $L^2$ may be a bond or $R^{5A}$-substituted $C_1$-$C_8$ alkylene. $L^2$ may be a bond or substituted or unsubstituted $C_1$-$C_5$ alkylene. $L^2$ may be a bond or $R^{5A}$-substituted $C_1$-$C_5$ alkylene. $L^2$ may be a bond or substituted or unsubstituted $C_1$-$C_3$ alkylene. $L^2$ may be a bond or $R^{5A}$-substituted $C_1$-$C_3$ alkylene. $L^2$ may be a bond. $L^2$ may be $R^{5A}$-substituted or unsubstituted methylene or $R^{5A}$-substituted or unsubstituted ethylene. $L^2$ may be unsubstituted methylene or unsubstituted ethylene. $L^2$ may be unsubstituted methylene. $L^2$ may be $R^{5A}$-substituted methylene where $R^{5A}$ is independently hydrogen, halogen or methyl.

$L^2$ may be a bond or substituted or unsubstituted 2 to 10 membered heteroalkylene. $L^2$ may be a bond or $R^{5A}$-substituted or unsubstituted 2 to 10 membered heteroalkylene. $L^2$ may be a bond or substituted or unsubstituted 2 to 8 membered heteroalkylene. $L^2$ may be a bond or $R^{5A}$-substituted 2 to 8 membered heteroalkylene. $L^2$ may be a bond or substituted or unsubstituted 2 to 5 membered heteroalkylene. $L^2$ may be a bond or $R^{5A}$-substituted 2 to 5 membered heteroalkylene. $L^2$ may be a bond or substituted or unsubstituted 2 to 3 membered heteroalkylene. $L^2$ may be a bond or $R^{5A}$-substituted 2 to 3 membered heteroalkylene. $L^2$ may be a bond. $L^2$ may be $R^{5A}$-substituted or unsubstituted aminomethylene or $R^{5A}$-substituted or unsubstituted aminoethylene. $L^2$ may be unsubstituted aminomethylene or unsubstituted aminoethylene. $L^2$ may be unsubstituted aminomethylene. $L^2$ may be $R^{5A}$-substituted aminomethylene where $R^{5A}$ is independently hydrogen, halogen or methyl. $L^2$ may be a bond. $L^2$ may be —$CH_2CH_2NH$—. $L^2$ may be —$CH_2NH$—. In embodiments, $L^2$ is substituted 3 to 6 membered heteroalkylene. In embodiments, Ring $L^2$ is unsubstituted $C_1$-$C_6$ alkylene. In embodiments, Ring $L^2$ is unsubstituted $C_1$-$C_4$ alkylene. In embodiments, $L^2$ is —$CH_2$—. In embodiments, $L^2$ is —$CH_2NHCOHNCH_2$—. In embodiments, $L^2$ is —$CH_2NHCO$—. In embodiments, $L^2$ is —$CH_2CH_2NHCONHCH_2$—.

$R^{5A}$ is independently hydrogen, halogen, oxo, —$N_3$, —$CF_3$, —$CCl_3$, —$CBr_3$, —$CI_3$, —CN, —CHO, —OH, —$NH_2$, —COOH, —$CONH_2$, —$NO_2$, —SH, —$SO_2$, —$SO_2Cl$, —$SO_2CH_3$—$SO_3H$, —$SO_4H$, —$SO_2NH_2$, —$NHNH_2$, —$ONH_2$, —NHC(O)$NHNH_2$, unsubstituted alkyl, unsubstituted heteroalkyl, unsubstituted cycloalkyl, unsubstituted heterocycloalkyl, unsubstituted aryl, or unsubstituted heteroaryl. $R^{5A}$ may independently be halogen, oxo, —$N_3$, —$CF_3$, —$CCl_3$, —$CBr_3$, —$CI_3$, —CN, —CHO, —OH, —$NH_2$, —COOH, —$CONH_2$, —$NO_2$, —SH, —$SO_2$, —$SO_2Cl$, —$SO_2CH_3$—$SO_3H$, —$SO_4H$, —$SO_2NH_2$, —$NHNH_2$, —$ONH_2$, —NHC(O)$NHNH_2$, unsubstituted alkyl, unsubstituted heteroalkyl, unsubstituted cycloalkyl, unsubstituted heterocycloalkyl, unsubstituted aryl, or unsubstituted heteroaryl.

In embodiments, $R^{5A}$ is independently hydrogen, halogen, oxo, —$N_3$, —$CF_3$, —$CCl_3$, —$CBr_3$, —$CI_3$, —CN, —CHO, —OH, —$NH_2$, —COOH, —$CONH_2$, —$NO_2$, —SH, —$SO_2$, —$SO_2Cl$, —$SO_2CH_3$—$SO_3H$, —$SO_4H$, —$SO_2NH_2$, —$NHNH_2$, —$ONH_2$, —NHC(O)$NHNH_2$, unsubstituted alkyl (e.g. $C_1$-$C_8$ alkyl, $C_1$-$C_6$ alkyl, or $C_1$-$C_4$ alkyl), unsubstituted heteroalkyl (e.g. 2 to 8 membered heteroalkyl, 2 to 6 membered heteroalkyl, or 2 to 4 membered heteroalkyl), unsubstituted cycloalkyl (e.g. $C_3$-$C_8$ cycloalkyl, $C_4$-$C_8$ cycloalkyl, or $C_5$-$C_6$ cycloalkyl), unsubstituted heterocycloalkyl (e.g. 3 to 8 membered heterocycloalkyl, 4 to 8 membered heterocycloalkyl, or 5 to 6 membered heterocycloalkyl), unsubstituted aryl (e.g. $C_6$-$C_{10}$ aryl or $C_6$ aryl), or unsubstituted heteroaryl (e.g. 5 to 10 membered heteroaryl, 5 to 9 membered heteroaryl, or 5 to 6 membered heteroaryl).

$R^{5A}$ may independently be halogen, oxo, —$N_3$, —$CF_3$, —$CCl_3$, —$CBr_3$, —$CI_3$, —CN, —CHO, —OH, —$NH_2$, —COOH, —$CONH_2$, —$NO_2$, —SH, —$SO_2$, —$SO_2Cl$, —$SO_2CH_3$—$SO_3H$, —$SO_4H$, —$SO_2NH_2$, —$NHNH_2$, —$ONH_2$, —NHC(O)$NHNH_2$, unsubstituted alkyl (e.g. $C_1$-$C_8$ alkyl, $C_1$-$C_6$ alkyl, or $C_1$-$C_4$ alkyl), unsubstituted heteroalkyl (e.g. 2 to 8 membered heteroalkyl, 2 to 6 membered heteroalkyl, or 2 to 4 membered heteroalkyl), unsubstituted cycloalkyl (e.g. $C_3$-$C_8$ cycloalkyl, $C_4$-$C_8$ cycloalkyl, or $C_5$-$C_6$ cycloalkyl), unsubstituted heterocycloalkyl (e.g. 3 to 8 membered heterocycloalkyl, 4 to 8 membered heterocycloalkyl, or 5 to 6 membered heterocycloalkyl), unsubstituted aryl (e.g. $C_6$-$C_{10}$ aryl or $C_6$ aryl), or unsubstituted heteroaryl (e.g. 5 to 10 membered heteroaryl, 5 to 9 membered heteroaryl, or 5 to 6 membered heteroaryl).

$L^3$ may be a bond, $R^6$-substituted or unsubstituted $C_1$-$C_{10}$ alkylene, $R^6$-substituted or unsubstituted 2 to 10 membered heteroalkylene, $R^6$-substituted or unsubstituted cycloalkylene, $R^6$-substituted or unsubstituted heterocycloalkylene, or $R^6$-substituted or unsubstituted alkylarylene. $L^3$ may be a bond or substituted or unsubstituted $C_1$-$C_{10}$ alkylene. $L^3$ may be a bond. $L^3$ may be substituted or unsubstituted $C_1$-$C_{10}$ alkylene. $L^3$ may be substituted $C_1$-$C_{10}$ alkylene. $L^3$ may be unsubstituted $C_1$-$C_{10}$ alkylene. $L^3$ may be $R^6$-substituted or unsubstituted $C_1$-$C_{10}$ alkylene. $L^3$ may be $R^6$-substituted $C_1$-$C_{10}$ alkylene. $L^3$ may be a bond or substituted or unsubstituted $C_1$-$C_8$ alkylene. $L^3$ may be substituted or unsubstituted $C_1$-$C_8$ alkylene. $L^3$ may be substituted $C_1$-$C_8$ alkylene. $L^3$ may be unsubstituted $C_1$-$C_8$ alkylene. $L^3$ may be $R^6$-substituted or unsubstituted $C_1$-$C_8$ alkylene. $L^3$ may be $R^6$-substituted $C_1$-$C_8$ alkylene. $L^3$ may be a bond or substituted or unsubstituted $C_1$-$C_5$ alkylene. $L^3$ may be substituted or unsubstituted $C_1$-$C_5$ alkylene. $L^3$ may be substituted $C_1$-$C_5$ alkylene. $L^3$ may be unsubstituted $C_1$-$C_5$ alkylene. $L^3$ may be $R^6$-substituted or unsubstituted $C_1$-$C_5$ alkylene. $L^3$ may be $R^6$-substituted $C_1$-$C_5$ alkylene. $L^3$ may be a bond or substituted or unsubstituted $C_1$-$C_3$ alkylene. $L^3$ may be substituted or unsubstituted $C_1$-$C_3$ alkylene. $L^3$ may be substituted $C_1$-$C_3$ alkylene. $L^3$ may be unsubstituted $C_1$-$C_3$ alkylene. $L^3$ may be $R^6$-substituted or unsubstituted $C_1$-$C_3$ alkylene. $L^3$ may be $R^6$-substituted $C_1$-$C_3$ alkylene. $L^3$ may be $R^6$-substituted $C_1$-$C_3$ alkylene, where $R^6$ is —NHC(O)$R^{6A}$ and $R^{6A}$ is as described herein. $L^3$ may be $R^6$-substituted $C_1$-$C_3$ alkylene, where $R^6$ is —NHC(O)$R^{6A}$ and $R^{6A}$ is —C(NCN)$R^{6C}$, —C(NH)$R^{6C}$, $R^{6C}$-substituted or unsubstituted alkyl, or $R^{6C}$-substituted or unsubstituted heteroalkyl.

$L^3$ may be substituted or unsubstituted 2 to 10 membered heteroalkylene. $L^3$ may be substituted 2 to 10 membered heteroalkylene. $L^3$ may be unsubstituted 2 to 10 membered heteroalkylene. $L^3$ may be $R^6$-substituted or unsubstituted 2 to 10 membered heteroalkylene. $L^3$ may be $R^6$-substituted 2 to 10 membered heteroalkylene. $L^3$ may be substituted or unsubstituted 2 to 8 membered heteroalkylene. $L^3$ may be substituted 2 to 8 membered heteroalkylene. $L^3$ may be unsubstituted 2 to 8 membered heteroalkylene. $L^3$ may be $R^6$-substituted or unsubstituted 2 to 8 membered heteroalkylene. $L^3$ may be $R^6$-substituted 2 to 8 membered heteroalkylene. $L^3$ may be substituted or unsubstituted 2 to 6 membered heteroalkylene. $L^3$ may be substituted 2 to 6 membered heteroalkylene. $L^3$ may be unsubstituted 2 to 6 membered heteroalkylene. $L^3$ may be $R^6$-substituted or unsubstituted 2 to 6 membered heteroalkylene. $L^3$ may be $R^6$-substituted 2 to 6 membered heteroalkylene.

$L^3$ may be substituted or unsubstituted $C_3$-$C_6$ cycloalkylene. $L^3$ may be substituted $C_3$-$C_6$ cycloalkylene. $L^3$ may be unsubstituted $C_3$-$C_6$ cycloalkylene. $L^3$ may be $R^6$-substituted or unsubstituted $C_3$-$C_6$ cycloalkylene. $L^3$ may be $R^6$-substituted $C_3$-$C_6$ cycloalkylene. $L^3$ may be substituted or unsubstituted $C_3$ cycloalkylene. $L^3$ may be $R^6$-substituted or unsubstituted $C_3$ cycloalkylene. $L^3$ may be unsubstituted $C_3$ cycloalkylene. $L^3$ may be substituted or unsubstituted $C_4$ cycloalkylene. $L^3$ may be $R^6$-substituted or unsubstituted $C_4$ cycloalkylene. $L^3$ may be unsubstituted $C_4$ cycloalkylene. $L^3$ may be substituted or unsubstituted $C_5$ cycloalkylene. $L^3$ may be $R^6$-substituted or unsubstituted $C_5$ cycloalkylene. $L^3$ may be unsubstituted $C_5$ cycloalkylene. $L^3$ may be substituted or unsubstituted $C_6$ cycloalkylene. $L^3$ may be $R^6$-substituted or unsubstituted $C_6$ cycloalkylene. $L^3$ may be unsubstituted $C_6$ cycloalkylene.

$L^3$ may be substituted or unsubstituted $C_6$-$C_{10}$ arylene. $L^3$ may be substituted $C_6$-$C_{10}$ arylene. $L^3$ may be unsubstituted $C_6$-$C_{10}$ arylene. $L^3$ may be $R^6$-substituted or unsubstituted $C_6$-$C_{10}$ arylene. $L^3$ may be $R^6$-substituted $C_6$-$C_{10}$ arylene. $L^3$ may be substituted or unsubstituted phenylene. $L^3$ may be $R^6$-substituted or unsubstituted phenylene. $L^3$ may be unsubstituted phenylene. $L^3$ may be substituted phenylene. $L^3$ may be $R^6$-substituted phenylene.

$L^3$ may be substituted or unsubstituted 5 to 6 membered heteroarylene. $L^3$ may be substituted 5 to 6 membered heteroarylene. $L^3$ may be unsubstituted 5 to 6 membered heteroarylene. $L^3$ may be $R^6$-substituted or unsubstituted 5 to 6 membered heteroarylene. $L^3$ may be $R^6$-substituted 5 to 6 membered heteroarylene. $L^3$ may be substituted or unsubstituted 5 to 10 membered heteroarylene. $L^3$ may be $R^6$-substituted or unsubstituted 5 to 10 membered heteroarylene. $L^3$ may be unsubstituted 5 to 10 membered heteroarylene. $L^3$ may be $R^6$-substituted 5 to 10 membered heteroarylene. $L^3$ may be substituted 5 to 10 membered heteroarylene. $L^3$ may be substituted or unsubstituted 5 membered heteroarylene. $L^3$ may be $R^6$-substituted or unsubstituted 5 membered heteroarylene. $L^3$ may be unsubstituted 5 membered heteroarylene. $L^3$ may be substituted or unsubstituted 6 membered heteroarylene. $L^3$ may be $R^6$-substituted or unsubstituted 6 membered heteroarylene. $L^3$ may be unsubstituted 6 membered heteroarylene.

$L^3$ may be substituted or unsubstituted alkylarylene (e.g. substituted or unsubstituted on the alkylene moiety or the arylene linker). $L^3$ may be unsubstituted alkylarylene. $L^3$ may be $R^6$-substituted or unsubstituted alkylarylene (e.g. $R^6$-substituted or unsubstituted on the alkylene moiety or the arylene linker). $L^3$ may be $R^6$-substituted alkylarylene. $L^3$ may be unsubstituted oxoalkylene or unsubstituted oxoheteroalkylene.

In embodiments, $L^3$ is substituted 2 to 8 membered heteroalkylene. In embodiments, $L^3$ is unsubstituted 2 to 8 membered heteroalkylene. In embodiments, $L^3$ is substituted 3 to 7 membered heteroalkylene. In embodiments, $L^3$ is unsubstituted 3 to 7 membered heteroalkylene. In embodiments, $L^3$ is substituted 4 to 6 membered heteroalkylene. In embodiments, $L^3$ is unsubstituted 4 to 6 membered heteroalkylene. In embodiments, $L^3$ is substituted 5 to 6 membered heteroalkylene. In embodiments, $L^3$ is unsubstituted 5 to 6 membered heteroalkylene. In embodiments, $L^3$ is unsubstituted $C_2$-$C_8$ alkylene. In embodiments, $L^3$ is unsubstituted $C_3$-$C_7$ alkylene. In embodiments, $L^3$ is unsubstituted $C_4$-$C_6$ alkylene. In embodiments, $L^3$ is unsubstituted $C_5$-$C_6$ alkylene. In embodiments, $L^3$ is —NHCO-(substituted or unsubstituted $C_5$-$C_6$ cycloalkylene)-NH—. In embodiments, $L^3$ is —NHCO-(substituted or unsubstituted $C_4$-$C_6$ cycloalkylene)-NH—. In embodiments, $L^3$ is —NHCO-(substituted or unsubstituted $C_3$-$C_7$ cycloalkylene)-NH—. In embodiments, $L^3$ is —NHCO-(substituted or unsubstituted $C_5$-$C_6$ cycloalkylene)-. In embodiments, $L^3$ is —NHCO-(substituted or unsubstituted $C_4$-$C_6$ cycloalkylene)-. In embodiments, $L^3$ is —NHCO-(substituted or unsubstituted $C_3$-$C_7$ cycloalkylene)-. In embodiments, $L^3$ is —NHCO-(substituted or unsubstituted 5 to 6 membered heteroarylene)-NH—. In embodiments, $L^3$ is —NHCO-(substituted or unsubstituted 5 to 10 membered heteroarylene)-NH—. In embodiments, $L^3$ is —NHCO-(substituted or unsubstituted 5 to 6 membered heteroarylene)-. In embodiments, $L^3$ is —NHCO-(substituted or unsubstituted 5 to 10 membered heteroarylene)-. In embodiments, $L^3$ is —NHCO-(substituted or unsubstituted 5 to 6 membered heterocycloalkylene)-NH—. In embodiments, $L^3$ is —NHCO-(substituted or unsubstituted 4 to 7 membered heterocycloalkylene)-NH—. In embodiments, $L^3$ is —NHCO-(substituted or unsubstituted 5 to 6 membered heterocycloalkylene)-. In embodiments, $L^3$ is —NHCO-(substituted or unsubstituted 4 to 7 membered heterocycloalkylene)-. In embodiments, $L^3$ is -(substituted or unsubstituted 4 to 7 membered heterocycloalkylene)-(unsubstituted $C_1$-$C_4$ alkylene)-. In embodiments, $L^3$ is -(substituted or unsubstituted 4 to 7 membered heterocycloalkylene)-(unsubstituted $C_1$-$C_4$ alkylene)-NH—. In embodiments, $L^3$ is -(substituted or unsubstituted 5 to 6 membered heteroarylene)-(unsubstituted $C_1$-$C_4$ alkylene)-. In embodiments, $L^3$ is -(substituted or unsubstituted 5 to 6 membered heteroarylene)-(unsubstituted $C_1$-$C_4$ alkylene)-NH—. In embodiments, $L^3$ is -(substituted or unsubstituted $C_4$-$C_7$ cycloalkylene)-(unsubstituted $C_1$-$C_4$ alkylene)-. In embodiments, $L^3$ is -(substituted or unsubstituted $C_4$-$C_7$ cycloalkylene)-(unsubstituted $C_1$-$C_4$ alkylene)-NH—. In embodiments, $L^3$ is —O-(substituted or unsubstituted $C_5$-$C_6$ cycloalkylene)-NH—. In embodiments, $L^3$ is —O-(substituted or unsubstituted $C_4$-$C_6$ cycloalkylene)-NH—. In embodiments, $L^3$ is —O-(substituted or unsubstituted $C_3$-$C_7$ cycloalkylene)-NH—. In embodiments, $L^3$ is —O-(substituted or unsubstituted $C_5$-$C_6$ cycloalkylene)-. In embodiments, $L^3$ is —O-(substituted or unsubstituted $C_4$-$C_6$ cycloalkylene)-. In embodiments, $L^3$ is —O-(substituted or unsubstituted $C_3$-$C_7$ cycloalkylene)-. In embodiments, $L^3$ is —O-(substituted or unsubstituted 5 to 6 membered heteroarylene)-NH—. In embodiments, $L^3$ is —O-(substituted or unsubstituted 5 to 6 membered heteroarylene)-. In embodiments, $L^3$ is —NHCO-(substituted or unsubstituted 5 to 6 membered heteroarylene)-NH—. In embodiments, $L^3$ is —NHCO-(substituted or unsubstituted 5 to 6 membered heteroarylene)-. In embodiments, $L^3$ is a substituted fused cycloalkylene-arylene. In embodiments, $L^3$ is an unsubstituted fused cycloalkylene-arylene. In embodiments, $L^3$ is a substituted fused heterocycloalkylene-heteroarylene. In embodiments, $L^3$ is an unsubstituted fused heterocycloalkylene-heteroarylene. In embodiments, $L^3$ is a substituted fused arylene-heterocycloalkylene-heteroarylene. In embodiments, $L^3$ is an unsubstituted fused arylene-heterocycloalkylene-heteroarylene.

In embodiments, $L^3$ is —NHCOCH$_2$CH$_2$CH$_2$CH$_2$—. In embodiments, $L^3$ is —NHCOCH$_2$CH$_2$CH$_2$—. In embodiments, $L^3$ is a bond. In embodiments, $L^3$ is —CH$_2$NH—. In embodiments, $L^3$ is —CH$_2$CH$_2$CH$_2$NH—. In embodiments, $L^3$ is —NH—. —NHCOCH$_2$CH$_2$—. In embodiments, $L^3$ is —CH$_2$CH$_2$CH$_2$CH$_2$CH$_2$CH$_2$CH$_2$NH—. In embodiments, $L^3$ is —CH$_2$CH$_2$CH$_2$CH$_2$CH$_2$CH$_2$CH$_2$—. In embodiments, $L^3$ is —CH$_2$CH$_2$—. In embodiments, $L^3$ is —CH$_2$CH$_2$CH$_2$—. In embodiments, $L^3$ is —CH$_2$CH$_2$CH$_2$CH$_2$—. In embodiments, $L^3$ is —CH$_2$CH$_2$CH$_2$CH$_2$—. In embodiments, $L^3$ is —CH$_2$CH$_2$CH$_2$CH$_2$CH$_2$NH—. In embodiments, $L^3$ is —NHCOCH$_2$CH$_2$CH$_2$NH—. In embodiments, $L^3$ is —NHCOCH$_2$CH$_2$NH—. In embodiments, $L^3$ is —NCOCH$_2$CH$_2$NH—. In embodiments, $L^3$ is —NHCOO—. In embodiments, $L^3$ is —NHCO—. In embodiments, $L^3$ is —NHCOOCH$_2$—. In embodiments, $L^3$ is —NHCOOCH$_2$CH$_2$NH—. In embodiments, $L^3$ is —OCH$_2$CH$_2$—. In embodiments, $L^3$ is —OCH$_2$CH$_2$NH—. In embodiments, $L^3$ is —NHCONH—. In embodiments, $L^3$ is —NHCONHCH$_2$CH$_2$—. In embodiments, $L^3$ is —NHCONHCH$_2$CH$_2$NH—. In embodiments, $L^3$ is —NHCH$_2$CH$_2$—. In embodiments, $L^3$ is —CONH—. In embodiments, $L^3$ is —CONHCH$_2$CH$_2$CH$_2$—. In embodiments, $L^3$ is —CONHCH$_2$CH$_2$CONH—. In embodiments, $L^3$ is —NHCH$_2$CH$_2$CH$_2$—. In embodiments, $L^3$ is —NHCH$_2$CH$_2$CH$_2$NH—. In embodiments, Y is —O—. In embodiments, $L^3$ is —OCH$_2$CH$_2$CH$_2$—. In embodiments, $L^3$ is —OCH$_2$CH$_2$CH$_2$NH—. In embodiments, $L^3$ is —CH$_2$CH$_2$CH$_2$CH$_2$NH—. In embodiments, $L^3$ is —CHCHCH$_2$NH—. In embodiments, $L^3$ is —CHCHCH$_2$—. In embodiments, $L^3$ is —CHCHCH$_2$NH—. In embodiments, $L^3$ is cyclohexyl. In embodiments, $L^3$ is unsubstituted cyclohexyl. In embodiments, $L^3$ is cyclopenyl. In embodiments, $L^3$ is unsubstituted cyclopentyl. In embodiments, $L^3$ is —NHCOPhNH—. In embodiments, $L^3$ is —NHCOPh-. In embodiments, $L^3$ is -Ph-. In embodiments, $L^3$ is -PhNH—. In embodiments, $L^3$ is —NHCO-cyclohexyl-NH—. In embodiments, $L^3$ is —NHCO-(unsubstituted cyclohexyl)-NH—. In embodiments, $L^3$ is —NHCO-cyclohexyl-. In embodiments, $L^3$ is —NHCO-(unsubstituted cyclohexyl)-. In embodiments, $L^3$ is —CH$_2$NHCOCH$_2$CH$_2$CH$_2$CH$_2$NH—. In embodiments, $L^3$ is —CH$_2$NHCO—. In embodiments, $L^3$ is —CH$_2$NH—. In embodiments, $L^3$ is —CH$_2$NHCOCH$_2$CH$_2$CH$_2$CH$_2$—. In embodiments, $L^3$ is —CH$_2$NHCOCH$_2$CH$_2$CH$_2$NH—. In embodiments, $L^3$ is —CH$_2$NHCOCH$_2$CH$_2$CH$_2$—. In embodiments, $L^3$ is —COCH$_2$CH$_2$CH$_2$CH$_2$NH—. In embodiments, $L^3$ is —COCH$_2$CH$_2$CH$_2$CH$_2$—. In embodiments, $L^3$ is —NHCH$_2$CH$_2$CH$_2$CH$_2$NH—. In embodiments, $L^3$ is —NHCH$_2$CH$_2$CH$_2$CH$_2$—.

In embodiments, $L^3$ is

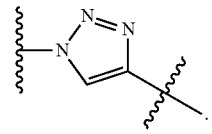 [SMILES: *c1cn(*)nn1]

In embodiments, $L^3$ is

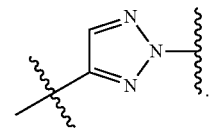 [SMILES: *c1cnn(*)n1]

In embodiments, $L^3$ is

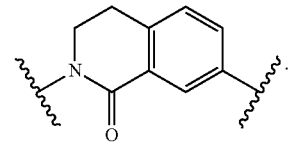

In embodiments, $L^3$ is

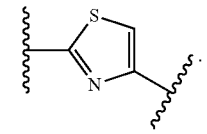 [SMILES: *c1csc(*)n1]

In embodiments, $L^3$ is

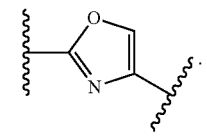 [SMILES: *c1coc(*)n1]

In embodiments, L³ is
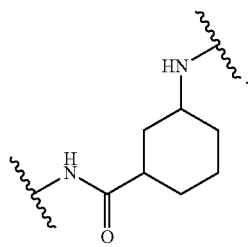 [SMILES: *NC(=O)C1CCCC(N*)C1]
In embodiments, L³ is
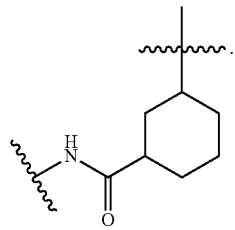 [SMILES: *NC(=O)C1CCCC(*)C1]
In embodiments, L³ is
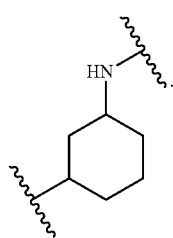 [SMILES: *NC1CCCC(*)C1]
In embodiments, L³ is
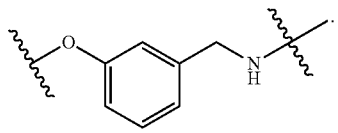 [SMILES: *NCc1cccc(O*)c1]
In embodiments, L³ is
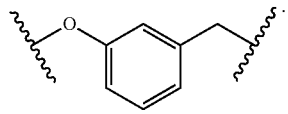 [SMILES: *Cc1cccc(O*)c1]
In embodiments, L³ is
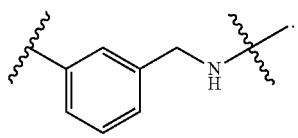 [SMILES: *NCc1cccc(*)c1]
In embodiments, L³ is
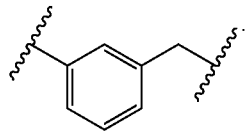 [SMILES: *Cc1cccc(*)c1]
In embodiments, L³ is
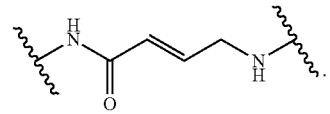 [SMILES: *NC/C=C/C(=O)N*]
In embodiments, L³ is
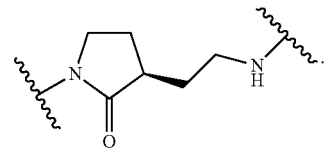 [SMILES: *NCC[C@@H]1CCN(*)C1=O]
In embodiments, L³ is
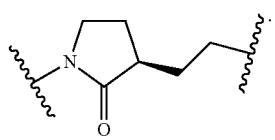 [SMILES: *CC[C@@H]1CCN(*)C1=O]
In embodiments, L³ is
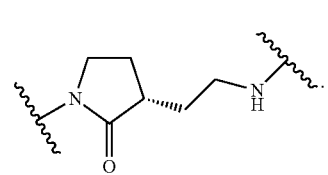 [SMILES: *NCC[C@H]1CCN(*)C1=O]
In embodiments, L³ is
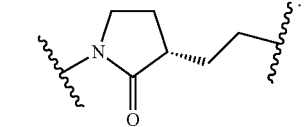 [SMILES: *CC[C@H]1CCN(*)C1=O]

In embodiments, L³ is

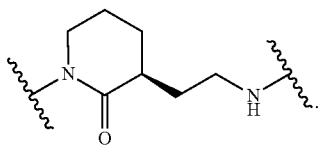 [SMILES: *NCC[C@@H]1CCCN(*)C1=O]

In embodiments, L³ is

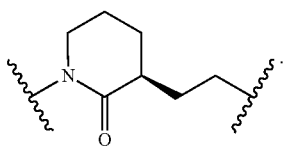 [SMILES: *CC[C@@H]1CCCN(*)C1=O]

In embodiments, L³ is

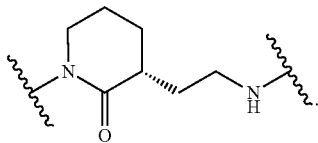 [SMILES: *NCC[C@H]1CCCN(*)C1=O]

In embodiments, L³ is

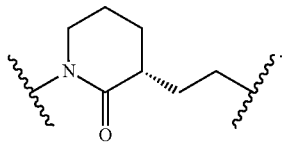 [SMILES: *CC[C@H]1CCCN(*)C1=O]

In embodiments, L³ is

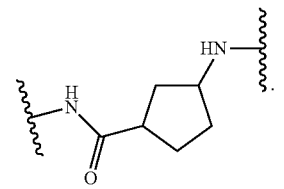 [SMILES: *NC(=O)C1CCC(N*)C1]

In embodiments, L³ is

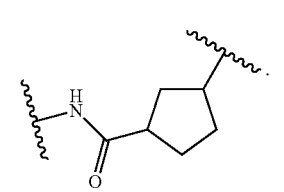 [SMILES: *NC(=O)C1CCC(*)C1]

In embodiments, L³ is

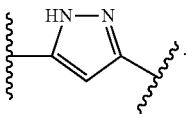 [SMILES: *c1cc(*)[nH]n1]

In embodiments, L³ is

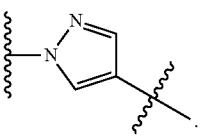 [SMILES: *c1cnn(*)c1]

$R^6$ is hydrogen, halogen, oxo, $-N_3$, $-CX^6_3$, $-CHX^6_2$, $-CH_2X^6$, $-CN$, $-COR^{6A}$, $-OR^{6A}$, $-NR^{6A}R^{6B}$, $-COOR^{6A}$, $-CONR^{6A}R^{6B}$, $-NHC(O)R^{6A}$, $-NO_2$, $-SR^{6A}$, $-SO_2$, $-SO_{n6}R^{6A}$, $-NHNR^{6A}R^{6B}$, $-ONR^{6A}R^{6B}$, $-NHC(O)NHNR^{6A}R^{6B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^6$ is hydrogen, halogen, oxo, $-N_3$, $-CX^6_3$, $-CHX^6_2$, $-CH_2X^6$, $-CN$, $-COR^{6A}$, $-OR^{6A}$, $-NR^{6A}R^{6B}$, $-COOR^{6A}$, $-CONR^{6A}R^{6B}$, $-NHC(O)R^{6A}$, $-NO_2$, $-SR^{6A}$, $-SO_2$, $-SO_{n6}R^{6A}$, $-NHNR^{6A}R^{6B}$, $-ONR^{6A}R^{6B}$, $-NHC(O)NHNR^{6A}R^{6B}$, $R^{6A}$-substituted or unsubstituted alkyl, $R^{6A}$-substituted or unsubstituted heteroalkyl, $R^{6A}$-substituted or unsubstituted cycloalkyl, $R^{6A}$-substituted or unsubstituted heterocycloalkyl, $R^{6A}$-substituted or unsubstituted aryl, or $R^{6A}$-substituted or unsubstituted heteroaryl.

$R^6$ may be $R^{6A}$-substituted or unsubstituted alkyl (e.g. $C_1$-$C_8$ alkyl, $C_1$-$C_6$ alkyl, or $C_1$-$C_4$ alkyl), $R^{6A}$-substituted or unsubstituted heteroalkyl (e.g. 2 to 8 membered heteroalkyl, 2 to 6 membered heteroalkyl, or 2 to 4 membered heteroalkyl), $R^{6A}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{6A}$-substituted or unsubstituted heterocycloalkyl (e.g. 3 to 8 membered heterocycloalkyl, 4 to 8 membered heterocycloalkyl, or 5 to 6 membered heterocycloalkyl), $R^{6A}$-substituted or unsubstituted aryl (e.g. $C_6$-$C_{10}$ aryl or $C_6$ aryl), or $R^{6A}$-substituted or unsubstituted heteroaryl (e.g. 5 to 10 membered heteroaryl, 5 to 9 membered heteroaryl, or 5 to 6 membered heteroaryl).

$R^6$ may be halogen, oxo, $-N_3$, $-CX^6_3$, $-CHX^6_2$, $-CH_2X^6$, $-CN$, $-COR^{6A}$, $-OR^{6A}$, $-NR^{6A}R^{6B}$, $-COOR^{6A}$, $-CONR^{6A}R^{6B}$, $-NHC(O)R^{6A}$, $-NO_2$, $-SR^{6A}$, $-SO_2$, $-SO_{n6}R^{6A}$, $-NHNR^{6A}R^{6B}$, $-ONR^{6A}R^{6B}$, $-NHC(O)NHNR^{6A}R^{6B}$, $R^{6A}$-substituted or unsubstituted alkyl, $R^{6A}$-substituted or unsubstituted heteroalkyl, $R^{6A}$-substituted or unsubstituted cycloalkyl, $R^{6A}$-substituted or unsubstituted heterocycloalkyl, $R^{6A}$-substituted or unsubstituted aryl, or $R^{6A}$-substituted or unsubstituted heteroaryl. $X^6$ is independently a halogen. $X^6$ is independently $-Cl$. $X^6$ is independently $-F$. $X^6$ is independently $-Br$. $X^6$ is independently a $-I$. The symbol n6 is 2, 3, or 4. The symbol n6 is 2. The symbol n6 is 3. The symbol n6 is 4.

$R^6$ may be hydrogen, halogen, oxo, $-N_3$, $-CX^6_3$, $-CHX^6_2$, $-CH_2X^6$, $-CN$, $-CHO$, $-OH$, $-NH_2$, —COOH, —CONH$_2$, —NO$_2$, —SH, —SO$_2$, —SO$_2$Cl, —SO$_2$CH$_3$—SO$_3$H, —SO$_4$H, —SO$_2$NH$_2$, —NHNH$_2$, —ONH$_2$, —NHC(O)NHNH$_2$, unsubstituted alkyl, unsubstituted heteroalkyl, unsubstituted cycloalkyl, unsubstituted heterocycloalkyl, unsubstituted aryl, or unsubstituted heteroaryl. R$^6$ may be hydrogen, halogen, oxo, —N$_3$, —CX$^6$$_3$, —CHX$^6$$_2$, —CH$_2$X$^6$, —CN, —CHO, —OH, —NH$_2$, —COOH, —CONH$_2$, —NO$_2$, —SH, —SO$_2$, —SO$_2$Cl, —SO$_2$CH$_3$—SO$_3$H, —SO$_4$H, —SO$_2$NH$_2$, —NHNH$_2$, —ONH$_2$, —NHC(O)NHNH$_2$, unsubstituted alkyl (e.g. C$_1$-C$_8$ alkyl, C$_1$-C$_6$ alkyl, or C$_1$-C$_4$ alkyl), unsubstituted heteroalkyl (e.g. 2 to 8 membered heteroalkyl, 2 to 6 membered heteroalkyl, or 2 to 4 membered heteroalkyl), unsubstituted cycloalkyl (e.g. C$_3$-C$_8$ cycloalkyl, C$_4$-C$_8$ cycloalkyl, or C$_5$-C$_6$ cycloalkyl), unsubstituted heterocycloalkyl (e.g. 3 to 8 membered heterocycloalkyl, 4 to 8 membered heterocycloalkyl, or 5 to 6 membered heterocycloalkyl), unsubstituted aryl (e.g. C$_6$-C$_{10}$ aryl or C$_6$ aryl), or unsubstituted heteroaryl (e.g. 5 to 10 membered heteroaryl, 5 to 9 membered heteroaryl, or 5 to 6 membered heteroaryl).

R$^6$ may be halogen, oxo, —N$_3$, —CX$^6$$_3$, —CHX$^6$$_2$, —CH$_2$X$^6$, —CN, —CHO, —OH, —NH$_2$, —COOH, —CONH$_2$, —NO$_2$, —SH, —SO$_2$, —SO$_2$Cl, —SO$_2$CH$_3$—SO$_3$H, —SO$_4$H, —SO$_2$NH$_2$, —NHNH$_2$, —ONH$_2$, —NHC(O)NHNH$_2$, unsubstituted alkyl (e.g. C$_1$-C$_8$ alkyl, C$_1$-C$_6$ alkyl, or C$_1$-C$_4$ alkyl), unsubstituted heteroalkyl (e.g. 2 to 8 membered heteroalkyl, 2 to 6 membered heteroalkyl, or 2 to 4 membered heteroalkyl), unsubstituted cycloalkyl (e.g. C$_3$-C$_8$ cycloalkyl, C$_4$-C$_8$ cycloalkyl, or C$_5$-C$_6$ cycloalkyl), unsubstituted heterocycloalkyl (e.g. 3 to 8 membered heterocycloalkyl, 4 to 8 membered heterocycloalkyl, or 5 to 6 membered heterocycloalkyl), unsubstituted aryl (e.g. C$_6$-C$_{10}$ aryl or C$_6$ aryl), or unsubstituted heteroaryl (e.g. 5 to 10 membered heteroaryl, 5 to 9 membered heteroaryl, or 5 to 6 membered heteroaryl).

R$^{6A}$ is hydrogen, halogen, oxo, —N$_3$, —CX$^{6A}$$_3$, —CHX$^{6A}$$_2$, —CH$_2$X$^{6A}$, —CN, —COR$^{6C}$, —OR$^{6C}$, —NHR$^{6C}$, —COOR$^{6C}$, —CONHR$^{6C}$, —NO$_2$, —SR$^{6C}$, —SO$_2$, —SO$_2$R$^{6C}$, —NHNHR$^{6C}$, —ONHR$^{6C}$, —NHC(O)NHNHR$^{6C}$, —C(NCN)R$^{6C}$, —C(NH)R$^{6C}$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, or a detectable moiety. X$^{6A}$ is independently a halogen. X$^{6A}$ is independently —Cl. X$^{6A}$ is independently —F. X$^{6A}$ is independently —Br. X$^{6A}$ is independently a —I.

R$^{6A}$ may be hydrogen, halogen, oxo, —N$_3$, —CX$^{6A}$$_3$, —CHX$^{6A}$$_2$, —CH$_2$X$^{6A}$, —CN, —CHO, —OH, —NH$_2$, —COOH, —CONH$_2$, —NO$_2$, —SH, —SO$_2$, —SO$_2$Cl, —SO$_2$CH$_3$—SO$_3$H, —SO$_4$H, —SO$_2$NH$_2$, —NHNH$_2$, —ONH$_2$, —NHC(O)NHNH$_2$, —C(NCN)R$^{6C}$, —C(NH)R$^{6C}$, R$^{6C}$-substituted or unsubstituted alkyl (e.g. C$_1$-C$_8$ alkyl, C$_1$-C$_6$ alkyl, or C$_1$-C$_4$ alkyl), R$^{6C}$-substituted or unsubstituted heteroalkyl (e.g. 2 to 8 membered heteroalkyl, 2 to 6 membered heteroalkyl, or 2 to 4 membered heteroalkyl), R$^{6C}$-substituted or unsubstituted cycloalkyl (e.g. C$_3$-C$_8$ cycloalkyl, C$_4$-C$_8$ cycloalkyl, or C$_5$-C$_6$ cycloalkyl), R$^{6C}$-substituted or unsubstituted heterocycloalkyl (e.g. 3 to 8 membered heterocycloalkyl, 4 to 8 membered heterocycloalkyl, or 5 to 6 membered heterocycloalkyl), R$^{6C}$-substituted or unsubstituted aryl (e.g. C$_6$-C$_{10}$ aryl or C$_6$ aryl), R$^{6C}$-substituted or unsubstituted heteroaryl (e.g. 5 to 10 membered heteroaryl, 5 to 9 membered heteroaryl, or 5 to 6 membered heteroaryl), or a detectable moiety.

R$^{6A}$ may be hydrogen, halogen, oxo, —N$_3$, —CX$^{6A}$$_3$, —CHX$^{6A}$$_2$, —CH$_2$X$^{6A}$, —CN, —CHO, —OH, —NH$_2$, —COOH, —CONH$_2$, —NO$_2$, —SH, —SO$_2$, —SO$_2$Cl, —SO$_2$CH$_3$—SO$_3$H, —SO$_4$H, —SO$_2$NH$_2$, —NHNH$_2$, —ONH$_2$, —NHC(O)NHNH$_2$, —C(NCN)R$^{6C}$, —C(NH)R$^{6C}$, R$^{6C}$-substituted or unsubstituted alkyl (e.g. C$_1$-C$_8$ alkyl, C$_1$-C$_6$ alkyl, or C$_1$-C$_4$ alkyl), R$^{6C}$-substituted or unsubstituted heteroalkyl (e.g. 2 to 8 membered heteroalkyl, 2 to 6 membered heteroalkyl, or 2 to 4 membered heteroalkyl), R$^{6C}$-substituted or unsubstituted cycloalkyl (e.g. C$_3$-C$_8$ cycloalkyl, C$_4$-C$_8$ cycloalkyl, or C$_5$-C$_6$ cycloalkyl), R$^{6C}$-substituted or unsubstituted heterocycloalkyl (e.g. 3 to 8 membered heterocycloalkyl, 4 to 8 membered heterocycloalkyl, or 5 to 6 membered heterocycloalkyl), R$^{6C}$-substituted or unsubstituted aryl (e.g. C$_6$-C$_{10}$ aryl or C$_6$ aryl), R$^{6C}$-substituted or unsubstituted heteroaryl (e.g. 5 to 10 membered heteroaryl, 5 to 9 membered heteroaryl, or 5 to 6 membered heteroaryl).

R$^{6A}$ may be halogen, oxo, —N$_3$, —CX$^{6A}$$_3$, —CHX$^{6A}$$_2$, —CH$_2$X$^{6A}$, —CN, —CHO, —OH, —NH$_2$, —COOH, —CONH$_2$, —NO$_2$, —SH, —SO$_2$, —SO$_2$Cl, —SO$_2$CH$_3$—SO$_3$H, —SO$_4$H, —SO$_2$NH$_2$, —NHNH$_2$, —ONH$_2$, —NHC(O)NHNH$_2$, —C(NCN)R$^{6C}$, —C(NH)R$^{6C}$, R$^{6C}$-substituted or unsubstituted alkyl (e.g. C$_1$-C$_8$ alkyl, C$_1$-C$_6$ alkyl, or C$_1$-C$_4$ alkyl), R$^{6C}$-substituted or unsubstituted heteroalkyl (e.g. 2 to 8 membered heteroalkyl, 2 to 6 membered heteroalkyl, or 2 to 4 membered heteroalkyl), R$^{6C}$-substituted or unsubstituted cycloalkyl (e.g. C$_3$-C$_8$ cycloalkyl, C$_4$-C$_8$ cycloalkyl, or C$_5$-C$_6$ cycloalkyl), R$^{6C}$-substituted or unsubstituted heterocycloalkyl (e.g. 3 to 8 membered heterocycloalkyl, 4 to 8 membered heterocycloalkyl, or 5 to 6 membered heterocycloalkyl), R$^{6C}$-substituted or unsubstituted aryl (e.g. C$_6$-C$_{10}$ aryl or C$_6$ aryl), R$^{6C}$-substituted or unsubstituted heteroaryl (e.g. 5 to 10 membered heteroaryl, 5 to 9 membered heteroaryl, or 5 to 6 membered heteroaryl), or a detectable moiety.

R$^{6A}$ may be halogen, oxo, —N$_3$, —CX$^{6A}$$_3$, —CHX$^{6A}$$_2$, —CH$_2$X$^{6A}$, —CN, —CHO, —OH, —NH$_2$, —COOH, —CONH$_2$, —NO$_2$, —SH, —SO$_2$, —SO$_2$Cl, —SO$_2$CH$_3$—SO$_3$H, —SO$_4$H, —SO$_2$NH$_2$, —NHNH$_2$, —ONH$_2$, —NHC(O)NHNH$_2$, —C(NCN)R$^{6C}$, —C(NH)R$^{6C}$, (e.g. C$_1$-C$_8$ alkyl, C$_1$-C$_6$ alkyl, or C$_1$-C$_4$ alkyl), R$^{6C}$-substituted or unsubstituted heteroalkyl (e.g. 2 to 8 membered heteroalkyl, 2 to 6 membered heteroalkyl, or 2 to 4 membered heteroalkyl), R$^{6C}$-substituted or unsubstituted cycloalkyl (e.g. C$_3$-C$_8$ cycloalkyl, C$_4$-C$_8$ cycloalkyl, or C$_5$-C$_6$ cycloalkyl), R$^{6C}$-substituted or unsubstituted heterocycloalkyl (e.g. 3 to 8 membered heterocycloalkyl, 4 to 8 membered heterocycloalkyl, or 5 to 6 membered heterocycloalkyl), R$^{6C}$-substituted or unsubstituted aryl (e.g. C$_6$-C$_{10}$ aryl or C$_6$ aryl), R$^{6C}$-substituted or unsubstituted heteroaryl (e.g. 5 to 10 membered heteroaryl, 5 to 9 membered heteroaryl, or 5 to 6 membered heteroaryl).

R$^{6A}$ may be halogen, oxo, —N$_3$, —CX$^{6A}$$_3$, —CHX$^{6A}$$_2$, —CH$_2$X$^{6A}$, —CN, —CHO, —OH, —NH$_2$, —COOH, —CONH$_2$, —NO$_2$, —SH, —SO$_2$, —SO$_2$Cl, —SO$_2$CH$_3$—SO$_3$H, —SO$_4$H, —SO$_2$NH$_2$, —NHNH$_2$, —ONH$_2$, —NHC(O)NHNH$_2$, unsubstituted alkyl, unsubstituted heteroalkyl, unsubstituted cycloalkyl, unsubstituted heterocycloalkyl, unsubstituted aryl, or unsubstituted heteroaryl. In embodiments, R$^{6A}$ is unsubstituted alkyl (e.g. C$_1$-C$_8$ alkyl, C$_1$-C$_6$ alkyl, or C$_1$-C$_4$ alkyl), unsubstituted heteroalkyl (e.g. 2 to 8 membered heteroalkyl, 2 to 6 membered heteroalkyl, or 2 to 4 membered heteroalkyl), unsubstituted cycloalkyl (e.g. C$_3$-C$_8$ cycloalkyl, C$_4$-C$_8$ cycloalkyl, or C$_5$-C$_6$ cycloalkyl), unsubstituted heterocycloalkyl (e.g. 3 to 8 membered heterocycloalkyl, 4 to 8 membered heterocycloalkyl, or 5 to 6 membered heterocycloalkyl), unsubstituted aryl (e.g. C$_6$-C$_{10}$ aryl or $C_6$ aryl), or unsubstituted heteroaryl (e.g. 5 to 10 membered heteroaryl, 5 to 9 membered heteroaryl, or 5 to 6 membered heteroaryl).

$R^{6C}$ is hydrogen, halogen, oxo, $-N_3$, $-CX^{6C}_3$, $-CHX^{6C}_2$, $-CH_2X^{6C}$, $-CN$, $-COR^{6D}$, $-OR^{6D}$, $-NR^{6D}R^{6E}$, $-COOR^{6D}$, $-CONR^{6D}R^{6E}$, $-NHC(O)R^{6D}$, $-NO_2$, $-SR^{6D}$, $-SO_{n6}R^{6D}$, $-NHNR^{6D}R^{6E}$, $-ONR^{6D}R^{6E}$, $-NHC(O)NHNR^{6D}R^{6E}$, $-C(NCN)R^{6D}$, $-C(NH)R^{6D}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. The symbol n6 is 2, 3, or 4. $X^{6C}$ is independently a halogen.

$R^{6C}$ is halogen, oxo, $-N_3$, $-CX^{6C}_3$, $-CHX^{6C}_2$, $-CH_2X^{6C}$, $-CN$, $-COR^{6D}$, $-OR^{6D}$, $-NR^{6D}R^{6E}$, $-COOR^{6D}$, $-CONR^{6D}R^{6E}$, $-NHC(O)R^{6D}$, $-NO_2$, $-SR^{6D}$, $-SO_{n6}R^{6D}$, $-NHNR^{6D}R^{6E}$, $-ONR^{6D}R^{6E}$, $-NHC(O)NHNR^{6D}R^{6E}$, $-C(NCN)R^{6D}$, $-C(NH)R^{6D}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^{6C}$ is hydrogen, halogen, oxo, $-N_3$, $-CX^{6C}_3$, $-CHX^{6C}_2$, $-CH_2X^{6C}$, $-CN$, $-COR^{6D}$, $-OR^{6D}$, $-NR^{6D}R^{6E}$, $-COOR^{6D}$, $-CONR^{6D}R^{6E}$, $-NHC(O)R^{6D}$, $-NO_2$, $-SR^{6D}$, $-SO_{n6}R^{6D}$, $-NHNR^{6D}R^{6E}$, $-ONR^{6D}R^{6E}$, $-NHC(O)NHNR^{6D}R^{6E}$, $-C(NCN)R^{6D}$, $-C(NH)R^{6D}$, $R^{6F}$-substituted or unsubstituted alkyl, $R^{6F}$-substituted or unsubstituted heteroalkyl, $R^{6F}$-substituted or unsubstituted cycloalkyl, $R^{6F}$-substituted or unsubstituted heterocycloalkyl, $R^{6F}$-substituted or unsubstituted aryl, or $R^{6F}$-substituted or unsubstituted heteroaryl. The symbol n6 is 2, 3, or 4. $X^{6C}$ is independently a halogen.

$R^{6C}$ is halogen, oxo, $-N_3$, $-CX^{6C}_3$, $-CHX^{6C}_2$, $-CH_2X^{6C}$, $-CN$, $-COR^{6D}$, $-OR^{6D}$, $-NR^{6D}R^{6E}$, $-COOR^{6D}$, $-CONR^{6D}R^{6E}$, $-NHC(O)R^{6D}$, $-NO_2$, $-SR^{6D}$, $-SO_{n6}R^{6D}$, $-NHNR^{6D}R^{6E}$, $-ONR^{6D}R^{6E}$, $-NHC(O)NHNR^{6D}R^{6E}$, $-C(NCN)R^{6D}$, $-C(NH)R^{6D}$, $R^{6F}$-substituted or unsubstituted alkyl, $R^{6F}$-substituted or unsubstituted heteroalkyl, $R^{6F}$-substituted or unsubstituted cycloalkyl, $R^{6F}$-substituted or unsubstituted heterocycloalkyl, $R^{6F}$-substituted or unsubstituted aryl, or $R^{6F}$ substituted or unsubstituted heteroaryl.

$R^{6C}$ may be hydrogen, halogen, oxo, $-N_3$, $-CX^{6C}_3$, $-CHX^{6C}_2$, $-CH_2X^{6C}$, $-CN$, $-CHO$, $-OH$, $-NH_2$, $-COOH$, $-CONH_2$, $-NO_2$, $-SH$, $-SO_2$, $-SO_2Cl$, $-SO_2CH_3$, $-SO_3H$, $-SO_4H$, $-SO_2NH_2$, $-NHNH_2$, $-ONH_2$, $-NHC(O)NHNH_2$, unsubstituted alkyl (e.g. $C_1$-$C_8$ alkyl, $C_1$-$C_6$ alkyl, or $C_1$-$C_4$ alkyl), unsubstituted heteroalkyl (e.g. 2 to 8 membered heteroalkyl, 2 to 6 membered heteroalkyl, or 2 to 4 membered heteroalkyl), unsubstituted cycloalkyl (e.g. $C_3$-$C_8$ cycloalkyl, $C_4$-$C_8$ cycloalkyl, or $C_5$-$C_6$ cycloalkyl), unsubstituted heterocycloalkyl (e.g. 3 to 8 membered heterocycloalkyl, 4 to 8 membered heterocycloalkyl, or 5 to 6 membered heterocycloalkyl), unsubstituted aryl (e.g. $C_6$-$C_{10}$ aryl or $C_6$ aryl), or unsubstituted heteroaryl (e.g. 5 to 10 membered heteroaryl, 5 to 9 membered heteroaryl, or 5 to 6 membered heteroaryl).

$R^{6C}$ may be halogen, oxo, $-N_3$, $-CX^{6C}_3$, $-CHX^{6C}_2$, $-CH_2C^{6C}$, $-CN$, $-CHO$, $-OH$, $-NH_2$, $-COOH$, $-CONH_2$, $-NO_2$, $-SH$, $-SO_2$, $-SO_2Cl$, $-SO_2CH_3$, $-SO_3H$, $-SO_4H$, $-SO_2NH_2$, $-NHNH_2$, $-ONH_2$, $-NHC(O)NHNH_2$, unsubstituted alkyl (e.g. $C_1$-$C_8$ alkyl, $C_1$-$C_6$ alkyl, or $C_1$-$C_4$ alkyl), unsubstituted heteroalkyl (e.g. 2 to 8 membered heteroalkyl, 2 to 6 membered heteroalkyl, or 2 to 4 membered heteroalkyl), unsubstituted cycloalkyl (e.g. $C_3$-$C_8$ cycloalkyl, $C_4$-$C_8$ cycloalkyl, or $C_5$-$C_6$ cycloalkyl), unsubstituted heterocycloalkyl (e.g. 3 to 8 membered heterocycloalkyl, 4 to 8 membered heterocycloalkyl, or 5 to 6 membered heterocycloalkyl), unsubstituted aryl (e.g. $C_6$-$C_{10}$ aryl or $C_6$ aryl), or unsubstituted heteroaryl (e.g. 5 to 10 membered heteroaryl, 5 to 9 membered heteroaryl, or 5 to 6 membered heteroaryl).

$R^{6F}$ may be unsubstituted alkyl (e.g. $C_1$-$C_8$ alkyl, $C_1$-$C_6$ alkyl, or $C_1$-$C_4$ alkyl), unsubstituted heteroalkyl (e.g. 2 to 8 membered heteroalkyl, 2 to 6 membered heteroalkyl, or 2 to 4 membered heteroalkyl), unsubstituted cycloalkyl (e.g. $C_3$-$C_8$ cycloalkyl, $C_4$-$C_8$ cycloalkyl, or $C_5$-$C_6$ cycloalkyl), unsubstituted heterocycloalkyl (e.g. 3 to 8 membered heterocycloalkyl, 4 to 8 membered heterocycloalkyl, or 5 to 6 membered heterocycloalkyl), unsubstituted aryl (e.g. $C_6$-$C_{10}$ aryl or $C_6$ aryl), or unsubstituted heteroaryl (e.g. 5 to 10 membered heteroaryl, 5 to 9 membered heteroaryl, or 5 to 6 membered heteroaryl), or a detectable moiety.

$R^{6F}$ may be unsubstituted alkyl (e.g. $C_1$-$C_8$ alkyl, $C_1$-$C_6$ alkyl, or $C_1$-$C_4$ alkyl), unsubstituted heteroalkyl (e.g. 2 to 8 membered heteroalkyl, 2 to 6 membered heteroalkyl, or 2 to 4 membered heteroalkyl), unsubstituted cycloalkyl (e.g. $C_3$-$C_8$ cycloalkyl, $C_4$-$C_8$ cycloalkyl, or $C_5$-$C_6$ cycloalkyl), unsubstituted heterocycloalkyl (e.g. 3 to 8 membered heterocycloalkyl, 4 to 8 membered heterocycloalkyl, or 5 to 6 membered heterocycloalkyl), unsubstituted aryl (e.g. $C_6$-$C_{10}$ aryl or $C_6$ aryl), or unsubstituted heteroaryl (e.g. 5 to 10 membered heteroaryl, 5 to 9 membered heteroaryl, or 5 to 6 membered heteroaryl). $X^{6F}$ is independently a halogen.

$R^{6F}$ may be hydrogen, halogen, oxo, $-N_3$, $-CX^{6F}_3$, $-CHX^{6F}_2$, $-CH_2X^{6F}$, $-CN$, $-CHO$, $-OH$, $-NH_2$, $-COOH$, $-CONH_2$, $-NO_2$, $-SH$, $-SO_2$, $-SO_2Cl$, $-SO_2CH_3$, $-SO_3H$, $-SO_4H$, $-SO_2NH_2$, $-NHNH_2$, $-ONH_2$, $-NHC(O)NHNH_2$, $R^{6G}$-substituted or unsubstituted alkyl, $R^{6G}$-substituted or unsubstituted heteroalkyl, $R^{6G}$-substituted or unsubstituted cycloalkyl, $R^{6G}$-substituted or unsubstituted heterocycloalkyl, $R^{6G}$-substituted or unsubstituted aryl, $R^{6G}$-substituted or unsubstituted heteroaryl, or a detectable moiety.

$R^{6F}$ may be hydrogen, halogen, oxo, $-N_3$, $-CX^{6F}_3$, $-CHX^{6F}_2$, $-CH_2X^{6F}$, $-CN$, $-CHO$, $-OH$, $-NH_2$, $-COOH$, $-CONH_2$, $-NO_2$, $-SH$, $-SO_2$, $-SO_2Cl$, $-SO_2CH_3$, $-SO_3H$, $-SO_4H$, $-SO_2NH_2$, $-NHNH_2$, $-ONH_2$, $-NHC(O)NHNH_2$, $R^{6G}$-substituted or unsubstituted alkyl, $R^{6G}$-substituted or unsubstituted heteroalkyl, $R^{6G}$-substituted or unsubstituted cycloalkyl, $R^{6G}$-substituted or unsubstituted heterocycloalkyl, $R^{6G}$-substituted or unsubstituted aryl, $R^{6G}$-substituted or unsubstituted heteroaryl.

$R^{6F}$ may be halogen, oxo, $-N_3$, $-CX^{6F}_3$, $-CHX^{6F}_2$, $-CH_2X^{6F}$, $-CN$, $-CHO$, $-OH$, $-NH_2$, $-COOH$, $-CONH_2$, $-NO_2$, $-SH$, $-SO_2$, $-SO_2Cl$, $-SO_2CH_3$, $-SO_3H$, $-SO_4H$, $-SO_2NH_2$, $-NHNH_2$, $-ONH_2$, $-NHC(O)NHNH_2$, $R^{6G}$-substituted or unsubstituted alkyl, $R^{6G}$-substituted or unsubstituted heteroalkyl, $R^{6G}$-substituted or unsubstituted cycloalkyl, $R^{6G}$-substituted or unsubstituted heterocycloalkyl, $R^{6G}$-substituted or unsubstituted aryl, $R^{6G}$-substituted or unsubstituted heteroaryl, or a detectable moiety.

$R^{6F}$ may be halogen, oxo, $-N_3$, $-CX^{6F}_3$, $-CHX^{6F}_2$, $-CH_2X^{6F}$, $-CN$, $-CHO$, $-OH$, $-NH_2$, $-COOH$, $-CONH_2$, $-NO_2$, $-SH$, $-SO_2$, $-SO_2Cl$, $-SO_2CH_3$, $-SO_3H$, $-SO_4H$, $-SO_2NH_2$, $-NHNH_2$, $-ONH_2$, $-NHC(O)NHNH_2$, $R^{6G}$-substituted or unsubstituted alkyl, $R^{6G}$-substituted or unsubstituted heteroalkyl, $R^{6G}$-substituted or unsubstituted cycloalkyl, $R^{6G}$-substituted or unsubstituted heterocycloalkyl, $R^{6G}$-substituted or unsubstituted aryl, or $R^{6G}$-substituted or unsubstituted heteroaryl.

$R^{6B}$, $R^{6D}$, $R^{6E}$, and $R^{6G}$ are independently hydrogen, halogen, oxo, —$N_3$, —$CF_3$, —$CCl_3$, —$CBr_3$, —$CI_3$, —CN, —CHO, —OH, —$NH_2$, —COOH, —$CONH_2$, —$NO_2$, —SH, —$SO_2$, —$SO_2Cl$, —$SO_2CH_3$—$SO_3H$, —$SO_4H$, —$SO_2NH_2$, —$NHNH_2$, —$ONH_2$, —NHC(O)$NHNH_2$, unsubstituted alkyl (e.g. $C_1$-$C_8$ alkyl, $C_1$-$C_6$ alkyl, or $C_1$-$C_4$ alkyl), unsubstituted heteroalkyl (e.g. 2 to 8 membered heteroalkyl, 2 to 6 membered heteroalkyl, or 2 to 4 membered heteroalkyl), unsubstituted cycloalkyl (e.g. $C_3$-$C_8$ cycloalkyl, $C_4$-$C_8$ cycloalkyl, or $C_5$-$C_6$ cycloalkyl), unsubstituted heterocycloalkyl (e.g. 3 to 8 membered heterocycloalkyl, 4 to 8 membered heterocycloalkyl, or 5 to 6 membered heterocycloalkyl), unsubstituted aryl (e.g. $C_6$-$C_{10}$ aryl or $C_6$ aryl), or unsubstituted heteroaryl (e.g. 5 to 10 membered heteroaryl, 5 to 9 membered heteroaryl, or 5 to 6 membered heteroaryl), or a detectable moiety.

$R^{6B}$, $R^{6D}$, $R^{6E}$, and $R^{6G}$ may independently be hydrogen, halogen, oxo, —$N_3$, —$CF_3$, —$CCl_3$, —$CBr_3$, —$CI_3$, —CN, —CHO, —OH, —$NH_2$, —COOH, —$CONH_2$, —$NO_2$, —SH, —$SO_2$, —$SO_2Cl$, —$SO_2CH_3$—$SO_3H$, —$SO_4H$, —$SO_2NH_2$, —$NHNH_2$, —$ONH_2$, —NHC(O)$NHNH_2$, unsubstituted alkyl (e.g. $C_1$-$C_8$ alkyl, $C_1$-$C_6$ alkyl, or $C_1$-$C_4$ alkyl), unsubstituted heteroalkyl (e.g. 2 to 8 membered heteroalkyl, 2 to 6 membered heteroalkyl, or 2 to 4 membered heteroalkyl), unsubstituted cycloalkyl (e.g. $C_3$-$C_8$ cycloalkyl, $C_4$-$C_8$ cycloalkyl, or $C_5$-$C_6$ cycloalkyl), unsubstituted heterocycloalkyl (e.g. 3 to 8 membered heterocycloalkyl, 4 to 8 membered heterocycloalkyl, or 5 to 6 membered heterocycloalkyl), unsubstituted aryl (e.g. $C_6$-$C_{10}$ aryl or $C_6$ aryl), or unsubstituted heteroaryl (e.g. 5 to 10 membered heteroaryl, 5 to 9 membered heteroaryl, or 5 to 6 membered heteroaryl).

$R^{6B}$, $R^{6D}$, $R^{6E}$, and $R^{6G}$ may independently be halogen, oxo, —$N_3$, —$CF_3$, —$CCl_3$, —$CBr_3$, —$CI_3$, —CN, —CHO, —OH, —$NH_2$, —COOH, —$CONH_2$, —$NO_2$, —SH, —$SO_2$, —$SO_2Cl$, —$SO_2CH_3$—$SO_3H$, —$SO_4H$, —$SO_2NH_2$, —$NHNH_2$, —$ONH_2$, —NHC(O)$NHNH_2$, unsubstituted alkyl (e.g. $C_1$-$C_8$ alkyl, $C_1$-$C_6$ alkyl, or $C_1$-$C_4$ alkyl), unsubstituted heteroalkyl (e.g. 2 to 8 membered heteroalkyl, 2 to 6 membered heteroalkyl, or 2 to 4 membered heteroalkyl), unsubstituted cycloalkyl (e.g. $C_3$-$C_8$ cycloalkyl, $C_4$-$C_8$ cycloalkyl, or $C_5$-$C_6$ cycloalkyl), unsubstituted heterocycloalkyl (e.g. 3 to 8 membered heterocycloalkyl, 4 to 8 membered heterocycloalkyl, or 5 to 6 membered heterocycloalkyl), unsubstituted aryl (e.g. $C_6$-$C_{10}$ aryl or $C_6$ aryl), or unsubstituted heteroaryl (e.g. 5 to 10 membered heteroaryl, 5 to 9 membered heteroaryl, or 5 to 6 membered heteroaryl), or a detectable moiety.

$R^{6B}$, $R^{6D}$, $R^{6E}$, and $R^{6G}$ may independently be halogen, oxo, —$N_3$, —$CF_3$, —$CCl_3$, —$CBr_3$, —$CI_3$, —CN, —CHO, —OH, —$NH_2$, —COOH, —$CONH_2$, —$NO_2$, —SH, —$SO_2$, —$SO_2Cl$, —$SO_2CH_3$—$SO_3H$, —$SO_4H$, —$SO_2NH_2$, —$NHNH_2$, —$ONH_2$, —NHC(O)$NHNH_2$, unsubstituted alkyl (e.g. $C_1$-$C_8$ alkyl, $C_1$-$C_6$ alkyl, or $C_1$-$C_4$ alkyl), unsubstituted heteroalkyl (e.g. 2 to 8 membered heteroalkyl, 2 to 6 membered heteroalkyl, or 2 to 4 membered heteroalkyl), unsubstituted cycloalkyl (e.g. $C_3$-$C_8$ cycloalkyl, $C_4$-$C_8$ cycloalkyl, or $C_5$-$C_6$ cycloalkyl), unsubstituted heterocycloalkyl (e.g. 3 to 8 membered heterocycloalkyl, 4 to 8 membered heterocycloalkyl, or 5 to 6 membered heterocycloalkyl), unsubstituted aryl (e.g. $C_6$-$C_{10}$ aryl or $C_6$ aryl), or unsubstituted heteroaryl (e.g. 5 to 10 membered heteroaryl, 5 to 9 membered heteroaryl, or 5 to 6 membered heteroaryl).

$R^1$ may independently be hydrogen, halogen, —$N_3$, —$CX_3$, —$CHX_2$, —$CH_2X$, —CN, —CHO, —OH, —$NH_2$, —COOH, —$CONH_2$, —$NO_2$, —SH, —$SO_2$, —$SO_2CH_3$—$SO_3H$, —$OSO_3H$, —$SO_2NH_2$, —$SO_2Ph$, —$NHNH_2$, —$ONH_2$, —NHC(O)$NHNH_2$, —$OPO_3H$, —$PO_3H_2$, substituted or unsubstituted alkyl (e.g. $C_1$-$C_8$ alkyl, $C_1$-$C_6$ alkyl, or $C_1$-$C_4$ alkyl), substituted or unsubstituted heteroalkyl (e.g. 2 to 8 membered heteroalkyl, 2 to 6 membered heteroalkyl, or 2 to 4 membered heteroalkyl), substituted or unsubstituted cycloalkyl (e.g. $C_3$-$C_8$ cycloalkyl, $C_4$-$C_8$ cycloalkyl, or $C_5$-$C_6$ cycloalkyl), substituted or unsubstituted heterocycloalkyl (e.g. 3 to 8 membered heterocycloalkyl, 4 to 8 membered heterocycloalkyl, or 5 to 6 membered heterocycloalkyl), substituted or unsubstituted aryl (e.g. $C_6$-$C_{10}$ aryl or $C_6$ aryl), substituted or unsubstituted heteroaryl (e.g. 5 to 10 membered heteroaryl, 5 to 9 membered heteroaryl, or 5 to 6 membered heteroaryl), or a detectable moiety. $R^1$ may independently be hydrogen, halogen, —$N_3$, —$CX_3$, —$CHX_2$, —$CH_2X$, —CN, —CHO, —OH, —$NH_2$, —COOH, —$CONH_2$, —$NO_2$, —SH, —$SO_2$, —$SO_2CH_3$—$SO_3H$, —$OSO_3H$, —$SO_2NH_2$, —$SO_2Ph$, —$NHNH_2$, —$ONH_2$, —NHC(O)$NHNH_2$, —$OPO_3H$, —$PO_3H_2$, substituted or unsubstituted alkyl (e.g. $C_1$-$C_8$ alkyl, $C_1$-$C_6$ alkyl, or $C_1$-$C_4$ alkyl), substituted or unsubstituted heteroalkyl (e.g. 2 to 8 membered heteroalkyl, 2 to 6 membered heteroalkyl, or 2 to 4 membered heteroalkyl), substituted or unsubstituted cycloalkyl (e.g. $C_3$-$C_8$ cycloalkyl, $C_4$-$C_8$ cycloalkyl, or $C_5$-$C_6$ cycloalkyl), substituted or unsubstituted heterocycloalkyl (e.g. 3 to 8 membered heterocycloalkyl, 4 to 8 membered heterocycloalkyl, or 5 to 6 membered heterocycloalkyl), substituted or unsubstituted aryl (e.g. $C_6$-$C_{10}$ aryl or $C_6$ aryl), substituted or unsubstituted heteroaryl (e.g. 5 to 10 membered heteroaryl, 5 to 9 membered heteroaryl, or 5 to 6 membered heteroaryl), or a detectable moiety.

$R^1$ may independently be halogen, —$N_3$, —$CX_3$, —$CHX_2$, —$CH_2X$, —CN, —CHO, —OH, —$NH_2$, —COOH, —$CONH_2$, —$NO_2$, —SH, —$SO_2$, —$SO_2CH_3$—$SO_3H$, —$OSO_3H$, —$SO_2NH_2$, —$SO_2Ph$, —$NHNH_2$, —$ONH_2$, —NHC(O)$NHNH_2$, —$OPO_3H$, —$PO_3H_2$, —$OCF_3$, —$OCHF_2$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, or a detectable moiety. $R^1$ may independently be halogen, —$N_3$, —$CX_3$, —$CHX_2$, —$CH_2X$, —CN, —CHO, —OH, —$NH_2$, —COOH, —$CONH_2$, —$NO_2$, —SH, —$SO_2CH_3$—$SO_3H$, —$OSO_3H$, —$SO_2NH_2$, —$SO_2Ph$, —$NHNH_2$, —$ONH_2$, —NHC(O)$NHNH_2$, —$OPO_3H$, —$PO_3H_2$, —$OCF_3$, —$OCHF_2$, substituted or unsubstituted alkyl (e.g. $C_1$-$C_8$ alkyl, $C_1$-$C_6$ alkyl, or $C_1$-$C_4$ alkyl), substituted or unsubstituted heteroalkyl (e.g. 2 to 8 membered heteroalkyl, 2 to 6 membered heteroalkyl, or 2 to 4 membered heteroalkyl), substituted or unsubstituted cycloalkyl (e.g. $C_3$-$C_8$ cycloalkyl, $C_4$-$C_8$ cycloalkyl, or $C_5$-$C_6$ cycloalkyl), substituted or unsubstituted heterocycloalkyl (e.g. 3 to 8 membered heterocycloalkyl, 4 to 8 membered heterocycloalkyl, or 5 to 6 membered heterocycloalkyl), substituted or unsubstituted aryl (e.g. $C_6$-$C_{10}$ aryl or $C_6$ aryl), substituted or unsubstituted heteroaryl (e.g. 5 to 10 membered heteroaryl, 5 to 9 membered heteroaryl, or 5 to 6 membered heteroaryl), or a detectable moiety.

$R^1$ may independently be halogen, —$N_3$, —$CX_3$, —$CHX_2$, —$CH_2X$, —CN, —CHO, —OH, —$NH_2$, —COOH, —$CONH_2$, —$NO_2$, —SH, —$SO_2$, —$SO_2CH_3$—$SO_3H$, —$OSO_3H$, —$SO_2NH_2$, —$SO_2Ph$, —$NHNH_2$, —$ONH_2$, —NHC(O)$NHNH_2$, —$OPO_3H$, —$PO_3H_2$, substituted or unsubstituted alkyl (e.g. $C_1$-$C_8$ alkyl, $C_1$-$C_6$ alkyl, or $C_1$-$C_4$ alkyl), substituted or unsubstituted heteroalkyl (e.g. 2 to 8 membered heteroalkyl, 2 to 6 membered heteroalkyl, or 2 to 4 membered heteroalkyl), substituted or unsubstituted cycloalkyl (e.g. $C_3$-$C_8$ cycloalkyl, $C_4$-$C_8$ cycloalkyl, or $C_5$-$C_6$ cycloalkyl), substituted or unsubstituted heterocycloalkyl (e.g. 3 to 8 membered heterocycloalkyl, 4 to 8 membered heterocycloalkyl, or 5 to 6 membered heterocycloalkyl), substituted or unsubstituted aryl (e.g. $C_6$-$C_{10}$ aryl or $C_6$ aryl), substituted or unsubstituted heteroaryl (e.g. 5 to 10 membered heteroaryl, 5 to 9 membered heteroaryl, or 5 to 6 membered heteroaryl). $R^1$ may independently be halogen, —$N_3$, —$CX_3$, —$CHX_2$, —$CH_2X$, —CN, —CHO, —OH, —$NH_2$, —COOH, —$CONH_2$, —$NO_2$, —SH, —$SO_2CH_3$, —$SO_3H$, —$OSO_3H$, —$SO_2NH_2$, —$SO_2Ph$, —$NHNH_2$, —$ONH_2$, —NHC(O)$NHNH_2$, —$OPO_3H$, —$PO_3H_2$, substituted or unsubstituted alkyl (e.g. $C_1$-$C_8$ alkyl, $C_1$-$C_6$ alkyl, or $C_1$-$C_4$ alkyl), substituted or unsubstituted heteroalkyl (e.g. 2 to 8 membered heteroalkyl, 2 to 6 membered heteroalkyl, or 2 to 4 membered heteroalkyl), substituted or unsubstituted cycloalkyl (e.g. $C_3$-$C_8$ cycloalkyl, $C_4$-$C_8$ cycloalkyl, or $C_5$-$C_6$ cycloalkyl), substituted or unsubstituted heterocycloalkyl (e.g. 3 to 8 membered heterocycloalkyl, 4 to 8 membered heterocycloalkyl, or 5 to 6 membered heterocycloalkyl), substituted or unsubstituted aryl (e.g. $C_6$-$C_{10}$ aryl or $C_6$ aryl), substituted or unsubstituted heteroaryl (e.g. 5 to 10 membered heteroaryl, 5 to 9 membered heteroaryl, or 5 to 6 membered heteroaryl). $R^1$ may independently be hydrogen, halogen, —$CX_3$, —$CHX_2$, —$CH_2X$, —CN, —OH, or —$NH_2$. $R^1$ may independently be hydrogen, halogen, oxo, $N_3$, —$CX_3$, —$CHX_2$, —$CH_2X$, —CN, —OH, —$NH_2$, —COOH, —$CONH_2$, —$NO_2$, —SH, —S(O)$_3$H, —S(O)$_4$H, —S(O)$_2NH_2$, —$SO_2Ph$, —$NHNH_2$, —$ONH_2$, —NHC(O)$NHNH_2$, —NHC(O)$NH_2$, —NHS(O)$_2H$, —NHC(O)H, —NHC(O)—OH, —NHOH, —$OCF_3$, or —$OCHF_2$. $R^1$ may independently be halogen, —$CX_3$, —$CHX_2$, —$CH_2X$, —CN, —OH, or —$NH_2$.

$R^1$ may independently be hydrogen, halogen, $N_3$, —$CX_3$, —$CHX_2$, —$CH_2X$, —CN, —OH, —$NH_2$, —COOH, —$CONH_2$, —$NO_2$, —SH, —S(O)$_3$H, —S(O)$_4$H, —S(O)$_2$$NH_2$, —$SO_2Ph$, —$NHNH_2$, —$ONH_2$, —NHC(O)$NHNH_2$, —NHC(O)$NH_2$, —NHS(O)$_2H$, —NHC(O)H, —NHC(O)—OH, —NHOH, —$OCF_3$, or —$OCHF_2$. $R^1$ may independently be halogen, $N_3$, —$CX_3$, —$CHX_2$, —$CH_2X$, —CN, —OH, —$NH_2$, —COOH, —$CONH_2$, —$NO_2$, —SH, —S(O)$_3$H, —S(O)$_4$H, —S(O)$_2NH_2$, —$SO_2Ph$, —$NHNH_2$, —$ONH_2$, —NHC(O)$NHNH_2$, —NHC(O)$NH_2$, —NHS(O)$_2$H, —NHC(O)H, —NHC(O)—OH, —NHOH, —$OCF_3$, —$OCHF_2$. $R^1$ may independently be hydrogen. $R^1$ may independently be —OMe. $R^1$ may independently be —$SCH_3$. X is independently —F, —Cl, —Br, or —I. X may independently be —F. X may independently be —Cl. X may independently be —Br. X may independently be —I.

In embodiments, $R^1$ is unsubstituted 2 to 3 membered heteroalkyl. In embodiments, $R^1$ is unsubstituted aryl. In embodiments, $R^1$ is —$SO_2$-(unsubstituted aryl or unsubstituted heteroaryl). In embodiments, $R^1$ is —$SO_2$-(unsubstituted $C_1$-$C_3$ alkyl). In embodiments, $R^1$ is —Cl. In embodiments, $R^1$ is —F. In embodiments, $R^1$ is —Br. In embodiments, $R^1$ is —$CH_3$. In embodiments, $R^1$ is —$OCH_3$. In embodiments, $R^1$ is —$SCH_3$. In embodiments, $R^1$ is unsubstituted phenyl. In embodiments, $R^1$ is —COOH. In embodiments, $R^1$ is —$SO_2Ph$. In embodiments, $R^1$ is —$SO_2CH_3$.

$R^1$ may be substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^1$ may be $R^7$-substituted or unsubstituted alkyl, $R^7$-substituted or unsubstituted heteroalkyl, $R^7$-substituted or unsubstituted cycloalkyl, $R^7$-substituted or unsubstituted heterocycloalkyl, $R^7$-substituted or unsubstituted aryl, or $R^7$-substituted or unsubstituted heteroaryl.

$R^1$ may independently be substituted or unsubstituted $C_1$-$C_{10}$ alkyl. $R^1$ may independently be substituted $C_1$-$C_{10}$ alkyl. $R^1$ may independently be unsubstituted $C_1$-$C_{10}$ alkyl. $R^1$ may independently be $R^7$-substituted or unsubstituted $C_1$-$C_{10}$ alkyl. $R^1$ may independently be $R^7$-substituted $C_1$-$C_{10}$ alkyl. $R^1$ may independently be substituted or unsubstituted $C_1$-$C_8$ alkyl. $R^1$ may independently be substituted $C_1$-$C_8$ alkyl. $R^1$ may independently be unsubstituted $C_1$-$C_8$ alkyl. $R^1$ may independently be $R^7$-substituted or unsubstituted $C_1$-$C_8$ alkyl. $R^1$ may independently be $R^7$-substituted $C_1$-$C_8$ alkyl. $R^1$ may independently be substituted or unsubstituted $C_1$-$C_5$ alkyl. $R^1$ may independently be substituted $C_1$-$C_5$ alkyl. $R^1$ may independently be unsubstituted $C_1$-$C_5$ alkyl. $R^1$ may independently be $R^7$-substituted or unsubstituted $C_1$-$C_5$ alkyl. $R^1$ may independently be $R^7$-substituted $C_1$-$C_5$ alkyl. $R^1$ may independently be substituted or unsubstituted $C_1$-$C_3$ alkyl. $R^1$ may independently be substituted $C_1$-$C_3$ alkyl. $R^1$ may independently be unsubstituted $C_1$-$C_3$ alkyl. $R^1$ may independently be $R^7$-substituted or unsubstituted $C_1$-$C_3$ alkyl. $R^1$ may independently be $R^7$-substituted $C_1$-$C_3$ alkyl.

$R^1$ may independently be substituted or unsubstituted 2 to 10 membered heteroalkyl. $R^1$ may independently be substituted 2 to 10 membered heteroalkyl. $R^1$ may independently be unsubstituted 2 to 10 membered heteroalkyl. $R^1$ may independently be $R^7$-substituted or unsubstituted 2 to 10 membered heteroalkyl. $R^1$ may independently be $R^7$-substituted 2 to 10 membered heteroalkyl. $R^1$ may independently be substituted or unsubstituted 2 to 8 membered heteroalkyl. $R^1$ may independently be substituted 2 to 8 membered heteroalkyl. $R^1$ may independently be unsubstituted 2 to 8 membered heteroalkyl. $R^1$ may independently be $R^7$-substituted or unsubstituted 2 to 8 membered heteroalkyl. $R^1$ may independently be $R^7$-substituted 2 to 8 membered heteroalkyl. $R^1$ may independently be substituted or unsubstituted 2 to 6 membered heteroalkyl. $R^1$ may independently be substituted 2 to 6 membered heteroalkyl. $R^1$ may independently be unsubstituted 2 to 6 membered heteroalkyl. $R^1$ may independently be $R^7$-substituted or unsubstituted 2 to 6 membered heteroalkyl. $R^1$ may independently be $R^7$-substituted 2 to 6 membered heteroalkyl.

$R^1$ may independently be substituted or unsubstituted $C_3$-$C_8$ cycloalkyl. $R^1$ may independently be unsubstituted $C_3$-$C_8$ cycloalkyl. $R^1$ may independently be substituted $C_3$-$C_8$ cycloalkyl. $R^1$ may independently be $R^7$-substituted or unsubstituted $C_3$-$C_8$ cycloalkyl. $R^1$ may independently be $R^7$-substituted $C_3$-$C_8$ cycloalkyl. $R^1$ may independently be substituted or unsubstituted $C_3$-$C_6$ cycloalkyl. $R^1$ may independently be substituted $C_3$-$C_6$ cycloalkyl. $R^1$ may independently be unsubstituted $C_3$-$C_6$ cycloalkyl. $R^1$ may independently be $R^7$-substituted or unsubstituted $C_3$-$C_6$ cycloalkyl. $R^1$ may independently be $R^7$-substituted $C_3$-$C_6$ cycloalkyl. $R^1$ may independently be substituted or unsubstituted $C_4$-$C_6$ cycloalkyl. $R^1$ may independently be substituted $C_4$-$C_6$ cycloalkyl. $R^1$ may independently be unsubstituted $C_4$-$C_6$ cycloalkyl. $R^1$ may independently be $R^7$-substituted or unsubstituted $C_4$-$C_6$ cycloalkyl. $R^1$ may independently be $R^7$-substituted $C_4$-$C_6$ cycloalkyl. $R^1$ may independently be substituted or unsubstituted $C_4$ cycloalkyl. $R^1$ may independently be substituted $C_4$ cycloalkyl. $R^1$ may independently be unsubstituted $C_4$ cycloalkyl. $R^1$ may independently be $R^7$-substituted or unsubstituted $C_4$ cycloalkyl. $R^1$ may independently be $R^7$-substituted $C_4$ cycloalkyl. $R^1$ may independently be substituted or unsubstituted $C_5$ cycloalkyl. $R^1$ may independently be substituted $C_5$ cycloalkyl. $R^1$ may independently be unsubstituted $C_5$ cycloalkyl. $R^1$ may independently be $R^7$-substituted or unsubstituted $C_5$ cycloalkyl. $R^1$ may independently be $R^7$-substituted $C_5$ cycloalkyl. $R^1$ may independently be substituted or unsubstituted $C_6$ cycloalkyl. $R^1$ may independently be substituted $C_6$ cycloalkyl. $R^1$ may independently be unsubstituted $C_6$ cycloalkyl. $R^1$ may independently be $R^7$-substituted or unsubstituted $C_6$ cycloalkyl. $R^1$ may independently be $R^7$-substituted $C_6$ cycloalkyl.

$R^1$ may independently be substituted or unsubstituted 3 to 8 membered heterocycloalkyl. $R^1$ may independently be unsubstituted 3 to 8 membered heterocycloalkyl. $R^1$ may independently be substituted 3 to 8 membered heterocycloalkyl. $R^1$ may independently be $R^7$-substituted or unsubstituted 3 to 8 membered heterocycloalkyl. $R^1$ may independently be $R^7$-substituted 3 to 8 membered heterocycloalkyl. $R^1$ may independently be substituted or unsubstituted 3 to 6 membered heterocycloalkyl. $R^1$ may independently be substituted 3 to 6 membered heterocycloalkyl. $R^1$ may independently be unsubstituted 3 to 6 membered heterocycloalkyl. $R^1$ may independently be $R^7$-substituted or unsubstituted 3 to 6 membered heterocycloalkyl. $R^1$ may independently be $R^7$-substituted 3 to 6 membered heterocycloalkyl. $R^1$ may independently be substituted or unsubstituted 4 to 6 membered heterocycloalkyl. $R^1$ may independently be substituted 4 to 6 membered heterocycloalkyl. $R^1$ may independently be unsubstituted 4 to 6 membered heterocycloalkyl. $R^1$ may independently be $R^7$-substituted or unsubstituted 4 to 6 membered heterocycloalkyl. $R^1$ may independently be $R^7$-substituted 4 to 6 membered heterocycloalkyl. $R^1$ may independently be substituted or unsubstituted 4 membered heterocycloalkyl. $R^1$ may independently be substituted 4 membered heterocycloalkyl. $R^1$ may independently be unsubstituted 4 membered heterocycloalkyl. $R^1$ may independently be $R^7$-substituted or unsubstituted 4 membered heterocycloalkyl. $R^1$ may independently be $R^7$-substituted 4 membered heterocycloalkyl. $R^1$ may independently be substituted or unsubstituted 5 membered heterocycloalkyl. $R^1$ may independently be substituted 5 membered heterocycloalkyl. $R^1$ may independently be unsubstituted 5 membered heterocycloalkyl. $R^1$ may independently be $R^7$-substituted or unsubstituted 5 membered heterocycloalkyl. $R^1$ may independently be $R^7$-substituted 5 membered heterocycloalkyl. $R^1$ may independently be substituted or unsubstituted 6 membered heterocycloalkyl. $R^1$ may independently be substituted 6 membered heterocycloalkyl. $R^1$ may independently be unsubstituted 6 membered heterocycloalkyl. $R^1$ may independently be $R^7$-substituted or unsubstituted 6 membered heterocycloalkyl. $R^1$ may independently be $R^7$-substituted 6 membered heterocycloalkyl.

$R^1$ may independently be substituted or unsubstituted $C_6$-$C_{10}$ aryl. $R^1$ may independently be substituted $C_6$-$C_{10}$ aryl. $R^1$ may independently be unsubstituted $C_6$-$C_{10}$ aryl. $R^1$ may independently be $R^7$-substituted or unsubstituted $C_6$-$C_{10}$ aryl. $R^1$ may independently be $R^7$-substituted $C_6$-$C_{10}$ aryl. $R^1$ may independently be substituted or unsubstituted $C_{10}$ aryl. $R^1$ may independently be substituted $C_{10}$ aryl. $R^1$ may independently be unsubstituted $C_{10}$ aryl. $R^1$ may independently be $R^7$-substituted or unsubstituted $C_{10}$ aryl. $R^1$ may independently be $R^7$-substituted $C_{10}$ aryl. $R^1$ may independently be substituted or unsubstituted $C_6$ aryl. $R^1$ may independently be substituted $C_6$ aryl. $R^1$ may independently be unsubstituted $C_6$ aryl. $R^1$ may independently be $R^7$-substituted or unsubstituted $C_6$ aryl. $R^1$ may independently be $R^7$-substituted $C_6$ aryl.

$R^1$ may independently be substituted or unsubstituted 5-10 membered heteroaryl. $R^1$ may independently be substituted 5-10 membered heteroaryl. $R^1$ may independently be unsubstituted 5-10 membered heteroaryl. $R^1$ may independently be $R^7$-substituted or unsubstituted 5-10 membered heteroaryl. $R^1$ may independently be $R^7$-substituted 5-10 membered heteroaryl. $R^1$ may independently be substituted or unsubstituted 5-6 membered heteroaryl. $R^1$ may independently be substituted 5-6 membered heteroaryl. $R^1$ may independently be unsubstituted 5-6 membered heteroaryl. $R^1$ may independently be $R^7$-substituted or unsubstituted 5-6 membered heteroaryl. $R^1$ may independently be $R^7$-substituted 5-6 membered heteroaryl. $R^1$ may independently be substituted or unsubstituted 5 membered heteroaryl. $R^1$ may independently be substituted 5 membered heteroaryl. $R^1$ may independently be unsubstituted 5 membered heteroaryl. $R^1$ may independently be $R^7$-substituted or unsubstituted 5 membered heteroaryl. $R^1$ may independently be $R^7$-substituted 5 membered heteroaryl. $R^1$ may independently be substituted or unsubstituted 6 membered heteroaryl. $R^1$ may independently be substituted 6 membered heteroaryl. $R^1$ may independently be unsubstituted 6 membered heteroaryl. $R^1$ may independently be $R^7$-substituted or unsubstituted 6 membered heteroaryl. $R^1$ may independently be $R^7$-substituted 6 membered heteroaryl.

$R^7$ is independently hydrogen, halogen, oxo, —$N_3$, —$CX^7_3$, —$CHX^7_2$, —$CH_2X^7$, —CN, —CHO, —OH, —$NH_2$, —COOH, —$CONH_2$, —$NO_2$, —SH, —$SO_2$, —$SO_2Cl$, —$SO_2CH_3$—$SO_3H$, —$SO_4H$, —$SO_2NH_2$, —$NHNH_2$, —$ONH_2$, —NHC(O)$NHNH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^7$ may independently be halogen, oxo, —$N_3$, —$CX^7_3$, —$CHX^7_2$, —$CH_2X^7$, —CN, —CHO, —OH, —$NH_2$, —COOH, —$CONH_2$, —$NO_2$, —SH, —$SO_2$, —$SO_2Cl$, —$SO_2CH_3$—$SO_3H$, —$SO_4H$, —$SO_2NH_2$, —$NHNH_2$, —$ONH_2$, —NHC(O)$NHNH_2$, substituted or unsubstituted alkyl (e.g. $C_1$-$C_8$ alkyl, $C_1$-$C_6$ alkyl, or $C_1$-$C_4$ alkyl), substituted or unsubstituted heteroalkyl (e.g. 2 to 8 membered heteroalkyl, 2 to 6 membered heteroalkyl, or 2 to 4 membered heteroalkyl), substituted or unsubstituted cycloalkyl (e.g. $C_3$-$C_8$ cycloalkyl, $C_4$-$C_8$ cycloalkyl, or $C_5$-$C_6$ cycloalkyl), substituted or unsubstituted heterocycloalkyl (e.g. 3 to 8 membered heterocycloalkyl, 4 to 8 membered heterocycloalkyl, or 5 to 6 membered heterocycloalkyl), substituted or unsubstituted aryl (e.g. $C_6$-$C_{10}$ aryl or $C_6$ aryl), substituted or unsubstituted heteroaryl (e.g. 5 to 10 membered heteroaryl, 5 to 9 membered heteroaryl, or 5 to 6 membered heteroaryl).

$R^7$ may independently be halogen, oxo, —$N_3$, —$CX^7_3$, —$CHX^7_2$, —$CH_2X^7$, —CN, —CHO, —OH, —$NH_2$, —COOH, —$CONH_2$, —$NO_2$, —SH, —$SO_2$, —$SO_2Cl$, —$SO_2CH_3$—$SO_3H$, —$SO_4H$, —$SO_2NH_2$, —$NHNH_2$, —$ONH_2$, —NHC(O)$NHNH_2$, substituted alkyl, substituted heteroalkyl, substituted or unsubstituted cycloalkyl, substituted or unsubstituted heterocycloalkyl, substituted or unsubstituted aryl, or substituted or unsubstituted heteroaryl.

$R^7$ may independently be halogen, oxo, —$N_3$, —$CX^7_3$, —$CHX^7_2$, —$CH_2X^7$, —CN, —CHO, —OH, —$NH_2$, —COOH, —$CONH_2$, —$NO_2$, —SH, —$SO_2$, —$SO_2Cl$, —$SO_2CH_3$—$SO_3H$, —$SO_4H$, —$SO_2NH_2$, —$NHNH_2$, —$ONH_2$, —NHC(O)$NHNH_2$, unsubstituted alkyl, unsubstituted heteroalkyl, unsubstituted cycloalkyl, unsubstituted heterocycloalkyl, unsubstituted aryl, or unsubstituted heteroaryl.

$R^7$ may independently be halogen, oxo, $-N_3$, $-CX^7{}_3$, $-CHX^7{}_2$, $-CH_2X^7$, $-CN$, $-CHO$, $-OH$, $-NH_2$, $-COOH$, $-CONH_2$, $-NO_2$, $-SH$, $-SO_2$, $-SO_2Cl$, $-SO_2CH_3-SO_3H$, $-SO_4H$, $-SO_2NH_2$, $-NHNH_2$, $-ONH_2$, $-NHC(O)NHNH_2$, unsubstituted alkyl (e.g. $C_1$-$C_8$ alkyl, $C_1$-$C_6$ alkyl, or $C_1$-$C_4$ alkyl), unsubstituted heteroalkyl (e.g. 2 to 8 membered heteroalkyl, 2 to 6 membered heteroalkyl, or 2 to 4 membered heteroalkyl), unsubstituted cycloalkyl (e.g. $C_3$-$C_8$ cycloalkyl, $C_4$-$C_8$ cycloalkyl, or $C_5$-$C_6$ cycloalkyl), unsubstituted heterocycloalkyl (e.g. 3 to 8 membered heterocycloalkyl, 4 to 8 membered heterocycloalkyl, or 5 to 6 membered heterocycloalkyl), unsubstituted aryl (e.g. $C_6$-$C_{10}$ aryl or $C_6$ aryl), or unsubstituted heteroaryl (e.g. 5 to 10 membered heteroaryl, 5 to 9 membered heteroaryl, or 5 to 6 membered heteroaryl). $X^7$ is independently $-F$, $-Cl$, $-Br$, or $-I$. $X^7$ may independently be $-F$. $X^7$ may independently be $-Cl$. $X^7$ may independently be $-Br$. $X^7$ may independently be $-I$.

In embodiments, $R^7$ is hydrogen, halogen, oxo, $-N_3$, $-CX^7{}_3$, $-CHX^7{}_2$, $-CH_2X^7$, $-CN$, $-CHO$, $-OH$, $-NH_2$, $-COOH$, $-CONH_2$, $-NO_2$, $-SH$, $-SO_2$, $-SO_2Cl$, $-SO_2CH_3-SO_3H$, $-SO_4H$, $-SO_2NH_2$, $-NHNH_2$, $-ONH_2$, $-NHC(O)NHNH_2$, $R^{20}$-substituted or unsubstituted alkyl, $R^{20}$-substituted or unsubstituted heteroalkyl, $R^{20}$-substituted or unsubstituted cycloalkyl, $R^{20}$-substituted or unsubstituted heterocycloalkyl, $R^{20}$-substituted or unsubstituted aryl, or $R^{20}$-substituted or unsubstituted heteroaryl.

In embodiments, $R^7$ is $R^{20}$-substituted or unsubstituted alkyl (e.g. $C_1$-$C_8$ alkyl, $C_1$-$C_6$ alkyl, or $C_1$-$C_4$ alkyl), $R^{20}$-substituted or unsubstituted heteroalkyl (e.g. 2 to 8 membered heteroalkyl, 2 to 6 membered heteroalkyl, or 2 to 4 membered heteroalkyl), $R^{20}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{20}$-substituted or unsubstituted heterocycloalkyl (e.g. 3 to 8 membered heterocycloalkyl, 4 to 8 membered heterocycloalkyl, or 5 to 6 membered heterocycloalkyl), $R^{20}$-substituted or unsubstituted aryl (e.g. $C_6$-$C_{10}$ aryl or $C_6$ aryl), $R^{20}$-substituted or unsubstituted heteroaryl (e.g. 5 to 10 membered heteroaryl, 5 to 9 membered heteroaryl, or 5 to 6 membered heteroaryl).

$R^{20}$ is halogen, oxo, $-N_3$, $-CX^{20}{}_3$, $-CHX^{20}{}_2$, $-CH_2X^{20}$, $-CN$, $-CHO$, $-OH$, $-NH_2$, $-COOH$, $-CONH_2$, $-NO_2$, $-SH$, $-SO_2$, $-SO_2Cl$, $-SO_2CH_3-SO_3H$, $-SO_4H$, $-SO_2NH_2$, $-NHNH_2$, $-ONH_2$, $-NHC(O)NHNH_2$, $R^{21}$-substituted or unsubstituted alkyl, $R^{21}$-substituted or unsubstituted heteroalkyl, $R^{21}$-substituted or unsubstituted cycloalkyl, $R^{21}$-substituted or unsubstituted heterocycloalkyl, $R^{21}$-substituted or unsubstituted aryl, or $R^{21}$-substituted or unsubstituted heteroaryl.

In embodiments, $R^{20}$ is $R^{21}$-substituted or unsubstituted alkyl (e.g. $C_1$-$C_8$ alkyl, $C_1$-$C_6$ alkyl, or $C_1$-$C_4$ alkyl), $R^{21}$-substituted or unsubstituted heteroalkyl (e.g. 2 to 8 membered heteroalkyl, 2 to 6 membered heteroalkyl, or 2 to 4 membered heteroalkyl), $R^{21}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{21}$-substituted or unsubstituted heterocycloalkyl (e.g. 3 to 8 membered heterocycloalkyl, 4 to 8 membered heterocycloalkyl, or 5 to 6 membered heterocycloalkyl), $R^{21}$-substituted or unsubstituted aryl (e.g. $C_6$-$C_{10}$ aryl or $C_6$ aryl), $R^{21}$-substituted or unsubstituted heteroaryl (e.g. 5 to 10 membered heteroaryl, 5 to 9 membered heteroaryl, or 5 to 6 membered heteroaryl) $X^{20}$ is independently $-F$, $-Cl$, $-Br$, or $-I$. $X^{20}$ may independently be $-F$. $X^{20}$ may independently be $-Cl$. $X^{20}$ may independently be $-Br$. $X^{20}$ may independently be $-I$.

$R^{21}$ is halogen, oxo, $-N_3$, $-CX^{21}{}_3$, $-CHX^{21}{}_2$, $-CH_2X^{21}$, $-CN$, $-CHO$, $-OH$, $-NH_2$, $-COOH$, $-CONH_2$, $-NO_2$, $-SH$, $-SO_2$, $-SO_2Cl$, $-SO_2CH_3-SO_3H$, $-SO_4H$, $-SO_2NH_2$, $-NHNH_2$, $-ONH_2$, $-NHC(O)NHNH_2$, $R^{22}$-substituted or unsubstituted alkyl, $R^{22}$-substituted or unsubstituted heteroalkyl, $R^{22}$-substituted or unsubstituted cycloalkyl, $R^{22}$-substituted or unsubstituted heterocycloalkyl, $R^{22}$-substituted or unsubstituted aryl, or $R^{22}$-substituted or unsubstituted heteroaryl.

In embodiments, $R^{21}$ is $R^{22}$-substituted or unsubstituted alkyl (e.g. $C_1$-$C_8$ alkyl, $C_1$-$C_6$ alkyl, or $C_1$-$C_4$ alkyl), $R^{22}$-substituted or unsubstituted heteroalkyl (e.g. 2 to 8 membered heteroalkyl, 2 to 6 membered heteroalkyl, or 2 to 4 membered heteroalkyl), $R^{22}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{22}$-substituted or unsubstituted heterocycloalkyl (e.g. 3 to 8 membered heterocycloalkyl, 4 to 8 membered heterocycloalkyl, or 5 to 6 membered heterocycloalkyl), $R^{22}$-substituted or unsubstituted aryl (e.g. $C_6$-$C_{10}$ aryl or $C_6$ aryl), $R^{22}$-substituted or unsubstituted heteroaryl (e.g. 5 to 10 membered heteroaryl, 5 to 9 membered heteroaryl, or 5 to 6 membered heteroaryl). $X^{21}$ is independently $-F$, $-Cl$, $-Br$, or $-I$. $X^{21}$ may independently be $-F$. $X^{21}$ may independently be $-Cl$. $X^{21}$ may independently be $-Br$. $X^{21}$ may independently be $-I$.

$R^{22}$ is halogen, oxo, $-N_3$, $-CX^{22}{}_3$, $-CHX^{22}{}_2$, $-CH_2X^{22}$, $-CN$, $-CHO$, $-OH$, $-NH_2$, $-COOH$, $-CONH_2$, $-NO_2$, $-SH$, $-SO_2$, $-SO_2Cl$, $-SO_2CH_3-SO_3H$, $-SO_4H$, $-SO_2NH_2$, $-NHNH_2$, $-ONH_2$, $-NHC(O)NHNH_2$, unsubstituted alkyl, unsubstituted heteroalkyl, unsubstituted cycloalkyl, unsubstituted heterocycloalkyl, unsubstituted aryl, or unsubstituted heteroaryl. In embodiments, $R^{22}$ is unsubstituted alkyl (e.g. $C_1$-$C_8$ alkyl, $C_1$-$C_6$ alkyl, or $C_1$-$C_4$ alkyl), unsubstituted heteroalkyl (e.g. 2 to 8 membered heteroalkyl, 2 to 6 membered heteroalkyl, or 2 to 4 membered heteroalkyl), unsubstituted cycloalkyl (e.g. $C_3$-$C_8$ cycloalkyl, $C_4$-$C_8$ cycloalkyl, or $C_5$-$C_6$ cycloalkyl), unsubstituted heterocycloalkyl (e.g. 3 to 8 membered heterocycloalkyl, 4 to 8 membered heterocycloalkyl, or 5 to 6 membered heterocycloalkyl), unsubstituted aryl (e.g. $C_6$-$C_{10}$ aryl or $C_6$ aryl), or unsubstituted heteroaryl (e.g. 5 to 10 membered heteroaryl, 5 to 9 membered heteroaryl, or 5 to 6 membered heteroaryl). $X^{22}$ is independently $-F$, $-Cl$, $-Br$, or $-I$. $X^{22}$ may independently be $-F$. $X^{22}$ may independently be $-Cl$. $X^{22}$ may independently be $-Br$. $X^{22}$ may independently be $-I$.

Each $R^{1A}$ may be any value of $R^1$, including $R^7$-substituted substituents, wherein $R^{1A}$ may be an $R^{7A}$-substituted substituent and $R^{7A}$ may have any value of $R^7$. The variables $R^{20A}$, $R^{21A}$, $R^{22A}$, $X^{20A}$, $X^{21A}$, and $X^{22A}$ may independently have any value of $R^{20}$, $R^{21}$, $R^{22}$, $X^{20}$, $X^{21}$, and $X^{22A}$, respectively. The variables upon which $R^{1B}$, $R^{1C}$, $R^{1D}$, and $R^{1E}$ depend may likewise by distinguished from each other and are independent of each other.

In embodiments, $R^1$ may independently be hydrogen, substituted or unsubstituted $C_1$-$C_5$ alkyl, or a detectable moiety. In embodiments, $R^1$ may independently be substituted or unsubstituted $C_1$-$C_5$ alkyl. $R^1$ may independently be a detectable moiety.

Two $R^1$ substituents attached to adjacent ring atoms (e.g., carbons) may optionally be joined to form a substituted or unsubstituted aryl or substituted or unsubstituted heteroaryl when z1 is an integer from 2 to 5. z1 may be 2. z1 may be 3. z1 may be 4. z1 may be 5. The two $R^1$ substituents attached to adjacent ring atoms (e.g., carbons) may optionally be joined to form a substituted or unsubstituted aryl. The two $R^1$ substituents attached to adjacent ring atoms (e.g., carbons) may optionally be joined to form a substituted aryl. The two $R^1$ substituents attached to adjacent ring atoms (e.g., carbons) may optionally be joined to form a unsubstituted aryl. The two $R^1$ substituents attached to adjacent ring atoms (e.g., carbons) may optionally be joined to form a $R^7$-substituted or unsubstituted aryl. The two $R^1$ substituents attached to adjacent ring atoms (e.g., carbons) may optionally be joined to form a $R^7$-substituted aryl.

The two $R^1$ substituents attached to adjacent ring atoms (e.g., carbons) may optionally be joined to form a substituted or unsubstituted $C_3$-$C_8$ cycloalkyl. The two $R^1$ substituents attached to adjacent ring atoms (e.g., carbons) may optionally be joined to form a substituted $C_3$-$C_8$ cycloalkyl. The two $R^1$ substituents attached to adjacent ring atoms (e.g., carbons) may optionally be joined to form a unsubstituted $C_3$-$C_8$ cycloalkyl. The two $R^1$ substituents attached to adjacent ring atoms (e.g., carbons) may optionally be joined to form a $R^7$-substituted or unsubstituted $C_3$-$C_8$ cycloalkyl. The two $R^1$ substituents attached to adjacent ring atoms (e.g., carbons) may optionally be joined to form a $R^7$-substituted $C_3$-$C_8$ cycloalkyl. The two $R^1$ substituents attached to adjacent ring atoms (e.g., carbons) may optionally be joined to form a substituted or unsubstituted $C_5$-$C_6$ cycloalkyl. The two $R^1$ substituents attached to adjacent ring atoms (e.g., carbons) may optionally be joined to form a substituted $C_5$-$C_6$ cycloalkyl. The two $R^1$ substituents attached to adjacent ring atoms (e.g., carbons) may optionally be joined to form a unsubstituted $C_5$-$C_6$ cycloalkyl. The two $R^1$ substituents attached to adjacent ring atoms (e.g., carbons) may optionally be joined to form a $R^7$-substituted or unsubstituted $C_5$-$C_6$ cycloalkyl. The two $R^1$ substituents attached to adjacent ring atoms (e.g., carbons) may optionally be joined to form a $R^7$-substituted $C_5$-$C_6$ cycloalkyl. The two $R^1$ substituents attached to adjacent ring atoms (e.g., carbons) may optionally be joined to form a substituted or unsubstituted $C_6$ cycloalkyl. The two $R^1$ substituents attached to adjacent ring atoms (e.g., carbons) may optionally be joined to form a substituted $C_6$ cycloalkyl. The two $R^1$ substituents attached to adjacent ring atoms (e.g., carbons) may optionally be joined to form a unsubstituted $C_6$ cycloalkyl. The two $R^1$ substituents attached to adjacent ring atoms (e.g., carbons) may optionally be joined to form a $R^7$-substituted or unsubstituted $C_6$ cycloalkyl. The two $R^1$ substituents attached to adjacent ring atoms (e.g., carbons) may optionally be joined to form a $R^7$-substituted $C_6$ cycloalkyl. Thus, in embodiments, the two $R^1$ substituents attached to adjacent ring atoms (e.g., carbons) are optionally joined to form a 5,5-, 5,6-, 6,5-, or 6,6-fused cycloalkyl.

The two $R^1$ substituents attached to adjacent ring carbons may optionally be joined to form a substituted or unsubstituted $C_6$-$C_{10}$ aryl. The two $R^1$ substituents attached to adjacent ring carbons may optionally be joined to form a substituted $C_6$-$C_{10}$ aryl. The two $R^1$ substituents attached to adjacent ring carbons may optionally be joined to form a unsubstituted $C_6$-$C_{10}$ aryl. The two $R^1$ substituents attached to adjacent ring carbons may optionally be joined to form a $R^7$-substituted or unsubstituted $C_6$-$C_{10}$ aryl. The two $R^1$ substituents attached to adjacent ring carbons may optionally be joined to form a $R^7$-substituted $C_6$-$C_{10}$ aryl. The two $R^1$ substituents attached to adjacent ring carbons may optionally be joined to form a substituted or unsubstituted $C_{10}$ aryl. The two $R^1$ substituents attached to adjacent ring carbons may optionally be joined to form a substituted $C_{10}$ aryl. The two $R^1$ substituents attached to adjacent ring carbons may optionally be joined to form a unsubstituted $C_{10}$ aryl. The two $R^1$ substituents attached to adjacent ring carbons may optionally be joined to form a $R^7$-substituted or unsubstituted $C_{10}$ aryl. The two $R^1$ substituents attached to adjacent ring carbons may optionally be joined to form a $R^7$-substituted $C_{10}$ aryl. The two $R^1$ substituents attached to adjacent ring carbons may optionally be joined to form a substituted or unsubstituted $C_6$ aryl (e.g. forming a napthyl). The two $R^1$ substituents attached to adjacent ring carbons may optionally be joined to form a substituted $C_6$ aryl (e.g. forming a napthyl). The two $R^1$ substituents attached to adjacent ring carbons may optionally be joined to form a unsubstituted $C_6$ aryl (e.g. forming a napthyl). The two $R^1$ substituents attached to adjacent ring carbons may optionally be joined to form a $R^7$-substituted or unsubstituted $C_6$ aryl (e.g. forming a napthyl). The two $R^1$ substituents attached to adjacent ring carbons may optionally be joined to form a $R^7$-substituted $C_6$ aryl (e.g. forming a napthyl). Thus, in embodiments, the two $R^1$ substituents attached to adjacent ring carbons may optionally joined to form a 6,6,6- or 6,6-fused aryl.

The two $R^1$ substituents attached to adjacent ring atoms (e.g., carbons) may optionally be joined to form a substituted or unsubstituted heteroaryl. The two $R^1$ substituents attached to adjacent ring atoms (e.g., carbons) may optionally be joined to form a substituted heteroaryl. The two $R^1$ substituents attached to adjacent ring atoms (e.g., carbons) may optionally be joined to form a unsubstituted heteroaryl. The two $R^1$ substituents attached to adjacent ring atoms (e.g., carbons) may optionally be joined to form a $R^7$-substituted or unsubstituted heteroaryl. The two $R^1$ substituents attached to adjacent ring atoms (e.g., carbons) may optionally be joined to form a $R^7$-substituted heteroaryl.

The two $R^1$ substituents attached to adjacent ring atoms (e.g., carbons) may optionally be joined to form a substituted or unsubstituted 3 to 8 membered heterocycloalkyl. The two $R^1$ substituents attached to adjacent ring atoms (e.g., carbons) may optionally be joined to form a substituted 3 to 8 membered heterocycloalkyl. The two $R^1$ substituents attached to adjacent ring atoms (e.g., carbons) may optionally be joined to form a unsubstituted 3 to 8 membered heterocycloalkyl. The two $R^1$ substituents attached to adjacent ring atoms (e.g., carbons) may optionally be joined to form a $R^7$-substituted or unsubstituted 3 to 8 membered heterocycloalkyl. The two $R^1$ substituents attached to adjacent ring atoms (e.g., carbons) may optionally be joined to form a $R^7$-substituted 3 to 8 membered heterocycloalkyl. The two $R^1$ substituents attached to adjacent ring atoms (e.g., carbons) may optionally be joined to form a substituted or unsubstituted 5 or 6 membered heterocycloalkyl. The two $R^1$ substituents attached to adjacent ring atoms (e.g., carbons) may optionally be joined to form a substituted 5 or 6 membered heterocycloalkyl. The two $R^1$ substituents attached to adjacent ring atoms (e.g., carbons) may optionally be joined to form a unsubstituted 5 or 6 membered heterocycloalkyl. The two $R^1$ substituents attached to adjacent ring atoms (e.g., carbons) may optionally be joined to form a $R^7$-substituted or unsubstituted 5 or 6 membered heterocycloalkyl. The two $R^1$ substituents attached to adjacent ring atoms (e.g., carbons) may optionally be joined to form a $R^7$-substituted 5 or 6 membered heterocycloalkyl. The two $R^1$ substituents attached to adjacent ring atoms (e.g., carbons) may optionally be joined to form a substituted or unsubstituted 6 membered heterocycloalkyl. The two $R^1$ substituents attached to adjacent ring atoms (e.g., carbons) may optionally be joined to form a substituted 6 membered heterocycloalkyl. The two $R^1$ substituents attached to adjacent ring atoms (e.g., carbons) may optionally be joined to form a unsubstituted 6 membered heterocycloalkyl. The two $R^1$ substituents attached to adjacent ring atoms (e.g., carbons) may optionally be joined to form a $R^7$-substituted or unsubstituted 6 membered heterocycloalkyl. The two $R^1$ substituents attached to adjacent ring atoms (e.g., carbons) may optionally be joined to form a $R^7$-substituted 6 membered heterocycloalkyl. Thus, in embodiments, the two $R^1$ substituents attached to adjacent ring atoms (e.g., carbons) may optionally joined to form a 5,5-, 5,6-, 6,5-, or 6,6-fused heterocycloalkyl.

The two $R^1$ substituents attached to adjacent ring atoms (e.g., carbons) may optionally be joined to form a substituted or unsubstituted 5 to 10 membered heteroaryl. The two $R^1$ substituents attached to adjacent ring atoms (e.g., carbons) may optionally be joined to form a substituted 5 to 10 membered heteroaryl. The two $R^1$ substituents attached to adjacent ring atoms (e.g., carbons) may optionally be joined to form a unsubstituted 5 to 10 membered heteroaryl. The two $R^1$ substituents attached to adjacent ring atoms (e.g., carbons) may optionally be joined to form a $R^7$-substituted or unsubstituted 5 to 10 membered heteroaryl. The two $R^1$ substituents attached to adjacent ring atoms (e.g., carbons) may optionally be joined to form a $R^7$-substituted 5 to 10 membered heteroaryl. The two $R^1$ substituents attached to adjacent ring atoms (e.g., carbons) may optionally be joined to form a substituted or unsubstituted 5 or 6 membered heteroaryl. The two $R^1$ substituents attached to adjacent ring atoms (e.g., carbons) may optionally be joined to form a substituted 5 or 6 membered heteroaryl. The two $R^1$ substituents attached to adjacent ring atoms (e.g., carbons) may optionally be joined to form a unsubstituted 5 or 6 membered heteroaryl. The two $R^1$ substituents attached to adjacent ring atoms (e.g., carbons) may optionally be joined to form a $R^7$-substituted or unsubstituted 5 or 6 membered heteroaryl. The two $R^1$ substituents attached to adjacent ring atoms (e.g., carbons) may optionally be joined to form a $R^7$-substituted 5 or 6 membered heteroaryl. The two $R^1$ substituents attached to adjacent ring atoms (e.g., carbons) may optionally be joined to form a substituted or unsubstituted 6 membered heteroaryl. The two $R^1$ substituents attached to adjacent ring atoms (e.g., carbons) may optionally be joined to form a substituted 6 membered heteroaryl. The two $R^1$ substituents attached to adjacent ring atoms (e.g., carbons) may optionally be joined to form a unsubstituted 6 membered heteroaryl. The two $R^1$ substituents attached to adjacent ring atoms (e.g., carbons) may optionally be joined to form a $R^7$-substituted or unsubstituted 6 membered heteroaryl. The two $R^1$ substituents attached to adjacent ring atoms (e.g., carbons) may optionally be joined to form a $R^7$-substituted 6 membered heteroaryl. Thus, in embodiments, the two $R^1$ substituents attached to adjacent ring atoms (e.g., carbons) may optionally be joined to form a 5,5-, 5,6-, 6,5-, or 6,6-fused heteroaryl.

Two $R^1$ substituents may be joined to form a substituted or unsubstituted cycloalkyl, substituted or unsubstituted heterocycloalkyl, substituted or unsubstituted aryl, or substituted or unsubstituted heteroaryl. Two $R^1$ substituents may be joined to form a substituted or unsubstituted cycloalkyl. Two $R^1$ substituents may be joined to form a substituted or unsubstituted heterocycloalkyl. Two $R^1$ substituents may be joined to form a substituted or unsubstituted aryl. Two $R^1$ substituents may be joined to form a substituted or unsubstituted heteroaryl. Two $R^1$ substituents may be joined to form an unsubstituted cycloalkyl. Two $R^1$ substituents may be joined to form an unsubstituted heterocycloalkyl. Two $R^1$ substituents may be joined to form an unsubstituted aryl. Two $R^1$ substituents may be joined to form an unsubstituted heteroaryl. Two $R^1$ substituents may be joined to form a substituted cycloalkyl. Two $R^1$ substituents may be joined to form a substituted heterocycloalkyl. Two $R^1$ substituents may be joined to form a substituted aryl. Two $R^1$ substituents may be joined to form a substituted heteroaryl.

In embodiments, the two $R^1$ substituents joined to form a ring described herein are two groups selected from $R^{1A}$, $R^{1B}$, $R^{1C}$, $R^{1D}$, and $R^{1E}$. The two $R^1$ substituents joined to form a ring may be $R^{1A}$ and $R^{1B}$. The two $R^1$ substituents joined to form a ring may be $R^{1A}$ and $R^{1C}$. The two $R^1$ substituents joined to form a ring may be $R^{1A}$ and $R^{1D}$. The two $R^1$ substituents joined to form a ring may be $R^{1A}$ and $R^{1E}$. The two $R^1$ substituents joined to form a ring may be $R^{1B}$ and $R^{1C}$. The two $R^1$ substituents joined to form a ring may be $R^{1B}$ and $R^{1D}$. The two $R^1$ substituents joined to form a ring may be $R^{1B}$ and $R^{1E}$. The two $R^1$ substituents joined to form a ring may be $R^{1C}$ and $R^{1D}$. The two $R^1$ substituents joined to form a ring may be $R^{1C}$ and $R^{1E}$. The two $R^1$ substituents joined to form a ring may be $R^{1D}$ and $R^{1E}$.

In embodiments, $R^2$ is $-NR^{3A}R^{3B}$, $-C(NH)NH_2$, $-C(NH)R^{3B}$, $-C(NR^{3A})NH_2$, $-C(NR^{3A})R^{3B}$, $-C(NCN)NH_2$, $-NH_2$, $-C(NH)NHR^{3B}$, $-C(NR^{3A})NHR^{3B}$, $-C(NCN)NHR^{3B}$, substituted or unsubstituted cycloalkyl, substituted or unsubstituted heterocycloalkyl, substituted or unsubstituted aryl, substituted or unsubstituted heteroaryl, substituted or unsubstituted fused ring cycloalkyl, substituted or unsubstituted fused ring heterocycloalkyl, substituted or unsubstituted fused ring aryl, or substituted or unsubstituted fused ring heteroaryl. $R^2$ may be $-NR^{3A}R^{3B}$. $R^2$ may be $-C(NH)NH_2$. $R^2$ may be $-C(NH)R^{3B}$. $R^2$ may be $-C(NR^{3A})NH_2$. $R^2$ may be $-C(NR^{3A})R^{3B}$. $R^2$ may be $-C(NCN)NH_2$. $R^2$ may be $-NH_2$. $R^2$ may be $-C(NH)NHR^{3B}$. $R^2$ may be $-C(NR^{3A})NHR^{3B}$. $R^2$ may be $-C(NCN)NHR^{3B}$. $R^2$ may be substituted or unsubstituted cycloalkyl. $R^2$ may be substituted or unsubstituted heterocycloalkyl. $R^2$ may be substituted or unsubstituted aryl. $R^2$ may be substituted or unsubstituted heteroaryl. $R^2$ may be substituted or unsubstituted fused ring cycloalkyl. $R^2$ may be substituted or unsubstituted fused ring heterocycloalkyl. $R^2$ may be substituted or unsubstituted fused ring aryl. $R^2$ may be substituted or unsubstituted fused ring heteroaryl.

$R^2$ may independently be substituted or unsubstituted $C_3$-$C_8$ cycloalkyl. $R^2$ may independently be unsubstituted $C_3$-$C_8$ cycloalkyl. $R^2$ may independently be substituted $C_3$-$C_8$ cycloalkyl. $R^2$ may independently be $R^8$-substituted or unsubstituted $C_3$-$C_8$ cycloalkyl. $R^2$ may independently be $R^8$-substituted $C_3$-$C_8$ cycloalkyl. $R^2$ may independently be substituted or unsubstituted $C_3$-$C_6$ cycloalkyl. $R^2$ may independently be substituted $C_3$-$C_6$ cycloalkyl. $R^2$ may independently be unsubstituted $C_3$-$C_6$ cycloalkyl. $R^2$ may independently be $R^8$-substituted or unsubstituted $C_3$-$C_6$ cycloalkyl. $R^2$ may independently be $R^8$-substituted $C_3$-$C_6$ cycloalkyl. $R^2$ may independently be substituted or unsubstituted $C_4$-$C_6$ cycloalkyl. $R^2$ may independently be substituted $C_4$-$C_6$ cycloalkyl. $R^2$ may independently be unsubstituted $C_4$-$C_6$ cycloalkyl. $R^2$ may independently be $R^8$-substituted or unsubstituted $C_4$-$C_6$ cycloalkyl. $R^2$ may independently be $R^8$-substituted $C_4$-$C_6$ cycloalkyl. $R^2$ may independently be substituted or unsubstituted $C_4$ cycloalkyl. $R^2$ may independently be substituted $C_4$ cycloalkyl. $R^2$ may independently be unsubstituted $C_4$ cycloalkyl. $R^2$ may independently be $R^8$-substituted or unsubstituted $C_4$ cycloalkyl. $R^2$ may independently be $R^8$-substituted $C_4$ cycloalkyl. $R^2$ may independently be substituted or unsubstituted $C_5$ cycloalkyl. $R^2$ may independently be substituted $C_5$ cycloalkyl. $R^2$ may independently be unsubstituted $C_5$ cycloalkyl. $R^2$ may independently be $R^8$-substituted or unsubstituted $C_5$ cycloalkyl. $R^2$ may independently be $R^8$-substituted $C_5$ cycloalkyl. $R^2$ may independently be substituted or unsubstituted $C_6$ cycloalkyl. $R^2$ may independently be substituted $C_6$ cycloalkyl. $R^2$ may independently be unsubstituted $C_6$ cycloalkyl. $R^2$ may independently be $R^8$-substituted or unsubstituted $C_6$ cycloalkyl. $R^2$ may independently be $R^8$-substituted $C_6$ cycloalkyl.

$R^2$ may independently be substituted or unsubstituted 3 to 8 membered heterocycloalkyl. $R^2$ may independently be unsubstituted 3 to 8 membered heterocycloalkyl. $R^2$ may independently be substituted 3 to 8 membered heterocycloalkyl. $R^2$ may independently be $R^8$-substituted or unsubstituted 3 to 8 membered heterocycloalkyl. $R^2$ may independently be $R^8$-substituted 3 to 8 membered heterocycloalkyl. $R^2$ may independently be substituted or unsubstituted 3 to 6 membered heterocycloalkyl. $R^2$ may independently be substituted 3 to 6 membered heterocycloalkyl. $R^2$ may independently be unsubstituted 3 to 6 membered heterocycloalkyl. $R^2$ may independently be $R^8$-substituted or unsubstituted 3 to 6 membered heterocycloalkyl. $R^2$ may independently be $R^8$-substituted 3 to 6 membered heterocycloalkyl. $R^2$ may independently be substituted or unsubstituted 4 to 6 membered heterocycloalkyl. $R^2$ may independently be substituted 4 to 6 membered heterocycloalkyl. $R^2$ may independently be unsubstituted 4 to 6 membered heterocycloalkyl. $R^2$ may independently be $R^8$-substituted or unsubstituted 4 to 6 membered heterocycloalkyl. $R^2$ may independently be $R^8$-substituted 4 to 6 membered heterocycloalkyl. $R^2$ may independently be substituted or unsubstituted 4 membered heterocycloalkyl. $R^2$ may independently be substituted 4 membered heterocycloalkyl. $R^2$ may independently be unsubstituted 4 membered heterocycloalkyl. $R^2$ may independently be $R^8$-substituted or unsubstituted 4 membered heterocycloalkyl. $R^2$ may independently be $R^8$-substituted 4 membered heterocycloalkyl. $R^2$ may independently be substituted or unsubstituted 5 membered heterocycloalkyl. $R^2$ may independently be substituted 5 membered heterocycloalkyl. $^{R2}$ may independently be unsubstituted 5 membered heterocycloalkyl. $R^2$ may independently be $R^8$-substituted or unsubstituted 5 membered heterocycloalkyl. $R^2$ may independently be $R^8$-substituted 5 membered heterocycloalkyl. $R^2$ may independently be substituted or unsubstituted 6 membered heterocycloalkyl. $R^2$ may independently be substituted 6 membered heterocycloalkyl. $R^2$ may independently be unsubstituted 6 membered heterocycloalkyl. $R^2$ may independently be $R^8$-substituted or unsubstituted 6 membered heterocycloalkyl. $R^2$ may independently be $R^8$-substituted 6 membered heterocycloalkyl.

$R^2$ may independently be substituted or unsubstituted $C_6$-$C_{10}$ aryl. $R^2$ may independently be substituted $C_6$-$C_{10}$ aryl. $R^2$ may independently be unsubstituted $C_6$-$C_{10}$ aryl. $R^2$ may independently be $R^8$-substituted or unsubstituted $C_6$-$C_{10}$ aryl. $R^2$ may independently be $R^8$-substituted $C_6$-$C_{10}$ aryl. $R^2$ may independently be substituted or unsubstituted $C_6$ aryl. $R^2$ may independently be substituted $C_6$ aryl. $R^2$ may independently be unsubstituted $C_6$ aryl. $R^2$ may independently be $R^8$-substituted or unsubstituted $C_6$ aryl. $R^2$ may independently be $R^8$-substituted $C_6$ aryl.

$R^2$ may independently be substituted or unsubstituted 5-10 membered heteroaryl. $R^2$ may independently be substituted 5-10 membered heteroaryl. $R^2$ may independently be unsubstituted 5-10 membered heteroaryl. $R^2$ may independently be $R^8$-substituted or unsubstituted 5-10 membered heteroaryl. $R^2$ may independently be $R^8$-substituted 5-10 membered heteroaryl. $R^2$ may independently be substituted or unsubstituted 5-6 membered heteroaryl. $R^2$ may independently be substituted 5-6 membered heteroaryl. $R^2$ may independently be unsubstituted 5-6 membered heteroaryl. $R^2$ may independently be R-substituted or unsubstituted 5-6 membered heteroaryl. $R^2$ may independently be $R^8$-substituted 5-6 membered heteroaryl. $R^2$ may independently be substituted or unsubstituted 5 membered heteroaryl. $R^2$ may independently be substituted 5 membered heteroaryl. $R^2$ may independently be unsubstituted 5 membered heteroaryl. $R^2$ may independently be $R^8$-substituted or unsubstituted 5 membered heteroaryl. $R^2$ may independently be $R^8$-substituted 5 membered heteroaryl. $R^2$ may independently be substituted or unsubstituted 6 membered heteroaryl. $R^2$ may independently be substituted 6 membered heteroaryl. $R^2$ may independently be unsubstituted 6 membered heteroaryl. $R^2$ may independently be $R^8$-substituted or unsubstituted 6 membered heteroaryl. $R^2$ may independently be $R^8$-substituted 6 membered heteroaryl. $R^2$ may independently be substituted pyridyl, substituted imidazolyl, substituted oxazolyl, substituted thiazolyl, substituted oxadiazolyl, substituted triazolyl or substituted thiadiazolyl. $R^2$ may independently be substituted pyridyl. $R^2$ may independently be substituted imidazolyl. $R^2$ may independently be substituted oxazolyl. $R^2$ may independently be substituted thiazolyl. $R^2$ may independently be substituted oxadiazolyl. $R^2$ may independently be substituted triazolyl. $R^2$ may independently be substituted thiadiazolyl. $R^2$ may independently be

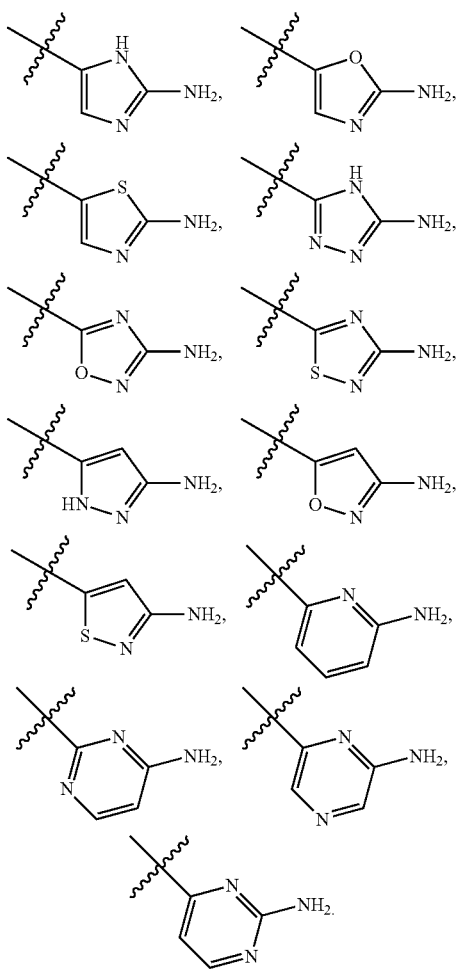

$R^2$ may independently be

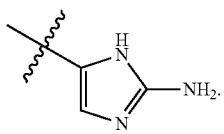 [SMILES: *c1cnc(N)[nH]1]

$R^2$ may independently be

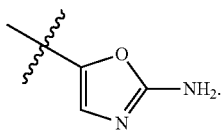 [SMILES: *c1cnc(N)o1]

$R^2$ may independently be

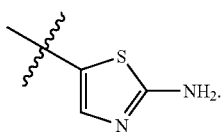 [SMILES: *c1cnc(N)s1]

$R^2$ may independently be

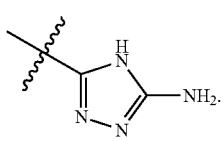

$R^2$ may independently be

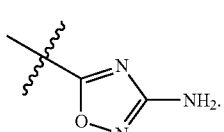

$R^2$ may independently be

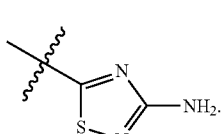

$R^2$ may independently be

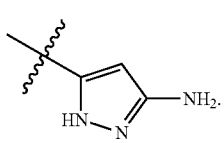 [SMILES: *c1cc(N)n[nH]1]

$R^2$ may independently be

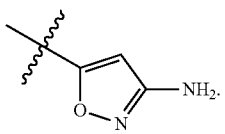 [SMILES: *c1cc(N)no1]

$R^2$ may independently be

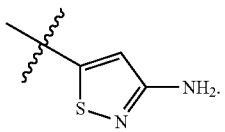 [SMILES: *c1cc(N)ns1]

$R^2$ may independently be

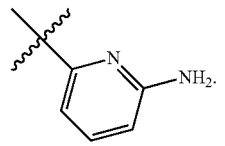 [SMILES: *c1cccc(N)n1]

$R^2$ may independently be

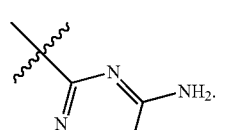

$R^2$ may independently be

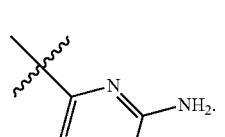

$R^2$ may independently be

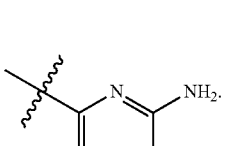

$R^2$ may independently be

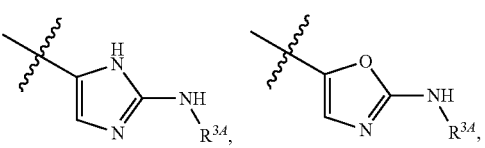

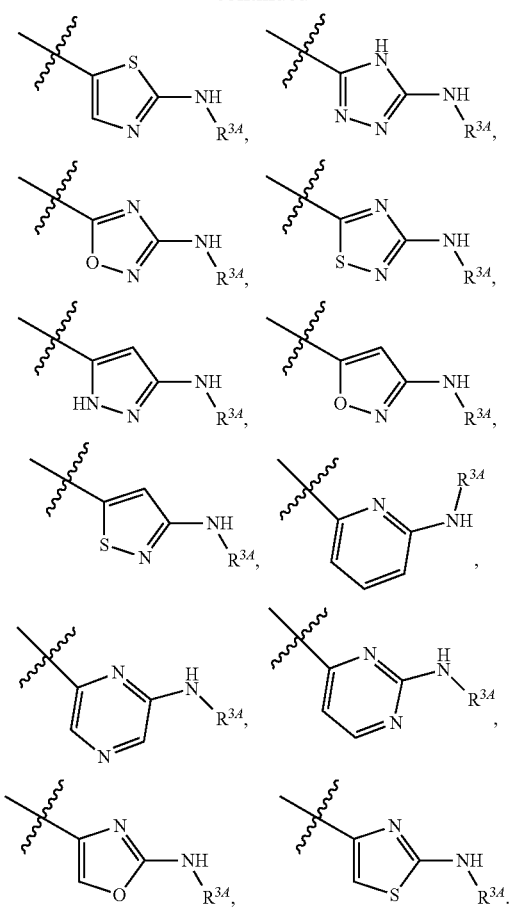
$R^2$ may independently be
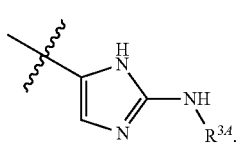
$R^2$ may independently be
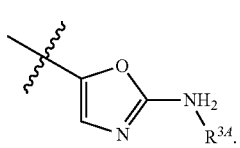
$R^2$ may independently be
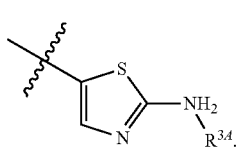
$R^2$ may independently be
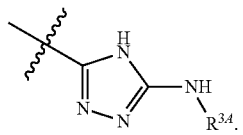
$R^2$ may independently be
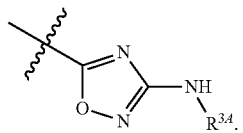
$R^2$ may independently be
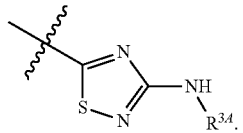
$R^2$ may independently be
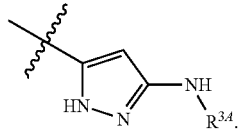
$R^2$ may independently be
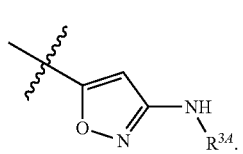
$R^2$ may independently be
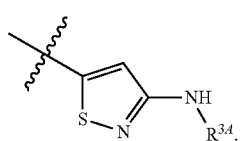
$R^2$ may independently be
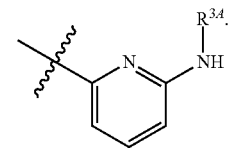

R² may independently be
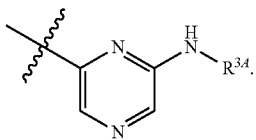
R² may independently be
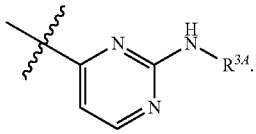
R² may independently be
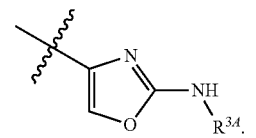
R² may independently be
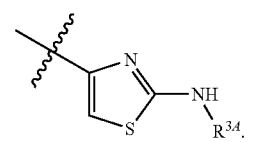
R² may independently be
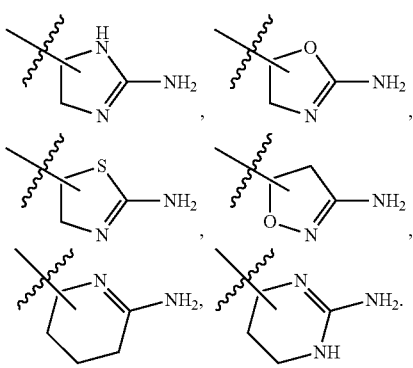
R² may independently be
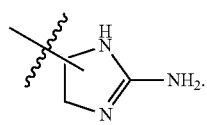
R² may independently be
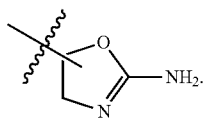
R² may independently be
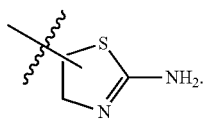
R² may independently be
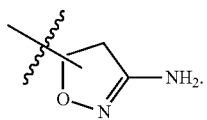
R² may independently be
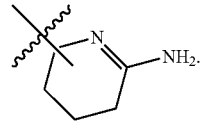
R² may independently be
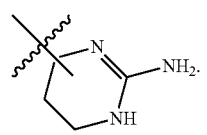
R² may may independently be
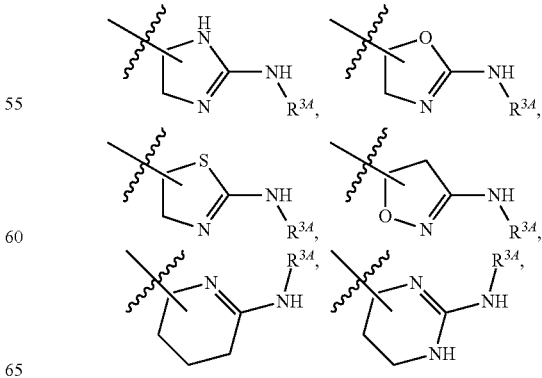

R² may independently be

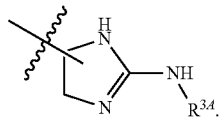

R² may independently be

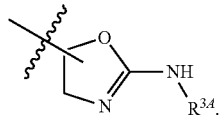

R² may independently be

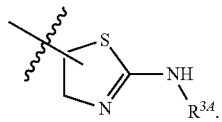

R² may independently be

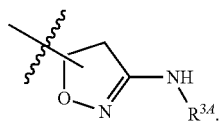

R² may independently be

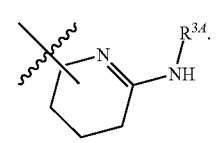

R² may independently be

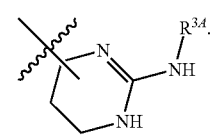

R² may independently be

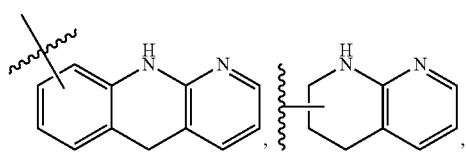

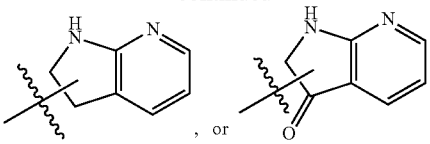, or

R² may independently be

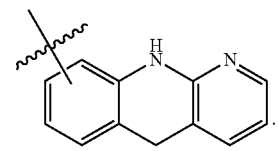

R² may independently be

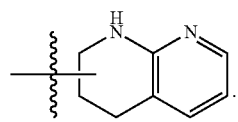

R² may independently be

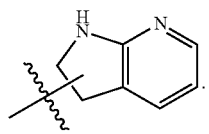

R² may independently be

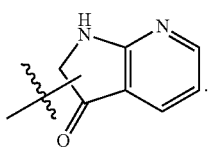

In embodiments, R² is a substituted fused heterocycloalkyl-heteroaryl. In embodiments, L³ is an unsubstituted fused heterocycloalkyl-heteroaryl. In embodiments, L³ is a substituted fused aryl-heterocycloalkyl-heteroaryl. In embodiments, L³ is an unsubstituted fused aryl-heterocycloalkyl-heteroaryl. In embodiments, R² is unsubstituted 5 to 6 membered heteroaryl. In embodiments, R² is substituted 5 to 6 membered heteroaryl. In embodiments, R² is unsubstituted 5 to 6 membered heterocycloalkyl. In embodiments, R² is substituted 5 to 6 membered heterocycloalkyl.

In embodiments, R² is a —NH-(substituted fused heterocycloalkyl-heteroaryl). In embodiments, L³ is an —NH-(unsubstituted fused heterocycloalkyl-heteroaryl). In embodiments, L³ is a —NH-(substituted fused aryl-heterocycloalkyl-heteroaryl). In embodiments, L³ is an —NH-(unsubstituted fused aryl-heterocycloalkyl-heteroaryl). In embodiments, R² is —NH-(unsubstituted 5 to 6 membered heteroaryl). In embodiments, R² is —NH-(substituted 5 to 6 membered heteroaryl). In embodiments, R² is —NH-(unsubstituted 5 to 6 membered heterocycloalkyl). In embodiments, R² is —NH-(substituted 5 to 6 membered heterocycloalkyl).

In embodiments, R² is unsubstituted pyridyl. In embodiments, R² is unsubstituted 2-pyridyl. In embodiments, R² is unsubstituted 3-pyridyl. In embodiments, R² is unsubstituted 4-pyridyl. In embodiments, R² is —C(NH)NH₂. In embodiments, R² is —NHC(NH)NH₂. In embodiments, R² is —C(NCN)NH₂. In embodiments, R² is —NHC(NCN)NH₂. In embodiments, R² is —NH₂-substituted pyridyl. In embodiments, R² is

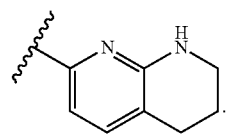 [SMILES: *c1ccc2c(n1)NCCC2]

In embodiments, R² is

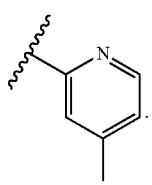 [SMILES: *c1cc(C)ccn1]

In embodiments, R² is

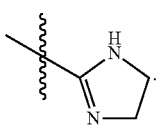 [SMILES: *C1=NCCN1]

In embodiments, R² is

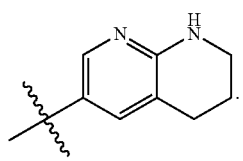 [SMILES: *c1cnc2c(c1)CCCN2]

In embodiments, R² is

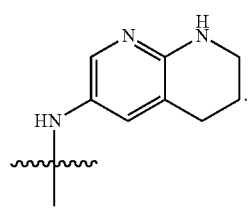 [SMILES: *Nc1cnc2c(c1)CCCN2]

In embodiments, R² is

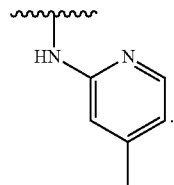 [SMILES: *Nc1cc(C)ccn1]

In embodiments, R² is

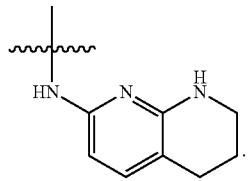 [SMILES: *Nc1ccc2c(n1)NCCC2]

In embodiments, R² is

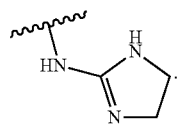

In embodiments, R² is

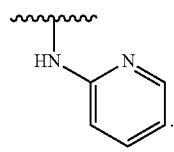

In embodiments, R² is

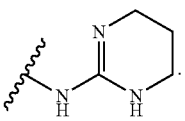

In embodiments, R² is

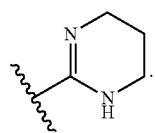

In embodiments, R² is

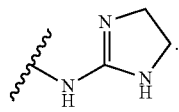

In embodiments, R² is

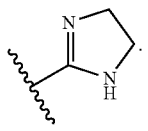

In embodiments, R² is

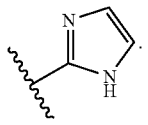

In embodiments, R² is

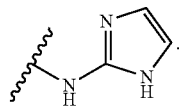 [SMILES: *Nc1ncc[nH]1]

In embodiments, R² is

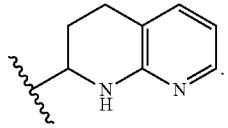 [SMILES: *C1CCc2cccnc2N1]

In embodiments, R² is

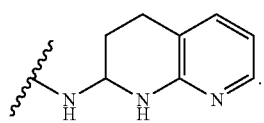 [SMILES: *NC1CCc2cccnc2N1]

In embodiments, R² is

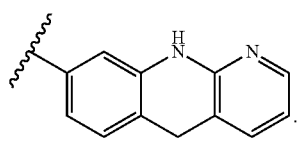 [SMILES: *c1ccc2c(c1)Nc1ncccc1C2]

In embodiments, R² is

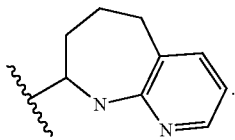 [SMILES: *C1CCCc2cccnc2N1]

In embodiments, R² is

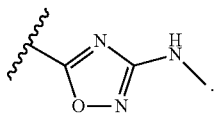 [SMILES: *c1nc(NC)no1]

In embodiments, R² is

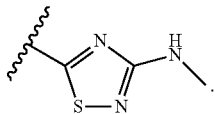 [SMILES: *c1nc(NC)ns1]

In embodiments, R² is

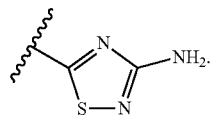 [SMILES: *c1nc(N)ns1]

In embodiments, R² is

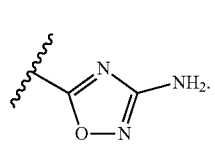 [SMILES: *c1nc(N)no1]

R² may independently be substituted or unsubstituted fused ring heterocycloalkyl. R² may independently be substituted fused ring heterocycloalkyl. R² may independently be unsubstituted fused ring heterocycloalkyl. R² may independently be R⁸-substituted or unsubstituted fused ring heterocycloalkyl. R² may independently be R⁸-substituted fused ring heterocycloalkyl. R² may independently be substituted or unsubstituted two fused ring heterocycloalkyl. R² may independently be substituted two fused ring heterocycloalkyl. R² may independently be unsubstituted two fused ring heterocycloalkyl. R² may independently be R⁸-substituted or unsubstituted two fused ring heterocycloalkyl. R² may independently be R⁸-substituted two fused ring heterocycloalkyl. R² may independently be substituted or unsubstituted three fused ring heterocycloalkyl. R² may independently be substituted three fused ring heterocycloalkyl. R² may independently be unsubstituted three fused ring heterocycloalkyl. R² may independently be R⁸-substituted or unsubstituted three fused ring heterocycloalkyl. R² may independently be R⁸-substituted three fused ring heterocycloalkyl. R² may independently be substituted or unsubstituted fused ring heterocycloalkyl wherein only one ring is a heterocycloalkyl. R² may independently be substituted fused ring heterocycloalkyl wherein only one ring is a heterocycloalkyl. $R^2$ may independently be unsubstituted fused ring heterocycloalkyl wherein only one ring is a heterocycloalkyl. $R^2$ may independently be $R^8$-substituted or unsubstituted fused ring heterocycloalkyl wherein only one ring is a heterocycloalkyl. $R^2$ may independently be $R^8$-substituted fused ring heterocycloalkyl wherein only one ring is a heterocycloalkyl.

$R^2$ may independently be substituted or unsubstituted fused ring aryl. $R^2$ may independently be substituted fused ring aryl. $R^2$ may independently be unsubstituted fused ring aryl. $R^2$ may independently be $R^8$-substituted or unsubstituted fused ring aryl. $R^2$ may independently be $R^8$-substituted fused ring aryl. $R^2$ may independently be substituted or unsubstituted two fused ring aryl. $R^2$ may independently be substituted two fused ring aryl. $R^2$ may independently be unsubstituted two fused ring aryl. $R^2$ may independently be $R^8$-substituted or unsubstituted two fused ring aryl. $R^2$ may independently be $R^8$-substituted two fused ring aryl. $R^2$ may independently be substituted or unsubstituted three fused ring aryl. $R^2$ may independently be substituted three fused ring aryl. $R^2$ may independently be unsubstituted three fused ring aryl. $R^2$ may independently be $R^8$-substituted or unsubstituted three fused ring aryl. $R^2$ may independently be $R^8$-substituted three fused ring aryl. $R^2$ may independently be substituted or unsubstituted fused ring aryl wherein only one ring is an aryl. $R^2$ may independently be substituted fused ring aryl wherein only one ring is an aryl. $R^2$ may independently be unsubstituted fused ring aryl wherein only one ring is an aryl. $R^2$ may independently be $R^8$-substituted or unsubstituted fused ring aryl wherein only one ring is an aryl. $R^2$ may independently be $R^8$-substituted fused ring aryl wherein only one ring is an aryl.

$R^2$ may independently be substituted or unsubstituted fused ring heteroaryl. $R^2$ may independently be substituted fused ring heteroaryl. $R^2$ may independently be unsubstituted fused ring heteroaryl. $R^2$ may independently be $R^8$-substituted or unsubstituted fused ring heteroaryl. $R^2$ may independently be $R^8$-substituted fused ring heteroaryl. $R^2$ may independently be substituted or unsubstituted two fused ring heteroaryl. $R^2$ may independently be substituted two fused ring heteroaryl. $R^2$ may independently be unsubstituted two fused ring heteroaryl. $R^2$ may independently be $R^8$-substituted or unsubstituted two fused ring heteroaryl. $R^2$ may independently be $R^8$-substituted two fused ring heteroaryl. $R^2$ may independently be substituted or unsubstituted three fused ring heteroaryl. $R^2$ may independently be substituted three fused ring heteroaryl. $R^2$ may independently be unsubstituted three fused ring heteroaryl. $R^2$ may independently be $R^8$-substituted or unsubstituted three fused ring heteroaryl. $R^2$ may independently be $R^8$-substituted three fused ring heteroaryl. $R^2$ may independently be substituted or unsubstituted fused ring heteroaryl wherein only one ring is a heteroaryl. $R^2$ may independently be substituted fused ring heteroaryl wherein only one ring is a heteroaryl. $R^2$ may independently be unsubstituted fused ring heteroaryl wherein only one ring is a heteroaryl. $R^2$ may independently be $R^8$-substituted or unsubstituted fused ring heteroaryl wherein only one ring is a heteroaryl. $R^2$ may independently be $R^8$-substituted fused ring heteroaryl wherein only one ring is a heteroaryl.

$R^8$ is hydrogen, halogen, oxo, $-N_3$, $-CX^8_3$, $-CHX^8_2$, $-CH_2X^8$, $-CN$, $-CHO$, $-OH$, $-NH_2$, $-COOH$, $-CONH_2$, $-NO_2$, $-SH$, $-SO_2$, $-SO_2Cl$, $-SO_2CH_3$, $-SO_3H$, $-SO_4H$, $-SO_2NH_2$, $-NHNH_2$, $-ONH_2$, $-NHC(O)NHNH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, $R^8$ is substituted or unsubstituted alkyl (e.g. $C_1$-$C_8$ alkyl, $C_1$-$C_6$ alkyl, or $C_1$-$C_4$ alkyl), substituted or unsubstituted heteroalkyl (e.g. 2 to 8 membered heteroalkyl, 2 to 6 membered heteroalkyl, or 2 to 4 membered heteroalkyl), substituted or unsubstituted cycloalkyl (e.g. $C_3$-$C_8$ cycloalkyl, $C_4$-$C_8$ cycloalkyl, or $C_5$-$C_6$ cycloalkyl), substituted or unsubstituted heterocycloalkyl (e.g. 3 to 8 membered heterocycloalkyl, 4 to 8 membered heterocycloalkyl, or 5 to 6 membered heterocycloalkyl), substituted or unsubstituted aryl (e.g. $C_6$-$C_{10}$ aryl or $C_6$ aryl), substituted or unsubstituted heteroaryl (e.g. 5 to 10 membered heteroaryl, 5 to 9 membered heteroaryl, or 5 to 6 membered heteroaryl).

$R^8$ may independently be halogen, oxo, $-N_3$, $-CX^8_3$, $-CHX^8_2$, $-CH_2X^8$, $-CN$, $-CHO$, $-OH$, $-NH_2$, $-COOH$, $-CONH_2$, $-NO_2$, $-SH$, $-SO_2$, $-SO_2Cl$, $-SO_2CH_3$, $-SO_3H$, $-SO_4H$, $-SO_2NH_2$, $-NHNH_2$, $-ONH_2$, $-NHC(O)NHNH_2$, substituted or unsubstituted alkyl (e.g. $C_1$-$C_8$ alkyl, $C_1$-$C_6$ alkyl, or $C_1$-$C_4$ alkyl), substituted or unsubstituted heteroalkyl (e.g. 2 to 8 membered heteroalkyl, 2 to 6 membered heteroalkyl, or 2 to 4 membered heteroalkyl), substituted or unsubstituted cycloalkyl (e.g. $C_3$-$C_8$ cycloalkyl, $C_4$-$C_8$ cycloalkyl, or $C_5$-$C_6$ cycloalkyl), substituted or unsubstituted heterocycloalkyl (e.g. 3 to 8 membered heterocycloalkyl, 4 to 8 membered heterocycloalkyl, or 5 to 6 membered heterocycloalkyl), substituted or unsubstituted aryl (e.g. $C_6$-$C_{10}$ aryl or $C_6$ aryl), substituted or unsubstituted heteroaryl (e.g. 5 to 10 membered heteroaryl, 5 to 9 membered heteroaryl, or 5 to 6 membered heteroaryl).

$R^8$ may independently be halogen, oxo, $-N_3$, $-CX^8_3$, $-CHX^8_2$, $-CH_2X$, $-CN$, $-CHO$, $-OH$, $-NH_2$, $-COOH$, $-CONH_2$, $-NO_2$, $-SH$, $-SO_2$, $-SO_2Cl$, $-SO_2CH_3$, $-SO_3H$, $-SO_4H$, $-SO_2NH_2$, $-NHNH_2$, $-ONH_2$, $-NHC(O)NHNH_2$, unsubstituted alkyl, unsubstituted heteroalkyl, unsubstituted cycloalkyl, unsubstituted heterocycloalkyl, unsubstituted aryl, or unsubstituted heteroaryl. In embodiments, $R^8$ is unsubstituted alkyl (e.g. $C_1$-$C_8$ alkyl, $C_1$-$C_6$ alkyl, or $C_1$-$C_4$ alkyl), unsubstituted heteroalkyl (e.g. 2 to 8 membered heteroalkyl, 2 to 6 membered heteroalkyl, or 2 to 4 membered heteroalkyl), unsubstituted cycloalkyl (e.g. $C_3$-$C_8$ cycloalkyl, $C_4$-$C_8$ cycloalkyl, or $C_5$-$C_6$ cycloalkyl), unsubstituted heterocycloalkyl (e.g. 3 to 8 membered heterocycloalkyl, 4 to 8 membered heterocycloalkyl, or 5 to 6 membered heterocycloalkyl), unsubstituted aryl (e.g. $C_6$-$C_{10}$ aryl or $C_6$ aryl), or unsubstituted heteroaryl (e.g. 5 to 10 membered heteroaryl, 5 to 9 membered heteroaryl, or 5 to 6 membered heteroaryl). $X^8$ is independently $-F$, $-Cl$, $-Br$, or $-I$. $X^8$ may independently be $-F$. $X^8$ may independently be $-Cl$. $X^8$ may independently be $-Br$. $X^8$ may independently be $-I$. In embodiments, $R^8$ is hydrogen, halogen, oxo, $-N_3$, $-CX^8_3$, $-CHX^8_2$, $-CH_2X^8$, $-CN$, $-CHO$, $-OH$, $-NH_2$, $-COOH$, $-CONH_2$, $-NO_2$, $-SH$, $-SO_2$, $-SO_2Cl$, $-SO_2CH_3$, $-SO_3H$, $-SO_4H$, $-SO_2NH_2$, $-NHNH_2$, $-ONH_2$, $-NHC(O)NHNH_2$, $R^{23}$-substituted or unsubstituted alkyl, $R^{23}$-substituted or unsubstituted heteroalkyl, $R^{23}$-substituted or unsubstituted cycloalkyl, $R^{23}$-substituted or unsubstituted heterocycloalkyl, $R^{23}$-substituted or unsubstituted aryl, or $R^{23}$-substituted or unsubstituted heteroaryl.

In embodiments, $R^8$ is $R^{23}$-substituted or unsubstituted alkyl (e.g. $C_1$-$C_6$ alkyl, $C_1$-$C_6$ alkyl, or $C_1$-$C_4$ alkyl), $R^{23}$-substituted or unsubstituted heteroalkyl (e.g. 2 to 8 membered heteroalkyl, 2 to 6 membered heteroalkyl, or 2 to 4 membered heteroalkyl), $R^{23}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{23}$-substituted or unsubstituted heterocycloalkyl (e.g. 3 to 8 membered heterocycloalkyl, 4 to 8 membered heterocycloalkyl, or 5 to 6 membered heterocloalkyl), $R^{23}$-substituted or unsubstituted aryl (e.g. $C_6$-$C_{10}$ aryl or $C_6$ aryl), $R^{23}$-substituted or unsubstituted heteroaryl (e.g. 5 to 10 membered heteroaryl, 5 to 9 membered heteroaryl, or 5 to 6 membered heteroaryl).

$R^{23}$ is halogen, oxo, —$N_3$, —$CX^{23}_3$, —$CHX^{23}_2$, —$CH_2X^{23}$, —CN, —CHO, —OH, —$NH_2$, —COOH, —$CONH_2$, —$NO_2$, —SH, —$SO_2$, —$SO_2Cl$, —$SO_2CH_3$— $SO_3H$, —$SO_4H$, —$SO_2NH_2$, —$NHNH_2$, —$ONH_2$, —NHC(O)$NHNH_2$, $R^{24}$-substituted or unsubstituted alkyl, $R^{24}$-substituted or unsubstituted heteroalkyl, $R^{24}$-substituted or unsubstituted cycloalkyl, $R^{24}$-substituted or unsubstituted heterocycloalkyl, $R^{24}$-substituted or unsubstituted aryl, or $R^{24}$-substituted or unsubstituted heteroaryl.

In embodiments, $R^{23}$ is $R^{24}$-substituted or unsubstituted alkyl (e.g. $C_1$-$C_8$ alkyl, $C_1$-$C_6$ alkyl, or $C_1$-$C_4$ alkyl), $R^{24}$-substituted or unsubstituted heteroalkyl (e.g. 2 to 8 membered heteroalkyl, 2 to 6 membered heteroalkyl, or 2 to 4 membered heteroalkyl), $R^{24}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{24}$-substituted or unsubstituted heterocycloalkyl (e.g. 3 to 8 membered heterocycloalkyl, 4 to 8 membered heterocycloalkyl, or 5 to 6 membered heterocycloalkyl), $R^{24}$-substituted or unsubstituted aryl (e.g. $C_6$-$C_{10}$ aryl or $C_6$ aryl), $R^{24}$-substituted or unsubstituted heteroaryl (e.g. 5 to 10 membered heteroaryl, 5 to 9 membered heteroaryl, or 5 to 6 membered heteroaryl). $X^{23}$ is independently —F, —Cl, —Br, or —I. $X^{23}$ may independently be —F. $X^{23}$ may independently be —Cl. $X^{23}$ may independently be —Br. $X^{23}$ may independently be —I.

$R^{24}$ is halogen, oxo, —$N_3$, —$CX^{24}_3$, —$CHX^{24}_2$, —$CH_2X^{24}$, —CN, —CHO, —OH, —$NH_2$, —COOH, —$CONH_2$, —$NO_2$, —SH, —$SO_2$, —$SO_2Cl$, —$SO_2CH_3$— $SO_3H$, —$SO_4H$, —$SO_2NH_2$, —$NHNH_2$, —$ONH_2$, —NHC(O)$NHNH_2$, $R^{25}$-substituted or unsubstituted alkyl, $R^{25}$-substituted or unsubstituted heteroalkyl, $R^{25}$-substituted or unsubstituted cycloalkyl, $R^{25}$-substituted or unsubstituted heterocycloalkyl, $R^{25}$-substituted or unsubstituted aryl, or $R^{25}$-substituted or unsubstituted heteroaryl.

In embodiments, $R^{24}$ is $R^{25}$-substituted or unsubstituted alkyl (e.g. $C_1$-$C_8$ alkyl, $C_1$-$C_6$ alkyl, or $C_1$-$C_4$ alkyl), $R^{25}$-substituted or unsubstituted heteroalkyl (e.g. 2 to 8 membered heteroalkyl, 2 to 6 membered heteroalkyl, or 2 to 4 membered heteroalkyl), $R^{25}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{25}$-substituted or unsubstituted heterocycloalkyl (e.g. 3 to 8 membered heterocycloalkyl, 4 to 8 membered heterocycloalkyl, or 5 to 6 membered heterocycloalkyl), $R^{25}$-substituted or unsubstituted aryl (e.g. $C_6$-$C_{10}$ aryl or $C_6$ aryl), $R^{25}$-substituted or unsubstituted heteroaryl (e.g. 5 to 10 membered heteroaryl, 5 to 9 membered heteroaryl, or 5 to 6 membered heteroaryl). $X^{24}$ is independently —F, —Cl, —Br, or —I. $X^{24}$ may independently be —F. $X^{24}$ may independently be —Cl. $X^{24}$ may independently be —Br. $X^{24}$ may independently be —I.

$R^{25}$ is halogen, oxo, —$N_3$, —$CX^{25}_3$, —$CHX^{25}_2$, —$CH_2X^{25}$, —CN, —CHO, —OH, —$NH_2$, —COOH, —$CONH_2$, —$NO_2$, —SH, —$SO_2$, —$SO_2Cl$, —$SO_2CH_3$— $SO_3H$, —$SO_4H$, —$SO_2NH_2$, —$NHNH_2$, —$ONH_2$, —NHC(O)$NHNH_2$, unsubstituted alkyl, unsubstituted heteroalkyl, unsubstituted cycloalkyl, unsubstituted heterocycloalkyl, unsubstituted aryl, or unsubstituted heteroaryl. In embodiments, $R^{25}$ is unsubstituted alkyl (e.g. $C_1$-$C_8$ alkyl, $C_1$-$C_6$ alkyl, or $C_1$-$C_4$ alkyl), unsubstituted heteroalkyl (e.g. 2 to 8 membered heteroalkyl, 2 to 6 membered heteroalkyl, or 2 to 4 membered heteroalkyl), unsubstituted cycloalkyl (e.g. $C_3$-$C_8$ cycloalkyl, $C_4$-$C_8$ cycloalkyl, or $C_5$-$C_6$ cycloalkyl), unsubstituted heterocycloalkyl (e.g. 3 to 8 membered heterocycloalkyl, 4 to 8 membered heterocycloalkyl, or 5 to 6 membered heterocycloalkyl), unsubstituted aryl (e.g. $C_6$-$C_{10}$ aryl or $C_6$ aryl), or unsubstituted heteroaryl (e.g. 5 to 10 membered heteroaryl, 5 to 9 membered heteroaryl, or 5 to 6 membered heteroaryl). $X^{25}$ is independently —F, —Cl, —Br, or —I. $X^{25}$ may independently be —F. $X^{25}$ may independently be —Cl. $X^{25}$ may independently be —Br. $X^{25}$ may independently be —I.

$R^{3A}$ may be hydrogen, —C(NH)$NH_2$, —C(NH)$R^{3D}$, —C($NR^{3C}$)$NH_2$, —C($NR^{3C}$)$R^{3D}$, —C(NCN)$NH_2$, $NH_2$, —C(NH)$NHR^{3D}$, —C($NR^{3C}$)$NHR^{3D}$, —C(NCN)$NHR^{3D}$, $R^{10}$-substituted or unsubstituted cycloalkyl, $R^{10}$-substituted or unsubstituted heterocycloalkyl, $R^{10}$-substituted or unsubstituted aryl, $R^{10}$-substituted or unsubstituted heteroaryl, or $R^{3A}$ and $R^{3B}$ are optionally joined to form a $R^{10}$-substituted or unsubstituted heterocycloalkyl or $R^{10}$-substituted or unsubstituted heteroaryl. $R^{3B}$ may be hydrogen, —C(NH)$NH_2$, —C(NH)$R^{3D}$, —C($NR^{3C}$)$NH_2$, —C($NR^{3C}$)$R^{3D}$, —C(NCN)$NH_2$, $NH_2$, —C(NH)$NHR^{3D}$, —C($NR^{3C}$)$NHR^{3D}$, —C(NCN)$NHR^{3D}$, $R^{10}$-substituted or unsubstituted cycloalkyl, $R^{10}$-substituted or unsubstituted heterocycloalkyl, $R^{10}$-substituted or unsubstituted aryl, $R^{10}$-substituted or unsubstituted heteroaryl, or $R^{3A}$ and $R^{3B}$ may optionally be joined to form a $R^{10}$-substituted or unsubstituted heterocycloalkyl or $R^{10}$-substituted or unsubstituted heteroaryl. $R^{3A}$ and $R^{3B}$ may be independently hydrogen, —C(NH)$NH_2$, —C(NH)$R^{3D}$, —C($NR^{3C}$)$NH_2$, —C($NR^3$)$R^{3D}$, —C(NCN)$NH_2$, $NH_2$, substituted or unsubstituted cycloalkyl, substituted or unsubstituted heterocycloalkyl, substituted or unsubstituted aryl, or substituted or unsubstituted heteroaryl. $R^{3A}$ and $R^{3B}$ may be independently hydrogen, —C(NH)$NH_2$, —C(NH)$R^{3D}$, —C($NR^{3C}$)$NH_2$, —C($NR^3$)$R^{3D}$, —C(NCN)$NH_2$, $NH_2$, substituted or unsubstituted alkyl (e.g. $C_1$-$C_8$ alkyl, $C_1$-$C_6$ alkyl, or $C_1$-$C_4$ alkyl), substituted or unsubstituted heteroalkyl (e.g. 2 to 8 membered heteroalkyl, 2 to 6 membered heteroalkyl, or 2 to 4 membered heteroalkyl), substituted or unsubstituted cycloalkyl (e.g. $C_3$-$C_8$ cycloalkyl, $C_4$-$C_8$ cycloalkyl, or $C_5$-$C_6$ cycloalkyl), substituted or unsubstituted heterocycloalkyl (e.g. 3 to 8 membered heterocycloalkyl, 4 to 8 membered heterocycloalkyl, or 5 to 6 membered heterocycloalkyl), substituted or unsubstituted aryl (e.g. $C_6$-$C_{10}$ aryl or $C_6$ aryl), substituted or unsubstituted heteroaryl (e.g. 5 to 10 membered heteroaryl, 5 to 9 membered heteroaryl, or 5 to 6 membered heteroaryl).

$R^{3A}$ and $R^{3B}$ may independently be —C(NH)$NH_2$, —C(NH)$R^{3D}$, —C($NR^{3C}$)$NH_2$, —C($NR^{3C}$)$R^{3D}$, —C(NCN)$NH_2$, $NH_2$, or a detectable moiety. $R^{3A}$ and $R^{3B}$ may be joined to form a substituted or unsubstituted 5 or 6 membered heterocycloalkyl or substituted or unsubstituted 5 or 6 membered heteroaryl. $R^{3A}$ and $R^{3B}$ may be joined to form an unsubstituted 5 or 6 membered heterocycloalkyl. $R^{3A}$ and $R^{3B}$ may be joined to form an unsubstituted 5 or 6 membered heteroaryl. $R^{3A}$ and $R^{3B}$ may be joined to form a substituted 5 or 6 membered heterocycloalkyl. $R^{3A}$ and $R^{3B}$ may be joined to form a substituted 5 or 6 membered heteroaryl. $R^{3A}$ and $R^{3B}$ may be joined to form an unsubstituted 5 membered heterocycloalkyl. $R^{3A}$ and $R^{3B}$ may be joined to form an unsubstituted 5 membered heteroaryl. $R^{3A}$ and $R^{3B}$ may be joined to form a substituted 5 membered heterocycloalkyl. $R^{3A}$ and $R^{3B}$ may be joined to form a substituted 5 membered heteroaryl. $R^{3A}$ and $R^{3B}$ may be joined to form an unsubstituted 6 membered heterocycloalkyl. $R^{3A}$ and $R^{3B}$ may be joined to form an unsubstituted 6 membered heteroaryl. $R^{3A}$ and $R^{3B}$ may be joined to form a substituted 6 membered heterocycloalkyl. $R^{3A}$ and $R^{3B}$ may be joined to form a substituted 6 membered heteroaryl.

$R^{3A}$ and $R^{3B}$ may independently be substituted or unsubstituted $C_1$-$C_{10}$ alkyl. $R^{3A}$ and $R^{3B}$ may independently be substituted $C_1$-$C_{10}$ alkyl. $R^{3A}$ and $R^{3B}$ may independently be unsubstituted $C_1$-$C_{10}$ alkyl. $R^{3A}$ and $R^{3B}$ may independently be $R^{10}$-substituted or unsubstituted $C_1$-$C_{10}$ alkyl. $R^{3A}$ and $R^{3B}$ may independently be $R^{10}$-substituted $C_1$-$C_{10}$ alkyl. $R^{3A}$ and $R^{3B}$ may independently be substituted or unsubstituted $C_1$-$C_8$ alkyl. $R^{3A}$ and $R^{3B}$ may independently be substituted $C_1$-$C_8$ alkyl. $R^{3A}$ and $R^{3B}$ may independently be unsubstituted $C_1$-$C_8$ alkyl. $R^{3A}$ and $R^{3B}$ may independently be $R^{10}$-substituted or unsubstituted $C_1$-$C_8$ alkyl. $R^{3A}$ and $R^{3B}$ may independently be $R^{10}$-substituted $C_1$-$C_8$ alkyl. $R^{3A}$ and $R^{3B}$ may independently be substituted or unsubstituted $C_1$-$C_5$ alkyl. $R^{3A}$ and $R^{3B}$ may independently be substituted $C_1$-$C_5$ alkyl. $R^{3A}$ and $R^{3B}$ may independently be unsubstituted $C_1$-$C_5$ alkyl. $R^{3A}$ and $R^{3B}$ may independently be $R^{10}$-substituted or unsubstituted $C_1$-$C_5$ alkyl. $R^{3A}$ and $R^{3B}$ may independently be $R^{10}$-substituted $C_1$-$C_5$ alkyl. $R^{3A}$ and $R^{3B}$ may independently be substituted or unsubstituted $C_1$-$C_3$ alkyl. $R^{3A}$ and $R^{3B}$ may independently be substituted $C_1$-$C_3$ alkyl. $R^{3A}$ and $R^{3B}$ may independently be unsubstituted $C_1$-$C_3$ alkyl. $R^{3A}$ and $R^{3B}$ may independently be $R^{10}$-substituted or unsubstituted $C_1$-$C_3$ alkyl. $R^{3A}$ and $R^{3B}$ may independently be $R^{10}$-substituted $C_1$-$C_3$ alkyl. In embodiments, one of $R^{3A}$ and $R^{3B}$ is hydrogen.

$R^{3A}$ and $R^{3B}$ may independently be substituted or unsubstituted 2 to 10 membered heteroalkyl. $R^{3A}$ and $R^{3B}$ may independently be substituted 2 to 10 membered heteroalkyl. $R^{3A}$ and $R^{3B}$ may independently be unsubstituted 2 to 10 membered heteroalkyl. $R^{3A}$ and $R^{3B}$ may independently be $R^{10}$-substituted or unsubstituted 2 to 10 membered heteroalkyl. $R^{3A}$ and $R^{3B}$ may independently be $R^{10}$-substituted 2 to 10 membered heteroalkyl. $R^{3A}$ and $R^{3B}$ may independently be substituted or unsubstituted 2 to 8 membered heteroalkyl. $R^{3A}$ and $R^{3B}$ may independently be substituted 2 to 8 membered heteroalkyl. $R^{3A}$ and $R^{3B}$ may independently be unsubstituted 2 to 8 membered heteroalkyl. $R^{3A}$ and $R^{3B}$ may independently be $R^{10}$-substituted or unsubstituted 2 to 8 membered heteroalkyl. $R^{3A}$ and $R^{3B}$ may independently be $R^{10}$-substituted 2 to 8 membered heteroalkyl. $R^{3A}$ and $R^{3B}$ may independently be substituted or unsubstituted 2 to 6 membered heteroalkyl. $R^{3A}$ and $R^{3B}$ may independently be substituted 2 to 6 membered heteroalkyl. $R^{3A}$ and $R^{3B}$ may independently be unsubstituted 2 to 6 membered heteroalkyl. $R^{3A}$ and $R^{3B}$ may independently be $R^{10}$-substituted or unsubstituted 2 to 6 membered heteroalkyl. $R^{3A}$ and $R^{3B}$ may independently be $R^{10}$-substituted 2 to 6 membered heteroalkyl. In embodiments, one of $R^{3A}$ and $R^{3B}$ is hydrogen.

$R^{3A}$ and $R^{3B}$ may independently be substituted or unsubstituted $C_3$-$C_8$ cycloalkyl. $R^{3A}$ and $R^{3B}$ may independently be unsubstituted $C_3$-$C_8$ cycloalkyl. $R^{3A}$ and $R^{3B}$ may independently be substituted $C_3$-$C_8$ cycloalkyl. $R^{3A}$ and $R^{3B}$ may independently be $R^{10}$-substituted or unsubstituted $C_3$-$C_8$ cycloalkyl. $R^{3A}$ and $R^{3B}$ may independently be $R^{10}$-substituted $C_3$-$C_8$ cycloalkyl. $R^{3A}$ and $R^{3B}$ may independently be substituted or unsubstituted $C_3$-$C_6$ cycloalkyl. $R^{3A}$ and $R^{3B}$ may independently be substituted $C_3$-$C_6$ cycloalkyl. $R^{3A}$ and $R^{3B}$ may independently be unsubstituted $C_3$-$C_6$ cycloalkyl. $R^{3A}$ and $R^{3B}$ may independently be $R^{10}$-substituted or unsubstituted $C_3$-$C_6$ cycloalkyl. $R^{3A}$ and $R^{3B}$ may independently be $R^{10}$-substituted $C_3$-$C_6$ cycloalkyl. $R^{3A}$ and $R^{3B}$ may independently be substituted or unsubstituted $C_4$-$C_6$ cycloalkyl. $R^{3A}$ and $R^{3B}$ may independently be substituted $C_4$-$C_6$ cycloalkyl. $R^{3A}$ and $R^{3B}$ may independently be unsubstituted $C_4$-$C_6$ cycloalkyl. $R^{3A}$ and $R^{3B}$ may independently be $R^{10}$-substituted or unsubstituted $C_4$-$C_6$ cycloalkyl. $R^{3A}$ and $R^{3B}$ may independently be $R^{10}$-substituted $C_4$-$C_6$ cycloalkyl. $R^{3A}$ and $R^{3B}$ may independently be substituted or unsubstituted $C_4$ cycloalkyl. $R^{3A}$ and $R^{3B}$ may independently be substituted $C_4$ cycloalkyl. $R^{3A}$ and $R^{3B}$ may independently be unsubstituted $C_4$ cycloalkyl. $R^{3A}$ and $R^{3B}$ may independently be $R^{10}$-substituted or unsubstituted $C_4$ cycloalkyl. $R^{3A}$ and $R^{3B}$ may independently be $R^{10}$-substituted $C_4$ cycloalkyl. $R^{3A}$ and $R^{3B}$ may independently be substituted or unsubstituted $C_5$ cycloalkyl. $R^{3A}$ and $R^{3B}$ may independently be substituted $C_5$ cycloalkyl. $R^{3A}$ and $R^{3B}$ may independently be unsubstituted $C_5$ cycloalkyl. $R^{3A}$ and $R^{3B}$ may independently be $R^{10}$-substituted or unsubstituted $C_5$ cycloalkyl. $R^{3A}$ and $R^{3B}$ may independently be $R^{10}$-substituted $C_5$ cycloalkyl. $R^{3A}$ and $R^{3B}$ may independently be substituted or unsubstituted $C_6$ cycloalkyl. $R^{3A}$ and $R^{3B}$ may independently be substituted $C_6$ cycloalkyl. $R^{3A}$ and $R^{3B}$ may independently be unsubstituted $C_6$ cycloalkyl. $R^{3A}$ and $R^{3B}$ may independently be $R^{10}$-substituted or unsubstituted $C_6$ cycloalkyl. $R^{3A}$ and $R^{3B}$ may independently be $R^{10}$-substituted $C_6$ cycloalkyl. In embodiments, one of $R^{3A}$ and $R^{3B}$ is hydrogen.

$R^{3A}$ and $R^{3B}$ may independently be substituted or unsubstituted 3 to 8 membered heterocycloalkyl. $R^{3A}$ and $R^{3B}$ may independently be unsubstituted 3 to 8 membered heterocycloalkyl. $R^{3A}$ and $R^{3B}$ may independently be substituted 3 to 8 membered heterocycloalkyl. $R^{3A}$ and $R^{3B}$ may independently be $R^{10}$-substituted or unsubstituted 3 to 8 membered heterocycloalkyl. $R^{3A}$ and $R^{3B}$ may independently be $R^{10}$-substituted 3 to 8 membered heterocycloalkyl. $R^{3A}$ and $R^{3B}$ may independently be substituted or unsubstituted 3 to 6 membered heterocycloalkyl. $R^{3A}$ and $R^{3B}$ may independently be substituted 3 to 6 membered heterocycloalkyl. $R^{3A}$ and $R^{3B}$ may independently be unsubstituted 3 to 6 membered heterocycloalkyl. $R^{3A}$ and $R^{3B}$ may independently be $R^{10}$-substituted or unsubstituted 3 to 6 membered heterocycloalkyl. $R^{3A}$ and $R^{3B}$ may independently be $R^{10}$-substituted 3 to 6 membered heterocycloalkyl. $R^{3A}$ and $R^{3B}$ may independently be substituted or unsubstituted 4 to 6 membered heterocycloalkyl. $R^{3A}$ and $R^{3B}$ may independently be substituted 4 to 6 membered heterocycloalkyl. $R^{3A}$ and $R^{3B}$ may independently be unsubstituted 4 to 6 membered heterocycloalkyl. $R^{3A}$ and $R^{3B}$ may independently be $R^{10}$-substituted or unsubstituted 4 to 6 membered heterocycloalkyl. $R^{3A}$ and $R^{3B}$ may independently be $R^{10}$-substituted 4 to 6 membered heterocycloalkyl. $R^{3A}$ and $R^{3B}$ may independently be substituted or unsubstituted 4 membered heterocycloalkyl. $R^{3A}$ and $R^{3B}$ may independently be substituted 4 membered heterocycloalkyl. $R^{3A}$ and $R^{3B}$ may independently be unsubstituted 4 membered heterocycloalkyl. $R^{3A}$ and $R^{3B}$ may independently be $R^{10}$-substituted or unsubstituted 4 membered heterocycloalkyl. $R^{3A}$ and $R^{3B}$ may independently be $R^{10}$-substituted 4 membered heterocycloalkyl. $R^{3A}$ and $R^{3B}$ may independently be substituted or unsubstituted 5 membered heterocycloalkyl. $R^{3A}$ and $R^{3B}$ may independently be substituted 5 membered heterocycloalkyl. $R^{3A}$ and $R^{3B}$ may independently be unsubstituted 5 membered heterocycloalkyl. $R^{3A}$ and $R^{3B}$ may independently be $R^{10}$-substituted or unsubstituted 5 membered heterocycloalkyl. $R^{3A}$ and $R^{3B}$ may independently be $R^{10}$-substituted 5 membered heterocycloalkyl. $R^{3A}$ and $R^{3B}$ may independently be substituted or unsubstituted 6 membered heterocycloalkyl. $R^{3A}$ and $R^{3B}$ may independently be substituted 6 membered heterocycloalkyl. $R^{3A}$ and $R^{3B}$ may independently be unsubstituted 6 membered heterocycloalkyl. $R^{3A}$ and $R^{3B}$ may independently be $R^{10}$-substituted or unsubstituted 6 membered heterocycloalkyl. $R^{3A}$ and $R^{3B}$ may independently be $R^{10}$-substituted 6 membered heterocycloalkyl. In embodiments, one of $R^{3A}$ and $R^{3B}$ is hydrogen.

$R^{3A}$ and $R^{3B}$ may independently be substituted or unsubstituted $C_6$-$C_{10}$ aryl. $R^{3A}$ and $R^{3B}$ may independently be substituted $C_6$-$C_{10}$ aryl. $R^{3A}$ and $R^{3B}$ may independently be unsubstituted $C_6$-$C_{10}$ aryl. $R^{3A}$ and $R^{3B}$ may independently be $R^{10}$-substituted or unsubstituted $C_6$-$C_{10}$ aryl. $R^{3A}$ and $R^{3B}$ may independently be $R^{10}$-substituted $C_6$-$C_{10}$ aryl. $R^{3A}$ and $R^{3B}$ may independently be substituted or unsubstituted $C_{10}$ aryl. $R^{3A}$ and $R^{3B}$ may independently be substituted $C_{10}$ aryl. $R^{3A}$ and $R^{3B}$ may independently be unsubstituted $C_{10}$ aryl. $R^{3A}$ and $R^{3B}$ may independently be $R^{10}$-substituted or unsubstituted $C_{10}$ aryl. $R^{3A}$ and $R^{3B}$ may independently be $R^{10}$-substituted $C_{10}$ aryl. $R^{3A}$ and $R^{3B}$ may independently be substituted or unsubstituted $C_{10}$ aryl. $R^{3A}$ and $R^{3B}$ may independently be substituted $C_{10}$ aryl. $R^{3A}$ and $R^{3B}$ may independently be unsubstituted $C_{10}$ aryl. $R^{3A}$ and $R^{3B}$ may independently be $R^{10}$-substituted or unsubstituted $C_{10}$ aryl. $R^{3A}$ and $R^{3B}$ may independently be $R^{10}$-substituted $C_{10}$ aryl. $R^{3A}$ and $R^{3B}$ may independently be substituted or unsubstituted $C_6$ aryl. $R^{3A}$ and $R^{3B}$ may independently be substituted $C_6$ aryl. $R^{3A}$ and $R^{3B}$ may independently be unsubstituted $C_6$ aryl. $R^{3A}$ and $R^{3B}$ may independently be $R^{10}$-substituted or unsubstituted $C_6$ aryl. $R^{3A}$ and $R^{3B}$ may independently be $R^{10}$-substituted $C_6$ aryl. In embodiments, one of $R^{3A}$ and $R^{3B}$ is hydrogen.

$R^{3A}$ and $R^{3B}$ may independently be substituted or unsubstituted 5-10 membered heteroaryl. $R^{3A}$ and $R^{3B}$ may independently be substituted 5-10 membered heteroaryl. $R^{3A}$ and $R^{3B}$ may independently be unsubstituted 5-10 membered heteroaryl. $R^{3A}$ and $R^{3B}$ may independently be $R^{10}$-substituted or unsubstituted 5-10 membered heteroaryl. $R^{3A}$ and $R^{3B}$ may independently be $R^{10}$-substituted 5-10 membered heteroaryl. $R^{3A}$ and $R^{3B}$ may independently be substituted or unsubstituted 5-6 membered heteroaryl. $R^{3A}$ and $R^{3B}$ may independently be substituted 5-6 membered heteroaryl. $R^{3A}$ and $R^{3B}$ may independently be unsubstituted 5-6 membered heteroaryl. $R^{3A}$ and $R^{3B}$ may independently be $R^{10}$-substituted or unsubstituted 5-6 membered heteroaryl. $R^{3A}$ and $R^{3B}$ may independently be $R^{10}$-substituted 5-6 membered heteroaryl. $R^{3A}$ and $R^{3B}$ may independently be substituted or unsubstituted 5 membered heteroaryl. $R^{3A}$ and $R^{3B}$ may independently be substituted 5 membered heteroaryl. $R^{3A}$ and $R^{3B}$ may independently be unsubstituted 5 membered heteroaryl. $R^{3A}$ and $R^{3B}$ may independently be $R^{10}$-substituted or unsubstituted 5 membered heteroaryl. $R^{3A}$ and $R^{3B}$ may independently be $R^{10}$-substituted 5 membered heteroaryl. $R^{3A}$ and $R^{3B}$ may independently be substituted or unsubstituted 6 membered heteroaryl. $R^{3A}$ and $R^{3B}$ may independently be substituted 6 membered heteroaryl. $R^{3A}$ and $R^{3B}$ may independently be unsubstituted 6 membered heteroaryl. $R^{3A}$ and $R^{3B}$ may independently be $R^{10}$-substituted or unsubstituted 6 membered heteroaryl. $R^{3A}$ and $R^{3B}$ may independently be $R^{10}$-substituted 6 membered heteroaryl. In embodiments, one of $R^{3A}$ and $R^{3B}$ is hydrogen.

$R^{3A}$ and $R^{3B}$ may be independently $R^{10}$-substituted or unsubstituted cycloalkyl, $R^{10}$-substituted or unsubstituted heterocycloalkyl, $R^{10}$-substituted or unsubstituted aryl, or $R^{10}$-substituted or unsubstituted heteroaryl. $R^{3A}$ and $R^{3B}$ may be independently substituted or unsubstituted 5 or 6 membered cycloalkyl, substituted or unsubstituted 5 or 6 membered heterocycloalkyl, substituted or unsubstituted 6 membered aryl or substituted or unsubstituted 5 or 6 membered heteroaryl. $R^{3A}$ and $R^{3B}$ may be independently hydrogen, —C(NH)NH₂, or —C(NCN)NH₂. $R^{3A}$ and $R^{3B}$ may be independently hydrogen or —C(NH)NH₂. $R^{3A}$ and $R^{3B}$ may be independently hydrogen or —C(NCN)NH₂. $R^{3A}$ and $R^{3B}$ may be independently —C(NH)NH₂, or —C(NCN)NH₂. $R^{3A}$ and $R^{3B}$ may be independently hydrogen or —C(NH)$R^{3C}$. $R^{3A}$ and $R^{3B}$ may be independently be hydrogen. $R^{3A}$ and $R^{3B}$ may independently be hydrogen and substituted or unsubstituted cycloalkyl as described herein. $R^{3A}$ and $R^{3B}$ may be independently hydrogen and substituted or unsubstituted heterocycloalkyl as described herein. $R^{3A}$ and $R^{3B}$ may be independently hydrogen and substituted or unsubstituted aryl as described herein. $R^{3A}$ and $R^{3B}$ may be independently hydrogen and substituted or unsubstituted heteroaryl as described herein. In embodiments, one of $R^{3A}$ and $R^{3B}$ is hydrogen.

$R^{3A}$ may be hydrogen and $R^{3B}$ may be pyrrolidinyl, pyrrolyl, tetrahydrofuranyl, furanyl, thiolanyl, thienyl, imidazolidinyl, pyrazolidinyl, imidazolyl, pyrazolyl, oxazolidinyl, isoxazolidinyl, oxazolyl, isoxazolyl, thiazolidinyl, isothiazolidinyl, thiazolyl, isothiazolyl, dioxolanyl, dithiolanyl, triazolyl, furazanyl, oxadiazolyl, thiadiazolyl, dithiazolyl, tetrazolyl, piperidinyl, pyridinyl, oxanyl, pyranyl, thianyl, thiopyranyl, piperazinyl, diazinyl, morpholinyl, oxazinyl, thiomorpholinyl, thiazinyl, dioxanyl, dioxinyl, dithianyl, dithiinyl, triazinyl, trioxanyl, trithianyl, or tetrazinyl. $R^{3B}$ may be hydrogen and $R^{3A}$ may be pyrrolidinyl, pyrrolyl, tetrahydrofuranyl, furanyl, thiolanyl, thienyl, imidazolidinyl, pyrazolidinyl, imidazolyl, pyrazolyl, oxazolidinyl, isoxazolidinyl, oxazolyl, isoxazolyl, thiazolidinyl, isothiazolidinyl, thiazolyl, isothiazolyl, dioxolanyl, dithiolanyl, triazolyl, furazanyl, oxadiazolyl, thiadiazolyl, dithiazolyl, tetrazolyl, piperidinyl, pyridinyl, oxanyl, pyranyl, thianyl, thiopyranyl, piperazinyl, diazinyl, morpholinyl, oxazinyl, thiomorpholinyl, thiazinyl, dioxanyl, dioxinyl, dithianyl, dithiinyl, triazinyl, trioxanyl, trithianyl, or tetrazinyl. $R^{3A}$ may be hydrogen and $R^{3B}$ may be unsubstituted pyrrolidinyl. $R^{3A}$ may be hydrogen and $R^{3B}$ may be unsubstituted pyrrolyl. $R^{3A}$ may be hydrogen and $R^{3B}$ may be unsubstituted tetrahydrofuranyl. $R^{3A}$ may be hydrogen and $R^{3B}$ may be unsubstituted furanyl. $R^{3A}$ may be hydrogen and $R^{3B}$ may be unsubstituted thiolanyl. $R^{3A}$ may be hydrogen and $R^{3B}$ may be unsubstituted thienyl. $R^{3A}$ may be hydrogen and $R^{3B}$ may be unsubstituted imidazolidinyl. $R^{3A}$ may be hydrogen and $R^{3B}$ may be unsubstituted pyrazolidinyl. $R^{3A}$ may be hydrogen and $R^{3B}$ may be unsubstituted imidazolyl. $R^{3A}$ may be hydrogen and $R^{3B}$ may be unsubstituted pyrazolyl. $R^{3A}$ may be hydrogen and $R^{3B}$ may be unsubstituted oxazolidinyl. $R^{3A}$ may be hydrogen and $R^{3B}$ may be unsubstituted isoxazolidinyl. $R^{3A}$ may be hydrogen and $R^{3B}$ may be unsubstituted oxazolyl. $R^{3A}$ may be hydrogen and $R^{3B}$ may be unsubstituted isoxazolyl. $R^{3A}$ may be hydrogen and $R^{3B}$ may be unsubstituted thiazolidinyl. $R^{3A}$ may be hydrogen and $R^{3B}$ may be unsubstituted isothiazolidinyl. $R^{3A}$ may be hydrogen and $R^{3B}$ may be unsubstituted thiazolyl. $R^{3A}$ may be hydrogen and $R^{3B}$ may be unsubstituted isothiazolyl. $R^{3A}$ may be hydrogen and $R^{3B}$ may be unsubstituted dioxolanyl. $R^{3A}$ may be hydrogen and $R^{3B}$ may be unsubstituted dithiolanyl. $R^{3A}$ may be hydrogen and $R^{3B}$ may be unsubstituted triazolyl. $R^{3A}$ may be hydrogen and $R^{3B}$ may be unsubstituted furazanyl. $R^{3A}$ may be hydrogen and $R^{3B}$ may be unsubstituted oxadiazolyl. $R^{3A}$ may be hydrogen and $R^{3B}$ may be unsubstituted thiadiazolyl. $R^{3A}$ may be hydrogen and $R^{3B}$ may be unsubstituted dithiazolyl. $R^{3A}$ may be hydrogen and $R^{3B}$ may be unsubstituted tetrazolyl. $R^{3A}$ may be hydrogen and $R^{3B}$ may be unsubstituted piperidinyl. $R^{3A}$ may be hydrogen and $R^{3B}$ may be unsubstituted pyridinyl. $R^{3A}$ may be hydrogen and $R^{3B}$ may be unsubstituted oxanyl. $R^{3A}$ may be hydrogen and $R^{3B}$ may be unsubstituted pyranyl. $R^{3A}$ may be hydrogen and $R^{3B}$ may be unsubstituted thianyl. $R^{3A}$ may be hydrogen and $R^{3B}$ may be unsubstituted thiopyranyl. $R^{3A}$ may be hydrogen and $R^{3B}$ may be unsubstituted piperazinyl. $R^{3A}$ may be hydrogen and $R^{3B}$ may be unsubstituted diazinyl. $R^{3A}$ may be hydrogen and $R^{3B}$ may be unsubstituted morpholinyl. $R^{3A}$ may be hydrogen and $R^{3B}$ may be unsubstituted oxazinyl. $R^{3A}$ may be hydrogen and $R^{3B}$ may be unsubstituted thiomorpholinyl. $R^{3A}$ may be hydrogen and $R^{3B}$ may be unsubstituted thiazinyl. $R^{3A}$ may be hydrogen and $R^{3B}$ may be unsubstituted dioxanyl. $R^{3A}$ may be hydrogen and $R^{3B}$ may be unsubstituted dioxinyl. $R^{3A}$ may be hydrogen and $R^{3B}$ may be unsubstituted dithianyl. $R^{3A}$ may be hydrogen and $R^{3B}$ may be unsubstituted dithiinyl. $R^{3A}$ may be hydrogen and $R^{3B}$ may be unsubstituted triazinyl. $R^{3A}$ may be hydrogen and $R^{3B}$ may be unsubstituted trioxanyl. $R^{3A}$ may be hydrogen and $R^{3B}$ may be unsubstituted trithianyl. $R^{3A}$ may be hydrogen and $R^{3B}$ may be unsubstituted tetrazinyl. $R^{3A}$ may be substituted or unsubstituted tetrazolyl. $R^{3A}$ may be substituted tetrazolyl. $R^{3A}$ may be unsubstituted tetrazolyl. $R^{3B}$ may be substituted or unsubstituted tetrazolyl. $R^{3B}$ may be substituted tetrazolyl. $R^{3B}$ may be unsubstituted tetrazolyl.

$R^{3A}$ may independently be hydrogen, —C(NH)NH$_2$, —C(NH)R$^{3D}$, —C(NR$^{3C}$)N$_2$, —C(NR$^{3C}$)R$^{3D}$, —C(NCN)NH$_2$, NH$_2$, substituted or unsubstituted cycloalkyl, substituted or unsubstituted heterocycloalkyl, substituted or unsubstituted aryl, or substituted or unsubstituted heteroaryl. $R^{3A}$ may independently be —C(NH)NH$_2$, —C(NH)R$^{3D}$, —C(NR$^{3C}$) NH$_2$, —C(NR$^3$)R$^{3D}$, —C(NCN)NH$_2$, NH$_2$, or a detectable moiety.

$R^{3A}$ may independently be substituted or unsubstituted $C_1$-$C_{10}$ alkyl. $R^{3A}$ may independently be substituted $C_1$-$C_{10}$ alkyl. $R^{3A}$ may independently be unsubstituted $C_1$-$C_{10}$ alkyl. $R^{3A}$ may independently be $R^{10}$-substituted or unsubstituted $C_1$-$C_{10}$ alkyl. $R^{3A}$ may independently be $R^{10}$-substituted $C_1$-$C_{10}$ alkyl. $R^{3A}$ may independently be substituted or unsubstituted $C_1$-$C_8$ alkyl. $R^{3A}$ may independently be substituted $C_1$-$C_8$ alkyl. $R^{3A}$ may independently be unsubstituted $C_1$-$C_8$ alkyl. $R^{3A}$ may independently be $R^{10}$-substituted or unsubstituted $C_1$-$C_8$ alkyl. $R^{3A}$ may independently be $R^{10}$-substituted $C_1$-$C_8$ alkyl. $R^{3A}$ may independently be substituted or unsubstituted $C_1$-$C_5$ alkyl. $R^{3A}$ may independently be substituted $C_1$-$C_5$ alkyl. $R^{3A}$ may independently be unsubstituted $C_1$-$C_5$ alkyl. $R^{3A}$ may independently be $R^{10}$-substituted or unsubstituted $C_1$-$C_5$ alkyl. $R^{3A}$ may independently be $R^{10}$-substituted $C_1$-$C_5$ alkyl. $R^{3A}$ may independently be substituted or unsubstituted $C_1$-$C_3$ alkyl. $R^{3A}$ may independently be substituted $C_1$-$C_3$ alkyl. $R^{3A}$ may independently be unsubstituted $C_1$-$C_3$ alkyl. $R^{3A}$ may independently be $R^{10}$-substituted or unsubstituted $C_1$-$C_3$ alkyl. $R^{3A}$ may independently be $R^{10}$-substituted $C_1$-$C_3$ alkyl. In embodiments, one of $R^{3A}$ is hydrogen.

$R^{3A}$ may independently be substituted or unsubstituted 2 to 10 membered heteroalkyl. $R^{3A}$ may independently be substituted 2 to 10 membered heteroalkyl. $R^{3A}$ may independently be unsubstituted 2 to 10 membered heteroalkyl. $R^{3A}$ may independently be $R^{10}$-substituted or unsubstituted 2 to 10 membered heteroalkyl. $R^{3A}$ may independently be $R^{10}$-substituted 2 to 10 membered heteroalkyl. $R^{3A}$ may independently be substituted or unsubstituted 2 to 8 membered heteroalkyl. $R^{3A}$ may independently be substituted 2 to 8 membered heteroalkyl. $R^{3A}$ may independently be unsubstituted 2 to 8 membered heteroalkyl. $R^{3A}$ may independently be $R^{10}$-substituted or unsubstituted 2 to 8 membered heteroalkyl. $R^{3A}$ may independently be $R^{10}$-substituted 2 to 8 membered heteroalkyl. $R^{3A}$ may independently be substituted or unsubstituted 2 to 6 membered heteroalkyl. $R^{3A}$ may independently be substituted 2 to 6 membered heteroalkyl. $R^{3A}$ may independently be unsubstituted 2 to 6 membered heteroalkyl. $R^{3A}$ may independently be $R^{10}$-substituted or unsubstituted 2 to 6 membered heteroalkyl. $R^{3A}$ may independently be $R^{10}$-substituted 2 to 6 membered heteroalkyl. In embodiments, $R^{3A}$ is hydrogen.

$R^{3A}$ may independently be substituted or unsubstituted $C_3$-$C_8$ cycloalkyl. $R^{3A}$ may independently be unsubstituted $C_3$-$C_8$ cycloalkyl. $R^{3A}$ may independently be substituted $C_3$-$C_8$ cycloalkyl. $R^{3A}$ may independently be $R^{10}$-substituted or unsubstituted $C_3$-$C_8$ cycloalkyl. $R^{3A}$ may independently be $R^{10}$-substituted $C_3$-$C_8$ cycloalkyl. $R^{3A}$ may independently be substituted or unsubstituted $C_3$-$C_6$ cycloalkyl. $R^{3A}$ may independently be substituted $C_3$-$C_6$ cycloalkyl. $R^{3A}$ may independently be unsubstituted $C_3$-$C_6$ cycloalkyl. $R^{3A}$ may independently be $R^{10}$-substituted or unsubstituted $C_3$-$C_6$ cycloalkyl. $R^{3A}$ may independently be $R^{10}$-substituted $C_3$-$C_6$ cycloalkyl. $R^{3A}$ may independently be substituted or unsubstituted $C_4$-$C_6$ cycloalkyl. $R^{3A}$ may independently be substituted $C_4$-$C_6$ cycloalkyl. $R^{3A}$ may independently be unsubstituted $C_4$-$C_6$ cycloalkyl. $R^{3A}$ may independently be $R^{10}$-substituted or unsubstituted $C_4$-$C_6$ cycloalkyl. $R^{3A}$ may independently be $R^{10}$-substituted $C_4$-$C_6$ cycloalkyl. $R^{3A}$ may independently be substituted or unsubstituted $C_4$ cycloalkyl. $R^{3A}$ may independently be substituted $C_4$ cycloalkyl. $R^{3A}$ may independently be unsubstituted $C_4$ cycloalkyl. $R^{3A}$ may independently be $R^{10}$-substituted or unsubstituted $C_4$ cycloalkyl. $R^{3A}$ may independently be $R^{10}$-substituted $C_4$ cycloalkyl. $R^{3A}$ may independently be substituted or unsubstituted $C_5$ cycloalkyl. $R^{3A}$ may independently be substituted $C_5$ cycloalkyl. $R^{3A}$ may independently be unsubstituted $C_5$ cycloalkyl. $R^{3A}$ may independently be $R^{10}$-substituted or unsubstituted $C_5$ cycloalkyl. $R^{3A}$ may independently be $R^{10}$-substituted $C_5$ cycloalkyl. $R^{3A}$ may independently be substituted or unsubstituted $C_6$ cycloalkyl. $R^{3A}$ may independently be substituted $C_6$ cycloalkyl. $R^{3A}$ may independently be unsubstituted $C_6$ cycloalkyl. $R^{3A}$ may independently be $R^{10}$-substituted or unsubstituted $C_6$ cycloalkyl. $R^{3A}$ may independently be $R^{10}$-substituted $C_6$ cycloalkyl.

$R^{3A}$ may independently be substituted or unsubstituted 3 to 8 membered heterocycloalkyl. $R^{3A}$ may independently be unsubstituted 3 to 8 membered heterocycloalkyl. $R^{3A}$ may independently be substituted 3 to 8 membered heterocycloalkyl. $R^{3A}$ may independently be $R^{10}$-substituted or unsubstituted 3 to 8 membered heterocycloalkyl. $R^{3A}$ may independently be $R^{10}$-substituted 3 to 8 membered heterocycloalkyl. $R^{3A}$ may independently be substituted or unsubstituted 3 to 6 membered heterocycloalkyl. $R^{3A}$ may independently be substituted 3 to 6 membered heterocycloalkyl. $R^{3A}$ may independently be unsubstituted 3 to 6 membered heterocycloalkyl. $R^{3A}$ may independently be $R^{10}$-substituted or unsubstituted 3 to 6 membered heterocycloalkyl. $R^{3A}$ may independently be $R^{10}$-substituted 3 to 6 membered heterocycloalkyl. $R^{3A}$ may independently be substituted or unsubstituted 4 to 6 membered heterocycloalkyl. $R^{3A}$ may independently be substituted 4 to 6 membered heterocycloalkyl. $R^{3A}$ may independently be unsubstituted 4 to 6 membered heterocycloalkyl. $R^{3A}$ may independently be $R^{10}$-substituted or unsubstituted 4 to 6 membered heterocycloalkyl. $R^{3A}$ may independently be $R^{10}$-substituted 4 to 6 membered heterocycloalkyl. $R^{3A}$ may independently be substituted or unsubstituted 4 membered heterocycloalkyl. $R^{3A}$ may independently be substituted 4 membered heterocycloalkyl. $R^{3A}$ may independently be unsubstituted 4 membered heterocycloalkyl. $R^{3A}$ may independently be $R^{10}$-substituted or unsubstituted 4 membered heterocycloalkyl. $R^{3A}$ may independently be $R^{10}$-substituted 4 membered heterocycloalkyl. $R^{3A}$ may independently be substituted or unsubstituted 5 membered heterocycloalkyl. $R^{3A}$ may independently be substituted 5 membered heterocycloalkyl. $R^{3A}$ may independently be unsubstituted 5 membered heterocycloalkyl. $R^{3A}$ may independently be $R^{10}$-substituted or unsubstituted 5 membered heterocycloalkyl. $R^{3A}$ may independently be $R^{10}$-substituted 5 membered heterocycloalkyl. $R^{3A}$ may independently be substituted or unsubstituted 6 membered heterocycloalkyl. $R^{3A}$ may independently be substituted 6 membered heterocycloalkyl. $R^{3A}$ may independently be unsubstituted 6 membered heterocycloalkyl. $R^{3A}$ may independently be $R^{10}$-substituted or unsubstituted 6 membered heterocycloalkyl. $R^{3A}$ may independently be $R^{10}$-substituted 6 membered heterocycloalkyl.

$R^{3A}$ may independently be substituted or unsubstituted $C_6$-$C_{10}$ aryl. $R^{3A}$ may independently be substituted $C_6$-$C_{10}$ aryl. $R^{3A}$ may independently be unsubstituted $C_6$-$C_{10}$ aryl. $R^{3A}$ may independently be $R^{10}$-substituted or unsubstituted $C_6$-$C_{10}$ aryl. $R^{3A}$ may independently be $R^{10}$-substituted $C_6$-$C_{10}$ aryl. $R^{3A}$ may independently be substituted or unsubstituted $C_{10}$ aryl. $R^{3A}$ may independently be substituted $C_{10}$ aryl. $R^{3A}$ may independently be unsubstituted $C_{10}$ aryl. $R^{3A}$ may independently be $R^{10}$-substituted or unsubstituted $C_{10}$ aryl. $R^{3A}$ may independently be $R^{10}$-substituted $C_{10}$ aryl. $R^{3A}$ may independently be substituted or unsubstituted $C_{10}$ aryl. $R^{3A}$ may independently be substituted $C_{10}$ aryl. $R^{3A}$ may independently be unsubstituted $C_{10}$ aryl. $R^{3A}$ may independently be $R^{10}$-substituted or unsubstituted $C_{10}$ aryl. $R^{3A}$ may independently be $R^{10}$-substituted $C_{10}$ aryl. $R^{3A}$ may independently be substituted or unsubstituted $C_6$ aryl. $R^{3A}$ may independently be substituted $C_6$ aryl. $R^{3A}$ may independently be unsubstituted $C_6$ aryl. $R^{3A}$ may independently be $R^{10}$-substituted or unsubstituted $C_6$ aryl. $R^{3A}$ may independently be $R^{10}$-substituted $C_6$ aryl.

$R^{3A}$ may independently be substituted or unsubstituted 5-10 membered heteroaryl. $R^{3A}$ may independently be substituted 5-10 membered heteroaryl. $R^{3A}$ may independently be unsubstituted 5-10 membered heteroaryl. $R^{3A}$ may independently be $R^{10}$-substituted or unsubstituted 5-10 membered heteroaryl. $R^{3A}$ may independently be $R^{10}$-substituted 5-10 membered heteroaryl. $R^{3A}$ may independently be substituted or unsubstituted 5-6 membered heteroaryl. $R^{3A}$ may independently be substituted 5-6 membered heteroaryl. $R^{3A}$ may independently be unsubstituted 5-6 membered heteroaryl. $R^{3A}$ may independently be $R^{10}$-substituted or unsubstituted 5-6 membered heteroaryl. $R^{3A}$ may independently be $R^{10}$-substituted 5-6 membered heteroaryl. $R^{3A}$ may independently be substituted or unsubstituted 5 membered heteroaryl. $R^{3A}$ may independently be substituted 5 membered heteroaryl. $R^{3A}$ may independently be unsubstituted 5 membered heteroaryl. $R^{3A}$ may independently be $R^{10}$-substituted or unsubstituted 5 membered heteroaryl. $R^{3A}$ may independently be $R^{10}$-substituted 5 membered heteroaryl. $R^{3A}$ may independently be substituted or unsubstituted 6 membered heteroaryl. $R^{3A}$ may independently be substituted 6 membered heteroaryl. $R^{3A}$ may independently be unsubstituted 6 membered heteroaryl. $R^{3A}$ may independently be $R^{10}$-substituted or unsubstituted 6 membered heteroaryl. $R^{3A}$ may independently be $R^{10}$-substituted 6 membered heteroaryl.

$R^{3A}$ may be independently $R^{10}$-substituted or unsubstituted cycloalkyl, $R^{10}$-substituted or unsubstituted heterocycloalkyl, $R^{10}$-substituted or unsubstituted aryl, or $R^{10}$-substituted or unsubstituted heteroaryl. $R^{3A}$ may be independently substituted or unsubstituted 5 or 6 membered cycloalkyl, substituted or unsubstituted 5 or 6 membered heterocycloalkyl, substituted or unsubstituted 6 membered aryl or substituted or unsubstituted 5 or 6 membered heteroaryl. $R^{3A}$ may be independently hydrogen, —C(NH)NH$_2$, or —C(NCN)NH$_2$. $R^{3A}$ may be independently hydrogen or —C(NH)NH$_2$. $R^{3A}$ may be independently hydrogen or —C(NCN)NH$_2$. $R^{3A}$ may be independently —C(NH)NH$_2$, or —C(NCN)NH$_2$. $R^{3A}$ may be independently hydrogen or —C(NH)$R^{3C}$. $R^{3A}$ may independently be hydrogen. $R^{3A}$ may independently be hydrogen or substituted or unsubstituted cycloalkyl as described herein. $R^{3A}$ may be independently hydrogen or substituted or unsubstituted heterocycloalkyl as described herein. $R^{3A}$ may be independently hydrogen or substituted or unsubstituted aryl as described herein. $R^{3A}$ may be independently hydrogen or substituted or unsubstituted heteroaryl as described herein.

$R^{3B}$ may independently be hydrogen, —C(NH)NH$_2$, —C(NH)$R^{3D}$, —C(NR$^{3C}$)NH$_2$, —C(NR$^{3C}$)R$^{3D}$, —C(NCN)NH$_2$, NH$_2$, substituted or unsubstituted cycloalkyl, substituted or unsubstituted heterocycloalkyl, substituted or unsubstituted aryl, or substituted or unsubstituted heteroaryl. $R^{3B}$ may independently be —C(NH)NH$_2$, —C(NH)$R^{3D}$, —C(NR$^{3C}$)$_2$, —C(NR$^{3C}$)R$^{3D}$, —C(NCN)NH$_2$, NH$_2$, or a detectable moiety.

$R^{3B}$ may independently be substituted or unsubstituted $C_1$-$C_{10}$ alkyl. $R^{3B}$ may independently be substituted $C_1$-$C_{10}$ alkyl. $R^{3B}$ may independently be unsubstituted $C_1$-$C_{10}$ alkyl. $R^{3B}$ may independently be $R^{10}$-substituted or unsubstituted $C_1$-$C_{10}$ alkyl. $R^{3B}$ may independently be $R^{10}$-substituted $C_1$-$C_{10}$ alkyl. $R^{3B}$ may independently be substituted or unsubstituted $C_1$-$C_8$ alkyl. $R^{3B}$ may independently be substituted $C_1$-$C_8$ alkyl. $R^{3B}$ may independently be unsubstituted $C_1$-$C_8$ alkyl. $R^{3B}$ may independently be $R^{10}$-substituted or unsubstituted $C_1$-$C_8$ alkyl. $R^{3B}$ may independently be $R^{10}$-substituted $C_1$-$C_8$ alkyl. $R^{3B}$ may independently be substituted or unsubstituted $C_1$-$C_5$ alkyl. $R^{3B}$ may independently be substituted $C_1$-$C_5$ alkyl. $R^{3B}$ may independently be unsubstituted $C_1$-$C_5$ alkyl. $R^{3B}$ may independently be $R^{10}$-substituted or unsubstituted $C_1$-$C_5$ alkyl. $R^{3B}$ may independently be $R^{10}$-substituted $C_1$-$C_5$ alkyl. $R^{3B}$ may independently be substituted or unsubstituted $C_1$-$C_3$ alkyl. $R^{3B}$ may independently be substituted $C_1$-$C_3$ alkyl. $R^{3B}$ may independently be unsubstituted $C_1$-$C_3$ alkyl. $R^{3B}$ may independently be $R^{10}$-substituted or unsubstituted $C_1$-$C_3$ alkyl. $R^{3B}$ may independently be $R^{10}$-substituted $C_1$-$C_3$ alkyl. In embodiments, one of $R^{3B}$ is hydrogen.

$R^{3B}$ may independently be substituted or unsubstituted 2 to 10 membered heteroalkyl. $R^{3B}$ may independently be substituted 2 to 10 membered heteroalkyl. $R^{3B}$ may independently be unsubstituted 2 to 10 membered heteroalkyl. $R^{3B}$ may independently be $R^{10}$-substituted or unsubstituted 2 to 10 membered heteroalkyl. $R^{3B}$ may independently be $R^{10}$-substituted 2 to 10 membered heteroalkyl. $R^{3B}$ may independently be substituted or unsubstituted 2 to 8 membered heteroalkyl. $R^{3B}$ may independently be substituted 2 to 8 membered heteroalkyl. $R^{3B}$ may independently be unsubstituted 2 to 8 membered heteroalkyl. $R^{3B}$ may independently be $R^{10}$-substituted or unsubstituted 2 to 8 membered heteroalkyl. $R^{3B}$ may independently be $R^{10}$-substituted 2 to 8 membered heteroalkyl. $R^{3B}$ may independently be substituted or unsubstituted 2 to 6 membered heteroalkyl. $R^{3B}$ may independently be substituted 2 to 6 membered heteroalkyl. $R^{3B}$ may independently be unsubstituted 2 to 6 membered heteroalkyl. $R^{3B}$ may independently be $R^{10}$-substituted or unsubstituted 2 to 6 membered heteroalkyl. $R^{3B}$ may independently be $R^{10}$-substituted 2 to 6 membered heteroalkyl. In embodiments, $R^{3B}$ is hydrogen.

$R^{3B}$ may independently be substituted or unsubstituted $C_3$-$C_8$ cycloalkyl. $R^{3B}$ may independently be unsubstituted $C_3$-$C_8$ cycloalkyl. $R^{3B}$ may independently be substituted $C_3$-$C_8$ cycloalkyl. $R^{3B}$ may independently be $R^{10}$-substituted or unsubstituted $C_3$-$C_8$ cycloalkyl. $R^{3B}$ may independently be $R^{10}$-substituted $C_3$-$C_8$ cycloalkyl. $R^{3B}$ may independently be substituted or unsubstituted $C_3$-$C_6$ cycloalkyl. $R^{3B}$ may independently be substituted $C_3$-$C_6$ cycloalkyl. $R^{3B}$ may independently be unsubstituted $C_3$-$C_6$ cycloalkyl. $R^{3B}$ may independently be $R^{10}$-substituted or unsubstituted $C_3$-$C_6$ cycloalkyl. $R^{3B}$ may independently be $R^{10}$-substituted $C_3$-$C_6$ cycloalkyl. $R^{3B}$ may independently be substituted or unsubstituted $C_4$-$C_6$ cycloalkyl. $R^{3B}$ may independently be substituted $C_4$-$C_6$ cycloalkyl. $R^{3B}$ may independently be unsubstituted $C_4$-$C_6$ cycloalkyl. $R^{3B}$ may independently be $R^{10}$-substituted or unsubstituted $C_4$-$C_6$ cycloalkyl. $R^{3B}$ may independently be $R^{10}$-substituted $C_4$-$C_6$ cycloalkyl. $R^{3B}$ may independently be substituted or unsubstituted $C_4$ cycloalkyl. $R^{3B}$ may independently be substituted $C_4$ cycloalkyl. $R^{3B}$ may independently be unsubstituted $C_4$ cycloalkyl. $R^{3B}$ may independently be $R^{10}$-substituted or unsubstituted $C_4$ cycloalkyl. $R^{3B}$ may independently be $R^{10}$-substituted $C_4$ cycloalkyl. $R^{3B}$ may independently be substituted or unsubstituted $C_5$ cycloalkyl. $R^{3B}$ may independently be substituted $C_5$ cycloalkyl. $R^{3B}$ may independently be unsubstituted $C_5$ cycloalkyl. $R^{3B}$ may independently be $R^{10}$-substituted or unsubstituted $C_5$ cycloalkyl. $R^{3B}$ may independently be $R^{10}$-substituted $C_5$ cycloalkyl. $R^{3B}$ may independently be substituted or unsubstituted $C_6$ cycloalkyl. $R^{3B}$ may independently be substituted $C_6$ cycloalkyl. $R^{3B}$ may independently be unsubstituted $C_6$ cycloalkyl. $R^{3B}$ may independently be $R^{10}$-substituted or unsubstituted $C_6$ cycloalkyl. $R^{3B}$ may independently be $R^{10}$-substituted $C_6$ cycloalkyl.

$R^{3B}$ may independently be substituted or unsubstituted 3 to 8 membered heterocycloalkyl. $R^{3B}$ may independently be unsubstituted 3 to 8 membered heterocycloalkyl. $R^{3B}$ may independently be substituted 3 to 8 membered heterocycloalkyl. $R^{3B}$ may independently be $R^{10}$-substituted or unsubstituted 3 to 8 membered heterocycloalkyl. $R^{3B}$ may independently be $R^{10}$-substituted 3 to 8 membered heterocycloalkyl. $R^{3B}$ may independently be substituted or unsubstituted 3 to 6 membered heterocycloalkyl. $R^{3B}$ may independently be substituted 3 to 6 membered heterocycloalkyl. $R^{3B}$ may independently be unsubstituted 3 to 6 membered heterocycloalkyl. $R^{3B}$ may independently be $R^{10}$-substituted or unsubstituted 3 to 6 membered heterocycloalkyl. $R^{3B}$ may independently be $R^{10}$-substituted 3 to 6 membered heterocycloalkyl. $R^{3B}$ may independently be substituted or unsubstituted 4 to 6 membered heterocycloalkyl. $R^{3B}$ may independently be substituted 4 to 6 membered heterocycloalkyl. $R^{3B}$ may independently be unsubstituted 4 to 6 membered heterocycloalkyl. $R^{3B}$ may independently be $R^{10}$-substituted or unsubstituted 4 to 6 membered heterocycloalkyl. $R^{3B}$ may independently be $R^{10}$-substituted 4 to 6 membered heterocycloalkyl. $R^{3B}$ may independently be substituted or unsubstituted 4 membered heterocycloalkyl. $R^{3B}$ may independently be substituted 4 membered heterocycloalkyl. $R^{3B}$ may independently be unsubstituted 4 membered heterocycloalkyl. $R^{3B}$ may independently be $R^{10}$-substituted or unsubstituted 4 membered heterocycloalkyl. $R^{3B}$ may independently be $R^{10}$-substituted 4 membered heterocycloalkyl. $R^{3B}$ may independently be substituted or unsubstituted 5 membered heterocycloalkyl. $R^{3B}$ may independently be substituted 5 membered heterocycloalkyl. $R^{3B}$ may independently be unsubstituted 5 membered heterocycloalkyl. $R^{3B}$ may independently be $R^{10}$-substituted or unsubstituted 5 membered heterocycloalkyl. $R^{3B}$ may independently be $R^{10}$-substituted 5 membered heterocycloalkyl. $R^{3B}$ may independently be substituted or unsubstituted 6 membered heterocycloalkyl. $R^{3B}$ may independently be substituted 6 membered heterocycloalkyl. $R^{3B}$ may independently be unsubstituted 6 membered heterocycloalkyl. $R^{3B}$ may independently be $R^{10}$-substituted or unsubstituted 6 membered heterocycloalkyl. $R^{3B}$ may independently be $R^{10}$-substituted 6 membered heterocycloalkyl.

$R^{3B}$ may independently be substituted or unsubstituted $C_6$-$C_{10}$ aryl. $R^{3B}$ may independently be substituted $C_6$-$C_{10}$ aryl. $R^{3B}$ may independently be unsubstituted $C_6$-$C_{10}$ aryl. $R^{3B}$ may independently be $R^{10}$-substituted or unsubstituted $C_6$-$C_{10}$ aryl. $R^{3B}$ may independently be $R^{10}$-substituted $C_6$-$C_{10}$ aryl. $R^{3B}$ may independently be substituted or unsubstituted $C_{10}$ aryl. $R^{3B}$ may independently be substituted $C_{10}$ aryl. $R^{3B}$ may independently be unsubstituted $C_{10}$ aryl. $R^{3B}$ may independently be $R^{10}$-substituted or unsubstituted $C_{10}$ aryl. $R^{3B}$ may independently be $R^{10}$-substituted $C_{10}$ aryl. $R^{3B}$ may independently be substituted or unsubstituted $C_{10}$ aryl. $R^{3B}$ may independently be substituted $C_{10}$ aryl. $R^{3B}$ may independently be unsubstituted $C_{10}$ aryl. $R^{3B}$ may independently be $R^{10}$-substituted or unsubstituted $C_{10}$ aryl. $R^{3B}$ may independently be $R^{10}$-substituted $C_{10}$ aryl. $R^{3B}$ may independently be substituted or unsubstituted $C_6$ aryl. $R^{3B}$ may independently be substituted $C_6$ aryl. $R^{3B}$ may independently be unsubstituted $C_6$ aryl. $R^{3B}$ may independently be $R^{10}$-substituted or unsubstituted $C_6$ aryl. $R^{3B}$ may independently be $R^{10}$-substituted $C_6$ aryl.

$R^{3B}$ may independently be substituted or unsubstituted 5-10 membered heteroaryl. $R^{3B}$ may independently be substituted 5-10 membered heteroaryl. $R^{3B}$ may independently be unsubstituted 5-10 membered heteroaryl. $R^{3B}$ may independently be $R^{10}$-substituted or unsubstituted 5-10 membered heteroaryl. $R^{3B}$ may independently be $R^{10}$-substituted 5-10 membered heteroaryl. $R^{3B}$ may independently be substituted or unsubstituted 5-6 membered heteroaryl. $R^{3B}$ may independently be substituted 5-6 membered heteroaryl. $R^{3B}$ may independently be unsubstituted 5-6 membered heteroaryl. $R^{3B}$ may independently be $R^{10}$-substituted or unsubstituted 5-6 membered heteroaryl. $R^{3B}$ may independently be $R^{10}$-substituted 5-6 membered heteroaryl. $R^{3B}$ may independently be substituted or unsubstituted 5 membered heteroaryl. $R^{3B}$ may independently be substituted 5 membered heteroaryl. $R^{3B}$ may independently be unsubstituted 5 membered heteroaryl. $R^{3B}$ may independently be $R^{10}$-substituted or unsubstituted 5 membered heteroaryl. $R^{3B}$ may independently be $R^{10}$-substituted 5 membered heteroaryl. $R^{3B}$ may independently be substituted or unsubstituted 6 membered heteroaryl. $R^{3B}$ may independently be substituted 6 membered heteroaryl. $R^{3B}$ may independently be unsubstituted 6 membered heteroaryl. $R^{3B}$ may independently be $R^{10}$-substituted or unsubstituted 6 membered heteroaryl. $R^{3B}$ may independently be $R^{10}$-substituted 6 membered heteroaryl.

$R^{3B}$ may be independently $R^{10}$-substituted or unsubstituted cycloalkyl, $R^{10}$-substituted or unsubstituted heterocycloalkyl, $R^{10}$-substituted or unsubstituted aryl, or $R^{10}$-substituted or unsubstituted heteroaryl. $R^{3B}$ may be independently substituted or unsubstituted 5 or 6 membered cycloalkyl, substituted or unsubstituted 5 or 6 membered heterocycloalkyl, substituted or unsubstituted 6 membered aryl or substituted or unsubstituted 5 or 6 membered heteroaryl. $R^{3B}$ may be independently hydrogen, —C(NH)NH$_2$, or —C(NCN)NH$_2$. $R^{3B}$ may be independently hydrogen or —C(NH)NH$_2$. $R^{3B}$ may be independently hydrogen or —C(NCN)NH$_2$. $R^{3B}$ may be independently —C(NH)NH$_2$, or —C(NCN)NH$_2$. $R^{3B}$ may be independently hydrogen or —C(NH)R$^{3C}$. $R^{3B}$ may independently be hydrogen. $R^{3B}$ may independently be hydrogen or substituted or unsubstituted cycloalkyl as described herein. $R^{3B}$ may be independently hydrogen or substituted or unsubstituted heterocycloalkyl as described herein. $R^{3B}$ may be independently hydrogen or substituted or unsubstituted aryl as described herein. $R^{3B}$ may be independently hydrogen or substituted or unsubstituted heteroaryl as described herein.

$R^{3B}$ may be hydrogen and $R^{3A}$ may be unsubstituted pyrrolidinyl. $R^{3B}$ may be hydrogen and $R^{3A}$ may be unsubstituted pyrrolyl. $R^{3B}$ may be hydrogen and $R^{3A}$ may be unsubstituted tetrahydrofuranyl. $R^{3B}$ may be hydrogen and $R^{3A}$ may be unsubstituted furanyl. $R^{3B}$ may be hydrogen and $R^{3A}$ may be unsubstituted thiolanyl. $R^{3B}$ may be hydrogen and $R^{3A}$ may be unsubstituted thienyl. $R^{3B}$ may be hydrogen and $R^{3A}$ may be unsubstituted imidazolidinyl. $R^{3B}$ may be hydrogen and $R^{3A}$ may be unsubstituted pyrazolidinyl. $R^{3B}$ may be hydrogen and $R^{3A}$ may be unsubstituted imidazolyl. $R^{3B}$ may be hydrogen and $R^{3A}$ may be unsubstituted pyrazolyl. $R^{3B}$ may be hydrogen and $R^{3A}$ may be unsubstituted oxazolidinyl. $R^{3B}$ may be hydrogen and $R^{3A}$ may be unsubstituted isoxazolidinyl. $R^{3B}$ may be hydrogen and $R^{3A}$ may be unsubstituted oxazolyl. $R^{3B}$ may be hydrogen and $R^{3A}$ may be unsubstituted isoxazolyl. $R^{3B}$ may be hydrogen and $R^{3A}$ may be unsubstituted thiazolidinyl. $R^{3B}$ may be hydrogen and $R^{3A}$ may be unsubstituted isothiazolidinyl. $R^{3B}$ may be hydrogen and $R^{3A}$ may be unsubstituted thiazolyl. $R^{3B}$ may be hydrogen and $R^{3A}$ may be unsubstituted isothiazolyl. $R^{3B}$ may be hydrogen and $R^{3A}$ may be unsubstituted dioxolanyl. $R^{3B}$ may be hydrogen and $R^{3A}$ may be unsubstituted dithiolanyl. $R^{3B}$ may be hydrogen and $R^{3A}$ may be unsubstituted triazolyl. $R^{3B}$ may be hydrogen and $R^{3A}$ may be unsubstituted furazanyl. $R^{3B}$ may be hydrogen and $R^{3A}$ may be unsubstituted oxadiazolyl. $R^{3B}$ may be hydrogen and $R^{3A}$ may be unsubstituted thiadiazolyl. $R^{3B}$ may be hydrogen and $R^{3A}$ may be unsubstituted dithiazolyl. $R^{3B}$ may be hydrogen and $R^{3A}$ may be unsubstituted tetrazolyl. $R^{3B}$ may be hydrogen and $R^{3A}$ may be unsubstituted piperidinyl. $R^{3B}$ may be hydrogen and $R^{3A}$ may be unsubstituted pyridinyl. $R^{3B}$ may be hydrogen and $R^{3A}$ may be unsubstituted oxanyl. $R^{3B}$ may be hydrogen and $R^{3A}$ may be unsubstituted pyranyl. $R^{3B}$ may be hydrogen and $R^{3A}$ may be unsubstituted thianyl. $R^{3B}$ may be hydrogen and $R^{3A}$ may be unsubstituted thiopyranyl. $R^{3B}$ may be hydrogen and $R^{3A}$ may be unsubstituted piperazinyl. $R^{3B}$ may be hydrogen and $R^{3A}$ may be unsubstituted diazinyl. $R^{3B}$ may be hydrogen and $R^{3A}$ may be unsubstituted morpholinyl. $R^{3B}$ may be hydrogen and $R^{3A}$ may be unsubstituted oxazinyl. $R^{3B}$ may be hydrogen and $R^{3A}$ may be unsubstituted thiomorpholinyl. $R^{3B}$ may be hydrogen and $R^{3A}$ may be unsubstituted thiazinyl. $R^{3B}$ may be hydrogen and $R^{3A}$ may be unsubstituted dioxanyl. $R^{3B}$ may be hydrogen and $R^{3A}$ may be unsubstituted dioxinyl. $R^{3B}$ may be hydrogen and $R^{3A}$ may be unsubstituted dithianyl. $R^{3B}$ may be hydrogen and $R^{3A}$ may be unsubstituted dithiinyl. $R^{3B}$ may be hydrogen and $R^{3A}$ may be unsubstituted triazinyl. $R^{3B}$ may be hydrogen and $R^{3A}$ may be unsubstituted trioxanyl. $R^{3B}$ may be hydrogen and $R^{3A}$ may be unsubstituted trithianyl. $R^{3B}$ may be hydrogen and $R^{3A}$ may be unsubstituted tetrazinyl.

$R^{3A}$ may be substituted pyrrolidinyl. $R^{3A}$ may be substituted pyrrolyl. $R^{3A}$ may be substituted tetrahydrofuranyl. $R^{3A}$ may be substituted furanyl. $R^{3A}$ may be substituted thiolanyl. $R^{3A}$ may be substituted thienyl. $R^{3A}$ may be substituted imidazolidinyl. $R^{3A}$ may be substituted pyrazolidinyl. $R^{3A}$ may be substituted imidazolyl. $R^{3A}$ may be substituted pyrazolyl. $R^{3A}$ may be substituted oxazolidinyl. $R^{3A}$ may be substituted isoxazolidinyl. $R^{3A}$ may be substituted oxazolyl. $R^{3A}$ may be substituted isoxazolyl. $R^{3A}$ may be substituted thiazolidinyl. $R^{3A}$ may be substituted isothiazolidinyl. $R^{3A}$ may be substituted thiazolyl. $R^{3A}$ may be substituted isothiazolyl. $R^{3A}$ may be substituted dioxolanyl. $R^{3A}$ may be substituted dithiolanyl. $R^{3A}$ may be substituted triazolyl. $R^{3A}$ may be substituted furazanyl. $R^{3A}$ may be substituted oxadiazolyl. $R^{3A}$ may be substituted thiadiazolyl. $R^{3A}$ may be substituted dithiazolyl. $R^{3A}$ may be substituted tetrazolyl. $R^{3A}$ may be substituted piperidinyl. $R^{3A}$ may be substituted pyridinyl. $R^{3A}$ may be substituted oxanyl. $R^{3A}$ may be substituted pyranyl. $R^{3A}$ may be substituted thianyl. $R^{3A}$ may be substituted thiopyranyl. $R^{3A}$ may be substituted piperazinyl. $R^{3A}$ may be substituted diazinyl. $R^{3A}$ may be substituted morpholinyl. $R^{3A}$ may be substituted oxazinyl. $R^{3A}$ may be substituted thiomorpholinyl. $R^{3A}$ may be substituted thiazinyl. $R^{3A}$ may be substituted dioxanyl. $R^{3A}$ may be substituted dioxinyl. $R^{3A}$ may be substituted dithianyl. $R^{3A}$ may be substituted dithiinyl. $R^{3A}$ may be substituted triazinyl. $R^{3A}$ may be substituted trioxanyl. $R^{3A}$ may be substituted trithianyl. $R^{3A}$ may be substituted tetrazinyl.

$R^{3B}$ may be substituted pyrrolidinyl. $R^{3B}$ may be substituted pyrrolyl. $R^{3B}$ may be substituted tetrahydrofuranyl. $R^{3B}$ may be substituted furanyl. $R^{3B}$ may be substituted thiolanyl. $R^{3B}$ may be substituted thienyl. $R^{3B}$ may be substituted imidazolidinyl. $R^{3B}$ may be substituted pyrazolidinyl. $R^{3B}$ may be substituted imidazolyl. $R^{3B}$ may be substituted pyrazolyl. $R^{3B}$ may be substituted oxazolidinyl. $R^{3B}$ may be substituted isoxazolidinyl. $R^{3B}$ may be substituted oxazolyl. $R^{3B}$ may be substituted isoxazolyl. $R^{3B}$ may be substituted thiazolidinyl. $R^{3B}$ may be substituted isothiazolidinyl. $R^{3B}$ may be substituted thiazolyl. $R^{3B}$ may be substituted isothiazolyl. $R^{3B}$ may be substituted dioxolanyl. $R^{3B}$ may be substituted dithiolanyl. $R^{3B}$ may be substituted triazolyl. $R^{3B}$ may be substituted furazanyl. $R^{3B}$ may be substituted oxadiazolyl. $R^{3B}$ may be substituted thiadiazolyl. $R^{3B}$ may be substituted dithiazolyl. $R^{3B}$ may be substituted tetrazolyl. $R^{3B}$ may be substituted piperidinyl. $R^{3B}$ may be substituted pyridinyl. $R^{3B}$ may be substituted oxanyl. $R^{3B}$ may be substituted pyranyl. $R^{3B}$ may be substituted thianyl. $R^{3B}$ may be substituted thiopyranyl. $R^{3B}$ may be substituted piperazinyl. $R^{3B}$ may be substituted diazinyl. $R^{3B}$ may be substituted morpholinyl. $R^{3B}$ may be substituted oxazinyl. $R^{3B}$ may be substituted thiomorpholinyl. $R^{3B}$ may be substituted thiazinyl. $R^{3B}$ may be substituted dioxanyl. $R^{3B}$ may be substituted dioxinyl. $R^{3B}$ may be substituted dithianyl. $R^{3B}$ may be substituted dithiinyl. $R^{3B}$ may be substituted triazinyl. $R^{3B}$ may be substituted trioxanyl. $R^{3B}$ may be substituted trithianyl. $R^{3B}$ may be substituted tetrazinyl.

$R^{3A}$ may be unsubstituted pyrrolidinyl. $R^{3A}$ may be unsubstituted pyrrolyl. $R^{3A}$ may be unsubstituted tetrahydrofuranyl. $R^{3A}$ may be unsubstituted furanyl. $R^{3A}$ may be unsubstituted thiolanyl. $R^{3A}$ may be unsubstituted thienyl. $R^{3A}$ may be unsubstituted imidazolidinyl. $R^{3A}$ may be unsubstituted pyrazolidinyl. $R^{3A}$ may be unsubstituted imidazolyl. $R^{3A}$ may be unsubstituted pyrazolyl. $R^{3A}$ may be unsubstituted oxazolidinyl. $R^{3A}$ may be unsubstituted isoxazolidinyl. $R^{3A}$ may be unsubstituted oxazolyl. $R^{3A}$ may be unsubstituted isoxazolyl. $R^{3A}$ may be unsubstituted thiazolidinyl. $R^{3A}$ may be unsubstituted isothiazolidinyl. $R^{3A}$ may be unsubstituted thiazolyl. $R^{3A}$ may be unsubstituted isothiazolyl. $R^{3A}$ may be unsubstituted dioxolanyl. $R^{3A}$ may be unsubstituted dithiolanyl. $R^{3A}$ may be unsubstituted triazolyl. $R^{3A}$ may be unsubstituted furazanyl. $R^{3A}$ may be unsubstituted oxadiazolyl. $R^{3A}$ may be unsubstituted thiadiazolyl. $R^{3A}$ may be unsubstituted dithiazolyl. $R^{3A}$ may be unsubstituted tetrazolyl. $R^{3A}$ may be unsubstituted piperidinyl. $R^{3A}$ may be unsubstituted pyridinyl. $R^{3A}$ may be unsubstituted oxanyl. $R^{3A}$ may be unsubstituted pyranyl. $R^{3A}$ may be unsubstituted thianyl. $R^{3A}$ may be unsubstituted thiopyranyl. $R^{3A}$ may be unsubstituted piperazinyl. $R^{3A}$ may be unsubstituted diazinyl. $R^{3A}$ may be unsubstituted morpholinyl. $R^{3A}$ may be unsubstituted oxazinyl. $R^{3A}$ may be unsubstituted thiomorpholinyl. $R^{3A}$ may be unsubstituted thiazinyl. $R^{3A}$ may be unsubstituted dioxanyl. $R^{3A}$ may be unsubstituted dioxinyl. $R^{3A}$ may be unsubstituted dithianyl. $R^{3A}$ may be unsubstituted dithiinyl. $R^{3A}$ may be unsubstituted triazinyl. $R^{3A}$ may be unsubstituted trioxanyl. $R^{3A}$ may be unsubstituted trithianyl. $R^{3A}$ may be unsubstituted tetrazinyl.

$R^{3B}$ may be unsubstituted pyrrolidinyl. $R^{3B}$ may be unsubstituted pyrrolyl. $R^{3B}$ may be unsubstituted tetrahydrofuranyl. $R^{3B}$ may be unsubstituted furanyl. $R^{3B}$ may be unsubstituted thiolanyl. $R^{3B}$ may be unsubstituted thienyl. $R^{3B}$ may be unsubstituted imidazolidinyl. $R^{3B}$ may be unsubstituted pyrazolidinyl. $R^{3B}$ may be unsubstituted imidazolyl. $R^{3B}$ may be unsubstituted pyrazolyl. $R^{3B}$ may be unsubstituted oxazolidinyl. $R^{3B}$ may be unsubstituted isoxazolidinyl. $R^{3B}$ may be unsubstituted oxazolyl. $R^{3B}$ may be unsubstituted isoxazolyl. $R^{3B}$ may be unsubstituted thiazolidinyl. $R^{3B}$ may be unsubstituted isothiazolidinyl. $R^{3B}$ may be unsubstituted thiazolyl. $R^{3B}$ may be unsubstituted isothiazolyl. $R^{3B}$ may be unsubstituted dioxolanyl. $R^{3B}$ may be unsubstituted dithiolanyl. $R^{3B}$ may be unsubstituted triazolyl. $R^{3B}$ may be unsubstituted furazanyl. $R^{3B}$ may be unsubstituted oxadiazolyl. $R^{3B}$ may be unsubstituted thiadiazolyl. $R^{3B}$ may be unsubstituted dithiazolyl. $R^{3B}$ may be unsubstituted tetrazolyl. $R^{3B}$ may be unsubstituted piperidinyl. $R^{3B}$ may be unsubstituted pyridinyl. $R^{3B}$ may be unsubstituted oxanyl. $R^{3B}$ may be unsubstituted pyranyl. $R^{3B}$ may be unsubstituted thianyl. $R^{3B}$ may be unsubstituted thiopyranyl. $R^{3B}$ may be unsubstituted piperazinyl. $R^{3B}$ may be unsubstituted diazinyl. $R^{3B}$ may be unsubstituted morpholinyl. $R^{3B}$ may be unsubstituted oxazinyl. $R^{3B}$ may be unsubstituted thiomorpholinyl. $R^{3B}$ may be unsubstituted thiazinyl. $R^{3B}$ may be unsubstituted dioxanyl. $R^{3B}$ may be unsubstituted dioxinyl. $R^{3B}$ may be unsubstituted dithianyl. $R^{3B}$ may be unsubstituted dithiinyl. $R^{3B}$ may be unsubstituted triazinyl. $R^{3B}$ may be unsubstituted trioxanyl. $R^{3B}$ may be unsubstituted trithianyl. $R^{3B}$ may be unsubstituted tetrazinyl.

$R^{3C}$ is hydrogen, halogen, oxo, $-N_3$, $-CX^{1C}_3$, $-CHX^{1C}_2$, $-CH_2X^{1C}$, $-CN$, $-CHO$, $-OH$, $-NH_2$, $-COOH$, $-CONH_2$, $-NO_2$, $-SH$, $-SO_2$, $-SO_2Cl$, $-SO_2CH_3$, $-SO_3H$, $-SO_4H$, $-SO_2NH_2$, $-NHNH_2$, $-ONH_2$, $-NHC(O)NHNH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^{3C}$ may be hydrogen, halogen, oxo, $-N_3$, $-CX^{1C}_3$, $-CHX^{1C}_2$, $-CH_2X^{1C}$, $-CN$, $-COR^{3E}$, $-OR^{3E}$, $-NR^{3E}R^{3F}$, $-COOR^{3E}$, $-CONR^{3E}R^{3F}$, $-NHC(O)R^{3E}$, $-NO_2$, $-SR^{3E}$, $-SO_{n3}R^{3E}$, $-NHNR^{3E}R^{3F}$, $-ONR^{3E}R^{3F}$, $-NHC(O)NHNR^{3E}R^{3F}$, $-C(NCN)R^{3E}$, $-C(NH)R^{3E}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl or a detectable moiety.

$R^{3C}$ may be hydrogen, halogen, oxo, $-N_3$, $-CX^{1C}_3$, $-CHX^{1C}_2$, $-CH_2X^{1C}$, $-CN$, $-COR^{3E}$, $-OR^{3E}$, $-NR^{3E}R^{3F}$, $-COOR^{3E}$, $-CONR^{3E}R^{3F}$, $-NHC(O)R^{3E}$, $-NO_2$, $-SR^{3E}$, $-SO_{n3}R^{3E}$, $-NHNR^{3E}R^{3F}$, $-ONR^{3E}R^{3F}$, $-NHC(O)NHNR^{3E}R^{3F}$, $-C(NCN)R^{3E}$, $-C(NH)R^{3E}$, substituted or unsubstituted alkyl (e.g. $C_1$-$C_8$ alkyl, $C_1$-$C_6$ alkyl, or $C_1$-$C_4$ alkyl), substituted or unsubstituted heteroalkyl (e.g. 2 to 8 membered heteroalkyl, 2 to 6 membered heteroalkyl, or 2 to 4 membered heteroalkyl), substituted or unsubstituted cycloalkyl (e.g. $C_3$-$C_8$ cycloalkyl, $C_4$-$C_8$ cycloalkyl, or $C_5$-$C_6$ cycloalkyl), substituted or unsubstituted heterocycloalkyl (e.g. 3 to 8 membered heterocycloalkyl, 4 to 8 membered heterocycloalkyl, or 5 to 6 membered heterocycloalkyl), substituted or unsubstituted aryl (e.g. $C_6$-$C_{10}$ aryl or $C_6$ aryl), substituted or unsubstituted heteroaryl (e.g. 5 to 10 membered heteroaryl, 5 to 9 membered heteroaryl, or 5 to 6 membered heteroaryl) or a detectable moiety.

$R^{3C}$ may be halogen, oxo, $-N_3$, $-CX^{1C}_3$, $-CHX^{1C}_2$, $-CH_2X^{1C}$, $-CN$, $-COR^{3E}$, $-OR^{3E}$, $-NR^{3E}R^{3F}$, $-COOR^{3E}$, $-CONR^{3E}R^{3F}$, $-NHC(O)R^{3E}$, $-NO_2$, $-SR^{3E}$, $-SO_{n3}R^{3E}$, $-NHNR^{3E}R^{3F}$, $-ONR^{3E}R^{3F}$, $-NHC(O)NHNR^{3E}R^{3F}$, $-C(NCN)R^{3E}$, $-C(NH)R^{3E}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl or a detectable moiety.

$R^{3C}$ may be halogen, oxo, $-N_3$, $-CX^{1C}_3$, $-CHX^{1C}_2$, $-CH_2X$, $-CN$, $-COR^{3E}$, $-OR^{3E}$, $-NR^{3E}R^{3F}$, $-COOR^{3E}$, $-CONR^{3E}R^{3F}$, $-NHC(O)R^{3E}$, $-NO_2$, $-SR^{3E}$, $-SO_{n3}R^{3E}$, $-NHNR^{3E}R^{3F}$, $-ONR^{3E}R^{3F}$, $-NHC(O)NHNR^{3E}R^{3F}$, $-C(NCN)R^{3E}$, $-C(NH)R^{3E}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{3C}$ may be substituted or unsubstituted tetrazolyl. $R^{3C}$ may be substituted tetrazolyl. $R^{3C}$ may be unsubstituted tetrazolyl.

$R^{3C}$ may be hydrogen, halogen, oxo, $-N_3$, $-CX^{1C}_3$, $-CHX^{1C}_2$, $-CH_2X^{1C}$, $-CN$, $-COR^{3E}$, $-OR^{3E}$, $-NR^{3E}R^{3F}$, $-COOR^{3E}$, $-CONR^{3E}R^{3F}$, $-NHC(O)R^{3E}$, $-NO_2$, $-SR^{3E}$, $-SO_{n3}R^{3E}$, $-NHNR^{3E}R^{3F}$, $-ONR^{3E}R^{3F}$, $-NHC(O)NHNR^{3E}R^{3F}$, $-C(NCN)R^{3E}$, $-C(NH)R^{3E}$, $R^{3G}$-substituted or unsubstituted alkyl, $R^{3G}$-substituted or unsubstituted heteroalkyl, $R^{3G}$-substituted or unsubstituted cycloalkyl, $R^{3G}$-substituted or unsubstituted heterocycloalkyl, $R^{3G}$-substituted or unsubstituted aryl, or $R^{3G}$-substituted or unsubstituted heteroaryl or a detectable moiety. $R^{3C}$ may be halogen, oxo, $-N_3$, $-CX^{1C}_3$, $-CHX^{1C}_2$, $-CH_2X^{1C}$, $-CN$, $-COR^{3E}$, $-OR^{3E}$, $-NR^{3E}R^{3F}$, $-COOR^{3E}$, $-CONR^{3E}R^{3F}$, $-NHC(O)R^{3E}$, $-NO_2$, $-SR^{3E}$, $-SO_{n3}R^{3E}$, $-NHNR^{3E}R^{3F}$, $-ONR^{3E}R^{3F}$, $-NHC(O)NHNR^{3E}R^{3F}$, $-C(NCN)R^{3E}$, $-C(NH)R^{3E}$, $R^{3G}$-substituted or unsubstituted alkyl, $R^{3G}$-substituted or unsubstituted heteroalkyl, $R^{3G}$-substituted or unsubstituted cycloalkyl, $R^{3G}$-substituted or unsubstituted heterocycloalkyl, $R^{3G}$-substituted or unsubstituted aryl, or $R^{3G}$-substituted or unsubstituted heteroaryl or a detectable moiety. $R^{3C}$ may be halogen, oxo, $-N_3$, $-CX^{1C}_3$, $-CHX^{1C}_2$, $-CH_2X^{1C}$, $-CN$, $-COR^{3E}$, $-OR^{3E}$, $-NR^{3E}R^{3F}$, $-COOR^{3E}$, $-CONR^{3E}R^{3F}$, $-NHC(O)R^{3E}$, $-NO_2$, $-SR^{3E}$, $-SO_{n3}R^{3E}$, $-NHNR^{3E}R^{3F}$, $-ONR^{3E}R^{3F}$, $-NHC(O)NHNR^{3E}R^{3F}$, $-C(NCN)R^{3E}$, $-C(NH)R^{3E}$, $R^{3G}$-substituted or unsubstituted alkyl, $R^{3G}$-substituted or unsubstituted heteroalkyl, $R^{3G}$-substituted or unsubstituted cycloalkyl, $R^{3G}$-substituted or unsubstituted heterocycloalkyl, $R^{3G}$-substituted or unsubstituted aryl, or $R^{3G}$-substituted or unsubstituted heteroaryl. The symbol n3 is 2, 3, or 4.

$R^{3E}$ and $R^{3F}$ are independently hydrogen, halogen, oxo, $-N_3$, $-CF_3$, $-CCl_3$, $-CBr_3$, $-CI_3$, $-CN$, $-CHO$, $-OH$, $-NH_2$, $-COOH$, $-CONH_2$, $-NO_2$, $-SH$, $-SO_2$, $-SO_2Cl$, $-SO_2CH_3$, $-SO_3H$, $-SO_4H$, —SO$_2$NH$_2$, —NHNH$_2$, —ONH$_2$, —NHC(O)NHNH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl or a detectable moiety. $R^{3E}$ and $R^{3F}$ are independently hydrogen, halogen, oxo, —N$_3$, —CF$_3$, —CCl$_3$, —CBr$_3$, —CI$_3$, —CN, —CHO, —OH, —NH$_2$, —COOH, —CONH$_2$, —NO$_2$, —SH, —SO$_2$, —SO$_2$Cl, —SO$_2$CH$_3$—SO$_3$H, —SO$_4$H, —SO$_2$NH$_2$, —NHNH$_2$, —ONH$_2$, —NHC(O)NHNH$_2$, substituted or unsubstituted alkyl (e.g. C$_1$-C$_8$ alkyl, C$_1$-C$_6$ alkyl, or C$_1$-C$_4$ alkyl), substituted or unsubstituted heteroalkyl (e.g. 2 to 8 membered heteroalkyl, 2 to 6 membered heteroalkyl, or 2 to 4 membered heteroalkyl), substituted or unsubstituted cycloalkyl (e.g. C$_3$-C$_8$ cycloalkyl, C$_4$-C$_8$ cycloalkyl, or C$_5$-C$_6$ cycloalkyl), substituted or unsubstituted heterocycloalkyl (e.g. 3 to 8 membered heterocycloalkyl, 4 to 8 membered heterocycloalkyl, or 5 to 6 membered heterocycloalkyl), substituted or unsubstituted aryl (e.g. C$_6$-C$_{10}$ aryl or C$_6$ aryl), substituted or unsubstituted heteroaryl (e.g. 5 to 10 membered heteroaryl, 5 to 9 membered heteroaryl, or 5 to 6 membered heteroaryl).

$R^{3E}$ and $R^{3F}$ may independently be hydrogen, halogen, oxo, —N$_3$, —CF$_3$, —CCl$_3$, —CBr$_3$, —CI$_3$, —CN, —CHO, —OH, —NH$_2$, —COOH, —CONH$_2$, —NO$_2$, —SH, —SO$_2$, —SO$_2$Cl, —SO$_2$CH$_3$—SO$_3$H, —SO$_4$H, —SO$_2$NH$_2$, —NHNH$_2$, —ONH$_2$, —NHC(O)NHNH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^{3E}$ and $R^{3F}$ may independently be hydrogen, halogen, oxo, —N$_3$, —CF$_3$, —CCl$_3$, —CBr$_3$, —CI$_3$, —CN, —CHO, —OH, —NH$_2$, —COOH, —CONH$_2$, —NO$_2$, —SH, —SO$_2$, —SO$_2$Cl, —SO$_2$CH$_3$—SO$_3$H, —SO$_4$H, —SO$_2$NH$_2$, —NHNH$_2$, —ONH$_2$, —NHC(O)NHNH$_2$, $R^{3G}$-substituted or unsubstituted alkyl, $R^{3G}$-substituted or unsubstituted heteroalkyl, $R^{3G}$-substituted or unsubstituted cycloalkyl, $R^{3G}$-substituted or unsubstituted heterocycloalkyl, $R^{3G}$-substituted or unsubstituted aryl, or $R^{3G}$-substituted or unsubstituted heteroaryl or a detectable moiety. $R^{3E}$ and $R^{3F}$ may independently be hydrogen, halogen, oxo, —N$_3$, —CF$_3$, —CCl$_3$, —CBr$_3$, —CI$_3$, —CN, —CHO, —OH, —NH$_2$, —COOH, —CONH$_2$, —NO$_2$, —SH, —SO$_2$, —SO$_2$Cl, —SO$_2$CH$_3$—SO$_3$H, —SO$_4$H, —SO$_2$NH$_2$, —NHNH$_2$, —ONH$_2$, —NHC(O)NHNH$_2$, $R^{3G}$-substituted or unsubstituted alkyl, $R^{3G}$-substituted or unsubstituted heteroalkyl, $R^{3G}$-substituted or unsubstituted cycloalkyl, $R^{3G}$-substituted or unsubstituted heterocycloalkyl, $R^{3G}$-substituted or unsubstituted aryl, or $R^{3G}$-substituted or unsubstituted heteroaryl.

$R^{3E}$ and $R^{3F}$ may independently be unsubstituted alkyl, unsubstituted heteroalkyl, unsubstituted cycloalkyl, unsubstituted heterocycloalkyl, unsubstituted aryl, unsubstituted heteroaryl, or a detectable moiety. $R^{3E}$ and $R^{3F}$ may independently be hydrogen, oxo, —N$_3$, —CF$_3$, —CCl$_3$, —CBr$_3$, —CI$_3$, —CN, —CHO, —OH, —NH$_2$, —COOH, —CONH$_2$, —NO$_2$, —SH, —SO$_2$, —SO$_2$Cl, —SO$_2$CH$_3$—SO$_3$H, —SO$_4$H, —SO$_2$NH$_2$, —NHNH$_2$, —ONH$_2$, —NHC(O)NHNH$_2$, unsubstituted alkyl, unsubstituted heteroalkyl, unsubstituted cycloalkyl, unsubstituted heterocycloalkyl, unsubstituted aryl, unsubstituted heteroaryl, or a detectable moiety.

$R^{3G}$ is halogen, oxo, —N$_3$, —CX$^{1G}_3$, —CHX$^{1G}_2$, —CH$_2$X$^{1G}$, —CN, —CHO, —OH, —NH$_2$, —COOH, —CONH$_2$, —NO$_2$, —SH, —SO$_2$, —SO$_2$Cl, —SO$_2$CH$_3$—SO$_3$H, —SO$_4$H, —SO$_2$NH$_2$, —NHNH$_2$, —ONH$_2$, —NHC(O)NHNH$_2$, unsubstituted alkyl, unsubstituted heteroalkyl, unsubstituted cycloalkyl, unsubstituted heterocycloalkyl, unsubstituted aryl, unsubstituted heteroaryl, or a detectable moiety.

In embodiments, $R^{3G}$ is unsubstituted alkyl (e.g. C$_1$-C$_8$ alkyl, C$_1$-C$_6$ alkyl, or C$_1$-C$_4$ alkyl), unsubstituted heteroalkyl (e.g. 2 to 8 membered heteroalkyl, 2 to 6 membered heteroalkyl, or 2 to 4 membered heteroalkyl), unsubstituted cycloalkyl (e.g. C$_3$-C$_8$ cycloalkyl, C$_4$-C$_8$ cycloalkyl, or C$_5$-C$_6$ cycloalkyl), unsubstituted heterocycloalkyl (e.g. 3 to 8 membered heterocycloalkyl, 4 to 8 membered heterocycloalkyl, or 5 to 6 membered heterocycloalkyl), unsubstituted aryl (e.g. C$_6$-C$_{10}$ aryl or C$_6$ aryl), or unsubstituted heteroaryl (e.g. 5 to 10 membered heteroaryl, 5 to 9 membered heteroaryl, or 5 to 6 membered heteroaryl).

$R^{3G}$ may be unsubstituted alkyl, unsubstituted heteroalkyl, unsubstituted cycloalkyl, unsubstituted heterocycloalkyl, unsubstituted aryl, unsubstituted heteroaryl, or a detectable moiety.

$R^{3D}$ is hydrogen, halogen, oxo, —N$_3$, —CX$^{1D}_3$, —CHX$^{1D}_2$, —CH$_2$X$^{1D}$, —CN, —CHO, —OH, —NH$_2$, —COOH, —CONH$_2$, —NO$_2$, —SH, —SO$_2$, —SO$_2$Cl, —SO$_2$CH$_3$—SO$_3$H, —SO$_4$H, —SO$_2$NH$_2$, —NHNH$_2$, —ONH$_2$, —NHC(O)NHNH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl or a detectable moiety. In embodiments $R^{3D}$ is substituted or unsubstituted alkyl (e.g. C$_1$-C$_8$ alkyl, C$_1$-C$_6$ alkyl, or C$_1$-C$_4$ alkyl), substituted or unsubstituted heteroalkyl (e.g. 2 to 8 membered heteroalkyl, 2 to 6 membered heteroalkyl, or 2 to 4 membered heteroalkyl), substituted or unsubstituted cycloalkyl (e.g. C$_3$-C$_8$ cycloalkyl, C$_4$-C$_8$ cycloalkyl, or C$_5$-C$_6$ cycloalkyl), substituted or unsubstituted heterocycloalkyl (e.g. 3 to 8 membered heterocycloalkyl, 4 to 8 membered heterocycloalkyl, or 5 to 6 membered heterocycloalkyl), substituted or unsubstituted aryl (e.g. C$_6$-C$_{10}$ aryl or C$_6$ aryl), substituted or unsubstituted heteroaryl (e.g. 5 to 10 membered heteroaryl, 5 to 9 membered heteroaryl, or 5 to 6 membered heteroaryl).

$R^{3D}$ may be hydrogen, halogen, oxo, —N$_3$, —CX$^{1D}_3$, —CHX$^{1D}_2$, —CH$_2$X$^{1D}$, —CN, —CHO, —OH, —NH$_2$, —COOH, —CONH$_2$, —NO$_2$, —SH, —SO$_2$, —SO$_2$Cl, —SO$_2$CH$_3$—SO$_3$H, —SO$_4$H, —SO$_2$NH$_2$, —NHNH$_2$, —ONH$_2$, —NHC(O)NHNH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{3D}$ may be substituted or unsubstituted tetrazolyl. $R^{3D}$ may be substituted tetrazolyl. $R^{3D}$ may be unsubstituted tetrazolyl.

$R^{3D}$ may be hydrogen, halogen, oxo, —N$_3$, —CX$^{1D}_3$, —CHX$^{1D}_2$, —CH$_2$X$^{1D}$, —CN, —CHO, —OH, —NH$_2$, —COOH, —CONH$_2$, —NO$_2$, —SH, —SO$_2$, —SO$_2$Cl, —SO$_2$CH$_3$—SO$_3$H, —SO$_4$H, —SO$_2$NH$_2$, —NHNH$_2$, —ONH$_2$, —NHC(O)NHNH$_2$, $R^{3H}$-substituted or unsubstituted alkyl, $R^{3H}$-substituted or unsubstituted heteroalkyl, $R^{3H}$-substituted or unsubstituted cycloalkyl, $R^{3H}$-substituted or unsubstituted heterocycloalkyl, $R^{3H}$-substituted or unsubstituted aryl, or $R^{3H}$-substituted or unsubstituted heteroaryl or a detectable moiety. $R^{3D}$ may be hydrogen, halogen, oxo, —N$_3$, —CX$^{1D}_3$, —CHX$^{1D}_2$, —CH$_2$X$^{1D}$, —CN, —CHO, —OH, —NH$_2$, —COOH, —CONH$_2$, —NO$_2$, —SH, —SO$_2$, —SO$_2$Cl, —SO$_2$CH$_3$—SO$_3$H, —SO$_4$H, —SO$_2$NH$_2$, —NHNH$_2$, —ONH$_2$, —NHC(O)NHNH$_2$, $R^{3H}$-substituted or unsubstituted alkyl, $R^{3H}$-substituted or unsubstituted heteroalkyl, $R^{3H}$-substituted or unsubstituted cycloalkyl, $R^{3H}$-substituted or unsubstituted heterocycloalkyl, $R^{3H}$-substituted or unsubstituted aryl, or $R^{3H}$-substituted or unsubstituted heteroaryl.

$R^{3D}$ may be hydrogen, halogen, oxo, —$N_3$, —$CX^{1D}{}_3$, —$CHX^{1D}{}_2$, —$CH_2X^{1D}$, —CN, —CHO, —OH, —$NH_2$, —COOH, —$CONH_2$, —$NO_2$, —SH, —$SO_2$, —$SO_2Cl$, —$SO_2CH_3$—$SO_3H$, —$SO_4H$, —$SO_2NH_2$, —$NHNH_2$, —$ONH_2$, —NHC(O)$NHNH_2$, unsubstituted alkyl, unsubstituted heteroalkyl, unsubstituted cycloalkyl, unsubstituted heterocycloalkyl, unsubstituted aryl, unsubstituted heteroaryl, or a detectable moiety. In embodiments, $R^{3D}$ may be hydrogen, halogen, oxo, —$N_3$, —$CX^{1D}{}_3$, —$CHX^{1D}{}_2$, —$CH_2X^{1D}$, —CN, —CHO, —OH, —$NH_2$, —COOH, —$CONH_2$, —$NO_2$, —SH, —$SO_2$, —$SO_2Cl$, —$SO_2CH_3$—$SO_3H$, —$SO_4H$, —$SO_2NH_2$, —$NHNH_2$, —$ONH_2$, —NHC(O)$NHNH_2$, unsubstituted alkyl (e.g. $C_1$-$C_8$ alkyl, $C_1$-$C_6$ alkyl, or $C_1$-$C_4$ alkyl), unsubstituted heteroalkyl (e.g. 2 to 8 membered heteroalkyl, 2 to 6 membered heteroalkyl, or 2 to 4 membered heteroalkyl), unsubstituted cycloalkyl (e.g. $C_3$-$C_8$ cycloalkyl, $C_4$-$C_8$ cycloalkyl, or $C_5$-$C_6$ cycloalkyl), unsubstituted heterocycloalkyl (e.g. 3 to 8 membered heterocycloalkyl, 4 to 8 membered heterocycloalkyl, or 5 to 6 membered heterocycloalkyl), unsubstituted aryl (e.g. $C_6$-$C_{10}$ aryl or $C_6$ aryl), or unsubstituted heteroaryl (e.g. 5 to 10 membered heteroaryl, 5 to 9 membered heteroaryl, or 5 to 6 membered heteroaryl), or a detectable moiety.

$R^{3D}$ may be unsubstituted alkyl, unsubstituted heteroalkyl, unsubstituted cycloalkyl, unsubstituted heterocycloalkyl, unsubstituted aryl, unsubstituted heteroaryl, or a detectable moiety.

$R^{3H}$ is halogen, oxo, —$N_3$, —$CX^{1H}{}_3$, —$CHX^{1H}{}_2$, —$CH_2X^{1H}$, —CN, —CHO, —OH, —$NH_2$, —COOH, —$CONH_2$, —$NO_2$, —SH, —$SO_2$, —$SO_2Cl$, —$SO_2CH_3$—$SO_3H$, —$SO_4H$, —$SO_2NH_2$, —$NHNH_2$, —$ONH_2$, —NHC(O)$NHNH_2$, unsubstituted alkyl, unsubstituted heteroalkyl, unsubstituted cycloalkyl, unsubstituted heterocycloalkyl, unsubstituted aryl, unsubstituted heteroaryl, or a detectable moiety. $R^{3H}$ may be unsubstituted alkyl, unsubstituted heteroalkyl, unsubstituted cycloalkyl, unsubstituted heterocycloalkyl, unsubstituted aryl, unsubstituted heteroaryl, or a detectable moiety. $R^{3H}$ may be halogen, oxo, —$N_3$, —$CX^{1H}{}_3$, —$CHX^{1H}{}_2$, —$CH_2X^{1H}$, —CN, —CHO, —OH, —$NH_2$, —COOH, —$CONH_2$, —$NO_2$, —SH, —$SO_2$, —$SO_2Cl$, —$SO_2CH_3$—$SO_3H$, —$SO_4H$, —$SO_2NH_2$, —$NHNH_2$, —$ONH_2$, —NHC(O)$NHNH_2$, unsubstituted alkyl, unsubstituted heteroalkyl, unsubstituted cycloalkyl, unsubstituted heterocycloalkyl, unsubstituted aryl, or unsubstituted heteroaryl $R^{3A}$ and $R^{3B}$ may independently be substituted or unsubstituted 4,5-dihydro-imidazole or substituted or unsubstituted 1,4,5,6-tetrahydropyrimidine. $R^{3A}$ and $R^{3B}$ may independently be $R^{10}$-substituted or unsubstituted 4,5-dihydro-imidazole. $R^{3A}$ and $R^{3B}$ may independently be unsubstituted 4,5-dihydro-imidazole. $R^{3A}$ and $R^{3B}$ may independently be $R^{10}$-substituted or unsubstituted 1,4,5,6-tetrahydropyrimidine. $R^{3A}$ and $R^{3B}$ may independently be unsubstituted 1,4,5,6-tetrahydropyrimidine. $R^{3A}$ and $R^{3B}$ may independently be hydrogen, substituted or unsubstituted 4,5-dihydro-imidazole or substituted or unsubstituted 1,4,5,6-tetrahydropyrimidine. $R^{3A}$ and $R^{3B}$ may independently be hydrogen or $R^{10}$-substituted or unsubstituted 4,5-dihydro-imidazole. $R^{3A}$ and $R^{3B}$ may independently be hydrogen or unsubstituted 4,5-dihydro-imidazole. $R^{3A}$ and $R^{3B}$ may independently be hydrogen or $R^{10}$-substituted or unsubstituted 1,4,5,6-tetrahydropyrimidine. $R^{3A}$ and $R^{3B}$ may independently be hydrogen or unsubstituted 1,4,5,6-tetrahydropyrimidine. In embodiments, one of $R^{3A}$ and $R^{3B}$ is hydrogen.

$R^{3A}$ and $R^{3B}$ may be joined together to form substituted or unsubstituted 4,5-dihydro-imidazole, substituted or unsubstituted 1,4,5,6-tetrahydropyrimidine, $R^{10}$-substituted or unsubstituted 4,5-dihydro-imidazole, unsubstituted 4,5-dihydro-imidazole, $R^{10}$-substituted or unsubstituted 1,4,5,6-tetrahydropyrimidine, unsubstituted 1,4,5,6-tetrahydropyrimidine. In embodiments, one of $R^{3A}$ and $R^{3B}$ is hydrogen.

$R^{3A}$ and $R^{3B}$ may be joined together to form a substituted or unsubstituted heterocycloalkyl or substituted or unsubstituted heteroaryl. $R^{3A}$ and $R^{3B}$ may be joined together to form a $R^{10}$-substituted heterocycloalkyl. $R^{3A}$ and $R^{3B}$ may be joined together to form a $R^{10}$-substituted 3 to 8 membered heterocycloalkyl. $R^{3A}$ and $R^{3B}$ may be joined together to form a $R^{10}$-substituted 4 to 6 membered heterocycloalkyl. $R^{3A}$ and $R^{3B}$ may be joined together to form a $R^{10}$-substituted 5 membered heterocycloalkyl. $R^{3A}$ and $R^{3B}$ may be joined together to form a $R^{10}$-substituted 6 membered heterocycloalkyl. $R^{3A}$ and $R^{3B}$ may be joined together to form a $R^{10}$-substituted heteroaryl. $R^{3A}$ and $R^{3B}$ may be joined together to form a $R^{10}$-substituted 5 to 8 membered heteroaryl. $R^{3A}$ and $R^{3B}$ may be joined together to form a $R^{10}$-substituted 5 membered heteroaryl. $R^{3A}$ and $R^{3B}$ may be joined together to form a $R^{10}$-substituted 6 membered heteroaryl. In embodiments, one of $R^{3A}$ and $R^{3B}$ is hydrogen.

$R^{10}$ is hydrogen, halogen, oxo, —$N_3$, —$CX^{10}{}_3$, —$CHX^{10}{}_2$, —$CH_2X^{10}$, —CN, —$COR^{10A}$, —$OR^{10A}$, —$NR^{10A}R^{10B}$, —$COOR^{10A}$, —$CONR^{10A}R^{10B}$, —NHC(O)$R^{10A}$, —$NO_2$, —$SR^{10A}$, —$SO_{n3}R^{10A}$, —$NHNR^{10A}R^{10B}$, —$ONR^{10A}R^{10B}$, —NHC(O)$NHNR^{10A}R^{10B}$, —C(NCN)$R^{10A}$, —C(NH)$R^{10A}$, $R^{10C}$-substituted or unsubstituted alkyl, $R^{10C}$-substituted or unsubstituted heteroalkyl, $R^{10C}$-substituted or unsubstituted cycloalkyl, $R^{10C}$-substituted or unsubstituted heterocycloalkyl, $R^{10C}$-substituted or unsubstituted aryl, or $R^{10C}$-substituted or unsubstituted heteroaryl.

In embodiments, $R^{10}$ is hydrogen, halogen, oxo, —$N_3$, —$CX^{10}{}_3$, —$CHX^{10}{}_2$, —$CH_2X^{10}$, —CN, —$COR^{10A}$, —$OR^{10A}$, —$NR^{10A}R^{10B}$, —$COOR^{10A}$, —$CONR^{10A}R^{10B}$, —NHC(O)$R^{10A}$, —$NO_2$, —$SR^{10A}$, —$SO^{n3}R^{10A}$, —$NHNR^{10A}R^{10B}$, —$ONR^{10A}R^{10B}$, —NHC(O)$NHNR^{10A}R^{10B}$, —C(NCN)$R^{10A}$, —C(NH)$R^{10A}$, $R^{10C}$-substituted or unsubstituted alkyl (e.g. $C_1$-$C_8$ alkyl, $C_1$-$C_6$ alkyl, or $C_1$-$C_4$ alkyl), $R^{10C}$-substituted or unsubstituted heteroalkyl (e.g. 2 to 8 membered heteroalkyl, 2 to 6 membered heteroalkyl, or 2 to 4 membered heteroalkyl), $R^{10C}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{10C}$-substituted or unsubstituted heterocycloalkyl (e.g. 3 to 8 membered heterocycloalkyl, 4 to 8 membered heterocycloalkyl, or 5 to 6 membered heterocycloalkyl), $R^{10C}$-substituted or unsubstituted aryl (e.g. $C_6$-$C_{10}$ aryl or $C_6$ aryl), $R^{10C}$-substituted or unsubstituted heteroaryl (e.g. 5 to 10 membered heteroaryl, 5 to 9 membered heteroaryl, or 5 to 6 membered heteroaryl).

$R^{10}$ may be halogen, oxo, —$N_3$, —$CX^{10}{}_3$, —$CHX^{10}{}_2$, —$CH_2X^{10}$, —CN, —$COR^{10}$, —$OR^{10}$, —$NR^{10A}R^{10B}$, —$COOR^{10A}$, —$CONR^{10A}R^{10B}$, —NHC(O)$R^{10A}$, —$NO_2$, —$SR^{10A}$, —$SO_{n3}R^{10A}$, —$NHNR^{10A}R^{10B}$, —$ONR^{10A}R^{10B}$, —NHC(O)$NHNR^{10A}R^{10B}$, —C(NCN)$R^{10A}$, —C(NH)$R^{10A}$, $R^{10C}$-substituted or unsubstituted alkyl, $R^{10C}$-substituted or unsubstituted heteroalkyl, $R^{10C}$-substituted or unsubstituted cycloalkyl, $R^{10C}$-substituted or unsubstituted heterocycloalkyl, $R^{10C}$-substituted or unsubstituted aryl, or $R^{10C}$-substituted or unsubstituted heteroaryl.

$R^{10}$ may be hydrogen, halogen, oxo, —$N_3$, —$CX^{10}{}_3$, —$CHX^{10}{}_2$, —$CH_2X^{10}$, —CN, —CHO, —OH, —$NH_2$, —COOH, —$CONH_2$, —$NO_2$, —SH, —$SO_2$, —$SO_2Cl$, —$SO_2CH_3$—$SO_3H$, —$SO_4H$, —$SO_2NH_2$, —$NHNH_2$, —$ONH_2$, —NHC(O)$NHNH_2$, unsubstituted alkyl, unsubstituted heteroalkyl, unsubstituted cycloalkyl, unsubstituted heterocycloalkyl, unsubstituted aryl, or unsubstituted heteroaryl. $R^{10}$ may be unsubstituted alkyl (e.g. $C_1$-$C_8$ alkyl, $C_1$-$C_6$ alkyl, or $C_1$-$C_4$ alkyl), unsubstituted heteroalkyl (e.g. 2 to 8 membered heteroalkyl, 2 to 6 membered heteroalkyl, or 2 to 4 membered heteroalkyl), unsubstituted cycloalkyl (e.g. $C_3$-$C_8$ cycloalkyl, $C_4$-$C_8$ cycloalkyl, or $C_5$-$C_6$ cycloalkyl), unsubstituted heterocycloalkyl (e.g. 3 to 8 membered heterocycloalkyl, 4 to 8 membered heterocycloalkyl, or 5 to 6 membered heterocycloalkyl), unsubstituted aryl (e.g. $C_6$-$C_{10}$ aryl or $C_6$ aryl), or unsubstituted heteroaryl (e.g. 5 to 10 membered heteroaryl, 5 to 9 membered heteroaryl, or 5 to 6 membered heteroaryl).

$R^{10A}$ and $R^{10B}$ are independently hydrogen, halogen, oxo, $-N_3$, $-CF_3$, $-CCl_3$, $-CBr_3$, $-CI_3$, $-CN$, $-CHO$, $-OH$, $-NH_2$, $-COOH$, $-CONH_2$, $-NO_2$, $-SH$, $-SO_2$, $-SO_2Cl$, $-SO_2CH_3$—$SO_3H$, $-SO_4H$, $-SO_2NH_2$, $-NHNH_2$, $-ONH_2$, $-NHC(O)NHNH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, $R^{10A}$ and $R^{10B}$ are independently hydrogen, halogen, oxo, $-N_3$, $-CF_3$, $-CCl_3$, $-CBr_3$, $-CI_3$, $-CN$, $-CHO$, $-OH$, $-NH_2$, $-COOH$, $-CONH_2$, $-NO_2$, $-SH$, $-SO_2$, $-SO_2Cl$, $-SO_2CH_3$—$SO_3H$, $-SO_4H$, $-SO_2NH_2$, $-NHNH_2$, $-ONH_2$, $-NHC(O)NHNH_2$, substituted or unsubstituted alkyl (e.g. $C_1$-$C_8$ alkyl, $C_1$-$C_6$ alkyl, or $C_1$-$C_4$ alkyl), substituted or unsubstituted heteroalkyl (e.g. 2 to 8 membered heteroalkyl, 2 to 6 membered heteroalkyl, or 2 to 4 membered heteroalkyl), substituted or unsubstituted cycloalkyl (e.g. $C_3$-$C_8$ cycloalkyl, $C_4$-$C_8$ cycloalkyl, or $C_5$-$C_6$ cycloalkyl), substituted or unsubstituted heterocycloalkyl (e.g. 3 to 8 membered heterocycloalkyl, 4 to 8 membered heterocycloalkyl, or 5 to 6 membered heterocycloalkyl), substituted or unsubstituted aryl (e.g. $C_6$-$C_{10}$ aryl or $C_6$ aryl), substituted or unsubstituted heteroaryl (e.g. 5 to 10 membered heteroaryl, 5 to 9 membered heteroaryl, or 5 to 6 membered heteroaryl).

$R^{10A}$ and $R^{10B}$ may independently be hydrogen, halogen, oxo, $-N_3$, $-CF_3$, $-CCl_3$, $-CBr_3$, $-CI_3$, $-CN$, $-CHO$, $-OH$, $-NH_2$, $-COOH$, $-CONH_2$, $-NO_2$, $-SH$, $-SO_2$, $-SO_2Cl$, $-SO_2CH_3$—$SO_3H$, $-SO_4H$, $-SO_2NH_2$, $-NHNH_2$, $-ONH_2$, $-NHC(O)NHNH_2$, $R^{10D}$-substituted or unsubstituted alkyl, $R^{10D}$-substituted or unsubstituted heteroalkyl, $R^{10D}$-substituted or unsubstituted cycloalkyl, $R^{10D}$-substituted or unsubstituted heterocycloalkyl, $R^{10D}$-substituted or unsubstituted aryl, or $R^{10D}$-substituted or unsubstituted heteroaryl.

$R^{10A}$ and $R^{10B}$ may independently be unsubstituted alkyl, unsubstituted heteroalkyl, unsubstituted cycloalkyl, unsubstituted heterocycloalkyl, unsubstituted aryl, unsubstituted heteroaryl, or a detectable moiety. $R^{10A}$ and $R^{10B}$ may independently be unsubstituted alkyl (e.g. $C_1$-$C_8$ alkyl, $C_1$-$C_6$ alkyl, or $C_1$-$C_4$ alkyl), unsubstituted heteroalkyl (e.g. 2 to 8 membered heteroalkyl, 2 to 6 membered heteroalkyl, or 2 to 4 membered heteroalkyl), unsubstituted cycloalkyl (e.g. $C_3$-$C_8$ cycloalkyl, $C_4$-$C_8$ cycloalkyl, or $C_5$-$C_6$ cycloalkyl), unsubstituted heterocycloalkyl (e.g. 3 to 8 membered heterocycloalkyl, 4 to 8 membered heterocycloalkyl, or 5 to 6 membered heterocycloalkyl), unsubstituted aryl (e.g. $C_6$-$C_{10}$ aryl or $C_6$ aryl), or unsubstituted heteroaryl (e.g. 5 to 10 membered heteroaryl, 5 to 9 membered heteroaryl, or 5 to 6 membered heteroaryl).

$R^{10A}$ and $R^{10B}$ may independently be hydrogen, halogen, oxo, $-N_3$, $-CF_3$, $-CCl_3$, $-CBr_3$, $-CI_3$, $-CN$, $-CHO$, $-OH$, $-NH_2$, $-COOH$, $-CONH_2$, $-NO_2$, $-SH$, $-SO_2$, $-SO_2Cl$, $-SO_2CH_3$—$SO_3H$, $-SO_4H$, $-SO_2NH_2$, $-NHNH_2$, $-ONH_2$, $-NHC(O)NHNH_2$, unsubstituted alkyl, unsubstituted heteroalkyl, unsubstituted cycloalkyl, unsubstituted heterocycloalkyl, unsubstituted aryl, unsubstituted heteroaryl, or a detectable moiety. $R^{10A}$ and $R^{10B}$ may independently be unsubstituted alkyl, unsubstituted heteroalkyl, unsubstituted cycloalkyl, unsubstituted heterocycloalkyl, unsubstituted aryl, unsubstituted heteroaryl, or a detectable moiety, or a detectable moiety.

$R^{10C}$ is hydrogen, halogen, oxo, $-N_3$, $-CX^{10C}_3$, $-CHX^{10C}_2$, $-CH_2X^{10C}$, $-CN$, $-COR^{10E}$, $-OR^{10E}$, $-NR^{10E}R^{10F}$, $-COOR^{10E}$, $-CONR^{10E}R^{10F}$, $-NHC(O)R^{10E}$, $-NO_2$, $-SR^{10E}$, $-SO^{n3}R^{10E}$, $-NHNR^{10E}R^{10F}$, $-ONR^{10E}R^{10F}$, $-NHC(O)NHNR^{10E}R^{10F}$, $-C(NCN)R^{10E}$, $-C(NH)R^{10E}$, $R^{10G}$-substituted or unsubstituted alkyl, $R^{10G}$-substituted or unsubstituted heteroalkyl, $R^{10G}$-substituted or unsubstituted cycloalkyl, $R^{10G}$-substituted or unsubstituted heterocycloalkyl, $R^{10G}$-substituted or unsubstituted aryl, or $R^{10G}$-substituted or unsubstituted heteroaryl, or a detectable moiety.

$R^{10C}$ may be oxo, $-N_3$, $-CX^{10C}_3$, $-CHX^{10C}_2$, $-CH_2X^{10C}$, $-CN$, $-CHO$, $-OH$, $-NH_2$, $-COOH$, $-CONH_2$, $-NO_2$, $-SH$, $-SO_2$, $-SO_2Cl$, $-SO_2CH_3$—$SO_3H$, $-SO_4H$, $-SO_2NH_2$, $-NHNH_2$, $-ONH_2$, $-NHC(O)NHNH_2$, unsubstituted alkyl, unsubstituted heteroalkyl, unsubstituted cycloalkyl, unsubstituted heterocycloalkyl, unsubstituted aryl, or unsubstituted heteroaryl, or a detectable moiety. $R^{10C}$ may be unsubstituted alkyl (e.g. $C_1$-$C_8$ alkyl, $C_1$-$C_6$ alkyl, or $C_1$-$C_4$ alkyl), unsubstituted heteroalkyl (e.g. 2 to 8 membered heteroalkyl, 2 to 6 membered heteroalkyl, or 2 to 4 membered heteroalkyl), unsubstituted cycloalkyl (e.g. $C_3$-$C_8$ cycloalkyl, $C_4$-$C_8$ cycloalkyl, or $C_5$-$C_6$ cycloalkyl), unsubstituted heterocycloalkyl (e.g. 3 to 8 membered heterocycloalkyl, 4 to 8 membered heterocycloalkyl, or 5 to 6 membered heterocycloalkyl), unsubstituted aryl (e.g. $C_6$-$C_{10}$ aryl or $C_6$ aryl), or unsubstituted heteroaryl (e.g. 5 to 10 membered heteroaryl, 5 to 9 membered heteroaryl, or 5 to 6 membered heteroaryl), or a detectable moiety.

$R^{10G}$ is hydrogen, halogen, oxo, $-N_3$, $-CX^{10G}_3$, $-CHX^{10G}_2$, $-CH_2X^{10G}$, $-CN$, $-CHO$, $-OH$, $-NH_2$, $-COOH$, $-CONH_2$, $-NO_2$, $-SH$, $-SO_2$, $-SO_2Cl$, $-SO_2CH_3$—$SO_3H$, $-SO_4H$, $-SO_2NH_2$, $-NHNH_2$, $-ONH_2$, $-NHC(O)NHNH_2$, $R^{10M}$-substituted or unsubstituted alkyl, $R^{10M}$-substituted or unsubstituted heteroalkyl, $R^{10M}$-substituted or unsubstituted cycloalkyl, $R^{10M}$-substituted or unsubstituted heterocycloalkyl, $R^{10M}$-substituted or unsubstituted aryl, or $R^{10M}$-substituted or unsubstituted heteroaryl, or a detectable moiety. $R^{10G}$ may be hydrogen, halogen, oxo, $-N_3$, $-CX^{10G}_3$, $-CHX^{10G}_2$, $-CH_2X^{10G}$, $-CN$, $-CHO$, $-OH$, $-NH_2$, $-COOH$, $-CONH_2$, $-NO_2$, $-SH$, $-SO_2$, $-SO_2Cl$, $-SO_2CH_3$—$SO_3H$, $-SO_4H$, $-SO_2NH_2$, $-NHNH_2$, $-ONH_2$, $-NHC(O)NHNH_2$, $R^{10M}$-substituted or unsubstituted alkyl (e.g. $C_1$-$C_8$ alkyl, $C_1$-$C_6$ alkyl, or $C_1$-$C_4$ alkyl), $R^{10M}$-substituted or unsubstituted heteroalkyl (e.g. 2 to 8 membered heteroalkyl, 2 to 6 membered heteroalkyl, or 2 to 4 membered heteroalkyl), $R^{10M}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{10M}$-substituted or unsubstituted heterocycloalkyl (e.g. 3 to 8 membered heterocycloalkyl, 4 to 8 membered heterocycloalkyl, or 5 to 6 membered heterocycloalkyl), $R^{10M}$-substituted or unsubstituted aryl (e.g. $C_6$-$C_{10}$ aryl or $C_6$ aryl), $R^{10M}$-substituted or unsubstituted heteroaryl (e.g. 5 to 10 membered heteroaryl, 5 to 9 membered heteroaryl, or 5 to 6 membered heteroaryl).

$R^{10G}$ may be oxo, $-N_3$—$CX^{10G}_3$, $-CHX^{10G}_2$, $-CH_2X^{10G}$, $-CN$, $-CHO$, $-OH$, $-NH_2$, $-COOH$, —CONH$_2$, —NO$_2$, —SH, —SO$_2$, —SO$_2$Cl, —SO$_2$CH$_3$—SO$_3$H, —SO$_4$H, —SO$_2$NH$_2$, —NHNH$_2$, —ONH$_2$, —NHC(O)NHNH$_2$, unsubstituted alkyl, unsubstituted heteroalkyl, unsubstituted cycloalkyl, unsubstituted heterocycloalkyl, unsubstituted aryl, or unsubstituted heteroaryl, or a detectable moiety. R$^{10G}$ may be oxo, —N$_3$, —CX$^{10G}{}_3$, —CHX$^{10G}{}_2$, —CH$_2$X$^{10G}$, —CN, —CHO, —OH, —NH$_2$, —COOH, —CONH$_2$, —NO$_2$, —SH, —SO$_2$, —SO$_2$Cl, —SO$_2$CH$_3$—SO$_3$H, —SO$_4$H, —SO$_2$NH$_2$, —NHNH$_2$, —ONH$_2$, —NHC(O)NHNH$_2$, unsubstituted alkyl (e.g. C$_1$-C$_8$ alkyl, C$_1$-C$_6$ alkyl, or C$_1$-C$_4$ alkyl), unsubstituted heteroalkyl (e.g. 2 to 8 membered heteroalkyl, 2 to 6 membered heteroalkyl, or 2 to 4 membered heteroalkyl), unsubstituted cycloalkyl (e.g. C$_3$-C$_8$ cycloalkyl, C$_4$-C$_8$ cycloalkyl, or C$_5$-C$_6$ cycloalkyl), unsubstituted heterocycloalkyl (e.g. 3 to 8 membered heterocycloalkyl, 4 to 8 membered heterocycloalkyl, or 5 to 6 membered heterocycloalkyl), unsubstituted aryl (e.g. C$_6$-C$_{10}$ aryl or C$_6$ aryl), or unsubstituted heteroaryl (e.g. 5 to 10 membered heteroaryl, 5 to 9 membered heteroaryl, or 5 to 6 membered heteroaryl), or a detectable moiety.

R$^{10D}$ is hydrogen, halogen, oxo, —N$_3$, —CX$^{10D}{}_3$, —CHX$^{10D}{}_2$, —CH$_2$X$^{10D}$, —CN, —COR$^{10E}$, —OR$^{10E}$, —NR$^{10H}$R$^{10J}$, —COOR$^{10H}$, —CONR$^{10H}$R$^{10J}$, —NHC(O)R$^{10H}$, —NO$_2$, —SR$^{10H}$, —SO$_{n3}$R$^{10H}$, —NHNR$^{10H}$R$^{10J}$, —ONR$^{10H}$R$^{10J}$, —NHC(O)NHNR$^{10H}$R$^{10J}$, —C(NCN)R$^{10H}$, —C(NH)R$^{10H}$, R$^{10K}$-substituted or unsubstituted alkyl, R$^{10K}$-substituted or unsubstituted heteroalkyl, R$^{10K}$-substituted or unsubstituted cycloalkyl, R$^{10K}$-substituted or unsubstituted heterocycloalkyl, R$^{10K}$-substituted or unsubstituted aryl, or R$^{10K}$-substituted or unsubstituted heteroaryl, or a detectable moiety. R$^{10D}$ may be hydrogen, halogen, oxo, —N$_3$, —CX$^{10D}{}_3$, —CHX$^{10D}{}_2$, —CH$_2$X$^{10D}$, —CN, —COR$^{10E}$, —OR$^{10E}$, —NR$^{10H}$R$^{10J}$, —COOR$^{10H}$, —CONR$^{10H}$R$^{10J}$, —NHC(O)R$^{10H}$, —NO$_2$, —SR$^{10H}$, —SO$_{n3}$R$^{10H}$, —NHNR$^{10H}$R$^{10J}$, —ONR$^{10H}$R$^{10J}$, —NHC(O)NHNR$^{10H}$R$^{10J}$, —C(NCN)R$^{10H}$, —C(NH)R$^{10H}$, R$^{10K}$-substituted or unsubstituted alkyl (e.g. C$_1$-C$_8$ alkyl, C$_1$-C$_6$ alkyl, or C$_1$-C$_4$ alkyl), R$^{10K}$-substituted or unsubstituted heteroalkyl (e.g. 2 to 8 membered heteroalkyl, 2 to 6 membered heteroalkyl, or 2 to 4 membered heteroalkyl), R$^{10K}$-substituted or unsubstituted cycloalkyl (e.g. C$_3$-C$_8$ cycloalkyl, C$_4$-C$_8$ cycloalkyl, or C$_5$-C$_6$ cycloalkyl), R$^{10K}$-substituted or unsubstituted heterocycloalkyl (e.g. 3 to 8 membered heterocycloalkyl, 4 to 8 membered heterocycloalkyl, or 5 to 6 membered heterocycloalkyl), R$^{10K}$-substituted or unsubstituted aryl (e.g. C$_6$-C$_{10}$ aryl or C$_6$ aryl), R$^{10K}$-substituted or unsubstituted heteroaryl (e.g. 5 to 10 membered heteroaryl, 5 to 9 membered heteroaryl, or 5 to 6 membered heteroaryl), or a detectable moiety.

R$^{10K}$ is hydrogen, halogen, oxo, —N$_3$, —CX$^{10K}{}_3$, —CHX$^{10K}{}_2$, —CH$_2$X$^{10K}$, —CN, —CHO, —OH, —NH$_2$, —COOH, —CONH$_2$, —NO$_2$, —SH, —SO$_2$, —SO$_2$Cl, —SO$_2$CH$_3$—SO$_3$H, —SO$_4$H, —SO$_2$NH$_2$, —NHNH$_2$, —ONH$_2$, —NHC(O)NHNH$_2$, R$^{10L}$-substituted or unsubstituted heteroalkyl, R$^{10L}$-substituted or unsubstituted cycloalkyl, R$^{10L}$-substituted or unsubstituted heterocycloalkyl, R$^{10L}$-substituted or unsubstituted aryl, or R$^{10L}$-substituted or unsubstituted heteroaryl, or a detectable moiety.

R$^{10E}$, R$^{10F}$, R$^{10H}$, R$^{10J}$, R$^{10L}$, and R$^{10M}$ are independently be hydrogen, halogen, oxo, —N$_3$, —CF$_3$, —CCl$_3$, —CBr$_3$, —CI$_3$, —CN, —CHO, —OH, —NH$_2$, —COOH, —CONH$_2$, —NO$_2$, —SH, —SO$_2$, —SO$_2$Cl, —SO$_2$CH$_3$—SO$_3$H, —SO$_4$H, —SO$_2$NH$_2$, —NHNH$_2$, —ONH$_2$, —NHC(O)NHNH$_2$, unsubstituted alkyl, or unsubstituted heteroalkyl, unsubstituted cycloalkyl, unsubstituted heterocycloalkyl, unsubstituted aryl, or substituted or unsubstituted heteroaryl, or a detectable moiety.

Each X$^{1C}$, X$^{1D}$, X$^{1G}$, X$^{1H}$, X$^{10}$, X$^{10C}$, X$^{10D}$, and X$^{10K}$ are independently halogen. In embodiments, X$^{1C}$ is —Cl. In embodiments, X$^{1D}$ is —Cl. In embodiments, X$^{1G}$ is —Cl. In embodiments, X$^{1H}$ is —Cl. In embodiments, X$^{10}$ is —Cl. In embodiments, X$^{10C}$ is —Cl. In embodiments, X$^{10D}$ is —Cl. In embodiments, X$^{10K}$ is —Cl. In embodiments, X$^{1C}$ is —Br. In embodiments, X$^{1D}$ is —Br. In embodiments, X$^{1G}$ is —Br. In embodiments, X$^{1H}$ is —Br. In embodiments, X$^{10}$ is —Br. In embodiments, X$^{10C}$ is —Br. In embodiments, X$^{10D}$ is —Br. In embodiments, X$^{10K}$ is —Br. In embodiments, X$^{1C}$ is —F. In embodiments, X$^{1D}$ is —F. In embodiments, X$^{1G}$ is —F. In embodiments, X$^{1H}$ is —F. In embodiments, X$^{10}$ is —F. In embodiments, X$^{10C}$ is —F. In embodiments, X$^{10D}$ is —F. In embodiments, X$^{10K}$ is —F. In embodiments, X$^{1C}$ is —I. In embodiments, X$^{1D}$ is —I. In embodiments, X$^{1G}$ is —I. In embodiments, X$^{1H}$ is —I. In embodiments, X$^{10}$ is —I. In embodiments, X$^{10C}$ is —I. In embodiments, X$^{10D}$ is —I. In embodiments, X$^{10K}$ is —I.

R$^{3A}$ and R$^{3B}$ may independently be hydrogen, —C(NH)NH$_2$, unsubstituted 4,5-dihydro-imidazole, unsubstituted 1,4,5,6-tetrahydropyrimidine, unsubstituted 1,2,3,4-tetrahydro-1,8-naphthyridine, or unsubstituted pyridine. R$^{3A}$ and R$^{3B}$ may independently be hydrogen. R$^{3A}$ and R$^{3B}$ may independently be —C(NH)NH$_2$. R$^{3A}$ and R$^{3B}$ may independently be unsubstituted 4,5-dihydro-imidazole. R$^{3A}$ and R$^{3B}$ may independently be unsubstituted 1,4,5,6-tetrahydropyrimidine. R$^{3A}$ and R$^{3B}$ may independently be unsubstituted 1,2,3,4-tetrahydro-1,8-naphthyridine. R$^{3A}$ and R$^{3B}$ may independently be or unsubstituted pyridine.

R$^{3A}$ may independently be hydrogen, —C(NH)NH$_2$, unsubstituted 4,5-dihydro-imidazole, unsubstituted 1,4,5,6-tetrahydropyrimidine, unsubstituted 1,2,3,4-tetrahydro-1,8-naphthyridine, or unsubstituted pyridine. R$^{3A}$ may independently be hydrogen. R$^{3A}$ may independently be —C(NH)NH$_2$. R$^{3A}$ may independently be unsubstituted 4,5-dihydro-imidazole. R$^{3A}$ may independently be unsubstituted 1,4,5,6-tetrahydropyrimidine. R$^{3A}$ may independently be unsubstituted 1,2,3,4-tetrahydro-1,8-naphthyridine. R$^{3A}$ may independently be or unsubstituted pyridine.

R$^{3B}$ may independently be hydrogen, —C(NH)NH$_2$, unsubstituted 4,5-dihydro-imidazole, unsubstituted 1,4,5,6-tetrahydropyrimidine, unsubstituted 1,2,3,4-tetrahydro-1,8-naphthyridine, or unsubstituted pyridine. R$^{3B}$ may independently be hydrogen. R$^{3B}$ may independently be —C(NH)NH$_2$. R$^{3B}$ may independently be unsubstituted 4,5-dihydro-imidazole. R$^{3B}$ may independently be unsubstituted 1,4,5,6-tetrahydropyrimidine. R$^{3B}$ may independently be unsubstituted 1,2,3,4-tetrahydro-1,8-naphthyridine. R$^{3B}$ may independently be or unsubstituted pyridine.

Y may be —C(O)N(R$^4$)—. Y may be —O—. Y may be —C(O)O— Y may be —S—. Y may be —N(SO$_2$R$^4$)—. Y may be —N(C(O)R$^4$)—. Y may be —N(C(O)OR$^4$)—. Y may be —N(R$^4$)C(O)—. Y may be —N(R$^4$)—. Y may be —N(R$^4$)C(O) N(R$^4$)—. Y may be —NHC(O)—, —NCH$_3$—, —NC(O)CH$_3$—, —NC(O)OCH$_3$—, —N(SO$_2$CH$_3$)—, —S—, —O—, —C(O)O—, substituted or unsubstituted 3 to 6 membered heterocycloalkylene, or 5 to 6 membered unsubstituted heteroarylene, or unsubstituted 6 membered arylene. Y may be —NHC(O)—. Y may be —NCH$_3$—. Y may be —NC(O)CH$_3$—. Y may be —NC(O)OCH$_3$—. Y may be —N(SO$_2$CH$_3$)—. Y may be —S—. Y may be —O—. Y may be C(O)O. Y may be —S. Y may be 5 to 6 membered unsubstituted heteroarylene. Y may be a bond. Y may be —C(O)N(R$^4$)—. Y may be —O—. Y may be —C(O)O—. Y may be —S—. Y may be —N(SO$_2$R$^4$)—.

Y may be —N(C(O)R⁴)—. Y may be —N(C(O)OR⁴)—. Y may be —N(R⁴)C(O)—. Y may be —N(R⁴)—. Y may be —N(R⁴)C(O)NH—. Y may be —NHC(O)N(R⁴)—. Y may be —N(R⁴)C(O)O—. Y may be —C(O)—. Y may be —N(R⁴)CH₂—. Y may be substituted or unsubstituted alkylene. Y may be substituted or unsubstituted heteroalkylene. Y may be substituted or unsubstituted cycloalkylene. Y may be substituted or unsubstituted heterocycloalkylene. Y may be substituted or unsubstituted arylene. Y may be substituted or unsubstituted heteroarylene. Y may be substituted alkylene. Y may be substituted heteroalkylene. Y may be substituted cycloalkylene. Y may be substituted heterocycloalkylene. Y may be substituted arylene. Y may be substituted heteroarylene. Y may be unsubstituted alkylene. Y may be unsubstituted heteroalkylene. Y may be unsubstituted cycloalkylene. Y may be unsubstituted heterocycloalkylene. Y may be unsubstituted arylene. Y may be unsubstituted heteroarylene. Y may be R¹¹-substituted or unsubstituted cycloalkylene. Y may be substituted or unsubstituted C₃-C₈ cycloalkylene. Y may be R¹¹-substituted or unsubstituted C₃-C₈ cycloalkylene. Y may be substituted or unsubstituted C₃-C₈ cycloalkylene. Y may be R¹¹-substituted or unsubstituted C₃-C₈ cycloalkylene. Y may be R¹¹-substituted or unsubstituted cycloalkylene. Y may be substituted or unsubstituted C₅-C₆ cycloalkylene. Y may be R¹¹-substituted or unsubstituted C₅-C₆ cycloalkylene. Y may be substituted C₅-C₆ cycloalkylene. Y may be unsubstituted C₅-C₆ cycloalkylene. Y may be R¹¹-substituted or unsubstituted C₅-C₆ cycloalkylene. Y may be substituted or unsubstituted C₆ cycloalkylene. Y may be R¹¹-substituted or unsubstituted C₆ arylene. Y may be unsubstituted C₆ cycloalkylene. Y may be R¹¹-substituted C₆ cycloalkylene. Y may be substituted or unsubstituted C₅ cycloalkylene. Y may be R¹¹-substituted or unsubstituted C₅ arylene. Y may be substituted C₅ cycloalkylene. Y may be unsubstituted C₅ cycloalkylene. Y may be R¹¹-substituted C₅ cycloalkylene. Y may be substituted or unsubstituted heterocycloalkylene. Y may be R¹-substituted or unsubstituted heterocycloalkylene. Y may be substituted or unsubstituted 3-8 membered heterocycloalkylene. Y may be R¹¹-substituted or unsubstituted 3-8 membered heterocycloalkylene. Y may be substituted or unsubstituted 3-6 membered heterocycloalkylene. Y may be R¹¹-substituted or unsubstituted 3-6 membered heterocycloalkylene. Y may be substituted or unsubstituted 3-5 membered heterocycloalkylene. Y may be R¹¹-substituted or unsubstituted 3-5 membered heterocycloalkylene. Y may be substituted or unsubstituted 4-6 membered heterocycloalkylene. Y may be R¹¹-substituted or unsubstituted 4-6 membered heterocycloalkylene. Y may be substituted or unsubstituted 5 membered heterocycloalkylene. Y may be R¹¹-substituted or unsubstituted 5 membered heterocycloalkylene. Y may be substituted or unsubstituted 6 membered heterocycloalkylene. Y may be R¹¹-substituted or unsubstituted 6 membered heterocycloalkylene. Y may be substituted or unsubstituted arylene. Y may be R¹¹-substituted or unsubstituted arylene. Y may be substituted or unsubstituted C₆-C₁₀ arylene. Y may be R¹¹-substituted or unsubstituted C₆-C₁₀ arylene. Y may be substituted or unsubstituted C₆-C₁₀ arylene. Y may be R¹¹-substituted C₆-C₁₀ arylene. Y may be substituted or unsubstituted C₆ arylene. Y may be R¹¹-substituted or unsubstituted C₆ arylene. Y may be substituted C₆ arylene. Y may be unsubstituted C₆ arylene. Y may be R¹-substituted C₆ arylene. Y may be substituted or unsubstituted heteroarylene. Y may be R¹¹-substituted or unsubstituted heteroarylene. Y may be substituted or unsubstituted 5-10 membered heteroarylene. Y may be R¹¹-substituted or unsubstituted 5-10 membered heteroarylene. Y may be substituted or unsubstituted 5-6 membered heteroarylene. Y may be R¹¹-substituted or unsubstituted 5-6 membered heteroarylene. Y may be substituted or unsubstituted 5 membered heteroarylene. Y may be R¹¹-substituted or unsubstituted 5 membered heteroarylene. Y may be substituted or unsubstituted 6 membered heteroarylene. Y may be R¹¹-substituted or unsubstituted 6 membered heteroarylene. Y may be unsubstituted 5 membered heteroarylene. Y may be R¹¹-substituted 5 membered heteroarylene. Y may be unsubstituted 6 membered heteroarylene. Y may be R¹¹-substituted 6 membered heteroarylene. Y may be unsubstituted 5 to 6 membered heteroarylene. Y may be

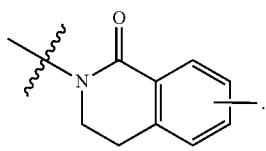

Y may be

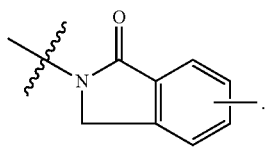

Y may be

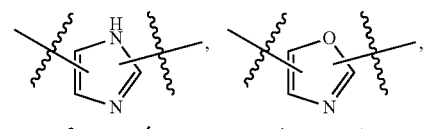

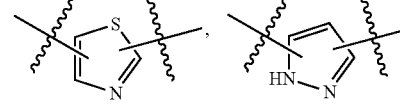

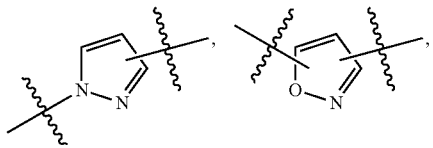

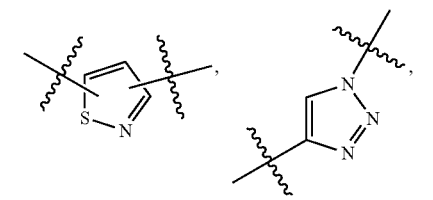

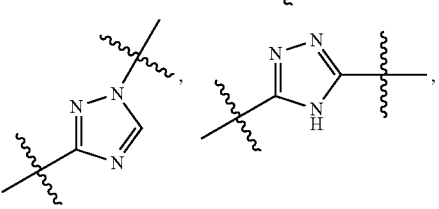

-continued
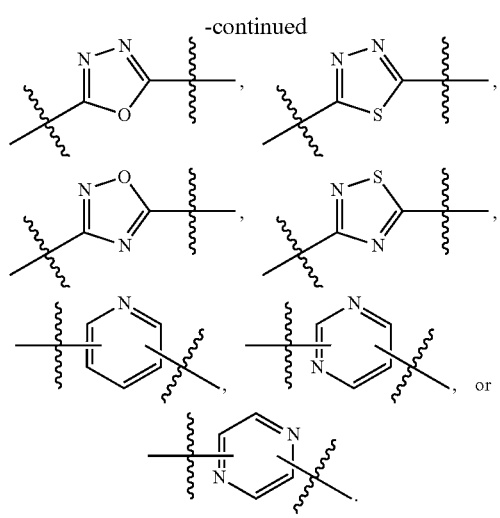
Y may be
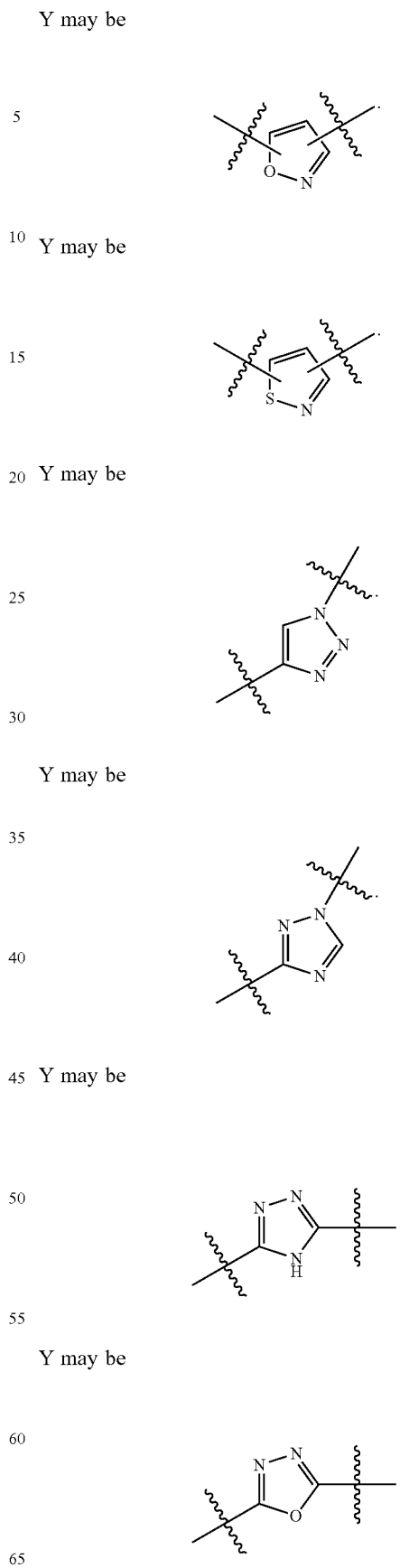
Y may be
Y may be
Y may be
Y may be
Y may be
Y may be
Y may be
Y may be
Y may be
Y may be Y may be

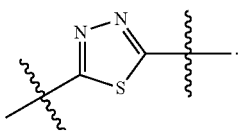 [SMILES: *c1nnc(*)s1]

Y may be

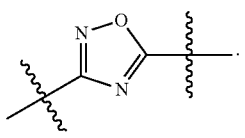 [SMILES: *c1noc(*)n1]

Y may be

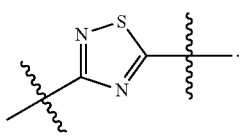 [SMILES: *c1nsc(*)n1]

Y may be

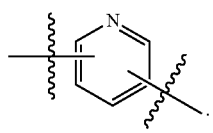

Y may be

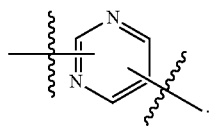

Y may be

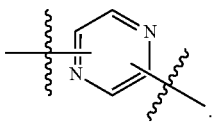

Y may independently be substituted or unsubstituted fused ring heterocycloalkyl. Y may independently be substituted fused ring heterocycloalkyl. Y may independently be unsubstituted fused ring heterocycloalkyl. Y may independently be $R^{11}$-substituted or unsubstituted fused ring heterocycloalkyl. Y may independently be $R^{11}$-substituted fused ring heterocycloalkyl. Y may independently be substituted or unsubstituted two fused ring heterocycloalkyl. Y may independently be substituted two fused ring heterocycloalkyl. Y may independently be unsubstituted two fused ring heterocycloalkyl. Y may independently be $R^{11}$-substituted or unsubstituted two fused ring heterocycloalkyl. Y may independently be $R^{11}$-substituted two fused ring heterocycloalkyl. Y may independently be substituted or unsubstituted three fused ring heterocycloalkyl. Y may independently be substituted three fused ring heterocycloalkyl. Y may independently be unsubstituted three fused ring heterocycloalkyl. Y may independently be $R^{11}$-substituted or unsubstituted three fused ring heterocycloalkyl. Y may independently be $R^{11}$-substituted three fused ring heterocycloalkyl. Y may independently be substituted or unsubstituted fused ring heterocycloalkyl wherein only one ring is a heterocycloalkyl. Y may independently be substituted fused ring heterocycloalkyl wherein only one ring is a heterocycloalkyl. Y may independently be unsubstituted fused ring heterocycloalkyl wherein only one ring is a heterocycloalkyl. Y may independently be $R^{11}$-substituted or unsubstituted fused ring heterocycloalkyl wherein only one ring is a heterocycloalkyl. Y may independently be $R^{11}$-substituted fused ring heterocycloalkyl wherein only one ring is a heterocycloalkyl.

Y may independently be substituted or unsubstituted fused ring aryl. Y may independently be substituted fused ring aryl. Y may independently be unsubstituted fused ring aryl. Y may independently be $R^{11}$-substituted or unsubstituted fused ring aryl. Y may independently be $R^{11}$-substituted fused ring aryl. Y may independently be substituted or unsubstituted two fused ring aryl. Y may independently be substituted two fused ring aryl. Y may independently be unsubstituted two fused ring aryl. Y may independently be $R^{11}$-substituted or unsubstituted two fused ring aryl. Y may independently be $R^{11}$-substituted two fused ring aryl. Y may independently be substituted or unsubstituted three fused ring aryl. Y may independently be substituted three fused ring aryl. Y may independently be unsubstituted three fused ring aryl. Y may independently be $R^{11}$-substituted or unsubstituted three fused ring aryl. Y may independently be $R^{11}$-substituted three fused ring aryl. Y may independently be substituted or unsubstituted fused ring aryl wherein only one ring is an aryl. Y may independently be substituted fused ring aryl wherein only one ring is an aryl. Y may independently be unsubstituted fused ring aryl wherein only one ring is an aryl. Y may independently be $R^1$-substituted or unsubstituted fused ring aryl wherein only one ring is an aryl. Y may independently be $R^{11}$-substituted fused ring aryl wherein only one ring is an aryl.

Y may independently be substituted or unsubstituted fused ring heteroaryl. Y may independently be substituted fused ring heteroaryl. Y may independently be unsubstituted fused ring heteroaryl. Y may independently be $R^{11}$-substituted or unsubstituted fused ring heteroaryl. Y may independently be $R^{11}$-substituted fused ring heteroaryl. Y may independently be substituted or unsubstituted two fused ring heteroaryl. Y may independently be substituted two fused ring heteroaryl. Y may independently be unsubstituted two fused ring heteroaryl. Y may independently be $R^{11}$-substituted or unsubstituted two fused ring heteroaryl. Y may independently be $R^{11}$-substituted two fused ring heteroaryl. Y may independently be substituted or unsubstituted three fused ring heteroaryl. Y may independently be substituted three fused ring heteroaryl. Y may independently be unsubstituted three fused ring heteroaryl. Y may independently be $R^{11}$-substituted or unsubstituted three fused ring heteroaryl. Y may independently be $R^{11}$-substituted three fused ring heteroaryl. Y may independently be substituted or unsubstituted fused ring heteroaryl wherein only one ring is a heteroaryl. Y may independently be substituted fused ring heteroaryl wherein only one ring is a heteroaryl. Y may independently be unsubstituted fused ring heteroaryl wherein only one ring is a heteroaryl. Y may independently be $R^{11}$-substituted or unsubstituted fused ring heteroaryl wherein only one ring is a heteroaryl. Y may independently be $R^{11}$-substituted fused ring heteroaryl wherein only one ring is a heteroaryl.

$R^{11}$ is hydrogen, halogen, oxo, $-N_3$, $-CF_3$, $-CCl_3$, $-CBr_3$, $-CI_3$, $-CN$, $-CHO$, $-OH$, $-NH_2$, $-COOH$, $-CONH_2$, $-NO_2$, $-SH$, $-SO_2CH_3$$-SO_3H$, $-SO_4H$, $-SO_2NH_2$, $-NHNH_2$, $-ONH_2$, $-NHC(O)NHNH_2$, unsubstituted alkyl, unsubstituted heteroalkyl, unsubstituted cycloalkyl, unsubstituted heterocycloalkyl, unsubstituted aryl, or unsubstituted heteroaryl. $R^{11}$ may be halogen, oxo, $-N_3$, $-CF_3$, $-CCl_3$, $-CBr_3$, $-CI_3$, $-CN$, $-CHO$, $-OH$, $-NH_2$, $-COOH$, $-CONH_2$, $-NO_2$, $-SH$, $-SO_2CH_3$$-SO_3H$, $-SO_4H$, $-SO_2NH_2$, $-NHNH_2$, $-ONH_2$, $-NHC(O)NHNH_2$, unsubstituted alkyl, unsubstituted heteroalkyl, unsubstituted cycloalkyl, unsubstituted heterocycloalkyl, unsubstituted aryl, or unsubstituted heteroaryl.

$R^{11}$ is hydrogen, halogen, oxo, $-N_3$, $-CF_3$, $-CCl_3$, $-CBr_3$, $-CI_3$, $-CN$, $-CHO$, $-OH$, $-NH_2$, $-COOH$, $-CONH_2$, $-NO_2$, $-SH$, $-SO_2CH_3$$-SO_3H$, $-SO_4H$, $-SO_2NH_2$, $-NHNH_2$, $-ONH_2$, $-NHC(O)NHNH_2$, unsubstituted alkyl (e.g. $C_1$-$C_8$ alkyl, $C_1$-$C_6$ alkyl, or $C_1$-$C_4$ alkyl), unsubstituted heteroalkyl (e.g. 2 to 8 membered heteroalkyl, 2 to 6 membered heteroalkyl, or 2 to 4 membered heteroalkyl), unsubstituted cycloalkyl (e.g. $C_3$-$C_8$ cycloalkyl, $C_4$-$C_8$ cycloalkyl, or $C_5$-$C_6$ cycloalkyl), unsubstituted heterocycloalkyl (e.g. 3 to 8 membered heterocycloalkyl, 4 to 8 membered heterocycloalkyl, or 5 to 6 membered heterocycloalkyl), unsubstituted aryl (e.g. $C_6$-$C_{10}$ aryl or $C_6$ aryl), or unsubstituted heteroaryl (e.g. 5 to 10 membered heteroaryl, 5 to 9 membered heteroaryl, or 5 to 6 membered heteroaryl).

$R^{11}$ may be halogen, oxo, $-N_3$, $-CF_3$, $-CCl_3$, $-CBr_3$, $-CI_3$, $-CN$, $-CHO$, $-OH$, $-NH_2$, $-COOH$, $-CONH_2$, $-NO_2$, $-SH$, $-SO_2CH_3$$-SO_3H$, $-SO_4H$, $-SO_2NH_2$, $-NHNH_2$, $-ONH_2$, $-NHC(O)NHNH_2$, unsubstituted alkyl (e.g. $C_1$-$C_8$ alkyl, $C_1$-$C_6$ alkyl, or $C_1$-$C_4$ alkyl), unsubstituted heteroalkyl (e.g. 2 to 8 membered heteroalkyl, 2 to 6 membered heteroalkyl, or 2 to 4 membered heteroalkyl), unsubstituted cycloalkyl (e.g. $C_3$-$C_8$ cycloalkyl, $C_4$-$C_8$ cycloalkyl, or $C_5$-$C_6$ cycloalkyl), unsubstituted heterocycloalkyl (e.g. 3 to 8 membered heterocycloalkyl, 4 to 8 membered heterocycloalkyl, or 5 to 6 membered heterocycloalkyl), unsubstituted aryl (e.g. $C_6$-$C_{10}$ aryl or $C_6$ aryl), or unsubstituted heteroaryl (e.g. 5 to 10 membered heteroaryl, 5 to 9 membered heteroaryl, or 5 to 6 membered heteroaryl).

In embodiments, Y is substituted 2 to 8 membered heteroalkylene. In embodiments, Y is unsubstituted 2 to 8 membered heteroalkylene. In embodiments, Y is substituted 3 to 7 membered heteroalkylene. In embodiments, Y is unsubstituted 3 to 7 membered heteroalkylene. In embodiments, Y is substituted 4 to 6 membered heteroalkylene. In embodiments, Y is unsubstituted 4 to 6 membered heteroalkylene. In embodiments, Y is substituted 5 to 6 membered heteroalkylene. In embodiments, Y is unsubstituted 5 to 6 membered heteroalkylene. In embodiments, Y is unsubstituted $C_2$-$C_8$ alkylene. In embodiments, Y is unsubstituted $C_3$-$C_7$ alkylene. In embodiments, Y is unsubstituted $C_4$-$C_6$ alkylene. In embodiments, Y is unsubstituted $C_5$-$C_6$ alkylene.

In embodiments, Y is —NHCO-(substituted or unsubstituted $C_5$-$C_6$ cycloalkylene)-NH—. In embodiments, Y is —NHCO-(substituted or unsubstituted $C_4$-$C_6$ cycloalkylene)-NH—. In embodiments, Y is —NHCO-(substituted or unsubstituted $C_3$-$C_7$ cycloalkylene)-NH—. In embodiments, Y is —NHCO-(substituted or unsubstituted $C_5$-$C_6$ cycloalkylene)-. In embodiments, Y is —NHCO-(substituted or unsubstituted $C_4$-$C_6$ cycloalkylene)-. In embodiments, Y is —NHCO-(substituted or unsubstituted $C_3$-$C_7$ cycloalkylene)-.

In embodiments, Y is —NHCO-(substituted or unsubstituted 5 to 6 membered heteroarylene)-NH—. In embodiments, Y is —NHCO-(substituted or unsubstituted 5 to 10 membered heteroarylene)-NH—. In embodiments, Y is —NHCO-(substituted or unsubstituted 5 to 6 membered heteroarylene)-. In embodiments, Y is —NHCO-(substituted or unsubstituted 5 to 10 membered heteroarylene)-. In embodiments, Y is —NHCO-(substituted or unsubstituted 5 to 6 membered heterocycloalkylene)-NH—. In embodiments, Y is —NHCO-(substituted or unsubstituted 4 to 7 membered heterocycloalkylene)-NH—. In embodiments, Y is —NHCO-(substituted or unsubstituted 5 to 6 membered heterocycloalkylene)-. In embodiments, Y is —NHCO-(substituted or unsubstituted 4 to 7 membered heterocycloalkylene)-. In embodiments, Y is -(substituted or unsubstituted 4 to 7 membered heterocycloalkylene)-(unsubstituted $C_1$-$C_4$ alkylene)-. In embodiments, Y is -(substituted or unsubstituted 4 to 7 membered heterocycloalkylene)-(unsubstituted $C_1$-$C_4$ alkylene)-NH—. In embodiments, Y is -(substituted or unsubstituted 5 to 6 membered heteroarylene)-(unsubstituted $C_1$-$C_4$ alkylene)-. In embodiments, Y is -(substituted or unsubstituted 5 to 6 membered heteroarylene)-(unsubstituted $C_1$-$C_4$ alkylene)-NH—. In embodiments, Y is -(substituted or unsubstituted $C_4$-$C_7$ cycloalkylene)-(unsubstituted $C_1$-$C_4$ alkylene)-. In embodiments, Y is -(substituted or unsubstituted $C_4$-$C_7$ cycloalkylene)-(unsubstituted $C_1$-$C_4$ alkylene)-NH—. In embodiments, Y is —O-(substituted or unsubstituted $C_5$-$C_6$ cycloalkylene)-NH—. In embodiments, Y is —O-(substituted or unsubstituted $C_4$-$C_6$ cycloalkylene)-NH—. In embodiments, Y is —O-(substituted or unsubstituted $C_3$-$C_7$ cycloalkylene)-NH—. In embodiments, Y is —O-(substituted or unsubstituted $C_5$-$C_6$ cycloalkylene)-. In embodiments, Y is —O-(substituted or unsubstituted $C_4$-$C_6$ cycloalkylene)-. In embodiments, Y is —O-(substituted or unsubstituted $C_3$-$C_7$ cycloalkylene)-. In embodiments, Y is —O-(substituted or unsubstituted 5 to 6 membered heteroarylene)-NH—. In embodiments, Y is —O-(substituted or unsubstituted 5 to 6 membered heteroarylene)-. In embodiments, Y is —NHCO-(substituted or unsubstituted 5 to 6 membered heteroarylene)-NH—. In embodiments, Y is —NHCO-(substituted or unsubstituted 5 to 6 membered heteroarylene)-. In embodiments, Y is a substituted fused cycloalkylene-arylene. In embodiments, Y is an unsubstituted fused cycloalkylene-arylene. In embodiments, Y is a substituted fused heterocycloalkylene-heteroarylene. In embodiments, Y is an unsubstituted fused heterocycloalkylene-heteroarylene. In embodiments, Y is a substituted fused arylene-heterocycloalkylene-heteroarylene. In embodiments, Y is an unsubstituted fused arylene-heterocycloalkyl ene-heteroarylene.

In embodiments, Y is —NHCOCH$_2$CH$_2$CH$_2$CH$_2$—. In embodiments, Y is —NHCOCH$_2$CH$_2$CH$_2$—. In embodiments, Y is a bond. In embodiments, Y is —CH$_2$NH—. In embodiments, Y is —CH$_2$CH$_2$CH$_2$NH—. In embodiments, Y is —NH—. In embodiments, Y is —NHCOCH$_2$CH$_2$—. In embodiments, Y is —CH$_2$CH$_2$CH$_2$CH$_2$CH$_2$CH$_2$NH—. In embodiments, Y is —CH$_2$CH$_2$CH$_2$CH$_2$CH$_2$CH$_2$—. In embodiments, Y is —CH$_2$CH$_2$—. In embodiments, Y is —CH$_2$CH$_2$CH$_2$—. In embodiments, Y is —CH$_2$CH$_2$CH$_2$CH$_2$—. In embodiments, Y is —CH$_2$CH$_2$CH$_2$CH$_2$CH$_2$—. In embodiments, Y is —CH$_2$CH$_2$CH$_2$CH$_2$CH$_2$NH—. In embodiments, Y is —NHCOCH$_2$CH$_2$CH$_2$CH$_2$NH—. In embodiments, Y is —NHCOCH$_2$CH$_2$CH$_2$NH—. In embodiments, Y is —NCOCH$_2$CH$_2$NH—. In embodiments, Y is —NHCOO—. In embodiments, Y is —NHCO—. In embodiments, Y is —NHCOOCH$_2$—. In embodiments, Y is —NHCOOCH$_2$CH$_2$NH—. In embodiments, Y is —OCH$_2$CH$_2$—. In embodiments, Y is —OCH$_2$CH$_2$NH—. In embodiments, Y is —NHCONH—. In embodiments, Y is —NHCONHCH$_2$CH$_2$—. In embodiments, Y is —NHCONHCH$_2$CH$_2$NH—. In embodiments, Y is —NHCH$_2$CH$_2$—. In embodiments, Y is —CONH—. In embodiments, Y is —CONHCH$_2$CH$_2$CH$_2$—. In embodiments, Y is —CONHCH$_2$CH$_2$CH$_2$NH—. In embodiments, Y is —NHCH$_2$CH$_2$CH$_2$—. In embodiments, Y is —NHCH$_2$CH$_2$CH$_2$NH—. In embodiments, Y is —O—. In embodiments, Y is —OCH$_2$CH$_2$CH$_2$CH$_2$—. In embodiments, Y is —OCH$_2$CH$_2$CH$_2$NH—. In embodiments, Y is —CH$_2$CH$_2$CH$_2$CH$_2$NH—. In embodiments, Y is —CHCHCH$_2$NH—.

In embodiments, Y is —CHCHCH$_2$—. In embodiments, Y is —CHCHCH$_2$NH—. In embodiments, Y is cyclohexyl. In embodiments, Y is unsubstituted cyclohexyl. In embodiments, Y is cyclopenyl. In embodiments, Y is unsubstituted cyclopentyl. In embodiments, Y is —NHCOPhNH—. In embodiments, Y is —NHCOPh-. In embodiments, Y is -Ph-. In embodiments, Y is -PhNH—. In embodiments, Y is —NHCO-cyclohexyl-NH—. In embodiments, Y is —NHCO-(unsubstituted cyclohexyl)-NH—. In embodiments, Y is —NHCO-cyclohexyl-. In embodiments, Y is —NHCO-(unsubstituted cyclohexyl)-. In embodiments, Y is —CH$_2$NHCOCH$_2$CH$_2$CH$_2$NH—. In embodiments, Y is —CH$_2$NHCO—. In embodiments, Y is —CH$_2$NH—. In embodiments, Y is —CH$_2$NHCOCH$_2$CH$_2$CH$_2$—. In embodiments, Y is —CH$_2$NHCOCH$_2$CH$_2$NH—. In embodiments, Y is —CH$_2$NHCOCH$_2$CH$_2$—. In embodiments, Y is —COCH$_2$CH$_2$CH$_2$NH—. In embodiments, Y is —COCH$_2$CH$_2$CH$_2$—. In embodiments, Y is —NHCH$_2$CH$_2$CH$_2$CH$_2$NH—. In embodiments, Y is —NHCH$_2$CH$_2$CH$_2$CH$_2$—.

In embodiments, Y is

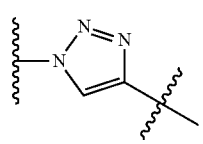

In embodiments, Y is

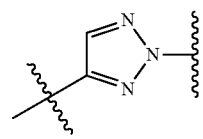

In embodiments, Y is

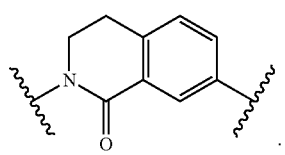 [SMILES: *c1ccc2c(c1)C(=O)N(*)CC2]

In embodiments, Y is

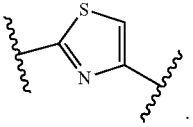

In embodiments, Y is

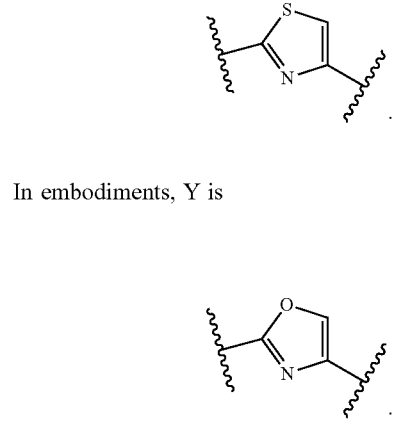

In embodiments, Y is

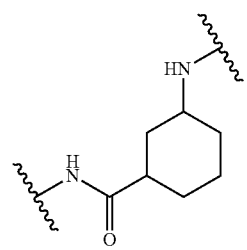

In embodiments, Y is

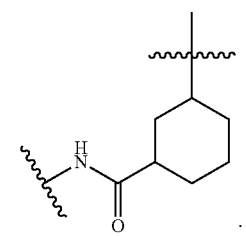 [SMILES: *NC(=O)C1CCCC(*)C1]

In embodiments, Y is

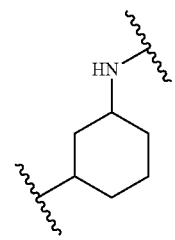

In embodiments, Y is
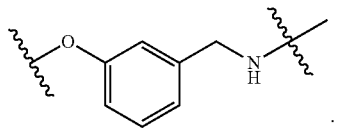 [SMILES: *NCc1cccc(O*)c1]
In embodiments, Y is
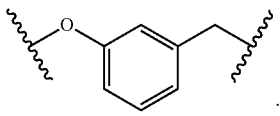 [SMILES: *Cc1cccc(O*)c1]
In embodiments, Y is
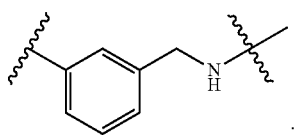 [SMILES: *NCc1cccc(*)c1]
In embodiments, Y is
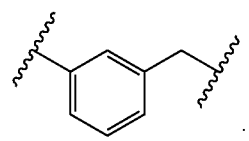 [SMILES: *Cc1cccc(*)c1]
In embodiments, Y is
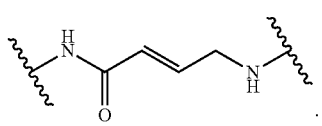 [SMILES: *NC/C=C/C(=O)N*]
In embodiments, Y is
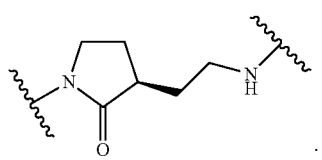 [SMILES: *NCC[C@@H]1CCN(*)C1=O]
In embodiments, Y is
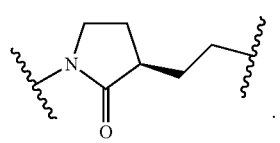 [SMILES: *CC[C@@H]1CCN(*)C1=O]
In embodiments, Y is
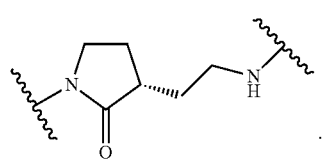 [SMILES: *NCC[C@H]1CCN(*)C1=O]
In embodiments, Y is
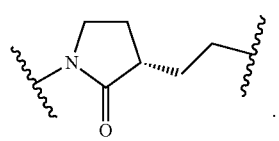 [SMILES: *CC[C@H]1CCN(*)C1=O]
In embodiments, Y is
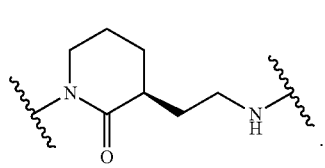 [SMILES: *NCC[C@@H]1CCCN(*)C1=O]
In embodiments, Y is
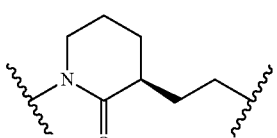
In embodiments, Y is
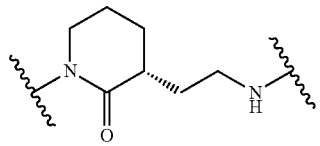
In embodiments, Y is
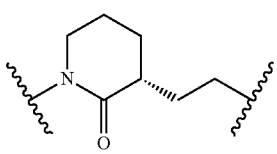

In embodiments, Y is

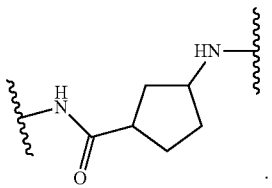 [SMILES: *NC(=O)C1CCC(N*)C1]

In embodiments, Y is

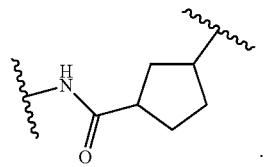 [SMILES: *NC(=O)C1CCC(*)C1]

In embodiments, Y is

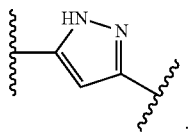 [SMILES: *c1cc(*)[nH]n1]

In embodiments, Y is

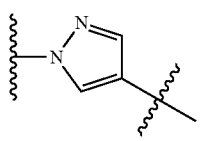

$R^4$ may be hydrogen. $R^4$ may be methyl. $R^4$ may be ethyl. $R^4$ may be propyl. $R^4$ may be isopropyl. $R^4$ may be unsubstituted methyl. $R^4$ may be unsubstituted ethyl. $R^4$ may be unsubstituted propyl.

$R^{12}$ may be hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, or $R^{12}$ may be a prodrug moiety. $R^{12}$ may be hydrogen, substituted or unsubstituted alkyl (e.g. $C_1$-$C_8$ alkyl, $C_1$-$C_6$ alkyl, or $C_1$-$C_4$ alkyl), substituted or unsubstituted heteroalkyl (e.g. 2 to 8 membered heteroalkyl, 2 to 6 membered heteroalkyl, or 2 to 4 membered heteroalkyl), substituted or unsubstituted cycloalkyl (e.g. $C_3$-$C_8$ cycloalkyl, $C_4$-$C_8$ cycloalkyl, or $C_5$-$C_6$ cycloalkyl), substituted or unsubstituted heterocycloalkyl (e.g. 3 to 8 membered heterocycloalkyl, 4 to 8 membered heterocycloalkyl, or 5 to 6 membered heterocycloalkyl), substituted or unsubstituted aryl (e.g. $C_6$-$C_{10}$ aryl or $C_6$ aryl), substituted or unsubstituted heteroaryl (e.g. 5 to 10 membered heteroaryl, 5 to 9 membered heteroaryl, or 5 to 6 membered heteroaryl), or $R^{12}$ may be a prodrug moiety. In embodiments, $R^{12}$ is a substituted or unsubstituted alkyl, or substituted or unsubstituted heteroalkyl.

$R^{12}$ may be hydrogen. $R^{12}$ may be substituted or unsubstituted alkyl. $R^{12}$ may be substituted or unsubstituted heteroalkyl. $R^{12}$ may be substituted or unsubstituted cycloalkyl. $R^{12}$ may be substituted or unsubstituted heterocycloalkyl. $R^{12}$ may be substituted or unsubstituted aryl. $R^{12}$ may be substituted or unsubstituted heteroaryl. $R^{12}$ may be a prodrug moiety. $R^{12}$ may be $R^{13}$-substituted or unsubstituted alkyl. $R^{12}$ may be $R^{13}$-substituted or unsubstituted heteroalkyl. $R^{12}$ may be $R^{13}$-substituted or unsubstituted cycloalkyl. $R^{12}$ may be $R^{13}$-substituted or unsubstituted heterocycloalkyl. $R^{12}$ may be $R^{13}$-substituted or unsubstituted aryl. $R^{12}$ may be $R^{13}$-substituted or unsubstituted heteroaryl. It will be understood that when $R^{12}$ is a prodrug moiety, the reaction that removes the prodrug moiety from the remainder of a compound described herein (e.g., prodrug) may, in embodiments, also remove the oxygen directly connected to $R^{12}$. In embodiments, where —$OR^{12}$ is removed, an —OH may replace the —$OR^{12}$.

In embodiments, $R^{12}$ is unsubstituted methyl. In embodiments, $R^{12}$ is unsubstituted ethyl. In embodiments, $R^{12}$ is unsubstituted propyl. In embodiments, $R^{12}$ is unsubstituted isopropyl. In embodiments, $R^{12}$ is unsubstituted t-butyl. In embodiments, $R^{12}$ is unsubstituted butyl. In embodiments, $R^{12}$ is unsubstituted $C_1$-$C_6$ alkyl. In embodiments, $R^{12}$ is substituted methyl. In embodiments, $R^{12}$ is substituted ethyl. In embodiments, $R^{12}$ is substituted propyl. In embodiments, $R^{12}$ is substituted isopropyl. In embodiments, $R^{12}$ is substituted t-butyl. In embodiments, $R^{12}$ is substituted butyl. In embodiments, $R^{12}$ is substituted $C_1$-$C_6$ alkyl. In embodiments, $R^{12}$ is $R^{13}$-substituted methyl. In embodiments, $R^{12}$ is $R^{13}$-substituted ethyl. In embodiments, $R^{12}$ is $R^{13}$-substituted propyl. In embodiments, $R^{12}$ is $R^{13}$-substituted isopropyl. In embodiments, $R^{12}$ is $R^{13}$-substituted t-butyl. In embodiments, $R^{12}$ is $R^{13}$-substituted butyl. In embodiments, $R^{12}$ is $R^{13}$-substituted $C_1$-$C_6$ alkyl. In embodiments, —$OR^{12}$ is a prodrug moiety. In embodiments, $R^{12}$ is a prodrug moiety.

In embodiments, $R^{12}$ is substituted or unsubstituted heteroalkyl (e.g. 2 to 8 membered heteroalkyl, 2 to 6 membered heteroalkyl, or 2 to 4 membered heteroalkyl). In embodiments, $R^{12}$ is substituted heteroalkyl (e.g. 2 to 8 membered heteroalkyl, 2 to 6 membered heteroalkyl, or 2 to 4 membered heteroalkyl). In embodiments, $R^{12}$ is unsubstituted heteroalkyl (e.g. 2 to 8 membered heteroalkyl, 2 to 6 membered heteroalkyl, or 2 to 4 membered heteroalkyl). In embodiments, $R^{12}$ is substituted or unsubstituted 2 to 8 membered heteroalkyl. In embodiments, $R^{12}$ is substituted or unsubstituted 2 to 6 membered heteroalkyl. In embodiments, $R^{12}$ is substituted or unsubstituted 2 to 4 membered heteroalkyl. In embodiments, $R^{12}$ is substituted 2 to 8 membered heteroalkyl. In embodiments, $R^{12}$ is substituted 2 to 6 membered heteroalkyl. In embodiments, $R^{12}$ is substituted 2 to 4 membered heteroalkyl. In embodiments, $R^{12}$ is unsubstituted 2 to 8 membered heteroalkyl. In embodiments, $R^{12}$ is unsubstituted 2 to 6 membered heteroalkyl. In embodiments, $R^{12}$ is unsubstituted 2 to 4 membered heteroalkyl. In embodiments, $R^{12}$ is $R^{13}$-substituted 2 to 8 membered heteroalkyl. In embodiments, $R^{12}$ is $R^{13}$-substituted 2 to 6 membered heteroalkyl. In embodiments, $R^{12}$ is $R^{13}$-substituted 2 to 4 membered heteroalkyl.

z1 is an integer from 0 to 5. z1 may be 0. z1 may be 1. z1 may be 2. z1 may be 3. z1 may be 4. z1 may be 5. z1 may be an integer between 0 and 3.

In embodiments, $R^2$ is —$NR^{3A}R^{3B}$, —$C(NH)NH_2$, —$C(NH)R^{3B}$, —$C(NR^{3A})NH_2$, —$C(NR^{3A})R^{3B}$, —$C(NCN)NH_2$, —$NH_2$, —$C(NH)NHR^{3B}$, —$C(NR^{3A})NHR^{3B}$, or —$C(NCN)NHR^{3B}$. In embodiments, $R^2$ is —$NR^{3A}R^{3B}$. $R^2$ may be —$C(NH)NH_2$. $R^2$ may be —$C(NH)R^{3B}$. $R^2$ may be —$C(NR^{3A})NH_2$. $R^2$ may be —$C(NR^{3A})R^{3B}$. $R^2$ may be —C(NCN)NH$_2$. R$^2$ may be —NH$_2$. R$^2$ may be —C(NH)NHR$^{3B}$. R$^2$ may be —C(NR$^{3A}$)NHR$^{3B}$. R$^2$ may be —C(NCN)NHR$^{3B}$. In embodiments, R$^2$ is a substituted or unsubstituted heteroaryl. In embodiments, R$^2$ is a substituted heteroaryl. In embodiments, R$^2$ is a substituted oxadiazolyl or substituted thiadiazolyl. In embodiments, R$^2$ is an oxadiazolyl substituted with —NH$_2$ or —NHMe. In embodiments, R$^2$ is a thiadiazolyl substituted with —NH$_2$ or —NHMe. In embodiments, R$^2$ is an unsubstituted fused ring heteroaryl. In embodiments, R$^2$ is

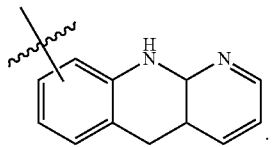

In embodiments, R$^2$ is

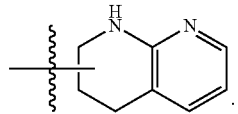

In embodiments, R$^2$ is —C(NH)NH$_2$.

In embodiments, L$^2$ is unsubstituted C$_1$-C$_5$ alkylene. In embodiments, L$^2$ is unsubstituted methylene.

In embodiments, L$^3$ is substituted or unsubstituted C$_1$-C$_8$ alkylene, substituted or unsubstituted 2 to 8 membered heteroalkylene, unsubstituted phenylene, unsubstituted 5 to 6 membered heteroarylene, or unsubstituted alkylarylene. In embodiments, L$^3$ is substituted or unsubstituted C$_1$-C$_7$ alkylene. In embodiments, L$^3$ is C$_1$-C$_7$ alkylene. In embodiments, L$^3$ is unsubstituted C$_1$-C$_7$ alkylene. In embodiments, L$^3$ is R$^6$-substituted C$_1$-C$_3$ alkylene; R$^6$ is —NHC(O)R$^{6A}$; R$^{6A}$ is —C(NCN)R$^{6C}$, —C(NH)R$^{6C}$, R$^{6C}$-substituted or unsubstituted alkyl, or R$^{6C}$-substituted or unsubstituted heteroalkyl; R$^{6C}$ is hydrogen, halogen, oxo, —N$_3$, —CF$_3$, —CCl$_3$, —CBr$_3$, —CI$_3$, —CN, —COR$^{6D}$, —OR$^{6D}$, —NR$^{6D}$R$^{6E}$, —COOR$^{6E}$, —CONR$^{6D}$R$^{6E}$, —NHC(O)R$^{6D}$, —NO$_2$, —SR$^{6D}$, —SO$_{n6}$R$^{6D}$, —NHNR$^{6D}$R$^{6E}$, —ONR$^{6D}$R$^{6E}$, —NHC(O)NHNR$^{6D}$R$^{6E}$, —C(NCN)R$^{6D}$, —C(NH)R$^{6D}$, R$^{6F}$-substituted or unsubstituted alkyl, R$^{6F}$-substituted or unsubstituted heteroalkyl, R$^{6F}$-substituted or unsubstituted cycloalkyl, R$^{6F}$-substituted or unsubstituted heterocycloalkyl, R$^{6F}$-substituted or unsubstituted aryl, or R$^{6F}$-substituted or unsubstituted heteroaryl; n6 is 2, 3, or 4; and R$^{6D}$, R$^{6E}$ and R$^{6F}$ are independently hydrogen, halogen, oxo, —N$_3$, —CF$_3$, —CCl$_3$, —CBr$_3$, —CI$_3$, —CN, —CHO, —OH, —NH$_2$, —COOH, —CONH$_2$, —NO$_2$, —SH, —SO$_2$, —SO$_2$Cl, —SO$_2$CH$_3$—SO$_3$H, —SO$_4$H, —SO$_2$NH$_2$, —NHNH$_2$, —ONH$_2$, —NHC(O)NHNH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, or a detectable moiety. In embodiments, R$^{6C}$ or R$^{6D}$ is a detectable moiety. In embodiments, R$^{6C}$ is a detectable moiety. In embodiments, R$^{6D}$ is a detectable moiety.

In embodiments, L$^3$ is substituted or unsubstituted C$_1$-C$_8$ alkylene, substituted or unsubstituted 2 to 8 membered heteroalkylene, unsubstituted phenylene, unsubstituted 5 to 6 membered heteroarylene, or unsubstituted alkylarylene. In embodiments, L$^3$ is substituted or unsubstituted C$_1$-C$_7$ alkylene. In embodiments, L$^3$ is R$^6$-substituted C$_1$-C$_3$ alkylene; R$^6$ is —NHC(O)R$^{6A}$; R$^{6A}$ is —C(NCN)R$^{6C}$, —C(NH)R$^{6C}$, R$^{6C}$-substituted or unsubstituted alkyl, or R$^{6C}$-substituted or unsubstituted heteroalkyl; R$^{6C}$ is hydrogen, halogen, oxo, —N$_3$, —CF$_3$, —CCl$_3$, —CBr$_3$, —CI$_3$, —CN, —COR$^{6D}$, —OR$^{6D}$, —NR$^{6D}$R$^{6E}$, —COOR$^{6E}$, —CONR$^{6D}$R$^{6E}$, —NHC(O)R$^{6D}$, —NO$_2$, —SR$^{6D}$, —SO$_{n6}$R$^{6D}$, —NHNR$^{6D}$R$^{6E}$, —ONR$^{6D}$R$^{6E}$, —NHC(O)NHNR$^{6D}$R$^{6E}$, —C(NCN)R$^{6D}$, —C(NH)R$^{6D}$, R$^{6F}$-substituted or unsubstituted alkyl, R$^{6F}$-substituted or unsubstituted heteroalkyl, R$^{6F}$-substituted or unsubstituted cycloalkyl, R$^{6F}$-substituted or unsubstituted heterocycloalkyl, R$^{6F}$-substituted or unsubstituted aryl, or R$^{6F}$-substituted or unsubstituted heteroaryl; n6 is 2, 3, or 4; and R$^{6D}$, R$^{6E}$ and R$^{6F}$ are independently hydrogen, halogen, oxo, —N$_3$, —CF$_3$, —CCl$_3$, —CBr$_3$, —CI$_3$, —CN, —CHO, —OH, —NH$_2$, —COOH, —CONH$_2$, —NO$_2$, —SH, —SO$_2$, —SO$_2$Cl, —SO$_2$CH$_3$—SO$_3$H, —SO$_4$H, —SO$_2$NH$_2$, —NHNH$_2$, —ONH$_2$, —NHC(O)NHNH$_2$, substituted or unsubstituted alkyl (e.g. C$_1$-C$_8$ alkyl, C$_1$-C$_6$ alkyl, or C$_1$-C$_4$ alkyl), substituted or unsubstituted heteroalkyl (e.g. 2 to 8 membered heteroalkyl, 2 to 6 membered heteroalkyl, or 2 to 4 membered heteroalkyl), substituted or unsubstituted cycloalkyl (e.g. C$_3$-C$_8$ cycloalkyl, C$_4$-C$_8$ cycloalkyl, or C$_5$-C$_6$ cycloalkyl), substituted or unsubstituted heterocycloalkyl (e.g. 3 to 8 membered heterocycloalkyl, 4 to 8 membered heterocycloalkyl, or 5 to 6 membered heterocycloalkyl), substituted or unsubstituted aryl (e.g. C$_6$-C$_{10}$ aryl or C$_6$ aryl), substituted or unsubstituted heteroaryl (e.g. 5 to 10 membered heteroaryl, 5 to 9 membered heteroaryl, or 5 to 6 membered heteroaryl), or a detectable moiety.

In embodiments, Y is a bond, —O—, —N(R$^4$)C(O)—, —N(R$^4$)C(O)NH—, —NHC(O)N(R$^4$)—, —N(R$^4$)C(O)O—, —N(R$^4$)C(O) N(R$^4$)—, substituted or unsubstituted 3 to 6 membered heterocycloalkylene, or substituted or unsubstituted 5 to 6 membered heteroarylene. In embodiments, Y is —NHC(O)—. In embodiments, Y is a bond. In embodiments, Y is —(NH)C(O)NH—. In embodiments, Y is —(NH)C(O)O—. In embodiments, Y is —N(R$^4$)C(O)N(R$^4$)—. In embodiments, Y is substituted 5 to 6 membered heterocycloalkylene. In embodiments, Y is unsubstituted 5 to 6 membered heteroarylene. In embodiments, R$^4$ is hydrogen. In embodiments, R$^4$ is unsubstituted methyl. In embodiments, R$^4$ is unsubstituted ethyl. In embodiments, R$^4$ is unsubstituted propyl. In embodiments, R$^4$ is unsubstituted butyl. In embodiments, R$^4$ is unsubstituted tert-butyl.

In embodiments, R$^1$ is independently hydrogen, halogen, —SO$_2$Me, —SO$_2$Ph, —COOH, substituted or unsubstituted C$_1$-C$_5$ alkyl, substituted or unsubstituted 2 to 5 membered heteroalkyl, or substituted or unsubstituted C$_6$-C$_{10}$ aryl. In embodiments, R$^1$ is independently hydrogen, halogen, substituted or unsubstituted C$_1$-C$_5$ alkyl, substituted or unsubstituted 2 to 5 membered heteroalkyl, or substituted or unsubstituted C$_6$-C$_{10}$ aryl. In embodiments, R$^1$ is independently halogen, —SO$_2$Me, —SO$_2$Ph, —COOH, substituted or unsubstituted C$_1$-C$_5$ alkyl, substituted or unsubstituted 2 to 5 membered heteroalkyl, or substituted or unsubstituted C$_6$-C$_{10}$ aryl. In embodiments, R$^1$ is independently halogen, substituted or unsubstituted C$_1$-C$_5$ alkyl, substituted or unsubstituted 2 to 5 membered heteroalkyl, or substituted or unsubstituted C$_6$-C$_{10}$ aryl.

In embodiments, R$^{3A}$ and R$^{3B}$ are independently hydrogen, —C(NH)NH$_2$, —C(NCN)NH$_2$, substituted or unsubstituted heterocycloalkyl, substituted or unsubstituted heteroaryl. In embodiments, R$^{3A}$ and R$^{3B}$ are joined to form a substituted or unsubstituted 5 or 6 membered heterocycloalkyl or substituted or unsubstituted 5 or 6 membered heteroaryl. In embodiments, $R^{3A}$ and $R^{3B}$ are independently hydrogen, —C(NH)NH$_2$, —C(NCN)NH$_2$, or substituted or unsubstituted 3 to 6 membered heterocycloalkyl, or substituted or unsubstituted 5 to 6 membered heteroaryl.

In embodiments, the compound has the formula:

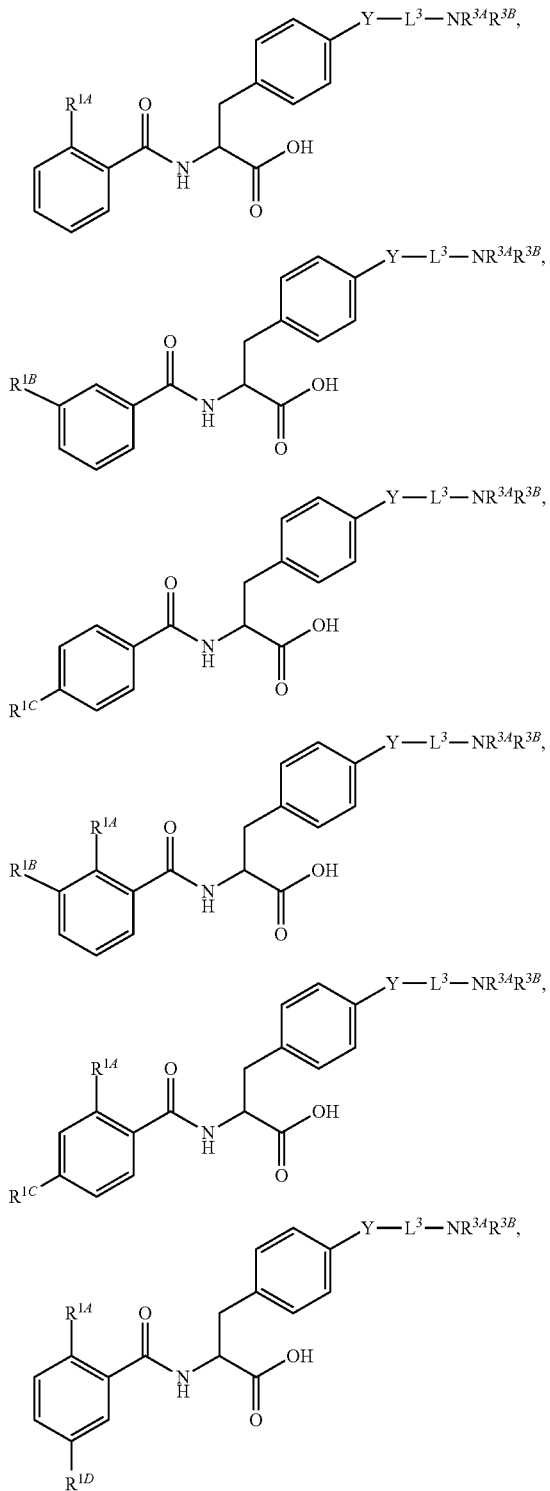

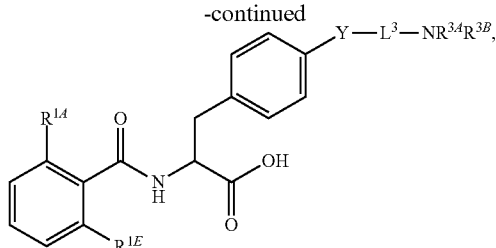

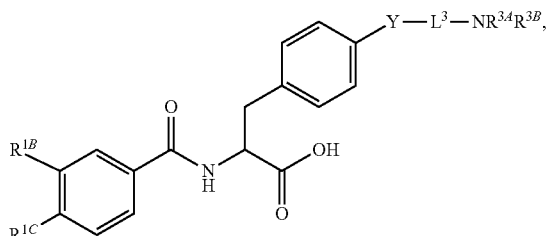

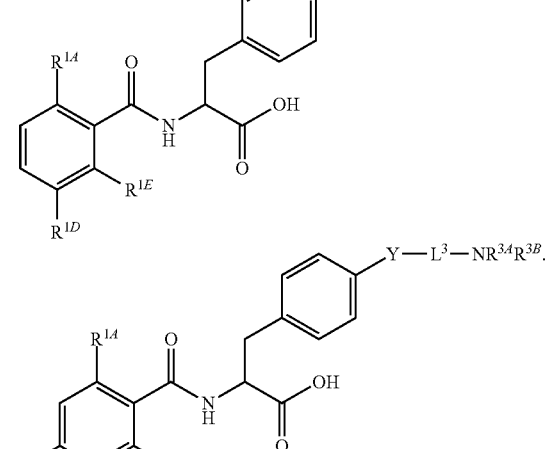

$Y$, $L^3$, $R^{3A}$, $R^{3B}$, $R^{1A}$, $R^{1B}$, $R^{1C}$, $R^{1D}$, and $R^{1E}$ are as described herein.

In embodiments, $R^{1A}$, $R^{1B}$, $R^{1C}$, $R^{1D}$, and $R^{1E}$ are independently hydrogen, halogen, —N$_3$, —CF$_3$, —CCl$_3$, —CBr$_3$, —CI$_3$, —CN, —CHO, —OH, —NH$_2$, —COOH, —CONH$_2$, —NO$_2$, —SH, —SO$_2$, —SO$_2$Cl, —SO$_2$CH$_3$, —SO$_2$Ph, —SO$_3$H, —OSO$_3$H, —SO$_2$NH$_2$, —NHNH$_2$, —ONH$_2$, —NHC(O)NHNH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, or a detectable moiety. In embodiments, $R^{1A}$, $R^{1B}$, $R^{1C}$, $R^{1D}$, and $R^{1E}$ are independently hydrogen, halogen, unsubstituted $C_1$-$C_3$ alkyl, unsubstituted 2 to 3 membered heteroalkyl, or unsubstituted phenyl. In embodiments, the two $R^1$ substituents joined to form a ring described herein are two groups selected from $R^{1A}$, $R^{1B}$, $R^{1C}$, $R^{1D}$, and $R^{1E}$. The two $R^1$ substituents joined to form a ring may be $R^{1A}$ and $R^{1B}$. The two $R^1$ substituents joined to form a ring may be $R^{1A}$ and $R^{1C}$. The two $R^1$ substituents joined to form a ring may be $R^{1A}$ and $R^{1D}$. The two $R^1$ substituents joined to form a ring may be $R^{1A}$ and $R^{1E}$. The two $R^1$ substituents joined to form a ring may be $R^{1B}$ and $R^{1C}$. The two $R^1$ substituents joined to form a ring may be $R^{1B}$ and $R^{1D}$. The two $R^1$ substituents joined to form a ring may be $R^{1B}$ and $R^{1E}$. The two $R^1$ substituents joined to form a ring may be $R^{1C}$ and $R^{1D}$. The two $R^1$ substituents joined to form a ring may be $R^{1C}$ and $R^{1E}$. The two $R^1$ substituents joined to form a ring may be $R^{1D}$ and $R^{1E}$. In embodiments of the compound having the formula:

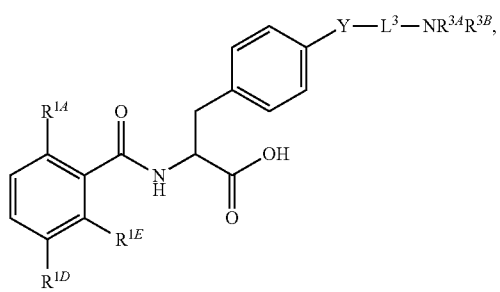

$R^{1D}$ and $R^{1E}$ are joined to form a ring described herein (e.g., substituted or unsubstituted cycloalkyl, substituted or unsubstituted heterocycloalkyl, substituted or unsubstituted aryl, or substituted or unsubstituted heteroaryl).

In embodiments, the compound has the formula:

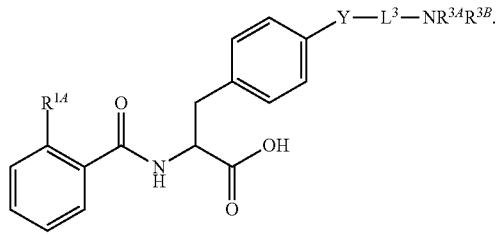

In embodiments, the compound has the formula:

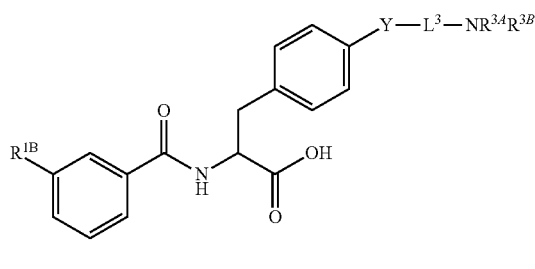

In embodiments, the compound has the formula:

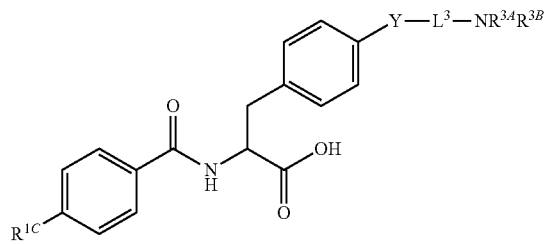

In embodiments, the compound has the formula:

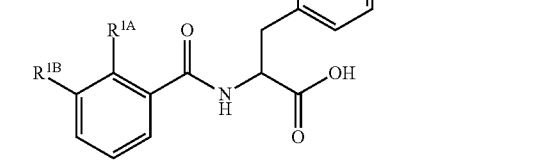

In embodiments, the compound has the formula:

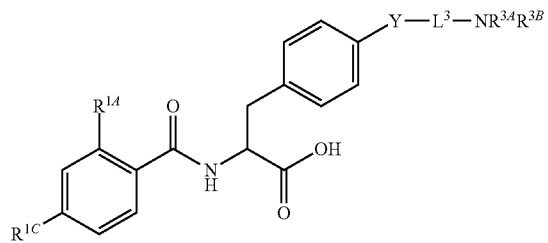

In embodiments, the compound has the formula:

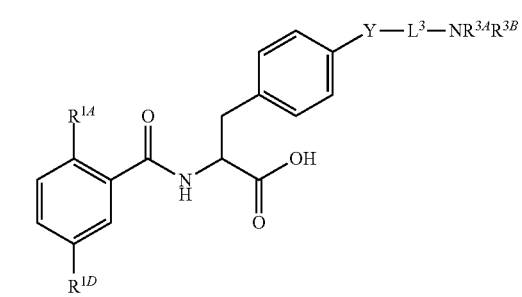

In embodiments, the compound has the formula:

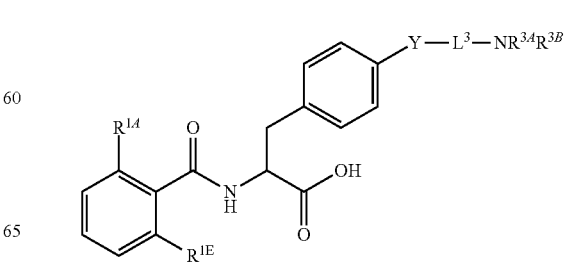

In embodiments, the compound has the formula:
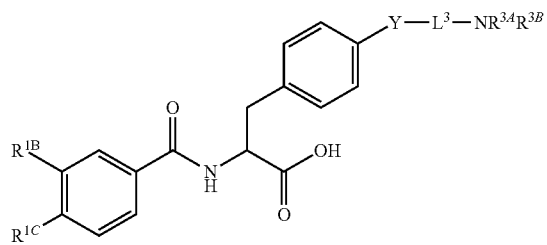
In embodiments, the compound has the formula:
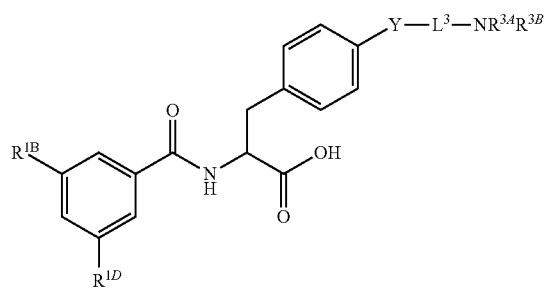
In embodiments, the compound has the formula:
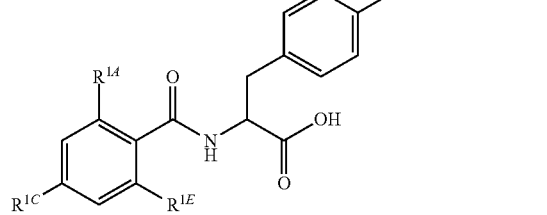
In embodiments, the compound has the formula:
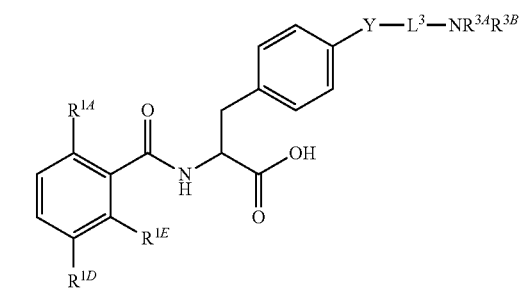
In each formula above, Y, $L^3$, $R^3$, $R^{3B}$, $R^{1A}$, $R^{1B}$, $R^{1C}$, $R^{1D}$, and $R^{1E}$ are as described herein.
In embodiments, the compound has the formula:
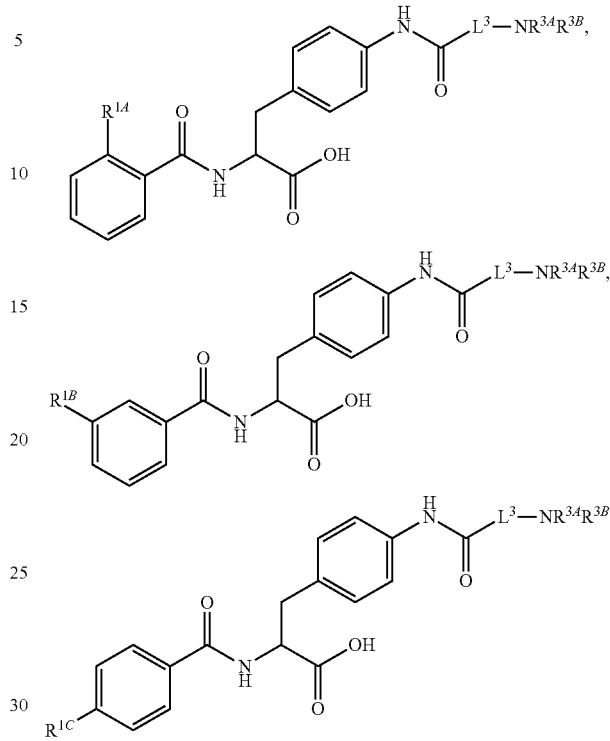
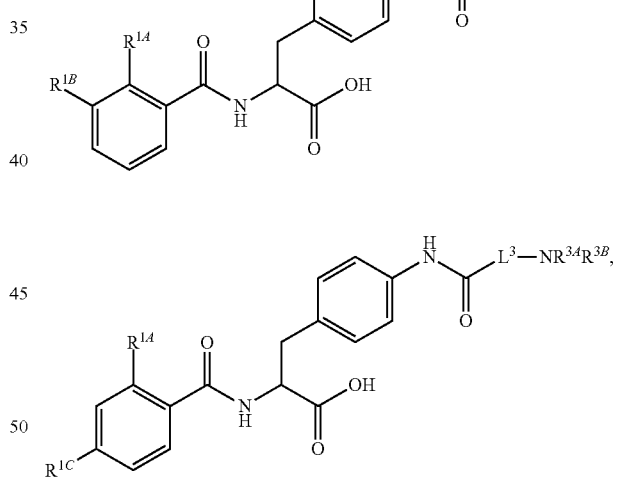
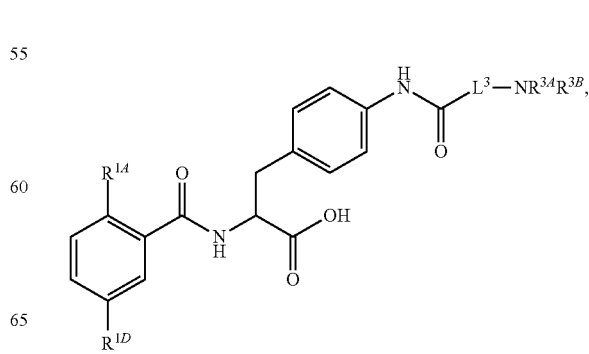

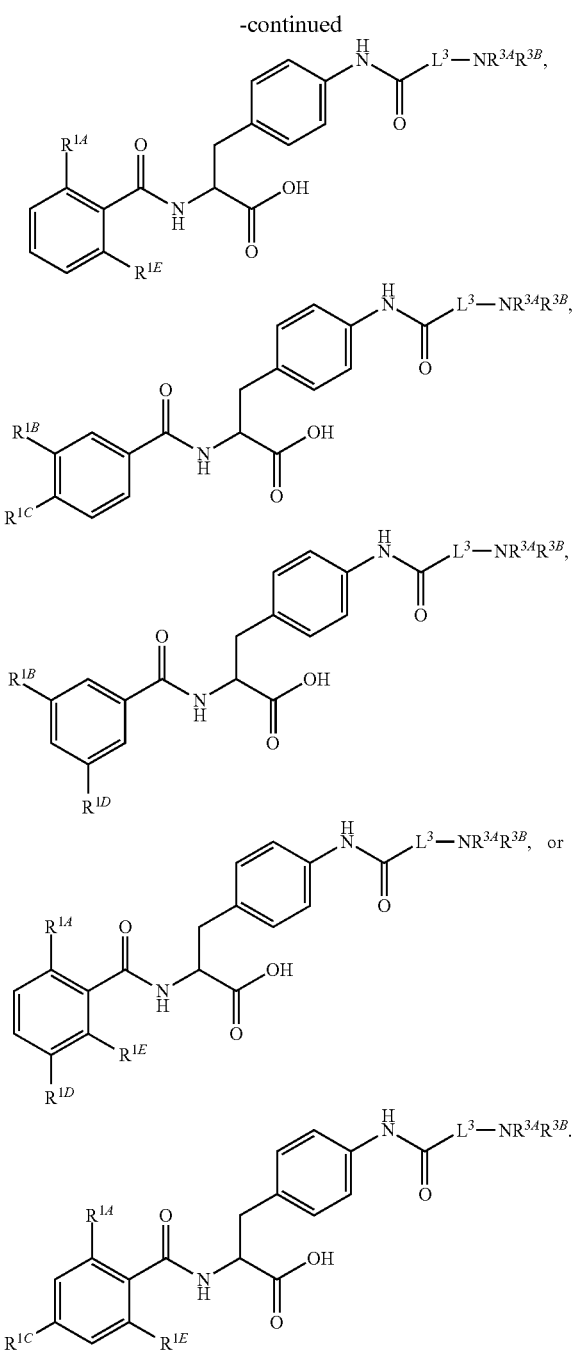

$L^3$, $R^{3A}$, $R^{3B}$, $R^{1A}$, $R^{1B}$, $R^{1C}$, $R^{1D}$, and $R^{1E}$ are as described herein.

In embodiments, $R^{1A}$, $R^{1B}$, $R^{1C}$, $R^{1D}$, and $R^{1E}$ are independently hydrogen, halogen, —$N_3$, —$CF_3$, —$CCl_3$, —$CBr_3$, —$CI_3$, —CN, —CHO, —OH, —$NH_2$, —COOH, —$CONH_2$, —$NO_2$, —SH, —$SO_2$, —$SO_2CH_3$, —$SO_2Ph$, —$SO_3H$, —$OSO_3H$, —$SO_2NH_2$, —$NHNH_2$, —$ONH_2$, —NHC(O)$NHNH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, or a detectable moiety. In embodiments, $R^{1A}$, $R^{1B}$, $R^{1C}$, $R^{1D}$, and $R^{1E}$ are independently hydrogen, halogen, —$N_3$, —$CF_3$, —$CCl_3$, —$CBr_3$, —$CI_3$, —CN, —CHO, —OH, —$NH_2$, —COOH, —$CONH_2$, —$NO_2$, —SH, —$SO_2$, —$SO_2CH_3$, —$SO_2Ph$, —$SO_3H$, —$OSO_3H$, —$SO_2NH_2$, —$NHNH_2$, —$ONH_2$, —NHC(O)$NHNH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, $R^{1A}$, $R^{1B}$, $R^{1C}$, $R^{1D}$, and $R^{1E}$ are independently hydrogen, halogen, unsubstituted $C_1$-$C_3$ alkyl, unsubstituted 2 to 3 membered heteroalkyl, or unsubstituted phenyl.

In embodiments, $R^{1A}$, $R^{1B}$, $R^{1C}$, $R^{1D}$, and $R^{1E}$ are independently hydrogen, halogen, —$N_3$, —$CF_3$, —$CCl_3$, —$CBr_3$, —$CI_3$, —CN, —CHO, —OH, —$NH_2$, —COOH, —$CONH_2$, —$NO_2$, —SH, —$SO_2$, —$SO_2CH_3$, —$SO_2Ph$, —$SO_3H$, —$OSO_3H$, —$SO_2NH_2$, —$NHNH_2$, —$ONH_2$, —NHC(O)$NHNH_2$, substituted or unsubstituted alkyl (e.g. $C_1$-$C_8$ alkyl, $C_1$-$C_6$ alkyl, or $C_1$-$C_4$ alkyl), substituted or unsubstituted heteroalkyl (e.g. 2 to 8 membered heteroalkyl, 2 to 6 membered heteroalkyl, or 2 to 4 membered heteroalkyl), substituted or unsubstituted cycloalkyl (e.g. $C_3$-$C_8$ cycloalkyl, $C_4$-$C_8$ cycloalkyl, or $C_5$-$C_6$ cycloalkyl), substituted or unsubstituted heterocycloalkyl (e.g. 3 to 8 membered heterocycloalkyl, 4 to 8 membered heterocycloalkyl, or 5 to 6 membered heterocycloalkyl), substituted or unsubstituted aryl (e.g. $C_6$-$C_{10}$ aryl or $C_6$ aryl), substituted or unsubstituted heteroaryl (e.g. 5 to 10 membered heteroaryl, 5 to 9 membered heteroaryl, or 5 to 6 membered heteroaryl), or a detectable moiety. In embodiments, $R^{1A}$, $R^{1B}$, $R^{1C}$, $R^{1D}$, and $R^{1E}$ are independently hydrogen, halogen, —$N_3$, —$CF_3$, —$CCl_3$, —$CBr_3$, —$CI_3$, —CN, —CHO, —OH, —$NH_2$, —COOH, —$CONH_2$, —$NO_2$, —SH, —$SO_2$, —$SO_2CH_3$, —$SO_2Ph$, —$SO_3H$, —$OSO_3H$, —$SO_2NH_2$, —$NHNH_2$, —$ONH_2$, —NHC(O)$NHNH_2$, substituted or unsubstituted alkyl (e.g. $C_1$-$C_8$ alkyl, $C_1$-$C_6$ alkyl, or $C_1$-$C_4$ alkyl), substituted or unsubstituted heteroalkyl (e.g. 2 to 8 membered heteroalkyl, 2 to 6 membered heteroalkyl, or 2 to 4 membered heteroalkyl), substituted or unsubstituted cycloalkyl (e.g. $C_3$-$C_8$ cycloalkyl, $C_4$-$C_8$ cycloalkyl, or $C_5$-$C_6$ cycloalkyl), substituted or unsubstituted heterocycloalkyl (e.g. 3 to 8 membered heterocycloalkyl, 4 to 8 membered heterocycloalkyl, or 5 to 6 membered heterocycloalkyl), substituted or unsubstituted aryl (e.g. $C_6$-$C_{10}$ aryl or $C_6$ aryl), substituted or unsubstituted heteroaryl (e.g. 5 to 10 membered heteroaryl, 5 to 9 membered heteroaryl, or 5 to 6 membered heteroaryl).

In embodiments, the compound has the formula:

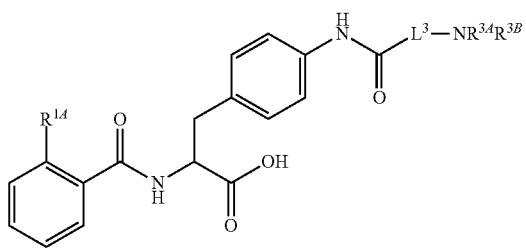

In embodiments, the compound has the formula:
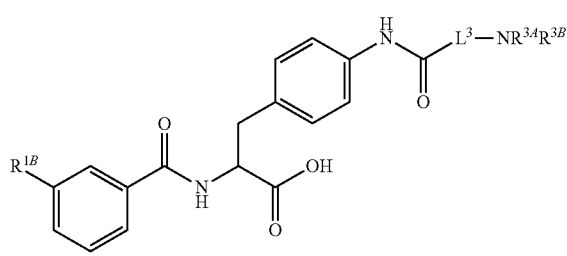
In embodiments, the compound has the formula:
In embodiments, the compound has the formula:
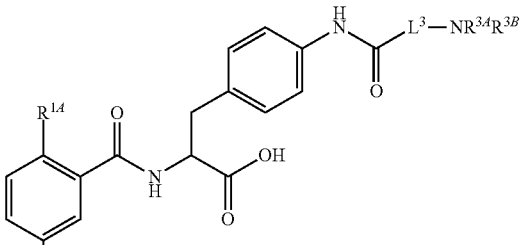
In embodiments, the compound has the formula:
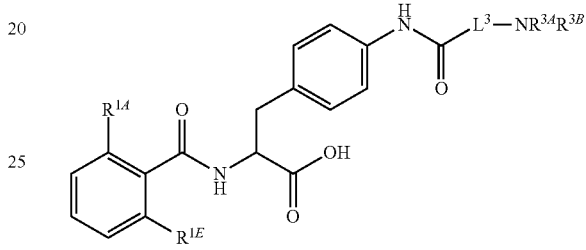
In embodiments, the compound has the formula:
In embodiments, the compound has the formula:
In embodiments, the compound has the formula:
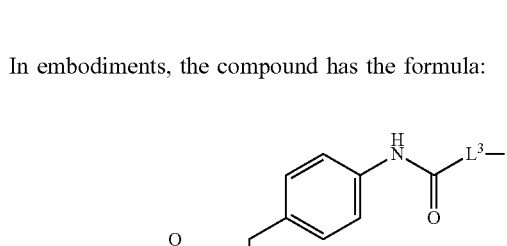

In embodiments, the compound has the formula:

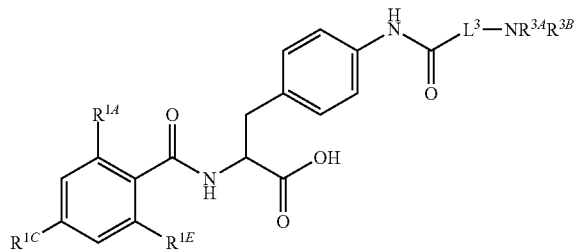

In embodiments, the compound has the formula:

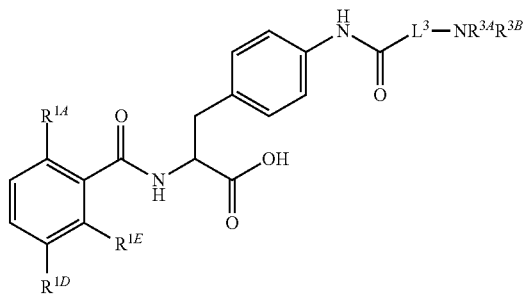

In each formula above, $L^3$, $R^{3A}$, $R^{3B}$, $R^{1A}$, $R^{1B}$, $R^{1C}$, $R^{1D}$, and $R^{1E}$ are as described herein.

In embodiments, $R^{1A}$ may be hydrogen, halogen, —N$_3$, —CF$_3$, —CCl$_3$, —CBr$_3$, —CI$_3$, —CN, —CHO, —OH, —NH$_2$, —COOH, —CONH$_2$, —NO$_2$, —SH, —SO$_2$CH$_3$, —SO$_2$Ph, —SO$_3$H, —OSO$_3$H, —SO$_2$NH$_2$, —NHNH$_2$, —ONH$_2$, —NHC(O)NHNH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, or a detectable moiety. $R^{1A}$ may be hydrogen. $R^{1A}$ may be halogen. $R^{1A}$ may be —N$_3$. $R^{1A}$ may be —CX$^{1A}{}_3$. $R^{1A}$ may be —CHX$^{1A}{}_2$. $R^{1A}$ may be —CH$_2$X$^{1A}$. $R^{1A}$ may be —CN. $R^{1A}$ may be —CHO. $R^{1A}$ may be —OH. $R^{1A}$ may be —NH$_2$. $R^{1A}$ may be —COOH. $R^{1A}$ may be —CONH$_2$. $R^{1A}$ may be —NO$_2$. $R^{1A}$ may be —SH. $R^{1A}$ may be —SO$_2$CH$_3$. $R^{1A}$ may be —SO$_2$Ph. $R^{1A}$ may be —SO$_3$H. $R^{1A}$ may be —OSO$_3$H. $R^{1A}$ may be —SO$_2$NH$_2$. $R^{1A}$ may be —NHNH$_2$. $R^{1A}$ may be —ONH$_2$. $R^{1A}$ may be —NHC(O)NHNH$_2$. $R^{1A}$ may be —OPO$_3$H. $R^{1A}$ may be —PO$_3$H$_2$. $R^{1A}$ may be —OCX$^{1A}{}_3$. $R^{1A}$ may be —OCHX$^{1A}{}_2$. $R^{1A}$ may be substituted alkyl. $R^{1A}$ may be substituted heteroalkyl. $R^{1A}$ may be substituted cycloalkyl. $R^{1A}$ may be substituted heterocycloalkyl. $R^{1A}$ may be substituted aryl. $R^{1A}$ may be substituted heteroaryl. $R^{1A}$ may be unsubstituted alkyl. $R^{1A}$ may be unsubstituted heteroalkyl. $R^{1A}$ may be unsubstituted cycloalkyl. $R^{1A}$ may be unsubstituted heterocycloalkyl. $R^{1A}$ may be unsubstituted aryl. $R^{1A}$ may be unsubstituted heteroaryl. $R^{1A}$ may be detectable moiety. $R^{1A}$ may be —F. $R^{1A}$ may be —Cl. $R^{1A}$ may be —Br. $R^{1A}$ may be —I. $R^{1A}$ may be —OCH$_3$. $R^{1A}$ may be —CH$_3$. $R^{1A}$ may be —CH$_2$CH$_3$. $R^{1A}$ may be —SCH$_3$. $R^{1A}$ may be unsubstituted phenyl. Each $X^{1A}$ is independently —F, —Cl, —Br, or —I.

In embodiments, $R^{1B}$ may be hydrogen, halogen, —N$_3$, —CF$_3$, —CCl$_3$, —CBr$_3$, —CI$_3$, —CN, —CHO, —OH, —NH$_2$, —COOH, —CONH$_2$, —NO$_2$, —SH, —SO$_2$CH$_3$, —SO$_2$Ph, —SO$_3$H, —OSO$_3$H, —SO$_2$NH$_2$, —NHNH$_2$, —ONH$_2$, —NHC(O)NHNH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, or a detectable moiety. $R^{1B}$ may be hydrogen. $R^{1B}$ may be halogen. $R^{1B}$ may be —N$_3$. $R^{1B}$ may be —CX$^{1B}{}_3$. $R^{1B}$ may be —CHX$^{1B}{}_2$. $R^{1B}$ may be —CH$_2$X$^{1B}$. $R^{1B}$ may be —CN. $R^{1B}$ may be —CHO. $R^{1B}$ may be —OH. $R^{1B}$ may be —NH$_2$. $R^{1B}$ may be —COOH. $R^{1B}$ may be —CONH$_2$. $R^{1B}$ may be —NO$_2$. $R^{1B}$ may be —SH. $R^{1B}$ may be —SO$_2$CH$_3$. $R^{1B}$ may be —SO$_2$Ph. $R^{1B}$ may be —SO$_3$H. $R^{1B}$ may be —OSO$_3$H. $R^{1B}$ may be —SO$_2$NH$_2$. $R^{1B}$ may be —NHNH$_2$. $R^{1B}$ may be —ONH$_2$. $R^{1B}$ may be —NHC(O)NHNH$_2$. $R^{1B}$ may be —OPO$_3$H. $R^{1B}$ may be —PO$_3$H$_2$. $R^{1B}$ may be —OCX$^{1B}{}_3$. $R^{1B}$ may be —OCHX$^{1B}$ 2. $R^{1B}$ may be substituted alkyl. $R^{1B}$ may be substituted heteroalkyl. $R^{1B}$ may be substituted cycloalkyl. $R^{1B}$ may be substituted heterocycloalkyl. $R^{1B}$ may be substituted aryl. $R^{1B}$ may be substituted heteroaryl. $R^{1B}$ may be unsubstituted alkyl. $R^{1B}$ may be unsubstituted heteroalkyl. $R^{1B}$ may be unsubstituted cycloalkyl. $R^{1B}$ may be unsubstituted heterocycloalkyl. $R^{1B}$ may be unsubstituted aryl. $R^{1B}$ may be unsubstituted heteroaryl. $R^{1B}$ may be detectable moiety. $R^{1B}$ may be —F. $R^{1B}$ may be —Cl. $R^{1B}$ may be —Br. $R^{1B}$ may be —I. $R^{1B}$ may be —OCH$_3$. $R^{1B}$ may be —CH$_3$. $R^{1B}$ may be —CH$_2$CH$_3$. $R^{1B}$ may be —SCH$_3$. $R^{1B}$ may be unsubstituted phenyl. Each $X^{1B}$ is independently —F, —Cl, —Br, or —I.

In embodiments, $R^{1C}$ may be hydrogen, halogen, —N$_3$, —CF$_3$, —CCl$_3$, —CBr$_3$, —CI$_3$, —CN, —CHO, —OH, —NH$_2$, —COOH, —CONH$_2$, —NO$_2$, —SH, —SO$_2$CH$_3$, —SO$_2$Ph, —SO$_3$H, —OSO$_3$H, —SO$_2$NH$_2$, —NHNH$_2$, —ONH$_2$, —NHC(O)NHNH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, or a detectable moiety. $R^{1C}$ may be hydrogen. $R^{1C}$ may be halogen. $R^{1C}$ may be —N$_3$. $R^{1C}$ may be —CX$^{1C}{}_3$. $R^{1C}$ may be —CHX$^{1C}{}_2$. $R^{1C}$ may be —CH$_2$X$^{1C}$. $R^{1C}$ may be —CN. $R^{1C}$ may be —CHO. $R^{1C}$ may be —OH. $R^{1C}$ may be —NH$_2$. $R^{1C}$ may be —COOH. $R^{1C}$ may be —CONH$_2$. $R^{1C}$ may be —NO$_2$. $R^{1C}$ may be —SH. $R^{1C}$ may be —SO$_2$CH$_3$. $R^{1C}$ may be —SO$_2$Ph. $R^{1C}$ may be —SO$_3$H. $R^{1C}$ may be —OSO$_3$H. $R^{1C}$ may be —SO$_2$NH$_2$. $R^{1C}$ may be —NHNH$_2$. $R^{1C}$ may be —ONH$_2$. $R^{1C}$ may be —NHC(O)NHNH$_2$. $R^{1C}$ may be —OPO$_3$H. $R^{1C}$ may be —PO$_3$H$_2$. $R^{1C}$ may be —OCX$^{1C}{}_3$. $R^{1C}$ may be —OCHX$^{1C}{}_2$. $R^{1C}$ may be substituted alkyl. $R^{1C}$ may be substituted heteroalkyl. $R^{1C}$ may be substituted cycloalkyl. $R^{1C}$ may be substituted heterocycloalkyl. $R^{1C}$ may be substituted aryl. $R^{1C}$ may be substituted heteroaryl. $R^{1C}$ may be unsubstituted alkyl. $R^{1C}$ may be unsubstituted heteroalkyl. $R^{1C}$ may be unsubstituted cycloalkyl. $R^{1C}$ may be unsubstituted heterocycloalkyl. $R^{1C}$ may be unsubstituted aryl. $R^{1C}$ may be unsubstituted heteroaryl. $R^{1C}$ may be detectable moiety. $R^{1C}$ may be —F. $R^{1C}$ may be —Cl. $R^{1C}$ may be —Br. $R^{1C}$ may be —I. $R^{1C}$ may be —OCH$_3$. $R^{1C}$ may be —CH$_3$. $R^{1C}$ may be —CH$_2$CH$_3$. $R^{1C}$ may be —SCH$_3$. $R^{1C}$ may be unsubstituted phenyl. Each $X^{1C}$ is independently —F, —Cl, —Br, or —I.

In embodiments, $R^{1D}$ may be hydrogen, halogen, —N$_3$, —CF$_3$, —CCl$_3$, —CBr$_3$, —CI$_3$, —CN, —CHO, —OH, —NH$_2$, —COOH, —CONH$_2$, —NO$_2$, —SH, —SO$_2$CH$_3$, —SO$_2$Ph, —SO$_3$H, —OSO$_3$H, —SO$_2$NH$_2$, —NHNH$_2$, —ONH$_2$, —NHC(O)NHNH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, or a detectable moiety. $R^{1D}$ may be hydrogen. $R^{1D}$ may be halogen. $R^{1D}$ may be —$N_3$. $R^{1D}$ may be —$CX^{1D}_3$. $R^{1D}$ may be —$CHX^{1D}_2$. $R^{1D}$ may be —$CH_2X^{1D}$. $R^{1D}$ may be —CN. $R^{1D}$ may be —CHO. $R^{1D}$ may be —OH. $R^{1D}$ may be —$NH_2$. $R^{1D}$ may be —COOH. $R^{1D}$ may be —$CONH_2$. $R^{1D}$ may be —$NO_2$. $R^{1D}$ may be —SH. $R^{1D}$ may be —$SO_2CH_3$. $R^{1D}$ may be —$SO_2Ph$. $R^{1D}$ may be —$SO_3H$. $R^{1D}$ may be —$OSO_3H$. $R^{1D}$ may be —$SO_2NH_2$. $R^{1D}$ may be —$NHNH_2$. $R^{1D}$ may be —$ONH_2$. $R^{1D}$ may be —$NHC(O)NHNH_2$. $R^{1D}$ may be —$OPO_3H$. $R^{1D}$ may be —$PO_3H_2$. $R^{1D}$ may be —$OCX^{1D}_3$. $R^{1D}$ may be —$OCHX^{1D}_2$. $R^{1D}$ may be substituted alkyl. $R^{1D}$ may be substituted heteroalkyl. $R^{1D}$ may be substituted cycloalkyl. $R^{1D}$ may be substituted heterocycloalkyl. $R^{1D}$ may be substituted aryl. $R^{1D}$ may be substituted heteroaryl. $R^{1D}$ may be unsubstituted alkyl. $R^{1D}$ may be unsubstituted heteroalkyl. $R^{1D}$ may be unsubstituted cycloalkyl. $R^{1D}$ may be unsubstituted heterocycloalkyl. $R^{1D}$ may be unsubstituted aryl. $R^{1D}$ may be unsubstituted heteroaryl. $R^{1D}$ may be detectable moiety. $R^{1D}$ may be —F. $R^{1D}$ may be —Cl. $R^{1D}$ may be —Br. $R^{1D}$ may be —I. $R^{1D}$ may be —$OCH_3$. $R^{1D}$ may be —$CH_3$. $R^{1D}$ may be —$CH_2CH_3$. $R^{1D}$ may be —$SCH_3$. $R^{1D}$ may be unsubstituted phenyl. Each $X^{1D}$ is independently —F, —Cl, —Br, or —I.

In embodiments, $R^{1E}$ may be hydrogen, halogen, —$N_3$, —$CF_3$, —$CCl_3$, —$CBr_3$, —$CI_3$, —CN, —CHO, —OH, —$NH_2$, —COOH, —$CONH_2$, —$NO_2$, —SH, —$SO_2CH_3$, —$SO_2Ph$, —$SO_3H$, —$OSO_3H$, —$SO_2NH_2$, —$NHNH_2$, —$ONH_2$, —$NHC(O)NHNH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, or a detectable moiety. $R^{1E}$ may be hydrogen. $R^{1E}$ may be halogen. $R^{1E}$ may be —$N_3$. $R^{1E}$ may be —$CX^{1E}_3$. $R^{1E}$ may be —$CHX^{1E}_2$. $R^{1E}$ may be —$CH_2X^{1E}$. $R^{1E}$ may be —CN. $R^{1E}$ may be —CHO. $R^{1E}$ may be —OH. $R^{1E}$ may be —$NH_2$. $R^{1E}$ may be —COOH. $R^{1E}$ may be —$CONH_2$. $R^{1E}$ may be —$NO_2$. $R^{1E}$ may be —SH. $R^{1E}$ may be —$SO_2CH_3$. $R^{1E}$ may be —$SO_2Ph$. $R^{1E}$ may be —$SO_3H$. $R^{1E}$ may be —$OSO_3H$. $R^{1E}$ may be —$SO_2NH_2$. $R^{1E}$ may be —$NHNH_2$. $R^{1E}$ may be —$ONH_2$. $R^{1E}$ may be —$NHC(O)NHNH_2$. $R^{1E}$ may be —$OPO_3H$. $R^{1E}$ may be —$PO_3H_2$. $R^{1E}$ may be —$OCX^{1E}_3$. $R^{1E}$ may be —$OCHX^{1E}_2$. $R^{1E}$ may be substituted alkyl. $R^{1E}$ may be substituted heteroalkyl. $R^{1E}$ may be substituted cycloalkyl. $R^{1E}$ may be substituted heterocycloalkyl. $R^{1E}$ may be substituted aryl. $R^{1E}$ may be substituted heteroaryl. $R^{1E}$ may be unsubstituted alkyl. $R^{1E}$ may be unsubstituted heteroalkyl. $R^{1E}$ may be unsubstituted cycloalkyl. $R^{1E}$ may be unsubstituted heterocycloalkyl. $R^{1E}$ may be unsubstituted aryl. $R^{1E}$ may be unsubstituted heteroaryl. $R^{1E}$ may be detectable moiety. $R^{1E}$ may be —F. $R^{1E}$ may be —Cl. $R^{1E}$ may be —Br. $R^{1E}$ may be —I. $R^{1E}$ may be —$OCH_3$. $R^{1E}$ may be —$CH_3$. $R^{1E}$ may be —$CH_2CH_3$. $R^{1E}$ may be —$SCH_3$. $R^{1E}$ may be unsubstituted phenyl. Each $X^{1E}$ is independently —F, —Cl, —Br, or —I.

In embodiments, the compound has the formula:

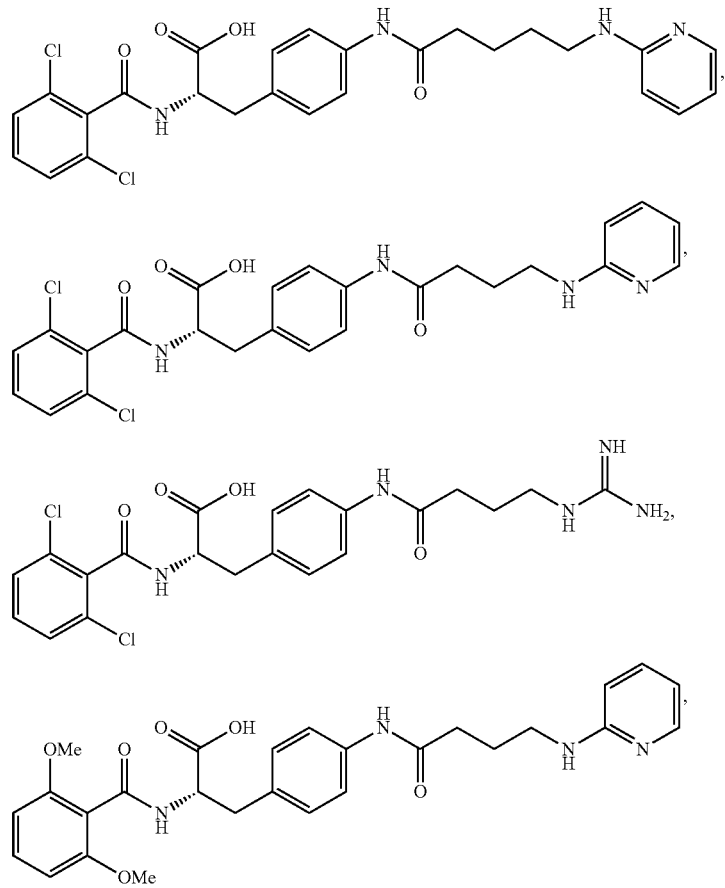

-continued
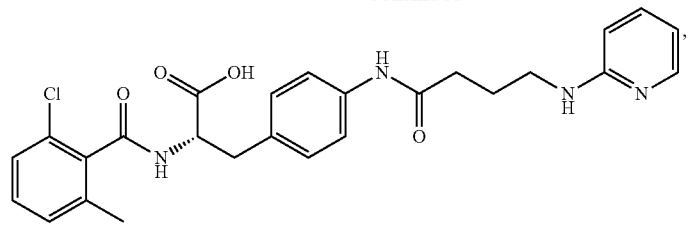
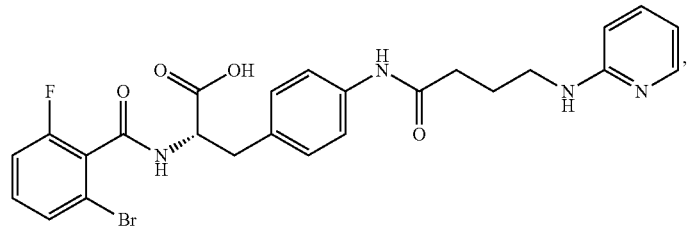
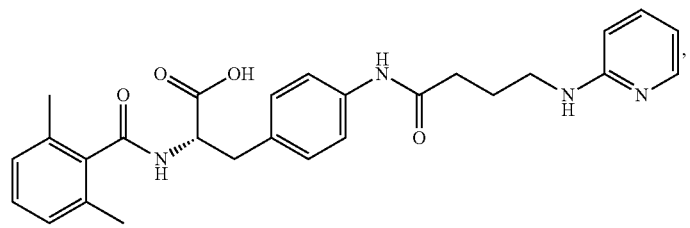
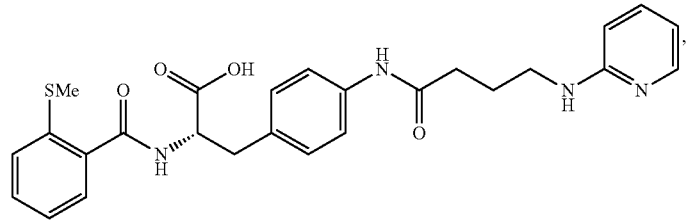
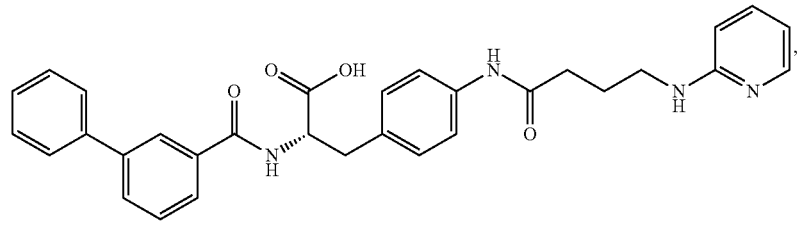
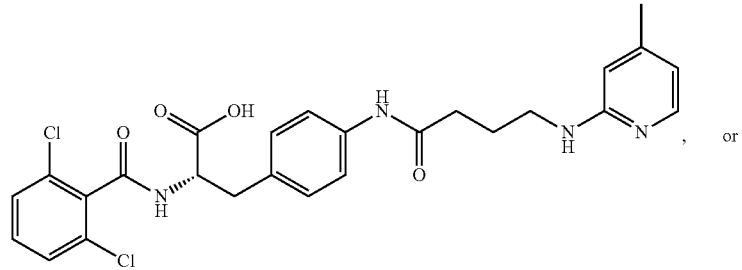
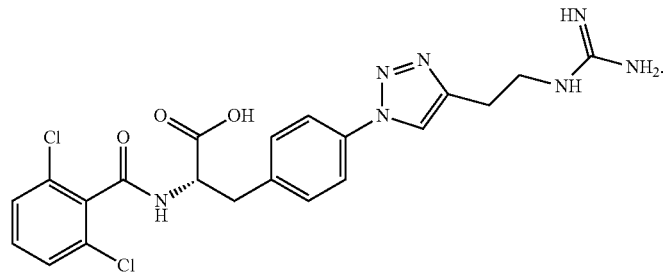

In embodiments, the compound has the formula:

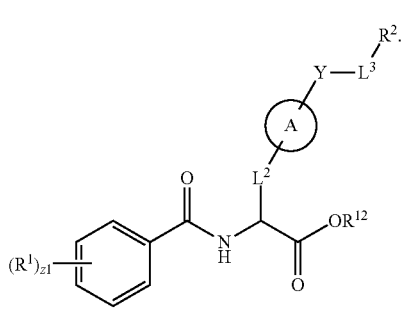
(Ia)

Ring A, Y, L², L³, R¹, R², R¹², and z1 are as described herein.

In embodiments, the compound has the formula:

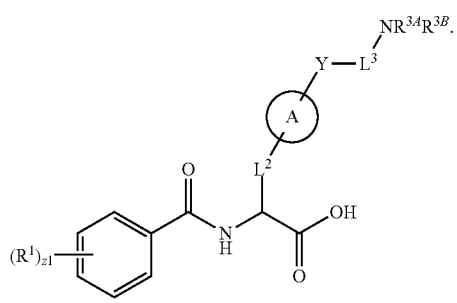
(Ib)

Ring A, Y, L², L³, R¹, R³⁴, R³ᴮ, and z1 are as described herein.

The compound of formula: (I) may have the formula:

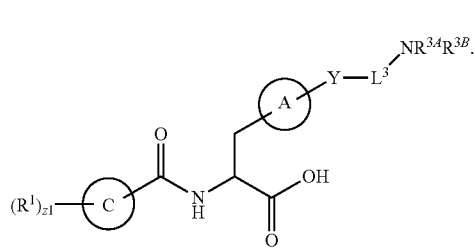
(II)

The compound of formula: (I) may have the formula:

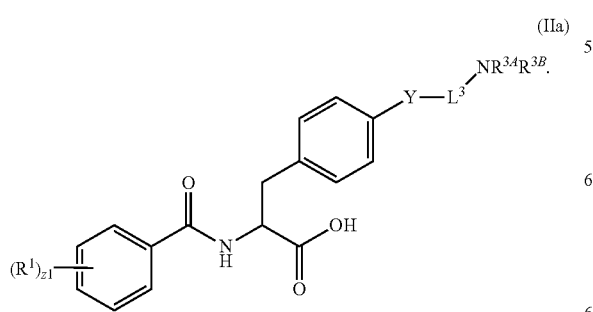
(IIa)

The compound of formula: (I) may have the formula:

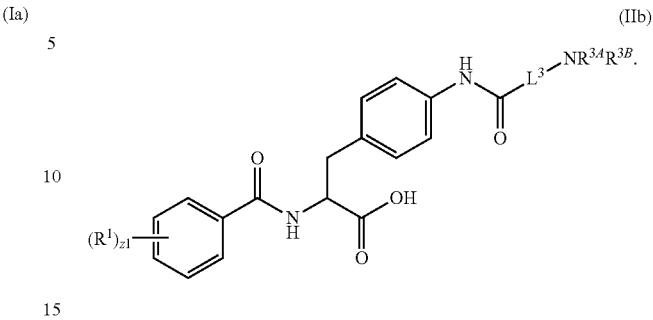
(IIb)

Ring A, Ring C, Y, L³, R¹, R³⁴, R³ᴮ, and z1 are as described herein, including embodiments thereof.

L³ may be substituted or unsubstituted $C_1$-$C_7$ alkylene, substituted or unsubstituted 2 to 7 membered heteroalkylene, alkylarylene. R¹ may be hydrogen, unsubstituted methyl, halogen, —OMe, —SMe, or phenyl. R³⁴ and R³ᴮ may independently be hydrogen, —C(NH)NH₂, —C(NCN)NH₂, or substituted or unsubstituted heterocycloalkyl, or substituted or unsubstituted heteroaryl.

The compound of formula: (I) may have the formula:

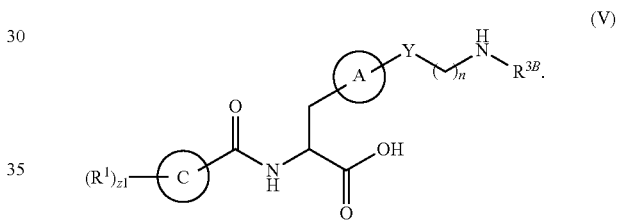
(V)

The compound of formula: (I) may have the formula:

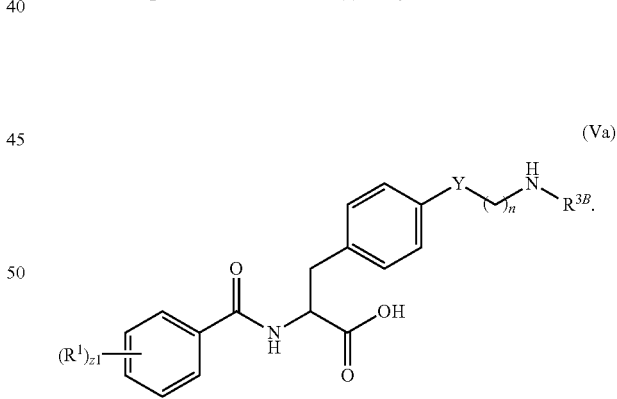
(Va)

Ring A, Ring C, R¹, R³ᴮ, and z1 are as described herein. The symbol n is an integer from 1 to 8. The symbol n may be 1. The symbol n may be 2. The symbol n may be 3. The symbol n may be 4. The symbol n may be 5. The symbol n may be 6. The symbol n may be 7. The symbol n may be 8. Y, R¹, R³ᴮ, and z1 are as described herein, including embodiments thereof.

The compound of formula: (I) may have the formula:
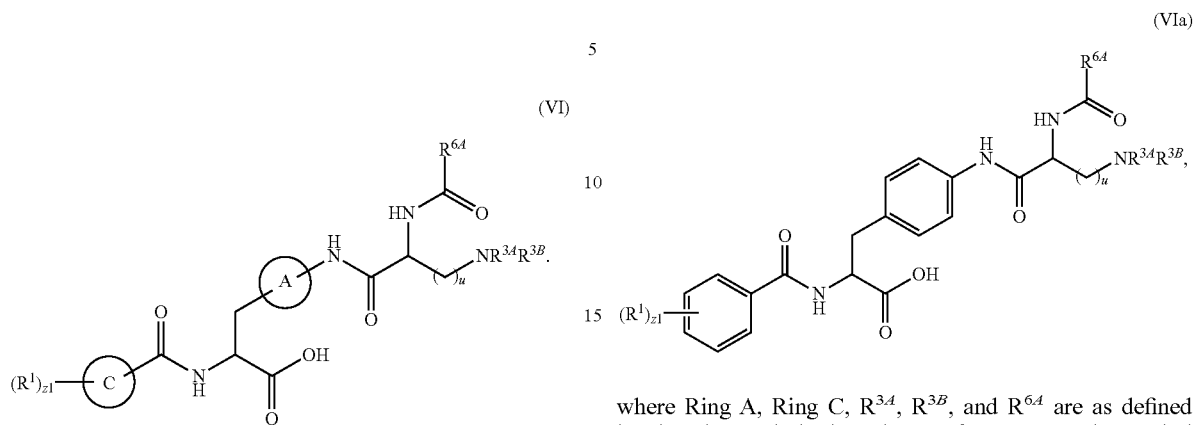
The compound of formula: (I) may have the formula:
where Ring A, Ring C, $R^{3A}$, $R^{3B}$, and $R^{6A}$ are as defined herein. The symbol u is an integer from 0 to 7. The symbol u may be an integer from 1 to 7.
The compound of formula: (VI) may have the formula:
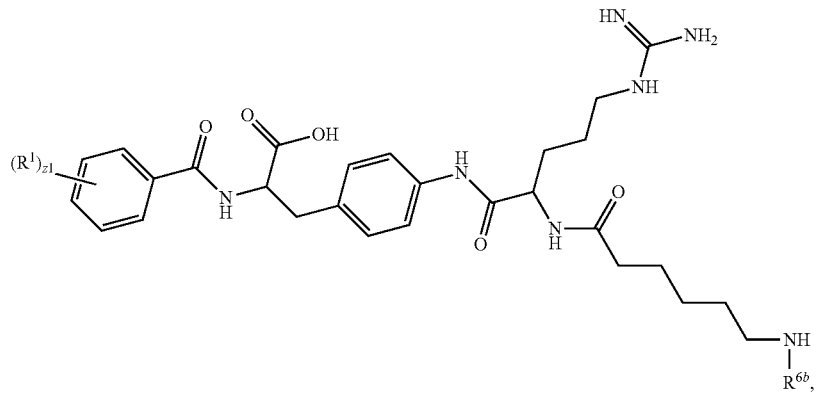
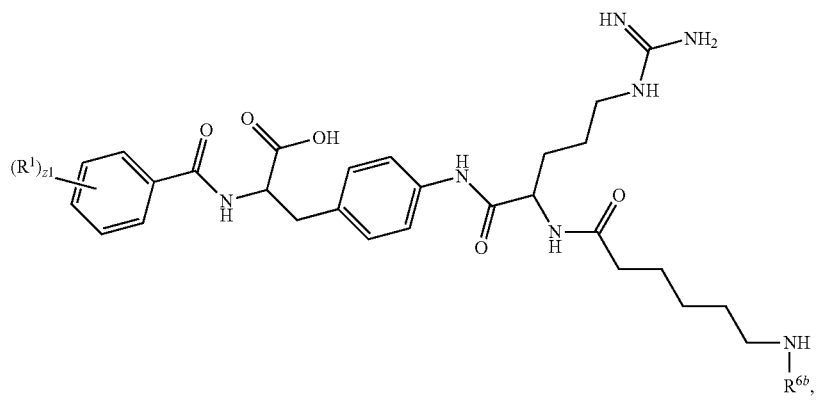

-continued

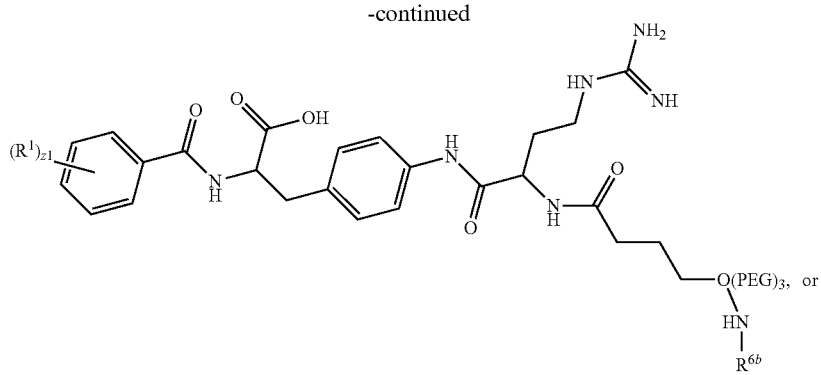

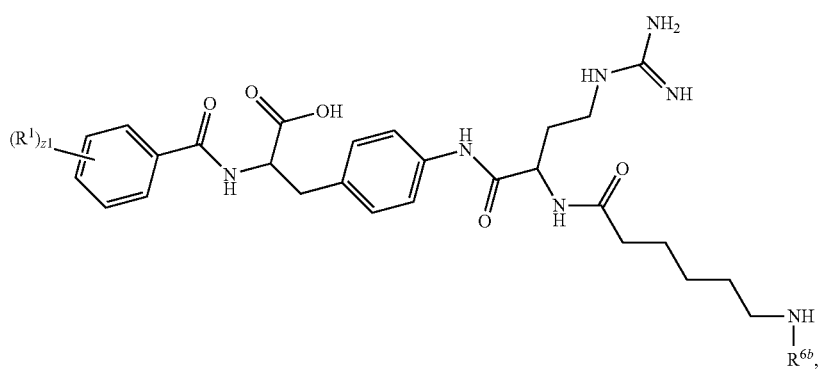

where $R^{6B}$ is a detectable moiety. The detectable moiety may be rhodamine, including analogues thereof, or fluorescein, including analogs thereof. The detectable moiety may be rhodamine, including analogues thereof. The rhodamine may be lissamine rhodamine sulfonyl or tetramethylrhodamine isothiocyanate. The detectable moiety may be fluorescein, including analogs thereof. The fluorescein may be fluorescein isothiocyanate.

The compounds described herein may be prodrugs having formula:

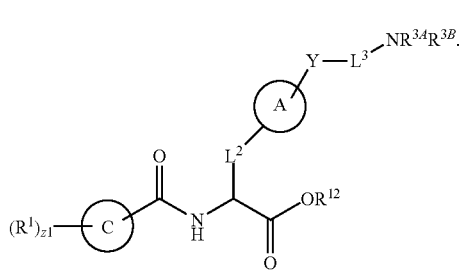

(IX)

The compound of formula: (I) may have the formula:

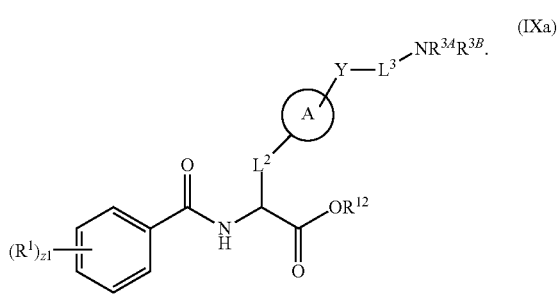

(IXa)

Ring A, Ring C, Y, $L^2$, $L^3$, $R^1$, $R^{3A}$, $R^{3B}$, $R^{12}$, and z1 are as described herein, including embodiments thereof. $R^{12}$ may be a hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, or $R^{12}$ may be a prodrug moiety. $R^{12}$ may be a pharmaceutically acceptable salt. $R^{12}$ may be a hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{12}$ may be a hydrogen, $R^{13}$-substituted or unsubstituted alkyl, $R^{13}$-substituted or unsubstituted heteroalkyl, $R^{13}$-substituted or unsubstituted cycloalkyl, $R^{13}$-substituted or unsubstituted heterocycloalkyl, $R^{13}$-substituted or unsubstituted aryl, or $R^{13}$-substituted or unsubstituted heteroaryl. $R^{12}$ may be a substituted or unsubstituted $C_1$-$C_5$ alkyl. $R^{12}$ may be $R^{13}$-substituted or unsubstituted $C_1$-$C_5$ alkyl. $R^{12}$ may be unsubstituted $C_1$-$C_3$ alkyl. $R^{12}$ may be unsubstituted methyl, unsubstituted ethyl, or unsubstituted propyl. $R^{12}$ may be a hydrogen. $R^{12}$ and the directly connected —O— may collectively be a prodrug moiety.

$R^{13}$ is hydrogen, halogen, oxo, —$N_3$, —$CF_3$, —$CCl_3$, —$CBr_3$, —$CI_3$, —CN, —CHO, —OH, —$NH_2$, —COOH, —$CONH_2$, —$NO_2$, —SH, —$SO_2$, —$SO_2Cl$, —$SO_2CH_3$— $SO_3H$, —$SO_4H$, —$SO_2NH_2$, —$NHNH_2$, —$ONH_2$, —NHC(O)$NHNH_2$, unsubstituted alkyl, unsubstituted heteroalkyl, unsubstituted cycloalkyl, unsubstituted heterocycloalkyl, unsubstituted aryl, or unsubstituted heteroaryl. $R^{13}$ may be halogen, oxo, —$N_3$, —$CF_3$, —$CCl_3$, —$CBr_3$, —$CI_3$, —CN, —CHO, —OH, —$NH_2$, —COOH, —$CONH_2$, —$NO_2$, —SH, —$SO_2$, —$SO_2Cl$, —$SO_2CH_3$—$SO_3H$, —$SO_4H$, —$SO_2NH_2$, —$NHNH_2$, —$ONH_2$, —NHC(O)$NHNH_2$, unsubstituted alkyl, unsubstituted heteroalkyl, unsubstituted cycloalkyl, unsubstituted heterocycloalkyl, unsubstituted aryl, or unsubstituted heteroaryl.

In another aspect is a compound having formula:

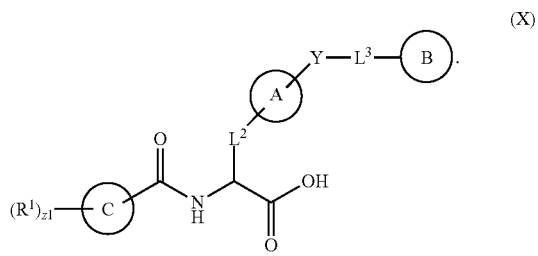

(X)

The compound of formula: (I) may have the formula:

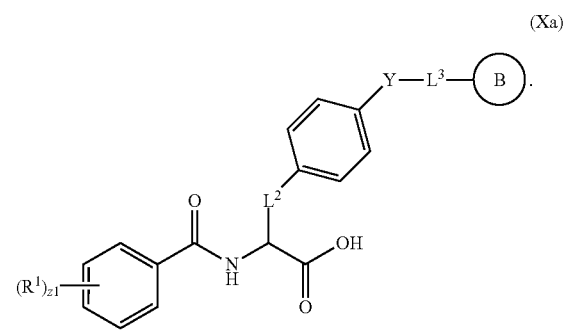

(Xa)

Y, $L^2$, $L^3$, $R^1$, and z1 are as described herein.

Ring B is a substituted or unsubstituted cycloalkyl, substituted or unsubstituted heterocycloalkyl, substituted or unsubstituted aryl, substituted or unsubstituted heteroaryl, substituted or unsubstituted fused ring aryl or substituted or unsubstituted fused ring heteroaryl.

Ring B may be aryl. Ring B may be 6 membered aryl. Ring B may be phenyl. Ring B may be unsubstituted phenyl. Ring B may be unsubstituted triazolyl. Ring B may be substituted triazolyl. Ring B may be unsubstituted tetrazolyl. Ring B may be substituted tetrazolyl. In embodiments, Ring B is phenyl. In embodiments, Ring B is cyclohexyl. In embodiments, Ring B is pyridyl. Ring B may be substituted $C_6$-$C_{10}$ aryl. Ring B may be substituted 5 to 10 membered heteroaryl. Ring B may be substituted aryl. Ring B may be unsubstituted aryl. Ring B may be substituted heteroaryl. Ring B may be unsubstituted heteroaryl. Ring B may be substituted or unsubstituted $C_6$-$C_{10}$ aryl. Ring B may be substituted or unsubstituted 5 to 10 membered heteroaryl. Ring B may be unsubstituted $C_6$-$C_{10}$ aryl. Ring B may be unsubstituted 5 to 10 membered heteroaryl.

Ring B may be a substituted or unsubstituted 4 to 6 membered heterocycloalkyl. Ring B may be a substituted or unsubstituted 5 or 6 membered heterocycloalkyl. Ring B may be substituted or unsubstituted 5 membered heterocycloalkyl. Ring B may be a heterocycloalkyl such as, for example, pyrrolidinyl, imidazolidinyl, oxazolidinyl, thiazolidinyl, dioxolanyl, dithiolanyl, piperidinyl, morpholinyl, dioxanyl, dithianyl, aziridinyl, azetidinyl, azepinyl, oxiranyl, oxetanyl, tetrahydrofuranyl, or tetrahydropyranyl. Ring B may be a substituted or unsubstituted heterocycloalkyl such as, for example, substituted or unsubstituted pyrrolidinyl, substituted or unsubstituted imidazolidinyl, substituted or unsubstituted oxazolidinyl, substituted or unsubstituted thiazolidinyl, substituted or unsubstituted dioxolanyl, substituted or unsubstituted dithiolanyl, substituted or unsubstituted piperidinylen, substituted or unsubstituted morpholinyl, substituted or unsubstituted dioxanyl, substituted or unsubstituted dithianyl, substituted or unsubstituted aziridinyl, substituted or unsubstituted azetidinyl, substituted or unsubstituted azepinyl, substituted or unsubstituted oxiranyl, substituted or unsubstituted oxetanyl, substituted or unsubstituted tetrahydrofuranyl, or substituted or unsubstituted tetrahydropyranyl. Ring B may be a substituted or unsubstituted 6 membered heterocycloalkyl. Ring B may be a unsubstituted 6 membered heterocycloalkyl. Ring B may be a unsubstituted 5 membered heterocycloalkyl. Ring B may be substituted or unsubstituted $C_3$-$C_8$ cycloalkyl. Ring B may be substituted or unsubstituted 3 to 8 membered heterocycloalkyl. Ring B may be unsubstituted $C_3$-$C_8$ cycloalkyl. Ring B may be substituted 3 to 8 membered heterocycloalkyl.

Ring B may be substituted or unsubstituted heteroaryl. Ring B may be substituted or unsubstituted 5 or 6 membered heteroaryl. Ring B may be substituted or unsubstituted 5 or 6 membered heteroaryl. Ring B may be a substituted or unsubstituted heteroaryl such as, for example, substituted or unsubstituted pyridinyl, substituted or unsubstituted pyrrolyl, substituted or unsubstituted furanyl, substituted or unsubstituted thiophenyl, substituted or unsubstituted imidazolyl, substituted or unsubstituted pyrazolyl, substituted or unsubstituted oxazolyl, substituted or unsubstituted thiazolyl, substituted or unsubstituted pyranyl, substituted or unsubstituted thiopyranyl, substituted or unsubstituted pyrazinyl, substituted or unsubstituted pyrimindyl, substituted or unsubstituted pyridazinyl, substituted or unsubstituted oxazinyl, substituted or unsubstituted thiazinyl, substituted or unsubstituted doxinyl, substituted or unsubstituted dithiinyl, substituted or unsubstituted azetyl, substituted or unsubstituted oxetyl, substituted or unsubstituted thietyl, substituted or unsubstituted azirinyl, substituted or unsubstituted oxirenyl or substituted or unsubstituted thirenyl. Ring B may be substituted or unsubstituted pyridinyl. Ring B may be substituted cycloalkyl. Ring B may be unsubstituted cycloalkyl. Ring B may be substituted heterocycloalkyl. Ring B may be unsubstituted heterocycloalkyl. Ring B may be substituted $C_3$-$C_8$ cycloalkyl. Ring B may be unsubstituted $C_3$-$C_8$ cycloalkyl. Ring B may be substituted 3 to 8 membered heterocycloalkyl. Ring B may be unsubstituted 3 to 8 membered heterocycloalkyl. In embodiments, Ring B is unsubstituted phenyl. In embodiments, Ring B is unsubstituted 5 to 6 membered heteroaryl.

In embodiments, Ring B is a $R^{15}$-substituted or unsubstituted cycloalkyl, $R^{15}$-substituted or unsubstituted heterocycloalkyl, $R^{15}$-substituted or unsubstituted aryl, $R^{15}$-substituted or unsubstituted heteroaryl, $R^{15}$-substituted or unsubstituted fused ring aryl or $R^{15}$-substituted or unsubstituted fused ring heteroaryl. In embodiments, Ring B is a substituted or unsubstituted cycloalkyl (e.g. $C_3$-$C_8$ cycloalkyl, $C_4$-$C_8$ cycloalkyl, or $C_5$-$C_6$ cycloalkyl), substituted or unsubstituted heterocycloalkyl (e.g. 3 to 8 membered heterocycloalkyl, 4 to 8 membered heterocycloalkyl, or 5 to 6 membered heterocycloalkyl), substituted or unsubstituted aryl (e.g. $C_6$-$C_{10}$ aryl or $C_6$ aryl), substituted or unsubstituted heteroaryl (e.g. 5 to 10 membered heteroaryl, 5 to 9 membered heteroaryl, or 5 to 6 membered heteroaryl).

Ring B may be substituted or unsubstituted fused ring aryl or substituted or unsubstituted fused ring heteroaryl. Ring B may be substituted or unsubstituted fused ring aryl or substituted or unsubstituted fused ring heteroaryl where only one ring is aromatic. Ring B may substituted or unsubstituted fused ring aryl or substituted or unsubstituted fused ring heteroaryl where each ring has at least one heteroatom. The heteroatom may be N, O, or S. The heteroatom may be N. Ring B may be substituted or unsubstituted 5,5-, 5,6-, 6,5-, or 6,6-fused ring described herein (e.g. a substituted or unsubstituted 5,5-, 5,6-, 6,5-, or 6,6-fused ring aryl or substituted or unsubstituted 5,5-, 5,6-, 6,5-, or 6,6-fused ring heteroaryl). Ring B may be substituted or unsubstituted 6,6-fused ring aryl or substituted or unsubstituted 6,6-fused ring heteroaryl. Ring B may be substituted or unsubstituted 6,6-fused ring aryl or substituted or unsubstituted 6,6-fused ring heteroaryl where only one ring is aromatic.

Ring B may be $R^{15}$-substituted or unsubstituted fused ring aryl or $R^{15}$-substituted or unsubstituted fused ring heteroaryl. Ring B may be $R^{15}$-substituted or unsubstituted fused ring aryl or $R^{15}$-substituted or unsubstituted fused ring heteroaryl where only one ring is aromatic. Ring B may $R^{15}$-substituted or unsubstituted fused ring aryl or $R^{15}$-substituted or unsubstituted fused ring heteroaryl where each ring has at least one heteroatom. The heteroatom may be N, O, or S. The heteroatom may be N. Ring B may be $R^{15}$-substituted or unsubstituted 5,5-, 5,6-, 6,5-, or 6,6-fused ring described herein (e.g. a $R^{15}$-substituted or unsubstituted 5,5-, 5,6-, 6,5-, or 6,6-fused ring aryl or $R^{15}$-substituted or unsubstituted 5,5-, 5,6-, 6,5-, or 6,6-fused ring heteroaryl). Ring B may be $R^{15}$-substituted or unsubstituted 6,6-fused ring aryl or $R^{15}$-substituted or unsubstituted 6,6-fused ring heteroaryl. Ring B may be $R^{15}$-substituted or unsubstituted 6,6-fused ring aryl or $R^{15}$-substituted or unsubstituted 6,6-fused ring heteroaryl where only one ring is aromatic.

$R^{15}$ is hydrogen, halogen, oxo, —$N_3$, —$CF_3$, —$CCl_3$, —$CBr_3$, —$CI_3$, —CN, —CHO, —OH, —$NH_2$, —$N(CH_3)_2$, —COOH, —$CONH_2$, —$NO_2$, —SH, —$SO_2$, —$SO_2Cl$, —$SO_2CH_3$—$SO_3H$, —$SO_4H$, —$SO_2NH_2$, —$NHNH_2$, —$ONH_2$, —$NHC(O)NHNH_2$, $R^{16}$-substituted or unsubstituted alkyl, $R^{16}$-substituted or unsubstituted heteroalkyl, $R^{16}$-substituted or unsubstituted cycloalkyl, $R^{16}$-substituted or unsubstituted heterocycloalkyl, $R^{16}$-substituted or unsubstituted aryl, or $R^{16}$-substituted or unsubstituted heteroaryl. $R^{15}$ may be halogen, oxo, —$N_3$, —$CF_3$, —$CCl_3$, —$CBr_3$, —$CI_3$, —CN, —CHO, —OH, —$NH_2$, —$N(CH_3)_2$, —COOH, —$CONH_2$, —$NO_2$, —SH, —$SO_2$, —$SO_2Cl$, —$SO_2CH_3$—$SO_3H$, —$SO_4H$, —$SO_2NH_2$, —$NHNH_2$, —$ONH_2$, —$NHC(O)NHNH_2$, $R^{16}$-substituted or unsubstituted alkyl, $R^{16}$-substituted or unsubstituted heteroalkyl, $R^{16}$-substituted or unsubstituted cycloalkyl, $R^{16}$-substituted or unsubstituted heterocycloalkyl, $R^{16}$-substituted or unsubstituted aryl, or $R^{16}$-substituted or unsubstituted heteroaryl.

$R^{16}$ is hydrogen, halogen, oxo, —$N_3$, —$CF_3$, —$CCl_3$, —$CBr_3$, —$CI_3$, —CN, —CHO, —OH, —$NH_2$, —$N(CH_3)_2$, —COOH, —$CONH_2$, —$NO_2$, —SH, —$SO_2$, —$SO_2Cl$, —$SO_2CH_3$—$SO_3H$, —$SO_4H$, —$SO_2NH_2$, —$NHNH_2$, —$ONH_2$, —$NHC(O)NHNH_2$, $R^{17}$-substituted or unsubstituted alkyl, $R^{17}$-substituted or unsubstituted heteroalkyl, $R^{17}$-substituted or unsubstituted cycloalkyl, $R^{17}$-substituted or unsubstituted heterocycloalkyl, $R^{17}$-substituted or unsubstituted aryl, or $R^{17}$-substituted or unsubstituted heteroaryl.

In embodiments, $R^{16}$ is hydrogen, halogen, oxo, —$N_3$, —$CF_3$, —$CCl_3$, —$CBr_3$, —$CI_3$, —CN, —CHO, —OH, —$NH_2$, —$N(CH_3)_2$, —COOH, —$CONH_2$, —$NO_2$, —SH, —$SO_2$, —$SO_2Cl$, —$SO_2CH_3$—$SO_3H$, —$SO_4H$, —$SO_2NH_2$, —$NHNH_2$, —$ONH_2$, —$NHC(O)NHNH_2$, $R^{17}$-substituted or unsubstituted alkyl (e.g. $C_1$-$C_8$ alkyl, $C_1$-$C_6$ alkyl, or $C_1$-$C_4$ alkyl), $R^{17}$-substituted or unsubstituted heteroalkyl (e.g. 2 to 8 membered heteroalkyl, 2 to 6 membered heteroalkyl, or 2 to 4 membered heteroalkyl), $R^{17}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{17}$-substituted or unsubstituted heterocycloalkyl (e.g. 3 to 8 membered heterocycloalkyl, 4 to 8 membered heterocycloalkyl, or 5 to 6 membered heterocycloalkyl), $R^{17}$-substituted or unsubstituted aryl (e.g. $C_6$-$C_{10}$ aryl or $C_6$ aryl), $R^{17}$-substituted or unsubstituted heteroaryl (e.g. 5 to 10 membered heteroaryl, 5 to 9 membered heteroaryl, or 5 to 6 membered heteroaryl).

$R^{16}$ may be halogen, oxo, —$N_3$, —$CF_3$, —$CCl_3$, —$CBr_3$, —$CI_3$, —CN, —CHO, —OH, —$NH_2$, —$N(CH_3)_2$, —COOH, —$CONH_2$, —$NO_2$, —SH, —$SO_2$, —$SO_2Cl$, —$SO_2CH_3$—$SO_3H$, —$SO_4H$, —$SO_2NH_2$, —$NHNH_2$, —$ONH_2$, —$NHC(O)NHNH_2$, $R^{17}$-substituted or unsubstituted alkyl, $R^{17}$-substituted or unsubstituted heteroalkyl, $R^{17}$-substituted or unsubstituted cycloalkyl, $R^{17}$-substituted or unsubstituted heterocycloalkyl, $R^{17}$-substituted or unsubstituted aryl, or $R^{17}$-substituted or unsubstituted heteroaryl.

In embodiments, $R^{16}$ is $R^{17}$-substituted or unsubstituted alkyl (e.g. $C_1$-$C_8$ alkyl, $C_1$-$C_6$ alkyl, or $C_1$-$C_4$ alkyl), $R^{17}$-substituted or unsubstituted heteroalkyl (e.g. 2 to 8 membered heteroalkyl, 2 to 6 membered heteroalkyl, or 2 to 4 membered heteroalkyl), $R^{17}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{17}$-substituted or unsubstituted heterocycloalkyl (e.g. 3 to 8 membered heterocycloalkyl, 4 to 8 membered heterocycloalkyl, or 5 to 6 membered heterocycloalkyl), $R^{17}$-substituted or unsubstituted aryl (e.g. $C_6$-$C_{10}$ aryl or $C_6$ aryl), $R^{17}$-substituted or unsubstituted heteroaryl (e.g. 5 to 10 membered heteroaryl, 5 to 9 membered heteroaryl, or 5 to 6 membered heteroaryl)

$R^{17}$ is hydrogen, halogen, oxo, —$N_3$, —$CF_3$, —$CCl_3$, —$CBr_3$, —$CI_3$, —CN, —CHO, —OH, —$NH_2$, —COOH, —$CONH_2$, —$NO_2$, —SH, —$SO_2$, —$SO_2Cl$, —$SO_2CH_3$—$SO_3H$, —$SO_4H$, —$SO_2NH_2$, —$NHNH_2$, —$ONH_2$, —$NHC(O)NHNH_2$, unsubstituted alkyl, unsubstituted heteroalkyl, unsubstituted cycloalkyl, unsubstituted heterocycloalkyl, unsubstituted aryl, or unsubstituted heteroaryl. $R^{17}$ may be halogen, oxo, —$N_3$, —$CF_3$, —$CCl_3$, —$CBr_3$, —$CI_3$, —CN, —CHO, —OH, —$NH_2$, —COOH, —$CONH_2$, —$NO_2$, —SH, —$SO_2$, —$SO_2Cl$, —$SO_2CH_3$—$SO_3H$, —$SO_4H$, —$SO_2NH_2$, —$NHNH_2$, —$ONH_2$, —$NHC(O)NHNH_2$, unsubstituted alkyl, unsubstituted heteroalkyl, unsubstituted cycloalkyl, unsubstituted heterocycloalkyl, unsubstituted aryl, or unsubstituted heteroaryl. Ring B may be

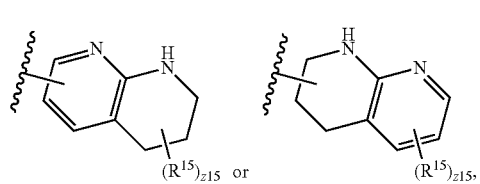

where $R^{15}$ is as described herein and z15 is an integer of 0 to 8. The symbol z15 may be 0, 1, or 2. The symbol z15 may be 0.

The compound may have the formula:

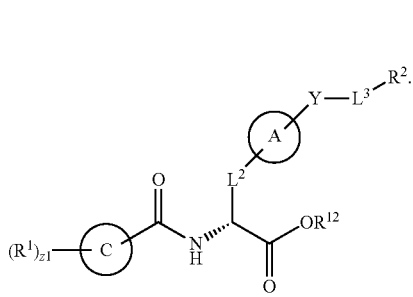

(Ii)

The compound may have the formula:

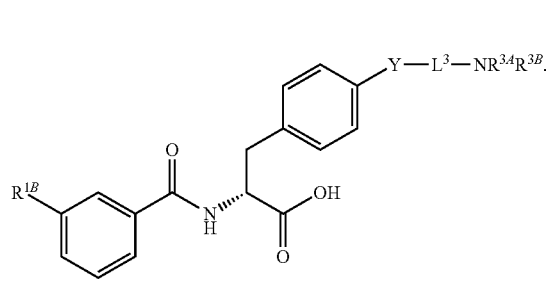

The compound may have the formula:

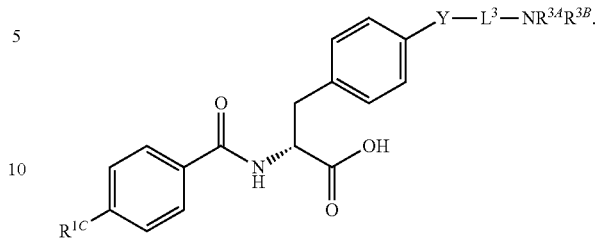

The compound may have the formula:

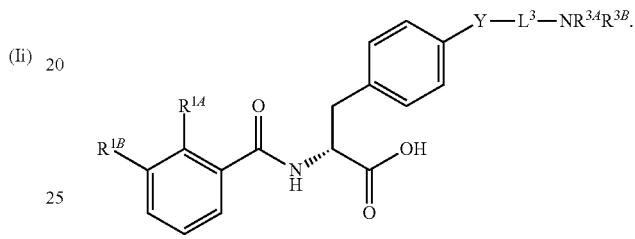

The compound may have the formula:

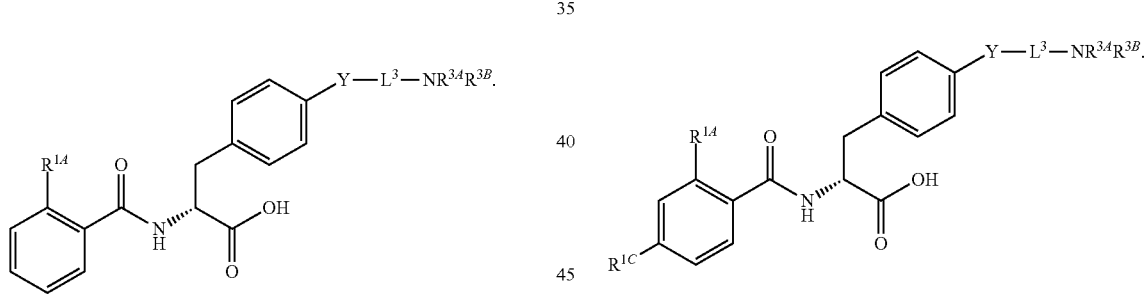

The compound may have the formula:

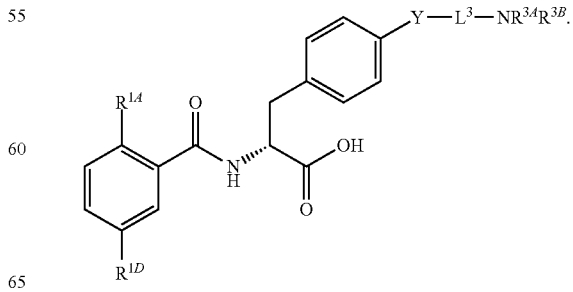

The compound may have the formula:
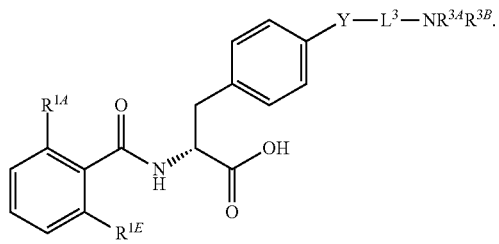
The compound may have the formula:
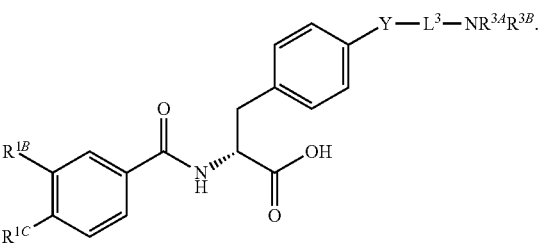
The compound may have the formula:
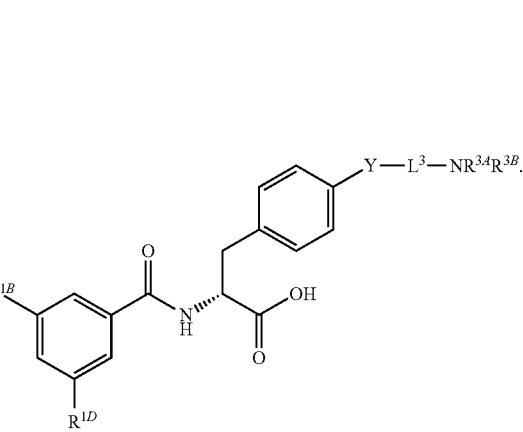
The compound may have the formula:
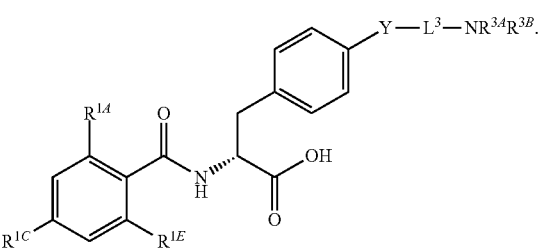
The compound may have the formula:
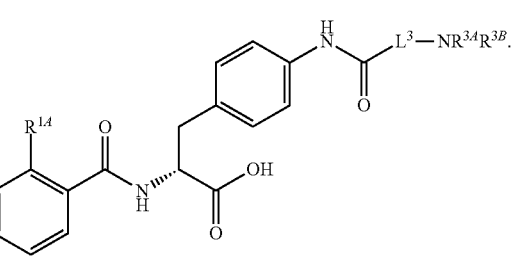
The compound may have the formula:
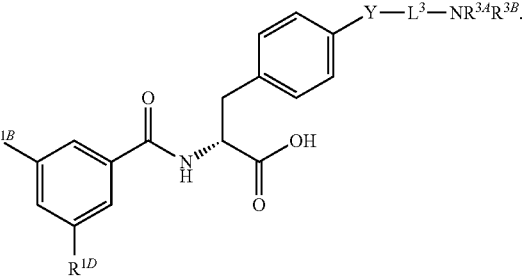
The compound may have the formula:
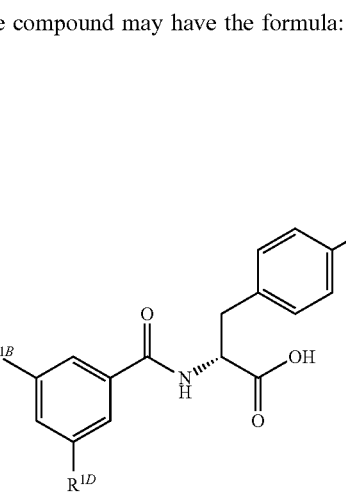
The compound may have the formula:
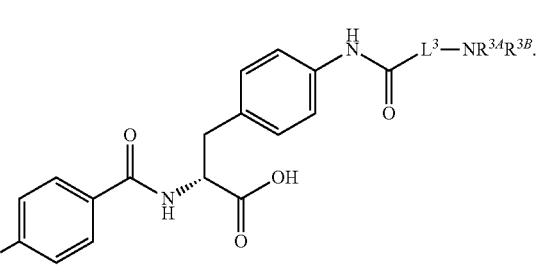

The compound may have the formula:
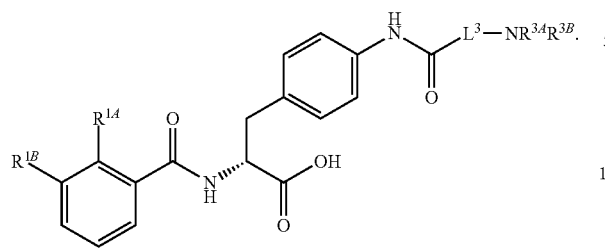
The compound may have the formula:
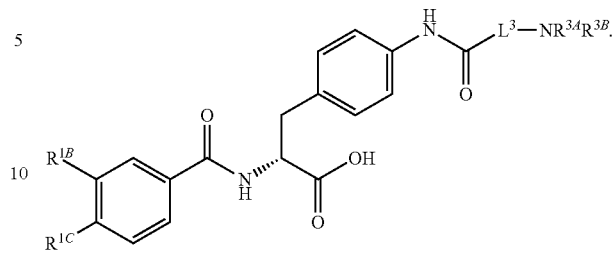
The compound may have the formula:
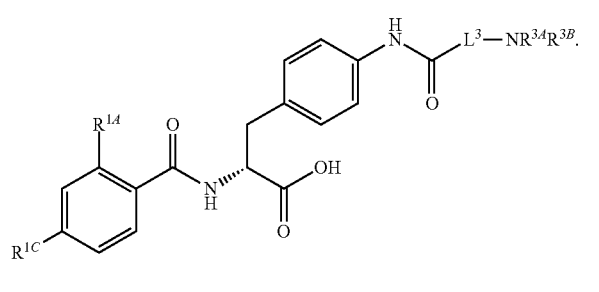
The compound may have the formula:
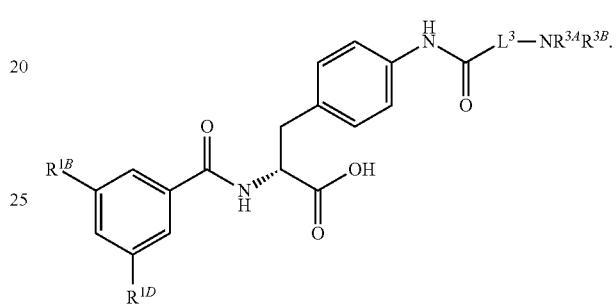
The compound may have the formula:
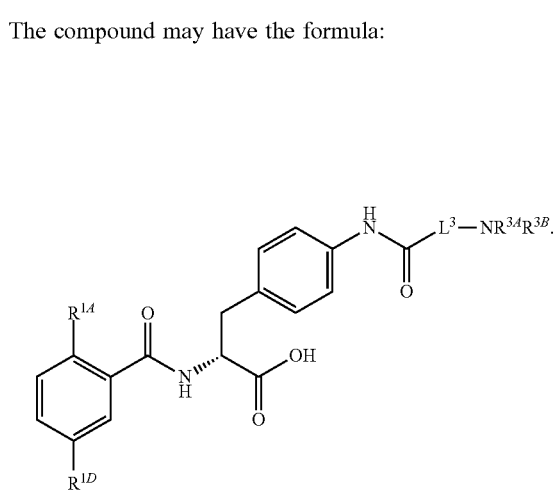
The compound may have the formula:
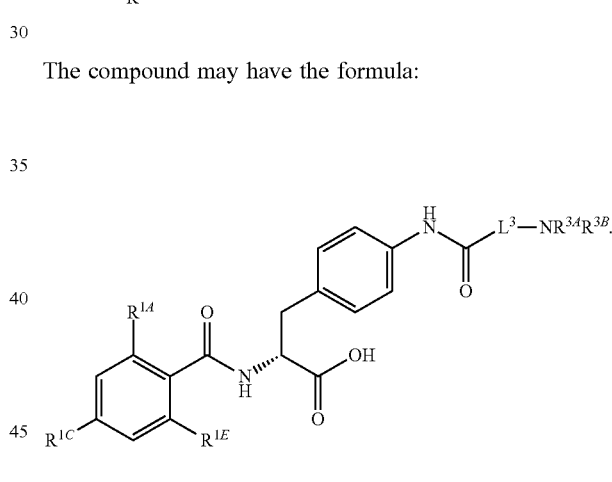
The compound may have the formula:
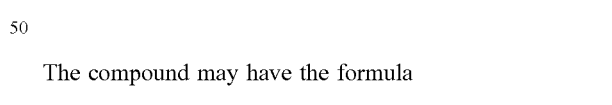
The compound may have the formula
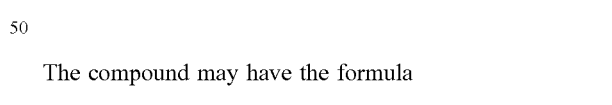

The compound may have the formula
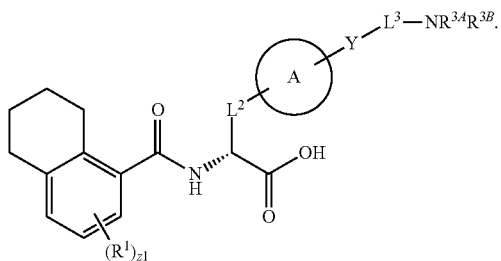
The compound may have the formula
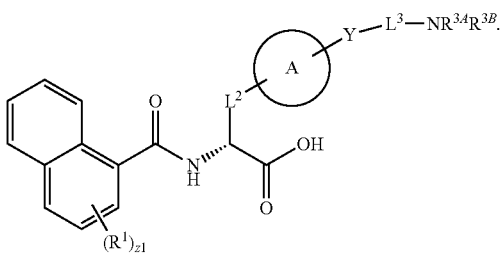
The compound may have the formula
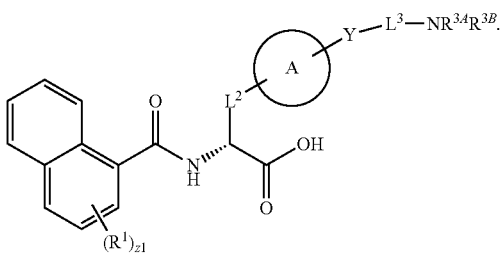
The compound may have the formula
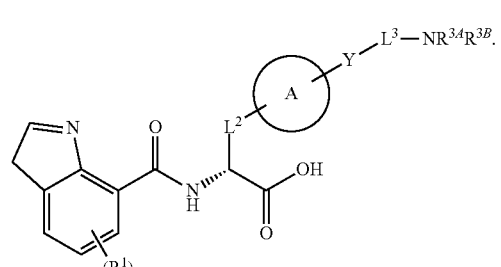
The compound may have the formula
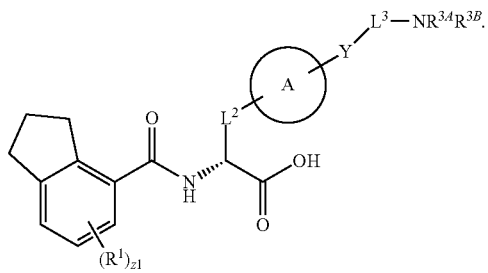
The compound may have the formula
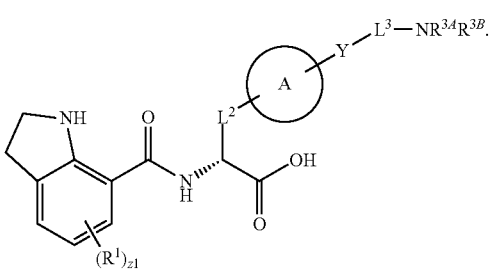
The compound may have the formula
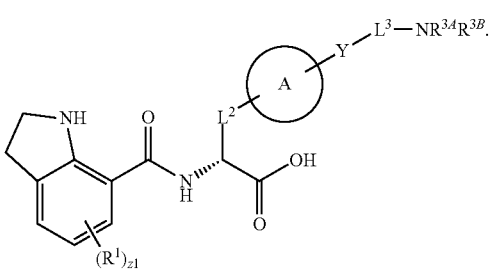
The compound may have the formula
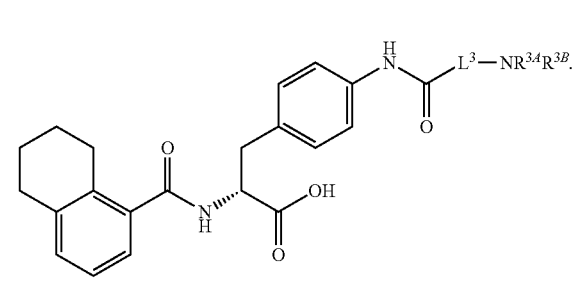

The compound may have the formula
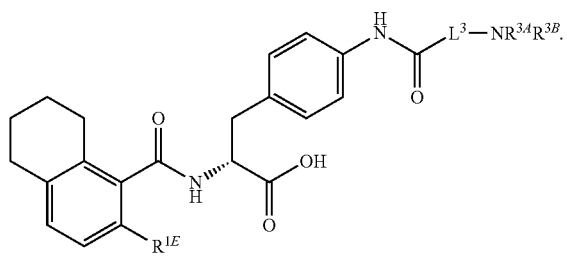
The compound may have the formula
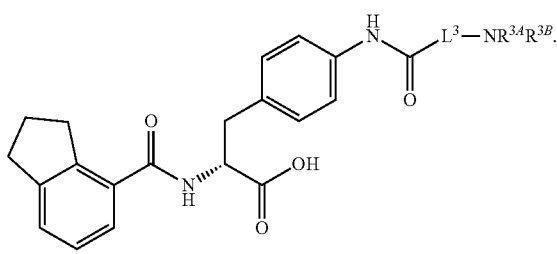
The compound may have the formula
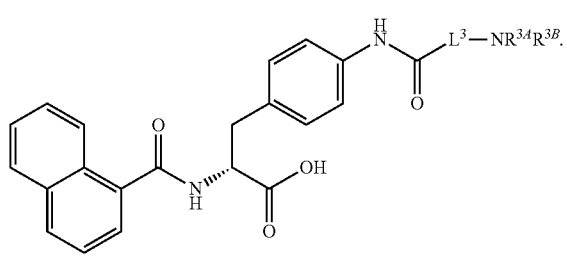
The compound may have the formula
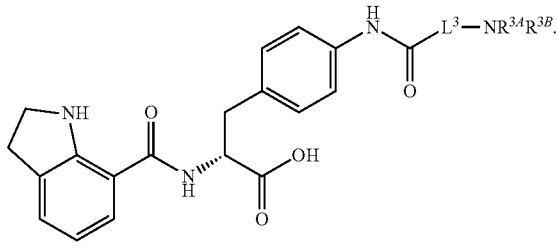
The compound may have the formula
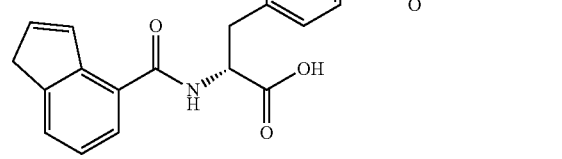
The compound may have the formula
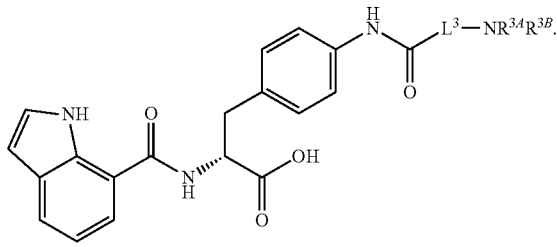
The compound may have the formula
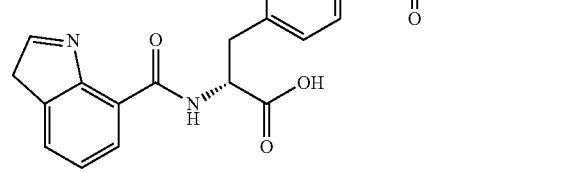
The compound may have the formula:
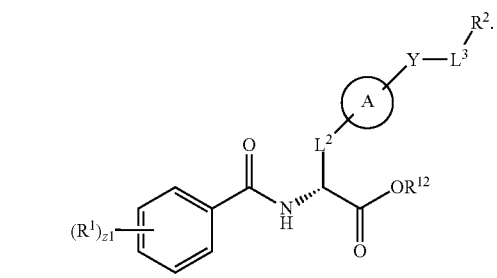

The compound may have the formula:
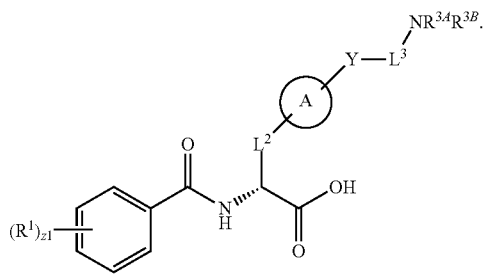
The compound may have the formula:
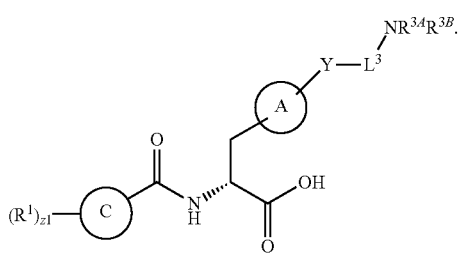
The compound may have the formula:
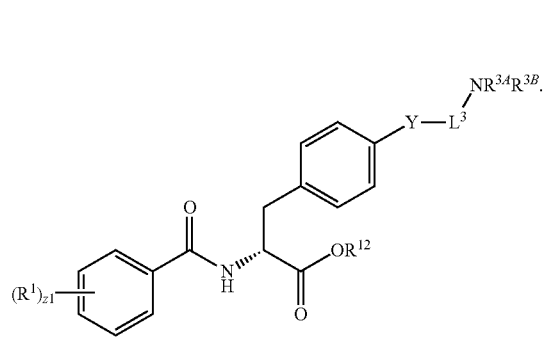
The compound may have the formula:
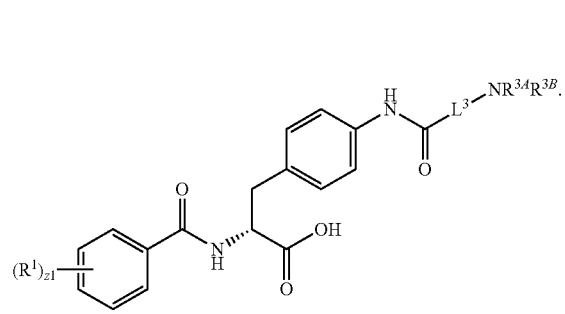
The compound may have the formula:
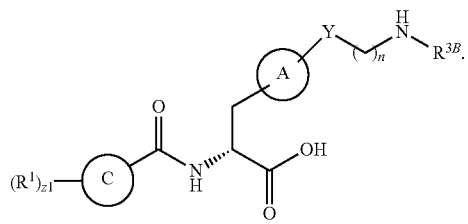
The compound may have the formula:
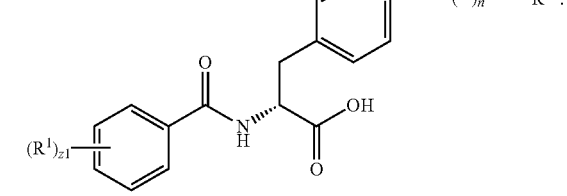
The compound may have the formula:
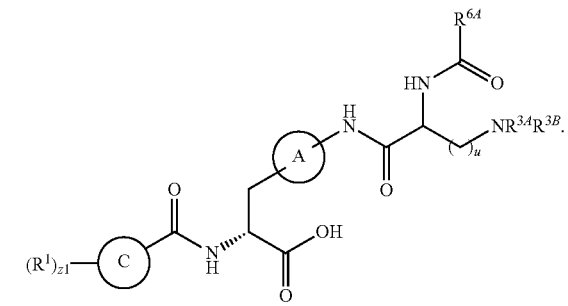
The compound may have the formula:
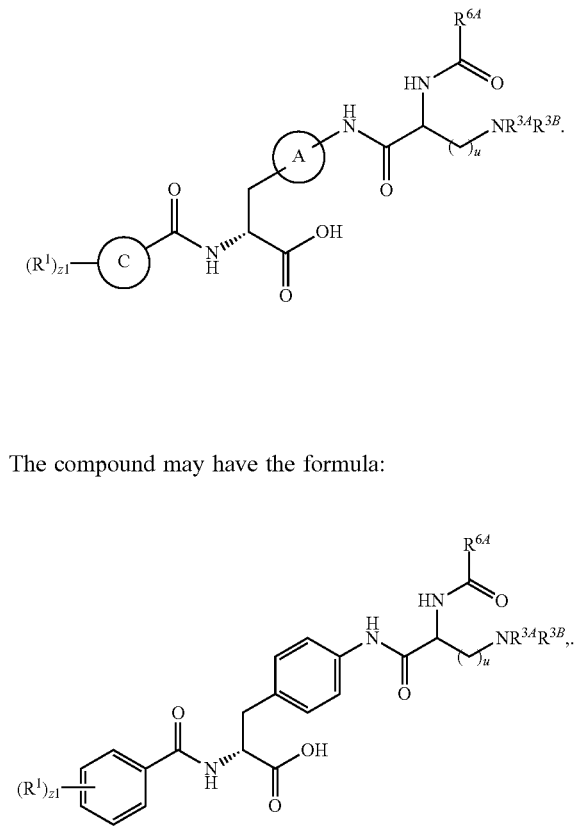

The compound may have the formula:
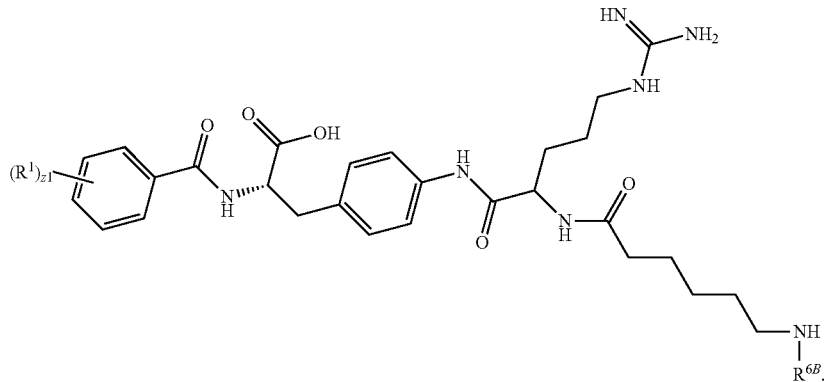
The compound may have the formula:
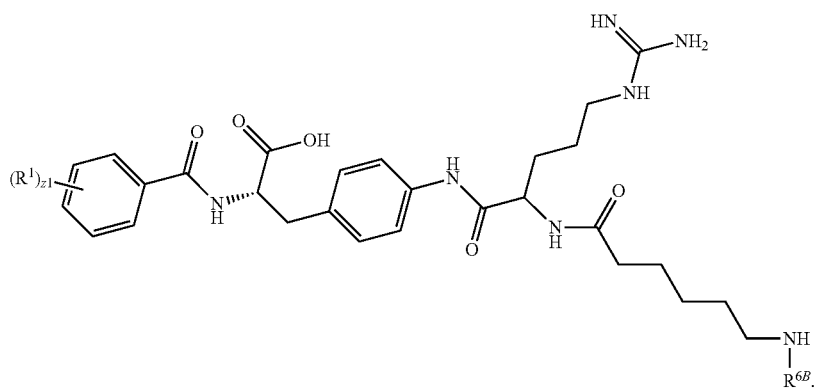
The compound may have the formula:
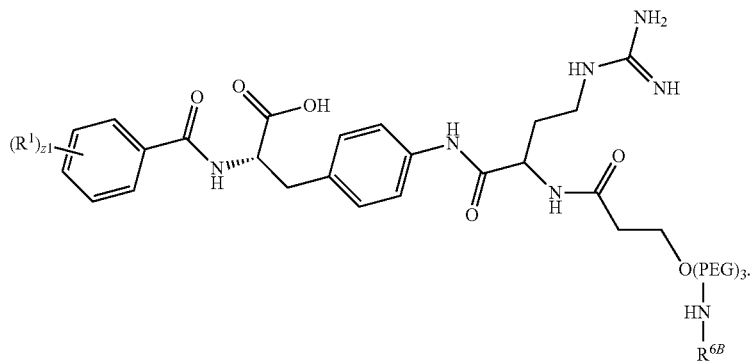

The compound may have the formula:

The compound may have the formula:

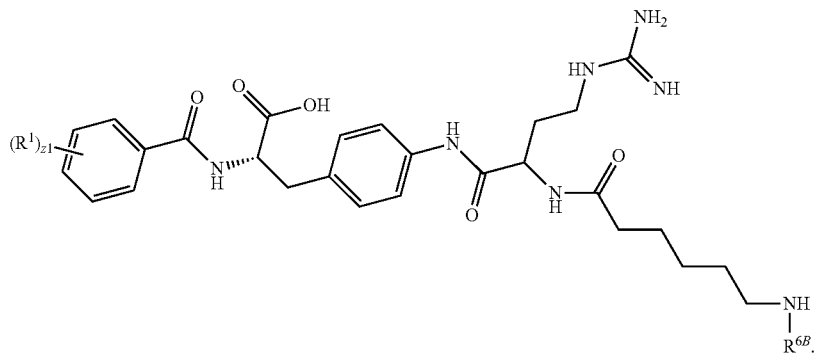

The compound may have the formula:

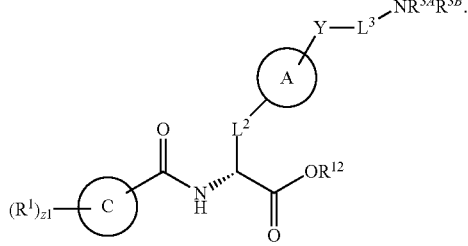

The compound may have the formula:

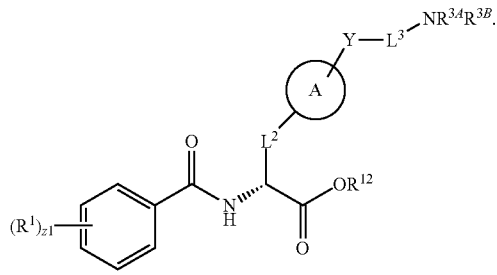

The compound may have the formula:

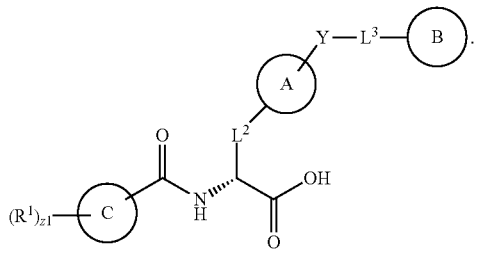

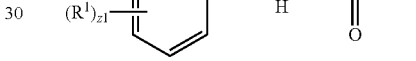

In the formulae above, Ring A, Ring B, Ring C, Y, $L^2$, $L^3$, $R^1$, $R^2$, $R^{3A}$, $R^{3B}$, $R^{12}$, $R^{6A}$, $R^{6B}$, $R^{1A}$, $R^{1B}$, $R^{1C}$, $R^{1D}$, $R^{1E}$, and z1 are as described herein (e.g., in an aspect, embodiment, figure, table, example, or claim). In embodiments, a compound may be the opposite enantiomer of a compound having one of the formulae described above. In embodiments, a compound may be the opposite stereoisomer of a compound having one of the formulae described above. In embodiments, a compound may be a racemic mixture of the enantiomer having one of the formulae described above and the opposite enantiomer. In embodiments, a compound may be a racemic mixture of the stereoisomer having one of the formulae described above and the opposite stereoisomer.

The compound may have the formula:

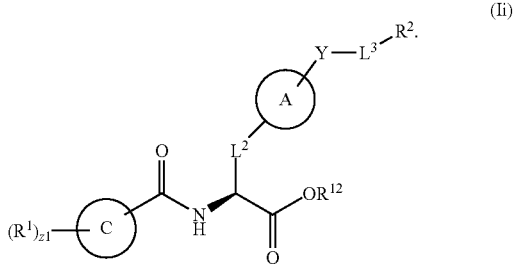

The compound may have the formula:
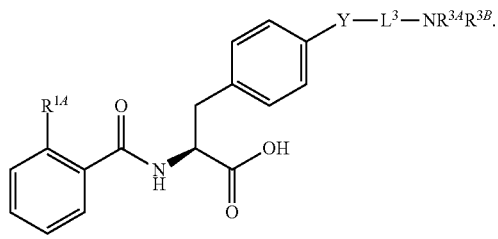
The compound may have the formula:
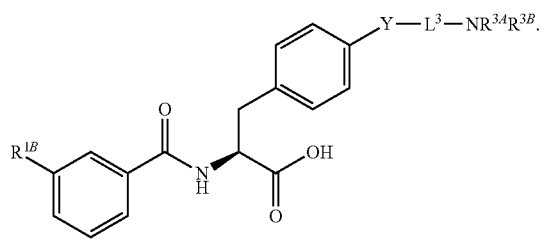
The compound may have the formula:
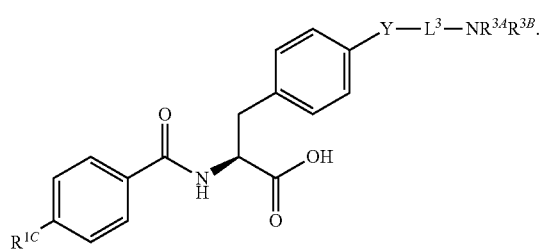
The compound may have the formula:
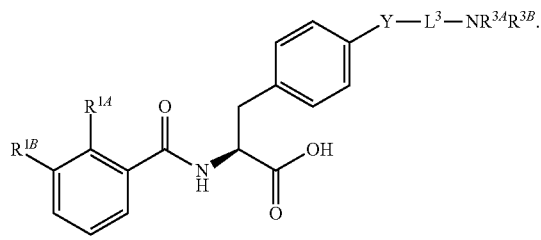
The compound may have the formula:
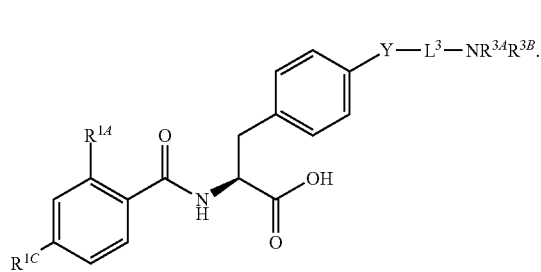
The compound may have the formula:
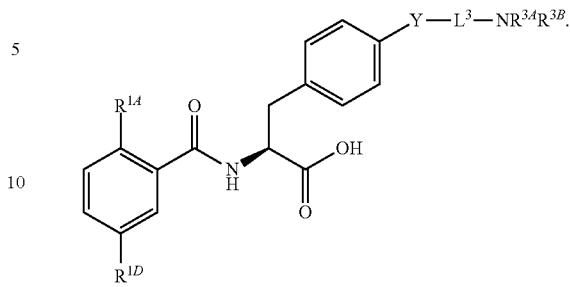
The compound may have the formula:
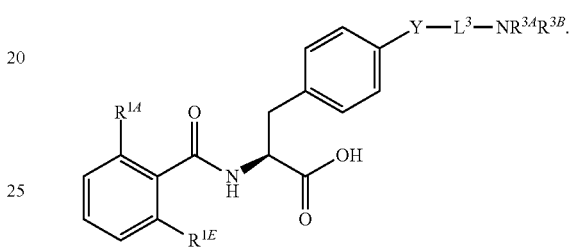
The compound may have the formula:
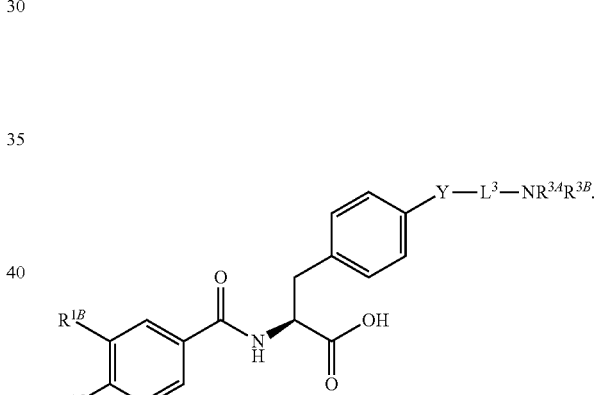
The compound may have the formula:
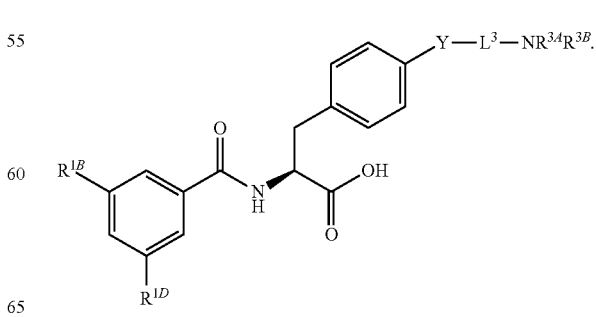

The compound may have the formula:
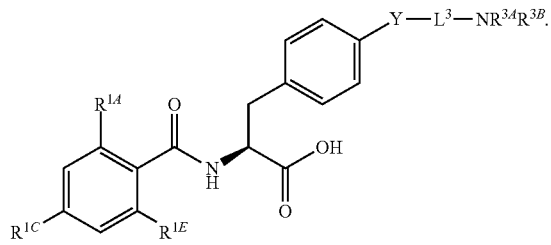
The compound may have the formula
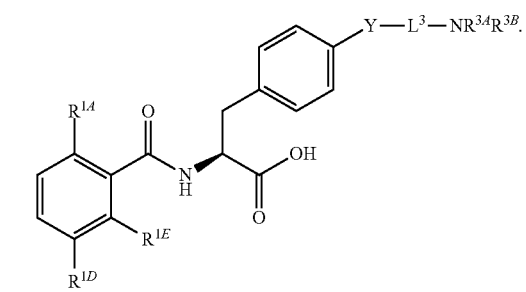
The compound may have the formula:
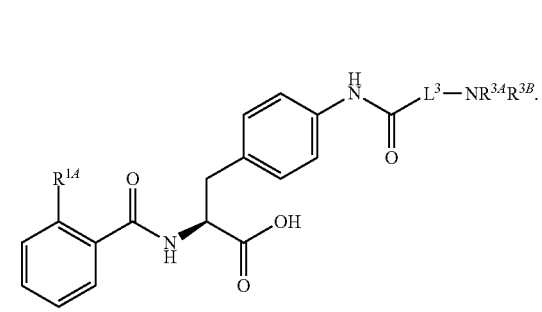
The compound may have the formula:
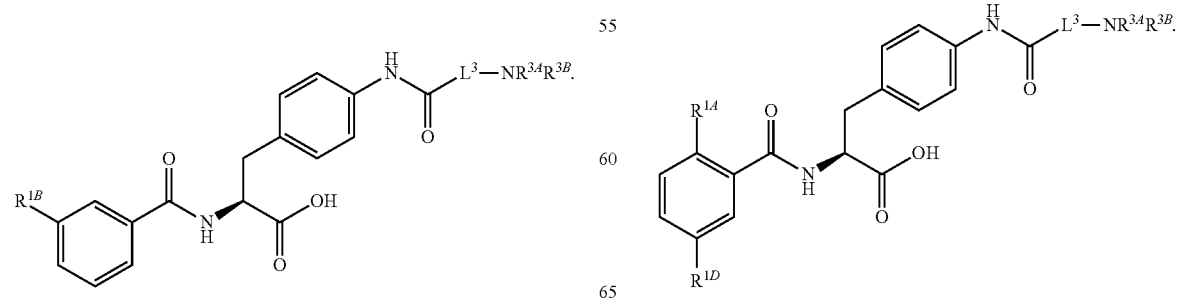
The compound may have the formula:
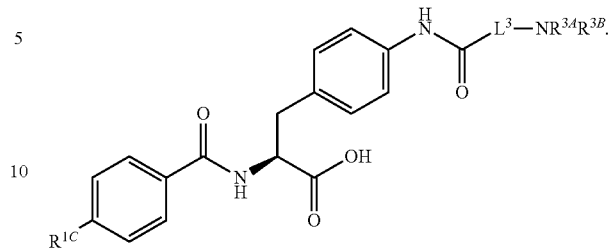
The compound may have the formula:
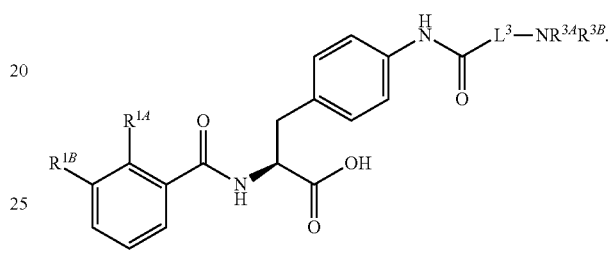
The compound may have the formula:
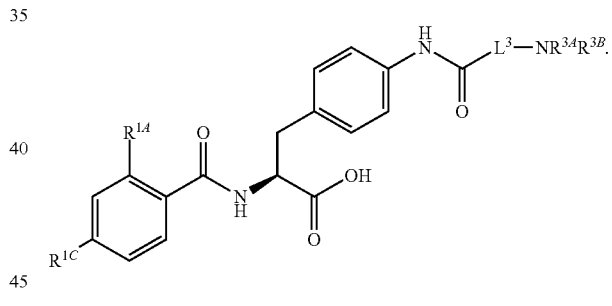
The compound may have the formula:
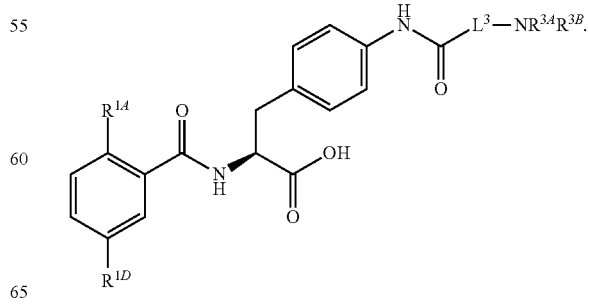

The compound may have the formula:
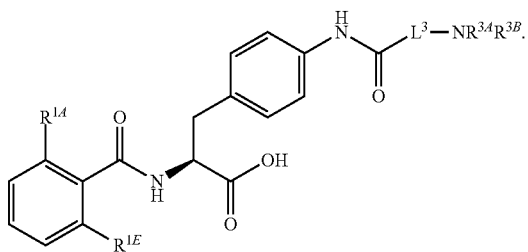
The compound may have the formula:
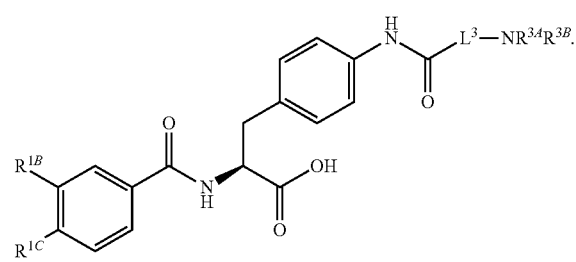
The compound may have the formula:
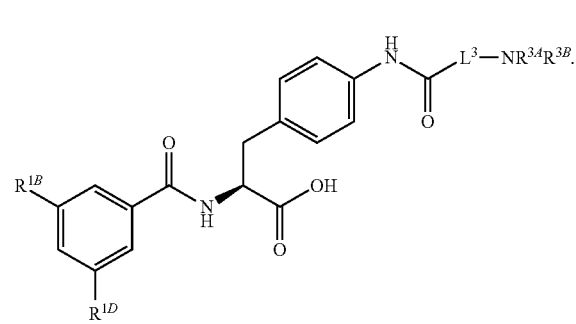
The compound may have the formula:
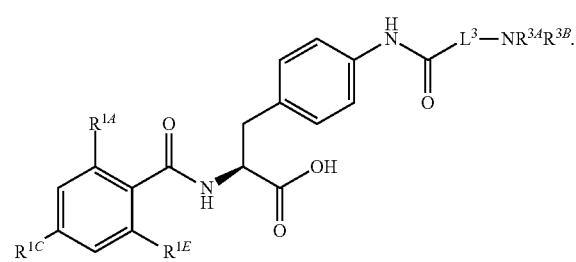
The compound may have the formula
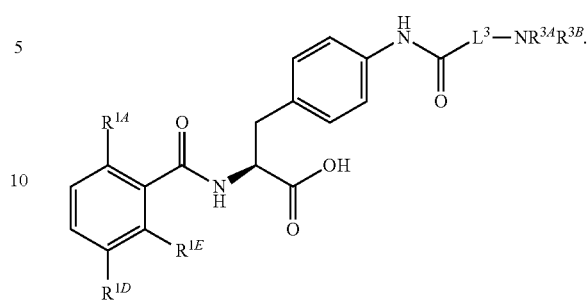
The compound may have the formula
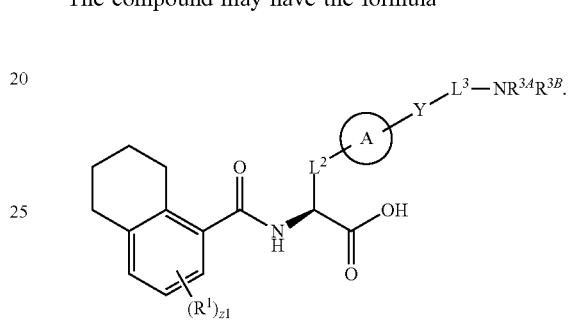
The compound may have the formula
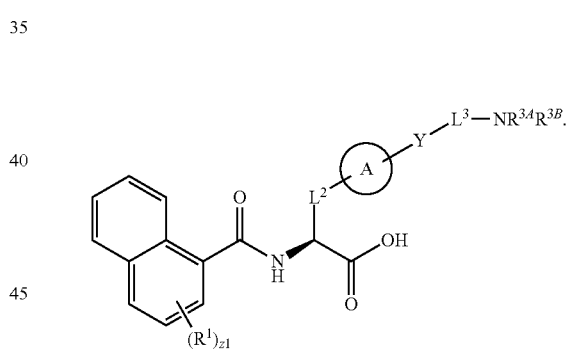
The compound may have the formula
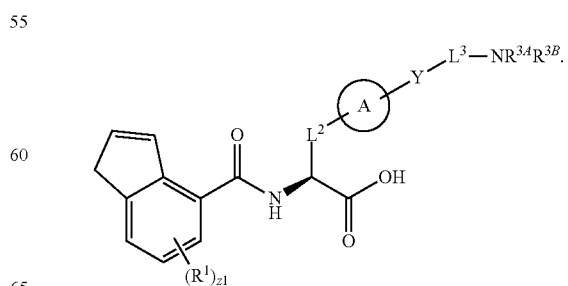

The compound may have the formula
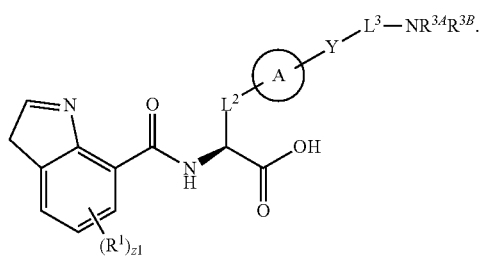
The compound may have the formula
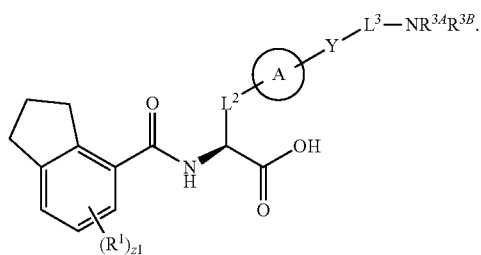
The compound may have the formula
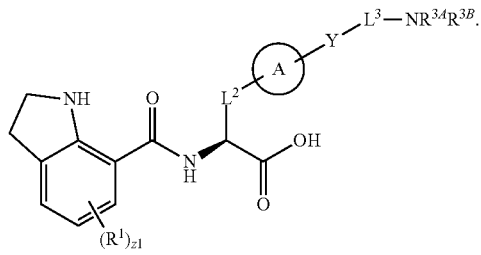
The compound may have the formula
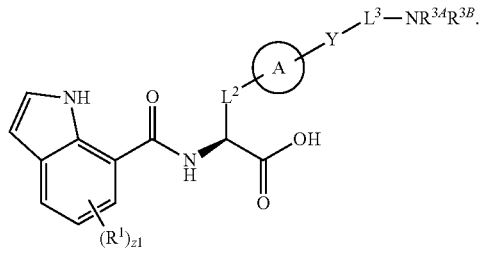
The compound may have the formula
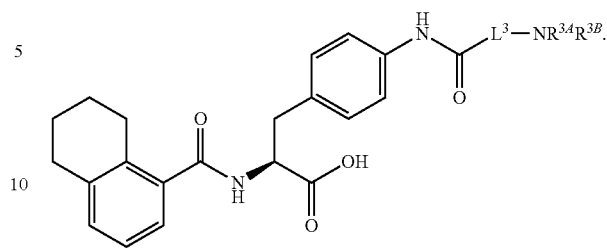
The compound may have the formula
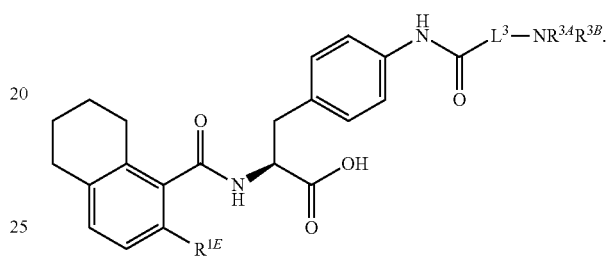
The compound may have the formula
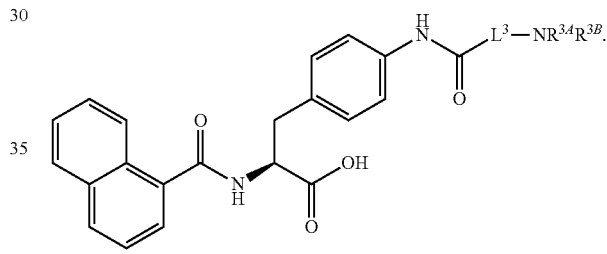
The compound may have the formula
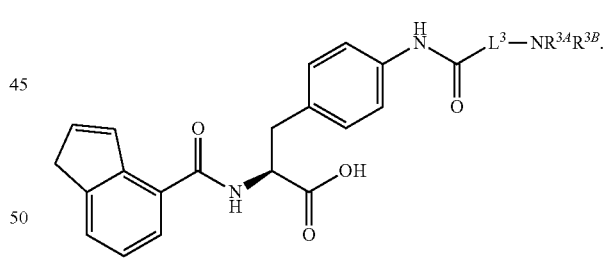
The compound may have the formula
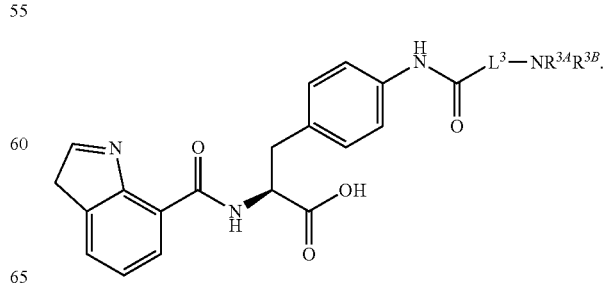

The compound may have the formula
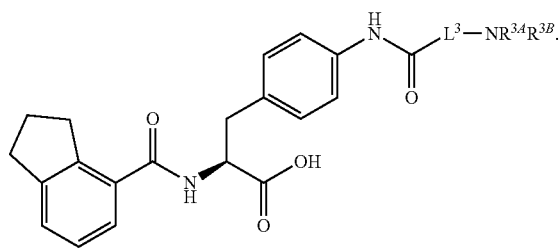
The compound may have the formula
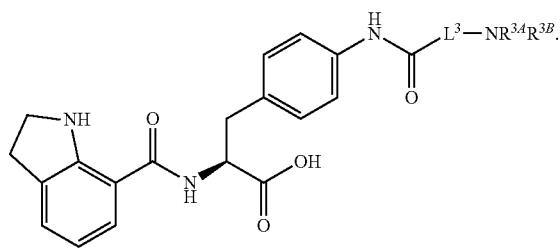
The compound may have the formula
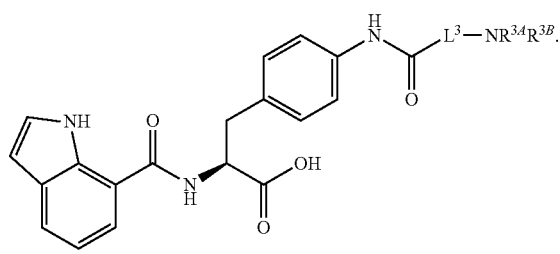
The compound may have the formula
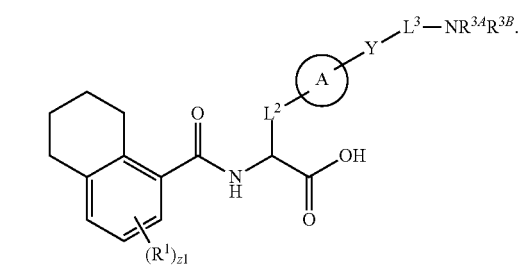
The compound may have the formula
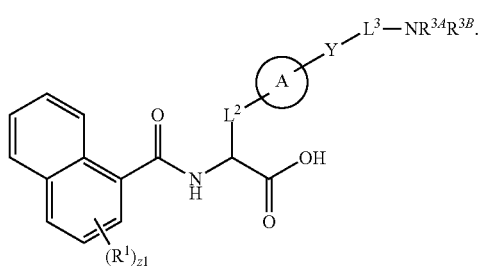
The compound may have the formula
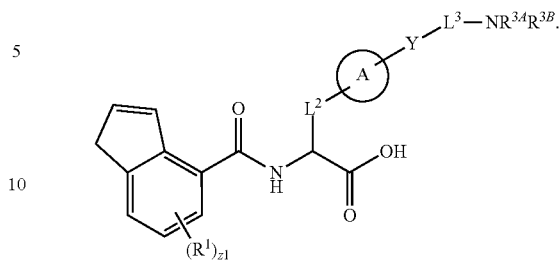
The compound may have the formula
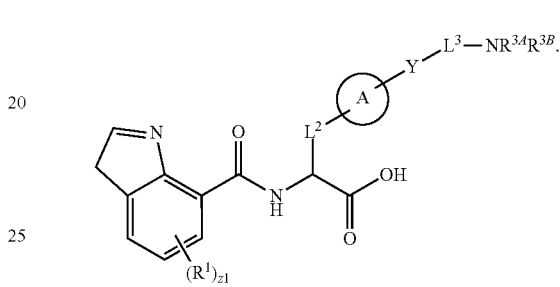
The compound may have the formula
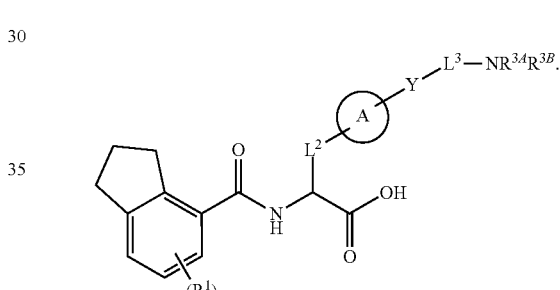
The compound may have the formula
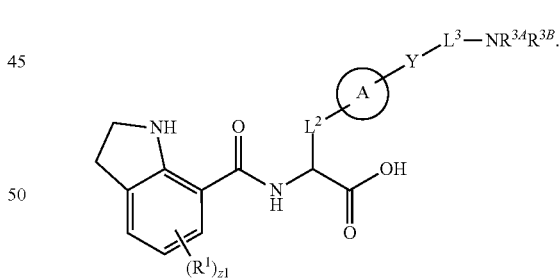
The compound may have the formula
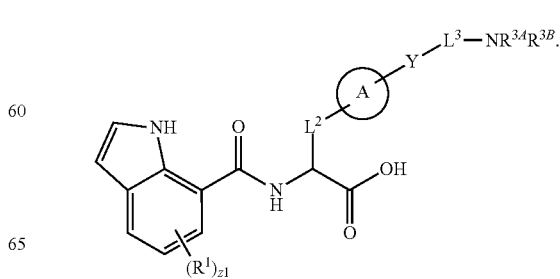

The compound may have the formula
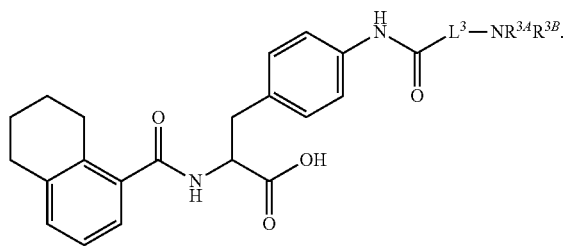
The compound may have the formula
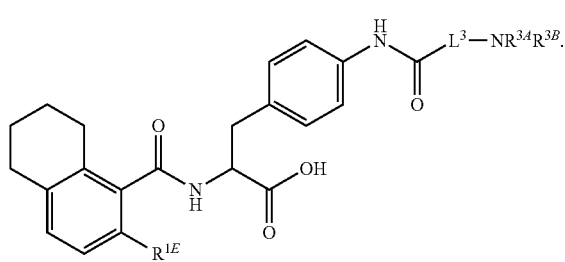
The compound may have the formula
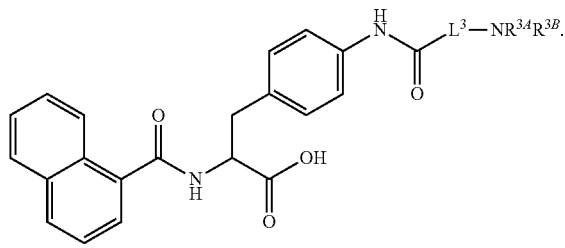
The compound may have the formula
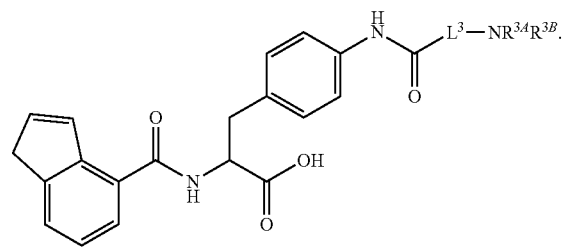
The compound may have the formula
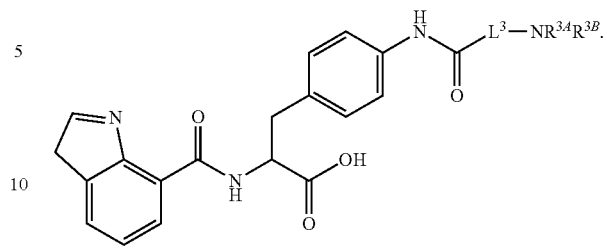
The compound may have the formula
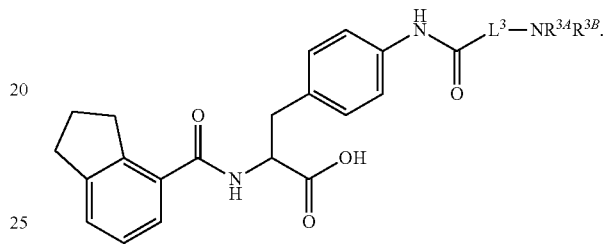
The compound may have the formula
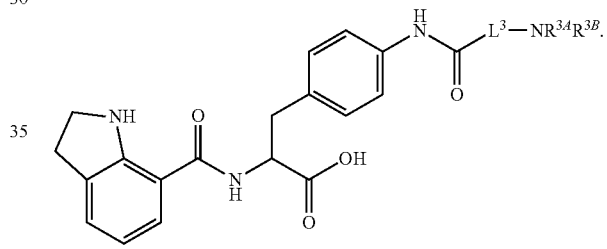
The compound may have the formula
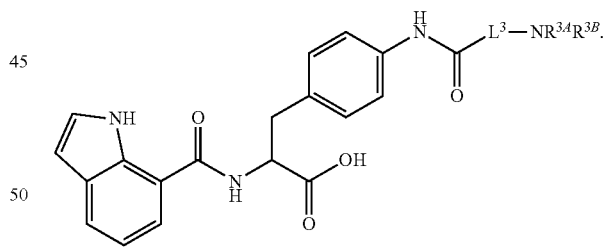
The compound may have the formula:
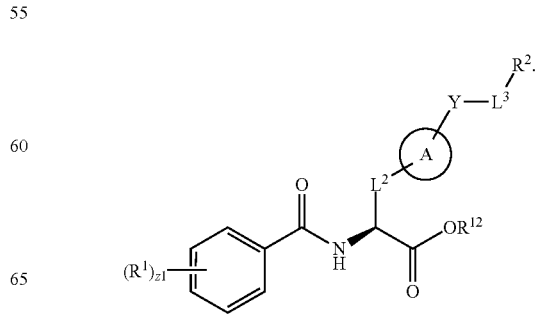

The compound may have the formula:
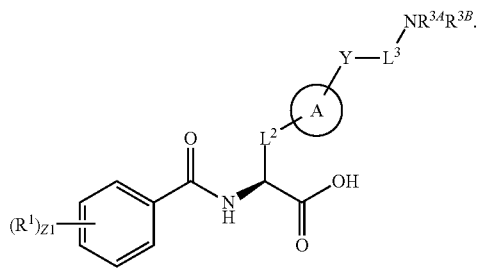
The compound may have the formula:
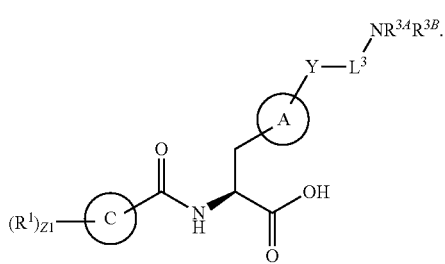
The compound may have the formula:
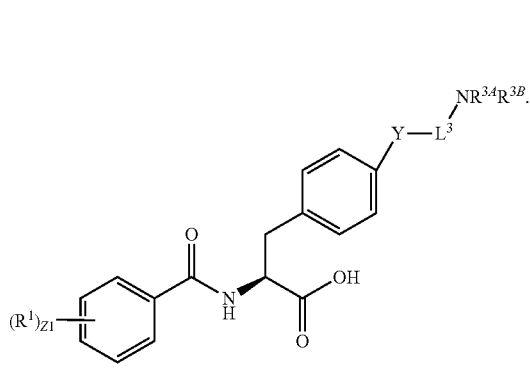
The compound may have the formula:
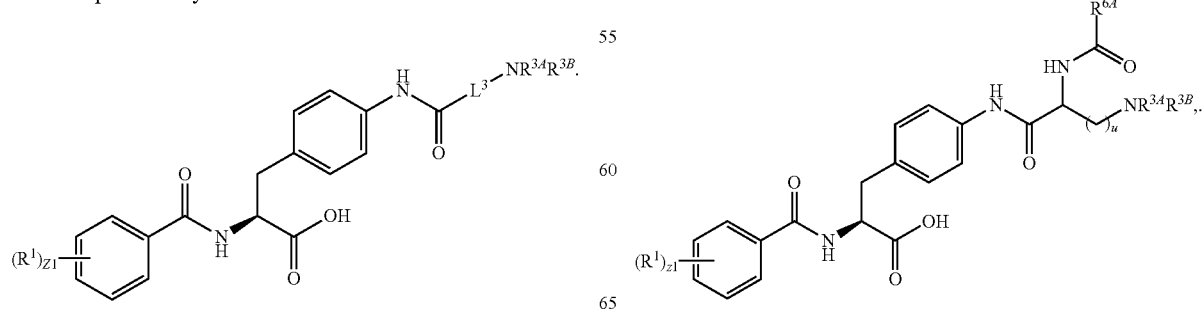
The compound may have the formula:
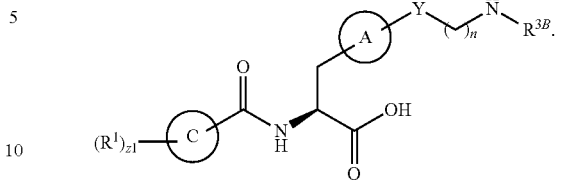
The compound may have the formula:
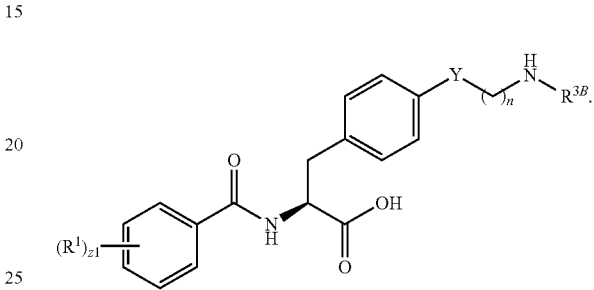
The compound may have the formula:
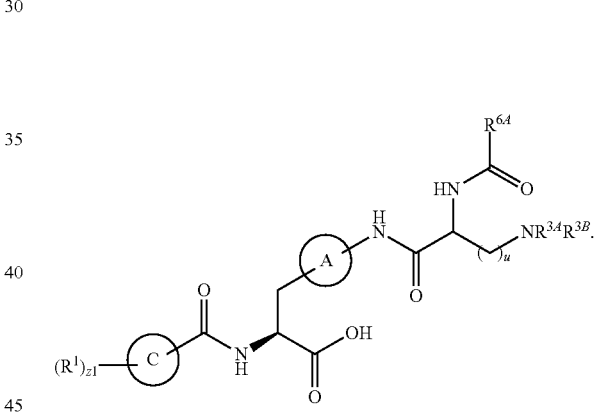
The compound may have the formula:
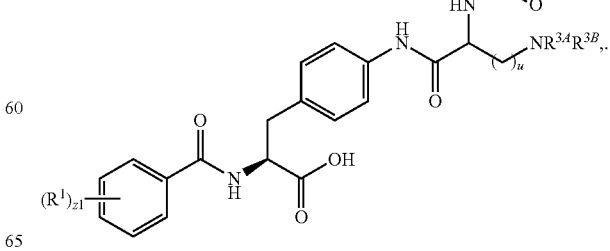

The compound may have the formula:
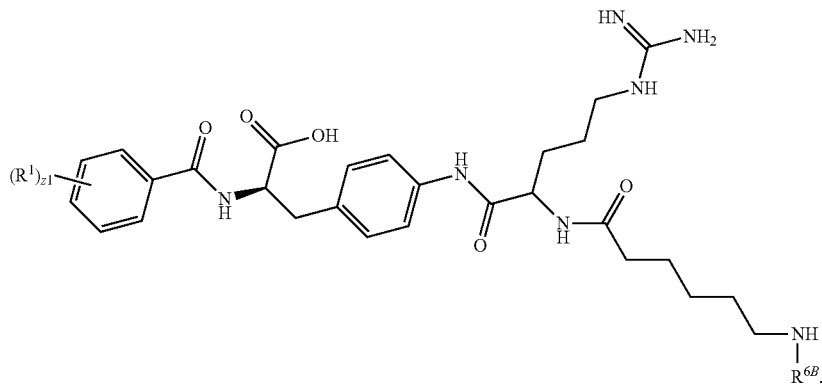
The compound may have the formula:
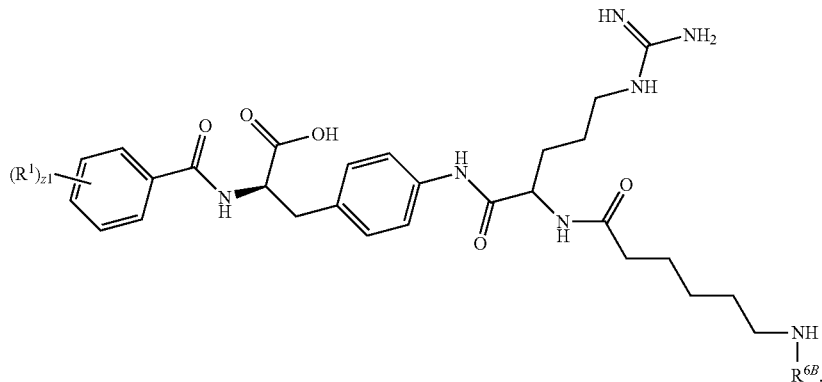
The compound may have the formula:
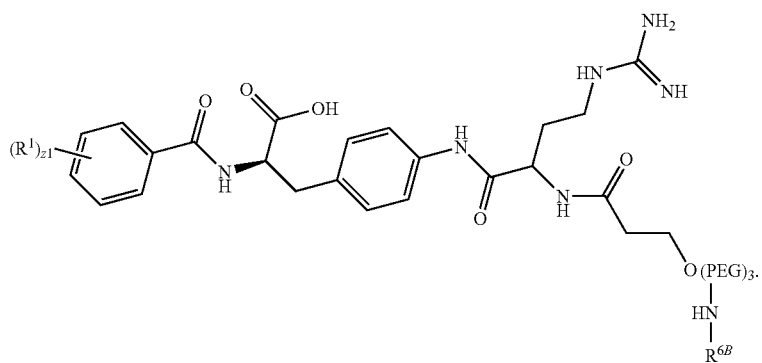

The compound may have the formula:

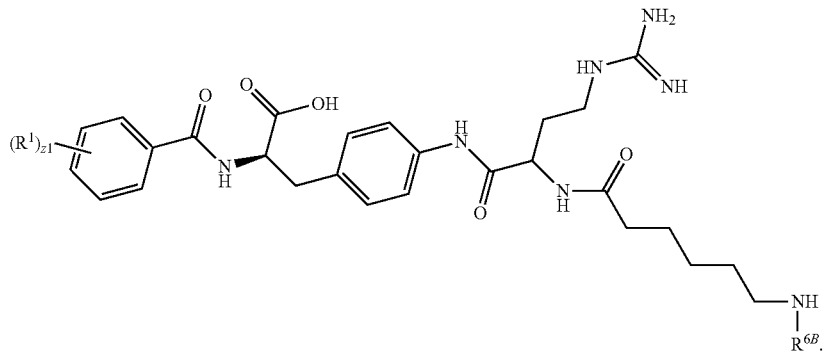

The compound may have the formula:

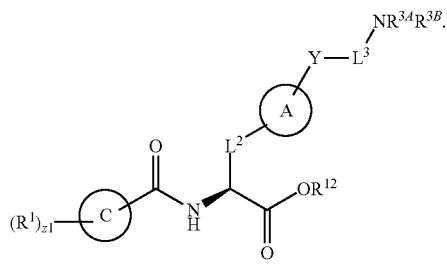

The compound may have the formula:

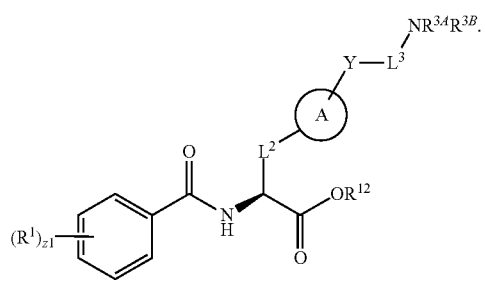

The compound may have the formula:

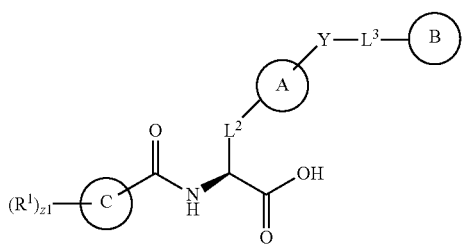

The compound may have the formula:

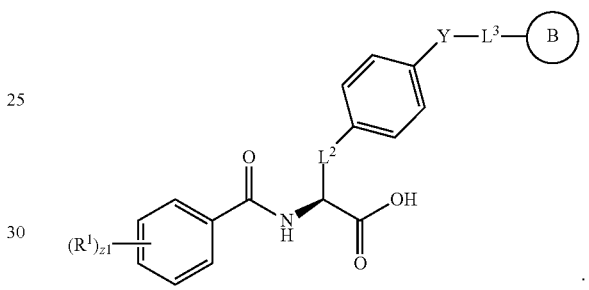

In the formulae above, Ring A, Ring B, Ring C, Y, $L^2$, $L^3$, $R^1$, $R^2$, $R^{3A}$, $R^{3B}$, $R^{12}$, $R^{6A}$, $R^{6B}$, $R^{1A}$, $R^{1B}$, $R^{1C}$, $R^{1D}$, $R^{1E}$, and z1 are as described herein (e.g., in an aspect, embodiment, figure, table, example, or claim). In embodiments, a compound may be the opposite enantiomer of a compound having one of the formulae described above. In embodiments, a compound may be the opposite stereoisomer of a compound having one of the formulae described above. In embodiments, a compound may be a racemic mixture of the enantiomer having one of the formulae described above and the opposite enantiomer. In embodiments, a compound may be a racemic mixture of the stereoisomer having one of the formulae described above and the opposite stereoisomer.

In embodiments, unless otherwise indicated, a compound described herein may be a racemic mixture of all stereoisomers. In embodiments, unless otherwise indicated, a compound described herein may be a racemic mixture of all enantiomers. In embodiments, unless otherwise indicated, a compound described herein may be a racemic mixture of two opposite stereoisomers. In embodiments, unless otherwise indicated, a compound described herein may be a racemic mixture of two opposite enantiomers. In embodiments, unless otherwise indicated, a compound described herein may be a single stereoisomer. In embodiments, unless otherwise indicated, a compound described herein may be a single enantiomer.

The compound may be a compound set forth in the examples, a figure, a claim, Table 1 or Table 2 or another table provided herein (e.g., in the Example section). In embodiments, any one or plurality of substituents (e.g., Ring A, Ring B, Ring C, Y, $L^2$, $L^3$, $R^1$, $R^2$, $R^{3A}$, $R^{3B}$, $R^{T2}$, $R^{6A}$, $R^{6B}$, $R^{1A}$, $R^{1B}$, $R^{1C}$, $R^{1D}$, $R^{1E}$, and z1) in one of the formulae described herein may be equal to the identify of that one or plurality, respectively, of substituents in one or a plurality of compounds described herein (e.g., compound in an example, figure, claim, Table 1, Table 2, or another table in the application).

In one aspect, provided herein is a method of modulating $\alpha_v\beta_1$ activity comprising contacting the $\alpha_v\beta_1$ with an effective amount of a compound of formula (I):

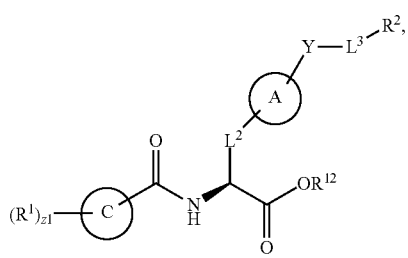

wherein the substituents are as described herein, including in embodiments. In one embodiment, $R^2$ excludes an optionally substituted heteroaryl, which includes at least one nitrogen atom. In embodiments, Ring A excludes pyridine. In embodiments, Ring A excludes thiophene.

In embodiments, $R^2$ is not heteroaryl. In embodiments, $R^2$ is not unsubstituted heteroaryl. In embodiments, $R^2$ is not substituted heteroaryl. In embodiments, $R^2$ is not a nitrogen containing heteroaryl. In embodiments, Ring A is not pyridine. In embodiments, Ring A is not thiophene.

In one aspect, provided herein is a compound of formula (I), wherein the substituents other than $R^2$ are as described herein, including in embodiments, and $R^2$ is an acyclic amidine or a cyclic or acyclic guanidine (e.g., as described herein). In embodiments, $R^2$ is —$NR^{3A}R^{3B}$, —$C(NH)NH_2$, —$C(NH)R^{3B}$, —$C(NR^{3A})NH_2$, —$C(NR^{3A})R^{3B}$, —$C(NCN)NH_2$, —$NH_2$, —$C(NH)NHR^{3B}$, —$C(NR^{3A})NHR^{3B}$, or —$C(NCN)NHR^{3B}$. In embodiments, $R^2$ is not a substituted or unsubstituted heteroaryl. In embodiments, $R^2$ is not a substituted heteroaryl. In embodiments, $R^2$ is not an unsubstituted heteroaryl. In embodiments, $R^2$ is not a substituted or unsubstituted nitrogen containing heteroaryl. In embodiments, $R^2$ is not a substituted nitrogen containing heteroaryl. In embodiments, $R^2$ is not an unsubstituted nitrogen containing heteroaryl. In embodiments, $R^2$ is not a substituted or unsubstituted 5 to 6 membered heteroaryl. In embodiments, $R^2$ is not a substituted 5 to 6 membered heteroaryl. In embodiments, $R^2$ is not an unsubstituted 5 to 6 membered heteroaryl. In embodiments, $R^2$ is not a substituted or unsubstituted nitrogen containing 5 to 6 membered heteroaryl. In embodiments, $R^2$ is not a substituted nitrogen containing 5 to 6 membered heteroaryl. In embodiments, $R^2$ is not an unsubstituted nitrogen containing 5 to 6 membered heteroaryl. In embodiments, Ring A is not a substituted or unsubstituted pyridyl. In embodiments, Ring A is not a substituted or unsubstituted thienyl. In embodiments, Ring A is not a substituted pyridyl. In embodiments, Ring A is not a substituted thienyl. In embodiments, Ring A is not an unsubstituted pyridyl. In embodiments, Ring A is not an unsubstituted thienyl. In embodiments, $R^2$ is an acyclic amidine (e.g., as described herein). In embodiments, $R^2$ is cyclic guanidine (e.g., as described herein). In embodiments, $R^2$ is an acyclic guanidine (e.g., as described herein). In embodiments, $R^2$ is an acyclic amidinyl (e.g., as described herein). In embodiments, $R^2$ is cyclic guanidinyl (e.g., as described herein). In embodiments, $R^2$ is an acyclic guanidinyl (e.g., as described herein).

In embodiments, the compound is not:

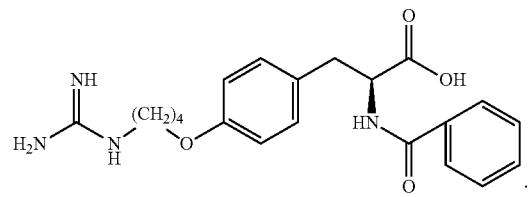

In embodiments, the compound is not:

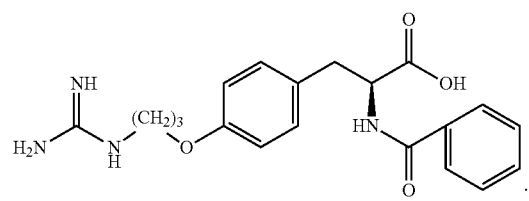

In one aspect, provided herein is a compound of formula (I), wherein Y is heteroaryl and $R^2$ is 2-aminopyridine. In embodiments, Y is heteroaryl and $R^2$ is heteroaryl. In embodiments, Y is substituted or unsubstituted heteroaryl and $R^2$ is substituted or unsubstituted heteroaryl. In embodiments, Y is substituted heteroaryl and $R^2$ is substituted heteroaryl. In embodiments, Y is unsubstituted heteroaryl and $R^2$ is unsubstituted heteroaryl. In embodiments, Y is substituted or unsubstituted heteroarylene and $R^2$ is 2-aminopyridine. In embodiments, Y is substituted heteroarylene and $R^2$ is 2-aminopyridine. In embodiments, Y is unsubstituted heteroarylene and $R^2$ is 2-aminopyridine. In embodiments, Y is substituted or unsubstituted heteroaryl and $R^2$ is substituted or unsubstituted heteroaryl. In embodiments, Y is substituted heteroaryl and $R^2$ is substituted heteroaryl. In embodiments, Y is substituted heteroaryl and $R^2$ is unsubstituted heteroaryl. In embodiments, Y is unsubstituted heteroaryl and $R^2$ is unsubstituted heteroaryl. In embodiments, Y is unsubstituted heteroaryl and $R^2$ is substituted heteroaryl.

In embodiments, Y is substituted or unsubstituted heteroarylene and $R^2$ is

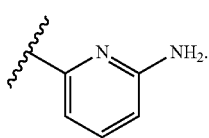 [SMILES: *c1cccc(N)n1]

In embodiments, Y is substituted heteroarylene and $R^2$ is

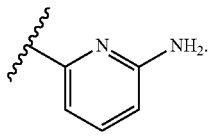 [SMILES: *c1cccc(N)n1]

In embodiments, Y is unsubstituted heteroarylene and $R^2$ is

[chemical structure: pyridine with $NH_2$ at 2-position, attachment at 6-position]

In embodiments, Y is substituted or unsubstituted heteroarylene and $R^2$ is

[chemical structure: 2-aminopyridine with NH linker]

In embodiments, Y is substituted heteroarylene and $R^2$ is

[chemical structure: 2-aminopyridine with NH linker]

In embodiments, Y is unsubstituted heteroarylene and $R^2$ is

[chemical structure: 2-aminopyridine with NH linker]

In embodiments, $L^2$ is not substituted alkylene. In embodiments, $L^2$ is not substituted $C_1$-$C_5$ alkylene. In embodiments, $L^2$ is not substituted $C_2$-$C_5$ alkylene. In embodiments, $L^2$ is not substituted $C_2$-$C_4$ alkylene. In embodiments, $L^2$ is not substituted $C_2$-$C_3$ alkylene. In embodiments, $L^2$ is not substituted $C_3$-$C_5$ alkylene. In embodiments, $L^2$ is not substituted $C_4$-$C_5$ alkylene. In embodiments, $L^2$ is not substituted methylene. In embodiments, $L^2$ is not unsubstituted methylene.

In embodiments, $L^2$ is not a substituted or unsubstituted heteroalkylene. In embodiments, $L^2$ is not a substituted or unsubstituted 2 to 5 membered heteroalkylene. In embodiments, $L^2$ is not a substituted or unsubstituted 2 to 4 membered heteroalkylene. In embodiments, $L^2$ is not a substituted or unsubstituted 2 to 3 membered heteroalkylene. In embodiments, $L^2$ is not a substituted or unsubstituted 3 to 4 membered heteroalkylene. In embodiments, $L^2$ is not a substituted or unsubstituted 3 to 5 membered heteroalkylene. In embodiments, $L^2$ is not a substituted 2 to 5 membered heteroalkylene. In embodiments, $L^2$ is not a substituted 2 to 4 membered heteroalkylene. In embodiments, $L^2$ is not a substituted 2 to 3 membered heteroalkylene. In embodiments, $L^2$ is not a substituted 3 to 4 membered heteroalkylene. In embodiments, $L^2$ is not a substituted 3 to 5 membered heteroalkylene. In embodiments, $L^2$ is not an unsubstituted 2 to 5 membered heteroalkylene. In embodiments, $L^2$ is not an unsubstituted 2 to 4 membered heteroalkylene. In embodiments, $L^2$ is not an unsubstituted 2 to 3 membered heteroalkylene. In embodiments, $L^2$ is not an unsubstituted 3 to 4 membered heteroalkylene. In embodiments, $L^2$ is not an unsubstituted 3 to 5 membered heteroalkylene.

In embodiments, $L^2$ is not a substituted 2 membered heteroalkylene. In embodiments, $L^2$ is not a substituted 3 membered heteroalkylene. In embodiments, $L^2$ is not a substituted 4 membered heteroalkylene. In embodiments, $L^2$ is not a substituted 5 membered heteroalkylene. In embodiments, $L^2$ is not an unsubstituted 2 membered heteroalkylene. In embodiments, $L^2$ is not an unsubstituted 3 membered heteroalkylene. In embodiments, $L^2$ is not an unsubstituted 4 membered heteroalkylene. In embodiments, $L^2$ is not an unsubstituted 5 membered heteroalkylene.

In embodiments, $L^2$ is not unsubstituted alkylene. In embodiments, $L^2$ is not unsubstituted $C_1$-$C_5$ alkylene. In embodiments, $L^2$ is not unsubstituted $C_2$-$C_5$ alkylene. In embodiments, $L^2$ is not unsubstituted $C_2$-$C_4$ alkylene. In embodiments, $L^2$ is not unsubstituted $C_2$-$C_3$ alkylene. In embodiments, $L^2$ is not unsubstituted $C_3$-$C_5$ alkylene. In embodiments, $L^2$ is not unsubstituted $C_4$-$C_5$ alkylene. In embodiments, $L^2$ is not unsubstituted methylene.

In embodiments, $L^2$ is substituted alkylene. In embodiments, $L^2$ is substituted $C_1$-$C_5$ alkylene. In embodiments, $L^2$ is substituted $C_2$-$C_5$ alkylene. In embodiments, $L^2$ is substituted $C_2$-$C_4$ alkylene. In embodiments, $L^2$ is substituted $C_2$-$C_3$ alkylene. In embodiments, $L^2$ is substituted $C_3$-$C_5$ alkylene. In embodiments, $L^2$ is substituted $C_4$-$C_5$ alkylene. In embodiments, $L^2$ is substituted methylene.

In embodiments, $L^2$ is a substituted or unsubstituted heteroalkylene. In embodiments, $L^2$ is a substituted or unsubstituted 2 to 5 membered heteroalkylene. In embodiments, $L^2$ is a substituted or unsubstituted 2 to 4 membered heteroalkylene. In embodiments, $L^2$ is a substituted or unsubstituted 2 to 3 membered heteroalkylene. In embodiments, $L^2$ is a substituted or unsubstituted 3 to 4 membered heteroalkylene. In embodiments, $L^2$ is a substituted or unsubstituted 3 to 5 membered heteroalkylene. In embodiments, $L^2$ is a substituted 2 to 5 membered heteroalkylene. In embodiments, $L^2$ is a substituted 2 to 4 membered heteroalkylene. In embodiments, $L^2$ is a substituted 2 to 3 membered heteroalkylene. In embodiments, $L^2$ is a substituted 3 to 4 membered heteroalkylene. In embodiments, $L^2$ is a substituted 3 to 5 membered heteroalkylene. In embodiments, $L^2$ is an unsubstituted 2 to 5 membered heteroalkylene. In embodiments, $L^2$ is an unsubstituted 2 to 4 membered heteroalkylene. In embodiments, $L^2$ is an unsubstituted 2 to 3 membered heteroalkylene. In embodiments, $L^2$ is an unsubstituted 3 to 4 membered heteroalkylene. In embodiments, $L^2$ is an unsubstituted 3 to 5 membered heteroalkylene.

In embodiments, $L^2$ is a substituted 2 membered heteroalkylene. In embodiments, $L^2$ is a substituted 3 membered heteroalkylene. In embodiments, $L^2$ is a substituted 4 membered heteroalkylene. In embodiments, $L^2$ is a substituted 5 membered heteroalkylene. In embodiments, $L^2$ is an unsubstituted 2 membered heteroalkylene. In embodiments, $L^2$ is an unsubstituted 3 membered heteroalkylene. In embodiments, $L^2$ is an unsubstituted 4 membered heteroalkylene. In embodiments, $L^2$ is an unsubstituted 5 membered heteroalkylene.

In embodiments, Ring A is substituted or unsubstituted cycloalkyl, substituted or unsubstituted heterocycloalkyl, or substituted or unsubstituted heteroaryl. In embodiments, Ring A is substituted or unsubstituted cycloalkyl. In embodiments, Ring A is substituted or unsubstituted heterocycloalkyl. In embodiments, Ring A is substituted or unsubstituted heteroaryl. In embodiments, Ring A is substituted cycloalkyl, substituted heterocycloalkyl, or substituted heteroaryl. In embodiments, Ring A is substituted cycloalkyl. In embodiments, Ring A is substituted heterocycloalkyl. In embodiments, Ring A is substituted heteroaryl. In embodiments, Ring A is unsubstituted cycloalkyl, unsubstituted heterocycloalkyl, or unsubstituted heteroaryl. In embodiments, Ring A is unsubstituted cycloalkyl. In embodiments, Ring A is unsubstituted heterocycloalkyl. In embodiments, Ring A is unsubstituted heteroaryl.

Ring A may be a substituted or unsubstituted heteroaryl such as, for example, substituted or unsubstituted pyrrolyl, substituted or unsubstituted furanyl, substituted or unsubstituted imidazolyl, substituted or unsubstituted pyrazolyl, substituted or unsubstituted oxazolyl, substituted or unsubstituted thiazolyl, substituted or unsubstituted pyranyl, substituted or unsubstituted thiopyranyl, substituted or unsubstituted pyrazinyl, substituted or unsubstituted pyrimindyl, substituted or unsubstituted pyridazinyl, substituted or unsubstituted oxazinyl, substituted or unsubstituted thiazinyl, substituted or unsubstituted doxinyl, substituted or unsubstituted dithiinyl, substituted or unsubstituted azetyl, substituted or unsubstituted oxetyl, substituted or unsubstituted thietyl, substituted or unsubstituted azirinyl, substituted or unsubstituted oxirenyl or substituted or unsubstituted thirenyl.

Y may be substituted heteroalkylene. Y may be substituted heteroalkylene with oxo. Y may be substituted alkylene. Y may be substituted alkylene with oxo. Y may be $R^{11}$-substituted heteroalkylene. Y may be $R^{11}$-substituted heteroalkylene, wherein $R^{11}$ is oxo. Y may be $R^{11}$-substituted alkylene. Y may be $R^{11}$-substituted alkylene, wherein $R^{11}$ is oxo.

In embodiments, the compound is not:

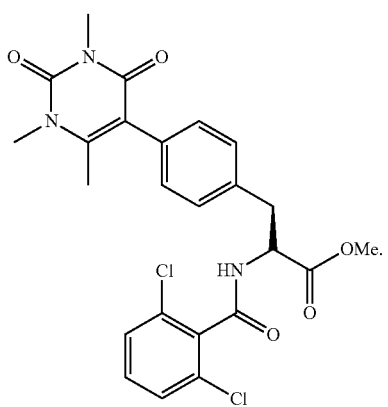

In embodiments, the compound is not:

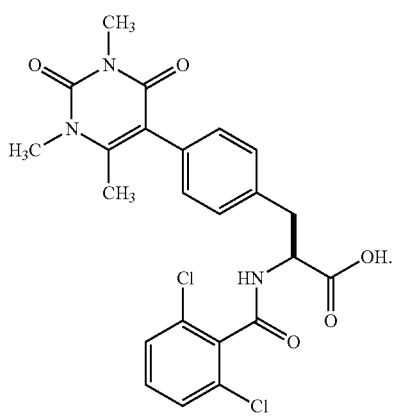

In embodiments, the compound is not:

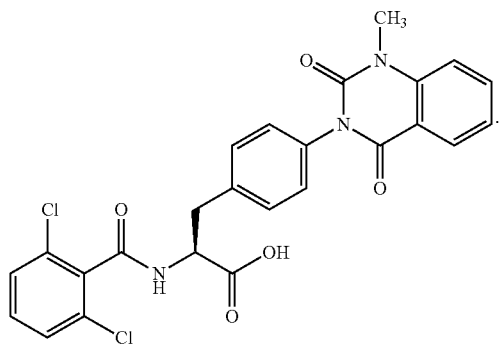 [SMILES: Cn1c(=O)n(-c2ccc(C[C@H](NC(=O)c3c(Cl)cccc3Cl)C(=O)O)cc2)c(=O)c2ccccc21]

In embodiments, the compound is not:

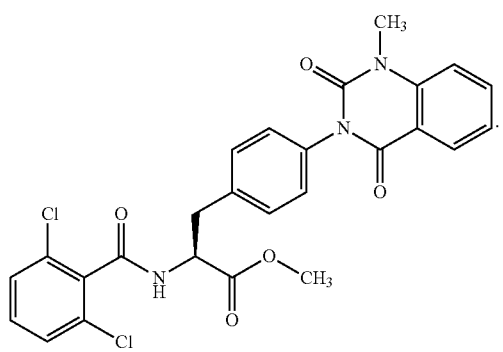 [SMILES: COC(=O)[C@H](Cc1ccc(-n2c(=O)c3ccccc3n(C)c2=O)cc1)NC(=O)c1c(Cl)cccc1Cl]

In embodiments, the compound is not:

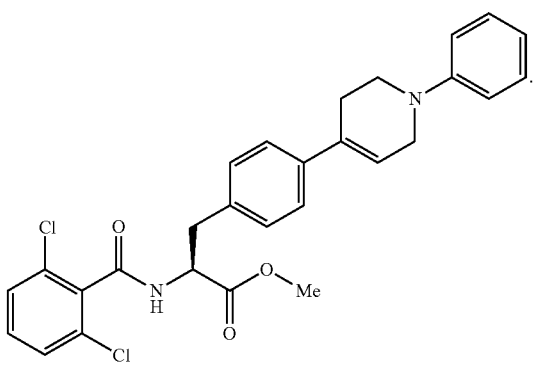 [SMILES: COC(=O)[C@H](Cc1ccc(C2=CCN(c3ccccc3)CC2)cc1)NC(=O)c1c(Cl)cccc1Cl]

In embodiments, the compound is not:

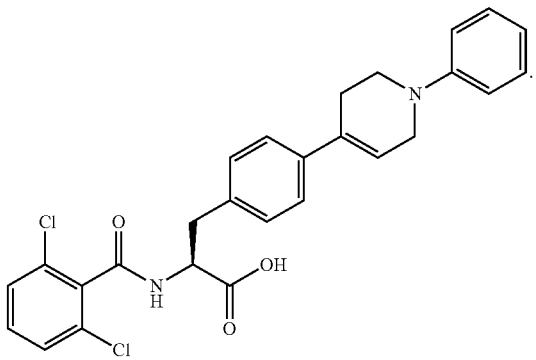 [SMILES: O=C(N[C@@H](Cc1ccc(C2=CCN(c3ccccc3)CC2)cc1)C(=O)O)c1c(Cl)cccc1Cl]

179
In embodiments, the compound is not:
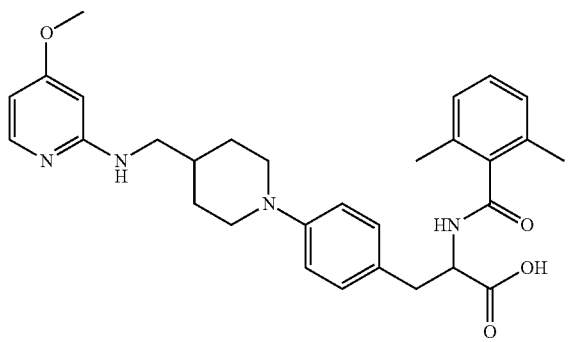
In embodiments, the compound is not:
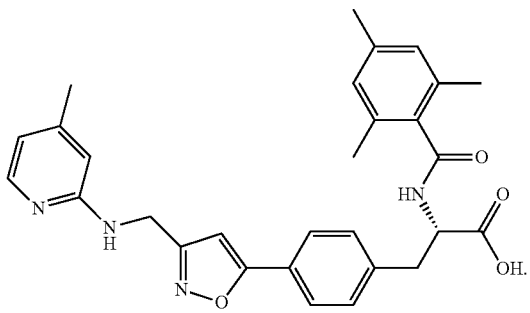 [SMILES: Cc1ccnc(NCc2cc(-c3ccc(C[C@H](NC(=O)c4c(C)cc(C)cc4C)C(=O)O)cc3)on2)c1]
In embodiments, the compound is not:
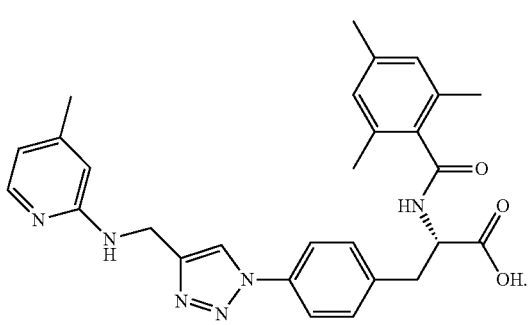 [SMILES: Cc1ccnc(NCc2cn(-c3ccc(C[C@H](NC(=O)c4c(C)cc(C)cc4C)C(=O)O)cc3)nn2)c1]
In embodiments, the compound is not:
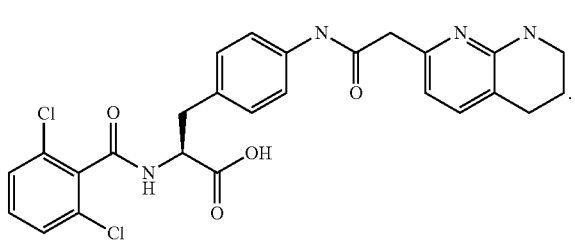 [SMILES: O=C(Cc1ccc2c(n1)NCCC2)Nc1ccc(C[C@H](NC(=O)c2c(Cl)cccc2Cl)C(=O)O)cc1]
180
In embodiments, the compound is not:
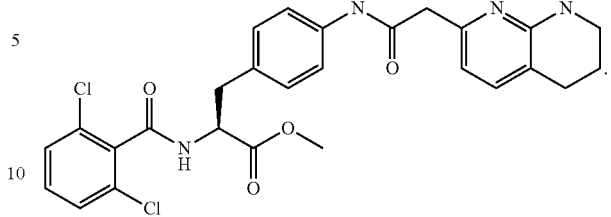
In embodiments, the compound is not:
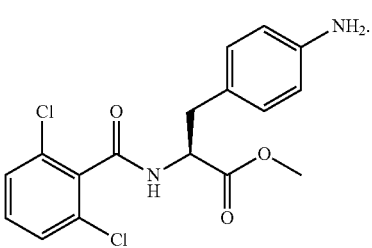 [SMILES: COC(=O)[C@H](Cc1ccc(N)cc1)NC(=O)c1c(Cl)cccc1Cl]
In embodiments, the compound is not:
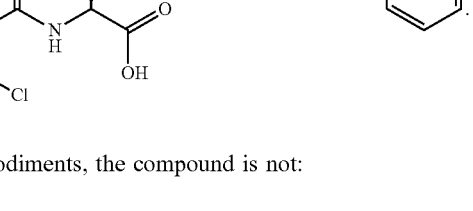
In embodiments, the compound is not:
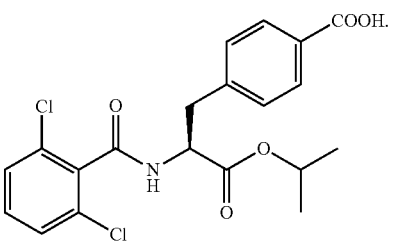 [SMILES: CC(C)OC(=O)[C@H](Cc1ccc(C(=O)O)cc1)NC(=O)c1c(Cl)cccc1Cl]

181
In embodiments, the compound is not:
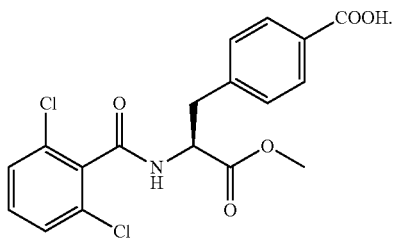 [SMILES: COC(=O)[C@H](Cc1ccc(C(=O)O)cc1)NC(=O)c1c(Cl)cccc1Cl]
In embodiments, the compound is not:
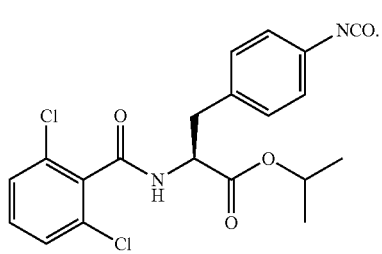
In embodiments, the compound is not:
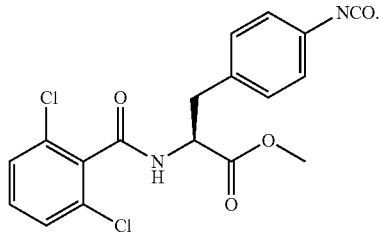
In embodiments, the compound is not:
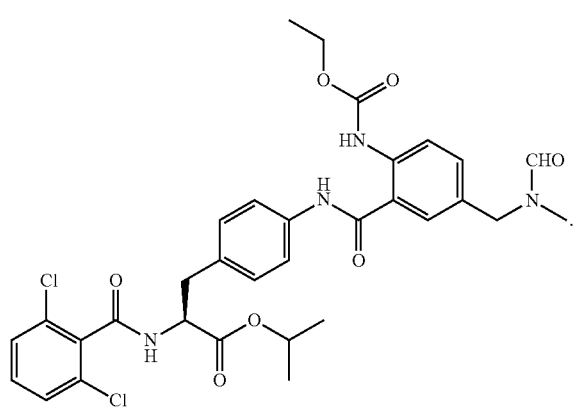 [SMILES: CCOC(=O)Nc1ccc(CN(C)C=O)cc1C(=O)Nc1ccc(C[C@H](NC(=O)c2c(Cl)cccc2Cl)C(=O)OC(C)C)cc1]
182
In embodiments, the compound is not:
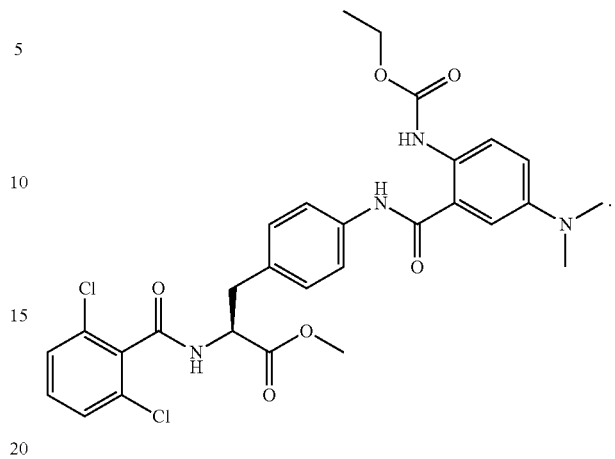
In embodiments, the compound is not:
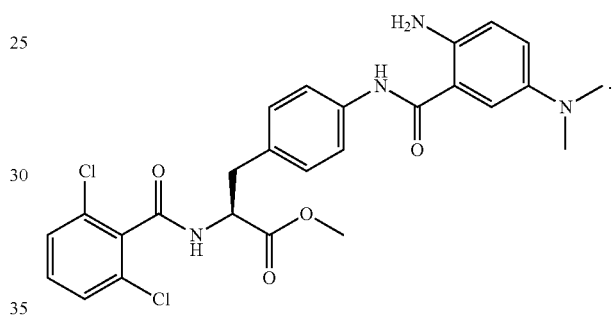
In embodiments, the compound is not:
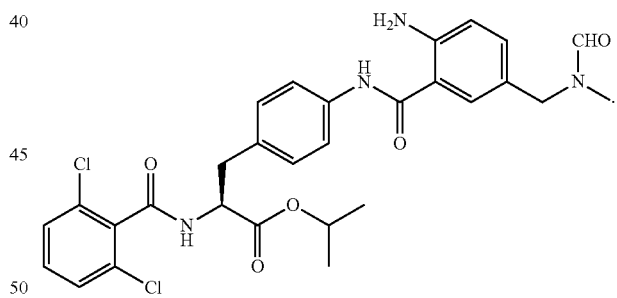
In embodiments, the compound is not:
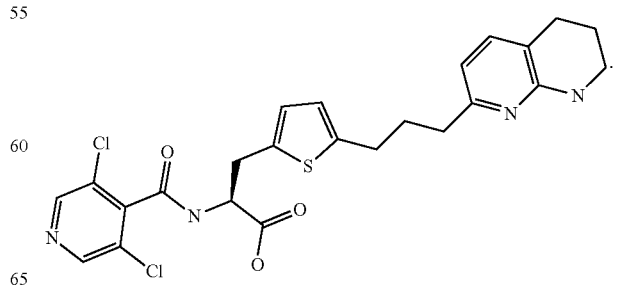

In embodiments, the compound is not:

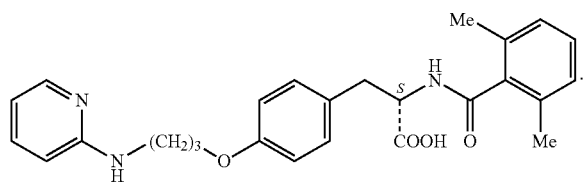

In embodiments, the compound is not:

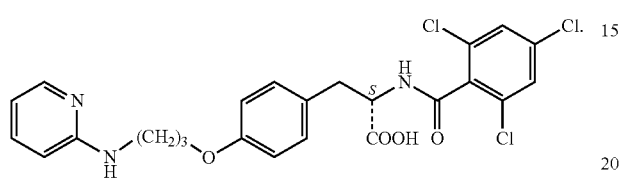

In embodiments, the compound is not:

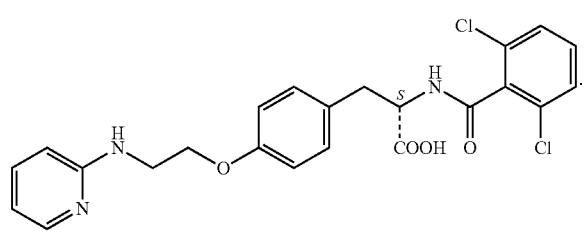

In embodiments, the compound is not:

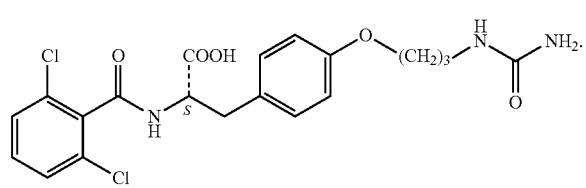

In embodiments, the compound is not:

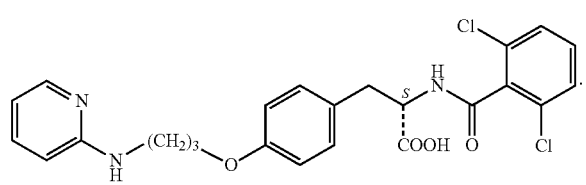

In embodiments, the compound is not:

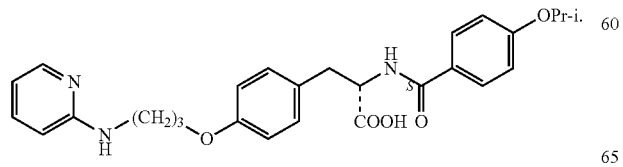

In embodiments, the compound is not:

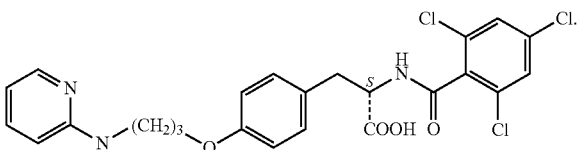

In embodiments, the compound is not:

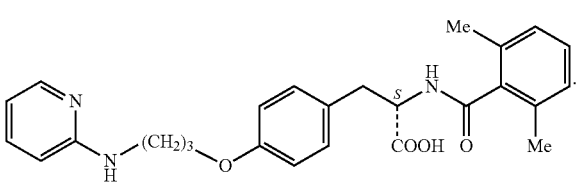

In embodiments, the compound is not:

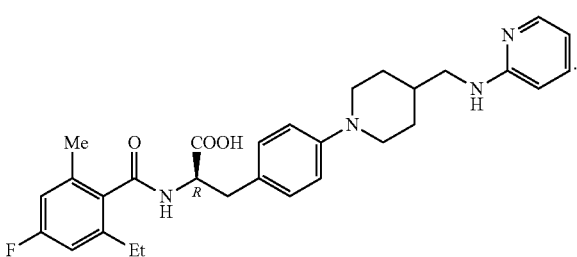

In embodiments, the compound is not:

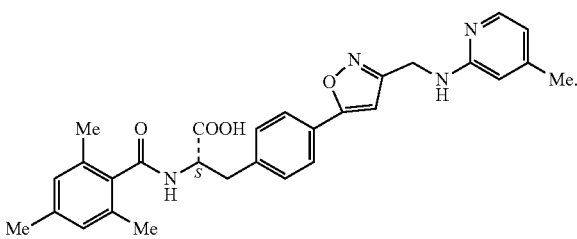

In embodiments, the compound is not:

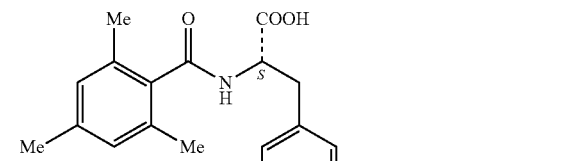

In embodiments, the compound is not:

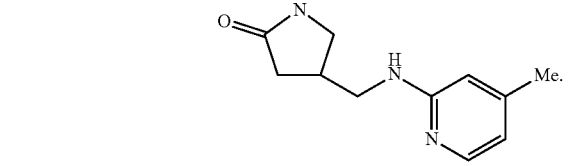

In embodiments, the compound is not:
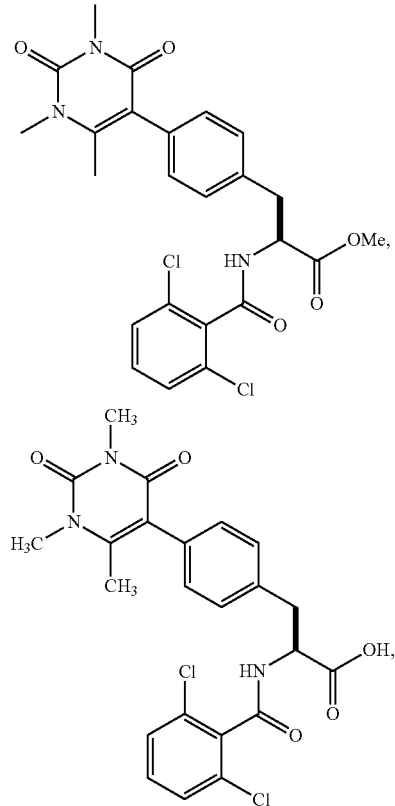
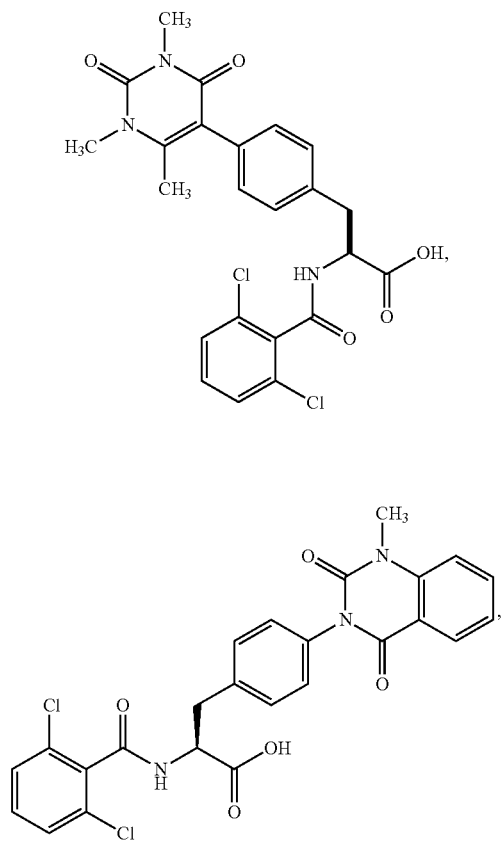
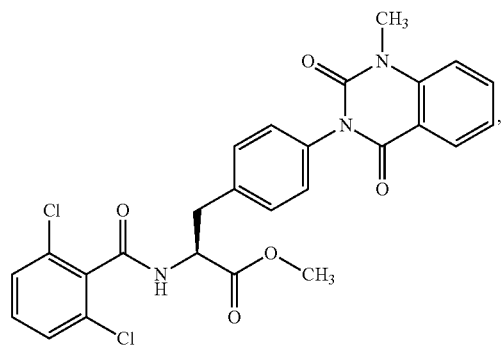
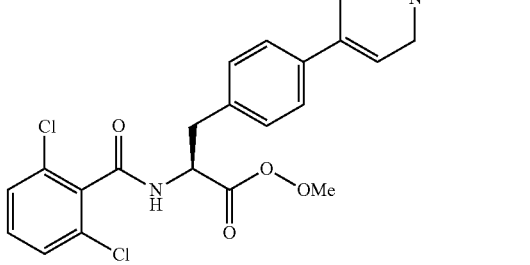
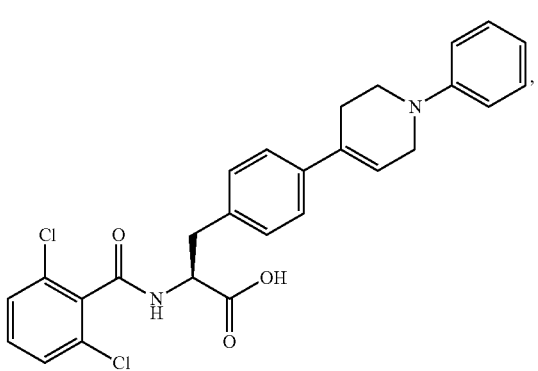
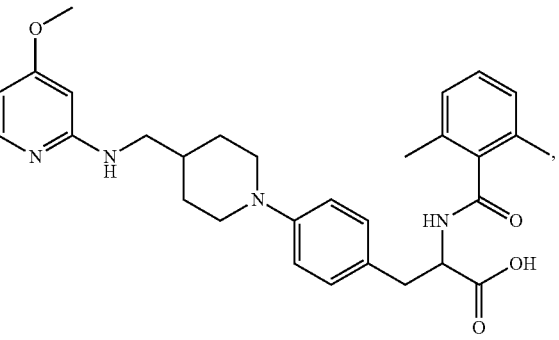
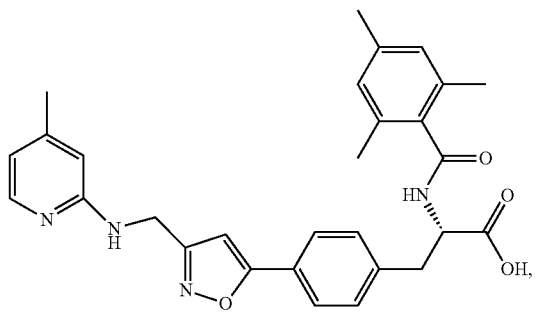

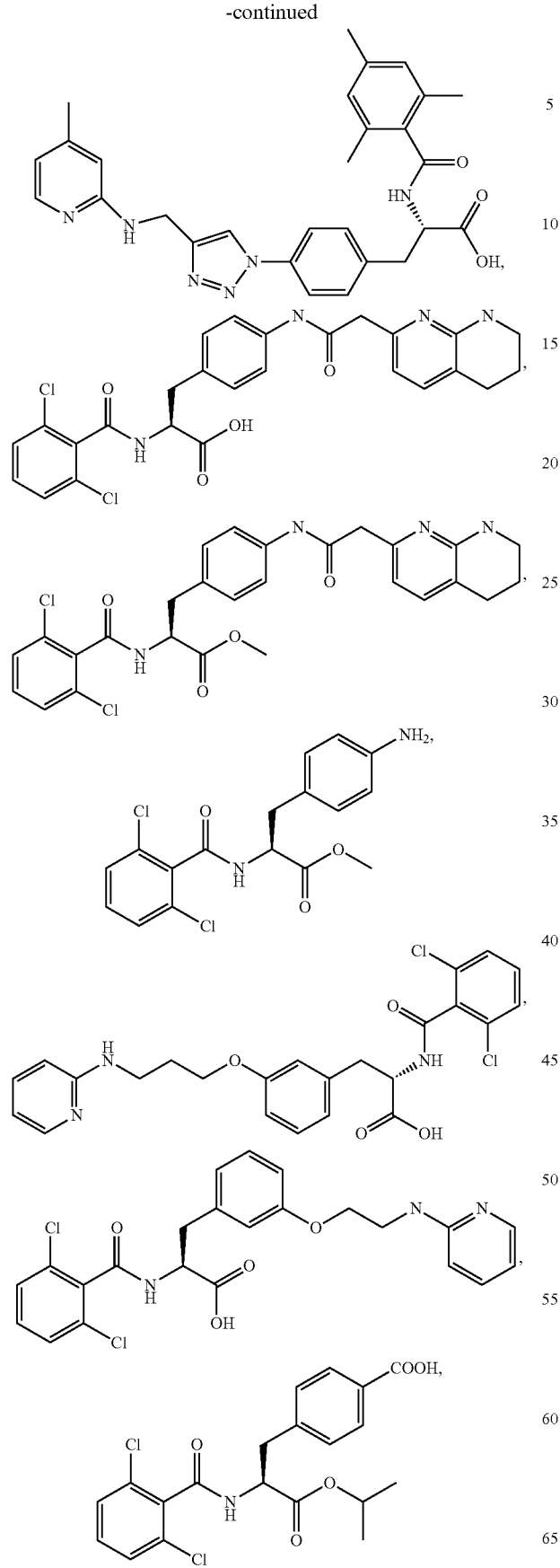
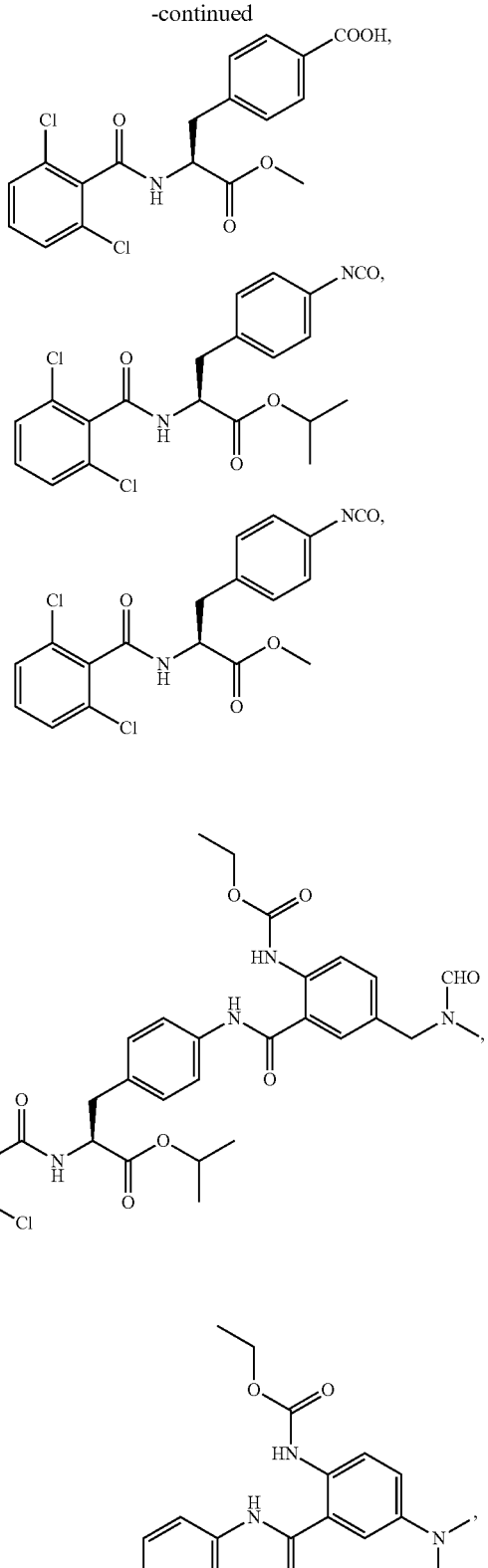

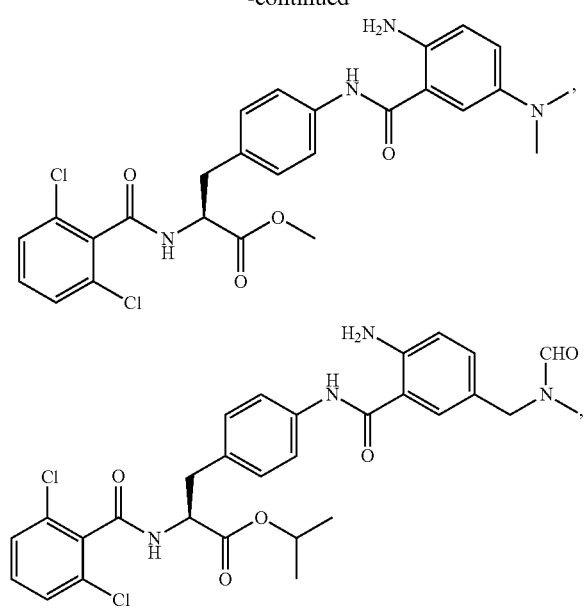
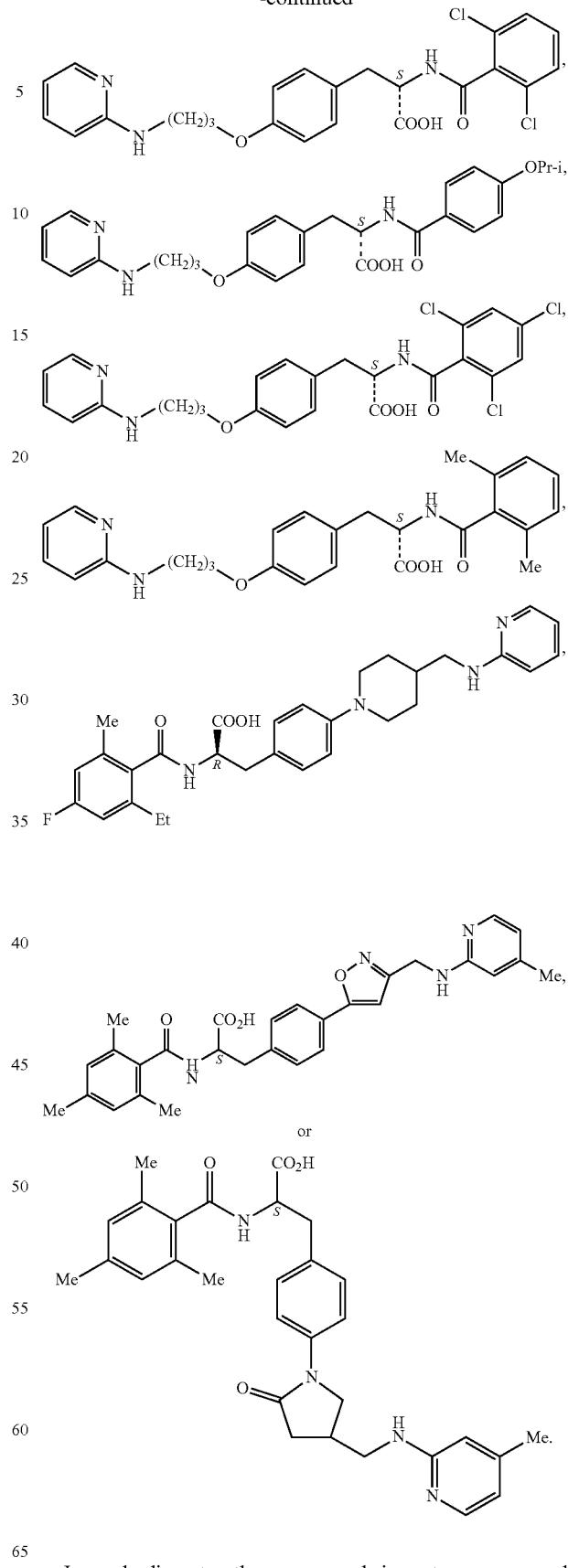
In embodiments, the compound is not a compound described within WO 2007/141473. In embodiments, the compound is not a compound described within WO 2008/125811. In embodiments, the compound is not a compound described within WO 2007/060408. In embodiments, the compound is not a compound described within WO 2001/042225. In embodiments, the compound is not a compound described within WO 2007/088041. In embodiments, the compound is not a compound described within WO 2002/016329. In embodiments, the compound is not a compound described within WO 2007/131764. In embodiments, the compound is not a compound described within WO 2007/131764 WO 2008/062859.

In embodiments, the compound is not a compound described within Bioorganic & Medicinal Chemistry Letters (2010), 20(1), 380-382. In embodiments, the compound is not a compound described within Bioorganic & Medicinal Chemistry Letters (2010), 20(1), 65-68. In embodiments, the compound is not a compound described within Biochimica et Biophysica Acta, (2014), 1840(9), 2978-2987. In embodiments, the compound is not a compound described within Sel. Org. React. Database (SORD) 2007, (20121004). In embodiments, the compound is not a compound described within Bioorganic & Medicinal Chemistry Letters (2012), 22(12), 4111-4116. In embodiments, the compound is not a compound described within Bioorganic & Medicinal Chemistry Letters (2012), 22(12), 4117-4121. In embodiments, the compound is not a compound described within Angewandte Chemie, International Edition (2009), 48(24), 4436-4440. In embodiments, the compound is not a compound described within ChemBioChem (2008), 9(9), 1397-1407. In embodiments, the compound is not a compound described within Angewandte Chemie, International Edition (2007), 46(19), 3571-3574.

II. Pharmaceutical Compositions

In another aspect is a pharmaceutical composition including a compound described herein. The compound may have a formula described herein, including embodiments and prodrugs thereof. The pharmaceutical composition may include a pharmaceutically acceptable excipient. Also provided herein is a pharmaceutical composition that includes a compound having formula: (X) and a pharmaceutically acceptable excipient.

In an aspect is provided a pharmaceutical composition including a compound described herein and a pharmaceutically acceptable excipient.

III. Methods for Treating Fibrosis

In an aspect is provided a method for treating fibrosis, the method including administering to a subject in need thereof a compound described herein. In embodiments, the fibrosis is pulmonary fibrosis, liver fibrosis, skin fibrosis, cardiac fibrosis, or kidney fibrosis. In embodiments, the fibrosis is pulmonary fibrosis. In embodiments, the fibrosis is liver fibrosis. In embodiments, the fibrosis is skin fibrosis. In embodiments, the fibrosis is cardiac fibrosis. In embodiments, the fibrosis is kidney fibrosis.

Provided herein are methods for treating fibrosis. In one aspect, is a method for treating fibrosis by administering to a subject in need thereof an $\alpha v\beta 1$-inhibitor, where the $\alpha v\beta 1$-inhibitor is an $\alpha v\beta 1$-inhibitor antibody, an $\alpha v\beta 1$-inhibitor RGD peptide, or an $\alpha v\beta 1$-inhibitor compound having the formulae described herein, including embodiments thereof. In an embodiment, is a method for treating fibrosis by administering to a subject in need thereof a therapeutically effective amount of an $\alpha v\beta 1$-inhibitor, where the $\alpha v\beta 1$-inhibitor is an $\alpha v\beta 1$-inhibitor antibody, an $\alpha v\beta 1$-inhibitor RGD peptide, or an $\alpha v\beta 1$-inhibitor compound having the formulae described herein, including embodiments thereof. The $\alpha v\beta 1$-inhibitor compound may be a compound having a formula described herein, including embodiments thereof. The $\alpha v\beta 1$ inhibitor-compound may be a compound having formula: (X), including embodiments thereof. The $\alpha v\beta 1$-inhibitor compound may be a pharmaceutical composition as described herein, including embodiments thereof.

The fibrosis may be pulmonary fibrosis, liver fibrosis, lung fibrosis, skin fibrosis, cardiac fibrosis, peritoneal fibrosis or kidney fibrosis. The fibrosis may be pulmonary fibrosis. The fibrosis may be idiopathic pulmonary fibrosis. The fibrosis may be liver fibrosis. The fibrosis may be skin fibrosis. The fibrosis may be cardiac fibrosis. The fibrosis may be kidney fibrosis. The fibrosis may be peritoneal fibrosis.

The $\alpha v\beta 1$-inhibitor may be an $\alpha v\beta 1$-inhibitor antibody. The $\alpha v\beta 1$-inhibitor antibody may be a humanized antibody. The $\alpha v\beta 1$-inhibitor antibody may be a recombinant immunoglobulin. When an $\alpha v\beta 1$-inhibitor antibody is a recombinant immunoglobulin, it may be formed using phage display.

The $\alpha v\beta 1$-inhibitor may be an $\alpha v\beta 1$-inhibitor RGD peptide. The $\alpha v\beta 1$-inhibitor RGD peptide is as described herein, including embodiments thereof. The $\alpha v\beta 1$-inhibitor RGD peptide may be Arg-Gly-Asp, Asp-Gly-Arg, cyclo-Gly-Arg-Gly-Asp-Ser-Pro, and KGD peptides include Cys-Asn-Thr-Leu-Lys-Gly-Asp-Cys or Asn-Thr-Leu-Lys-Gly-Asp.

The $\alpha v\beta 1$-inhibitor may be an $\alpha v\beta 1$-inhibitor compound. The $\alpha v\beta 1$-inhibitor compound may have a formula described herein, including embodiments thereof. The $\alpha v\beta 1$-inhibitor compound may have formula: (X), including embodiments thereof.

IV. Methods of Detecting $\alpha V\beta 1$ Expression

In an aspect is provided a method of detecting $\alpha v\beta 1$ expression in a cell, the method including; (i) contacting a cell with a compound described herein; (ii) allowing the compound to bind to the cell; and (iii) detecting the compound, thereby detecting $\alpha v\beta 1$ expression in a cell.

Further provided herein are methods of detecting $\alpha v\beta 1$ expression in a cell. In one aspect is a method of detecting $\alpha v\beta 1$ expression in a cell by contacting a cell with an $\alpha v\beta 1$-specific moiety and allowing the $\alpha v\beta 1$-specific moiety to bind to the cell. The $\alpha v\beta 1$-specific moiety is detected, thereby detecting $\alpha v\beta 1$ expression in a cell. The detection may be performed using techniques known in the art (e.g. fluorescence detection or radiolabel detection). The cell may form part of an organism (e.g. a human). The cell may be a skin myofibroblast, a lung myofibroblast, or a hepatic myofibroblast. The cell may be a skin myofibroblast. The cell may be a lung myofibroblast. The cell may be a hepatic myofibroblast.

The detection may be performed by detecting a detectable moiety bound to the αvβ1-specific ligand. The detectable moiety may be covalently attached to the αvβ1-specific moiety. The detectable moiety may be non-covalently attached αvβ1-specific moiety. The αvβ1-specific moiety may be an αvβ1-specific antibody. The αvβ1-specific moiety may be an αvβ1-specific RGD peptide. The αvβ1-specific moiety may be an αvβ1-specific compound, where the compound is a compound described herein. The αvβ1-specific compound may be a compound having a formula described herein, including embodiments thereof. The αvβ1-specific compound may be a compound having the formula: (X), including embodiments thereof.

V. Methods of Inhibition

Further provided here are methods for determining inhibition of αvβ1 integrin binding. In one aspect is a method for determining whether a test compound inhibits αvβ1 integrin binding by combining an αvβ1 integrin-expressing cell and a test compound in a reaction vessel. The reaction vessel is covalently bonded to an αvβ1 ligand (e.g. a composition that binds to αvβ1). The method includes determining whether the αvβ1 integrin-expressing cell binds to the αvβ1 ligand in the presence of the test compound, thereby determining whether the test compound inhibits αvβ1 integrin binding. The reaction vessel may be a cell culture dish. The αvβ1 ligand may be fibronectin. The αvβ1 ligand may be latency associated peptide of TGFβ.

In an aspect is provided a method of inhibiting TGFβ activation, the method including: (i) contacting a cell expressing αvβ1 integrin with a compound described herein; (ii) allowing the compound to bind to αvβ1 in the presence of TGFβ; (iii) comparing a level of activated TGFβ to a control to thereby identify a lower level of TGFβ activation and inhibition of TGFβ activation. In embodiments, the cell is a skin myofibroblast, a lung myofibroblast, renal myofibroblast, or a hepatic myofibroblast.

In another aspect is a method of inhibiting TGFβ activation by contacting a cell expressing αvβ1 integrin with an αvβ1-inhibitor and allowing the αvβ1-inhibitor to bind to αvβ1 in the presence of latent TGFβ. The method includes comparing a level of activated TGFβ to a control to thereby identify a level of TGFβ activation and identify inhibition of TGFβ activation. The control may be, for example, inactivated TGFβ, a level prior to administration of the αvβ1 inhibitor-compound, or a known level of TGFβ activation. The αvβ1-inhibitor may be an αvβ1 inhibitor-compound where the αvβ1 inhibitor-compound is as described herein (e.g. formula described herein, including embodiments and prodrugs thereof). The αvβ1-inhibitor compound may be a compound having the formula: (X), including embodiments and prodrugs thereof. The TGFβ may be latent TGFβ. The cell may form part of an organism (e.g. a human). The cell may be a skin myofibroblast, a lung myofibroblast, renal myofibroblast, or a hepatic myofibroblast. The cell may be a skin myofibroblast. The cell may be a lung myofibroblast. The cell may be a hepatic myofibroblast. The cell may be a renal myofibroblast. The method may further include adding an exogenous source of TGFβ and determining the activation of the exogenous TGFβ.

The binding of the αvβ1 inhibitor may be determined using the methods of detection described herein. The level of TGFβ activation may be determined using the methods of detection described herein.

VI. Embodiments

Embodiment P1

A compound having the formula:

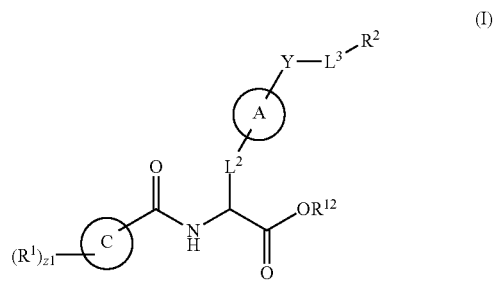

(I)

wherein, Ring A is substituted or unsubstituted cycloalkyl, substituted or unsubstituted heterocycloalkyl, substituted or unsubstituted aryl, or substituted or unsubstituted heteroaryl; Ring C is aryl or heteroaryl; $L^2$ is independently a bond or substituted, unsubstituted $C_1$-$C_{10}$ alkylene, or unsubstituted 2 to 5 membered heteroalkylene; $L^3$ is a bond, substituted or unsubstituted $C_1$-$C_{10}$ alkylene, substituted or unsubstituted 2 to 10 membered heteroalkylene, substituted or unsubstituted cycloalkylene, substituted or unsubstituted heterocycloalkylene, substituted or unsubstituted arylene, substituted or unsubstituted heteroarylene, or substituted or unsubstituted alkylarylene; Y is a bond, —C(O)N($R^4$)—, —O—, —C(O)O—, —S—, —N($SO_2$—$R^4$)—, —N(C(O)$R^4$)—, —N(C(O)O$R^4$)—, —($NR^4$)C(O)—, —N($R^4$)—, —($NR^4$)C(O)NH—, —NHC(O)N($R^4$)—, —($NR^4$)C(O)O—, —C(O)—, —($NR^4$)$CH_2$—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene; $R^1$ is independently hydrogen, halogen, —$N_3$, —$CX_3$, —$CHX_2$, —$CH_2X$, —CN, —CHO, —OH, —$NH_2$, —COOH, —$CONH_2$, —$NO_2$, —SH, —$SO_2$, —$SO_2CH_3$, —$SO_3H$, —$OSO_3H$, —$SO_2NH_2$, —$SO_2$Ph, —$NHNH_2$, —$ONH_2$, —NHC(O)$NHNH_2$, —$OPO_3H$, —$PO_3H_2$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, or a detectable moiety; $R^2$ is —$NR^{3A}R^{3B}$, —C(NH)$NH_2$, —C(NH)$R^{3B}$, —C($NR^{3A}$)$NH_2$, —C($NR^{3A}$)$R^{3B}$, —C(NCN)$NH_2$, —$NH_2$, —C(NH)$NHR^{3B}$, —C($NR^{3A}$)$NHR^{3B}$, —C(NCN)$NHR^{3B}$, substituted or unsubstituted cycloalkyl, substituted or unsubstituted heterocycloalkyl, substituted or unsubstituted aryl, substituted or unsubstituted heteroaryl, substituted or unsubstituted fused ring cycloalkyl, substituted or unsubstituted fused ring heterocycloalkyl, substituted or unsubstituted fused ring aryl, or substituted or unsubstituted fused ring heteroaryl; $R^{3A}$ and $R^{3B}$ are independently hydrogen, —C(NH)$NH_2$, —C(NH)$R^{3D}$, —C($NR^{3C}$)$NH_2$, —C($NR^{3C}$)$R^{3D}$, —C(NCN)$NH_2$, —$NH_2$, —C(NH)$NHR^{3D}$, —C($NR^{3C}$)$NHR^{3D}$, —C(NCN)$NHR^{3D}$, substituted or unsubstituted cycloalkyl, substituted or unsubstituted heterocycloalkyl, substituted or unsubstituted aryl, substituted or unsubstituted heteroaryl, or $R^{3A}$ and $R^{3B}$ are optionally joined to form a substituted or unsubstituted heterocycloalkyl or substituted or unsubstituted heteroaryl; $R^{3C}$ is independently hydrogen, halogen, —$N_3$, —$CX^{1C}_3$, —$CHX^{1C}_2$, —$CH_2X^{1C}$, —CN, —CHO, —OH, —$NH_2$, —COOH, —$CONH_2$, —$NO_2$, —SH, —$SO_2$, —$SO_2CH_3$—$SO_3H$, —$SO_4H$, —$SO_2NH_2$, —$NHNH_2$, —$ONH_2$, —$NHC(O)NHNH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{3D}$ is independently hydrogen, halogen, —$N_3$, —$CX^{1D}_3$, —$CHX^{1D}_2$, —$CH_2X^{1D}$, —CN, —CHO, —OH, —$NH_2$, —COOH, —$CONH_2$, —$NO_2$, —SH, —$SO_2$, —$SO_2CH_3$—$SO_3H$, —$SO_4H$, —$SO_2NH_2$, —$NHNH_2$, —$ONH_2$, —$NHC(O)NHNH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^4$ is independently hydrogen or unsubstituted $C_1$-$C_5$ alkyl;

$R^{12}$ is hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, or a prodrug moiety; each X, $X^{1C}$ and $X^{1D}$ is independently —F, —Cl, —Br, or —I; and z1 is an integer from 0 to 5.

Embodiment P2

The compound of Embodiment P1, wherein $R^{12}$ is hydrogen.

Embodiment P3

The compound of Embodiment P1, wherein $R^{12}$ is a prodrug moiety.

Embodiment P4

The compound of one of Embodiments P1 to P3, wherein Ring C is phenyl and z1 is an integer between 0 to 3.

Embodiment P5

The compound of one of Embodiments P1 to P3, wherein Ring C is 5 to 6 membered heteroaryl and z1 is an integer between 0 to 3.

Embodiment P6

The compound of one of Embodiments P1 to P3, wherein Ring C is pyridyl and z1 is an integer between 0 to 3.

Embodiment P7

The compound of one of Embodiments P1 to P6, wherein Ring A is unsubstituted phenyl.

Embodiment P8

The compound of one of Embodiments P1 to P6, wherein Ring A is unsubstituted 5 to 6 membered heteroaryl.

Embodiment P9

The compound of one of Embodiments P1 to P6, wherein Ring A is substituted or unsubstituted 5 to 6 membered heterocycloalkyl.

Embodiment P10

The compound of one of Embodiments P1 to P6, wherein Ring A is

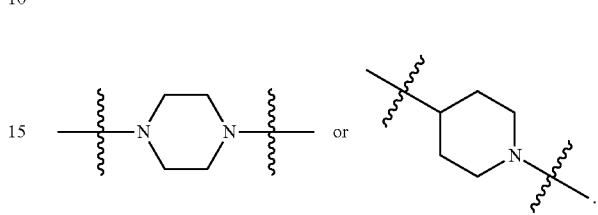

Embodiment P11

The compound of one of Embodiments P1 to 10, wherein $R^2$ is —$NR^{3A}R^{3B}$.

Embodiment P12

The compound of one of Embodiments P1 to P10, wherein $R^2$ is a substituted or unsubstituted heteroaryl.

Embodiment P13

The compound of one of Embodiments P1 to P10, wherein $R^2$ is a substituted heteroaryl.

Embodiment P14

The compound of one of Embodiments P1 to P10, wherein $R^2$ is a substituted pyridyl, substituted imidazolyl, substituted oxazolyl, substituted thiazolyl, substituted oxadiazolyl, substituted triazolyl or substituted thiadiazolyl.

Embodiment P15

The compound of one of Embodiments P1 to P10, wherein $R^2$ is a substituted heterocycloalkyl.

Embodiment P16

The compound of one of Embodiments P1 to P10, wherein $R^2$ is

Embodiment P17

The compound of one of Embodiments P1 to P10, wherein $R^2$ is

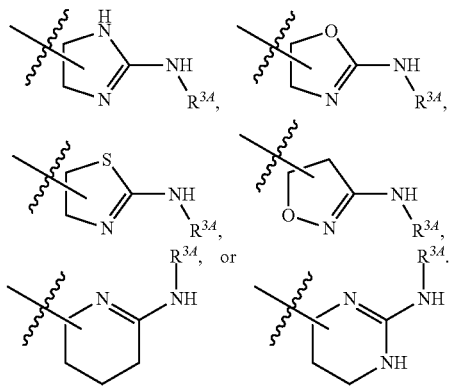

Embodiment P18

The compound of one of Embodiments P1 to P10, wherein $R^2$ is an unsubstituted fused ring heteroaryl.

Embodiment P19

The compound of one of Embodiments P1 to P10, wherein $R^2$ is

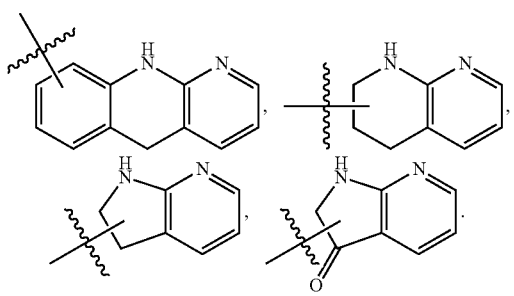

Embodiment P20

The compound of one of Embodiments P1 to P10, wherein $R^2$ is

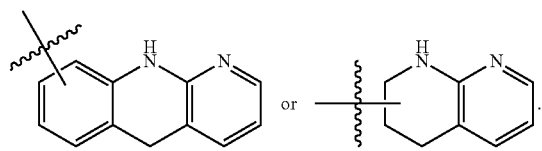

Embodiment P21

The compound of one of Embodiments P1 to P10, wherein $R^2$ is —C(NH)NH$_2$, —C(NH)R$^{3B}$, —C(NR$^{3A}$)NH$_2$, —C(NR$^{3A}$)R$^{3B}$, —C(NCN)NH$_2$, —NH$_2$, —C(NH)NHR$^{3B}$, —C(NR$^{3A}$)NHR$^{3B}$, or —C(NCN)NHR$^{3B}$.

Embodiment P22

The compound of one of Embodiments P1 to P10, wherein $R^2$ is —C(NH)NH$_2$.

Embodiment P23

The compound of one of Embodiments P1 to P22, wherein $L^2$ is unsubstituted $C_1$-$C_5$ alkylene or unsubstituted 2 to 5 membered heteroalkylene.

Embodiment P24

The compound of one of Embodiments P1 to P22, wherein $L^2$ is unsubstituted $C_1$-$C_5$ alkylene.

Embodiment P25

The compound of one of Embodiments P1 to P22, wherein $L^2$ is —CH$_2$CH$_2$NH—.

Embodiment P26

The compound of one of Embodiments P1 to P22, wherein $L^2$ is unsubstituted methylene.

Embodiment P27

The compound of one of Embodiments P1 to P22, wherein $L^2$ is a bond.

Embodiment P28

The compound of any one of Embodiments P1 to P27, wherein $L^3$ is substituted or unsubstituted $C_1$-$C_8$ alkylene, substituted or unsubstituted 2 to 8 membered heteroalkylene, unsubstituted phenylene, unsubstituted 5 to 6 membered heteroarylene, or unsubstituted alkylarylene.

Embodiment P29

The compound of any one of Embodiments P1 to P27, wherein $L^3$ is substituted or unsubstituted $C_1$-$C_7$ alkylene.

Embodiment P30

The compound of any one of Embodiments P1 to P27, wherein $L^3$ is $R^6$-substituted $C_1$-$C_3$ alkylene; $R^6$ is —NHC(O)R$^{6A}$; R$^{6A}$ is —C(NCN)R$^{6C}$, —C(NH)R$^{6C}$, R$^{6C}$-substituted or unsubstituted alkyl, or R$^{6C}$-substituted or unsubstituted heteroalkyl; R$^{6C}$ is hydrogen, halogen, oxo, —N$_3$, —CF$_3$, —CCl$_3$, —CBr$_3$, —CI$_3$, —CN, —COR$^{6D}$, —OR$^{6D}$, —NR$^{6D}$R$^{6E}$, —COOR$^{6E}$, —CONR$^{6D}$R$^{6E}$, —NHC(O)R$^{6D}$, —NO$_2$, —SR$^{6D}$, —SO$_{n6}$R$^{6D}$, —NHNR$^{6D}$R$^{6E}$, —ONR$^{6D}$R$^{6E}$, —NHC(O)NHNR$^{6D}$R$^{6E}$, —C(NCN)R$^{6D}$, —C(NH)R$^{6D}$, R$^{6F}$-substituted or unsubstituted alkyl, R$^{6F}$-substituted or unsubstituted heteroalkyl, R$^{6F}$-substituted or unsubstituted cycloalkyl, R$^{6F}$-substituted or unsubstituted heterocycloalkyl, R$^{6F}$-substituted or unsubstituted aryl, or R$^{6F}$ substituted or unsubstituted heteroaryl; n6 is 2, 3, or 4; and R$^{6D}$, R$^{6E}$ and R$^{6F}$ are independently hydrogen, halogen, oxo, —N$_3$, —CF$_3$, —CCl$_3$, —CBr$_3$, —CI$_3$, —CN, —CHO, —OH, —NH$_2$, —COOH, —CONH$_2$, —NO$_2$, —SH, —SO$_2$, —SO$_2$Cl, —SO$_2$CH$_3$—SO$_3$H, —SO$_4$H, —SO$_2$NH$_2$, —NHNH$_2$, —ONH$_2$, —NHC(O)NHNH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, or a detectable moiety.

Embodiment P31

The compound of Embodiment P30, wherein $R^{6C}$ or $R^{6D}$ is a detectable moiety.

Embodiment P32

The compound of any one of Embodiments P1 to P31, wherein Y is a bond, —O—, —(NR$^4$)C(O)—, —(NR$^4$)C(O)NH—, —NHC(O)N(R$^4$)—, —(NR$^4$)C(O)O—, —C(O)—, —(NR$^4$)CH$_2$—, substituted or unsubstituted 3 to 6 membered heterocycloalkylene, or substituted or unsubstituted 5 to 6 membered heteroarylene.

Embodiment P33

The compound of any one of Embodiments P1 to P31, wherein Y is —NHC(O)—.

Embodiment P34

The compound of any one of Embodiments P1 to P31, wherein Y is a bond.

Embodiment P35

The compound of any one of Embodiments P1 to P31, wherein Y is —(NH)C(O)NH—.

Embodiment P36

The compound of any one of Embodiments P1 to P31, wherein Y is —(NH)C(O)O—.

Embodiment P37

The compound of any one of Embodiments P1 to P31, wherein Y is substituted or unsubstituted 5 to 6 membered heterocycloalkylene Embodiment P38

The compound of any one of Embodiments P1 to P31, wherein Y is unsubstituted 5 to 6 membered heteroarylene.

Embodiment P39

The compound of any one of Embodiments P1 to P31, wherein Y is

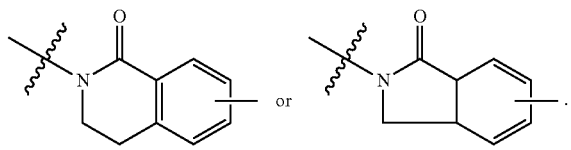

Embodiment P40

The compound of any one of Embodiments P1 to P31, wherein Y is

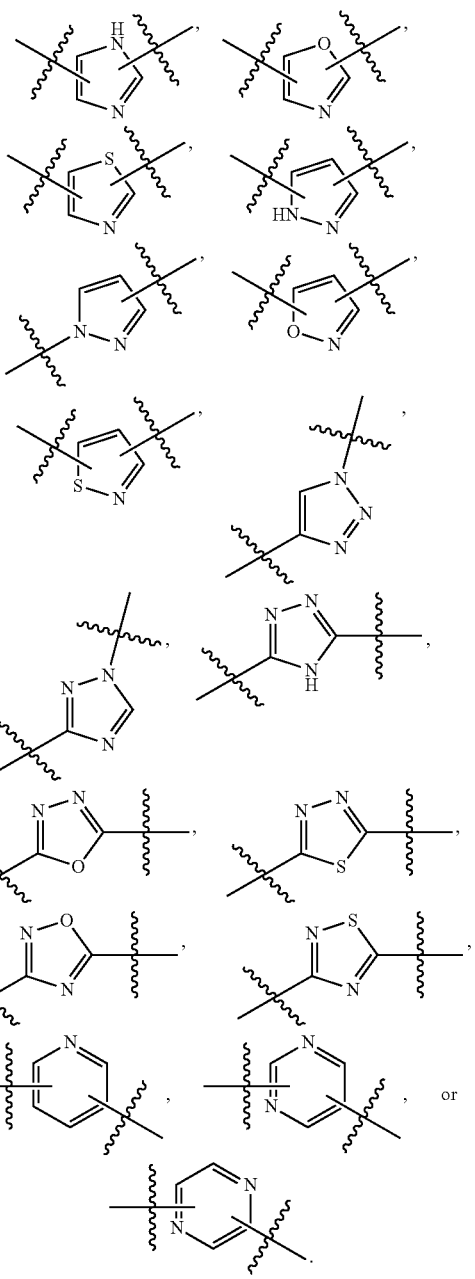

Embodiment P41

The compound of any one of Embodiments P1 to P40, wherein $R^1$ is independently hydrogen, halogen, —OMe, —SMe, —SO$_2$Me, —SO$_2$Ph, —COOH, substituted or unsubstituted C$_1$-C$_5$ alkyl, substituted or unsubstituted 2 to 5 membered heteroalkyl, or substituted or unsubstituted C$_6$-C$_{10}$ aryl.

Embodiment P42

The compound of any one of Embodiments P1 to P40, wherein $R^1$ is independently hydrogen, halogen, substituted or unsubstituted C$_1$-C$_5$ alkyl, substituted or unsubstituted 2 to 5 membered heteroalkyl, or substituted or unsubstituted C$_6$-C$_{10}$ aryl.

Embodiment P43

The compound of any one of Embodiments P1 to P42, wherein $R^{3A}$ and $R^{3B}$ are independently hydrogen, —C(NH)NH$_2$, —C(NCN)NH$_2$, substituted or unsubstituted heterocycloalkyl, or substituted or unsubstituted heteroaryl.

Embodiment P44

The compound of any one of Embodiments P1 to P42, wherein $R^{3A}$ and $R^{3B}$ are joined to form a substituted or unsubstituted 5 or 6 membered heterocycloalkyl or substituted or unsubstituted 5 or 6 membered heteroaryl.

Embodiment P45

The compound of any one of Embodiments P1 to P42, wherein $R^{3A}$ and $R^{3B}$ are independently hydrogen, —C(NH)NH$_2$, —C(NCN)NH$_2$, or substituted or unsubstituted 3 to 6 membered heterocycloalkyl, or substituted or unsubstituted 5 to 6 membered heteroaryl.

Embodiment P46

The compound of any one of Embodiments P1 to P45 having the formula:

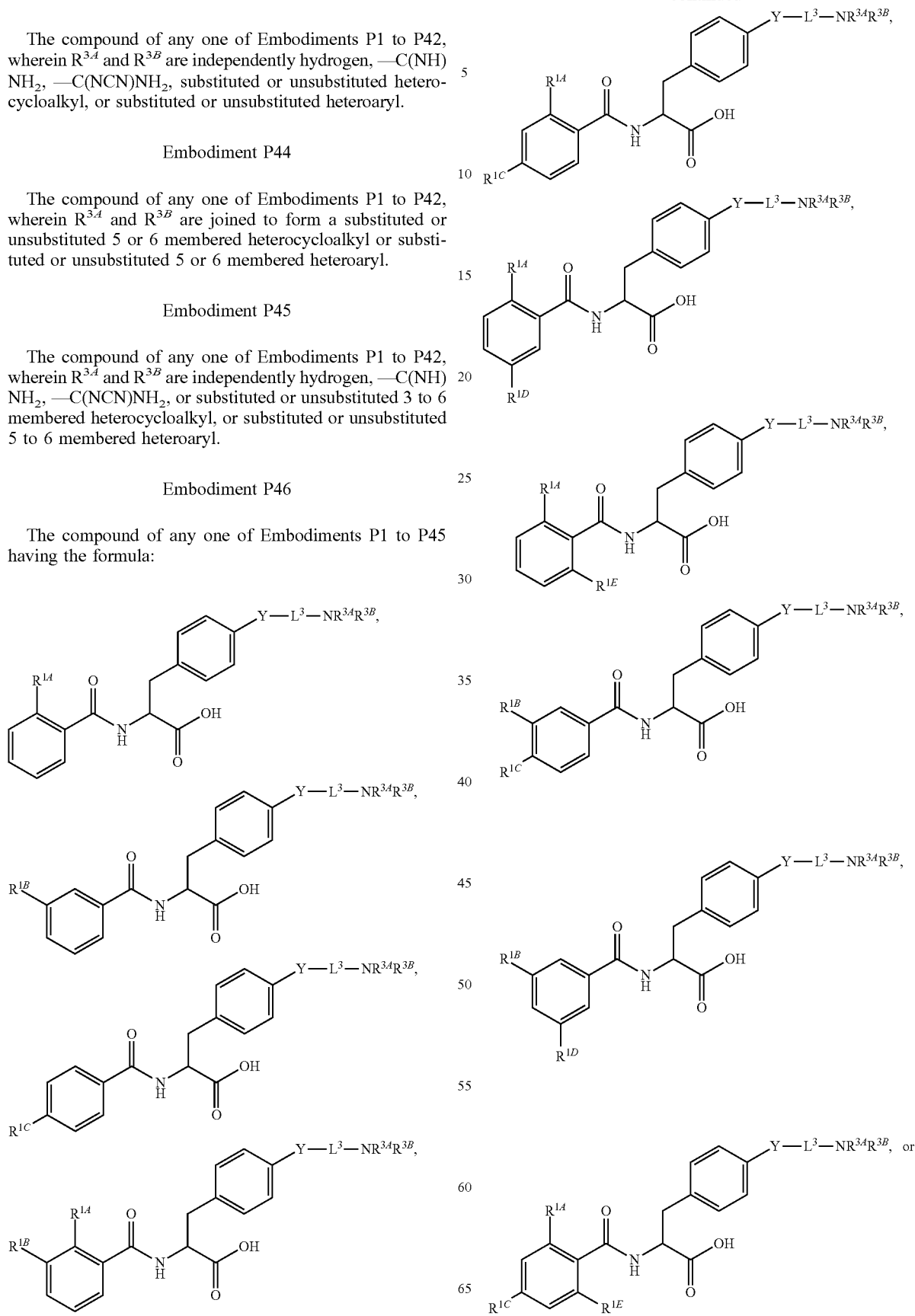

-continued

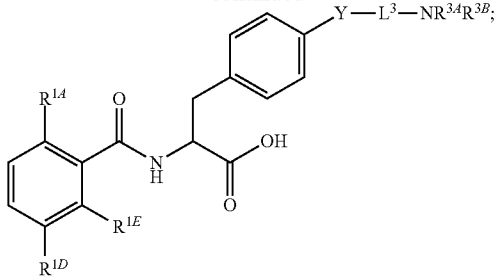

wherein $R^{1A}$, $R^{1B}$, $R^{1C}$, $R^{1D}$, and $R^{1E}$ are independently hydrogen, halogen, —$N_3$, —$CF_3$, —$CCl_3$, —$CBr_3$, —$CI_3$, —CN, —CHO, —OH, —$NH_2$, —COOH, —$CONH_2$, —$NO_2$, —SH, —$SO_2$, —$SO_2Cl$, —$SO_2CH_3$—$SO_3H$, —$OSO_3H$, —$SO_2NH_2$, —$NHNH_2$, —$ONH_2$, —NHC(O)$NHNH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, or a detectable moiety.

Embodiment P47

The compound of Embodiment P46, wherein $R^{1A}$, $R^{1B}$, $R^{1C}$, $R^{1D}$, and $R^{1E}$ are independently hydrogen, halogen, unsubstituted $C_1$-$C_3$ alkyl, unsubstituted 2 to 3 membered heteroalkyl, or unsubstituted phenyl.

Embodiment P48

The compound of Embodiment P46, wherein two substituents selected from $R^{1A}$, $R^{1B}$, $R^{1C}$, $R^{1D}$, and $R^{1E}$, are joined to form a substituted or unsubstituted cycloalkyl, substituted or unsubstituted heterocycloalkyl, substituted or unsubstituted aryl, substituted or unsubstituted heteroaryl.

Embodiment P49

The compound of Embodiment P46, wherein two substituents selected from $R^{1A}$, $R^{1B}$, $R^{1C}$, $R^{1D}$, and $R^{1E}$, connected to adjacent ring atoms, are joined to form a substituted or unsubstituted cycloalkyl, substituted or unsubstituted heterocycloalkyl, substituted or unsubstituted aryl, substituted or unsubstituted heteroaryl.

Embodiment P50

The compound of any one of Embodiments P46 to P49 having the formula:

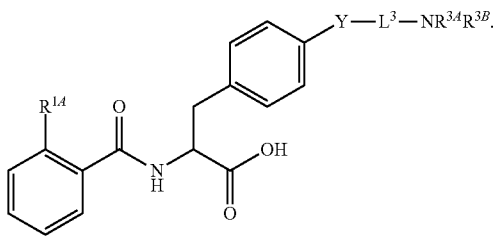

Embodiment P51

The compound of any one of Embodiments P46 to P49 having the formula:

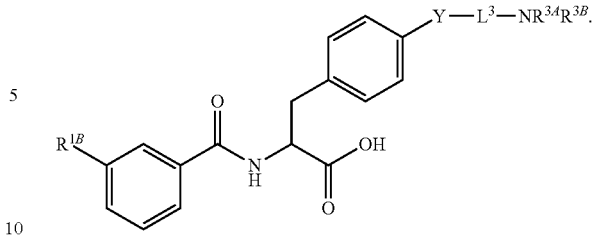

Embodiment P52

The compound of any one of Embodiments P46 to P49 having the formula:

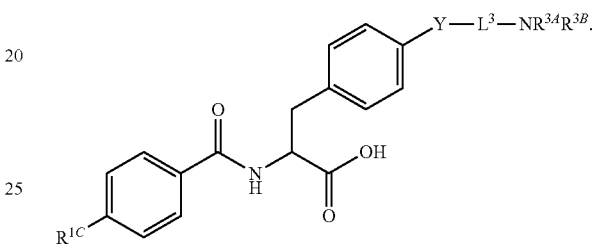

Embodiment P53

The compound of any one of Embodiments P46 to P49 having the formula:

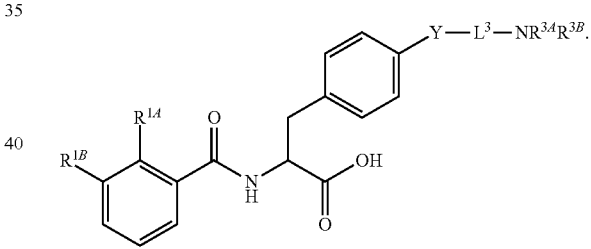

Embodiment P54

The compound of any one of Embodiments P46 to P49 having the formula:

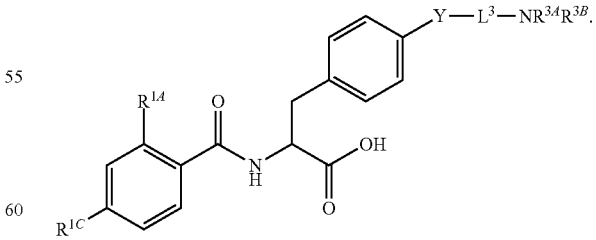

Embodiment P55

The compound of any one of Embodiments P46 to P49 having the formula:

205

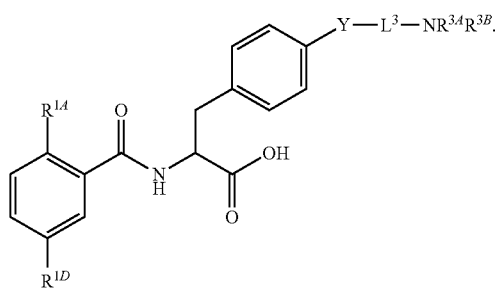

Embodiment P56

The compound of any one of Embodiments P46 to P49 having the formula:

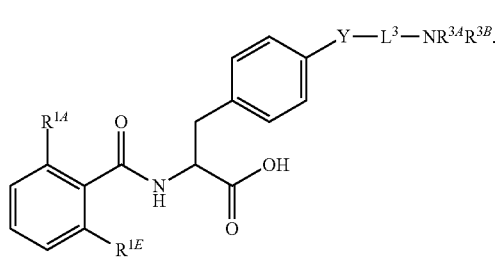

Embodiment P57

The compound of any one of Embodiments P46 to P49 having the formula:

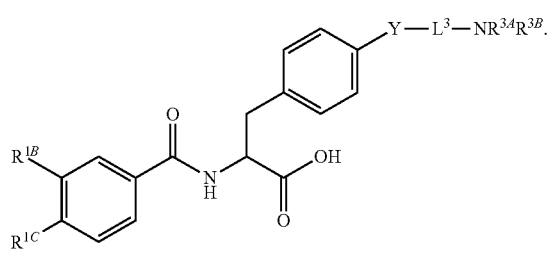

Embodiment P58

The compound of any one of Embodiments P46 to P49 having the formula:

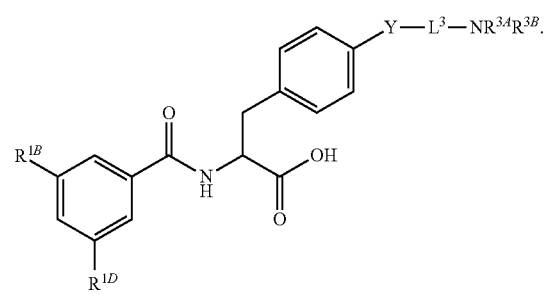

206

Embodiment P59

The compound of any one of Embodiments P46 to P49 having the formula:

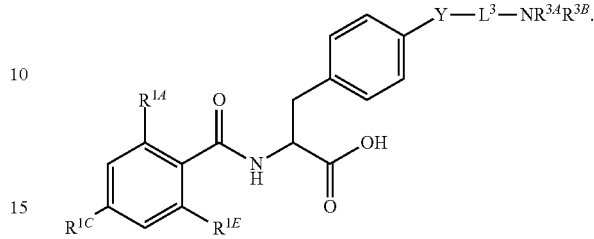

Embodiment P60

The compound of any one of Embodiments P46 to P49 having the formula:

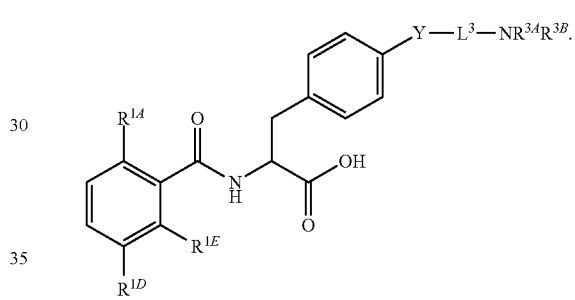

Embodiment P61

The compound of any one of Embodiments P4 to P45 having the formula:

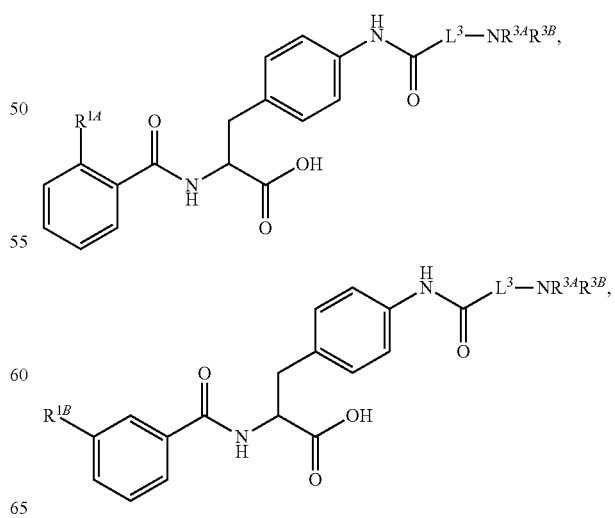

-continued

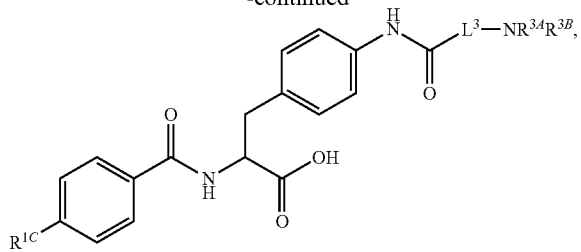

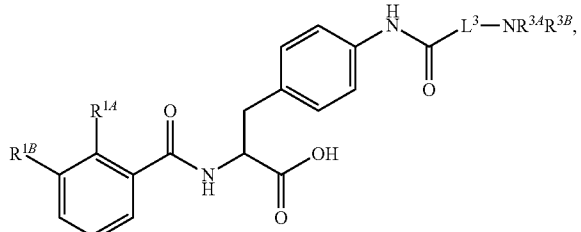

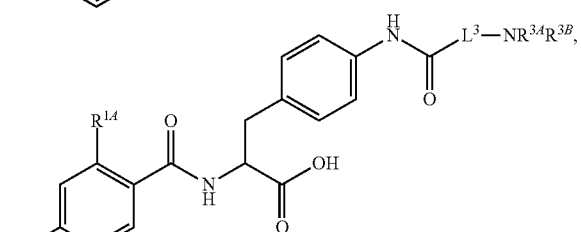

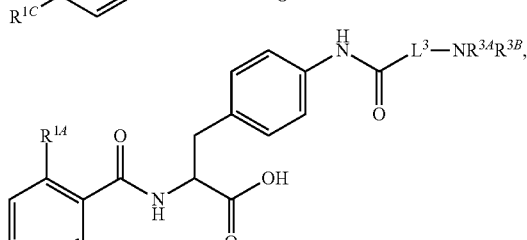

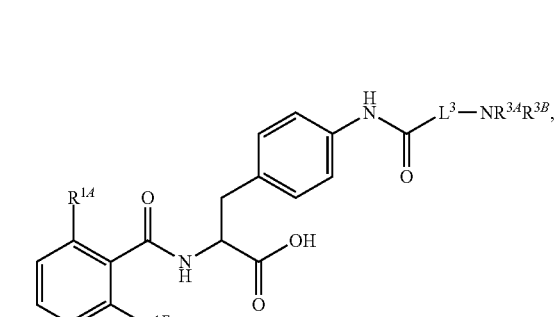

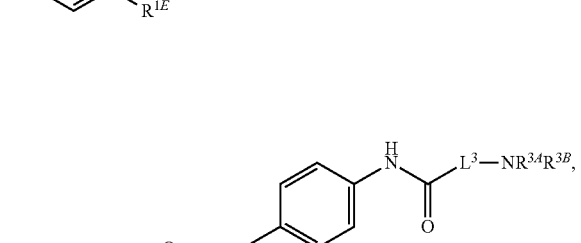

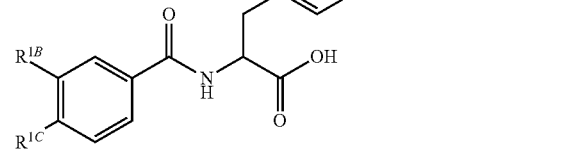

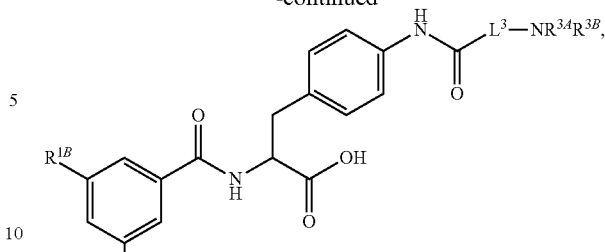

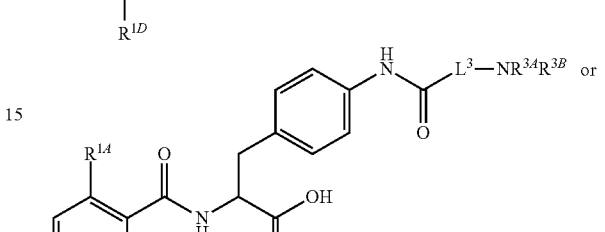

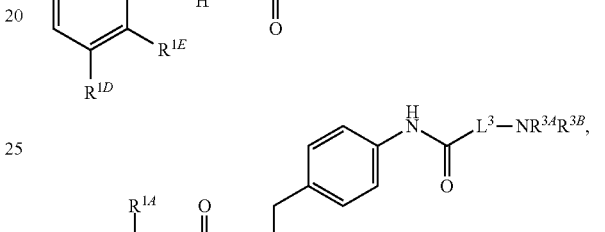

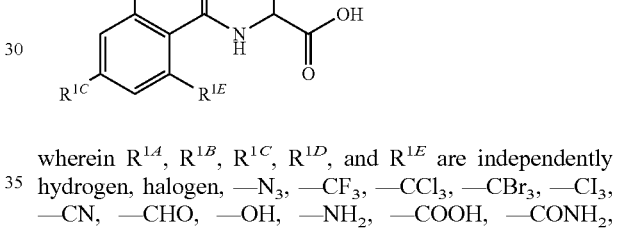

wherein $R^{1A}$, $R^{1B}$, $R^{1C}$, $R^{1D}$, and $R^{1E}$ are independently hydrogen, halogen, —N$_3$, —CF$_3$, —CCl$_3$, —CBr$_3$, —CI$_3$, —CN, —CHO, —OH, —NH$_2$, —COOH, —CONH$_2$, —NO$_2$, —SH, —SO$_2$, —SO$_2$CH$_3$—SO$_3$H, —OSO$_3$H, —SO$_2$NH$_2$, —NHNH$_2$, —ONH$_2$, —NHC(O)NHNH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, or a detectable moiety.

Embodiment P62

The compound of Embodiment P61, wherein $R^{1A}$, $R^{1B}$, $R^{1C}$, $R^{1D}$, and $R^{1E}$ are independently hydrogen, halogen, unsubstituted C$_1$-C$_3$ alkyl, unsubstituted 2 to 3 membered heteroalkyl, or unsubstituted phenyl.

Embodiment P63

The compound of Embodiment P61, wherein two substituents selected from $R^{1A}$, $R^{1B}$, $R^{1C}$, $R^{1D}$, and $R^{1E}$, are joined to form a substituted or unsubstituted cycloalkyl, substituted or unsubstituted heterocycloalkyl, substituted or unsubstituted aryl, substituted or unsubstituted heteroaryl.

Embodiment P64

The compound of Embodiment P61, wherein two substituents selected from $R^{1A}$, $R^{1B}$, $R^{1C}$, $R^{1D}$, and $R^{1E}$, connected to adjacent ring atoms, are joined to form a substituted or unsubstituted cycloalkyl, substituted or unsubstituted heterocycloalkyl, substituted or unsubstituted aryl, substituted or unsubstituted heteroaryl.

Embodiment P65

The compound of any one of Embodiments P61 to P64 having the formula:

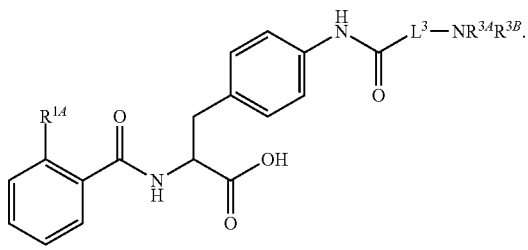

Embodiment P66

The compound of any one of Embodiments P61 to P64 having the formula:

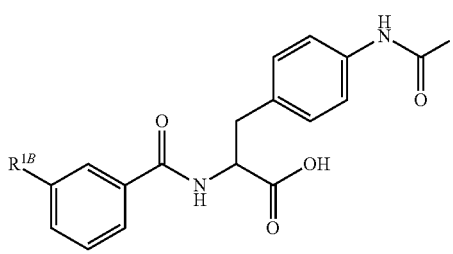

Embodiment P67

The compound of any one of Embodiments P61 to P64 having the formula:

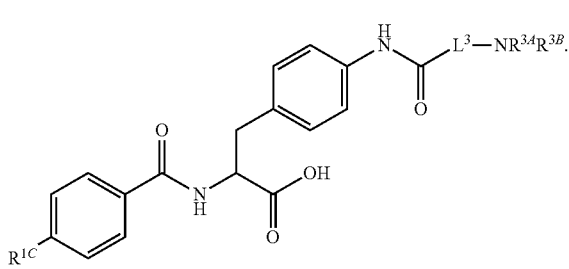

Embodiment P68

The compound of any one of Embodiments P61 to P64 having the formula:

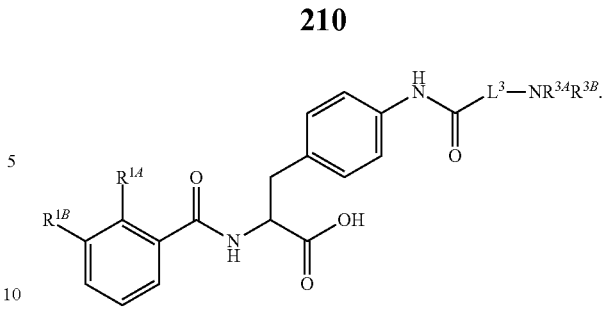

Embodiment P69

The compound of any one of Embodiments P61 to P64 having the formula:

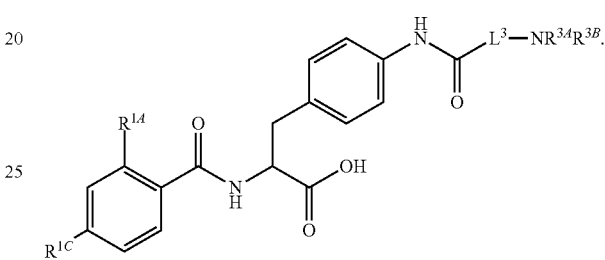

Embodiment P70

The compound of any one of Embodiments P61 to P64 having the formula:

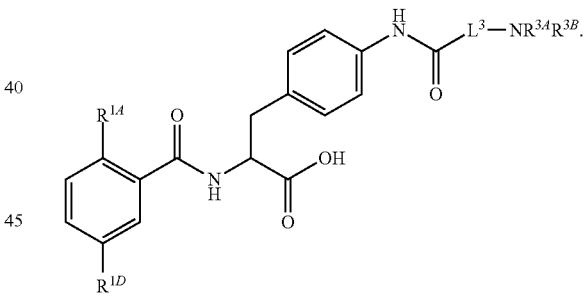

Embodiment P71

The compound of any one of Embodiments P61 to P64 having the formula:

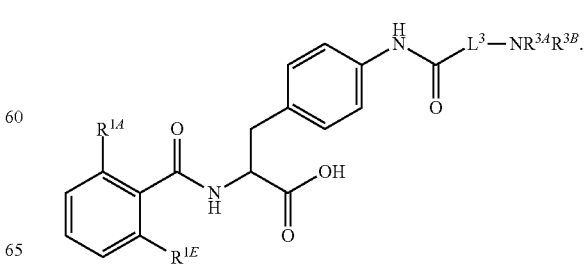

Embodiment P72

The compound of any one of Embodiments P61 to P64 having the formula:

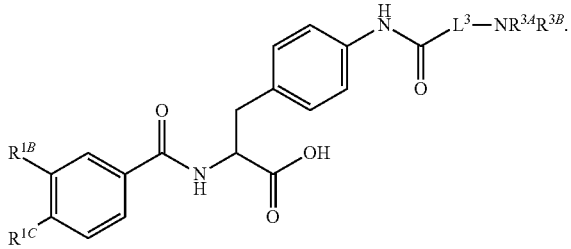

Embodiment P73

The compound of any one of Embodiments P61 to P64 having the formula:

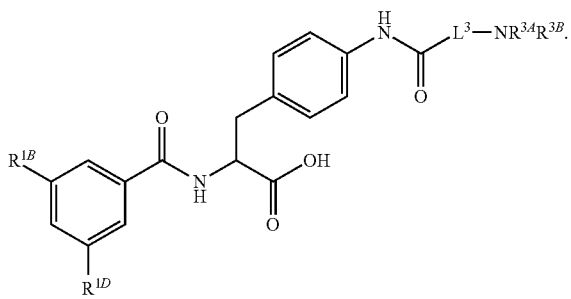

Embodiment P74

The compound of any one of Embodiments P61 to P64 having the formula:

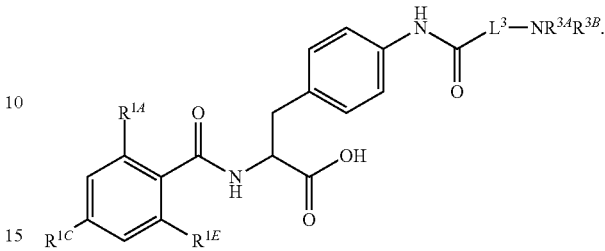

Embodiment P75

The compound of any one of Embodiments P61 to P64 having the formula:

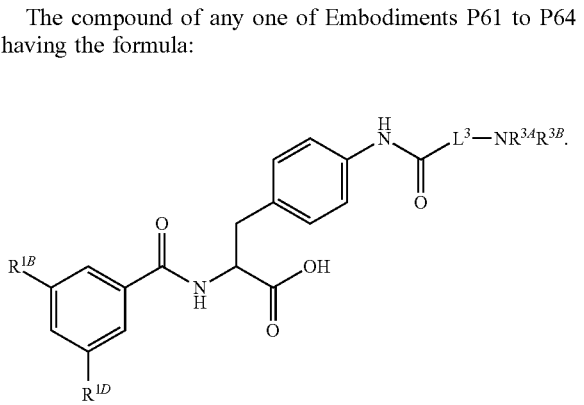

Embodiment P76

The compound of Embodiment P1 having formula:

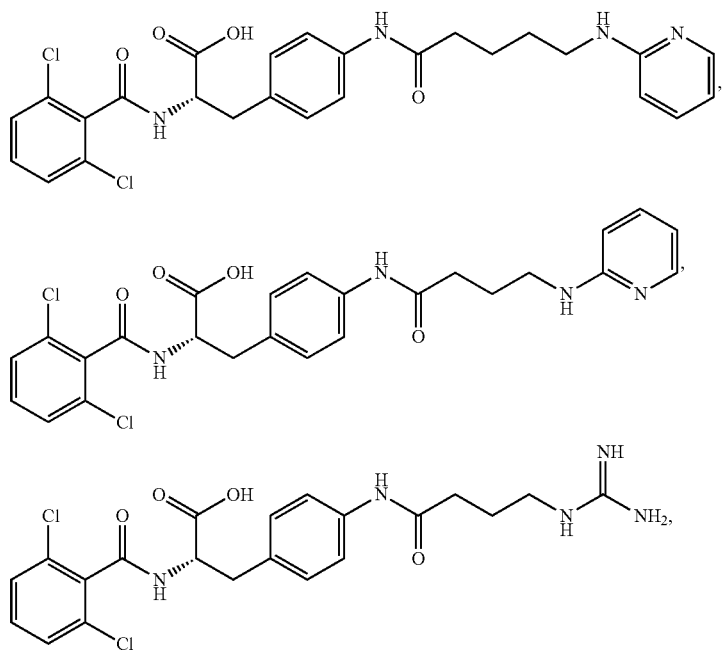

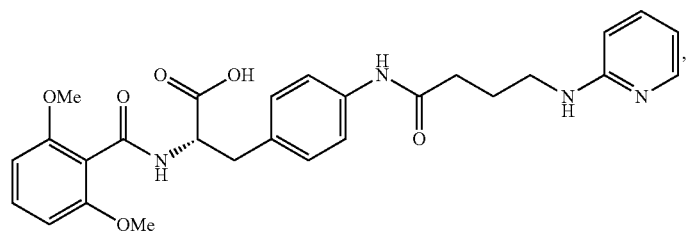
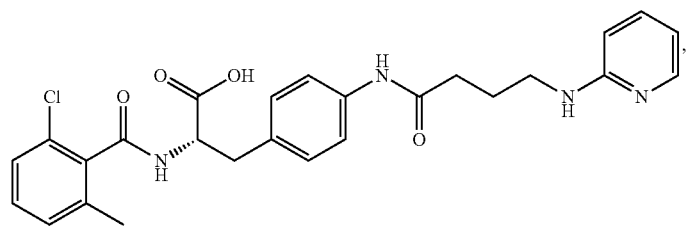
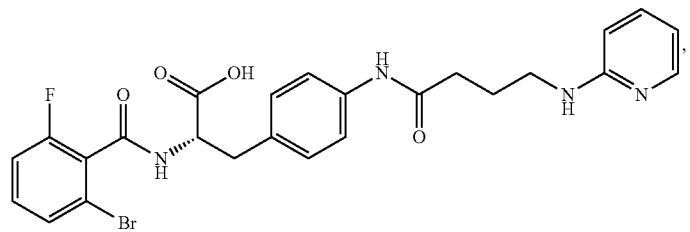
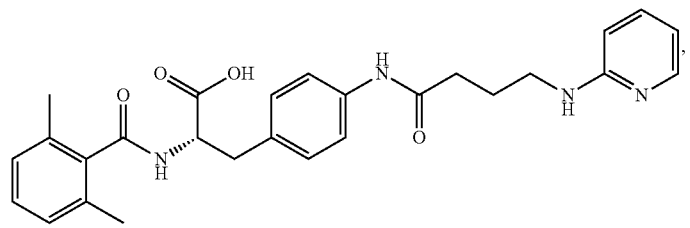
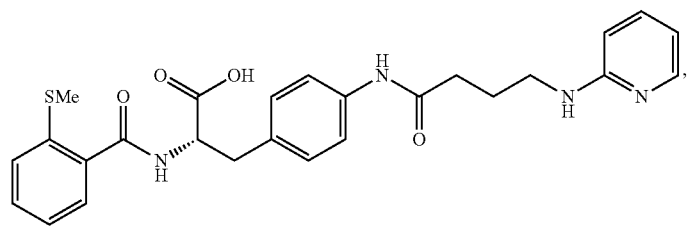
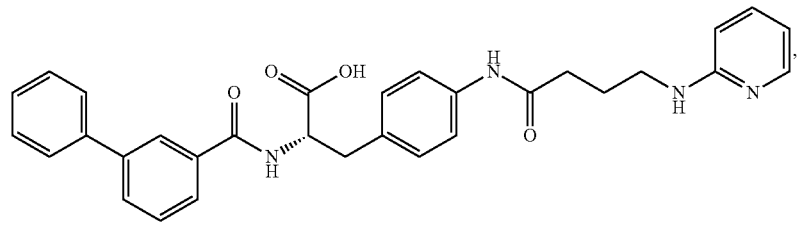
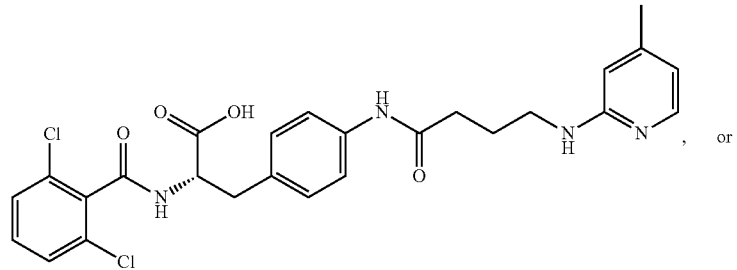, or

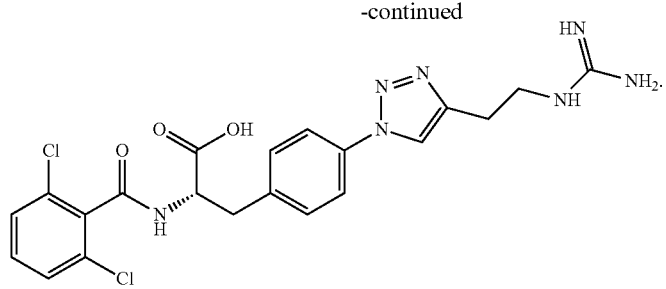

Embodiment P77

A pharmaceutical composition comprising the compound of any one of Embodiments P1 to P76 and a pharmaceutically acceptable excipient.

Embodiment P78

A method of detecting αvβ1 expression in a cell, said method comprising: (i) contacting a cell with a compound of one of Embodiments P1 to P76; (ii) allowing said compound to bind to said cell; and (iii) detecting said compound, thereby detecting αvβ1 expression in a cell.

Embodiment P79

A method of inhibiting TGFβ activation, said method comprising: (i) contacting a cell expressing αvβ1 integrin with a compound of one of Embodiments P1 to P76; (ii) allowing said compound to bind to αvβ1 in the presence of TGFβ; and (iii) comparing a level of activated TGFβ to a control to thereby identify a lower level of TGFβ activation and inhibition of TGFβ activation.

Embodiment P80

The method of Embodiment P79, wherein said cell is a skin myofibroblast, a lung myofibroblast, renal myofibroblast, or a hepatic myofibroblast.

Embodiment P81

A method for treating fibrosis, said method comprising administering to a subject in need thereof an effective amount of a compound having the formula of any one of Embodiments P1 to P76.

Embodiment P82

The method of Embodiment P81, wherein said fibrosis is pulmonary fibrosis, liver fibrosis, skin fibrosis, cardiac fibrosis, or kidney fibrosis.

Embodiment 83

The method of Embodiment P81, wherein said fibrosis is pulmonary fibrosis.

Embodiment P84

The method of Embodiment P81, wherein said fibrosis is liver fibrosis.

Embodiment P85

The method of Embodiment P81, wherein said fibrosis is skin fibrosis.

Embodiment P86

The method of Embodiment P81, wherein said fibrosis is cardiac fibrosis.

Embodiment P87

The method of Embodiment P81, wherein said fibrosis is kidney fibrosis.

VII. Additional Embodiments

Embodiment 1

A compound having the formula:

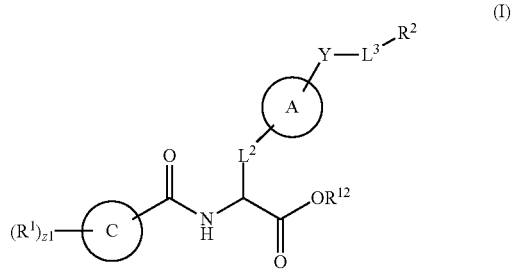

(I)

wherein, Ring A is substituted or unsubstituted cycloalkyl, substituted or unsubstituted heterocycloalkyl, substituted or unsubstituted aryl, or substituted or unsubstituted heteroaryl; Ring C is aryl or heteroaryl; $L^2$ is independently a bond or substituted, unsubstituted $C_1$-$C_{10}$ alkylene, or unsubstituted 2 to 10 (e.g., 2 to 5) membered heteroalkylene; $L^3$ is a bond, substituted or unsubstituted $C_1$-$C_{10}$ alkylene, substituted or unsubstituted 2 to 10 membered heteroalkylene, substituted or unsubstituted cycloalkylene, substituted or unsubstituted heterocycloalkylene, substituted or unsubstituted arylene, substituted or unsubstituted heteroarylene, or substituted or unsubstituted alkylarylene; Y is a bond, —C(O)N($R^4$)—, —O—, —C(O)O—, —S—, —N($SO_2R^4$)—, —N(C(O)$R^4$)—, —N(C(O)O$R^4$)—, —N($R^4$)C(O)—, —N($R^4$)—, —N($R^4$)C(O)NH—, —NHC(O)N($R^4$)—, —N($R^4$)C(O)O—, —C(O)—, —N($R^4$)$CH_2$—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;

$R^1$ is independently hydrogen, halogen, $-N_3$, $-CX_3$, $-CHX_2$, $-CH_2X$, $-CN$, $-CHO$, $-OH$, $-NH_2$, $-COOH$, $-CONH_2$, $-NO_2$, $-SH$, $-SO_2$, $-SO_2CH_3$ $-SO_3H$, $-OSO_3H$, $-SO_2NH_2$, $-SO_2Ph$, $-NHNH_2$, $-ONH_2$, $-NHC(O)NHNH_2$, $-OPO_3H$, $-PO_3H_2$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, or a detectable moiety; $R^2$ is $-NR^{3A}R^{3B}$, $-C(NH)NH_2$, $-C(NH)R^{3B}$, $-C(NR^{3A})NH_2$, $-C(NR^{3A})R^{3B}$, $-C(NCN)NH_2$, $-NH_2$, $-C(NH)NHR^{3B}$, $-C(NR^{3A})NHR^{3B}$, $-C(NCN)NHR^{3B}$, substituted or unsubstituted cycloalkyl, substituted or unsubstituted heterocycloalkyl, substituted or unsubstituted aryl, substituted or unsubstituted heteroaryl, substituted or unsubstituted fused ring cycloalkyl, substituted or unsubstituted fused ring heterocycloalkyl, substituted or unsubstituted fused ring aryl, or substituted or unsubstituted fused ring heteroaryl; $R^{3A}$ and $R^{3B}$ are independently hydrogen, $-C(NH)NH_2$, $-C(NH)R^{3D}$, $-C(NR^{3C})NH_2$, $-C(NR^{3C})R^{3D}$, $-C(NCN)NH_2$, $-NH_2$, $-C(NH)NHR^{3D}$, $-C(NR^{3C})NHR^{3D}$, $-C(NCN)NHR^{3D}$, substituted or unsubstituted cycloalkyl, substituted or unsubstituted heterocycloalkyl, substituted or unsubstituted aryl, substituted or unsubstituted heteroaryl, or $R^{3A}$ and $R^{3B}$ are optionally joined to form a substituted or unsubstituted heterocycloalkyl or substituted or unsubstituted heteroaryl; $R^{3C}$ is hydrogen, halogen, $-N_3$, $-CX^{1C}_3$, $-CHX^{1C}_2$, $-CH_2X^{1C}$, $-CN$, $-CHO$, $-OH$, $-NH_2$, $-COOH$, $-CONH_2$, $-NO_2$, $-SH$, $-SO_2$, $-SO_2CH_3$ $-SO_3H$, $-SO_4H$, $-SO_2NH_2$, $-NHNH_2$, $-ONH_2$, $-NHC(O)NHNH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{3D}$ is hydrogen, halogen, $-N_3$, $-CX^{1D}_3$, $-CHX^{1D}_2$, $-CH_2X^{1D}$, $-CN$, $-CHO$, $-OH$, $-NH_2$, $-COOH$, $-CONH_2$, $-NO_2$, $-SH$, $-SO_2$, $-SO_2CH_3$ $-SO_3H$, $-SO_4H$, $-SO_2NH_2$, $-NHNH_2$, $-ONH_2$, $-NHC(O)NHNH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^4$ is hydrogen or unsubstituted $C_1$-$C_5$ alkyl; $R^{12}$ is hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, or a prodrug moiety; each X, $X^{1C}$ and $X^{1D}$ is independently $-F$, $-Cl$, $-Br$, or $-I$; and z1 is an integer from 0 to 5.

Embodiment 2

The compound of Embodiment 1, wherein $R^{12}$ is hydrogen.

Embodiment 3

The compound of Embodiment 1, wherein $R^{12}$ is a prodrug moiety.

Embodiment 4

The compound of one of Embodiments 1 to 3, wherein Ring C is phenyl and z1 is an integer between 0 to 3.

Embodiment 5

The compound of one of Embodiments 1 to 3, wherein Ring C is 5 to 6 membered heteroaryl and z1 is an integer between 0 to 3.

Embodiment 6

The compound of one of Embodiments 1 to 3, wherein Ring C is pyridyl and z1 is an integer between 0 to 3.

Embodiment 7

The compound of one of Embodiments 1 to 6, wherein Ring A is unsubstituted phenyl.

Embodiment 8

The compound of one of Embodiments 1 to 6, wherein Ring A is unsubstituted 5 to 6 membered heteroaryl.

Embodiment 9

The compound of one of Embodiments 1 to 6, wherein Ring A is substituted or unsubstituted 5 to 6 membered heterocycloalkyl.

Embodiment 10

The compound of one of Embodiments 1 to 6, wherein Ring A is

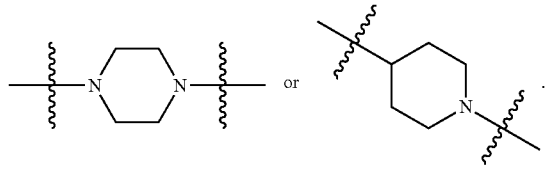 [SMILES: *N1CCN(*)CC1 ; *C1CCN(*)CC1]

Embodiment 11

The compound of one of Embodiments 1 to 10, wherein $R^2$ is $-NR^{3A}R^{3B}$.

Embodiment 12

The compound of one of Embodiments 1 to 12, wherein $R^2$ is a substituted or unsubstituted heteroaryl.

Embodiment 13

The compound of one of Embodiments 1 to 10, wherein R2 is a substituted heteroaryl.

Embodiment 14

The compound of one of Embodiments 1 to 10, wherein $R^2$ is a substituted pyridyl, substituted imidazolyl, substituted oxazolyl, substituted thiazolyl, substituted oxadiazolyl, substituted triazolyl or substituted thiadiazolyl.

Embodiment 15

The compound of one of Embodiments 1 to 10, wherein $R^2$ is a substituted heterocycloalkyl.

Embodiment 16

The compound of one of Embodiments 1 to 10, wherein $R^2$ is

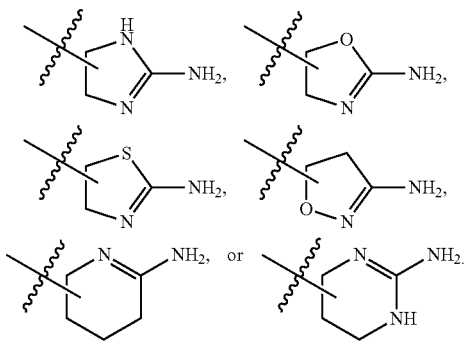

Embodiment 17

The compound of one of Embodiments 1 to 10, wherein $R^2$ is

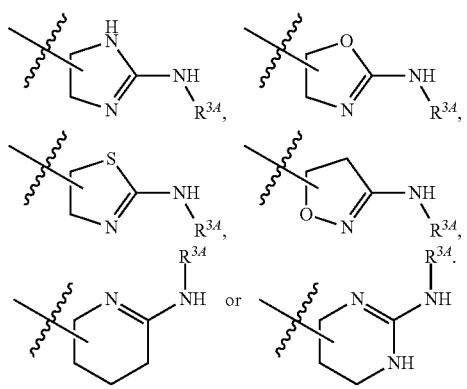

Embodiment 18

The compound of one of Embodiments 1 to 10, wherein $R^2$ is an unsubstituted fused ring heteroaryl.

Embodiment 19

The compound of one of Embodiments 1 to 10, wherein $R^2$ is

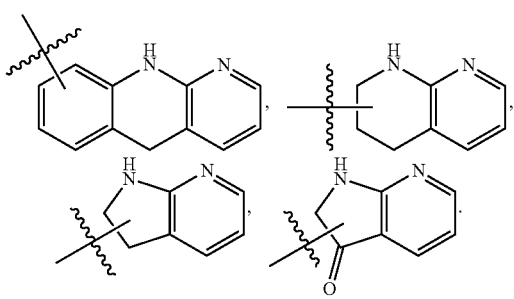

Embodiment 20

The compound of one of Embodiments 1 to 10, wherein $R^2$ is

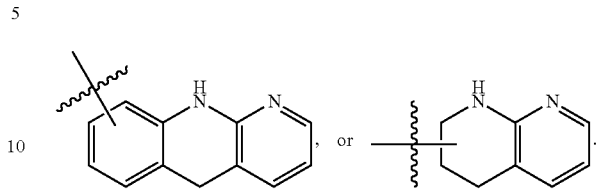

Embodiment 21

The compound of one of Embodiments 1 to 10, wherein $R^2$ is —C(NH)NH$_2$, —C(NH)R$^{3B}$, —C(NR$^{3A}$)NH$_2$, —C(NR$^{3A}$)R$^{3B}$, —C(NCN)NH$_2$, —NH$_2$, —C(NH)NHR$^{3B}$, —C(NR$^{3A}$)NHR$^{3B}$, or —C(NCN)NHR$^{3B}$.

Embodiment 22

The compound of one of Embodiments 1 to 10, wherein $R^2$ is —C(NH)NH$_2$.

Embodiment 23

The compound of one of Embodiments 1 to 22, wherein $L^2$ is unsubstituted C$_1$-C$_5$ alkylene or unsubstituted 2 to 5 membered heteroalkylene.

Embodiment 24

The compound of one of Embodiments 1 to 22, wherein $L^2$ is unsubstituted C$_1$-C$_5$ alkylene.

Embodiment 25

The compound of one of Embodiments 1 to 22, wherein $L^2$ is —CH$_2$CH$_2$NH—.

Embodiment 26

The compound of one of Embodiments 1 to 22, wherein $L^2$ is unsubstituted methylene.

Embodiment 27

The compound of one of Embodiments 1 to 22, wherein $L^2$ is a bond.

Embodiment 28

The compound of any one of Embodiments 1 to 27, wherein $L^3$ is substituted or unsubstituted C$_1$-C$_8$ alkylene, substituted or unsubstituted 2 to 8 membered heteroalkylene, unsubstituted phenylene, unsubstituted 5 to 6 membered heteroarylene, or unsubstituted alkylarylene.

Embodiment 29

The compound of any one of Embodiments 1 to 27, wherein $L^3$ is substituted or unsubstituted C$_1$-C$_7$ alkylene.

Embodiment 30

The compound of any one of Embodiments 1 to 27, wherein $L^3$ is R$^6$-substituted C$_1$-C$_3$ alkylene; R$^6$ is —NHC (O)R$^{6A}$; R$^{6A}$ is —C(NCN)R$^{6C}$, —C(NH)R$^{6C}$, R$^{6C}$-substituted or unsubstituted alkyl, or R$^{6C}$-substituted or unsubstituted heteroalkyl; R$^{6C}$ is hydrogen, halogen, oxo, —N$_3$, —CF$_3$, —CCl$_3$, —CBr$_3$, —CI$_3$, —CN, —COR$^{6D}$, —OR$^{6D}$, —NR$^{6D}$R$^{6E}$, —COOR$^{6E}$, —CONR$^{6D}$R$^{6E}$, —NHC(O)R$^{6D}$, —NO$_2$, —SR$^{6D}$, —SO$_{n6}$R$^{6D}$, —NHNR$^{6D}$R$^{6E}$, —ONR$^{6D}$R$^{6E}$, —NHC(O)NHNR$^{6D}$R$^{6E}$, —C(NCN)R$^{6D}$, —C(NH)R$^{6D}$, R$^{6F}$-substituted or unsubstituted alkyl, R$^{6F}$-substituted or unsubstituted heteroalkyl, R$^{6F}$-substituted or unsubstituted cycloalkyl, R$^{6F}$-substituted or unsubstituted heterocycloalkyl, R$^{6F}$-substituted or unsubstituted aryl, or R$^{6F}$ substituted or unsubstituted heteroaryl; n6 is 2, 3, or 4; and R$^{6D}$, R$^{6E}$ and R$^{6F}$ are independently hydrogen, halogen, oxo, —N$_3$, —CF$_3$, —CCl$_3$, —CBr$_3$, —CI$_3$, —CN, —CHO, —OH, —NH$_2$, —COOH, —CONH$_2$, —NO$_2$, —SH, —SO$_2$, —SO$_2$Cl, —SO$_2$CH$_3$—SO$_3$H, —SO$_4$H, —SO$_2$NH$_2$, —NHNH$_2$, —ONH$_2$, —NHC(O)NHNH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, or a detectable moiety.

Embodiment 31

The compound of Embodiments 30, wherein R$^{6C}$ or R$^{6D}$ is a detectable moiety.

Embodiment 32

The compound of any one of Embodiments 1 to 31, wherein Y is a bond, —O—, —N(R$^4$)C(O)—, —N(R$^4$)C(O)NH—, —NHC(O)N(R$^4$)—, —N(R$^4$)C(O)O—, —C(O)—, —N(R$^4$)CH$_2$—, substituted or unsubstituted 3 to 6 membered heterocycloalkylene, or substituted or unsubstituted 5 to 6 membered heteroarylene.

Embodiment 33

The compound of any one of Embodiments 1 to 31, wherein Y is —NHC(O)—.

Embodiment 34

The compound of any one of Embodiments 1 to 31, wherein Y is a bond.

Embodiment 35

The compound of any one of Embodiments 1 to 31, wherein Y is —(NH)C(O)NH—.

Embodiment 36

The compound of any one of Embodiments 1 to 31, wherein Y is —(NH)C(O)O—.

Embodiment 37

The compound of any one of Embodiments 1 to 31, wherein Y is substituted or unsubstituted 5 to 6 membered heterocycloalkylene Embodiment 38

The compound of any one of Embodiments 1 to 31, wherein Y is unsubstituted 5 to 6 membered heteroarylene.

Embodiment 39

The compound of any one of Embodiments 1 to 31, wherein Y is

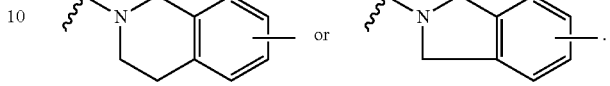

Embodiment 40

The compound of any one of Embodiments 1 to 31, wherein Y is

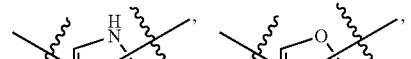

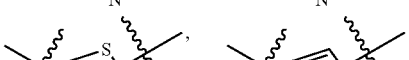

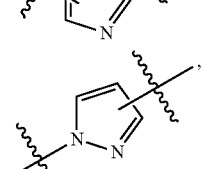 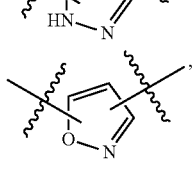

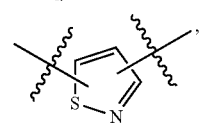 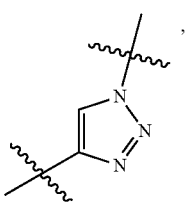

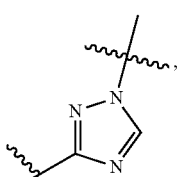 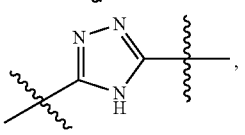

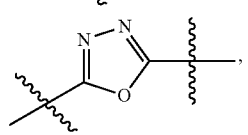 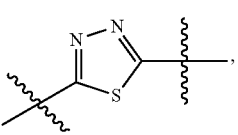

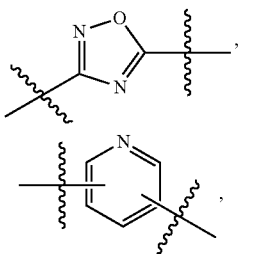 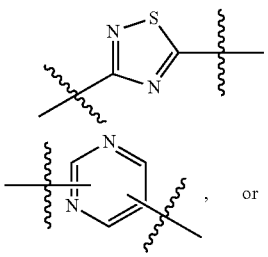, or

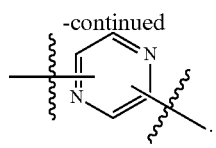

Embodiment 41

The compound of any one of Embodiments 1 to 40, wherein $R^1$ is independently hydrogen, halogen, —OMe, —SMe, —SO$_2$Me, —SO$_2$Ph, —COOH, substituted or unsubstituted $C_1$-$C_5$ alkyl, substituted or unsubstituted 2 to 5 membered heteroalkyl, or substituted or unsubstituted $C_6$-$C_{10}$ aryl.

Embodiment 42

The compound of any one of Embodiments 1 to 40, wherein $R^1$ is independently hydrogen, halogen, substituted or unsubstituted $C_1$-$C_5$ alkyl, substituted or unsubstituted 2 to 5 membered heteroalkyl, or substituted or unsubstituted $C_6$-$C_{10}$ aryl.

Embodiment 43

The compound of any one of Embodiments 1 to 42, wherein $R^{3A}$ and $R^{3B}$ are independently hydrogen, —C(NH)NH$_2$, —C(NCN)NH$_2$, substituted or unsubstituted heterocycloalkyl, or substituted or unsubstituted heteroaryl.

Embodiment 44

The compound of any one of Embodiments 1 to 42, wherein $R^{3A}$ and $R^{3B}$ are joined to form a substituted or unsubstituted 5 or 6 membered heterocycloalkyl or substituted or unsubstituted 5 or 6 membered heteroaryl.

Embodiment 45

The compound of any one of Embodiments 1 to 42, wherein $R^{3A}$ and $R^{3B}$ are independently hydrogen, —C(NH)NH$_2$, —C(NCN)NH$_2$, or substituted or unsubstituted 3 to 6 membered heterocycloalkyl, or substituted or unsubstituted 5 to 6 membered heteroaryl.

Embodiment 46

The compound of any one of Embodiments 1 to 45 having the formula:

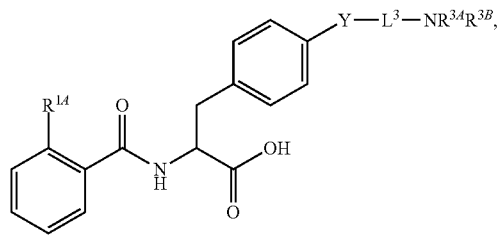

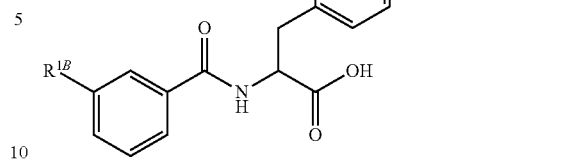

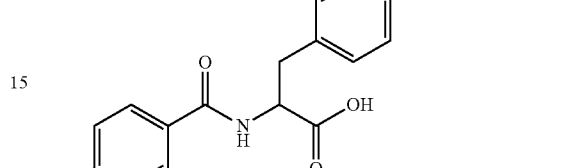

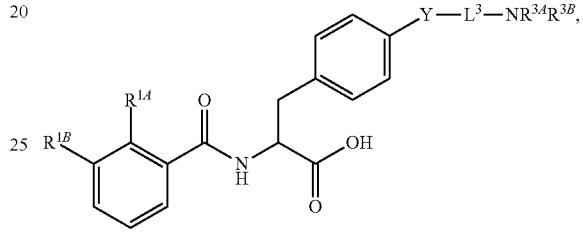

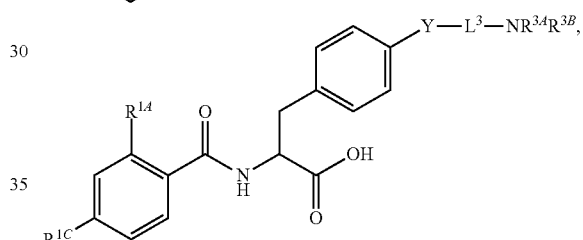

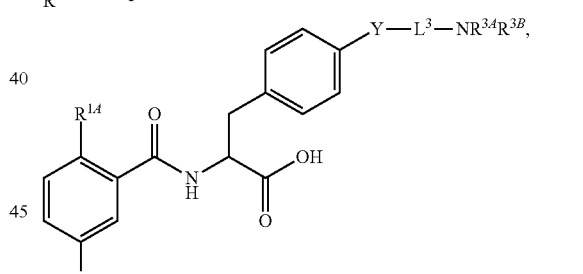

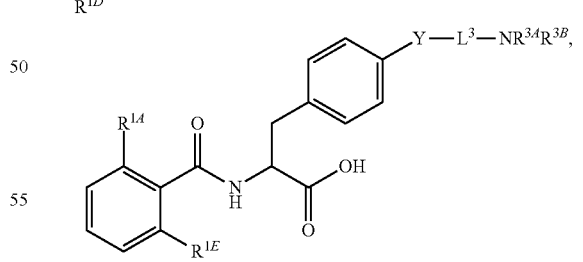

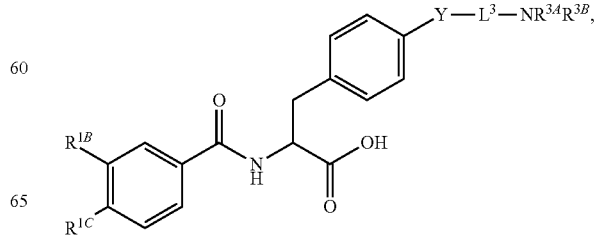

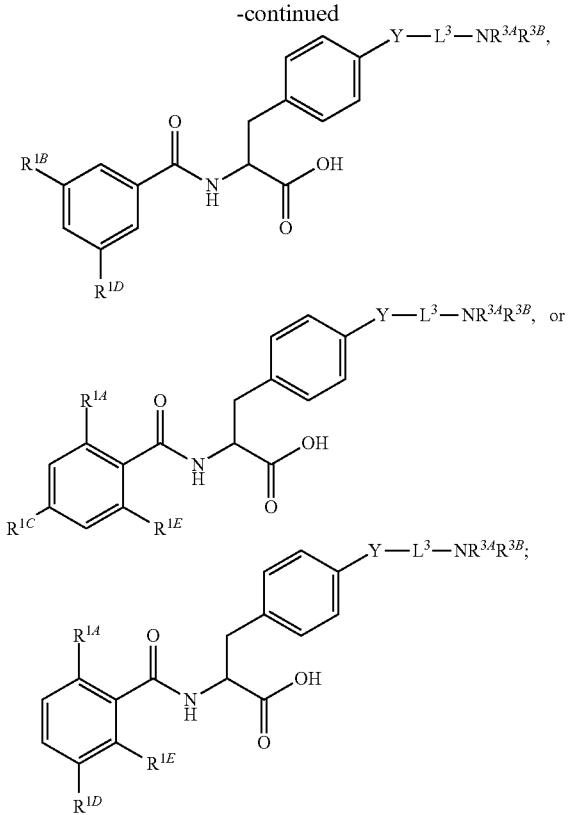

wherein $R^{1A}$, $R^{1B}$, $R^{1C}$, $R^{1D}$, and $R^{1E}$ are independently hydrogen, halogen, —$N_3$, —$CF_3$, —$CCl_3$, —$CBr_3$, —$CI_3$, —CN, —CHO, —OH, —$NH_2$, —COOH, —$CONH_2$, —$NO_2$, —SH, —$SO_2$, —$SO_2Cl$, —$SO_2CH_3$—$SO_3H$, —$OSO_3H$, —$SO_2NH_2$, —$NHNH_2$, —$ONH_2$, —NHC(O)NHNH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, or a detectable moiety.

Embodiment 47

The compound of Embodiment 46, wherein $R^{1A}$, $R^{1B}$, $R^{1C}$, $R^{1D}$, and $R^{1E}$ are independently hydrogen, halogen, unsubstituted $C_1$-$C_3$ alkyl, unsubstituted 2 to 3 membered heteroalkyl, or unsubstituted phenyl.

Embodiment 48

The compound of Embodiment 46, wherein two substituents selected from $R^{1A}$, $R^{1B}$, $R^{1C}$, $R^{1D}$, and $R^{1E}$, are joined to form a substituted or unsubstituted cycloalkyl, substituted or unsubstituted heterocycloalkyl, substituted or unsubstituted aryl, substituted or unsubstituted heteroaryl.

Embodiment 49

The compound of Embodiment 46, wherein two substituents selected from $R^{1A}$, $R^{1B}$, $R^{1C}$, $R^{1D}$, and $R^{1E}$, connected to adjacent ring atoms, are joined to form a substituted or unsubstituted cycloalkyl, substituted or unsubstituted heterocycloalkyl, substituted or unsubstituted aryl, substituted or unsubstituted heteroaryl.

Embodiment 50

The compound of any one of Embodiments 46 to 49 having the formula:

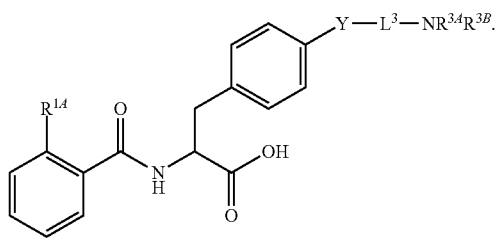

Embodiment 51

The compound of any one of Embodiments 46 to 49 having the formula:

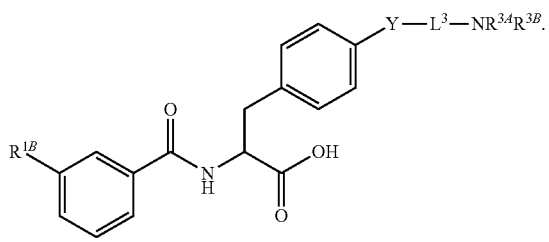

Embodiment 52

The compound of any one of Embodiments 46 to 49 having the formula:

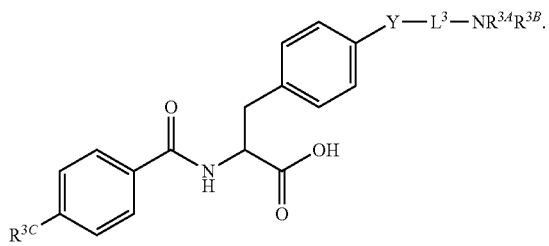

Embodiment 53

The compound of any one of Embodiments 46 to 49 having the formula:

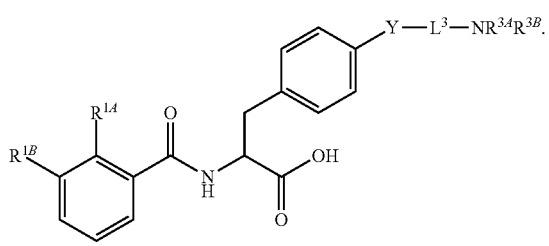

Embodiment 54

The compound of any one of Embodiments 46 to 49 having the formula:

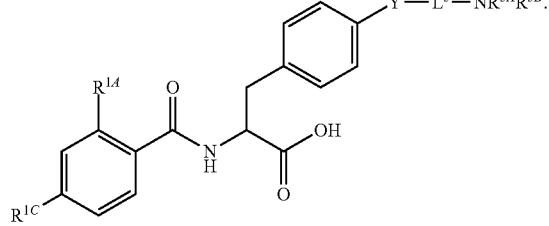

Embodiment 55

The compound of any one of Embodiments 46 to 49 having the formula:

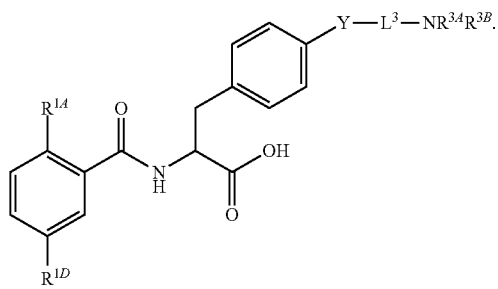

Embodiment 56

The compound of any one of Embodiments 46 to 49 having the formula:

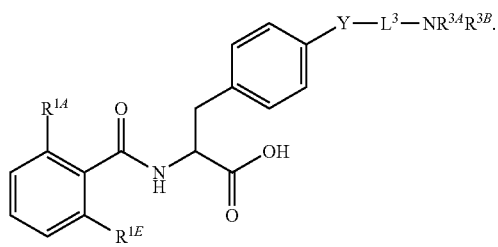

Embodiment 57

The compound of any one of Embodiments 46 to 49 having the formula:

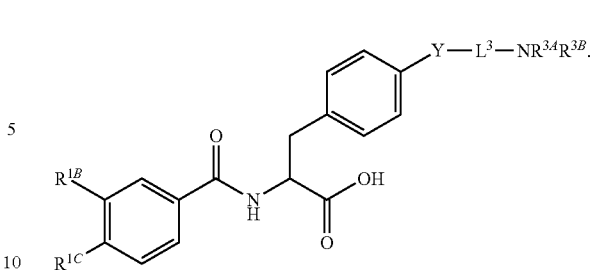

Embodiment 58

The compound of any one of Embodiments 46 to 49 having the formula:

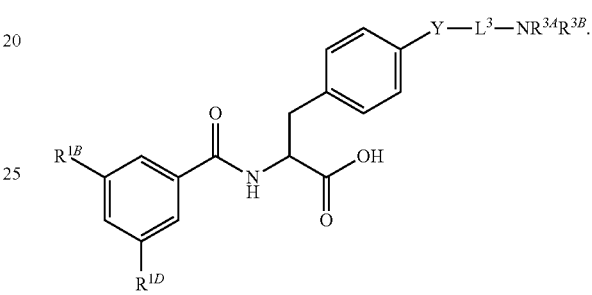

Embodiment 59

The compound of any one of Embodiments 46 to 49 having the formula:

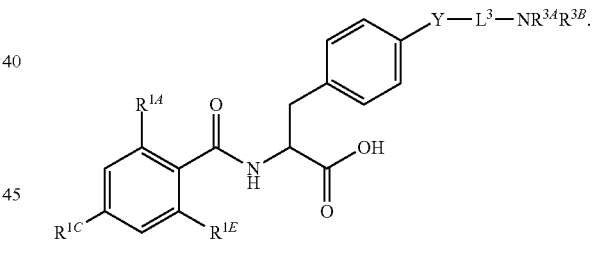

Embodiment 60

The compound of any one of Embodiments 46 to 49 having the formula:

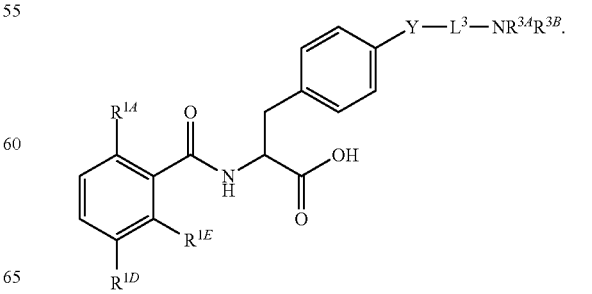

Embodiment 61

The compound of any one of Embodiments 1 to 45 having the formula:

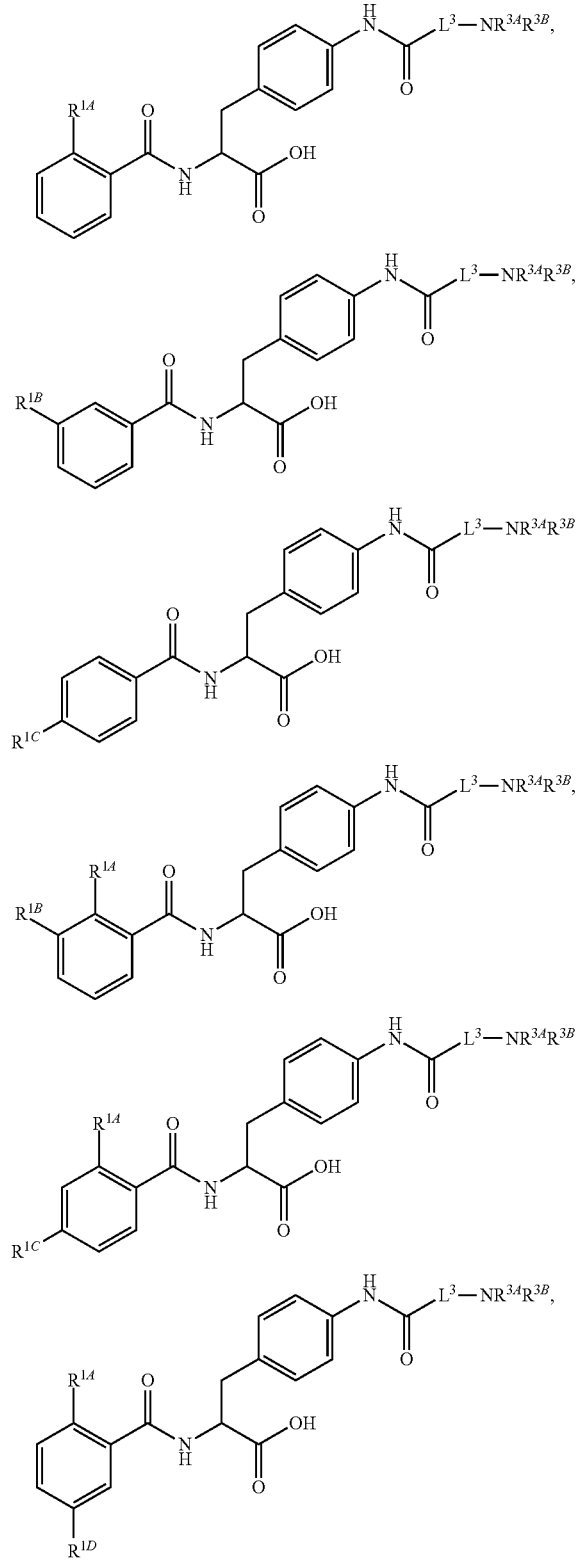

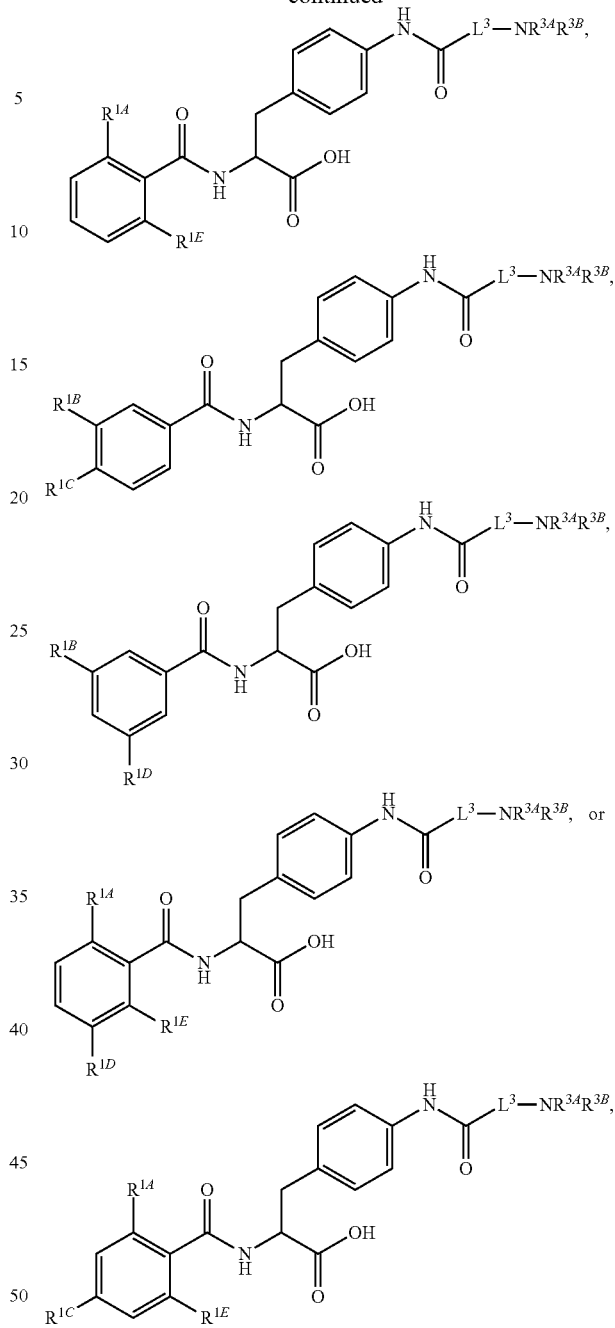

wherein $R^{1A}$, $R^{5B}$, $R^{1C}$, $R^{1D}$, and $R^{1E}$ are independently hydrogen, halogen, —$N_3$, —$CF_3$, —$CCl_3$, —$CBr_3$, —$Cl_3$, —CN, —CHO, —OH, —$NH_2$, —COOH, —$CONH_2$, —$NO_2$, —SH, —$SO_2$, —$SO_2CH_3$—$SO_3H$, —$OSO_3H$, —$SO_2NH_2$, —$NHNH_2$, —$ONH_2$, —NHC(O)$NHNH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, or a detectable moiety.

Embodiment 62

The compound of Embodiment 61, wherein $R^{1A}$, $R^{1B}$, $R^{1C}$, $R^{1D}$, and $R^{1E}$ are independently hydrogen, halogen, unsubstituted $C_1$-$C_3$ alkyl, unsubstituted 2 to 3 membered heteroalkyl, or unsubstituted phenyl.

Embodiment 63

The compound of Embodiment 61, wherein two substituents selected from $R^{1A}$, $R^{1B}$, $R^{1C}$, $R^{1D}$, and $R^{1E}$, are joined to form a substituted or unsubstituted cycloalkyl, substituted or unsubstituted heterocycloalkyl, substituted or unsubstituted aryl, substituted or unsubstituted heteroaryl.

Embodiment 64

The compound of Embodiment 61, wherein two substituents selected from $R^{1A}$, $R^{1B}$, $R^{1C}$, $R^{1D}$, and $R^{1E}$, connected to adjacent ring atoms, are joined to form a substituted or unsubstituted cycloalkyl, substituted or unsubstituted heterocycloalkyl, substituted or unsubstituted aryl, substituted or unsubstituted heteroaryl.

Embodiment 65

The compound of any one of Embodiments 61 to 64 having the formula:

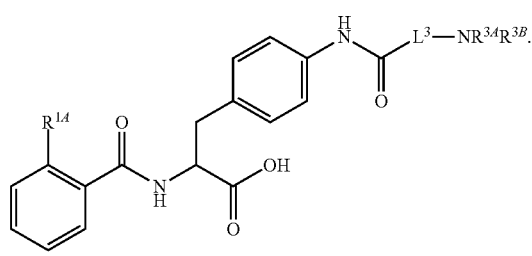

Embodiment 66

The compound of any one of Embodiments 61 to 64 having the formula:

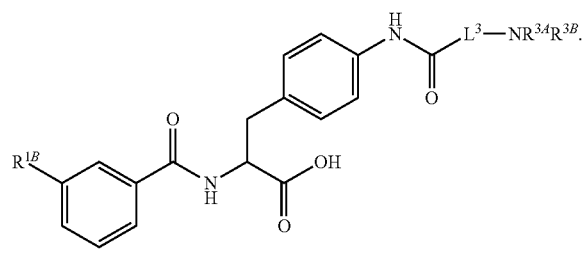

Embodiment 67

The compound of any one of Embodiments 61 to 64 having the formula:

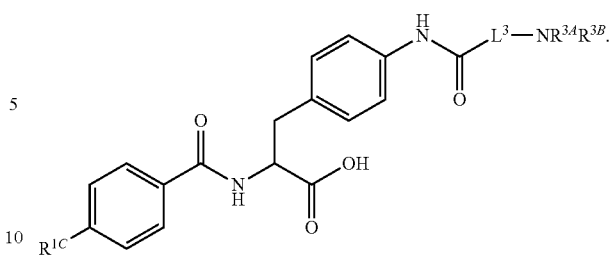

Embodiment 68

The compound of any one of Embodiments 61 to 64 having the formula:

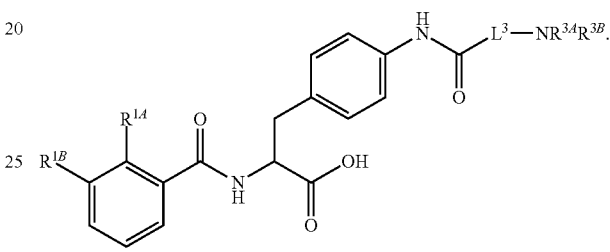

Embodiment 69

The compound of any one of Embodiments 61 to 64 having the formula:

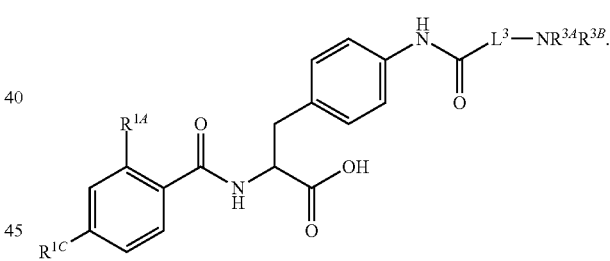

Embodiment 70

The compound of any one of Embodiments 61 to 64 having the formula:

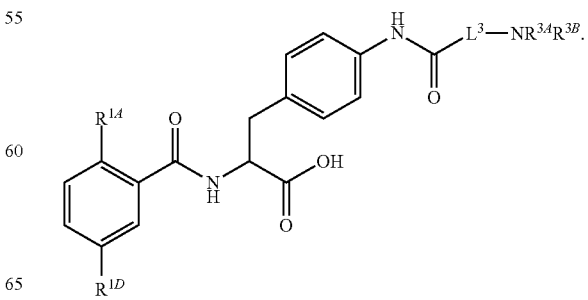

Embodiment 71

The compound of any one of Embodiments 61 to 64 having the formula:

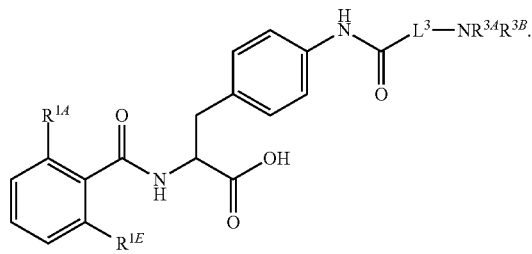

Embodiment 72

The compound of any one of Embodiments 61 to 64 having the formula:

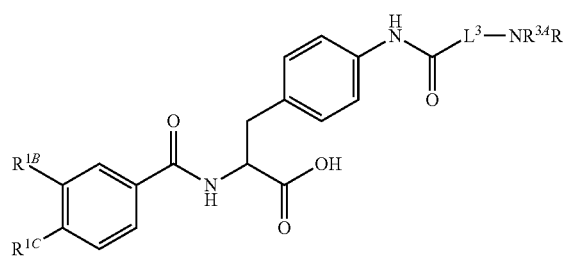

Embodiment 73

The compound of any one of Embodiments 61 to 64 having the formula:

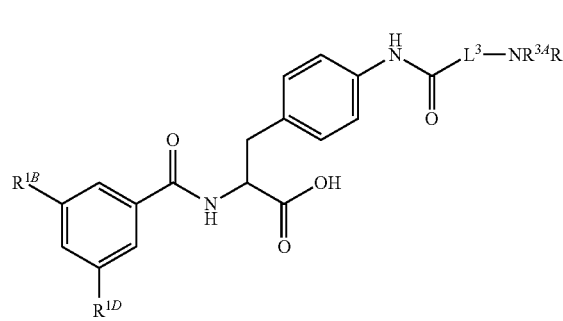

Embodiment 74

The compound of any one of Embodiments 61 to 64 having the formula:

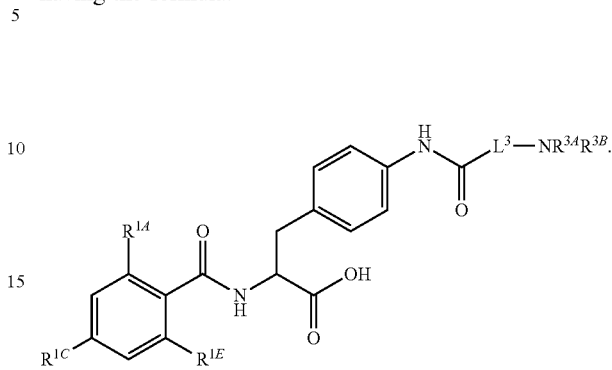

Embodiment 75

The compound of any one of Embodiments 61 to 64 having the formula:

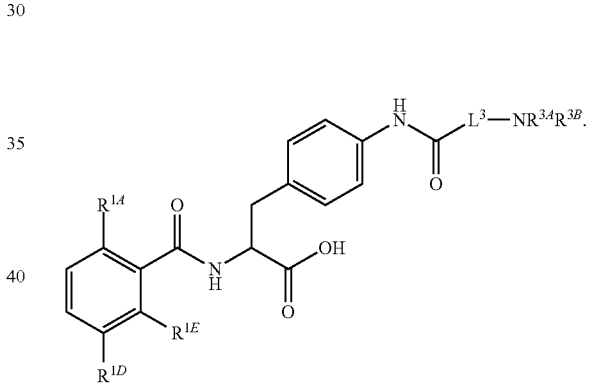

Embodiment 76

The compound of Embodiment 1 having formula:

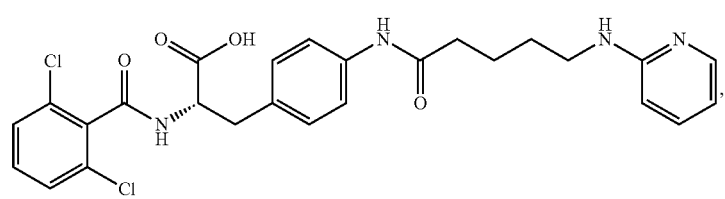

-continued
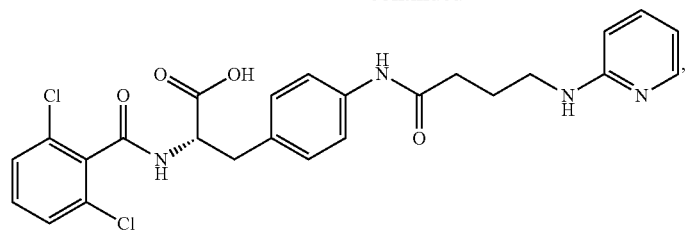
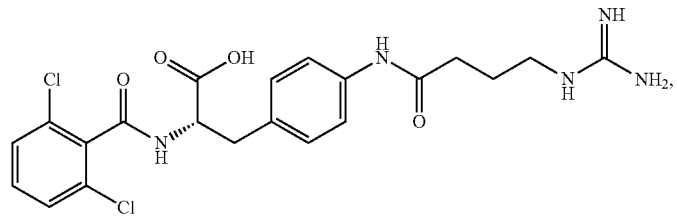
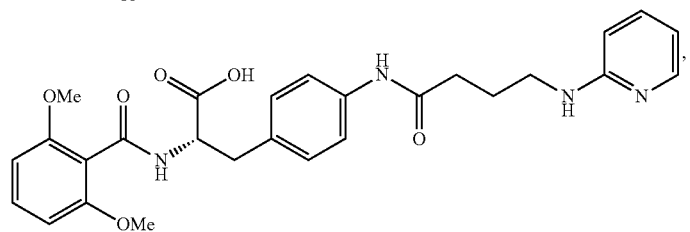
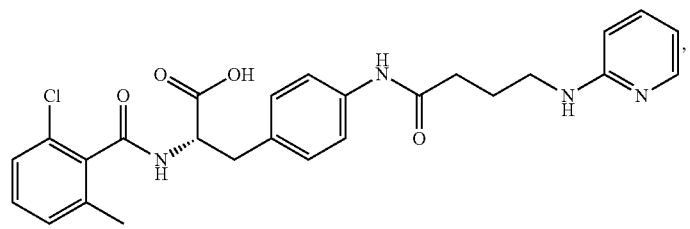
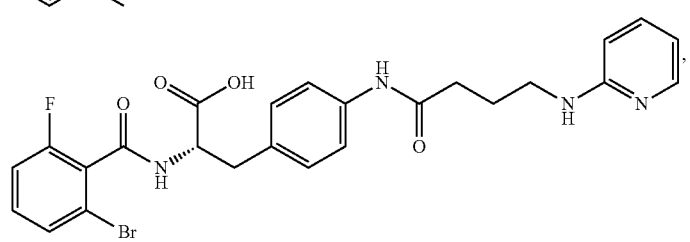
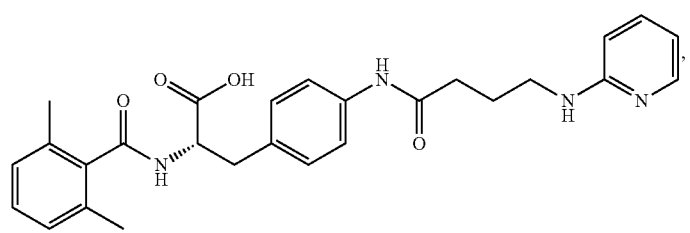
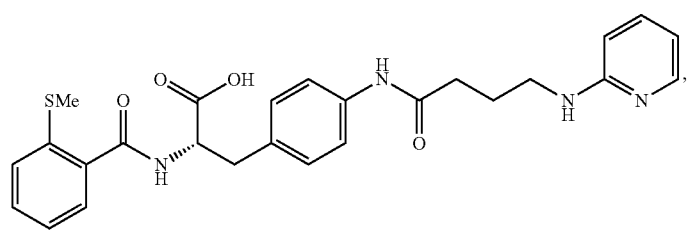

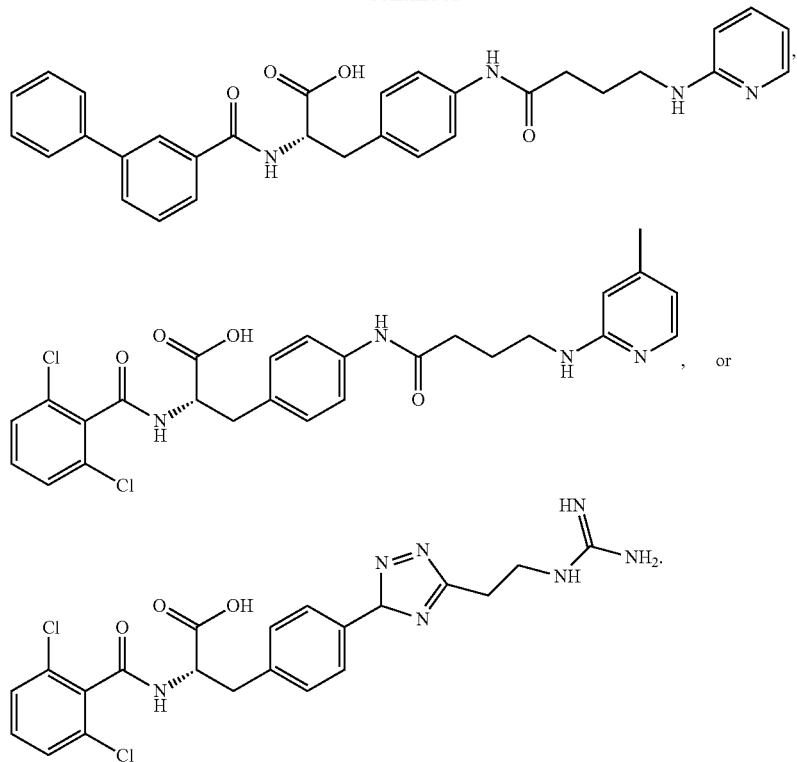

Embodiment 77

A pharmaceutical composition comprising the compound of any one of Embodiments 1 to 76 and a pharmaceutically acceptable excipient.

Embodiment 78

A method of detecting αvβ1 expression in a cell, said method comprising: (i) contacting a cell with a compound of one of Embodiments 1 to 76; (ii) allowing said compound to bind to said cell; and (iii) detecting said compound, thereby detecting αvβ1 expression in a cell.

Embodiment 79

A method of inhibiting TGFβ activation, said method comprising: (i) contacting a cell expressing αvβ1 integrin with a compound of one of Embodiments 1 to 76; (ii) allowing said compound to bind to αvβ1 in the presence of TGFβ; and (iii) comparing a level of activated TGFβ to a control to thereby identify a lower level of TGFβ activation and inhibition of TGFβ activation.

Embodiment 80

The method of Embodiment 79, wherein said cell is a skin myofibroblast, a lung myofibroblast, renal myofibroblast, or a hepatic myofibroblast.

Embodiment 81

A method for treating fibrosis, said method comprising administering to a subject in need thereof an effective amount of a compound having the formula of any one of Embodiments 1 to 76.

Embodiment 82

The method of Embodiment 81, wherein said fibrosis is pulmonary fibrosis, liver fibrosis, skin fibrosis, cardiac fibrosis, or kidney fibrosis.

Embodiment 83

The method of Embodiment 81, wherein said fibrosis is pulmonary fibrosis.

Embodiment 84

The method of Embodiment 81, wherein said fibrosis is liver fibrosis.

Embodiment 85

The method of Embodiment 81, wherein said fibrosis is skin fibrosis.

Embodiment 86

The method of Embodiment 81, wherein said fibrosis is cardiac fibrosis.

Embodiment 87

The method of Embodiment 81, wherein said fibrosis is kidney fibrosis.

Embodiment 88

A method of detecting αvβ1 expression in a cell, said method comprising: (i) contacting a cell with a compound of one of Embodiments 1 to 76, wherein the compound comprises a detectable moiety; (ii) allowing said compound to bind to said cell; and (iii) detecting said compound, thereby detecting αvβ1 expression in a cell.

Embodiment 89

A method of inhibiting TGFβ activation, said method comprising: (i) contacting a cell expressing αvβ1 integrin with a compound of one of Embodiments 1 to 76; (ii) allowing said compound to bind to αvβ1 in the presence of TGFβ.

Embodiment 90

The method of Embodiment 89, further comprising comparing a level of activated TGFβ to a control to thereby identify a lower level of TGFβ activation and inhibition of TGFβ activation.

Embodiment 91

The method of Embodiments 89 or 90, wherein said cell is a skin myofibroblast, a lung myofibroblast, renal myofibroblast, or a hepatic myofibroblast.

Embodiment 92

The compound of Embodiment 1, wherein $R^{12}$ is a substituted or unsubstituted alkyl, or substituted or unsubstituted heteroalkyl.

VIII. Examples

Example 1

Solid phase synthesis schematic for synthesis of compounds described herein.

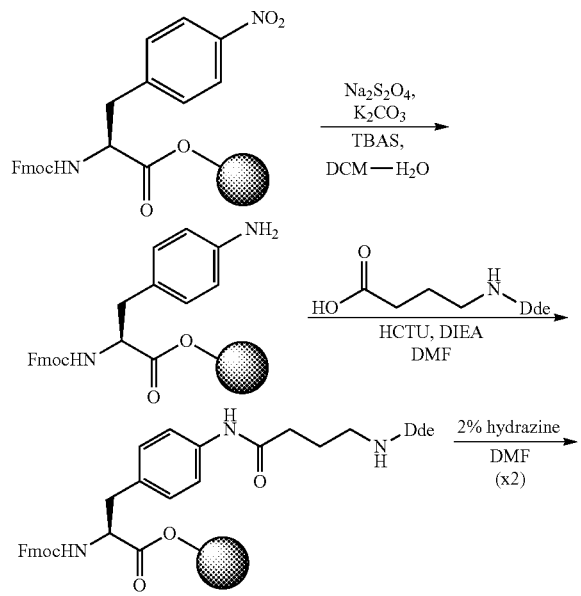

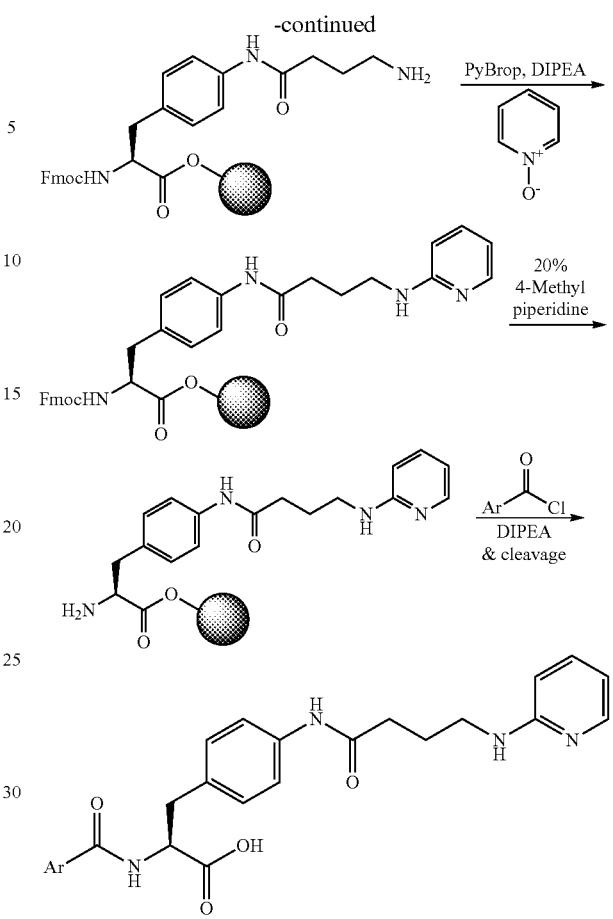

[General Method A] Fmoc-(p-NO2)-Phe-Wang resin (20 g, 0.55 meq/g, 11 mmol) was treated with a solution of sodium dithionite (17.4 g, 110 mmol), potassium carbonate (21.2 g, 154 mmol), tetra-n-butylammonium sulfate (3.73 g, 11 mmol) in dichloromethane-H$_2$O (1:1, 300 mL) for 2 h with nitrogen bubbling. The resin was washed with dichloromethane-H$_2$O (1:1, 300 mL) (×3), dimethylformamide (200 mL, ×3), methanol (200 mL, ×3), and dichloromethane (200 mL, ×3). A portion of resin (10 g) was then treated with a Dde protected aminobutanoic acid (9 g, 6.0 eq) in DMF (100 mL) and DIPEA (14.1 mL, 14.5 eq) followed by a solution of HCTU (12.3 g, 5.5 mmol) in DMF (50 mL). After overnight agitation by nitrogen bubbling, the resin was filtered and washed with DMF (×3). The Dde protecting group was then removed by treatment with 2% hydrazine (5.5 mL) in DMF (45 mL) for 5 min and the deprotection step was repeated. The resin was filtered and washed with DMF (×3), DCM (×3), MeOH (×3) and dried. A portion of resin (5 g) was treated with a solution of pyridine N-oxide (1.2 g), PyBroP (6.5 eq), DIPEA (18.75 eq) in DCM (40 mL) for 3 h and the resin was filtered and washed with DCM (×3), MeOH (×3) and dried. A portion of resin (500 mg) was then treated for 20 min with a mixture of substituted benzoic acid (5 eq), HCTU (5 eq), and DIEA (10 eq) at 75° C. The resin was filtered, and washed with DMF thoroughly. Then the resin was washed with DMF thoroughly and washed with DCM and MeOH. The product was cleaved from the resin by 3-hr treatment with a mixture of TFA:TIPS:H$_2$O (95:2.5:2.5) and was purified by preparative RP-HPLC. LC-MS profile (solvent A, solvent B' (Vydac 218TP54, 300 Å, solvent A, solvent B', flow rate: 0.9 ml/min, gradient: 5% to 100% solvent B' for 30 min, detection: 254 nm). HPLC profile (condition 1) solvent A, solvent B' (Vydac 218TP54, 300 Å, solvent A, solvent B', flow rate: 0.9 ml/min, gradient: 5% to 100% solvent B' for 30 min, detection: 254 nm).

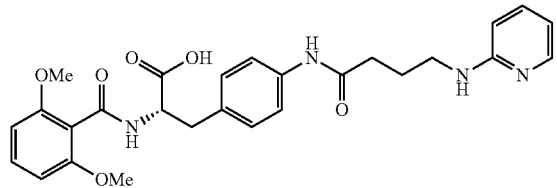 [SMILES: COc1cccc(OC)c1C(=O)N[C@@H](Cc1ccc(NC(=O)CCCNc2ccccn2)cc1)C(=O)O]

[HIJ-886] Prepared from 2,6-dimethoxy benzoic acid as a substituted benzoic acid by General Method A. (S)-2-(2,6-dimethoxybenzamido)-3-(4-(4-(pyridin-2-ylamino)butanamido)phenyl)propanoic acid; retention time 15.00 min, m/z=507.9 (MH+).

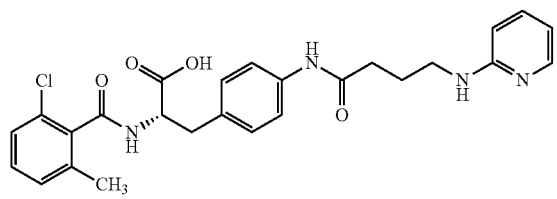 [SMILES: Cc1cccc(Cl)c1C(=O)N[C@@H](Cc1ccc(NC(=O)CCCNc2ccccn2)cc1)C(=O)O]

[HIJ-888] Prepared from 2-chloro-6-methyl benzoic acid as a substituted benzoic acid by General Method A. (S)-2-(2-chloro-6-methylbenzamido)-3-(4-(4-(pyridin-2-ylamino)butanamido)phenyl)propanoic acid; retention time 15.6 min, m/z=495.8 (MH+).

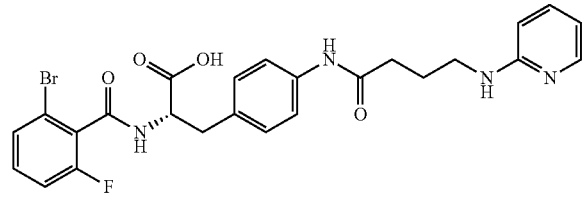 [SMILES: O=C(CCCNc1ccccn1)Nc1ccc(C[C@H](NC(=O)c2c(F)cccc2Br)C(=O)O)cc1]

[HIJ-889] Prepared from 2-bromo-6-fluorobenzoic acid by General Method A (S)-2-(2-bromo-6-fluorobenzamido)-3-(4-(4-(pyridin-2-ylamino)butanamido)phenyl)propanoic acid); retention time 15.65 min, m/z=543.8, 545.6 (MH+).

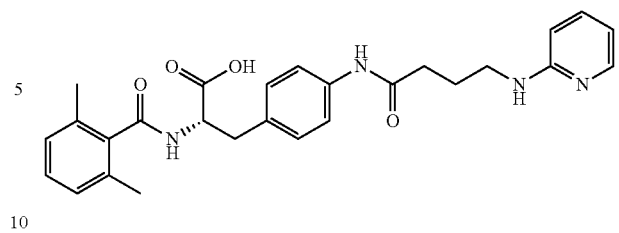

[HIJ-890] Prepared from 2,6-dimethylbenzoic acid by General Method A. (S)-2-(2,6-dimethylbenzamido)-3-(4-(4-(pyridin-2-ylamino)butanamido)phenyl)propanoic acid; retention time 15.39 min, m/z=475.9 (MH+).

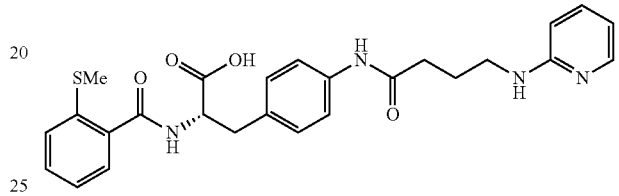

[HIJ-891] Prepared from 2-(methylthio)benzoic acid by General Method A. (S)-2-(2-(methylthio)benzamido)-3-(4-(4-(pyridin-2-ylamino)butanamido)phenyl)propanoic acid); retention time 15.53 min, m/z=493.8 (MH+)

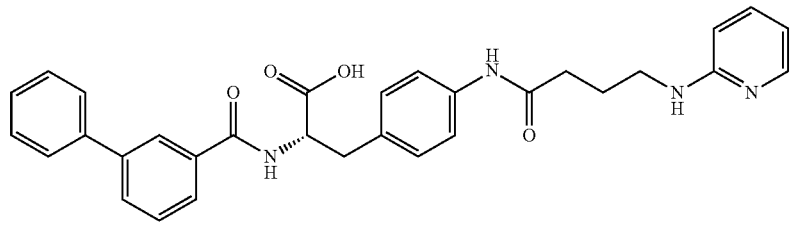 [SMILES: O=C(CCCNc1ccccn1)Nc1ccc(C[C@H](NC(=O)c2cccc(-c3ccccc3)c2)C(=O)O)cc1]

[HIJ-892] Prepared from [1,1'-biphenyl]-3-carboxylic acid by General Method A. (S)-2-([1,1'-biphenyl]-3-carboxamido)-3-(4-(4-(pyridin-2-ylamino)butanamido)phenyl) propanoic acid; retention time 18.85 min, m/z=523.9 (MH+)

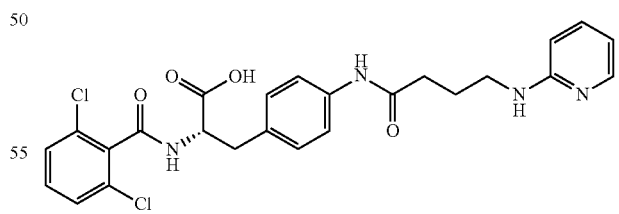

[YT-103] Prepared from 2,6-dichlorobenzoic acid by General Method A. (S)-2-(2,6-dichlorobenzamido)-3-(4-(4-(pyridin-2-ylamino)butanamido)phenyl)propanoic acid; retention time (condition: 19×100 mm Altantis T3 OBD, solvent A, solvent B', flow rate: 15 ml/min, gradient: 8% solvent B' for 3 min, 8% to 15% solvent B' for 1 min, 15% to 24% solvent B' for 30 min, detection: 254 nm) 19.46 min, m/z=515.4 (MH+).

[HIJ-899]

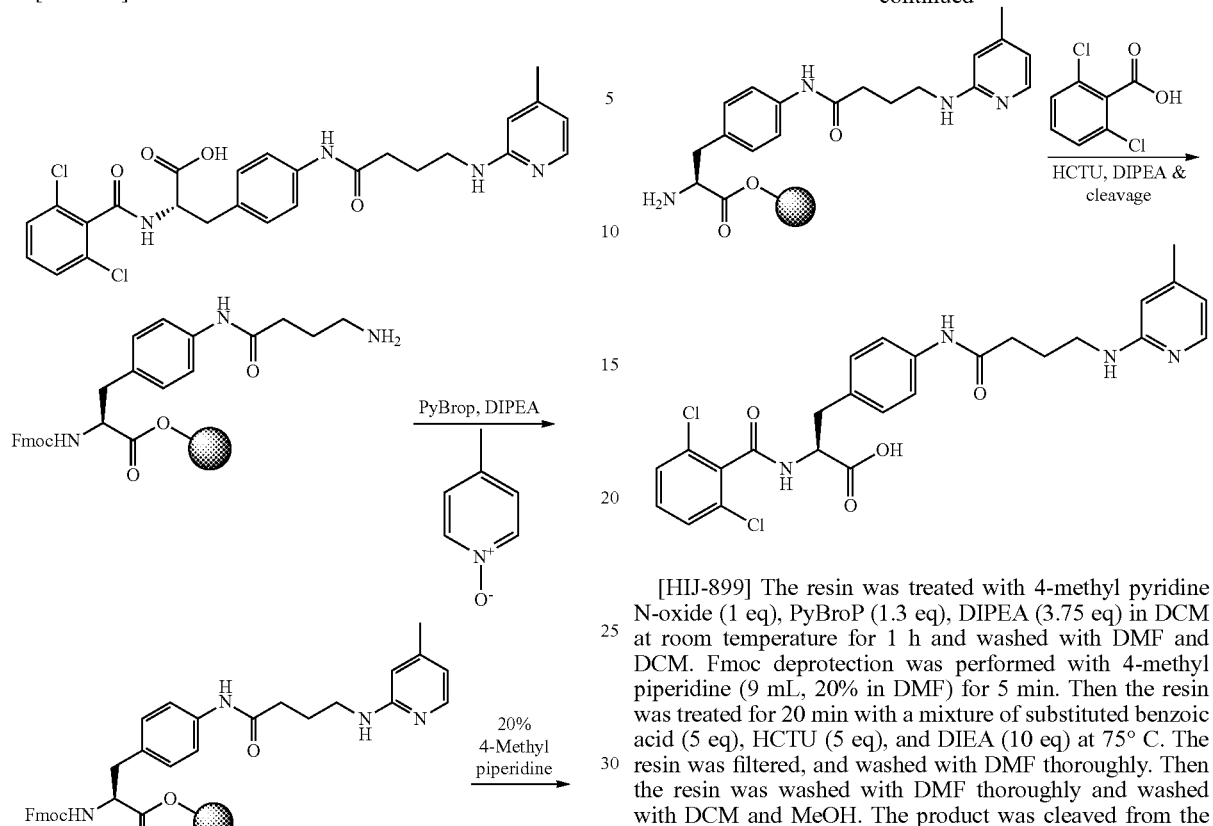
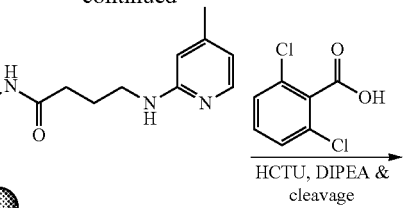

[HIJ-899] The resin was treated with 4-methyl pyridine N-oxide (1 eq), PyBroP (1.3 eq), DIPEA (3.75 eq) in DCM at room temperature for 1 h and washed with DMF and DCM. Fmoc deprotection was performed with 4-methyl piperidine (9 mL, 20% in DMF) for 5 min. Then the resin was treated for 20 min with a mixture of substituted benzoic acid (5 eq), HCTU (5 eq), and DIEA (10 eq) at 75° C. The resin was filtered, and washed with DMF thoroughly. Then the resin was washed with DMF thoroughly and washed with DCM and MeOH. The product was cleaved from the resin by 3-hr treatment with a mixture of TFA:TIPS:H2O (95:2.5:2.5) and was purified by RP-HPLC. Retention time 16.34 min, m/z=529.9 (MH+)

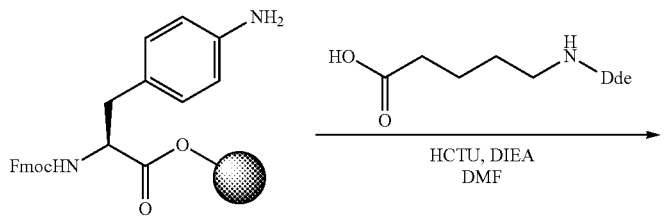
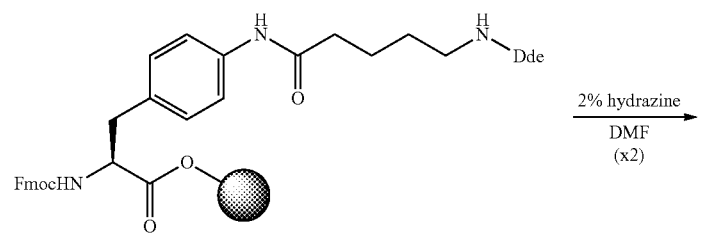
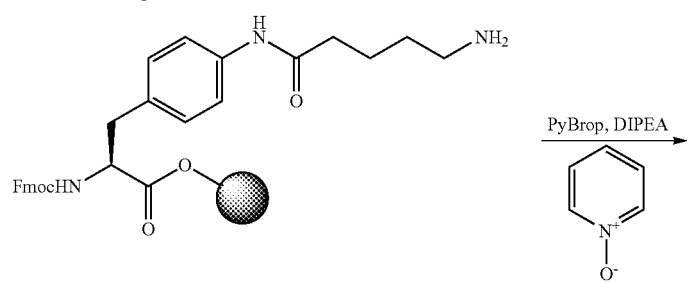

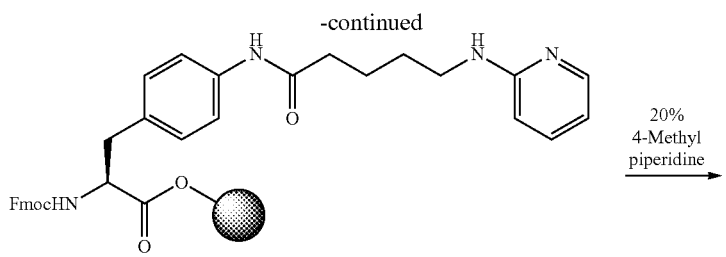

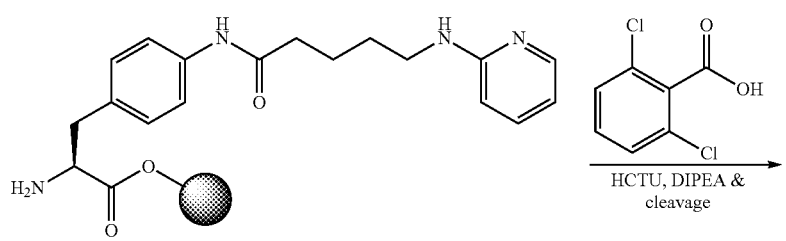

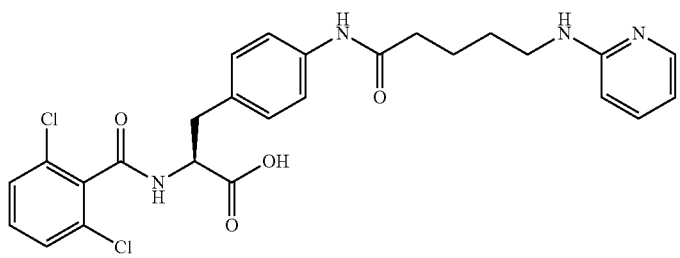

[YT-43] The resin was then treated with a Dde protected aminopentanoic acid (6.0 eq) in DMF (100 mL) and DIPEA (12 eq) followed by a solution of HCTU (5.5 eq) in DMF (50 mL). After overnight agitation by nitrogen bubbling, the resin was filtered and washed with DMF (×3). The Dde protecting group was then removed by treatment with 2% hydrazine (5.5 mL) in DMF (45 mL) for 5 min and the deprotection step was repeated. The resin was filtered and washed with DMF (×3), DCM (×3), MeOH (×3) and dried. A portion of resin (5 g) was treated with a solution of pyridine N-oxide (1.2 g), PyBroP (6.5 eq), DIPEA (18.75 eq) in DCM (40 mL) for 3 h and the resin was filtered and washed with DCM (×3), MeOH (×3) and dried. A portion of resin (500 mg) was then treated for 20 min with a mixture of 2,6-dichlorobenzoic acid (5 eq), HCTU (5 eq), and DIEA (10 eq) at 75° C. The resin was filtered, and washed with DMF thoroughly. Then the resin was washed with DMF thoroughly and washed with DCM and MeOH. The product was cleaved from the resin by 3-hr treatment with a mixture of TFA:TIPS:H$_2$O (95:2.5:2.5) and was purified by RP-HPLC. Retention time (condition: 19×100 mm Altantis T3 OBD, solvent A, solvent B', flow rate: 13 ml/min, gradient: 8% solvent B' for 5 min, 8% to 20% solvent B' for 1 min, 20% to 23% solvent B' for 24 min, detection: 254 nm) 13.46 min, m/z=528 (MH+)

[JM-39]

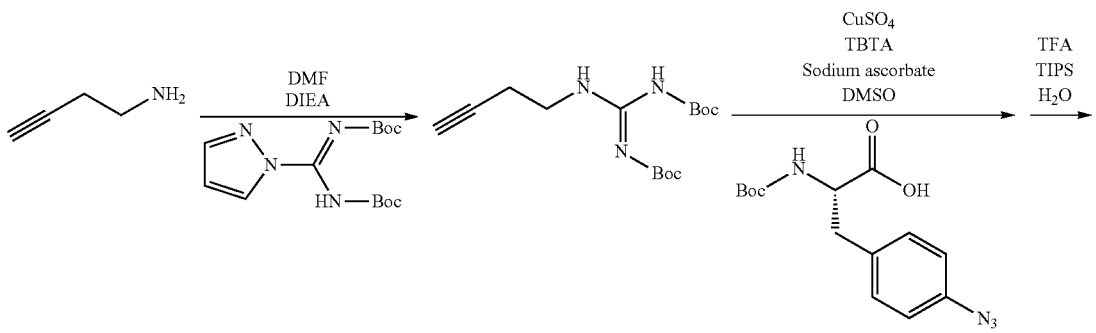

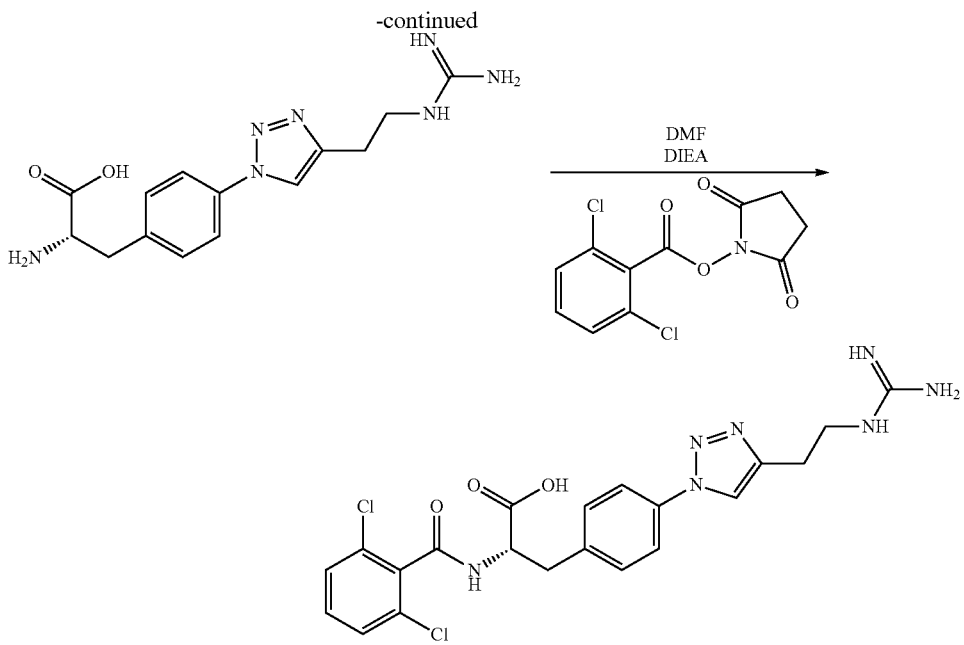

2,5-dioxopyrrolidin-1-yl 2,6-dichlorobenzoate (S)-2-amino-3-(4-(4-(2-guanidinoethyl)-1H-1,2,3-triazol-1-yl)phenyl)propanoic acid

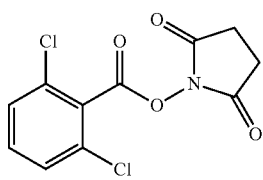 [SMILES: O=C(ON1C(=O)CCC1=O)c1c(Cl)cccc1Cl]

To a mixture of 2,6-dichlorobenzoic acid (2.00 g, 10.0 mmol) and N-hydroxysucccinimide (1.44 g, 12.6 mmol) in DMF (50 mL) was added N-(3-dimethyl aminopropyl)-N'-ethylcarbodiimide hydrochloride (3.01 g, 15.7 mmol). After stirring for 18 hours, the mixture was diluted with ethyl acetate (100 mL), washed three times with water (100 mL), washed with brine (50 mL), dried over anhydrous magnesium sulfate, and concentrated in vacuo to provide 2,5-dioxopyrrolidin-1-yl 2,6-dichlorobenzoate. $^1$H NMR (300 MHz, CDCl$_3$) δ (ppm) 7.42 (s, 3H), 2.93 (s, 4H).

1-(but-3-yn-1-yl)-2,3-di-Boc-guanidine

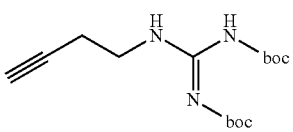

To a solution of 3-butyn-1-amine hydrochloride (250 mg, 2.37 mmol) in 6 mL DMF was added N,N-diisopropylethylamine (1.23 mL, 7.10 mmol) followed by N,N'-Di-Boc-1H-pyrazole-1-carboxamidine (808 mg, 2.60 mmol). The mixture was stirred for 3 days. Water (20 mL) was added. The resulting solid was filtered and washed with water to provide 1-(but-3-yn-1-yl)-2,3-di-Boc-guanidine. MS (m/z) 312 (MH+).

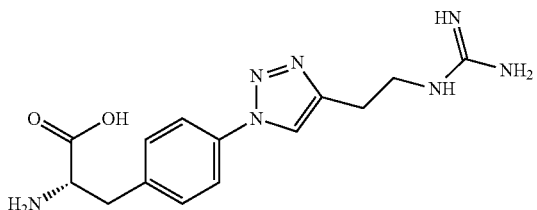

To a mixture of Boc-4-azido-L-phenylalanine (100 mg, 0.326 mmol) and 1-(but-3-yn-1-yl)-2,3-di-Boc-guanidine (111 mg, 0.359 mmol) in water (1 mL) and DMSO (2 mL) was added sodium ascorbate (6.5 mg, 0.0033 mmol), tris[(1-benzyl-1H-1,2,3-triazol-4-yl)methyl]amine (1.7 mg, 0.0033 mmol) in 0.25 mL DMSO, and cupric sulfate (0.5 mg, 0.003 mmol). The mixture was stirred at room temperature for 30 minutes then at 60° C. for 30 minutes. DMSO (2 mL) was added. After an additional 30 minutes at 60° C., the mixture was cooled and diluted with water. The mixture was extracted with ethyl acetate. The organic layer was washed with brine, dried over anhydrous magnesium sulfate, and concentrated in vacuo. The resulting residue was stirred in a mixture of trifluroacetic acid (1.9 mL), triisopropylsilane (0.05 mL), and water (0.05 mL) for 2.5 hours. The mixture was concentrated to provide (S)-2-amino-3-(4-(4-(2-guanidinoethyl)-1H-1,2,3-triazol-1-yl)phenyl)propanoic acid. MS (m/z)=318 (MH+).

(S)-2-(2,6-dichlorobenzamido)-3-(4-(4-(2-guanidinoethyl)-1H-1,2,3-triazol-1-yl)phenyl)propanoic acid

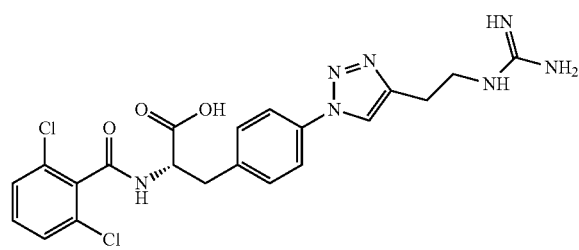 [SMILES: N=C(N)NCCc1cn(-c2ccc(C[C@H](NC(=O)c3c(Cl)cccc3Cl)C(=O)O)cc2)nn1]

[JM-39]
2,5-dioxopyrrolidin-1-yl 2,6-dichlorobenzoate (30 mg, 0.10 mmol) and N,N-diisopropylethylamine (0.07 mL, 0.42 mmol) were added to a mixture of (S)-2-amino-3-(4-(4-(2-guanidinoethyl)-1H-1,2,3-triazol-1-yl)phenyl)propanoic acid (33 mg, 0.10 mmol) in DMF (1 mL). After stirring for four days, the mixture was concentrated in vacuo. The crude residue was purified by preparative TLC (50% methanol in dichloromethane). (S)-2-amino-3-(4-(4-(2-guanidinoethyl)-1H-1,2,3-triazol-1-yl)phenyl)propanoic acid. Retention time 17.2 min, MS (m/z)=490 (MH+).

[General Method I] Amino compound on resin was agitated with a premixed solution of pyridine N-oxide (1 eq), PyBroP (1.3 eq), DIPEA (3.75 eq) in DCM at room temperature for 1 h. The resin was washed with DMF, DCM and MeOH. The product was cleaved from the resin by 3-hr treatment with a mixture of TFA:TIPS:H$_2$O (95:2.5:2.5) and was purified by RP-HPLC.

[YT-43] (n=4) Prepared by general method I. retention time (condition: 19×100 mm Altantis T3 OBD, solvent A, solvent B', flow rate: 13 ml/min, gradient: 8% solvent B' for 5 min, 8% to 20% solvent B' for 1 min, 20% to 23% solvent B' for 24 min, detection: 254 nm) 13.46 min, m/z=528 (MH+)

[YT-103] (n=3) Prepared by general method I. retention time (condition: 19×100 mm Altantis T3 OBD, solvent A, solvent B', flow rate: 15 ml/min, gradient: 8% solvent B' for 3 min, 8% to 15% solvent B' for 1 min, 15% to 24% solvent B' for 30 min, detection: 254 nm) 19.46 min, m/z=515.4 (MH+)

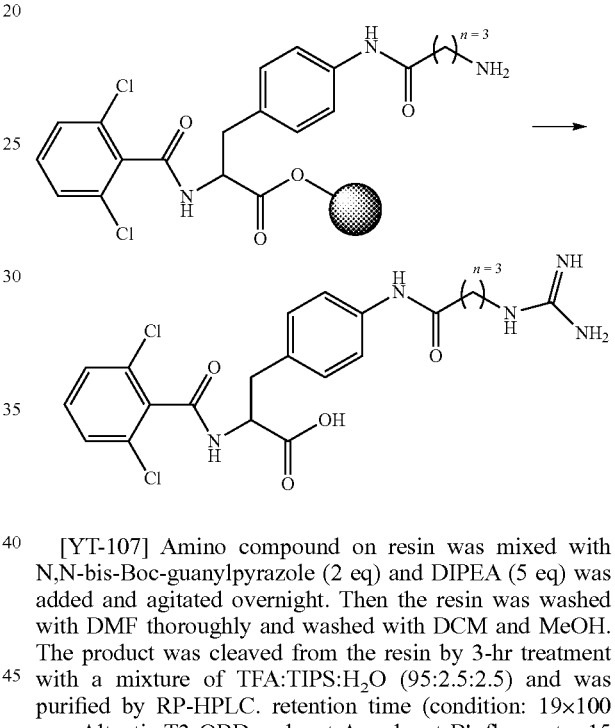

[YT-107] Amino compound on resin was mixed with N,N-bis-Boc-guanylpyrazole (2 eq) and DIPEA (5 eq) was added and agitated overnight. Then the resin was washed with DMF thoroughly and washed with DCM and MeOH. The product was cleaved from the resin by 3-hr treatment with a mixture of TFA:TIPS:H$_2$O (95:2.5:2.5) and was purified by RP-HPLC. retention time (condition: 19×100 mm Altantis T3 OBD, solvent A, solvent B', flow rate: 15 ml/min, gradient: 8% solvent B' for 3 min, 8% to 15% solvent B' for 1 min, 15% to 24% solvent B' for 30 min, detection: 254 nm) 16.14 min, m/z=480.3 (MH+)

TABLE 1

Table 5: IC$_{50}$ data of compounds

| Name | Structure of compound synthesized | Cell Adhesion Assay IC50 range (nM) A: below 100 nM B: 100 nM-10 μM |
|---|---|---|
| YT-43 | | B |

TABLE 1-continued

Table 5: IC$_{50}$ data of compounds

| Name | Structure of compound synthesized | Cell Adhesion Assay IC50 range (nM) A: below 100 nM B: 100 nM-10 μM |
|---|---|---|
| YT-103 | | A |
| YT-101 | | B |
| YT-107 | | B |
| YT-115 | | B |
| YT-119 | | A |
| HIJ-886 | | B |

TABLE 1-continued

Table 5: IC$_{50}$ data of compounds

| Name | Structure of compound synthesized | Cell Adhesion Assay IC50 range (nM) A: below 100 nM B: 100 nM-10 μM |
|---|---|---|
| HIJ-888 | | B |
| HIJ-889 | | A |
| HIJ-890 | | A |
| HIJ-891 | | B |
| HIJ-892 | | B |
| HU-899 | | A |

TABLE 1-continued
Table 5: IC$_{50}$ data of compounds
| Name | Structure of compound synthesized | Cell Adhesion Assay IC50 range (nM) A: below 100 nM B: 100 nM-10 μM |
|---|---|---|
| JM-39 | 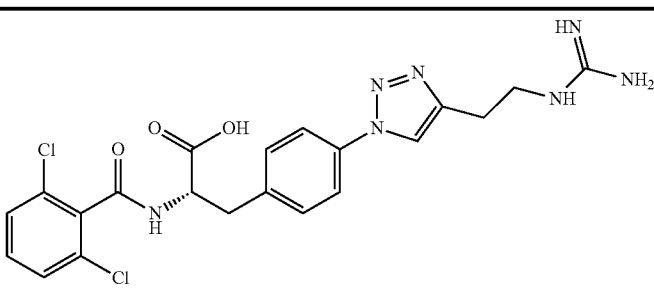 | B |
| JM-61 | 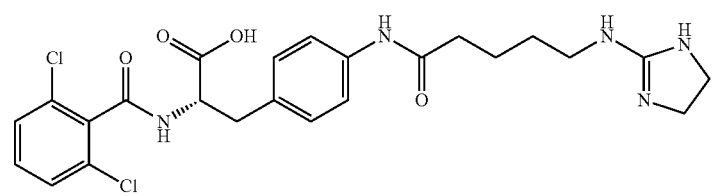 [SMILES: O=C(CCCCNC1=NCCN1)Nc1ccc(C[C@H](NC(=O)c2c(Cl)cccc2Cl)C(=O)O)cc1] | B |
| JM-141 | 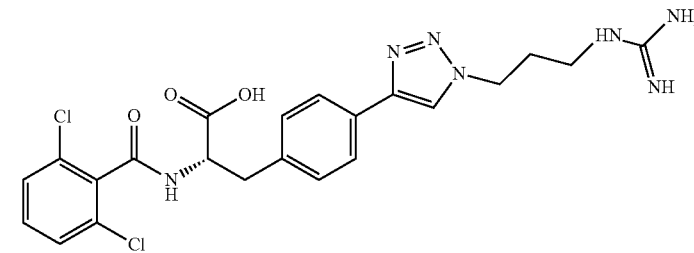 | A |
| JM-175 | 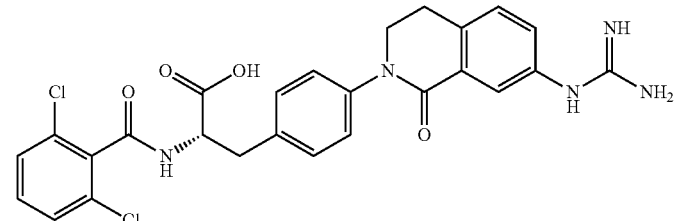 | B |
| JM-185 | 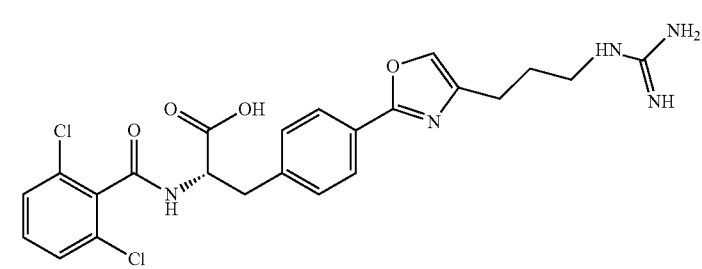 [SMILES: N=C(N)NCCCc1coc(-c2ccc(C[C@H](NC(=O)c3c(Cl)cccc3Cl)C(=O)O)cc2)n1] | B |
| JM-192 | 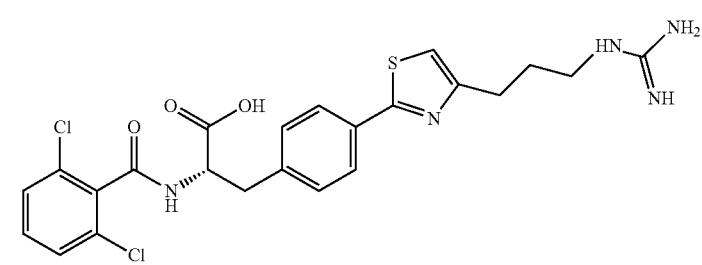 [SMILES: N=C(N)NCCCc1csc(-c2ccc(C[C@H](NC(=O)c3c(Cl)cccc3Cl)C(=O)O)cc2)n1] | B |

TABLE 1-continued

Table 5: IC$_{50}$ data of compounds

| Name | Structure of compound synthesized | Cell Adhesion Assay IC50 range (nM) A: below 100 nM B: 100 nM-10 μM |
|---|---|---|
| JM-230 | (structure) | B |

"A" indicates an IC$_{50}$ value in the Cell Adhesion Assay less than about 100 nM. "B" indicates an IC$_{50}$ value in the Cell Adhesion Assay between about 100 nM and about 10 μM.

TABLE 2

Compounds 12 (structure)

13 (structure)

14 (structure)

TABLE 2-continued
Compounds
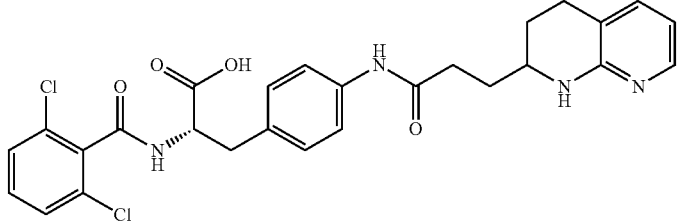 [SMILES: O=C(CCC1CCc2cccnc2N1)Nc1ccc(C[C@H](NC(=O)c2c(Cl)cccc2Cl)C(=O)O)cc1]
15
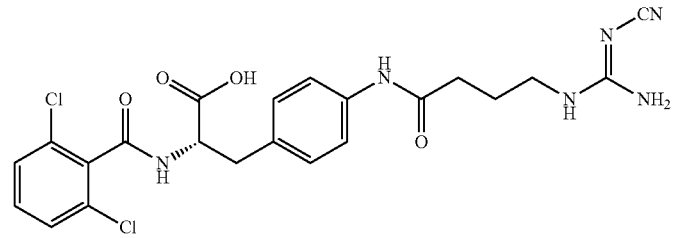 [SMILES: N#C/N=C(\N)NCCCC(=O)Nc1ccc(C[C@H](NC(=O)c2c(Cl)cccc2Cl)C(=O)O)cc1]
16
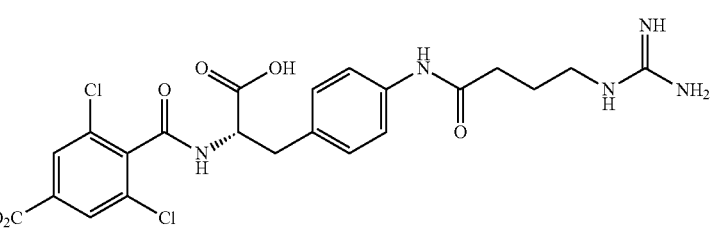
17
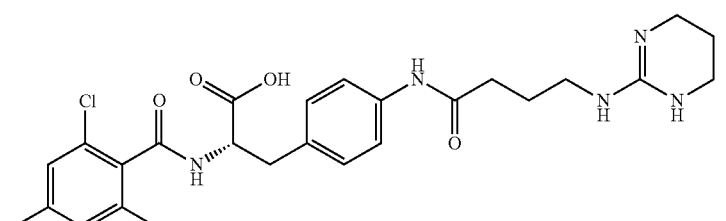
18
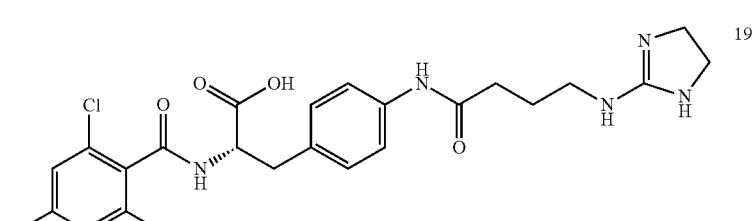
19
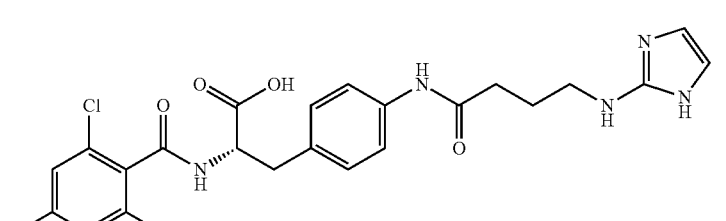
20

TABLE 2-continued
Compounds
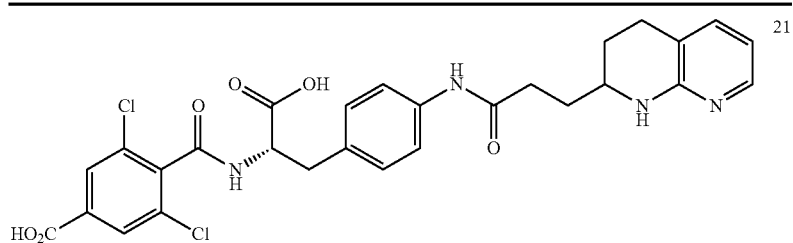
21
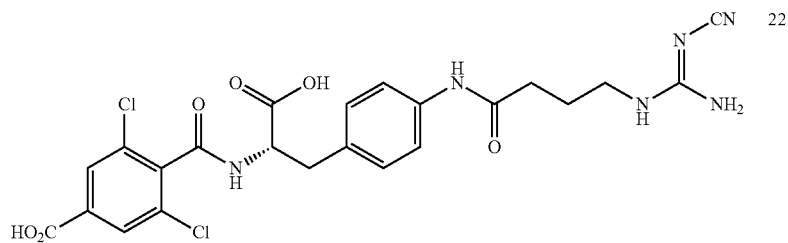
22
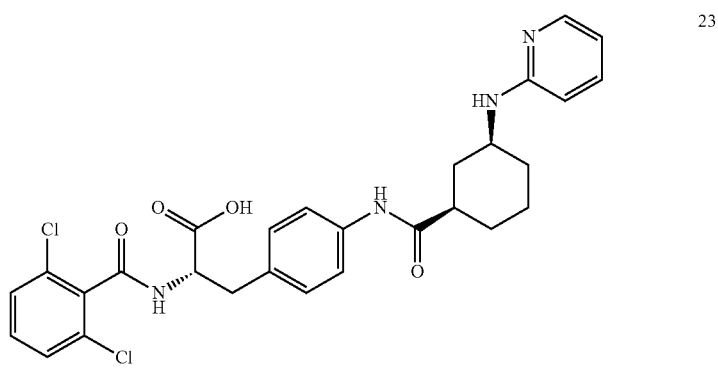
23
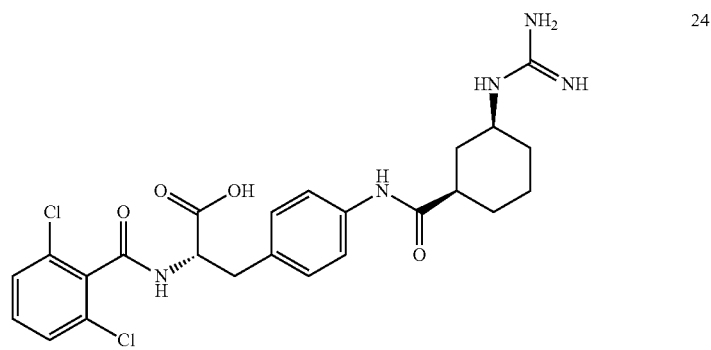
24
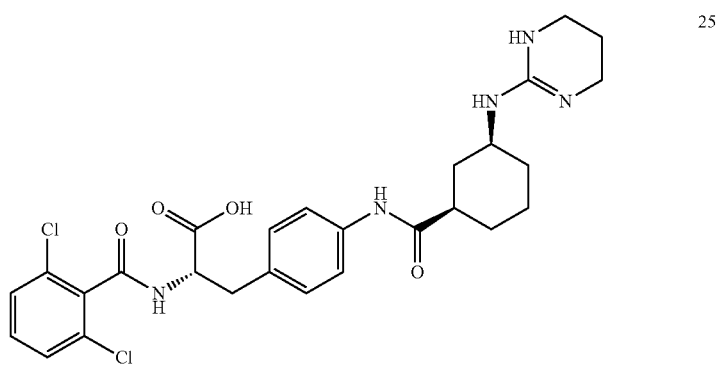
25

TABLE 2-continued
Compounds
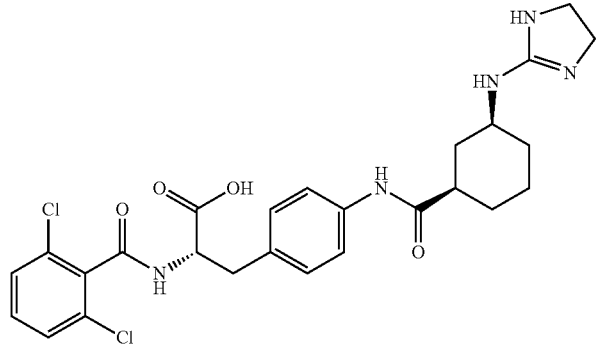 [SMILES: O=C(N[C@@H](Cc1ccc(NC(=O)[C@@H]2CCC[C@H](NC3=NCCN3)C2)cc1)C(=O)O)c1c(Cl)cccc1Cl] 26
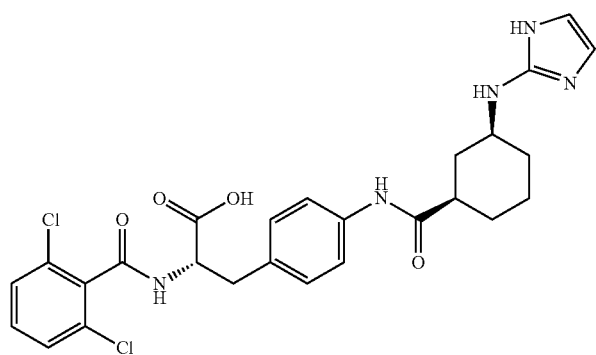 [SMILES: O=C(N[C@@H](Cc1ccc(NC(=O)[C@@H]2CCC[C@H](Nc3ncc[nH]3)C2)cc1)C(=O)O)c1c(Cl)cccc1Cl] 27
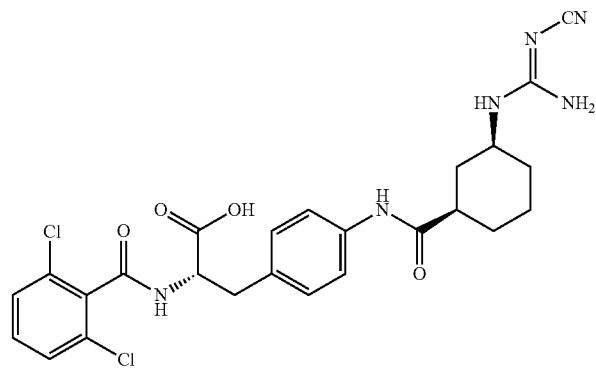 [SMILES: N#C/N=C(\N)N[C@H]1CCC[C@@H](C(=O)Nc2ccc(C[C@H](NC(=O)c3c(Cl)cccc3Cl)C(=O)O)cc2)C1] 28
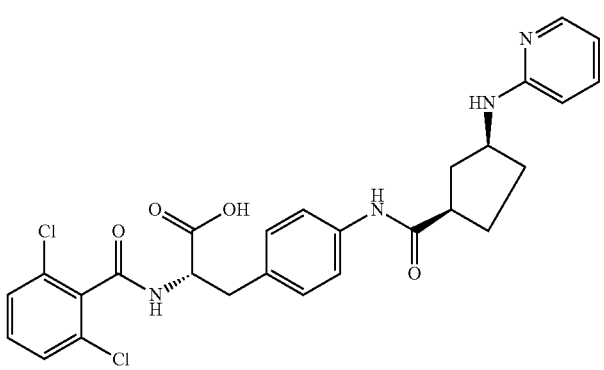 [SMILES: O=C(N[C@@H](Cc1ccc(NC(=O)[C@@H]2CC[C@H](Nc3ccccn3)C2)cc1)C(=O)O)c1c(Cl)cccc1Cl] 29

TABLE 2-continued
| Compounds | |
|---|---|
| 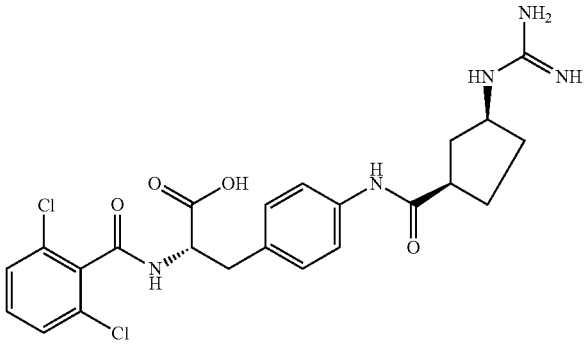 [SMILES: N=C(N)N[C@H]1CC[C@@H](C(=O)Nc2ccc(C[C@H](NC(=O)c3c(Cl)cccc3Cl)C(=O)O)cc2)C1] | 30 |
| 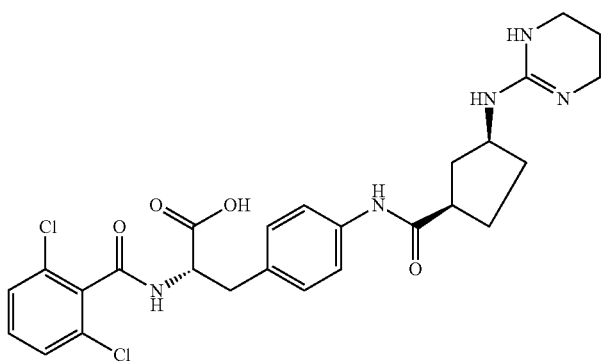 [SMILES: O=C(N[C@@H](Cc1ccc(NC(=O)[C@@H]2CC[C@H](NC3=NCCCN3)C2)cc1)C(=O)O)c1c(Cl)cccc1Cl] | 31 |
| 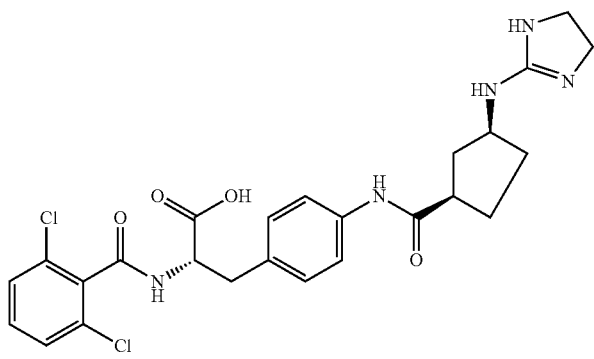 [SMILES: O=C(N[C@@H](Cc1ccc(NC(=O)[C@@H]2CC[C@H](NC3=NCCN3)C2)cc1)C(=O)O)c1c(Cl)cccc1Cl] | 32 |
| 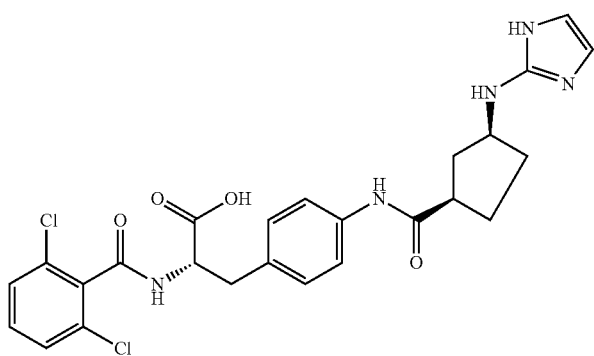 [SMILES: O=C(N[C@@H](Cc1ccc(NC(=O)[C@@H]2CC[C@H](Nc3ncc[nH]3)C2)cc1)C(=O)O)c1c(Cl)cccc1Cl] | 33 |

TABLE 2-continued

Compounds

| | |
|---|---|
| (structure) | 34 |
| (structure) | 35 |
| (structure) | 36 |
| (structure) | 37 |
| (structure) | 38 |

TABLE 2-continued
Compounds
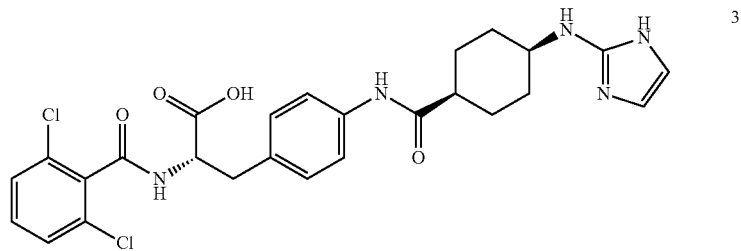 39
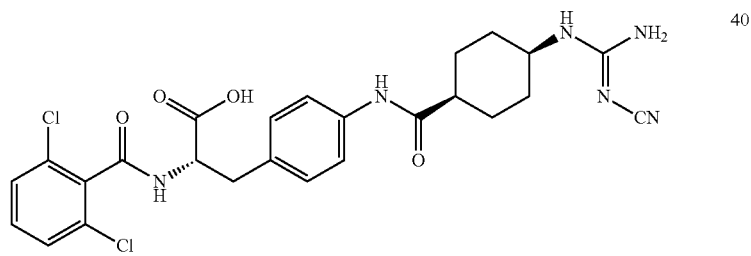 40
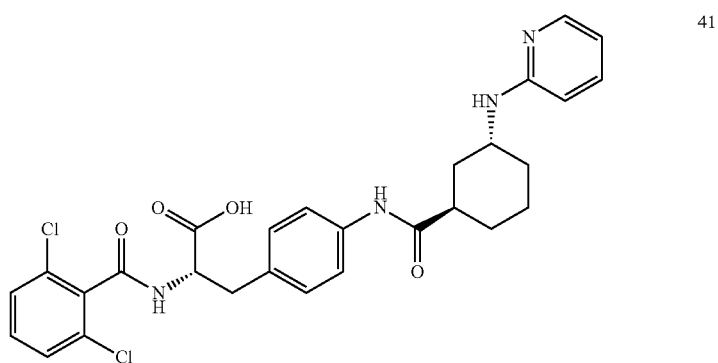 41
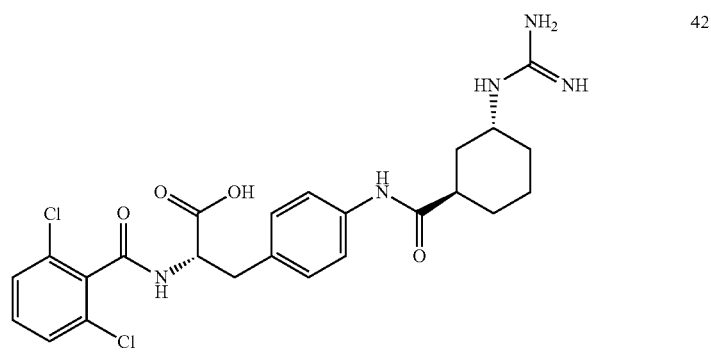 42
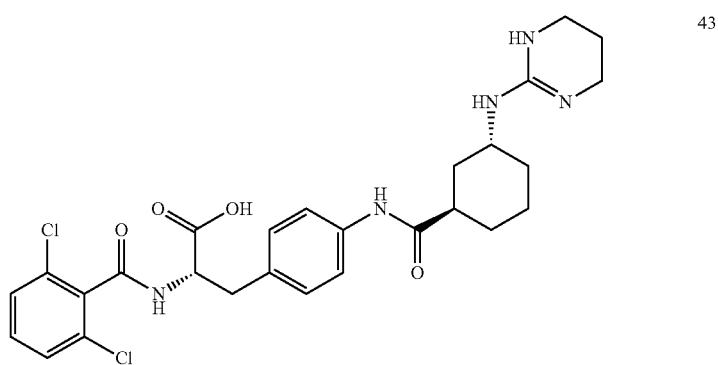 43

TABLE 2-continued
Compounds
44
45
46
47

TABLE 2-continued
Compounds
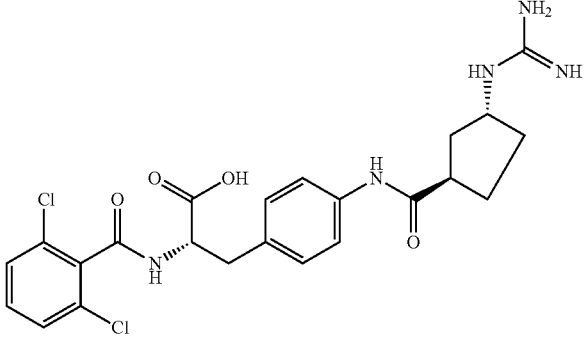 [SMILES: N=C(N)N[C@@H]1CC[C@@H](C(=O)Nc2ccc(C[C@H](NC(=O)c3c(Cl)cccc3Cl)C(=O)O)cc2)C1]
48
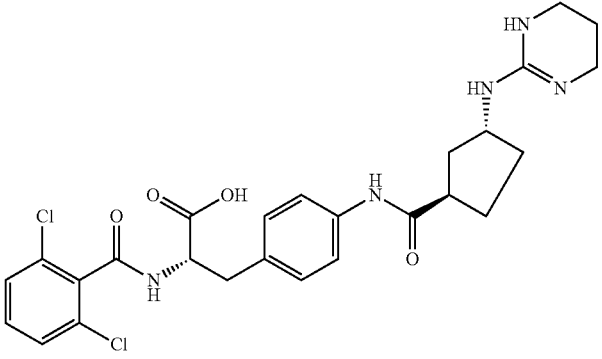 [SMILES: O=C(N[C@@H](Cc1ccc(NC(=O)[C@@H]2CC[C@@H](NC3=NCCCN3)C2)cc1)C(=O)O)c1c(Cl)cccc1Cl]
49
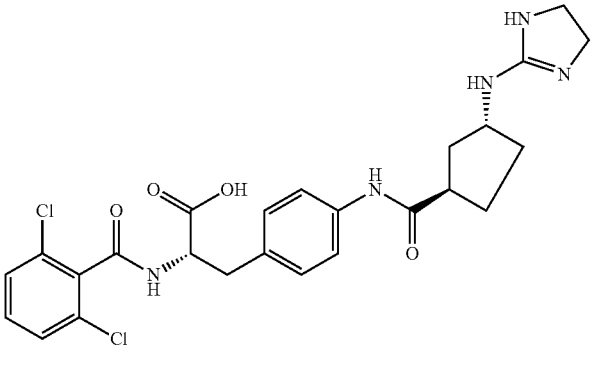 [SMILES: O=C(N[C@@H](Cc1ccc(NC(=O)[C@@H]2CC[C@@H](NC3=NCCN3)C2)cc1)C(=O)O)c1c(Cl)cccc1Cl]
50
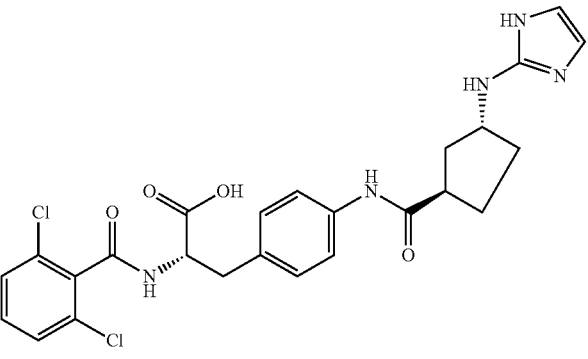 [SMILES: O=C(N[C@@H](Cc1ccc(NC(=O)[C@@H]2CC[C@@H](Nc3ncc[nH]3)C2)cc1)C(=O)O)c1c(Cl)cccc1Cl]
51

TABLE 2-continued

Compounds

| | |
|---|---|
| (structure) | 52 |
| (structure) | 53 |
| (structure) | 54 |
| (structure) | 55 |
| (structure) | 56 |

TABLE 2-continued
Compounds
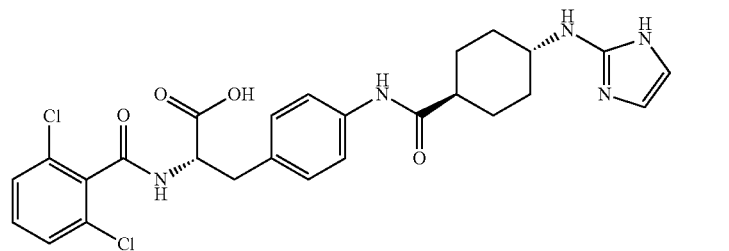 [SMILES: O=C(N[C@@H](Cc1ccc(NC(=O)[C@H]2CC[C@H](Nc3ncc[nH]3)CC2)cc1)C(=O)O)c1c(Cl)cccc1Cl]
57
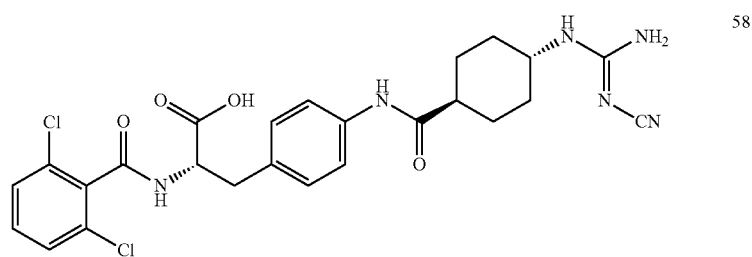
58
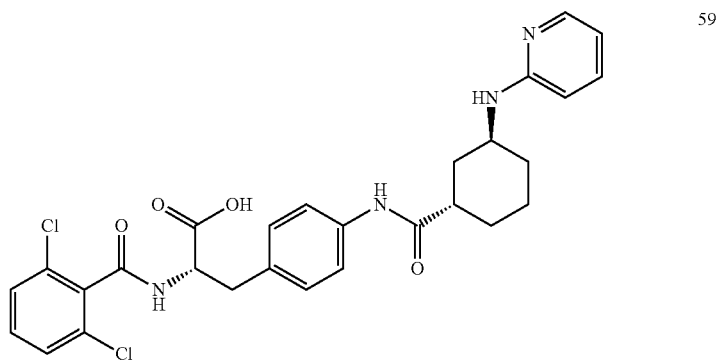
59
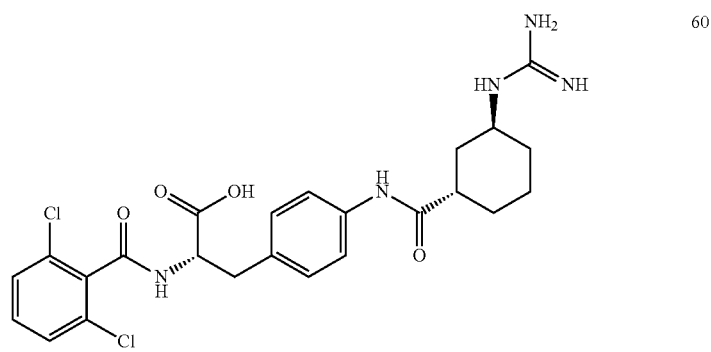
60
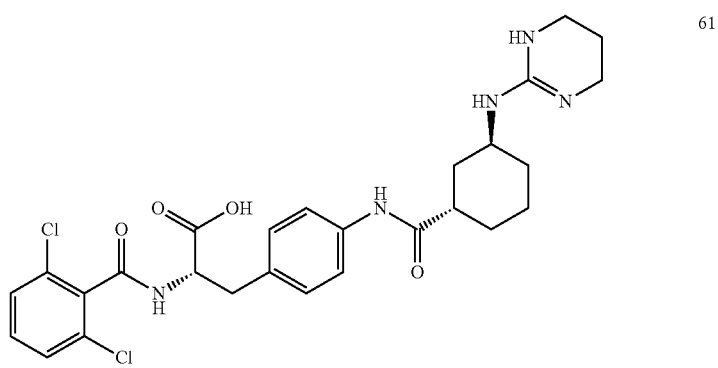
61

TABLE 2-continued

Compounds

62

63

64

65

TABLE 2-continued
Compounds
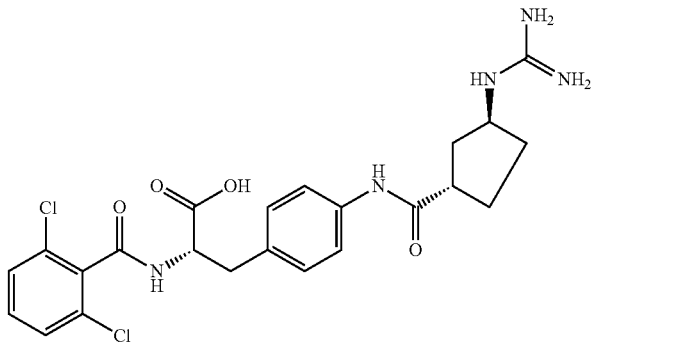 [SMILES: N=C(N)N[C@H]1CC[C@H](C(=O)Nc2ccc(C[C@H](NC(=O)c3c(Cl)cccc3Cl)C(=O)O)cc2)C1]
66
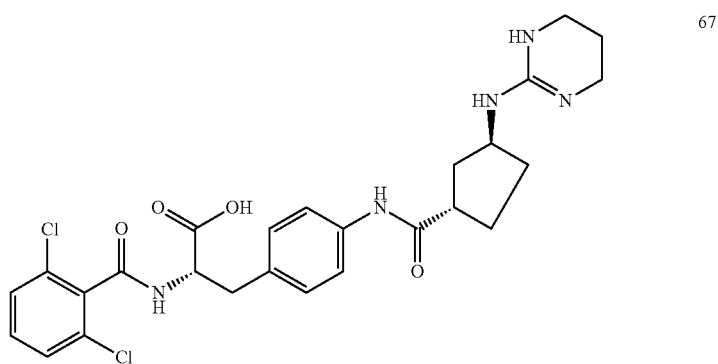
67
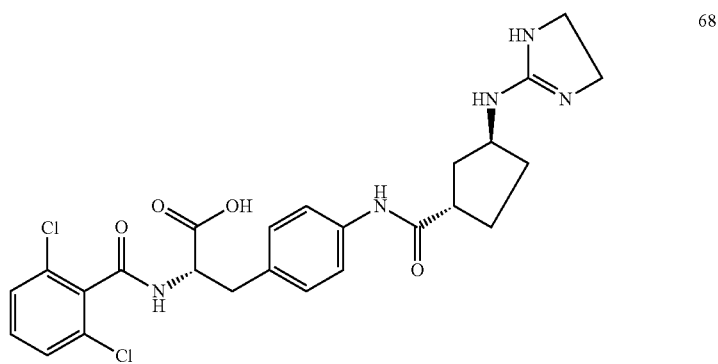
68
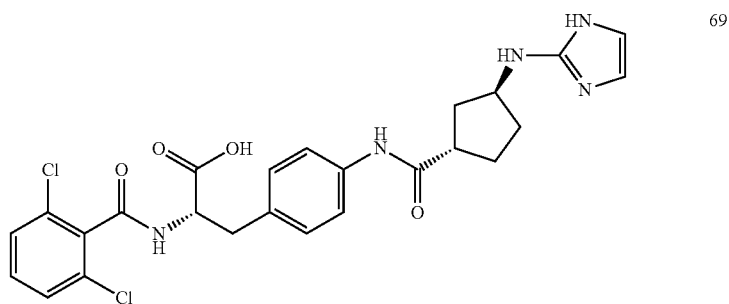
69

TABLE 2-continued
Compounds
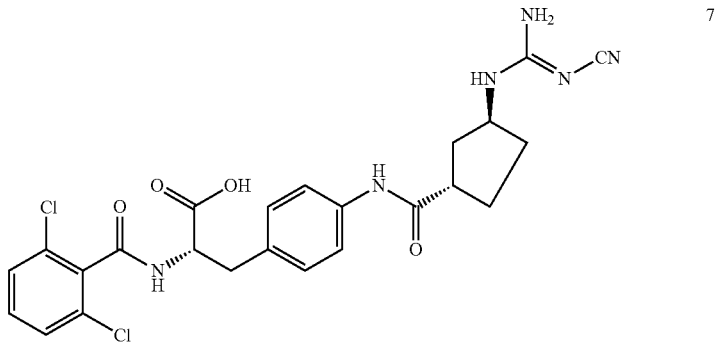
70
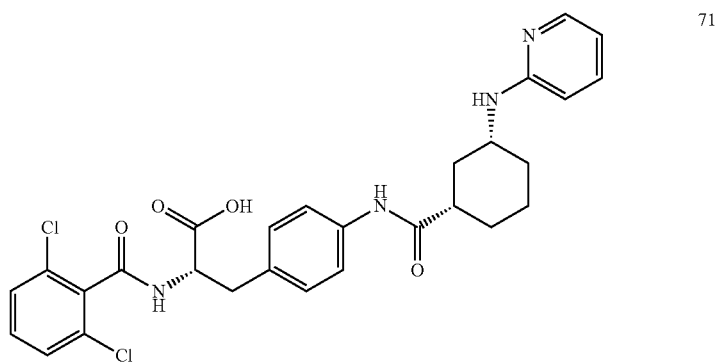
71
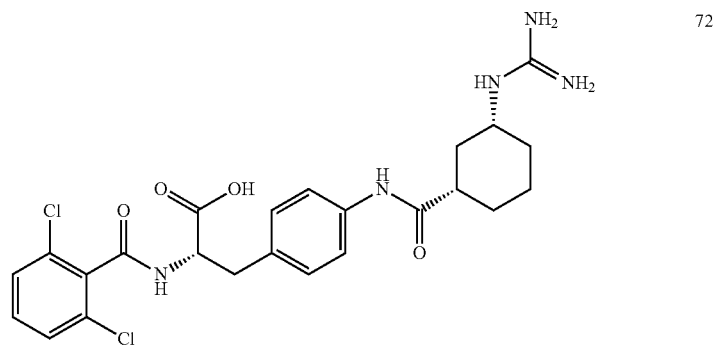
72
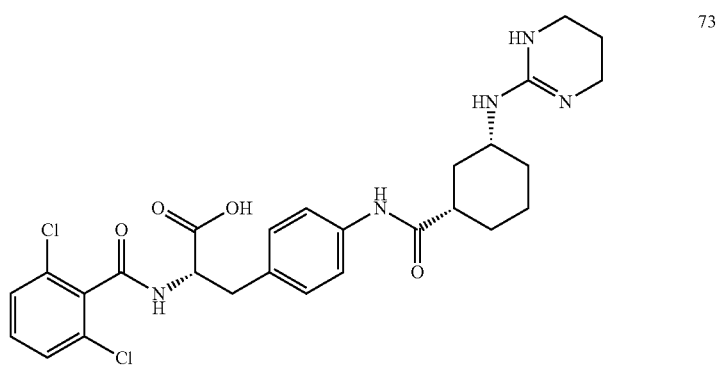
73

TABLE 2-continued
Compounds
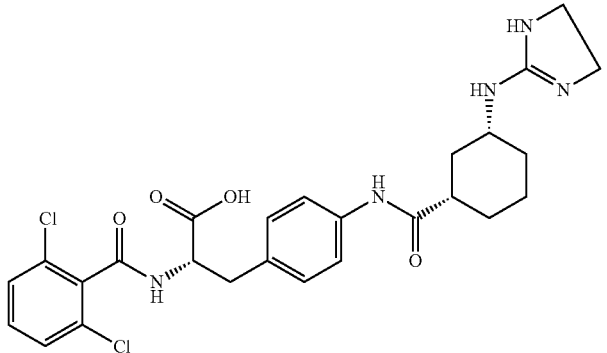 [SMILES: O=C(N[C@@H](Cc1ccc(NC(=O)[C@H]2CCC[C@@H](NC3=NCCN3)C2)cc1)C(=O)O)c1c(Cl)cccc1Cl]
74
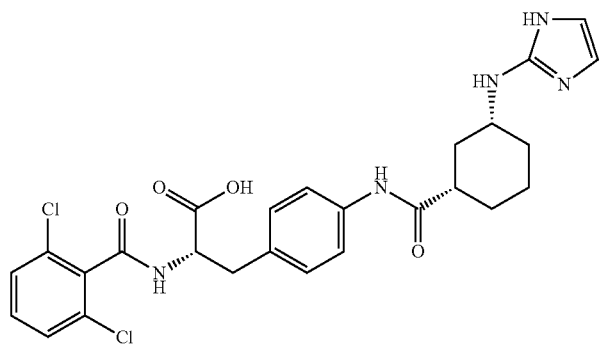 [SMILES: O=C(N[C@@H](Cc1ccc(NC(=O)[C@H]2CCC[C@@H](Nc3ncc[nH]3)C2)cc1)C(=O)O)c1c(Cl)cccc1Cl]
75
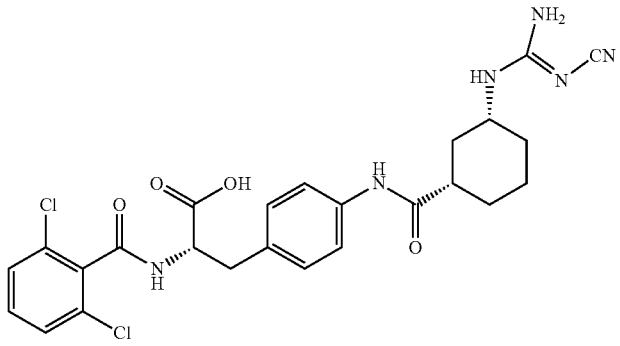 [SMILES: N#C/N=C(\N)N[C@@H]1CCC[C@H](C(=O)Nc2ccc(C[C@H](NC(=O)c3c(Cl)cccc3Cl)C(=O)O)cc2)C1]
76
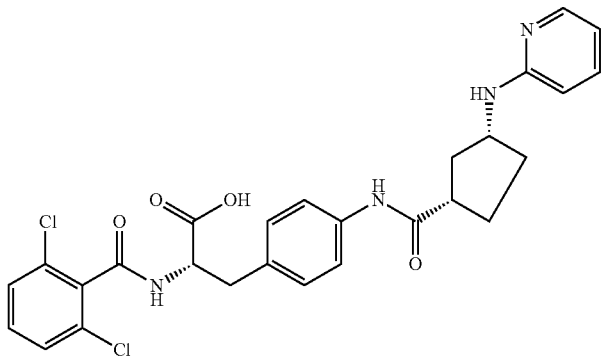 [SMILES: O=C(N[C@@H](Cc1ccc(NC(=O)[C@H]2CC[C@@H](Nc3ccccn3)C2)cc1)C(=O)O)c1c(Cl)cccc1Cl]
77

TABLE 2-continued
Compounds
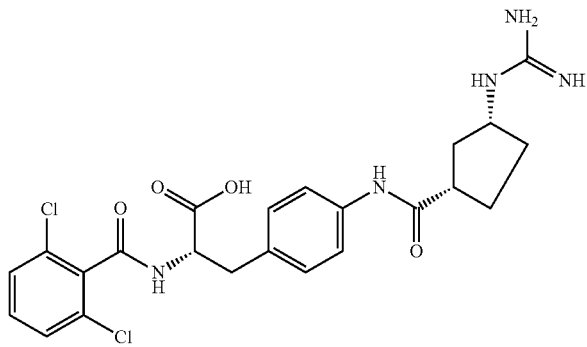 [SMILES: N=C(N)N[C@@H]1CC[C@H](C(=O)Nc2ccc(C[C@H](NC(=O)c3c(Cl)cccc3Cl)C(=O)O)cc2)C1]
78
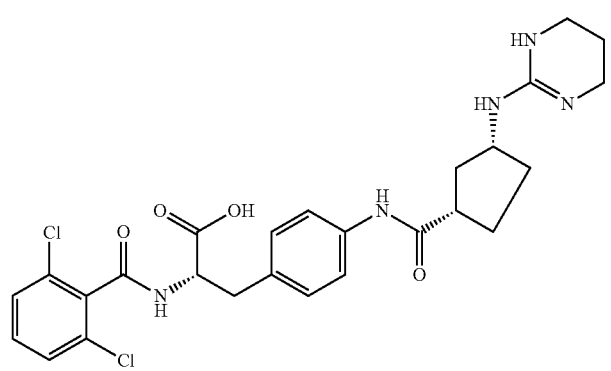 [SMILES: O=C(N[C@@H](Cc1ccc(NC(=O)[C@H]2CC[C@@H](NC3=NCCCN3)C2)cc1)C(=O)O)c1c(Cl)cccc1Cl]
79
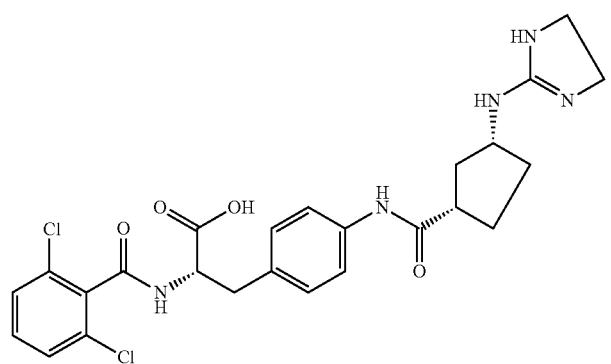 [SMILES: O=C(N[C@@H](Cc1ccc(NC(=O)[C@H]2CC[C@@H](NC3=NCCN3)C2)cc1)C(=O)O)c1c(Cl)cccc1Cl]
80
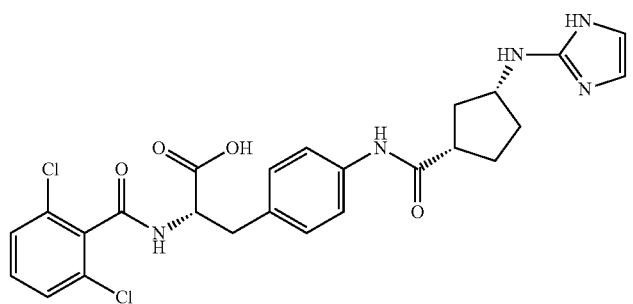 [SMILES: O=C(N[C@@H](Cc1ccc(NC(=O)[C@H]2CC[C@@H](Nc3ncc[nH]3)C2)cc1)C(=O)O)c1c(Cl)cccc1Cl]
81

TABLE 2-continued

Compounds 82, 83, 84, 85, 86, 87 (chemical structures)

TABLE 2-continued

| Compounds |
|---|
| 88 (structure) |
| 89 (structure) |
| 90 (structure) |
| 91 (structure) |
| 92 (structure) |
| 93 (structure) |

TABLE 2-continued
Compounds
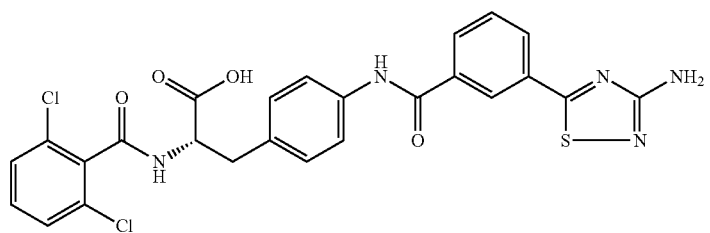 [SMILES: Nc1noc(-c2cccc(C(=O)Nc3ccc(C[C@H](NC(=O)c4c(Cl)cccc4Cl)C(=O)O)cc3)c2)n1]
94
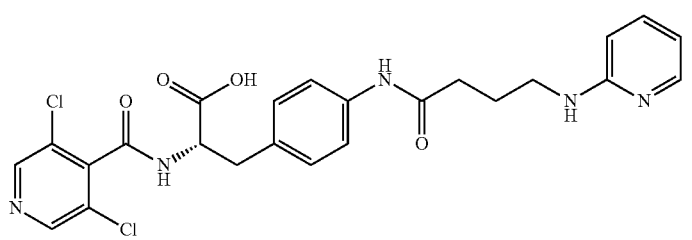 [SMILES: O=C(CCCNc1ccccn1)Nc1ccc(C[C@H](NC(=O)c2c(Cl)cncc2Cl)C(=O)O)cc1]
95
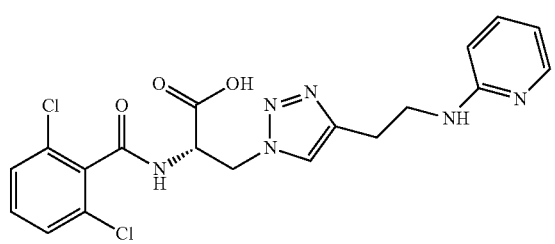 [SMILES: O=C(N[C@@H](Cn1cc(CCNc2ccccn2)nn1)C(=O)O)c1c(Cl)cccc1Cl]
96
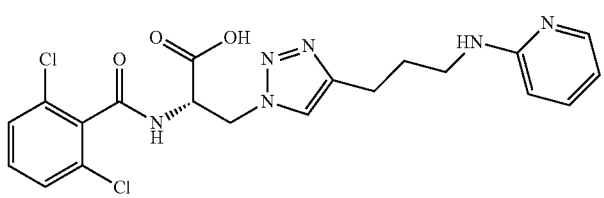 [SMILES: O=C(N[C@@H](Cn1cc(CCCNc2ccccn2)nn1)C(=O)O)c1c(Cl)cccc1Cl]
97
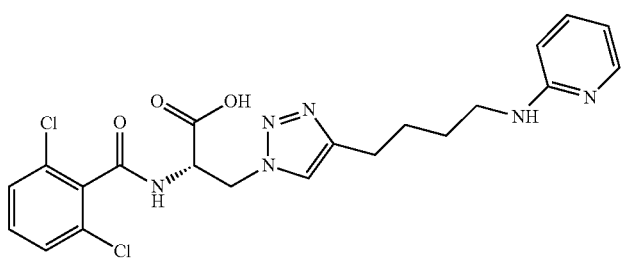 [SMILES: O=C(N[C@@H](Cn1cc(CCCCNc2ccccn2)nn1)C(=O)O)c1c(Cl)cccc1Cl]
98
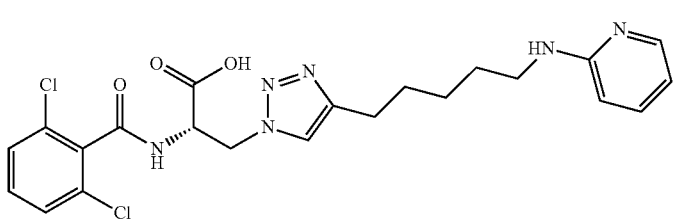 [SMILES: O=C(N[C@@H](Cn1cc(CCCCCNc2ccccn2)nn1)C(=O)O)c1c(Cl)cccc1Cl]
99

TABLE 2-continued
Compounds
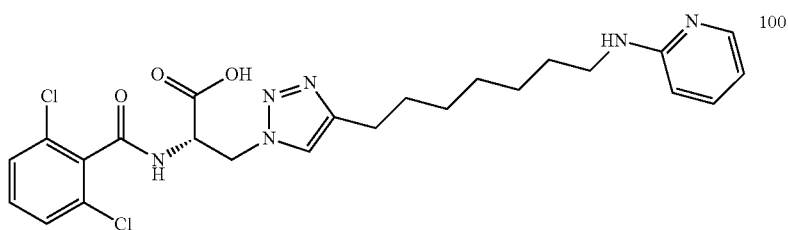
100
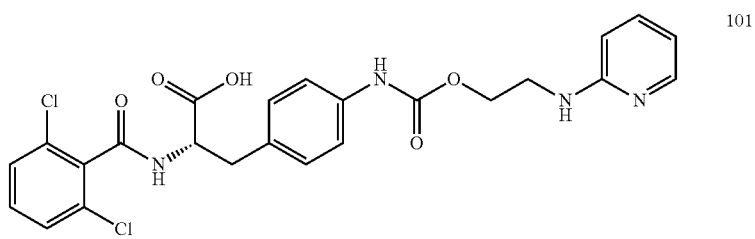
101
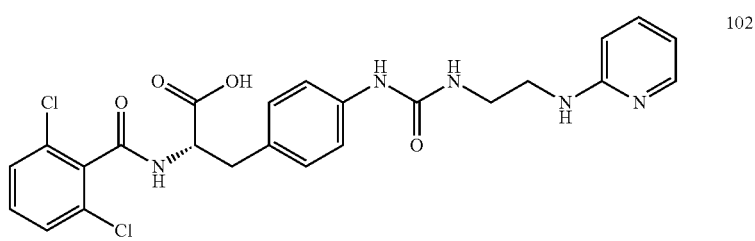
102
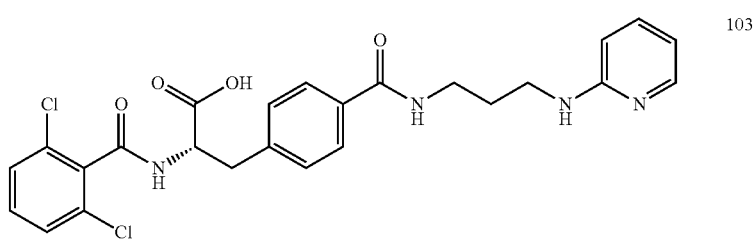
103
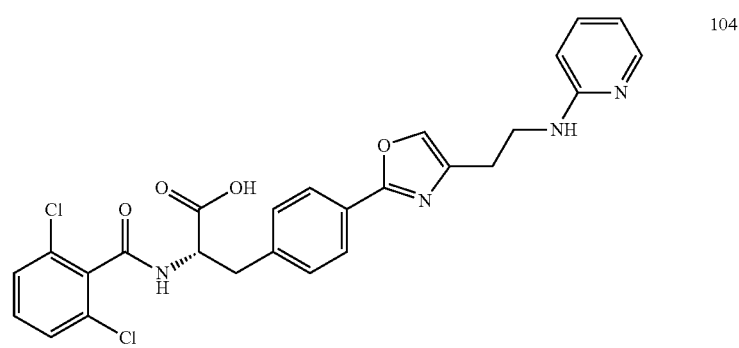
104

TABLE 2-continued
Compounds
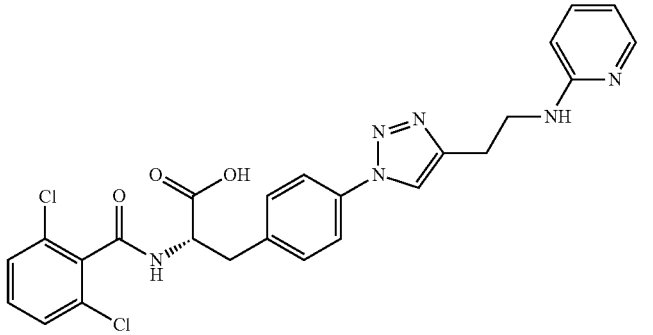 [SMILES: O=C(N[C@@H](Cc1ccc(-n2cc(CCNc3ccccn3)nn2)cc1)C(=O)O)c1c(Cl)cccc1Cl]
105
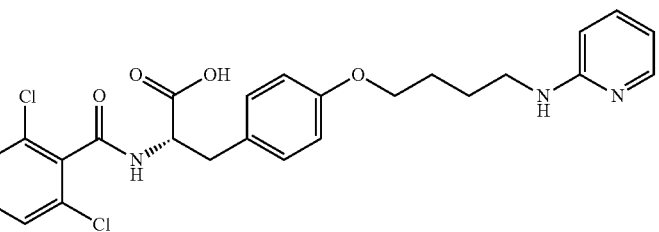
106
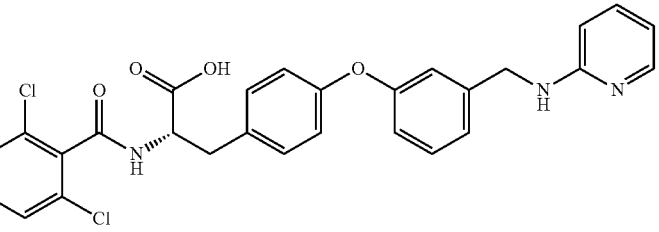
107
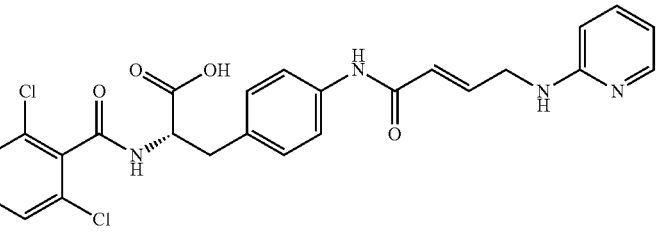
108
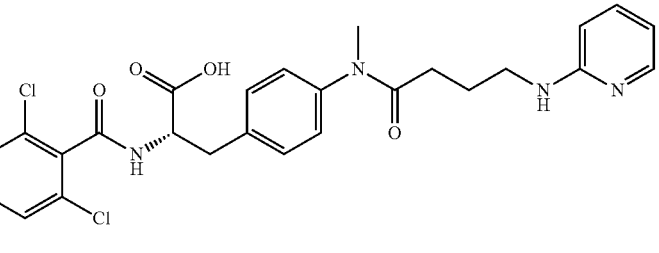
109
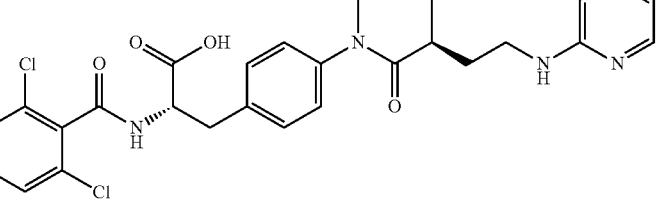
110

TABLE 2-continued
Compounds
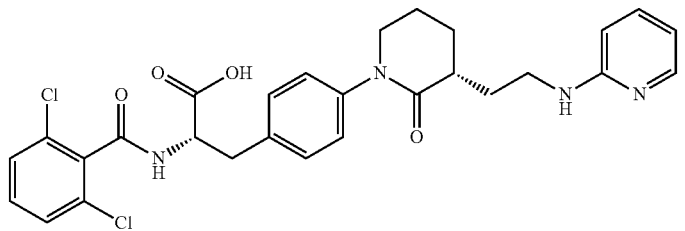 [SMILES: O=C(N[C@@H](Cc1ccc(N2CCC[C@H](CCNc3ccccn3)C2=O)cc1)C(=O)O)c1c(Cl)cccc1Cl]
111
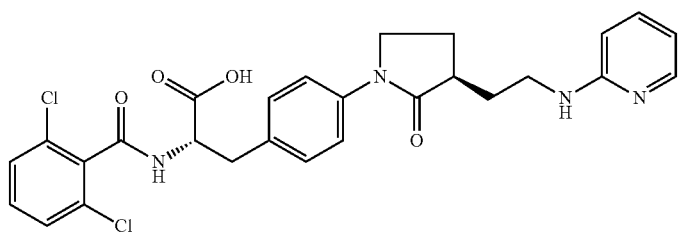 [SMILES: O=C(N[C@@H](Cc1ccc(N2CC[C@@H](CCNc3ccccn3)C2=O)cc1)C(=O)O)c1c(Cl)cccc1Cl]
112
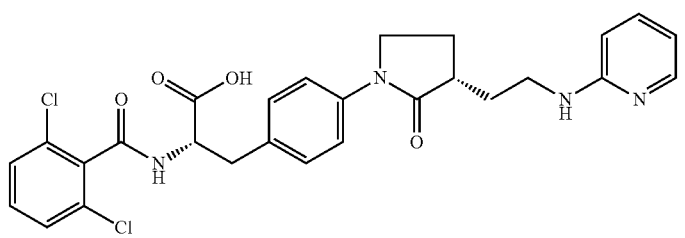 [SMILES: O=C(N[C@@H](Cc1ccc(N2CC[C@H](CCNc3ccccn3)C2=O)cc1)C(=O)O)c1c(Cl)cccc1Cl]
113
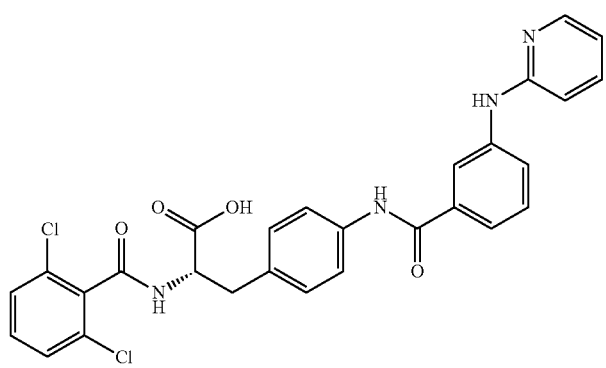 [SMILES: O=C(Nc1ccc(C[C@H](NC(=O)c2c(Cl)cccc2Cl)C(=O)O)cc1)c1cccc(Nc2ccccn2)c1]
114
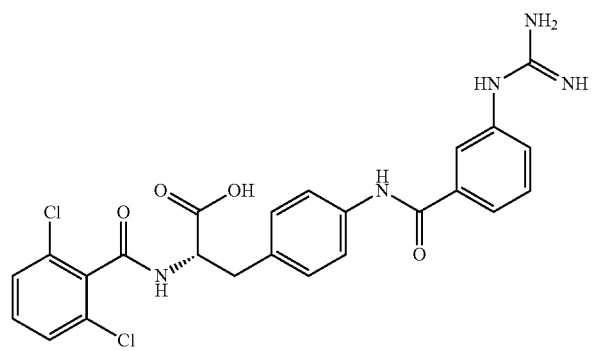 [SMILES: N=C(N)Nc1cccc(C(=O)Nc2ccc(C[C@H](NC(=O)c3c(Cl)cccc3Cl)C(=O)O)cc2)c1]
115

TABLE 2-continued
Compounds
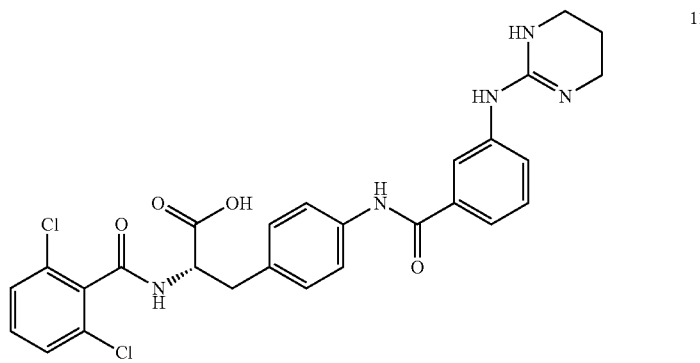 116
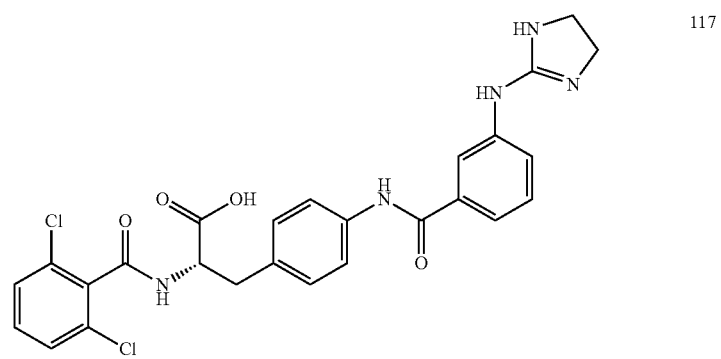 117
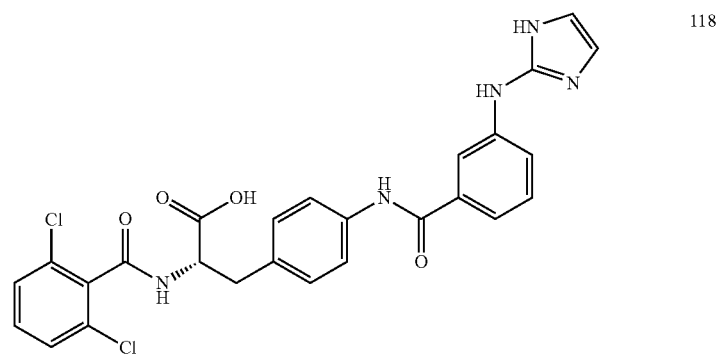 118
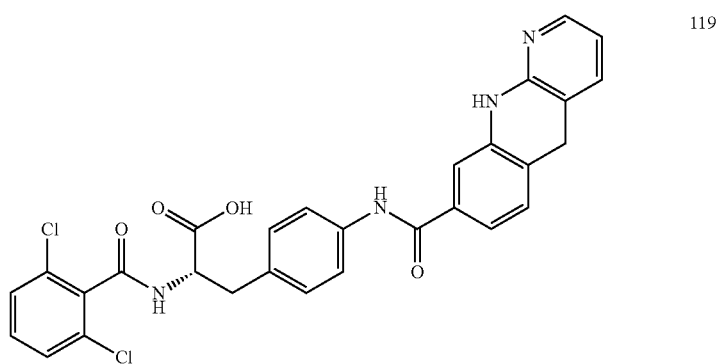 119

TABLE 2-continued
Compounds
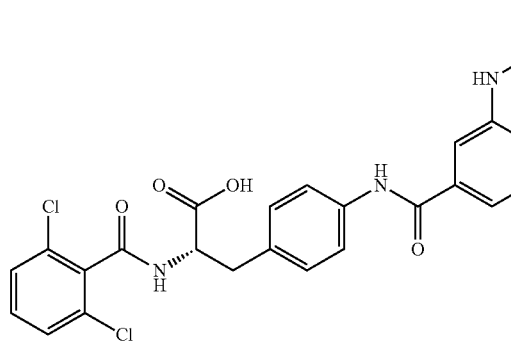
120
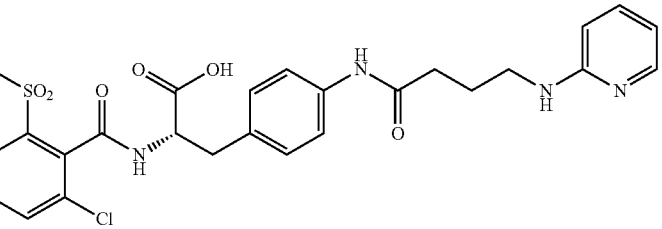
121
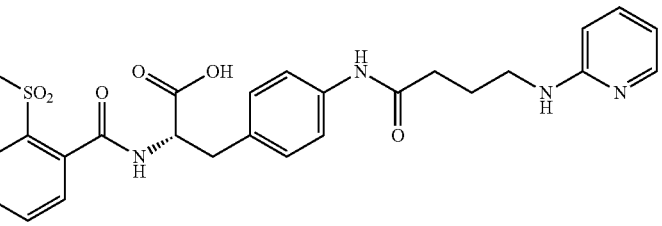
122
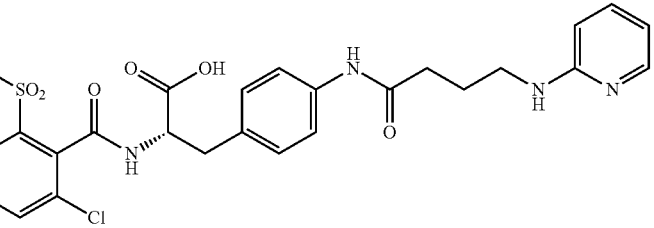
123
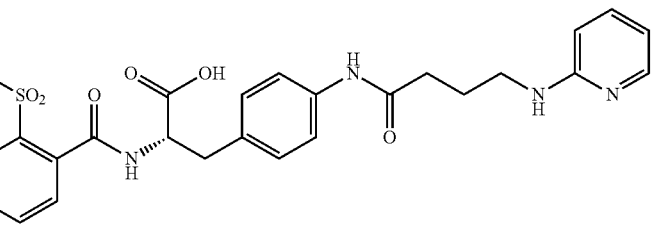
124
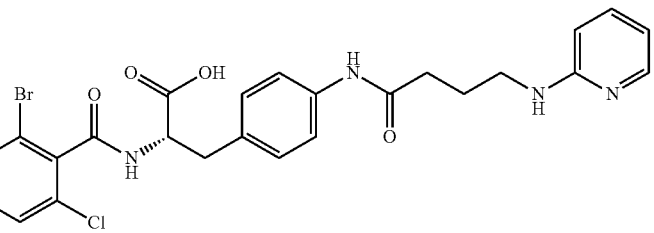
125

TABLE 2-continued

Compounds

TABLE 2-continued
Compounds
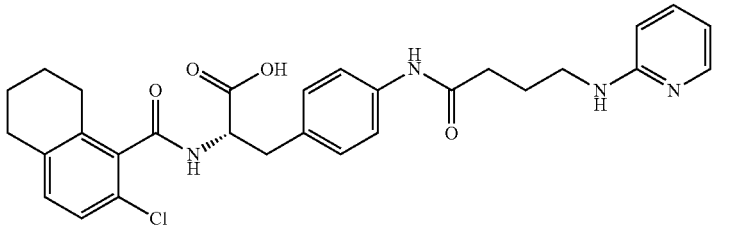 [SMILES: O=C(CCCNc1ccccn1)Nc1ccc(C[C@H](NC(=O)c2c(Cl)ccc3c2CCCC3)C(=O)O)cc1]
132
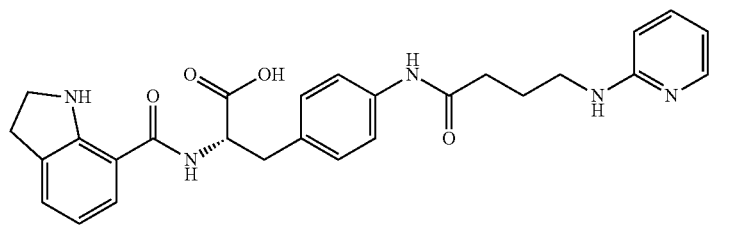 [SMILES: O=C(CCCNc1ccccn1)Nc1ccc(C[C@H](NC(=O)c2cccc3c2NCC3)C(=O)O)cc1]
133
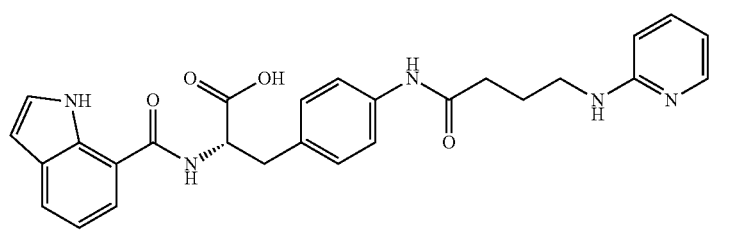 [SMILES: O=C(CCCNc1ccccn1)Nc1ccc(C[C@H](NC(=O)c2cccc3cc[nH]c23)C(=O)O)cc1]
134
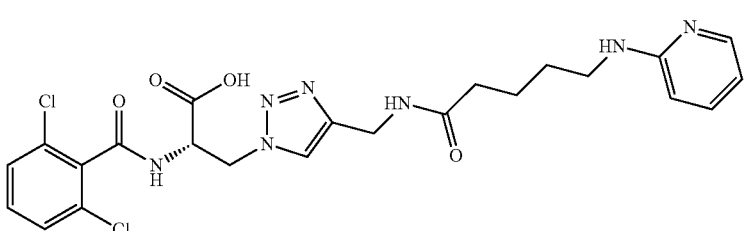
135
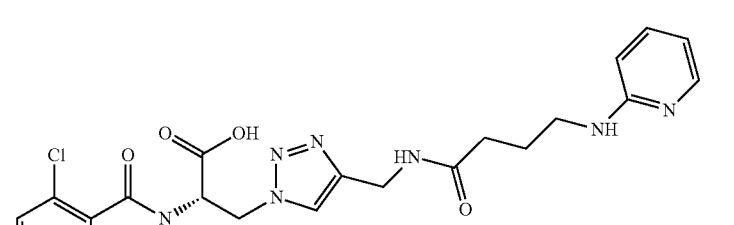
136
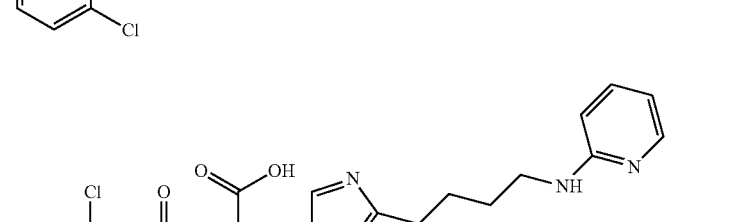
137

TABLE 2-continued
Compounds
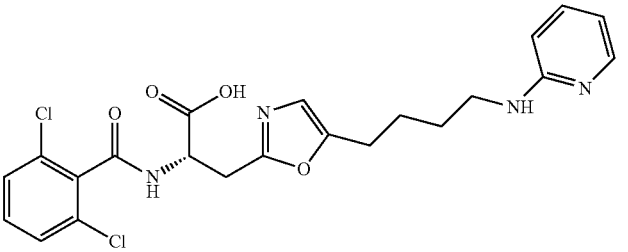 [SMILES: O=C(N[C@@H](Cc1ncc(CCCCNc2ccccn2)o1)C(=O)O)c1c(Cl)cccc1Cl]
138
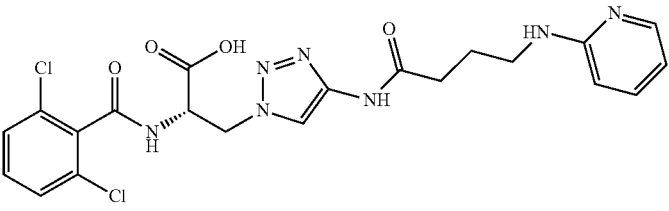 [SMILES: O=C(CCCNc1ccccn1)Nc1cn(C[C@H](NC(=O)c2c(Cl)cccc2Cl)C(=O)O)nn1]
139
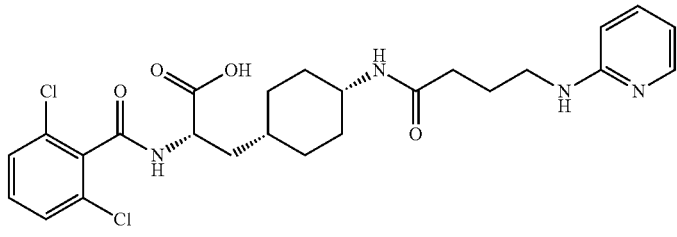 [SMILES: O=C(CCCNc1ccccn1)N[C@H]1CC[C@@H](C[C@H](NC(=O)c2c(Cl)cccc2Cl)C(=O)O)CC1]
140
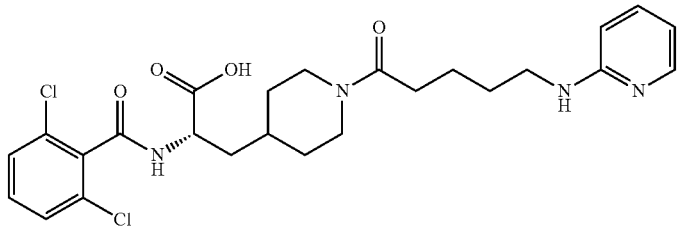 [SMILES: O=C(N[C@@H](CC1CCN(C(=O)CCCCNc2ccccn2)CC1)C(=O)O)c1c(Cl)cccc1Cl]
141
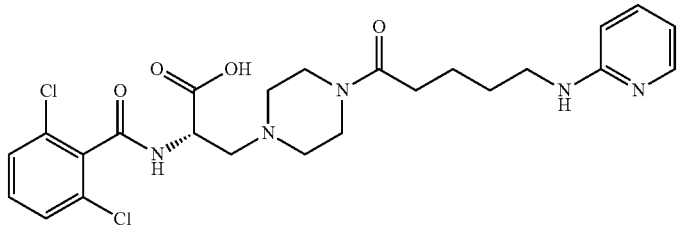 [SMILES: O=C(N[C@@H](CN1CCN(C(=O)CCCCNc2ccccn2)CC1)C(=O)O)c1c(Cl)cccc1Cl]
142
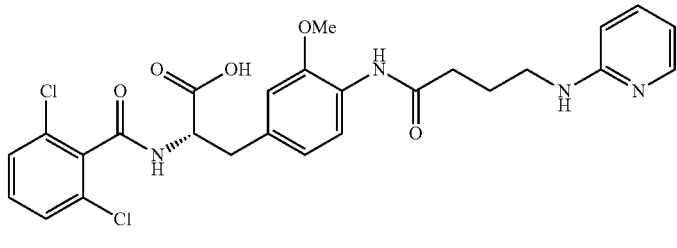 [SMILES: COc1cc(C[C@H](NC(=O)c2c(Cl)cccc2Cl)C(=O)O)ccc1NC(=O)CCCNc1ccccn1]
143

TABLE 2-continued
Compounds
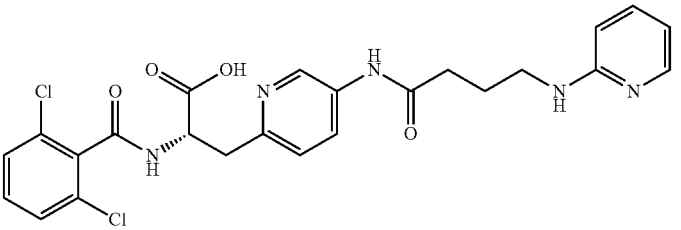 [SMILES: O=C(CCCNc1ccccn1)Nc1ccc(C[C@H](NC(=O)c2c(Cl)cccc2Cl)C(=O)O)nc1]
144
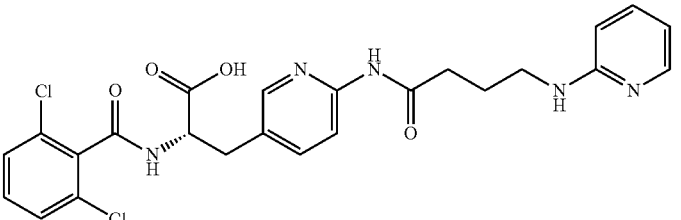
145
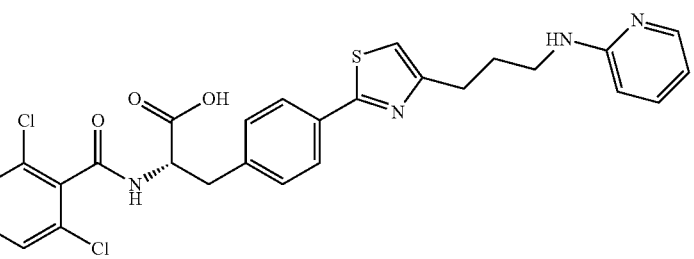
146
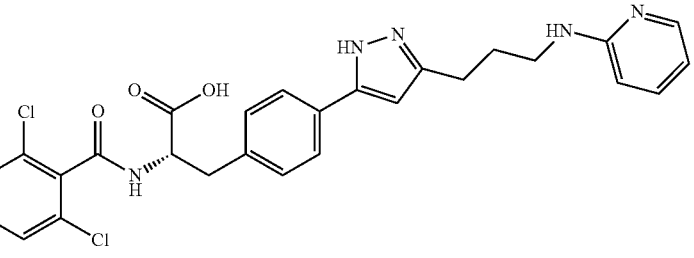
147
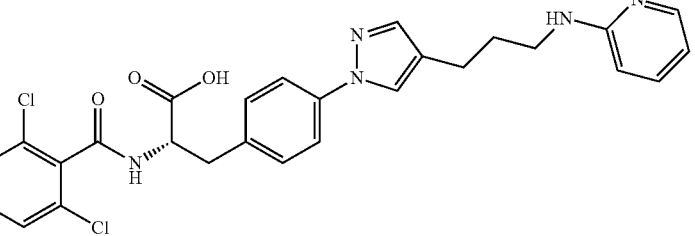
148
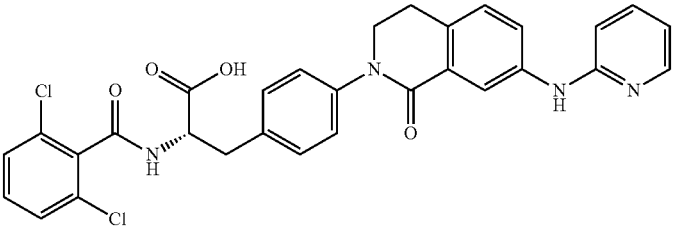 [SMILES: O=C(N[C@@H](Cc1ccc(N2CCc3ccc(Nc4ccccn4)cc3C2=O)cc1)C(=O)O)c1c(Cl)cccc1Cl]
149

TABLE 2-continued
Compounds
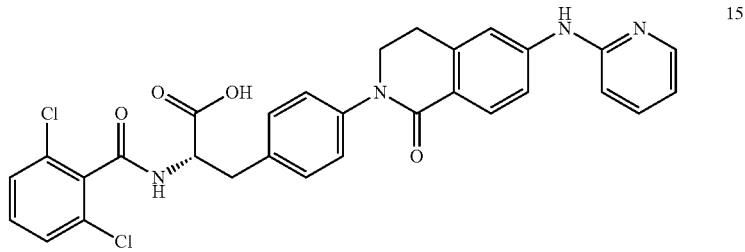
150
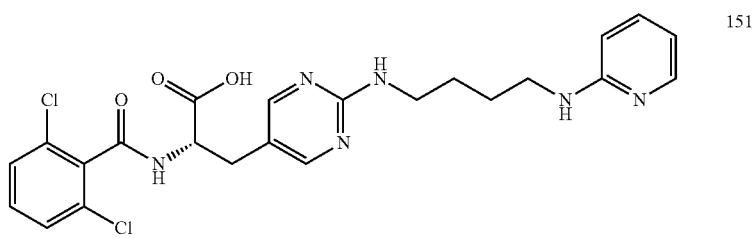
151
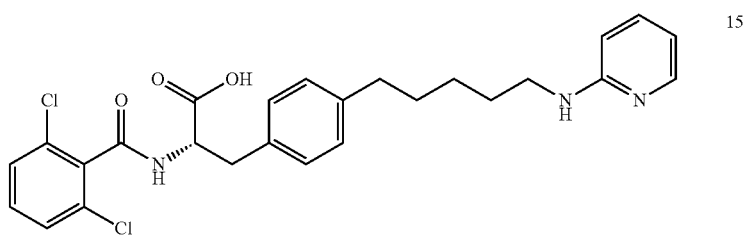
152
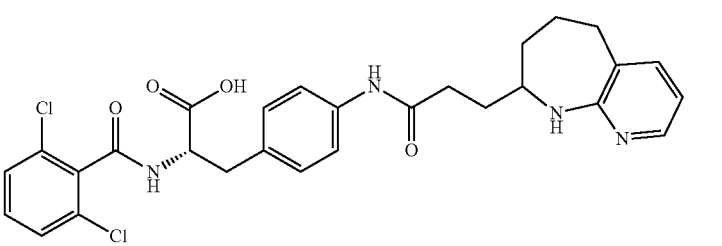 [SMILES: O=C(CCC1CCCc2cccnc2N1)Nc1ccc(C[C@H](NC(=O)c2c(Cl)cccc2Cl)C(=O)O)cc1]
153
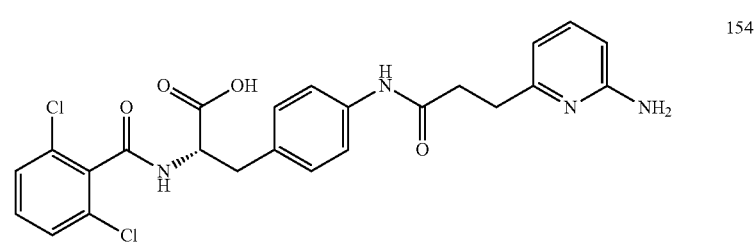
154
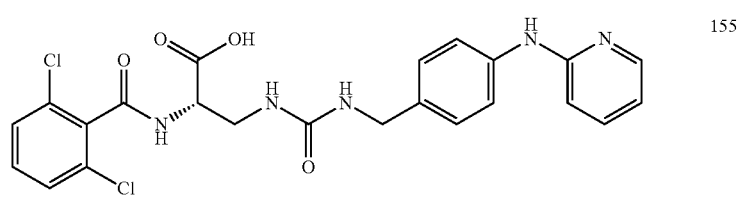
155

TABLE 2-continued

Compounds

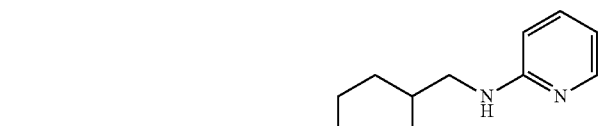

156

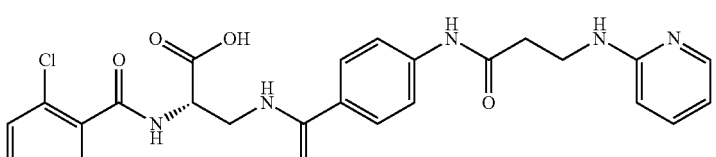

157

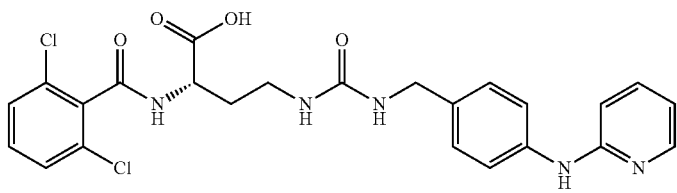 [SMILES: O=C(NCC[C@H](NC(=O)c1c(Cl)cccc1Cl)C(=O)O)NCc1ccc(Nc2ccccn2)cc1]

158

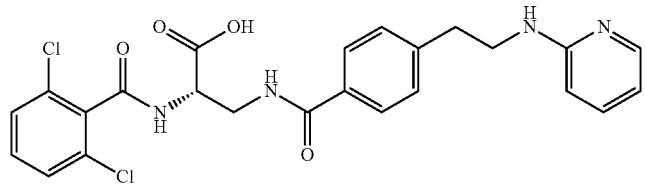 [SMILES: O=C(NC[C@H](NC(=O)c1c(Cl)cccc1Cl)C(=O)O)c1ccc(CCNc2ccccn2)cc1]

159

Example 2

Fibrosis models Lung and liver fibrosis are induced as described previously [1, 2]. For $CCl_4$—Induced liver fibrosis, mice are injected intraperitoneally (i.p.) with 1 ul/g body weight sterile $CCl_4$ in a 1:3 ratio with olive oil or olive oil (control), twice weekly for six weeks. ALZET osmotic pumps (Durect, Cupertino, Calif.) are inserted after three weeks of treatment to deliver either a compound described herein or an inactive control small molecule, each dissolved in 50% DMSO (in sterile water) and administered at a dose of 70 mg/kg/day. Livers are harvested 24 hours after the last $CCl_4$ injection. For bleomycin-induced lung fibrosis, 3 U/kg bleomycin (bleo) or water (control) are administered by direct airway intubation with a microsprayer (PennCentury, city). ALZET osmotic pumps are inserted 14 days after treatment, as above and lungs are harvested at 28 days [1].

Primary Cell Isolation

Primary mouse lung fibroblasts are isolated from 4-12 day old mice using a previously reported method, with minor modifications [3]. Mice lungs are removed, pooled together and digested in enzyme solution for total 1 h with removal of dispersed cells every 10 minutes. The enzyme solution consist of Hanks buffered salt solution (HBSS, without Ca or Mg) with 0.3 mg/ml of type I collagenase (Sigma), and 0.5 mg/ml of trypsin (Sigma) in a shaking water bath maintained at 37° C. After each digestion interval, dispersed cells are passed through a sterile filter (70 m) into DMEM-Ham's F-12 media (Sigma), 10% fetal bovine serum, and undigested lung tissue placed in fresh enzyme solution. Once digestion is complete, erythrocytes are lysed at room temperature 10 min using red blood cell lysing buffer (Sigma). Then, the cells are pelleted by centrifugation, and cultured in DMEM medium with 10% fetal bovine serum, 1% penicillin/streptomycin in 100 mm tissue culture dishes. The nonadherent cells are aspirated, and the adherent fibroblast were grown in culture. Primary murine hepatic stellate cells are isolated and passaged as described previously [1]. Mouse liver are perfused through the inferior vena cava sequentially with liver perfusion media (Invitrogen). 0.3% pronase (Roche) and 0.02% collagenase (Sigma). The liver is excised and minced with scissors and further digested in 0.044% pronase and 0.008% DNAse (Roche). The cell suspension are shaken (200-250 rpm) at 37° C. for 10 minutes and strained through a sterile filter (70 μm). To remove hepatocytes the cell suspension are centrifuged at 90×g for 2 minutes, the supernatant collected, DNAse added and this procedure is repeated twice. The supernatant are centrifuged at 700×g for 7 minutes to collect the non-parenchymal cell fraction. Collected cells are re-suspended in 10 ml of complete DMEM (10% fetal bovine serum, 1% penicillin/streptomycin) and allowed to differentiate in culture into myofibroblasts before use.

Hydroxyproline Assay

Mouse lung, liver, and kidney tissue are homogenized with trichloroacetic acid and incubated overnight at 110° C. in HCl. Samples are reconstituted in water, and hydroxyproline content is measured using the chloramine T assay [4].

Immunoprecipitation and Western Blotting

Cells are lysed in RIPA buffer (50 mM Tris-HCL, ph 7.4, 10 mM MgCl2, 125 mM NaCl, 2% NP-40), cell lysates are centrifuged at 14,000 rpm for ten minutes at 4° C. and the supernatant collected. 10 µg of anti-αv antibody (for human fibroblast L230, and for murine fibroblast RMV-7, is added to the supernatant and this is rotated at 4° C. for two hours, followed by the addition of 30 µl of prewashed protein G sepharose slurry (GE Healthcare) for one hour at 4° C. The beads are washed three times with PBS/protease inhibitor mixture, and once with PBS only. Laemmli sample buffer is added and the samples are boiled for five minutes followed by SDS-PAGE and western blotting using the following antibodies: αv integrin 611012, 1:500 (BD Biosciences), β1 integrin 04-11-09, 1:500 (Millipore).

TGFB Activation Assay

Test cells are plated at 50K cells/well in 96-well plates together with mink lung epithelial cells expressing firefly luciferase downstream of the TGFβ 3 sensitive portion of the plasminogen activator inhibitor 1 promoter (15K cells/well) [1]. Cells are co-cultured for 16 hours and TGFβ activity is calculated by measurement of luminescence in the presence and absence of TGFβ-blocking antibody, 1D11.

Integrin-Specific Adhesion Assays

The effects of compounds on cell adhesion mediated by α5β1, α8β1, αvβ1, αvβ3, αvβ5, αvβ6, and αvβ8 are measured using pairs of cell lines and ligands selected to isolate the effect of each individual integrin. For α5β1 we utilize the colon carcinoma cell line, SW480, plated on 0.3 µg/ml fibronectin, for α8β1, we utilize SW480 cells transfected with human α8 adhering to 1 µg/ml recombinant TGFβ1 LAP [5], for αvβ1 we use Chinese Hamster Ovary Cells (CHO cells) transfected with human αv adhering to 0.3 µg/ml fibronectin [6], for αvβ3 we use SW480 cells transfected with human β3, for αvβ5 we use wild type SW480 cells adhering to 0.1 µg/ml vitronectin. For αvβ6 we use SW480 cells transfected with human β6 adhering to 0.01 µg/ml recombinant human TGFβ1 LAP. For αvβ8 we use glioma cell line (SNB19) expressing β8 adhering to 1 µg/ml recombinant human TGFβ1 LAP.

The effects of the compound on cell adhesion mediated by αvβ1 integrin were measured using Chinese Hamster Ovary Cells (CHO cells) transfected with human αv adhering to 0.3 µg/ml fibronectin. In every case, we confirmed that adhesion could be inhibited by blocking antibodies to αv and β1. Cells were resuspended in DMEM for 30 min at 4° C. with 10-fold dilutions of the compound with a starting concentration of 10 µM. Each sample was then added to triplicate wells of a 96-well plate which had been coated overnight at 4° C. with the relevant ligand, washed, blocked by 1 hr incubation with 1% BSA, and washed again. Cells were allowed to attach for 30-60 min at 37° C. After incubation, non-adherent cells were removed by discarding the media and spinning the plate top-side down at 500 rpm for 5 minutes. Cells were then fixed and stained with 40 ul of 0.5% Crystal violet, 1% Formaldehyde, 20% Methanol for 30 minutes and lysed with 2% Trition-X. Absorbance was measured at 595 nm in a Microplate reader. For all assays, concentration-response curves were constructed by non-linear regression analysis and $IC_{50}$ values using Graphpad PRISM (ver 6.0).

Tissue Staining

Paraffin-embedded sections are processed as described previously [1]. 5 µM sections are stained Hematoxylin and Eosin or with picrosirius red. Pictures are taken from random fields from each section, at a final magnification of 10×. Staining area is calculated by pixel counting with NIH image J. For florescence microscopy, fixed livers and lungs are transferred to 30% sucrose in PBS overnight, embedded in OCT, then cryosectioned at 5 µm. Cryosections are permeabilized and blocked with 0.3% Triton X-100 and 3% BSA in PBS. Sections are incubated with primary antibodies (rabbit anti-phospho-Smad3 Epitomics, 1880-1, 1:100; rat anti-PDGFRb eBiosciences 14-1402, 1:100) overnight at 4° C., then with fluorophore-conjugated secondary antibodies (Invitrogen). Confocal imaging is performed on a Zeiss LSM5 Pascal microscope. Phospho-Smad immunofluorescent staining was quantified as described [7].

Statistics

All data are presented as mean±S.E.M unless otherwise noted. Statistical significance is calculated using a one way analysis of variance and Tukey test to determine post-hoc significance between individual groups. p-values are defined using Student's t test for paired comparisons. Differences with a P value of less than 0.05 are considered statistically significant.

Example 3

Fibrosis is a pathologic process, characterized by overproduction of extracellular matrix (ECM) as a response to tissue injury. Nearly 45% of all deaths in the developed world can be attributed to some type of chronic fibroproliferative disease (1, 2). Despite their high prevalence, current therapeutic options for fibrotic diseases are quite limited to elimination of triggering stimuli and organ transplantation. No effective agent exists that can directly halt the disease progression at the cellular level, which represents a major unmet medical need. However, our understanding of fibrogenesis has rapidly grown for the last two decades to shed light on new therapeutic targets in the vast complexity of fibrogenesis pathways (3-10). Cellular damage triggers the recruitment of inflammatory cells, which in turn secrete cytokines that induce the accumulation of activated fibroblasts. These so-called myofibroblasts are key executors of fibrosis as they are the main producers of collagen and other ECM. The origin of myofibroblasts is still under debate (11) but it is generally agreed that transforming growth factor beta (TGFβ) plays a role as a central pro-fibrotic factor in fibroblast activation and differentiation to myofibroblasts. TGFβ is secreted as a latent form and requires integrin binding to be fully active, which suggests that inhibition of integrin binding to the latent TGFβ complex is a promising therapeutic target.

Integrins are a family of transmembrane receptors consisting of two non-covalently bound α and β subunits (12, 13). In the process of fibroblast activation, there is a positive feedback loop between TGFβ and αv integrins (14, 15). In fact, epithelium-derived αvβ6 integrin is known to directly activate TGFβ in pulmonary fibrosis, and an αvβ6 blocking antibody is currently in phase II clinical trials for pulmonary fibrosis (16-18). In contrast to αvβ6 which is restricted to the epithelium, other αv integrins (αvβ1, αvβ3, αvβ5 and αvβ8) are expressed in myofibroblasts in many organs. Despite the fact that myofibroblasts are responsible for the majority of ECM production, little is known concerning the role of these αv integrins in fibrosis. We produced mice lacking all αv integrins on myofibroblasts (αv f/f PDGFRPβ Cre+) and found they are protected from CCl4-induced liver fibrosis. These mice are also protected from renal fibrosis induced by unilateral ureteral obstruction and pulmonary fibrosis induced by bleomycin. However, global deletion of αvβ3 or αvβ5 or fibroblast-specific deletion of αvβ8 (mice with global β8 deletion die in utero) did not protect against hepatic fibrosis. These results strongly suggest that hepatic protection is mostly due to the loss of αvβ1 integrin. However, experimental validation to identify the critical role of αvβ1 integrin in fibrosis poses a very challenging problem: it is not possible to study the in vivo role of αvβ1 using knockout mice since mice lacking β1 on myofibroblasts do not survive. Effective blocking monoclonal antibodies against αvβ1 integrin are not available, either. Thus pharmacological modulation of αvβ1 integrin by small molecules is a very attractive route to test the role of αvβ1 integrin in tissue fibrosis.

Given that 16 of 24 integrins contain either an αv chain or β1 chain, it is important to develop potent, selective αvβ1 integrin inhibitors. These molecules can be used to probe the role of αvβ1 integrin in tissue fibrosis as well as other diseases. In preliminary studies we prepared a small series of αvβ1 antagonists by combining fragments known to target the αv and β1 subunits based on our earlier published studies (19, 20).

Select compounds inhibit TGFβ activation by cultured liver myofibroblasts, whereas antibodies that block αvβ3, αvβ5 and αvβ8 do not. Encouraged by these data, we will conduct in-depth studies of cell adhesion inhibition mediate by all RGD-binding integrins. We will also initiate extensive structure-activity relationships (SAR) to obtain a panel of small molecules with the greatest potency and selectivity against αvβ1. The best compound thus identified will be tested in cell-based assays as well as a mouse liver fibrosis model as described below. In addition, large-scale preparation will be pursued to ensure a sufficient supply for animal studies.

αvβ1 integrin inhibition is effective in cell adhesion assay/mouse liver fibrosis model: Inhibitors are tested in cell adhesion assay to test their potency/selectivity. A panel of cell lines and integrin ligands were developed to allow rapid examination of potency and specificity of inhibitors against all 8 integrins that recognize RGD sequences in ligands. A subset of these are used to generate the data. These cell lines are used to calculate $IC_{50}$ concentrations for each inhibitor synthesized to rapidly generate structure activity information to drive subsequent modification and synthesis. Inhibitors are evaluated for showing better potency/selectivity in $CCl_4$-induced liver fibrosis. A general inhibitor of αv integrins can reverse fibrosis in this model when administered as a continuous subcutaneous infusion (from Alzet pumps) beginning 3 weeks after $CCl_4$ initiation. However, global inhibition of all αv integrins is likely to cause unacceptable side effects. We will therefore take a similar approach for each of the most promising αvβ1 inhibitors herein, using Alzet pumps to administer the inhibitor, or an inactive relative, to groups of 10 mice treated with either vehicle or $CCl_4$ 3× weekly for 6 weeks. As above, pumps will be inserted after 3 weeks of CCl4 treatment. Small molecules that are effective will be further tested in the UUO model of renal fibrosis and the bleomycin model of pulmonary fibrosis. Again we will examine therapeutic rather than prophylactic efficacy by beginning treatment in each model after the onset of fibrosis.

Example 4

Solid phase synthesis schematic for synthesis of compounds described herein.

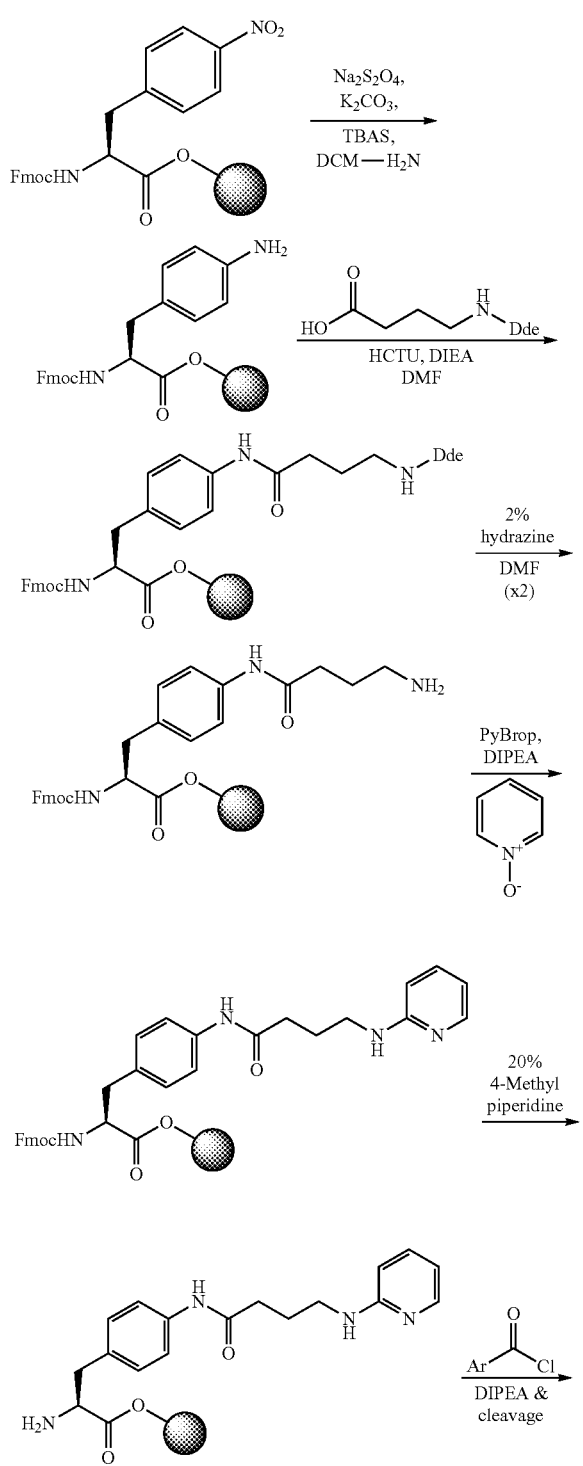

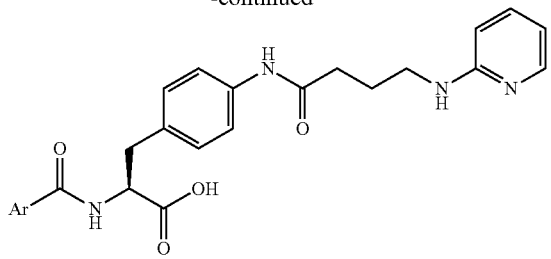

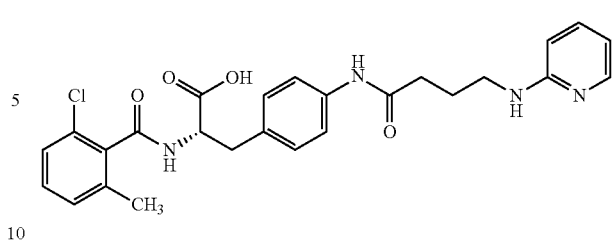

[General Method A] Fmoc-(p-NO2)-Phe-Wang resin (20 g, 0.55 meq/g, 11 mmol) was treated with a solution of sodium dithionite (17.4 g, 110 mmol), potassium carbonate (21.2 g, 154 mmol), tetra-n-butylammonium sulfate (3.73 g, 11 mmol) in dichloromethane-$H_2O$ (1:1, 300 mL) for 2 h with nitrogen bubbling. The resin was washed with dichloromethane-$H_2O$ (1:1, 300 mL) (×3), dimethylformamide (200 mL, ×3), methanol (200 mL, ×3), and dichloromethane (200 mL, ×3). A portion of resin (10 g) was then treated with a Dde protected aminobutanoic acid (9 g, 6.0 eq) in DMF (100 mL) and DIPEA (14.1 mL, 14.5 eq) followed by a solution of HCTU (12.3 g, 5.5 mmol) in DMF (50 mL). After overnight agitation by nitrogen bubbling, the resin was filtered and washed with DMF (×3). The Dde protecting group was then removed by treatment with 2% hydrazine (5.5 mL) in DMF (45 mL) for 5 min and the deprotection step was repeated. The resin was filtered and washed with DMF (×3), DCM (×3), MeOH (×3) and dried. A portion of resin (5 g) was treated with a solution of pyridine N-oxide (1.2 g), PyBroP (6.5 eq), DIPEA (18.75 eq) in DCM (40 mL) for 3 h and the resin was filtered and washed with DCM (×3), MeOH (×3) and dried. A portion of resin (500 mg) was then treated for 20 min with a mixture of substituted benzoic acid (5 eq), HCTU (5 eq), and DIEA (10 eq) at 75° C. The resin was filtered, and washed with DMF thoroughly. Then the resin was washed with DMF thoroughly and washed with DCM and MeOH. The product was cleaved from the resin by 3-hr treatment with a mixture of TFA:TIPS:$H_2O$ (95:2.5:2.5) and was purified by preparative RP-HPLC. Column 19×100 mm Altantis T3 OBD, solvent A (0.1% trifluoroacetic acid in $H_2O$), solvent B'(0.1% trifluoroacetic acid in a mixture of isopropanol/acetonitrile/water (60/30/10)), flow rate: 15 ml/min, gradient: 8% solvent B' for 3 min, 8% to 15% solvent B' for 1 min, 15% to 24% solvent B' for 30 min, detection: 254 nm. LC-MS profile (solvent A, solvent B'(Vydac 218TP54, 300 Å, solvent A, solvent B', flow rate: 0.9 ml/min, gradient: 5% to 100% solvent B' for 30 min, detection: 254 nm).

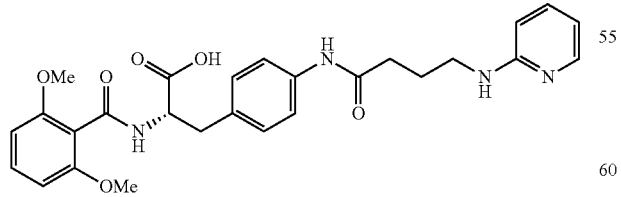

[HIJ-886] Prepared from 2,6-dimethoxy benzoic acid as a substituted benzoic acid by General Method A. (S)-2-(2,6-dimethoxybenzamido)-3-(4-(4-(pyridin-2-ylamino)butanamido)phenyl)propanoic acid; retention time (condition 1) 15.00 min, m/z=507.9 (MH+).

[HIJ-888] Prepared from 2-chloro-6-methyl benzoic acid as a substituted benzoic acid by General Method A. (S)-2-(2-chloro-6-methylbenzamido)-3-(4-(4-(pyridin-2-ylamino)butanamido)phenyl)propanoic acid; retention time (condition 1) 3.79 min, m/z=495.8 (MH+).

YT-101-115, 119

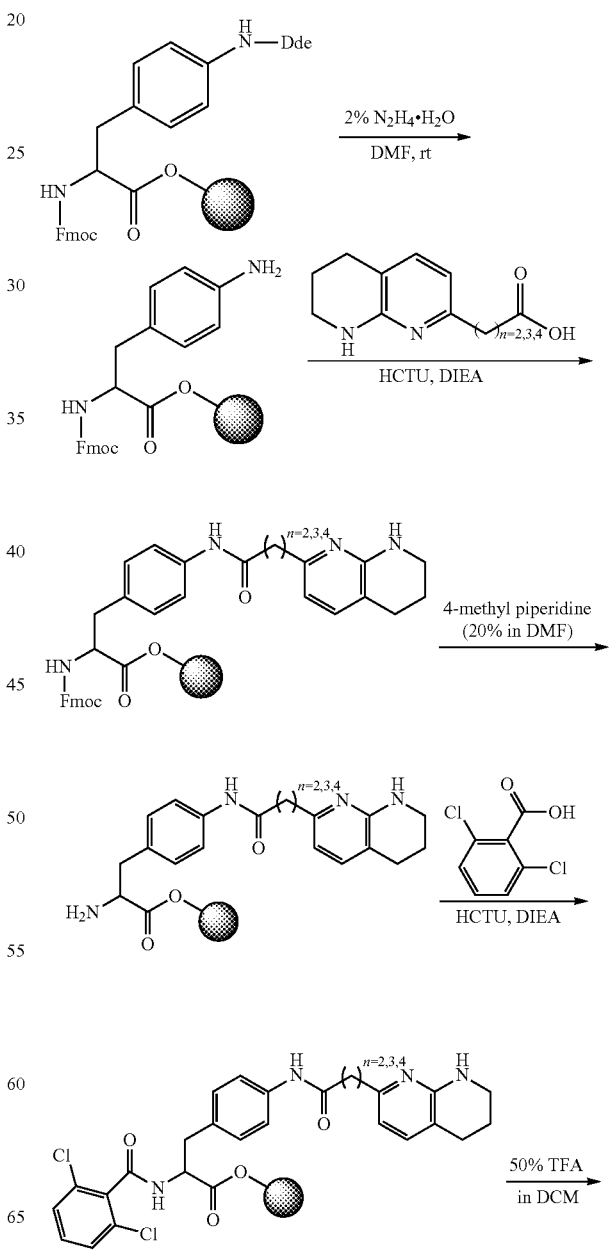

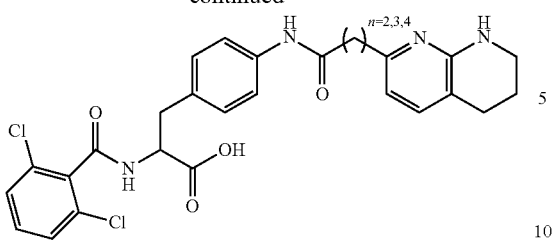

Fmoc-(p-NH-Dde)-Phe-Wang resin (1 mmol) was treated with hydrazinehydrate (7 mL, 2% in DMF) for 15 min to remove Dde protecting group. The deprotection step was repeated once and filtered, wash with DMF thoroughly. Then a portion of resin (0.2 mmol) was taken and stirred for 5 min with a mixture of tetrahydronaphthyridine acid (5 eq), HCTU (5 eq), and DIPEA (10 eq). The resin was filtered, and washed with DMF thoroughly. Then the resin was treated with 4-methyl piperidine (10 mL, 20% in DMF) for 15 min to remove Fmoc protecting group. The deprotection step was repeated once and filtered, wash with DMF thoroughly. Then a portion of resin (0.2 mmol) was taken. For compounds YT-115, YT-119 and YT-101, a mixture of 2,6-Dichlorobenzoic acid (5 eq), HCTU (5 eq) and DIPEA (10 eq) in DMF (10 mL) was added and stirred for 1 h at 75° C. A mixture of TFA:TIPS:$H_2O$ (95:2.5:2.5) was then used for cleavage from resin. The crude product was purified by RP-HPLC.

[YT-101] (n=3) retention time (condition 6: 19×100 mm Altantis T3 OBD, solvent A, solvent B', flow rate: 15 ml/min, gradient: 8% solvent B' for 5 min, 8% to 18% solvent B' for 1 min, 18% to 24% solvent B' for 24 min, detection: 254 nm) 20.77 min, m/z=537 (MH+)

[YT-115] (n=4) retention time (condition 10: 19×100 mm Altantis T3 OBD, solvent A, solvent B', flow rate: 15 ml/min, gradient: 8% solvent B' for 3 min, 8% to 19% solvent B' for 1 min, 19% to 23% solvent B' for 24 min, detection: 254 nm) 22.92 min, m/z=569.7 (MH+)

[YT-119] (n=2) retention time (condition 1: 19×100 mm Altantis T3 OBD, solvent A, solvent B', flow rate: 15 ml/min, gradient: 8% solvent B' for 3 min, 8% to 19.5% solvent B' for 1 min, 19.5% to 21% solvent B' for 24 min, detection: 254 nm) 16.46 min, m/z=541.9 (MH+)

[JM-61]

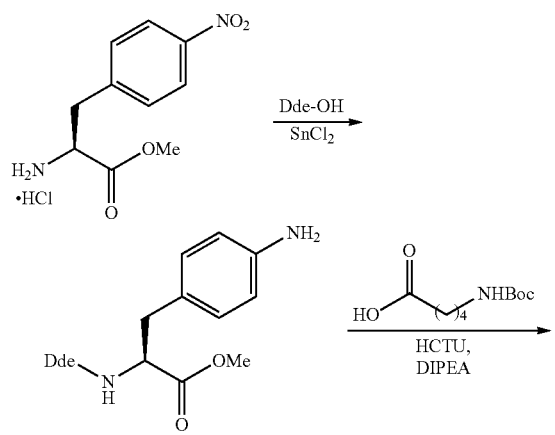

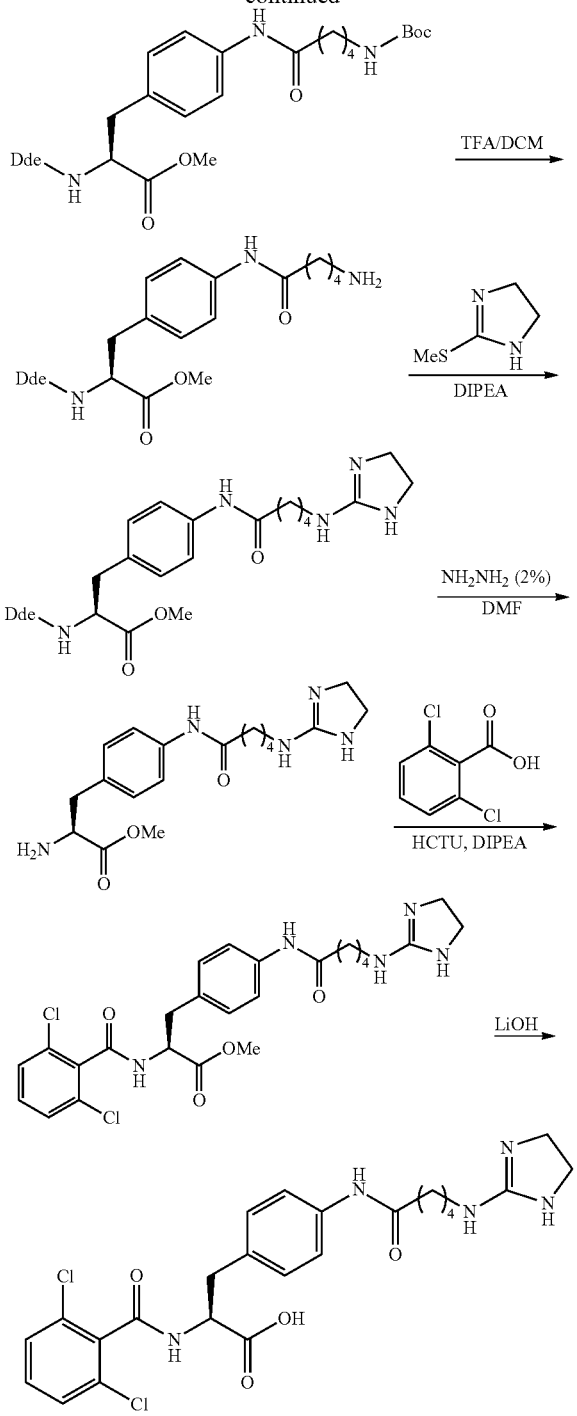

A mixture of 4-NO2 phenylalanine methyl ester (1.3 g, 5 mmol), DIPEA (0.87 mL, 5 mmol), and 2-acetyldimedone (0.9 g, 5 mmol) in MeOH (35 mL) was refluxed for 3 h and cooled down. SnCl2-2H2O (5.6 g, 25 mmol) was added to the mixture and refluxed for additional 2 h and cooled. The reaction mixture was poured into ice and neutralized with saturated $NaHCO_3$ solution to pH=8. Ethyl acetate was added and the mixture was filtered through a pad of Celite. The organic layer was washed with brine, dried over anhydrous $Na_2SO_4$, and concentrated to provide the amine as a yellow solid (1.74 g, 97%) ESI-MS: 359.8 (MH+) 1H NMR (300 MHz, CDCl3) δ ppm 1.04 (s, 6H) 2.27 (s, 3H) 2.33 (s, 2H) 2.43 (s, 2H) 2.96 (dd, J=13.94, 8.85 Hz, 1 H) 3.18 (dd, J=13.94, 4.71 Hz, 1H) 3.63 (br. s, 2H) 3.78 (s, 3H) 4.53 (td, J=8.48, 4.90 Hz, 1H) 6.61 (d, J=8.29 Hz, 2H) 6.96 (d, J=8.29 Hz, 2H) 13.89 (d, J=7.72 Hz, 1H). To the amine (1.1 g, 3.1 mmol) in DMF (5.5 mL) was added Boc-5-aminovaleric acid (0.78 g, 3.6 mmol), HCTU (1.5 g, 3.6 mmol), and DIPEA (1.6 mL, 9.0 mmol). The mixture was stirred for 5 hours at rt. The mixture was diluted with ethyl acetate, washed with 10% aq. citric acid, washed with sat. aq. NaHCO3, washed twice with water, washed with brine, dried over anhydrous Na2SO4, and concentrated to provide the crude amide. (1.8 g, quant.) ESI-MS: 559.0 (MH+) 1H NMR (300 MHz, CDCl3) δ ppm 1.03 (s, 6H) 1.44 (s, 9H) 1.52-1.66 (m, 2H) 1.68-1.83 (m, 2H) 2.27 (s, 3H) 2.31-2.50 (m, 6H) 3.04 (dd, J=13.85, 8.76 Hz, 1H) 3.13-3.31 (m, 3H) 3.78 (s, 3H) 4.58 (td, J=8.48, 4.90 Hz, 1H) 4.67 (m, 1H) 7.13 (d, J=8.29 Hz, 2H) 7.49 (d, J=8.29 Hz, 2H) 7.56 (br. s, 1H) 13.93 (d, J=8.29 Hz, 1H). 1.7 g (3.0 mmol) of crude Boc-amine was stirred in dichloromethane (8 mL) and trifluoroacetic acid (4 mL) for 90 minutes. The mixture was concentrated to provide 2.6 g of crude amine trifluoroacetate salt. ESI-MS: 458.8 (MH+) 1H NMR (300 MHz, DMSO-d6) δ ppm 0.94 (s, 6H) 1.47-1.69 (m, 4H) 2.20-2.38 (m, 5H) 2.71-2.86 (m, 2H) 2.97-3.08 (m, 1H) 3.09-3.19 (m, 1H) 3.71 (s, 3H) 4.99 (td, J=7.49, 5.37 Hz, 1H) 7.07 (d, J=8.48 Hz, 2H) 7.50 (d, J=8.48 Hz, 2H) 7.65 (br. s, 3H) 9.91 (s, 1H) 13.53 (d, J=8.10 Hz, 1H). To a mixture of a portion of amine trifluoroacetate salt (0.71 g, 1.2 mmol) in DCM (3 mL) was added 2-(methylthio)-4,5-dihydro-1H-imidazole hydroiodide salt (0.42 g, 0.93 mmol) and DIPEA (0.7 mL, 4 mmol). The mixture was stirred for 18 hours at rt. The mixture was diluted with ethyl acetate, washed with water twice, washed with brine, dried over anhydrous Na2SO4, and concentrated. The crude residue was purified by flash chromatography (40 g column silica, gradient elution 0 to 30% MeOH/DCM) to provide the cyclic guanidine. ESI-MS: 527.1 (MH+). The Dde amine (26 mg, 0.05 mmol) was stirred in DMF (1 mL) and 25% aq. hydrazine hydrate (0.1 mL) for 90 minutes. The mixture was concentrated under reduced pressure to give the crude amine (26 mg). The amine was dissolved in DMF (1 mL) and 2,6-dichlorobenzoic acid (14 mg, 0.075 mmol), HCTU (31 mg, 0.075 mmol), and DIPEA (0.017 mL, 0.1 mmol). After 1 h stirring, the mixture was diluted with water and extracted with ethyl acetate. The combined organic layers were dried over anhydrous MgSO4 and concentrated. The crude residue was purified by flash chromatography (40 g column silica, gradient elution 0 to 30% MeOH/DCM) to provide the amide methyl ester (7 mg). Methyl ester was hydrolyzed by treatment with aqueous LiOH (1M, 0.12 mL) in THF-H2O (2:1, 1.5 mL) for 6 h. The mixture was neutralized and purified by RP-HPLC. ESI-MS: 520.7 (MH+).

[JM-141]

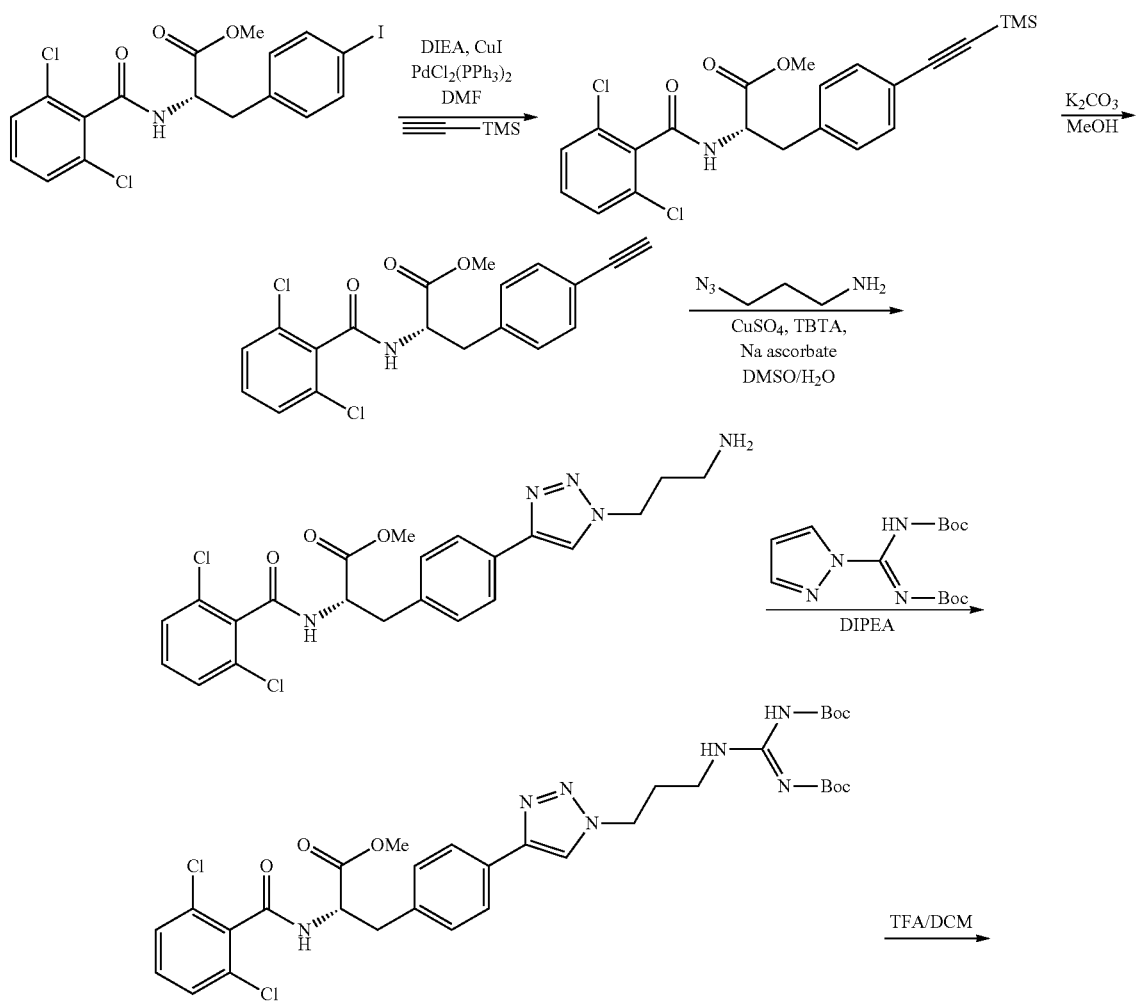

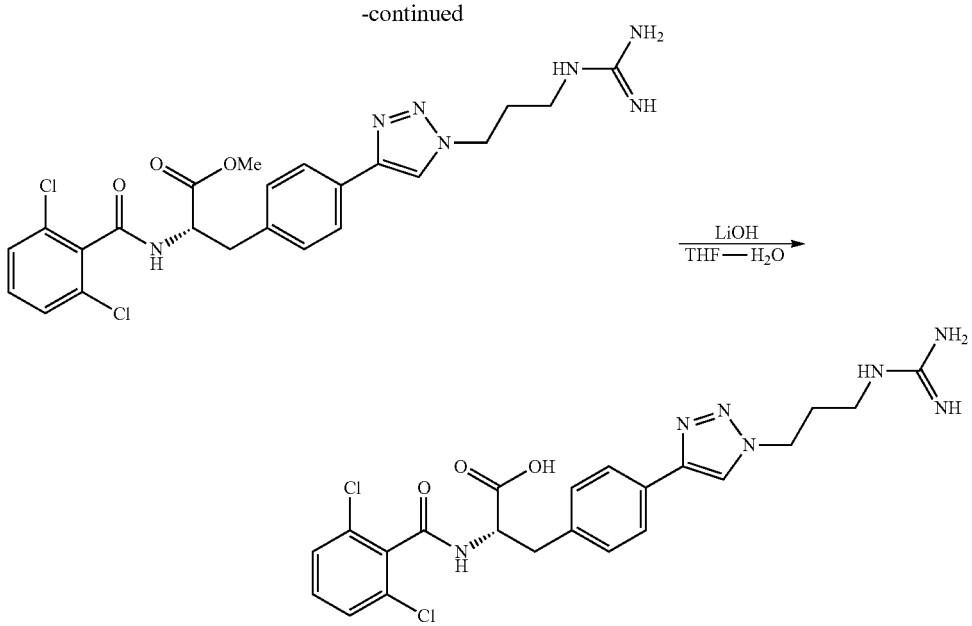

To methyl (S)-2-(2,6-dichlorobenzamido)-3-(4-iodophenyl)propanoate (261 mg, 0.546 mmol) prepared by the precedent (WO 2007141473 A1) and CuI (5 mg, 5 mol %) in degassed DMF (3 mL) was added DIPEA (0.25 mL, 1.53 mmol), Pd(PPh$_3$)$_2$Cl$_2$ (4 mg) and TMS acetylene (0.15 mL, 1.09 mmol). The mixture was stirred at 45° C. for 2.5 h. The mixture was partitioned with water and ethyl acetate and the organic layer was concentrated under reduced pressure. The crude TMS alkyne was dissolved in MeOH (3 mL) and potassium carbonate (82 mg, 0.06 mmol) was added and stirred for 1 h. Water and ethyl acetate were added and the organic layer was washed with water. The organic layer was washed with brine, dried over Na2SO4 and concentrated under reduced pressure. ESI-MS: 531.8 (MH+). The alkyne (50 mg, 0.132 mmol) was added to a solution of 3-azidopropan-1-amine (13 mg, 0.132 mmol) in DMSO-H2O (2L1, 1.5 mL) and sodium ascorbate (2.6 mg, 0.1 eq), TBTA (0.7 mg, 0.01 eq) and CuSO4 (0.2 mg, 0.01 eq). After 30 min at 80° C., another TBTA (2 mg) and sodium ascorbate (7 mg) were added. After additional 30 min, additional batch of 3-azidopropan-1-amine (5 mg) was added. After 20 minutes, the mixture was cooled and water and ethyl acetate were added and the organic layer was washed with sat. sodium bicarbonate solution. The organic layer was concentrated under reduced pressure. ESI-MS: 476.7 (MH+). To the above crude amine in DMF (1 mL) was added tert-butyl ((tert-butoxycarbonyl)imino)(1H-pyrazol-1-yl)methyl)carbamate (31 mg, 0.1 mmol) and stirred for 1.5 h. Water and ethyl acetate were added and the organic layer was separated and concentrated under reduced pressure. ESI-MS: 718.9 (MH+). The bis-Boc guanidine was stirred in TFA (50% in DCM, 2 mL) for 1.5 h and concentrated. ESI-MS: 518.8 (MH+). The ester (41 mg) was dissolved in THF (1 mL) and aqueous LiOH solution (1M, 0.24 mL) was added. After 1.5 h, the solution was acidified by addition of 1M HCl and purified by RP-HPLC. condition: 19×100 mm Altantis T3 OBD, solvent A, solvent B', flow rate: 10 ml/min, gradient: 5% solvent B for 5 min, 5% to 100% solvent B for 25 min, detection: 254 nm) 20.0 min, ESI-MS: 504 (MH+).

[JM-175]

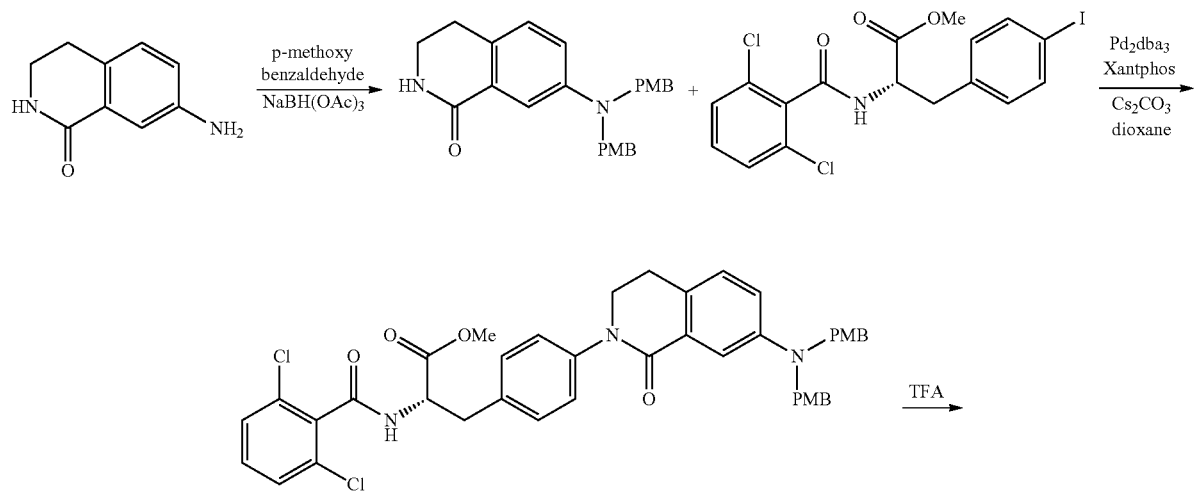

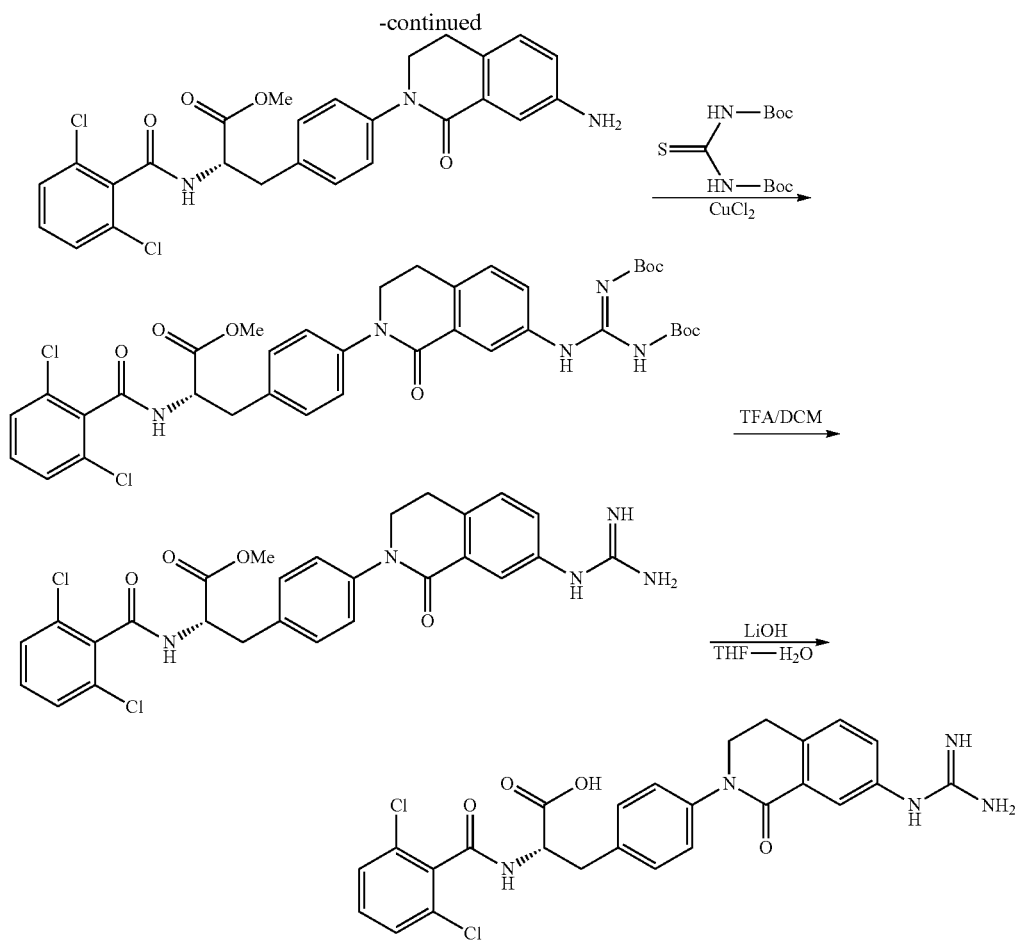

To a mixture of 7-amino-3,4-dihydroisoquinolin-1(2H)-one (122 mg, 0.752 mmol) and p-methoxybenzaldehyde (0.2 mL, 1.65 mmol) in DCE (2 mL) was added AcOH (4 drops) and NaBH(OAc)₃ (349 mg, 1.65 mmol). After stirring overnight, additional NaBH(OAc)₃ (100 mg) was added and stirred for 4 h. Saturated NaHCO3 solution and ethyl acetate was added. The organic layer was washed with water and dried over MgSO₄ and concentrated under reduced pressure. The product was purified by silica gel column chromatography (0 to 100% EtOAc in hexane) ESI-MS: 403.9 (MH+). The dihydrosioquinolinone (39 mg, 0.096 mmol), methyl (S)-2-(2,6-dichlorobenzamido)-3-(4-iodophenyl)propanoate (46 mg, 0.096 mmol), xantphos (3.3 mg, 0.0058 mmol), Pd₂dba₃ (2 mg, 0.002 mmol), and Cs₂CO₃ (44 mg, 0.13 mmol) were dissolved in dioxane (1 mL). The reaction vessel was degassed and heated at 65° C. for 1 h and kept stirring at 100° C. for 4 h. The reaction mixture was cooled and partitioned between ethyl acetate and water. The organic layer was washed with brine, dried over MgSO₄ and concentrated. The product was purified by preparative TLC. ESI-MS: 752.9 (MH+). The bis PMB amine (14 mg, 0.018 mmol) was stirred in TFA (1 mL) at 65° C. for 3 h and concentrated. ESI-MS: 512.8 (MH+). To a mixture of crude aniline (18 mg) in DMF (1 mL) was added trimethylamine (0.03 mL), bis-Boc thiourea (16 mg, 0.06 mmol), and then CuCl₂ (8 mg, 0.06 mmol). After 30 min, water and EtOAc were added and the organic layer was separated, concentrated and purified by preparative HPLC. ESI-MS: 754.9 (MH+). The bis-guanidine was stirred in TFA (50% in DCM, 1 mL) for 1.5 h and concentrated to yield the guanidine (4 mg). ESI-MS: 554.8 (MH+). To the crude methyl ester in THF (0.5 mL) was added aq. LiOH (1M, 0.06 mL). After 1.5 h, the mixture was acidified with aq. HCl (1M) and purified by RP-HPLC. condition: 19×100 mm Altantis T3 OBD, solvent A, solvent B', flow rate: 10 ml/min, gradient: 5% solvent B' for 5 min, 5% to 100% solvent B' for 25 min, detection: 254 nm) 19.5 min, ESI-MS: 540.8 (MH+)

[JM-185]

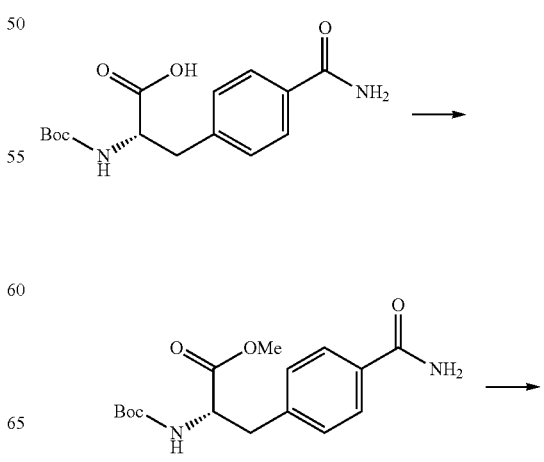

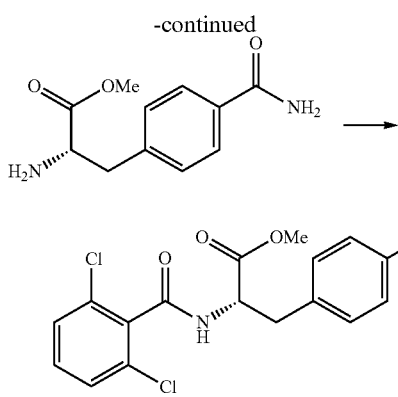

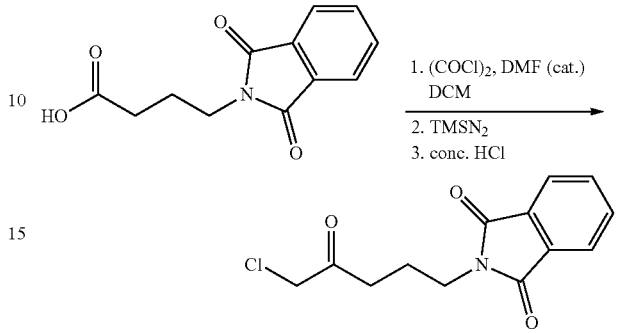

methyl (S)-3-(4-carbamoylphenyl)-2-(2, 6-dichlorobenzamido)propanoate was obtained after silica gel column chromatography. (377 mg, 63% over three steps). ESI-MS: 395.6 (MH+), 417.8 (MNa+)

To the Boc-L-4-carbamoyl phenylalanine (500 mg, 1.62 mmol) in DCM (10 mL) was added EDC (341 mg, 1.78 mmol), HOBt (241 mg, 1.78 mmol) and MeOH (3 mL). After stirring for 3 h, the mixture was partitioned between ethyl acetate and sat. aq. NaHCO3 solution. The organic layer was washed with brine, dried over Na$_2$SO$_4$, and concentrated under reduced pressure. ESI-MS: 323.6 (MH+), 345.6 (MNa+). The crude Boc amine was stirred in TFA (20% in DCM, 10 mL) for 1 h. The mixture was concentrated ESI-MS: 223.6 (MH+). A mixture of crude amine, 2,6-dichlorobenzoic acid (290 mg, 1.52 mmol), HCTU (629 mg, 1.52 mmol) and DIPEA (0.79 mL, 4.56 mmol) in DMF (5 mL) was stirred for 3 h. The reaction mixture was then diluted with water and extracted with ethyl acetate. The organic layer was washed with brine, dried over Na2SO4, and concentrated under reduced pressure. The To a mixture of the acid (248 mg) in DCM (3 mL) was added oxalyl chloride (0.1 mL) and DMF (1 drop). After evolution of gas, the mixture was concentrated and dissolved in CH3CN-THF (1:1, 6 mL) and cooled to 0° C. TMSdiazomethane (2M in hexanes, 0.64 mL) was added dropwise and stirred at rt for 30 min and re-cooled to 0° C. Concentrated hydrochloric acid (0.18 mL) was added dropwise and after stirring at rt for 30 min, ethyl acetate and sat. aq. NaHCO3 were added. The organic layer was dried over MgSO4 and concentrated to yield 2-(5-chloro-4-oxopentyl) isoindoline-1,3-dione. 1H NMR (300 MHz, CDCl$_3$) δ ppm 1.95-2.1 (m, 2H) 2.6-2.7 (m, 2H) 3.7-3.8 (m, 2H) 4.09 (s, 2H) 7.65-7.75 (m, 2H) 7.80-7.90 (m, 2H).

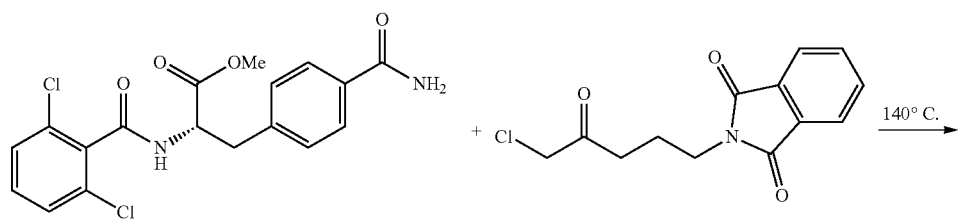

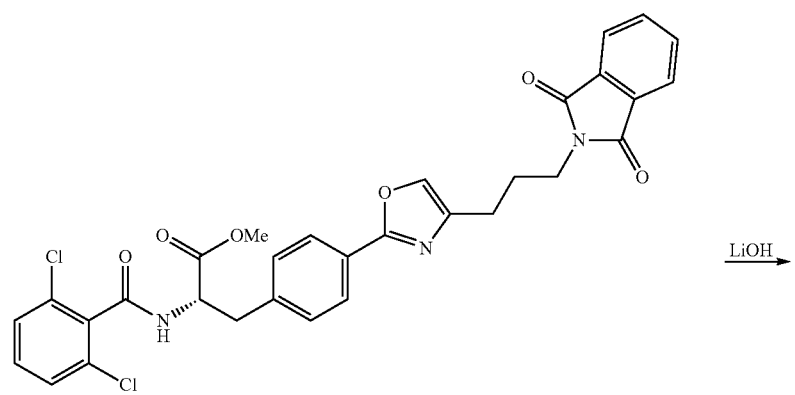

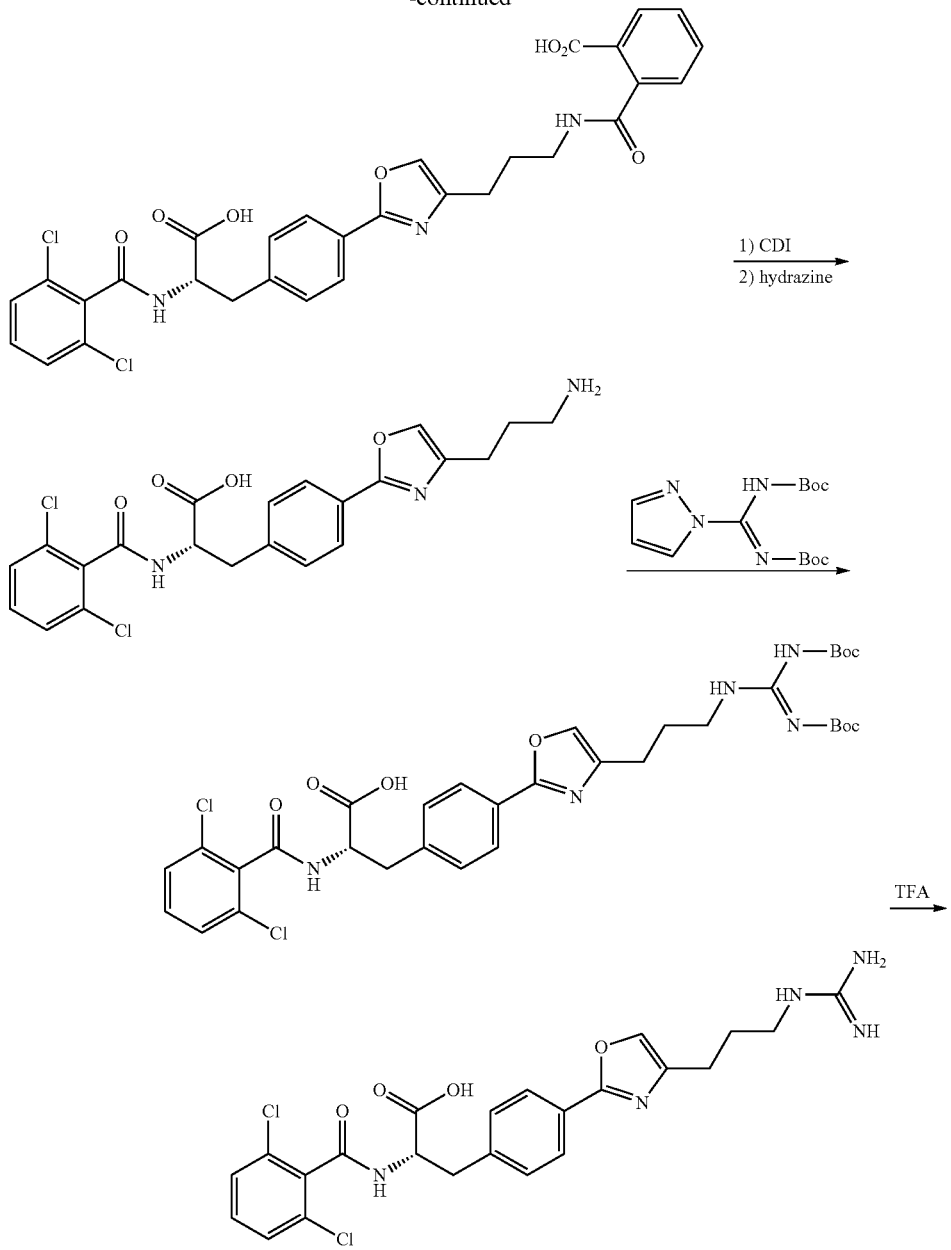

A mixture of 2-(5-chloro-4-oxopentyl)isoindoline-1,3-dione (56 mg, 0.20 mmol) and methyl (S)-3-(4-carbamoylphenyl)-2-(2,6-dichlorobenzamido)propanoate (76 mg, 0.19 mmol) were placed in a vial with a stirred bar and heated to 140° C. After 45 min, the solids melted and after heating for 4 h, the mixture was cooled and the product was purified by preparative TLC. ESI-MS: 606.8 (MH+). The ester was dissolved in THF (1 mL) and LiOH solution (1M, 0.2 mL) was added. After 1 h, the mixture was acidified with 1M HCl. Ethyl acetate and water were added and the organic layer was separated, dried over MgSO4 and concentrated. ESI-MS: 610.8 (MH+). To a mixture of diacid in THF (1 mL) was added CDI (7.3 mg). After 1 h, sat. NaHCO3 solution (1 mL) was added and stirred for 5 min. The mixture was acidified with 5% HCl solution and extracted with ethyl acetate. The organic layer was washed with water and concentrated. ESI-MS: 592.7 (MH+). To the phthalimide in EtOH (1 mL) was added hydrazine hydrate (25% aqueous solution, 0.02 mL) and stirred for 30 min. The reaction mixture was then heated to 80° C. and stirred for 1 h. Another hydrazine hydrate (0.05 mL) was added and kept heating for 3 h. The mixture was cooled to rt and stirred overnight. The reaction mixture was concentrated. ESI-MS: 462.6 (MH+). To the crude mixture in DMF (1 mL) was added tert-butyl (((tert-butoxycarbonyl)imino)(1H-pyrazol-1-yl)methyl)carbamate (31 mg, 0.1 mmol) and triethylamine (0.03 mL, 0.2 mmol). After stirring at rt for 90 min, the mixture was concentrated and the product was purified by preparative TLC. ESI-MS: 704.9 (MH+). The bis-Boc guanidine was stirred in TFA (50% in DCM, 1 mL) for 1 h and concentrated. The product was purified by RP-HPLC. condition: 19×100 mm Altantis T3 OBD, solvent A, solvent B', flow rate: 7 ml/min, gradient: 5% solvent B for 5 min, 5% to 100% solvent B for 30 min, detection: 254 nm) 23 min, ESI-MS: 504.6 (MH+)

[JM-192]

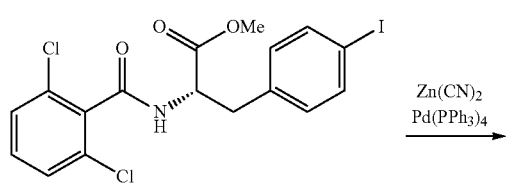

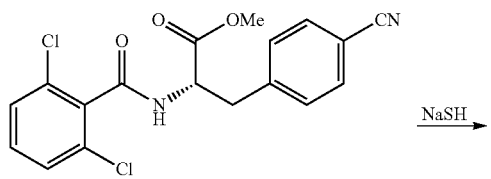

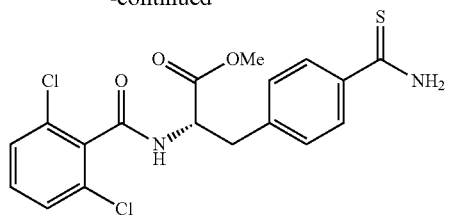

To a degassed solution of methyl (S)-2-(2,6-dichlorobenzamido)-3-(4-iodophenyl)propanoate (134 mg, 0.280 mmol) prepared by the precedent (WO 2007141473 A1) and Zn(CN)₂ (33 mg, 0.280 mmol) in DMF (1 mL) was added Pd(PPh₃)₄ (32 mg, 0.028 mmol) and heated at 80° C. After 5 h, an additional Pd(PPh₃)₄ (25 mg) was added and stirred overnight at 80° C. The reaction mixture was diluted with ethyl acetate and water. The organic layer was washed with water and centrated and the product was purified by preparative TLC. ESI-MS: 377.7 (MH+) To a mixture of the nitrile (44 mg, 0.12 mmol) in DMF-water (1:1, 1 mL) was added NH4Cl (32 mg, 0.59 mmol) and NaSH (33 mg, 0.59 mmol). After 45 min, DMF (1 mL) was added and stirred overnight. The mixture was diluted with ethyl acetate and water. The organic layer was washed with water and concentrated. The product was purified by preparative TLC. ESI-MS: 411.7 (MH+)

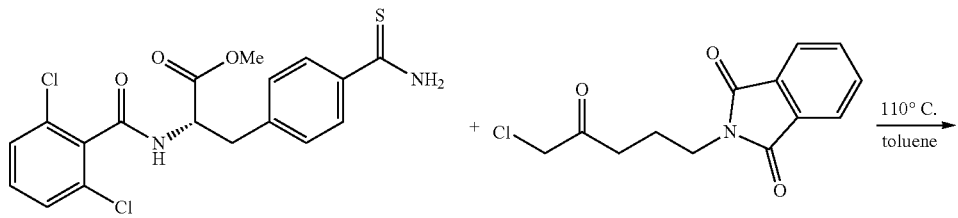

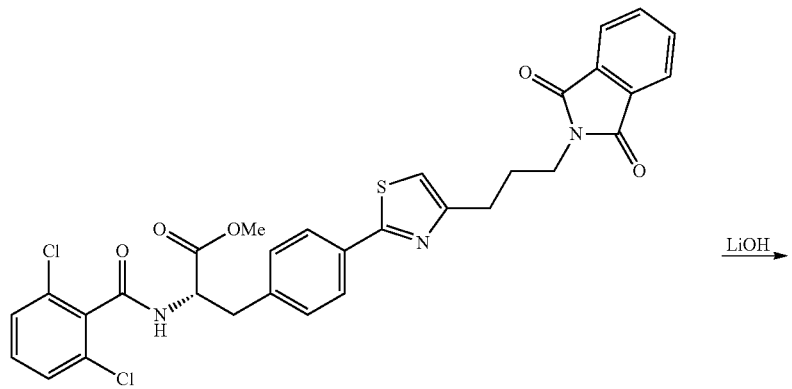

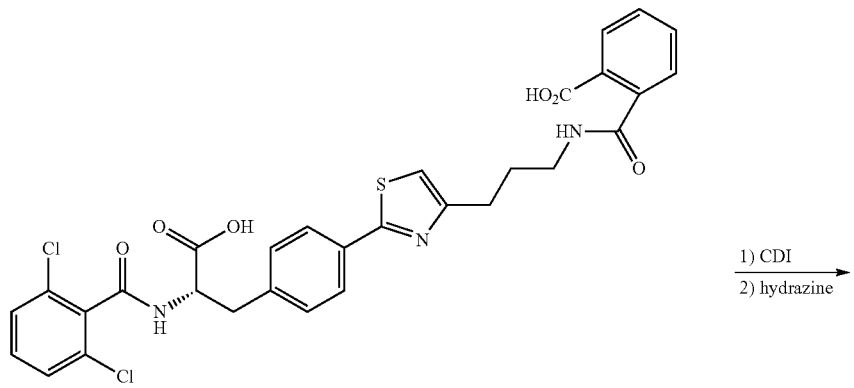

-continued

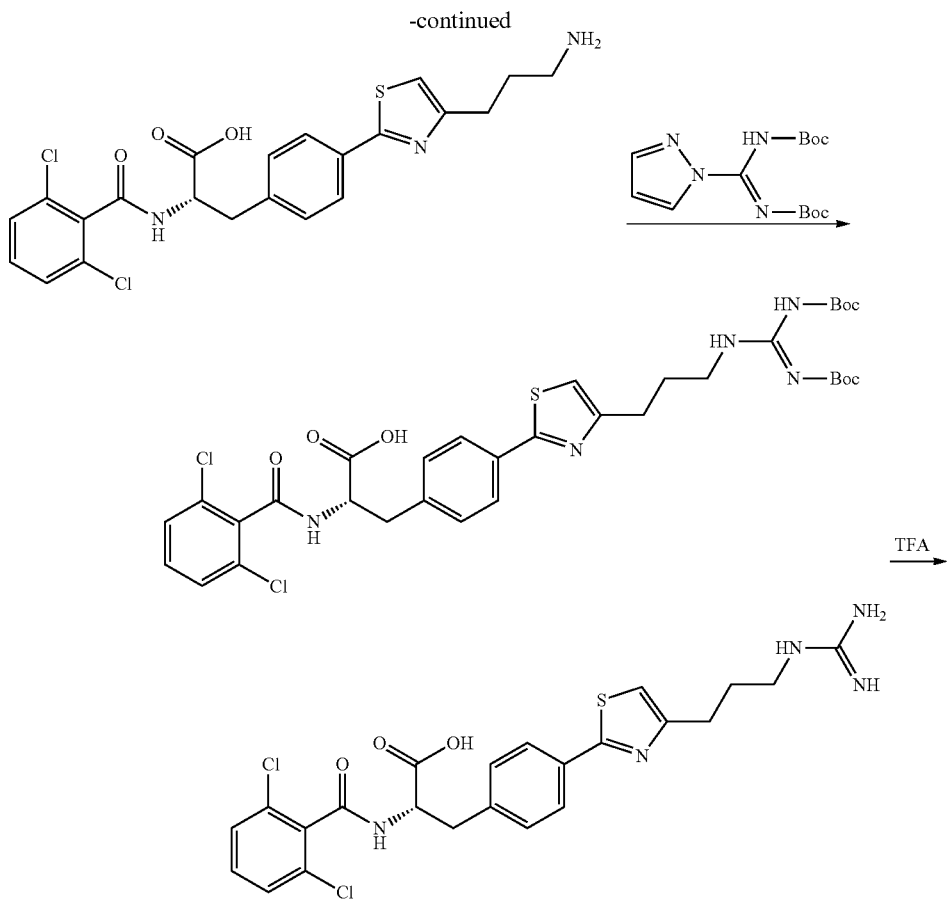

A mixture of methyl (S)-3-(4-carbamothioylphenyl)-2-(2,6-dichlorobenzamido)propanoate (13 mg, 0.032 mmol) and 2-(5-chloro-4-oxopentyl)isoindoline-1,3-dione (11 mg, 0.041 mmol) in toluene (0.5 mL) was heated at 110° C. After 2.5 h, additional 2-(5-chloro-4-oxopentyl)isoindoline-1,3-dione (10 mg) was added and heated for 3 h. The mixture was cooled and the product was purified by preparative TLC (12 mg). ESI-MS: 622.8 (MH+). To the methyl ester in THF (1 mL) was added aq. LiOH (1M, 0.06 mL). After 1 h, another aq. LiOH (1M, 0.05 mL) was added and stirred for 1 h. The solution was acidified with 1M HCl and partitioned between water and ethyl acetate. The organic layer was separated and concentrated. ESI-MS: 626.7 (MH+). The crude mixture was dissolved in THF (1 mL) and CDI (10 mg) was added. After 45 min, sat. NaHCO3 (mL) was added and stirred for 5 min. The mixture was acidified with 5% HCl solution and extracted with ethyl acetate. The organic layer was washed with water and concentrated. ESI-MS: 608.7 (MH+). To the phthalimide in EtOH (0.5 mL) was added hydrazine hydrate (25% aqueous solution, 0.02 mL) and the mixture was stirred for 2 h at 80° C. Another hydrazine hydrate (0.05 mL) was added and kept heating for 2 h. The mixture was cooled to rt and stirred overnight. The reaction mixture was concentrated. ESI-MS: 478.6 (MH+). To the crude mixture in DMF (0.5 mL) was added tert-butyl (((tert-butoxycarbonyl)imino)(1H-pyrazol-1-yl)methyl)carbamate (10 mg, 0.032 mmol) and triethylamine (0.02 mL). After stirring at rt for 2 h, the mixture was concentrated and the product was purified by preparative TLC. ESI-MS: 720.9 (MH+). The bis-Boc guanidine was stirred in TFA (50% in DCM, 1 mL) for 1 h and concentrated. The product was purified by RP-HPLC. condition: 19×100 mm Altantis T3 OBD, solvent A, solvent B', flow rate: 7 ml/min, gradient: 5% solvent B for 5 min, 5% to 100% solvent B for 30 min, detection: 254 nm) 24 min, ESI-MS: 520.7 (MH+)

[JM-230]

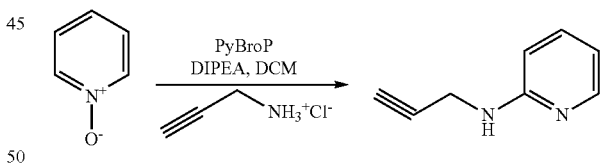

To a mixture of amine (300 mg, 3.28 mmol) and pyridine N-oxide (249 mg, 2.62 mmol) in DCM (11 mL) were added DIPEA (2.3 mL, 13.1 mmol) and PyBroP (566 mg, 3.41 mmol) and stirred overnight. Ethyl acetate and sat. aq. NaHCO3 was added. The organic layer was washed with water, brine and dried over MgSO4 and concentrated. 1H NMR (300 MHz, CDCl$_3$) δ ppm 2.0-2.05 (m, 1H), 2.45-2.65 (m, 2H) 3.55-3.70 (m, 2H) 6.35-6.45 (m, 1H) 6.55-6.65 (m, 1H) 7.35-7.45 (m, 1H) 8.15-8.05 (m, 1H).

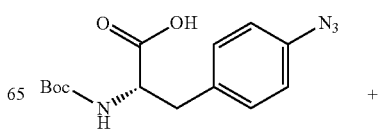

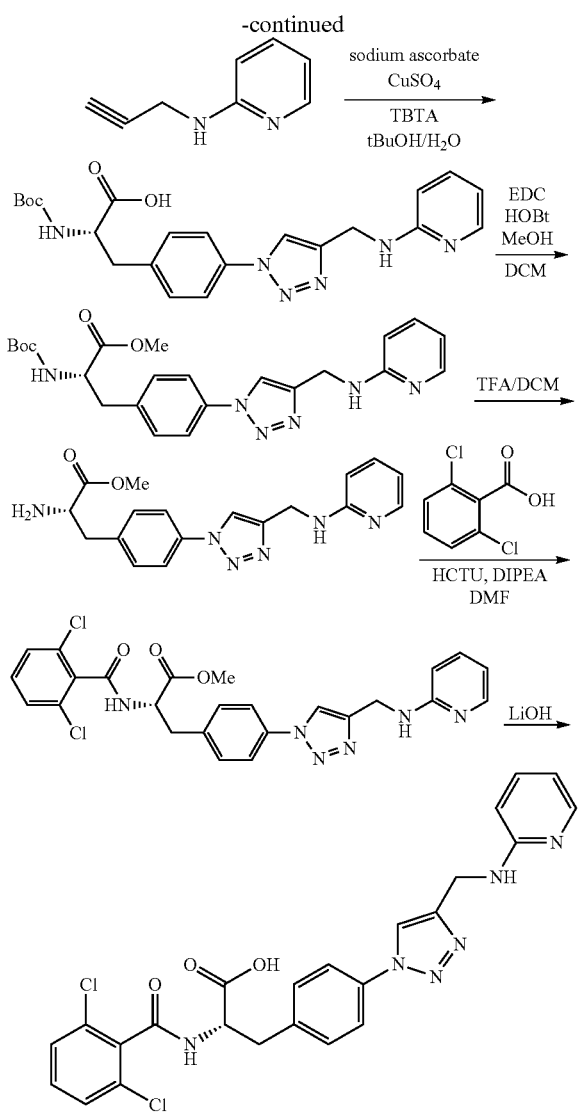

A mixture of (S)-3-(4-azidophenyl)-2-((tert-butoxycarbonyl)amino)propanoic acid (100 mg, 0.326 mmol) and N-(prop-2-yn-1-yl)pyridin-2-amine (86 mg, 0.653 mmol), sodium ascorbate (6.4 mg, 0.032 mmol), CuSO4 (0.5 mg, 0.00326 mmol), TBTA (1.7 mg, 0.00326 mmol) were stirred in tBuOH-water (2:1, 1.5 mL) for 90 min at 60° C. Additional N-(prop-2-yn-1-yl)pyridin-2-amine (66 mg) was added and kept stirring for 1 h at 60° C. The mixture was cooled and concentrated. ESI-MS: 439.8 (MH+). To the crude acid in DCM (2 mL) was added EDC (52 mg, 0.271 mmol), HoBt (37 mg, 0.271 mmol) and MeOH (1 mL). After stirring overnight, the mixture was purified by preparative TLC (38 mg). ESI-MS: 453.5 (MH+). The Boc protected amine was stirred in TFA (50% in DCM, 1 mL) for 2 h and concentrated. ESI-MS: 353.6 (MH+). The half of crude amine was dissolved in DMF (1 mL) and 2,6-dichlorobenzoic acid (10 mg, 0.055 mmol), HCTU (23 mg, 0.055 mmol), and DIPEA (0.04 mL, 0.21 mmol) were added. After stirring for 48 h, the mixture was diluted with ethyl acetate and water. The organic layer was concentrated and the product was purified by preparative TLC (14 mg). ESI-MS: 525.7 (MH+). The ester (10 mg) was stirred in THF (1 mL) and aq. LiOH (1M, 0.1 mL) was added. The mixture was stirred for 1 h and acidified with 1M HCl and concentrated. The product was purified by RP-HPLC. condition: 19×100 mm Altantis T3 OBD, solvent A, solvent B', flow rate: 7 ml/min, gradient: 5% solvent B for 5 min, 5% to 100% solvent B for 30 min, detection: 254 nm) 20 min, ESI-MS: 511.6 (MH+).

The Integrin specific adhesion assays were measured using Chinese Hamster Ovary Cells (CHO cells) transfected with human αv adhering to 0.3 µg/ml fibronectin. In every case, we confirmed that adhesion could be inhibited by blocking antibodies to the relevant integrin (complex-specific blocking antibodies in all cases except αvβ1 for which we showed equivalent effects of blocking αv and β1). Cells were resuspended in DMEM for 30 min at 4° C. with 10-fold dilutions of the compound with a starting concentration of 10 µM. Each sample was then added to triplicate wells of a 96-well plate which had been coated overnight at 4° C. with the relevant ligand, washed, blocked by 1 hr incubation with 1% BSA, and washed again. Cells were allowed to attach for 30-60 min at 37° C. After incubation, non-adherent cells were removed by discarding the media and spinning the plate top-side down at 500 rpm for 5 minutes. Cells were then fixed and stained with 40 ul of 0.5% Crystal violet, 1% Formaldehyde, 20% Methanol for 30 minutes and lysed with 2% Trition-X. Absorbance was measured at 595 nm in a Microplate reader. For all assays, concentration-response curves were constructed by non-linear regression analysis and $IC_{50}$ values using Graphpad PRISM (ver 6.0).

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method for treating fibrosis, said method comprising administering to a subject in need thereof an effective amount of a compound, or a salt thereof, having the formula:

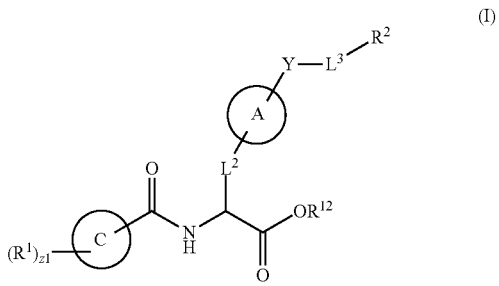

(I)

wherein,

Ring A is substituted or unsubstituted aryl, or substituted or unsubstituted heteroaryl;

Ring C is aryl or heteroaryl;

$L^2$ is independently a bond or substituted, unsubstituted $C_1$-$C_{10}$ alkylene, or unsubstituted 2 to 10 membered heteroalkylene;

$L^3$ is a bond, substituted or unsubstituted $C_1$-$C_{10}$ alkylene, substituted or unsubstituted 2 to 10 membered heteroalkylene, substituted or unsubstituted cycloalkylene, substituted or unsubstituted heterocycloalkylene, substituted or unsubstituted arylene, substituted or unsubstituted heteroarylene, or substituted or unsubstituted alkylarylene;

Y is —C(O)N($R^4$)—, —O—, —C(O)O—, —S—, —N($SO_2R^4$)—, —N(C(O)$R^4$)—, —N(C(O)O$R^4$)—, —N($R^4$)C(O)—, —N($R^4$)—, —N($R^4$)C(O)NH—, —NHC(O)N($R^4$)—, —N($R^4$)C(O)O—, —C(O)—, —N($R^4$)$CH_2$—, substituted or unsubstituted alkylene, substituted or unsubstituted heteroalkylene, or substituted or unsubstituted arylene;

$R^1$ is independently halogen, —$N_3$, —$CX_3$, —$CHX_2$, —$CH_2X$, —CN, —CHO, —OH, —$NH_2$, —COOH, —$CONH_2$, —$NO_2$, —SH, —$SO_2$, —$SO_2CH_3$, —$SO_3H$, —$OSO_3H$, —$SO_2NH_2$, —$SO_2Ph$, —$NHNH_2$, —$ONH_2$, —NHC(O)$NHNH_2$, —$OPO_3H$, —$PO_3H_2$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, or a detectable moiety;

$R^2$ is —$NR^{3A}R^{3B}$, —C(NH)$NH_2$, —C(NH)$R^{3B}$, —C($NR^{3A}$)$NH_2$, —C($NR^{3A}$)$R^{3B}$, —C(NCN)$NH_2$, —$NH_2$, —C(NH)$NHR^{3B}$, —C($NR^{3A}$)$NHR^{3B}$, —C(NCN)$NHR^{3B}$, substituted or unsubstituted cycloalkyl, substituted or unsubstituted heterocycloalkyl, substituted or unsubstituted aryl, substituted or unsubstituted heteroaryl, substituted or unsubstituted fused ring cycloalkyl, substituted or unsubstituted fused ring heterocycloalkyl, substituted or unsubstituted fused ring aryl, or substituted or unsubstituted fused ring heteroaryl;

$R^{3A}$ and $R^{3B}$ are independently hydrogen, —C(NH)$NH_2$, —C(NH)$R^{3D}$, —C($NR^{3C}$)$NH_2$, —C($NR^{3C}$)$R^{3D}$, —C(NCN)$NH_2$, —$NH_2$, —C(NH)$NHR^{3D}$, —C($NR^{3C}$)$NHR^{3D}$, —C(NCN)$NHR^{3D}$, substituted or unsubstituted cycloalkyl, substituted or unsubstituted heterocycloalkyl, substituted or unsubstituted aryl, substituted or unsubstituted heteroaryl, wherein $R^{3A}$ and $R^{3B}$ are optionally joined to form a substituted or unsubstituted heterocycloalkyl or substituted or unsubstituted heteroaryl;

$R^{3C}$ is hydrogen, halogen, —$N_3$, —$CX^{1C}_3$, —$CHX^{1C}_2$, —$CH_2X^{1C}$, —CN, —CHO, —OH, —$NH_2$, —COOH, —$CONH_2$, —$NO_2$, —SH, —$SO_2$, —$SO_2CH_3$, —$SO_3H$, —$SO_4H$, —$SO_2NH_2$, —$NHNH_2$, —$ONH_2$, —NHC(O)$NHNH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{3D}$ is hydrogen, halogen, —$N_3$, —$CX^{1D}_3$, —$CHX^{1D}_2$, —$CH_2X^{1D}$, —CN, —CHO, —OH, —$NH_2$, —COOH, —$CONH_2$, —$NO_2$, —SH, —$SO_2$, —$SO_2CH_3$, —$SO_3H$, —$SO_4H$, —$SO_2NH_2$, —$NHNH_2$, —$ONH_2$, —NHC(O)$NHNH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^4$ is hydrogen or unsubstituted $C_1$-$C_5$ alkyl;

$R^{12}$ is hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, or a prodrug moiety;

each X, $X^{1C}$ and $X^{1D}$ is independently —F, —Cl, —Br, or —I; and z1 is an integer from 0 to 5.

2. The method of claim 1, wherein said fibrosis is pulmonary fibrosis, liver fibrosis, skin fibrosis, cardiac fibrosis, or kidney fibrosis.

3. The method of claim 1, wherein $R^{12}$ is a substituted or unsubstituted alkyl, or substituted or unsubstituted heteroalkyl.

4. The method of claim 1, wherein Ring C is phenyl or Ring C is 5 to 6 membered heteroaryl and z1 is an integer between 0 to 3.

5. The method of claim 1, wherein Ring A is unsubstituted phenyl or unsubstituted 5 to 6 membered heteroaryl.

6. The method of claim 1, wherein $R^2$ is —$NR^{3A}R^{3B}$ or substituted or unsubstituted heteroaryl.

7. The method of claim 1, wherein $R^2$ is a substituted pyridyl, substituted imidazolyl, substituted oxazolyl, substituted thiazolyl, substituted oxadiazolyl, substituted triazolyl or substituted thiadiazolyl.

8. The method of claim 1, wherein $R^2$ is a substituted heterocycloalkyl.

9. The method of claim 1, wherein $R^2$ is —C(NH)$NH_2$, —C(NH)$R^{3B}$, —C($NR^{3A}$)$NH_2$, —C($NR^{3A}$)$R^{3B}$, —C(NCN)$NH_2$, —$NH_2$, —C(NH)$NHR^{3B}$, —C($NR^{3A}$)$NHR^{3B}$, or —C(NCN)$NHR^{3B}$.

10. The method of claim 1, wherein $L^2$ is unsubstituted $C_1$-$C_5$ alkylene or unsubstituted 2 to 5 membered heteroalkylene.

11. The method of claim 1, wherein $L^3$ is substituted or unsubstituted $C_1$-$C_8$ alkylene, substituted or unsubstituted 2 to 8 membered heteroalkylene, unsubstituted phenylene, unsubstituted 5 to 6 membered heteroarylene, or unsubstituted alkylarylene.

12. The method of claim 1, wherein $L^3$ is $R^6$-substituted $C_1$-$C_3$ alkylene;

$R^6$ is —NHC(O)$R^{6A}$;

$R^{6A}$ is —C(NCN)$R^{6C}$, —C(NH)$R^{6C}$, $R^{6C}$-substituted or unsubstituted alkyl, or $R^{6C}$-substituted or unsubstituted heteroalkyl;

$R^{6C}$ is hydrogen, halogen, oxo, —$N_3$, —$CF_3$, —$CCl_3$, —$CBr_3$, —$CI_3$, —CN, —$COR^{6D}$, —$OR^{6D}$, —$NR^{6D}R^{6E}$, —$COOR^{6E}$, —$CONR^{6D}R^{6E}$, —NHC(O)$R^{6D}$, —$NO_2$, —$SR^{6D}$, —$SO_{n6}R^{6D}$, —$NHNR^{6D}R^{6E}$, —$ONR^{6D}R^{6E}$, —NHC(O)$NHNR^{6D}R^{6E}$, —C(NCN)$R^{6D}$, —C(NH)$R^{6D}$, $R^{6E}$-substituted or unsubstituted alkyl, $R^{6E}$-substituted or unsubstituted heteroalkyl, $R^{6E}$-substituted or unsubstituted cycloalkyl, $R^{6E}$-substituted or unsubstituted heterocycloalkyl, $R^{6E}$-substituted or unsubstituted aryl, or $R^{6E}$-substituted or unsubstituted heteroaryl;

n6 is 2, 3, or 4; and $R^{6D}$, $R^{6E}$ and $R^{6F}$ are independently hydrogen, halogen, oxo, —$N_3$, —$CF_3$, —$CCl_3$, —$CBr_3$, —$CI_3$, —CN, —CHO, —OH, —$NH_2$, —COOH, —$CONH_2$, —$NO_2$, —SH, —$SO_2$, —$SO_2Cl$, —$SO_2CH_3$, —$SO_3H$, —$SO_4H$, —$SO_2NH_2$, —$NHNH_2$, —$ONH_2$, —NHC(O)$NHNH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, or a detectable moiety.

13. The method of claim 1, wherein $R^{6C}$ or $R^{6D}$ is a detectable moiety.

14. The method of claim 1, wherein Y is —O—, —N($R^4$)C(O)—, —N($R^4$)C(O)NH—, —NHC(O)N($R^4$)—, —N($R^4$)C(O)O—, —C(O)—, or —N($R^4$)$CH_2$.

15. The method of claim 1, wherein $R^1$ is independently hydrogen, halogen, —OMe, —SMe, —SO$_2$Me, —SO$_2$Ph, —COOH, substituted or unsubstituted $C_1$-$C_5$ alkyl, substituted or unsubstituted 2 to 5 membered heteroalkyl, or substituted or unsubstituted $C_6$-$C_{10}$ aryl.

16. The method of claim 1, wherein the compound, or salt thereof, has the formula:

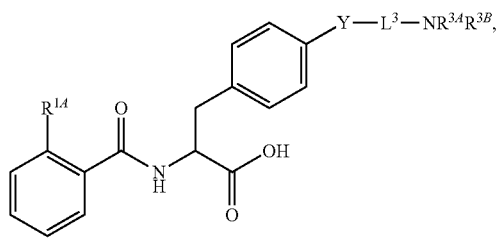

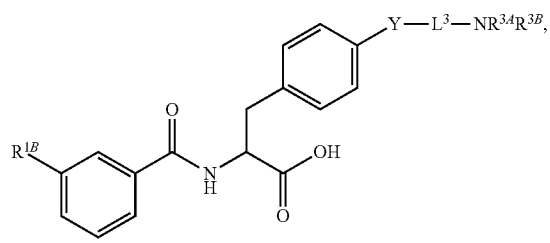

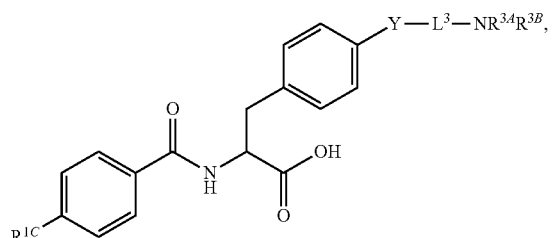

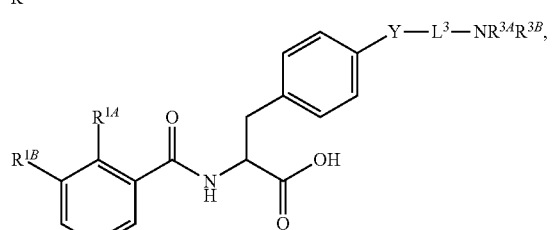

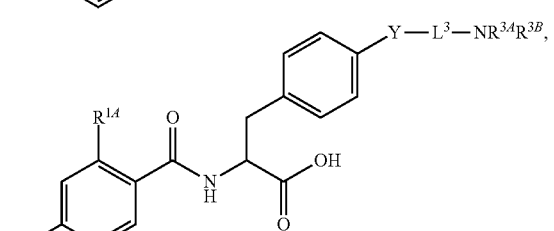

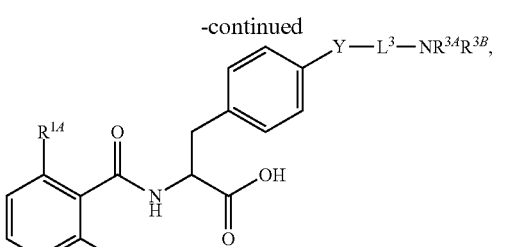

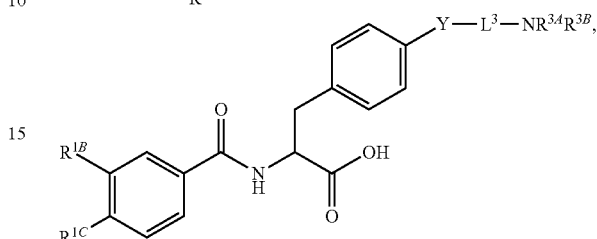

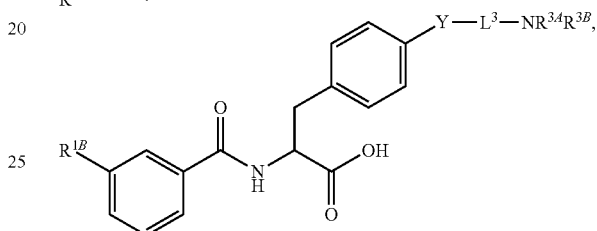

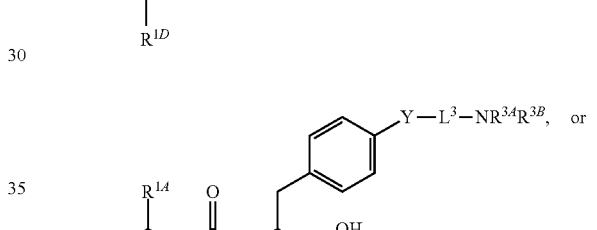

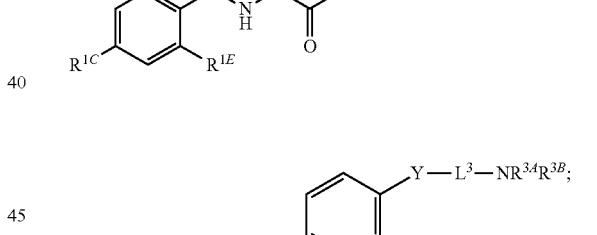

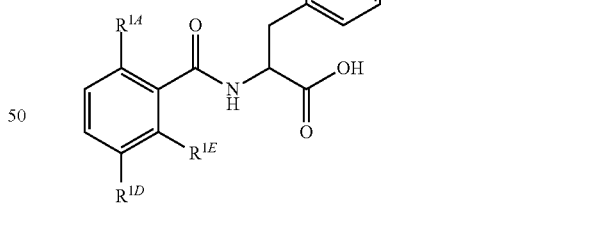

wherein $R^{1A}$, $R^{1B}$, $R^{1C}$, $R^{1D}$, and $R^{1E}$ are independently hydrogen, halogen, —N$_3$, —CF$_3$, —CCl$_3$, —CBr$_3$, —CI$_3$, —CN, —CHO, —OH, —NH$_2$, —COOH, —CONH$_2$, —NO$_2$, —SH, —SO$_2$, —SO$_2$Cl, —SO$_2$CH$_3$ —SO$_3$H, —OSO$_3$H, —SO$_2$NH$_2$, —NHNH$_2$, —ONH$_2$, —NHC(O)NHNH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, or a detectable moiety.

17. The method of claim 1, wherein said fibrosis is pulmonary fibrosis.

18. The method of claim 1, wherein the compound, or salt thereof, has the formula:

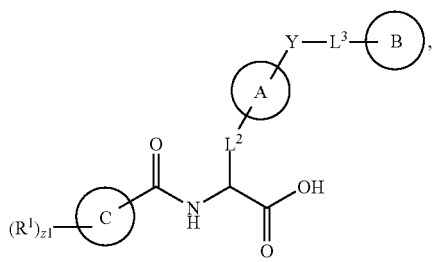

wherein,

Ring B is a substituted or unsubstituted cycloalkyl, substituted or unsubstituted heterocycloalkyl, substituted or unsubstituted aryl, substituted or unsubstituted heteroaryl, substituted or unsubstituted fused ring aryl or substituted or unsubstituted fused ring heteroaryl.

19. The method of claim 1, wherein the compound, or salt thereof, has the formula:

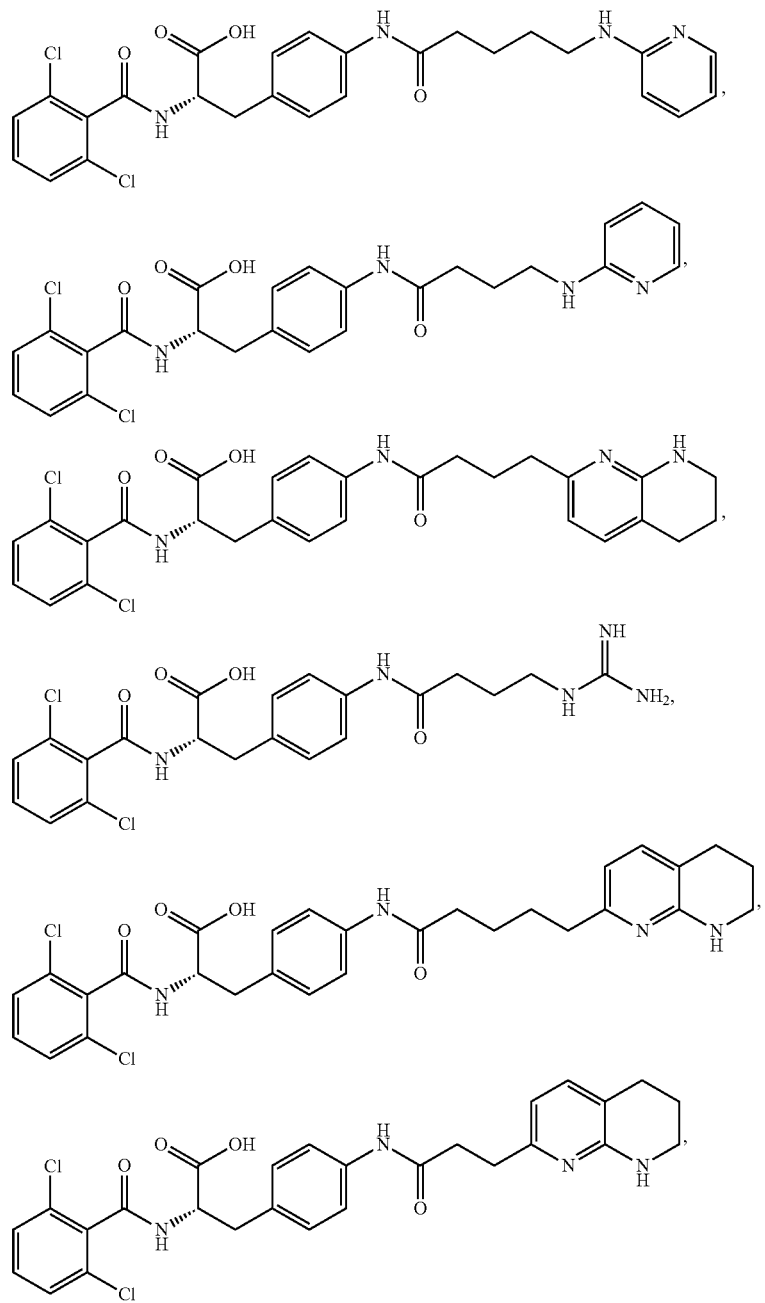

-continued
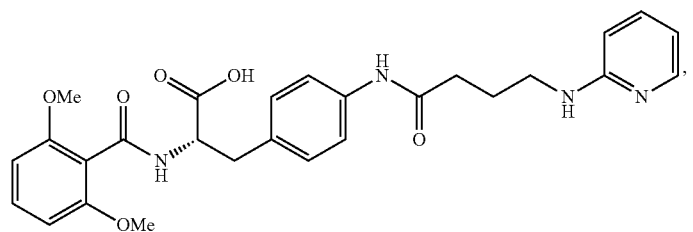
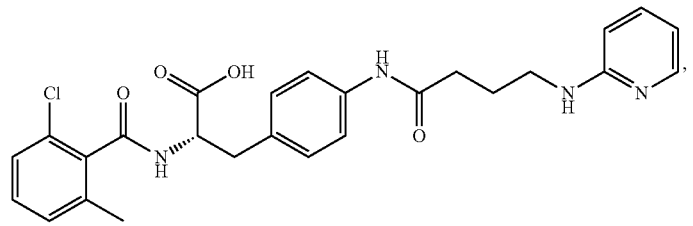
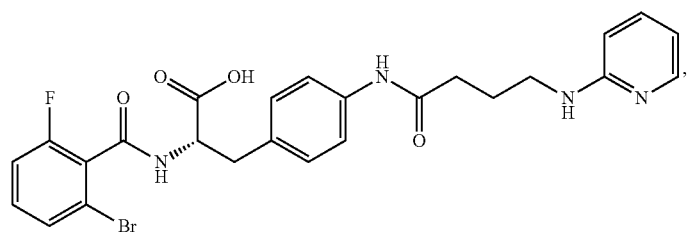
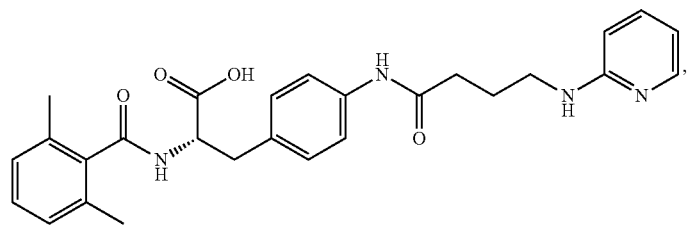
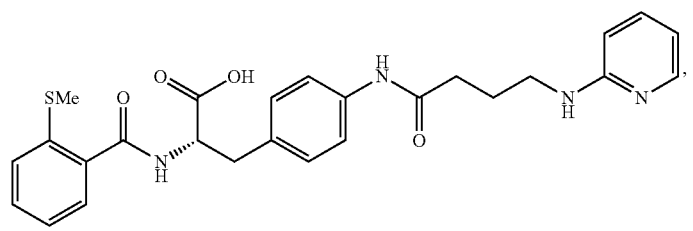
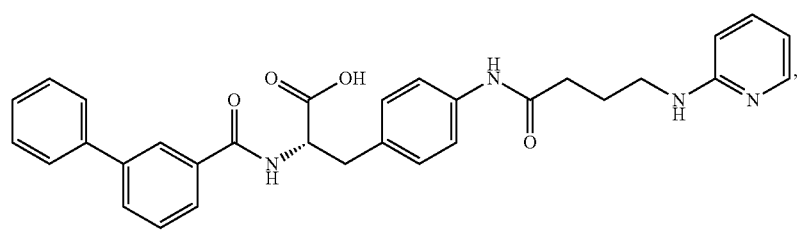
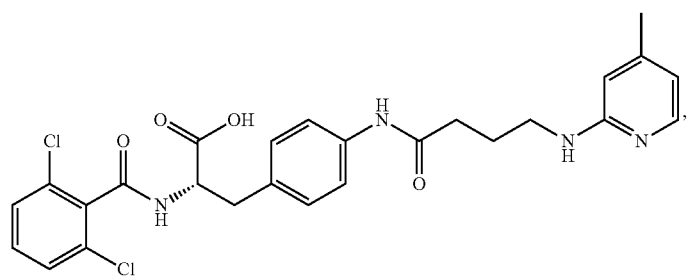

-continued
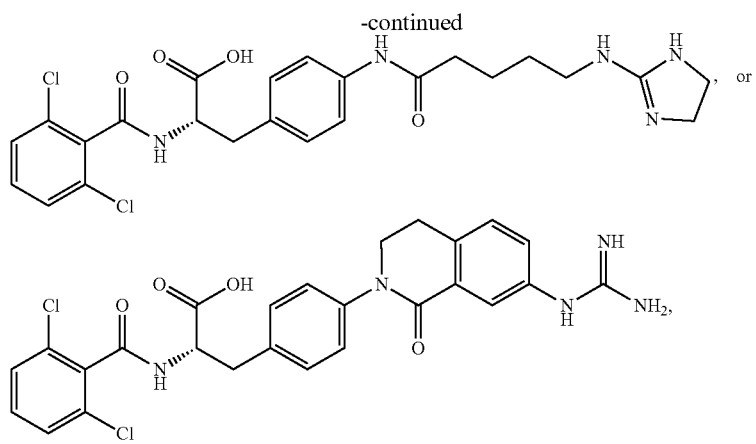
* * * * *